(12) United States Patent
He et al.

(10) Patent No.: US 9,938,301 B2
(45) Date of Patent: Apr. 10, 2018

(54) DIHYDROPYRIMIDO FUSED RING DERIVATIVE AS HBV INHIBITOR

(71) Applicant: QILU PHARMACEUTICAL CO., LTD., Shandong (CN)

(72) Inventors: Haiying He, Shanghai (CN); Kai Zhou, Shanghai (CN); Hua Qin, Shanghai (CN); Xiaolin Li, Shanghai (CN); Yuedong Zhou, Shanghai (CN); Xiaofei Wang, Shanghai (CN); Xuemei Chi, Shanghai (CN); Jian Li, Shanghai (CN); Shuhui Chen, Shanghai (CN)

(73) Assignee: QILU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 15/314,599

(22) PCT Filed: May 27, 2015

(86) PCT No.: PCT/CN2015/079870
§ 371 (c)(1),
(2) Date: Nov. 29, 2016

(87) PCT Pub. No.: WO2015/180631
PCT Pub. Date: Dec. 3, 2015

(65) Prior Publication Data
US 2017/0197986 A1 Jul. 13, 2017

(30) Foreign Application Priority Data

May 30, 2014 (CN) .......................... 2014 1 0240665
Dec. 31, 2014 (CN) .......................... 2014 1 0850212
May 22, 2015 (CN) .......................... 2015 1 0268946

(51) Int. Cl.
| C07D 487/04 | (2006.01) |
| C07D 498/04 | (2006.01) |
| C07D 471/04 | (2006.01) |
| C07D 487/10 | (2006.01) |
| C07D 513/04 | (2006.01) |

(52) U.S. Cl.
CPC ......... *C07D 513/04* (2013.01); *C07D 471/04* (2013.01); *C07D 487/04* (2013.01); *C07D 498/04* (2013.01)

(58) Field of Classification Search
CPC .. C07D 487/04; C07D 498/04; C07D 471/04; C07D 487/10
See application file for complete search history.

(56) References Cited

U.S. PATENT DOCUMENTS

| 6,696,451 B1 | 2/2004 | Stoltefuss et al. |
| 7,514,565 B2 | 4/2009 | Stoltefuss et al. |
| 9,340,538 B2 | 5/2016 | Zhang et al. |
| 2004/0167135 A1 | 8/2004 | Stoltefuss et al. |
| 2007/0117812 A1 | 5/2007 | Stoltefuss et al. |
| 2015/0152096 A1 | 6/2015 | Zhang et al. |

FOREIGN PATENT DOCUMENTS

| CN | 1305471 A | 7/2001 |
| CN | 103570626 A | 2/2014 |
| CN | 103626752 A | 3/2014 |
| CN | 103664897 A | 3/2014 |
| CN | 103664899 A | 3/2014 |
| CN | 103664925 A | 3/2014 |
| CN | 105153164 A | 12/2015 |
| WO | 01/45712 A1 | 6/2001 |

OTHER PUBLICATIONS

Hong et al. (Journal of the American Chemical Society (1992), 114(18), 7001-6).*
Sergio G. Duron et al., "Synthesis and Determination of Absolute Configuration of the Bicyclic Guanidine Core of Batzelladine A", Organic Letters 2001 vol. 3, No. 10, pp. 1551-1554.
Kjell Undheim et al., "N-Quaternary Compounds—Part VIII. Synthesis and Properties of Dihydrothiazolo[3,2-c]pyrimidinium-8-oxides", Acta Chemica Scandinavica 23 (1969) No. 7, pp. 2437-2451.
Supplementary European Search Report dated Feb. 17, 2017 corresponding to EP 15799888.1.
International Search Report dated Sep. 8, 2015 issued in corresponding PCT/CN2015/079870 application (4 pages).
English Abstract of CN 103570626 A published Feb. 12, 2014.
English Abstract of CN 103626752 A published Mar. 12, 2014.
English Abstract of CN 103664897 A published Mar. 26, 2014.
English Abstract of CN 103664899 A published Mar. 26, 2014.
English Abstract of CN 103664925 A published Mar. 26, 2014.
K. Deres et al., "Inhibition of Hepatitis B Virus Replication by Drug-Induced Depletion of Nucleocapsids", Science, vol. 299 (2003) pp. 893-896.
H.J. Hacker et al., "Antivirals Interacting with Hepatitis B Virus Core Protein and Core Mutations May Misdirect Capsid Assembly in a Similar Fashion", Biochemistry Pharmacology, vol. 66 (2003) pp. 2273-2279.

(Continued)

*Primary Examiner* — Bruck Kifle
(74) *Attorney, Agent, or Firm* — Millen, White, Zelano & Branigan, P.C.

(57) ABSTRACT

Disclosed is a dihydropyrimido fused ring derivative as a HBV inhibitor, and in particular relates to a compound shown as formula (I) or a pharmaceutically acceptable salt thereof.

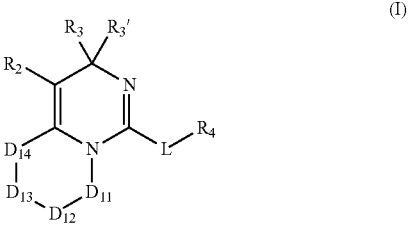

18 Claims, No Drawings

(56) References Cited

OTHER PUBLICATIONS

S.M. Berge et al., "Pharmaceutical Salts", Journal of Pharmaceutical Sciences, vol. 66, No. 1 (1977) pp. 1-19.
H. Maehr, "A Proposed New Convention for Graphic Presentation of Molecular Geometry and Topography", Journal of Chemical Education, vol. 62, No. 2 (Feb. 1965) pp. 114-120.
Remington: The Science and Practice of Pharmacy, 21st Ed., Lippincott, Williams&Wilkins (2005) 358 pages.
English Translation of Chinese Patent Application No. 201410850212.9 (not published).
English Translation of Chinese Patent Application No. 201510268946.0 (not published).
Office Action dated Mar. 21, 2016 issued in corresponding TW 2015-46073 A application (4 pages).
Written Opinion of the International Searching Authority dated Sep. 8, 2015 issued in corresponding PCT/CN2015/079870 application (5 pages).

\* cited by examiner

DIHYDROPYRIMIDO FUSED RING DERIVATIVE AS HBV INHIBITOR

TECHNICAL FIELD

The present invention relates to a dihydropyrimido fused ring derivative as a HBV inhibitor, and particularly to a compound represented by formula (I) or a pharmaceutically acceptable salt thereof.

PRIOR ART

Hepatitis B virus belongs to Hepadnaviridae family. It can cause acute and or persistent/progressive chronic diseases. Hepatitis B virus also causes many other clinical manifestations in pathomorphology, in particular, chronic liver inflammation, hepatic cirrhosis and hepatocellular canceration. Furthermore, co-infection with hepatitis D will cause adverse effects during the development of the disease.

The conventional medicaments licensed for treating chronic hepatitis include interferon and lamivudine. However, interferon only has moderate activity but relatively high toxic side effects; although lamivudine has good activity, its drug resistance increases rapidly during therapy and rebound effects often occur after discontinuation of therapy, and the $IC_{50}$ value of lamivudine(3-TC)> is 300 nM (Science, 299 (2003), 893-896).

Deres et al have reported a type of heteroaromaticly substituted dihydropyrimidine (HAP) compounds represented by Bay41_4109, Bay39_5493, and this type of compounds could play a role in inhibiting replication of HBV by preventing the forming of normal nucleocapsids. Bay41-4109 has demonstrated better drug metabolic parameters during clinical studies (Science, 299 (2003), 893-896). Researches on its mechanisms have found that the heteroaromaticly substituted dihydropyrimidine (HAP) compounds change the angle between the dimmers that forms the nucleocapsid by interacting with 113-143 amino acid residues of the core protein, leading to the formation of unstable swollen nucleocapsid and accelerating the degradation of the core protein (Biochem. Pharmacol. 66 (2003), 2273-2279).

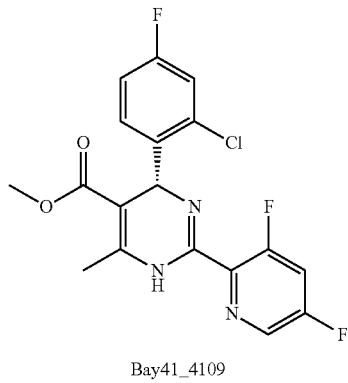 [SMILES: COC(=O)C1=C(C)NC(c2ncc(F)cc2F)=N[C@H]1c1ccc(F)cc1Cl]

Bay41_4109

Currently, there is still a need of a new compound capable of effectively acting as an antiviral drug, particularly a medicament for treating and/or preventing Hepatitis B.

CONTENTS OF THE INVENTION

One objective of the invention is to provide a compound represented by formula (I) or a pharmaceutically acceptable salt thereof,

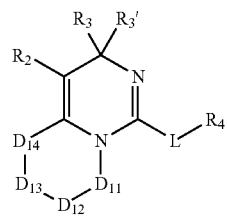

(I)

wherein, 0 to 2 of $D_{11-14}$ are separately and independently selected from a single bond, —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, —C(=O)O—, —C(=O)—, —C(=S)—, —S(=O)— or —S(=O)$_2$—, and the rest are selected from —C($R_{d1}$)($R_{d2}$)—;

L is selected from a single bond, —O—, —S—, —NH—, —C(=O)—, —C(=S)—, —S(=O)—, —S(=O)$_2$—, —C(=O)N($R_{d3}$)—, —N($R_{d4}$)—, —[C($R_{d1}$)($R_{d2}$)]$_{0-6}$;

$R_2$ is selected from

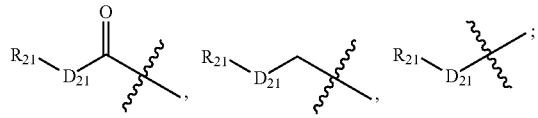

$D_{21}$ is selected from a single bond, —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, —[C($R_{d1}$)($R_{d2}$)]$_{0-6}$;

$R_3$, $R_4$ are separately and independently selected from the following groups optionally substituted by $R_{01}$: $C_{1-10}$ alkyl or heteroalkyl, 3-6 membered cycloalkyl or heterocycloalkyl, 6-10 membered aromatic ring group or heteroaromatic ring group;

$R_3'$, $R_{21}$, $R_{d1-8}$ are separately and independently selected from H, F, Cl, Br, I, OH, $NH_2$, CN, —COOH, or selected from the following groups optionally substituted by $R_{01}$: $C_{1-4}$ alkyl, —$C_{0-4}$ alkylphenyl, —$C_{0-4}$ alkyl-3-6 membered heterocyclyl, 3-6 membered heterocyclylacyl-, benzenesulfonamido or heterobenzenesulfonamido, -$D_{01}$-$D_{02}$-$D_{03}$-H,

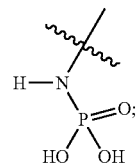

$D_{01}$ is selected from a single bond, —$C_{1-4}$ alkyl-;
$D_{02}$ is selected from O, S, NH, —C(=O)—, —S(=O)$_2$—, —C(=O)O—, —C(=O)NH—, —C(=S)NH—, —S(=O)$_2$ NH—, —S(=O)NH—, —NHC(=O)O—, —NHC(=O)NH—, —NHS(=O)$_2$NH—, —C(=O)NHS(=O)$_2$—, —NHS(=O)NH—, —C(=O)NHS(=O)—, —NHS(=O)$_2$O—, —NHS(=O)O—, —C(=N)—, —NH—C(=N)—;
$D_{03}$ is selected from a single bond, —$C_{1-4}$ alkyl-, —$C_{2-4}$ alkenyl-, —$C_{3-6}$ cycloalkyl-, -3-6 membered heterocycloalkyl-, 5-6 membered aryl, 5-6 membered heteroaryl;
optionally, $R_3$ and $R_3'$ are together linked to the same carbon atom or heteroatom to form a 3-12 membered ring which is optionally substituted;

"hetero" represents a heteroatom or heteroatom group, which is selected from —C(=O)N(R$_{d3}$)—, —N(R$_{d4}$)—, —C(=NR$_{d5}$)—, —S(=O)$_2$N(R$_{d6}$)—, —S(=O) N(R$_{d7}$)—, —O—, —S—, =O, =S, —C(=O)O—, —C(=O)—, —C(=S)—, —S(=O), —S(=O)$_2$— or/and —P(=O)(OR$_{d8}$)$_2$;

R$_{01}$ is selected from F, Cl, Br, I, CN, OH, SH, NH$_2$, CHO, COOH, =NH, =O, =S, or the following groups optionally substituted by R$_{001}$: C$_{1-10}$ alkyl, C$_{1-10}$ alkylamino, N,N-di (C$_{1-10}$ alkyl)amino, C$_{1-10}$ alkoxy, C$_{1-10}$ alkylacyl, C$_{1-10}$ alkoxycarbonyl, —C$_{1-5}$ alkyl-C(=O)O—C$_{1-10}$ alkyl, C$_{1-10}$ alkylsulfonyl, C$_{1-10}$ alkylsulfinyl, 3-10 membered cycloalkyl, 3-10 membered cycloalkylamino, 3-10 membered heterocycloalkylamino, 3-10 membered cycloalkoxy, 3-10 membered cycloalkylacyl, 3-10 membered cycloalkoxycarbonyl, 3-10 membered cycloalkylsulfonyl, 3-10 membered cycloalkylsulfinyl;

R$_{001}$ is selected from F, Cl, Br, I, CN, OH, N(CH$_3$)$_2$, NH(CH$_3$), NH$_2$, CHO, COOH, =NH, =O, =S, trihalomethyl, dihalomethyl, monohalomethyl, aminomethyl, hydroxymethyl, methyl, methoxy, formyl, methoxycarbonyl, methylsulfonyl, methylsulfinyl;

in any of the above described cases, the number of R$_{01}$, R$_{001}$ is separately and independently selected from 0, 1, 2 or 3, and the number of heteroatom or heteroatom group is separately and independently selected from 1, 2 or 3.

In some embodiments of the invention, the above described compound or pharmaceutically acceptable salt thereof has a structure shown as formula (□):

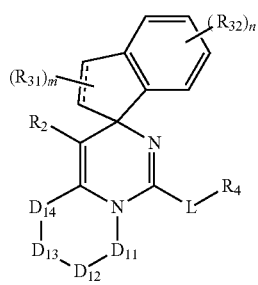

(  )

wherein, R$_{31-32}$ are separately and independently selected from H, F, Cl, Br, I, OH, NH$_2$, CN, —COOH, or selected from the following groups optionally substituted by 1, 2 or 3 R$_{01}$: C$_{1-4}$ alkyl, —C$_{0-4}$ alkylphenyl, —C$_{0-4}$ alkyl-3-6 membered heterocyclyl, 3-6 membered heterocyclylacyl-, benzenesulfonamido or heterobenzenesulfonamido, -D$_{01}$-D$_{02}$-D$_{03}$-H,

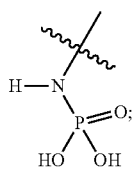

D$_{01}$ is selected from a single bond, —C$_{1-4}$ alkyl-; D$_{02}$ is selected from O, S, NH, —C(=O)—, —S(=O)$_2$—, —C(=O)O—, —C(=O)NH—, —C(=S)NH—, —S(=O)$_2$ NH—, —S(=O)NH—, —NHC(=O)O—, —NHC(=O)NH—, —NHS(=O)$_2$NH—, —C(=O)NHS(=O)$_2$—, —NHS(=O)NH—, —C(=O)NHS(=O)—, —NHS(=O)$_2$ O—, —NHS(=O)O—, —C(=N)—, —NH—C(=N)—; D$_{03}$ is selected from a single bond, —C$_{1-4}$ alkyl-, —C$_{2-4}$ alkenyl-, —C$_{3-6}$ cycloalkyl-, -3-6 membered heterocycloalkyl-, 5-6 membered aryl, 5-6 membered heteroaryl;

m, n are separately and independently selected from 1 or 2;

----- represents a single bond or double bond.

In some embodiments of the invention, the above described -D$_{03}$-H is selected from: H, Me, Et,

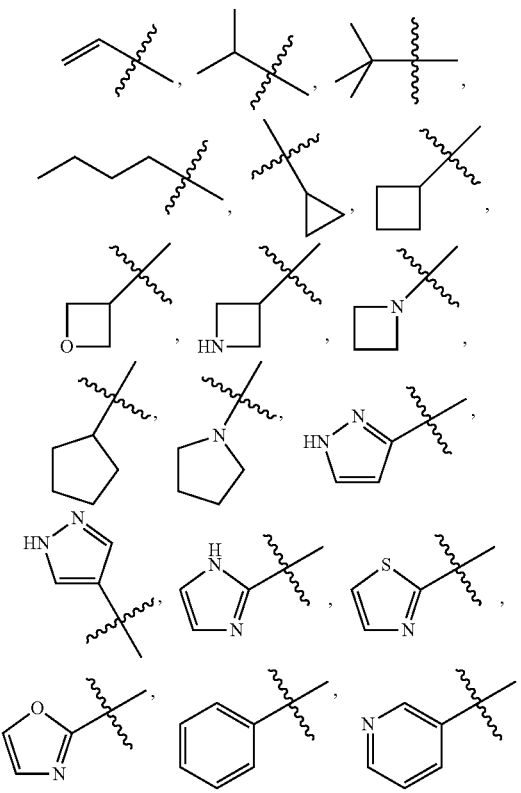

In some embodiments of the invention, R$_{01}$ is selected from halogen, CN, =NH, =O, =S, COOH, or the following groups optionally substituted by 1, 2 or 3 R$_{001}$: hydroxyl, amino, C$_{1-4}$ alkyl, C$_{1-4}$ alkoxy, C$_{0-4}$ alkyl-C(=O)O—C$_{1-4}$ alkyl;

particularly, R$_{01}$ is selected from F, Cl, Br, I, OH, CN, NH$_2$, =NH, =O, =S, —SMe, Me, Et,

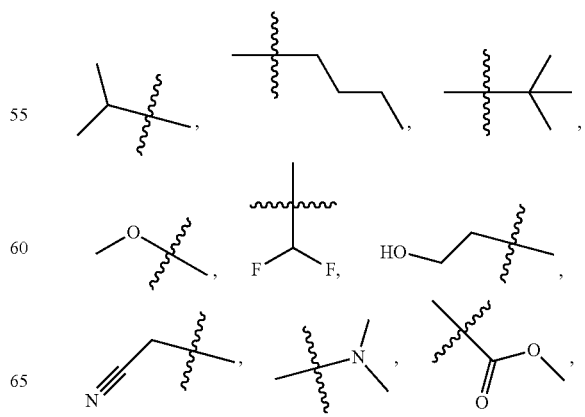

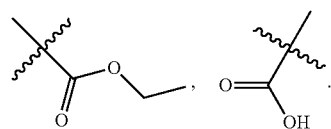
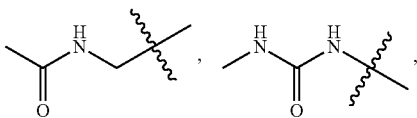
In some embodiments of the invention, the above described $R_3'$, $R_{21}$, $R_{d1-d8}$, $R_{31-32}$ are separately and independently selected from H, F, Cl, Br, I, OH, $NH_2$, CN, —COOH, or selected from the following groups optionally substituted by 1, 2 or 3 $R_{01}$: $CH_3$,
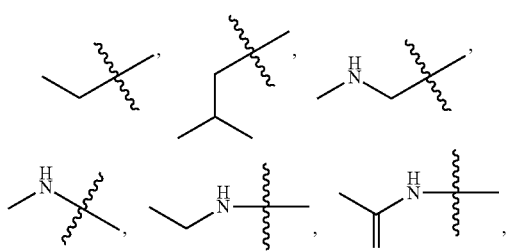
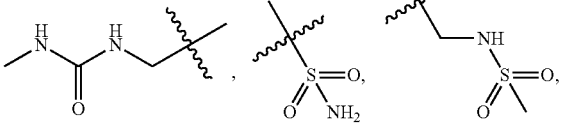
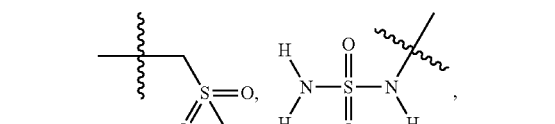
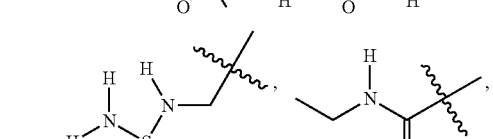

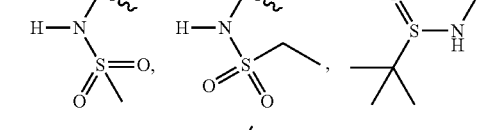
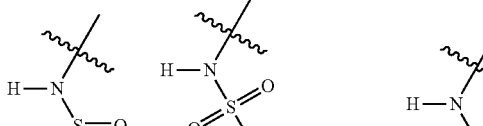
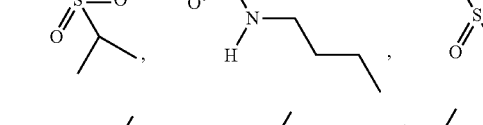
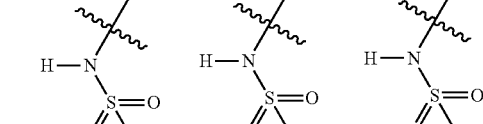
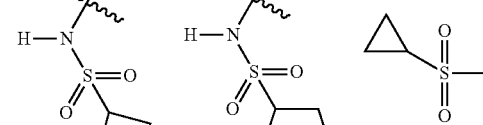
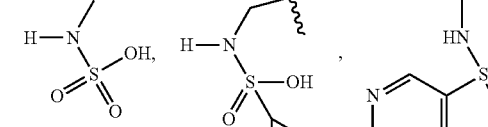

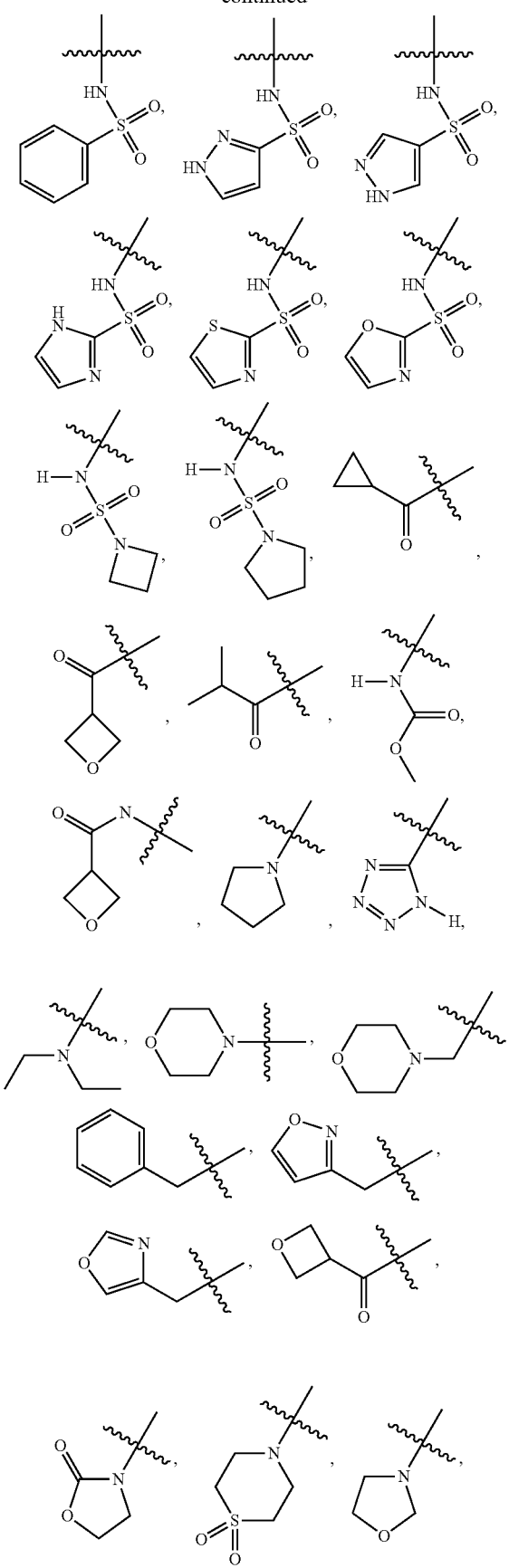
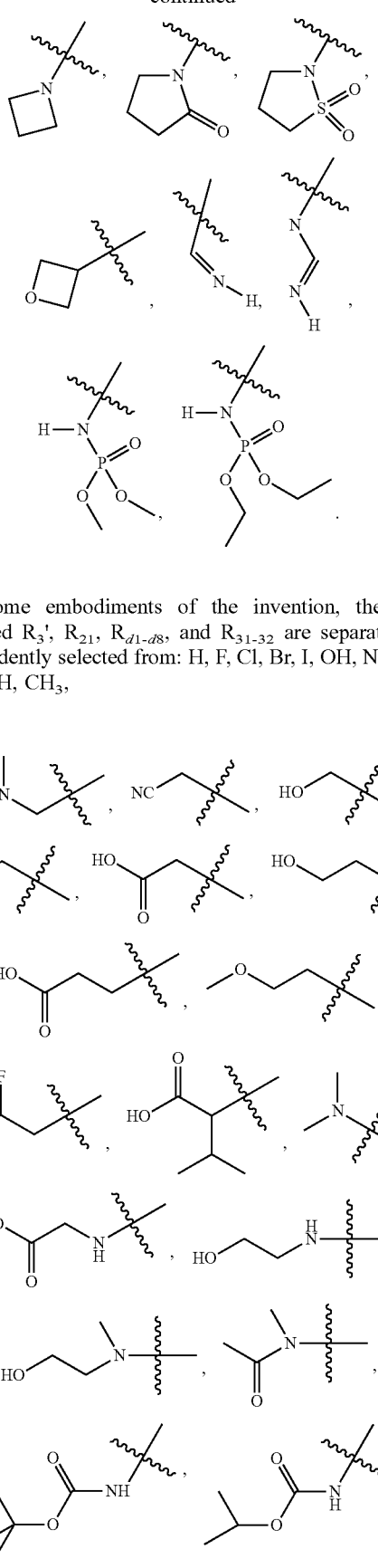
In some embodiments of the invention, the above described $R_3'$, $R_{21}$, $R_{d1-d8}$, and $R_{31-32}$ are separately and independently selected from: H, F, Cl, Br, I, OH, $NH_2$, CN, —COOH, $CH_3$, -continued
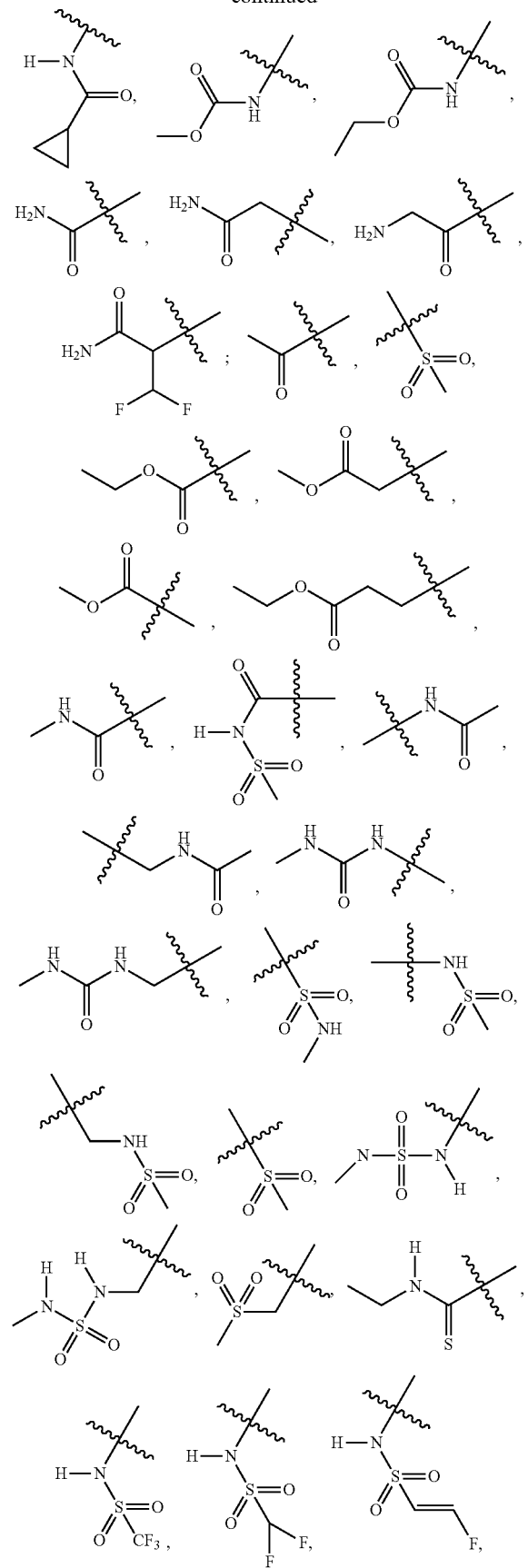
-continued
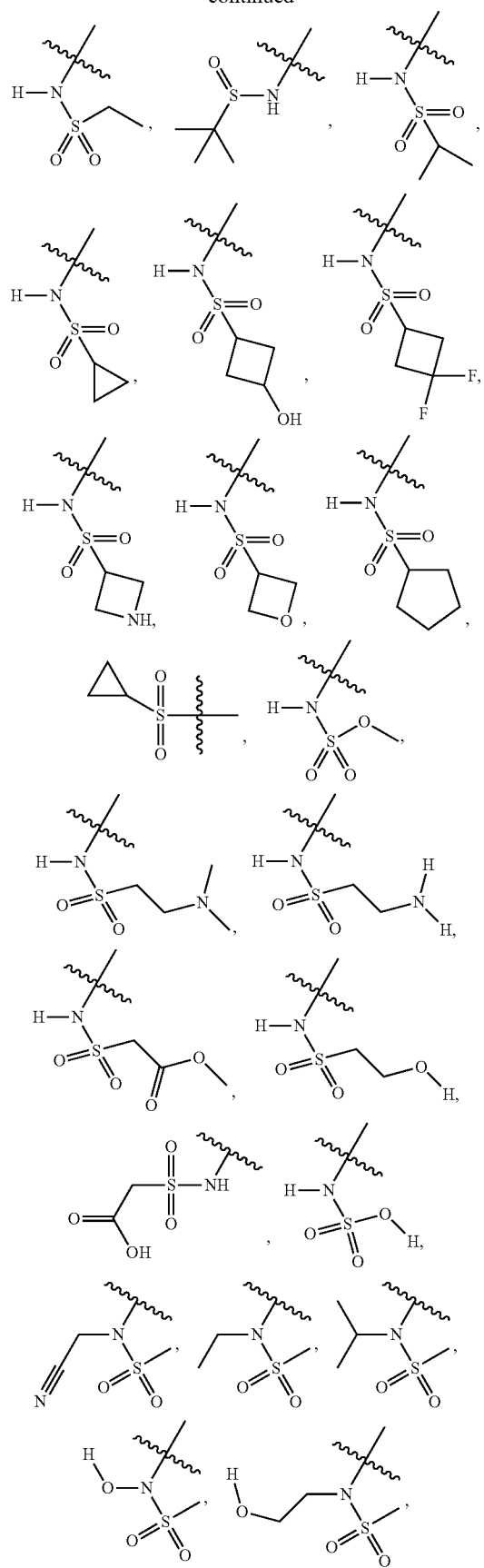

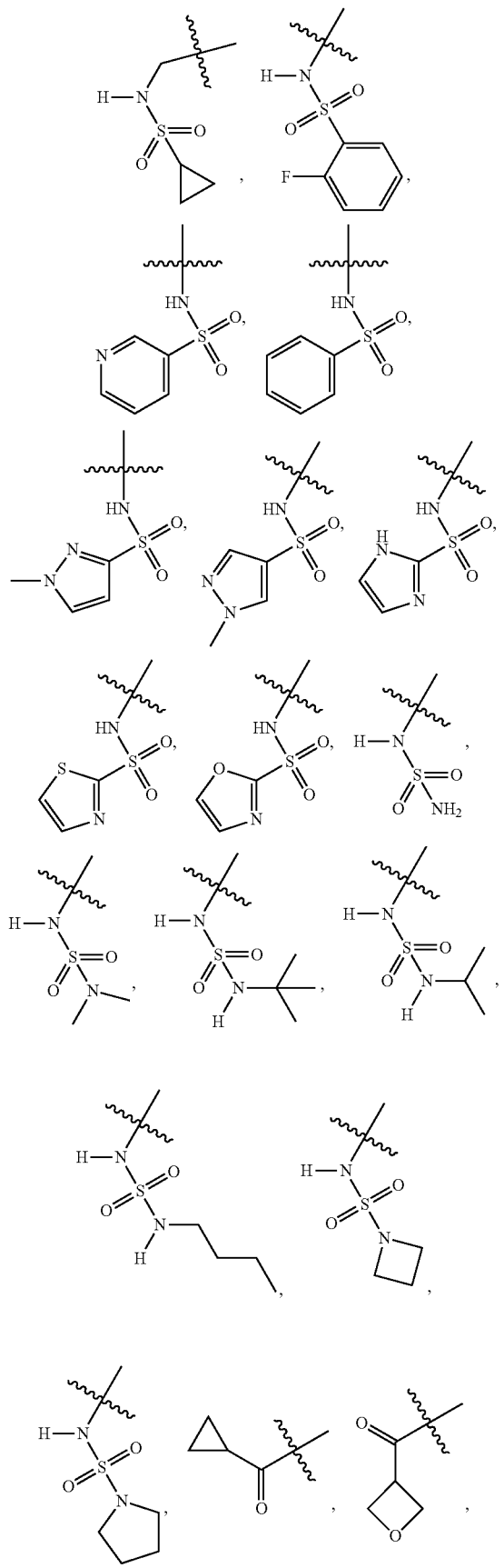
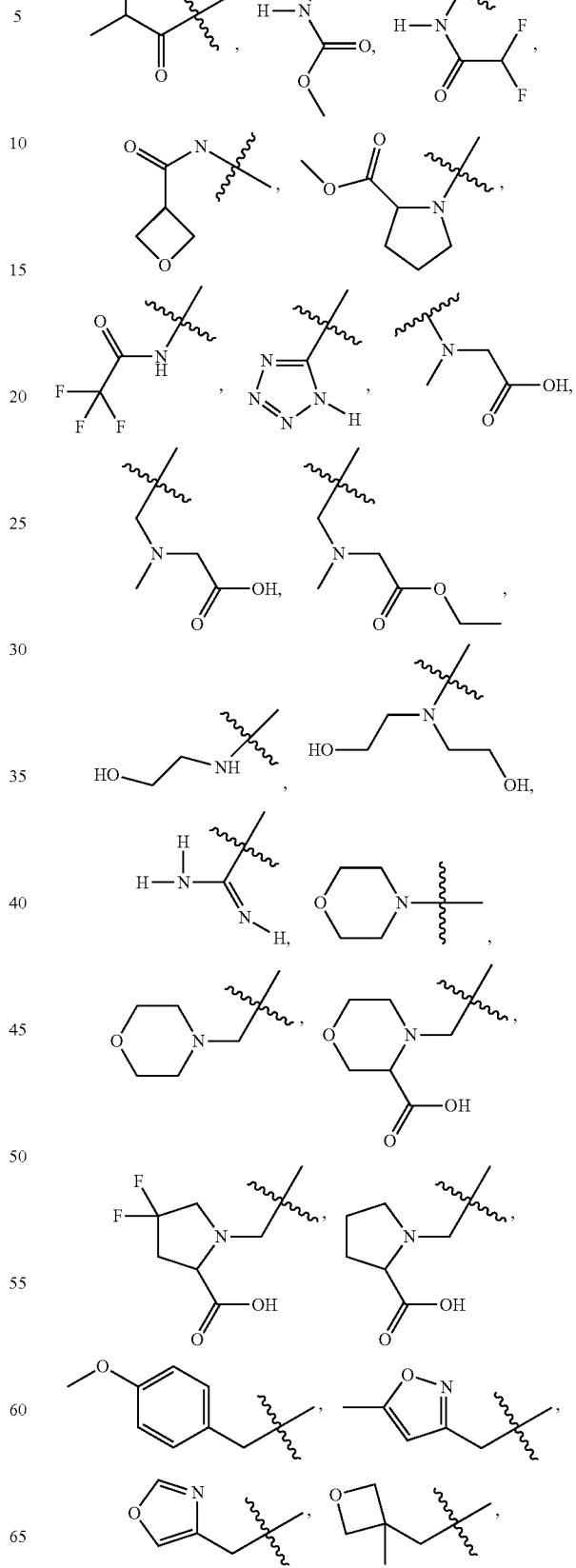

-continued
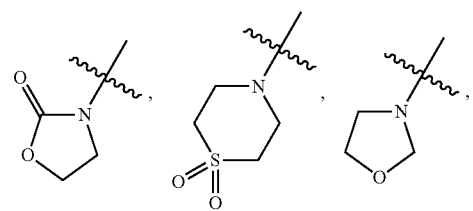
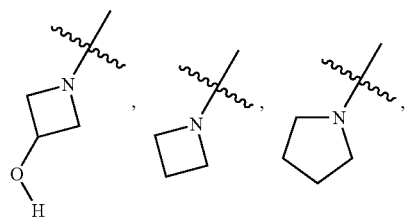
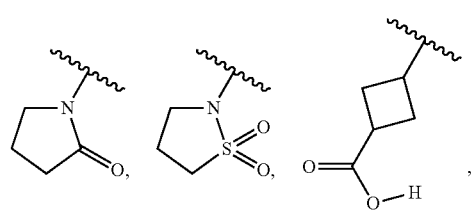
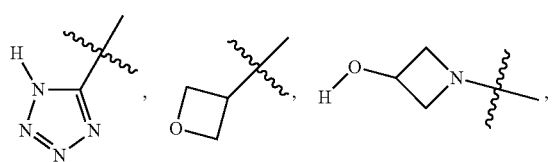
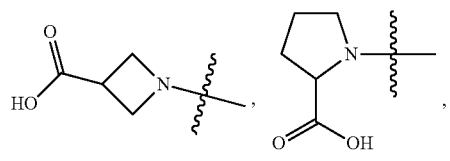
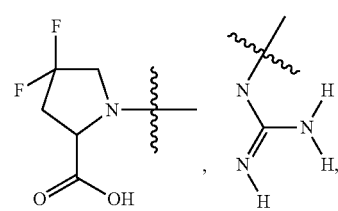
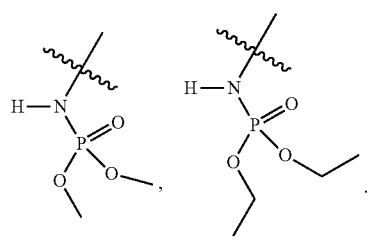
In some embodiments of the invention, the structural unit
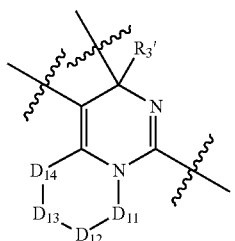
is selected from:
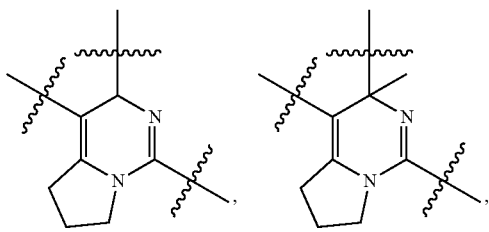
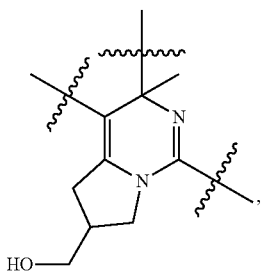
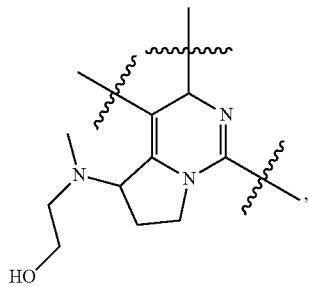
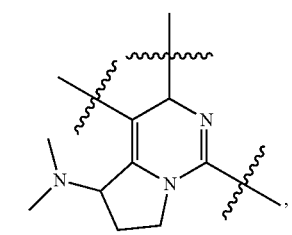
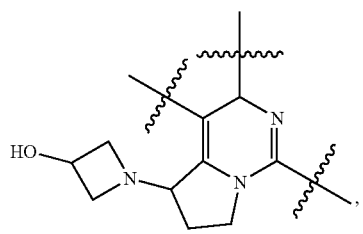

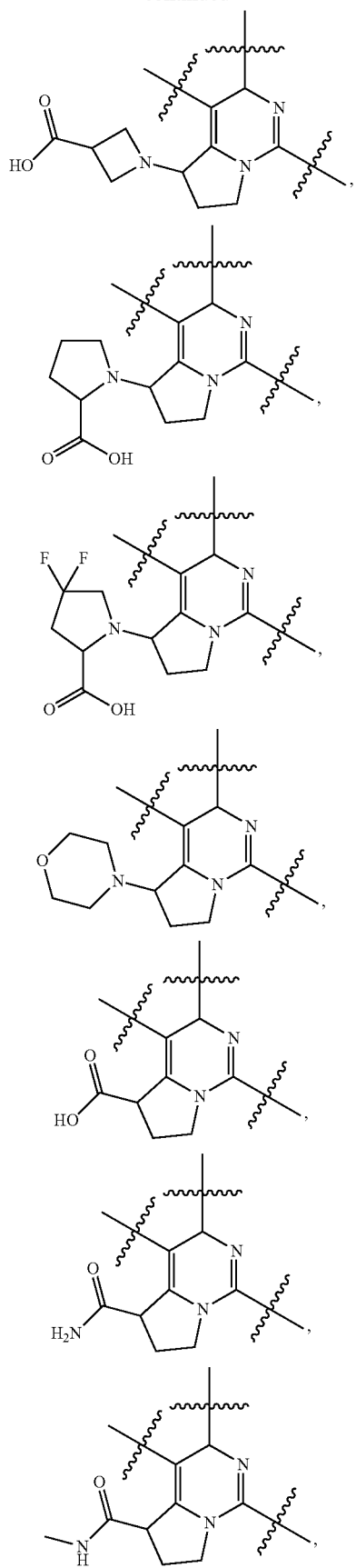
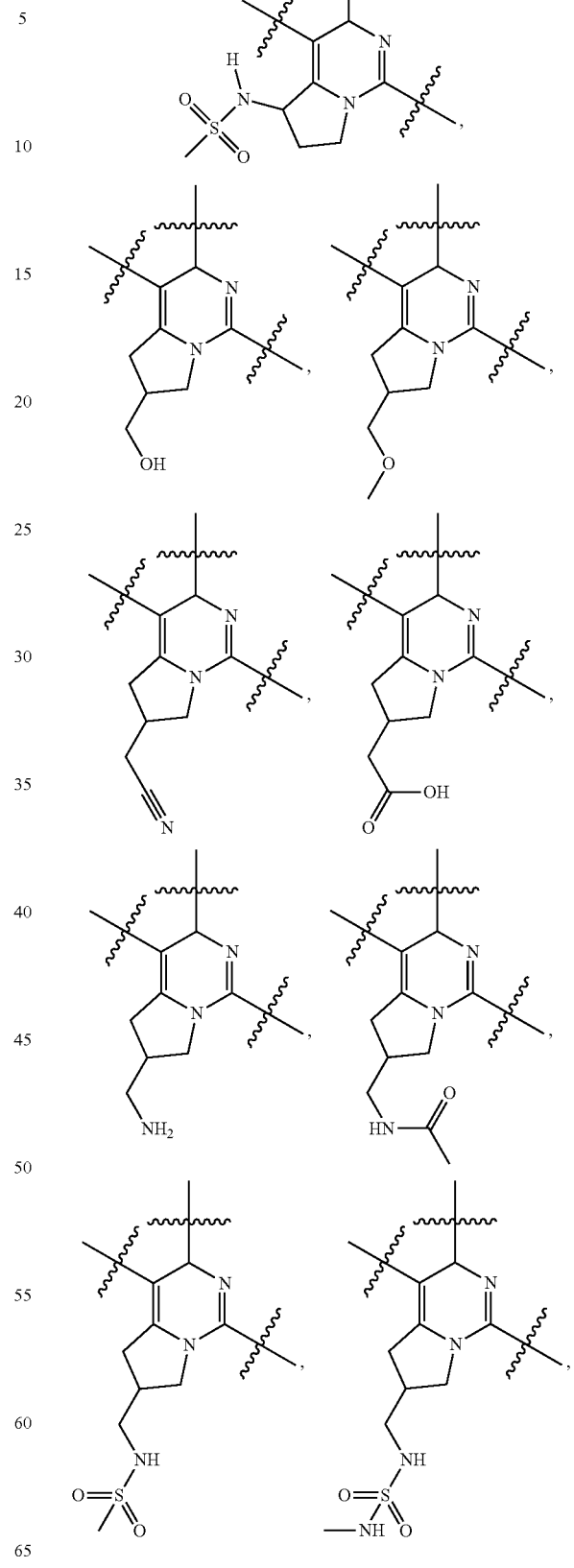

-continued
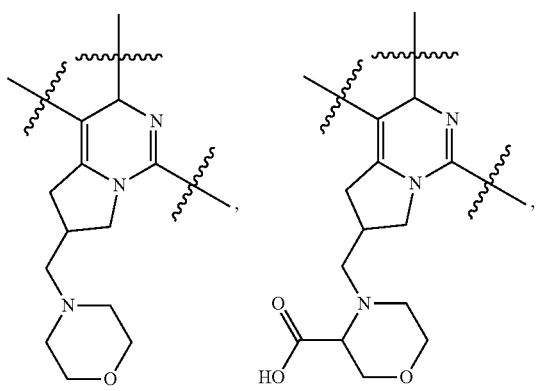
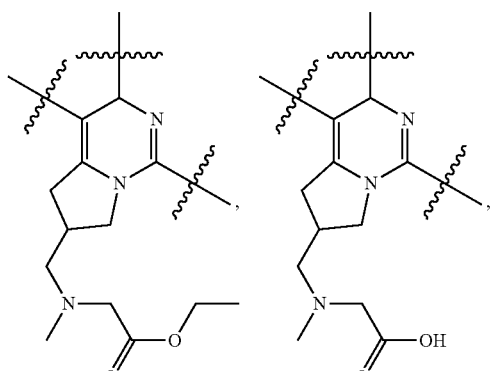
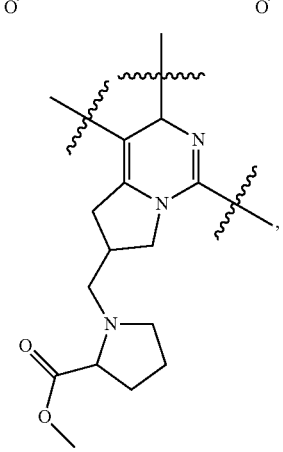
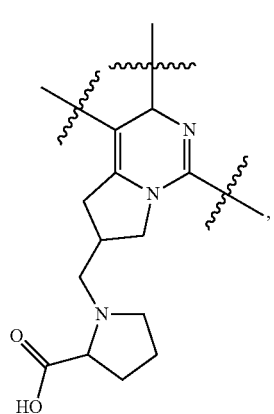
-continued
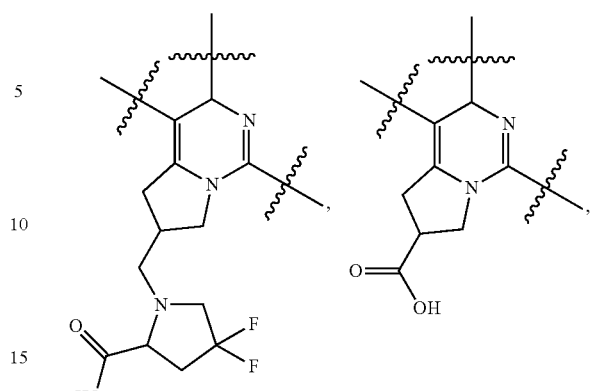
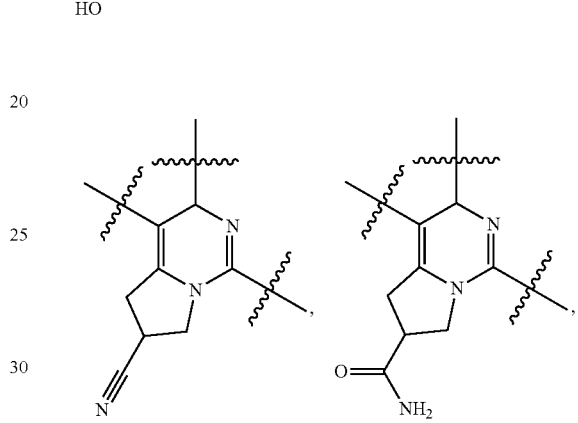
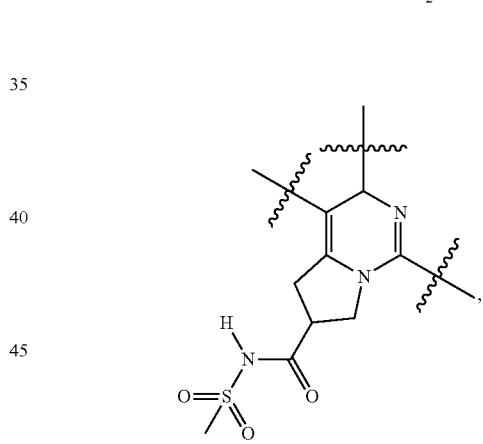
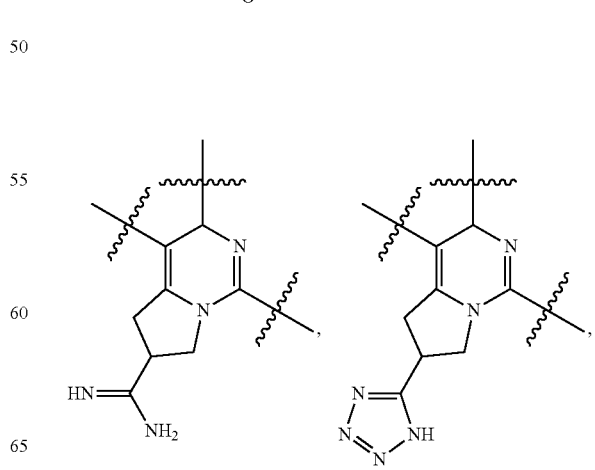

-continued
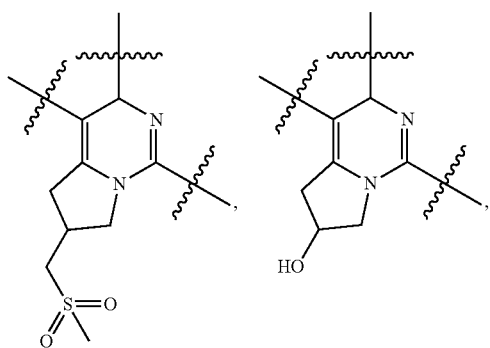
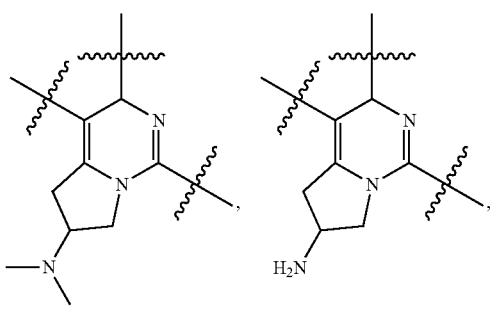
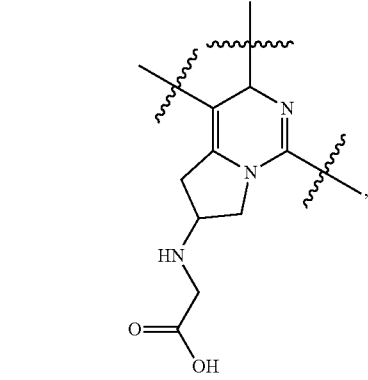
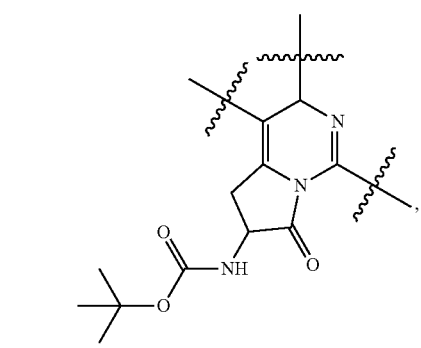
-continued
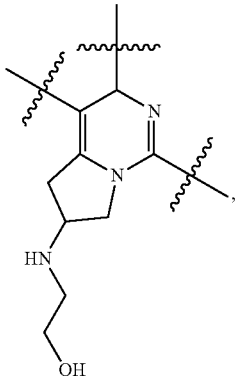
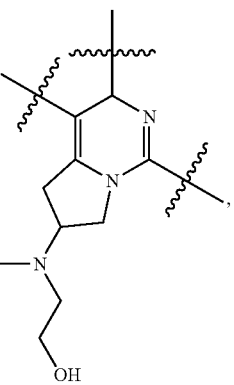
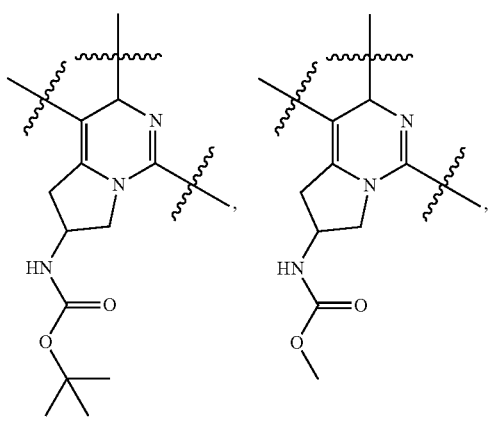
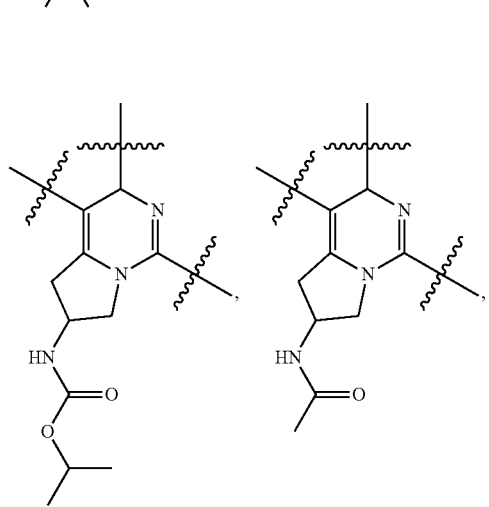

-continued
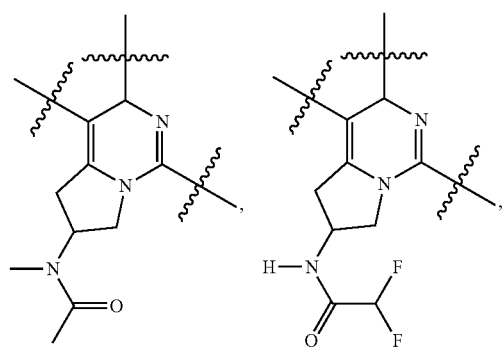
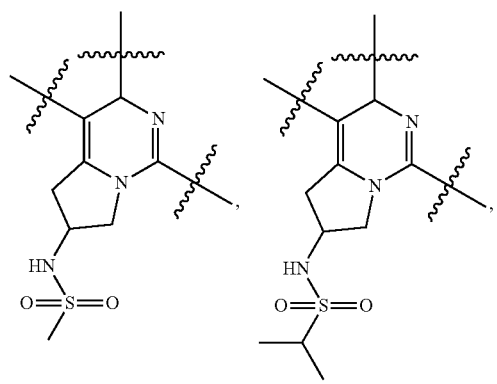
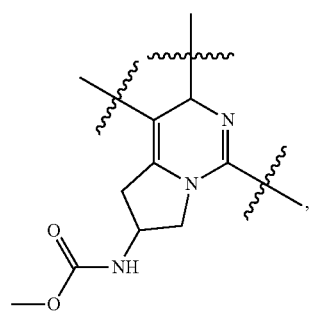
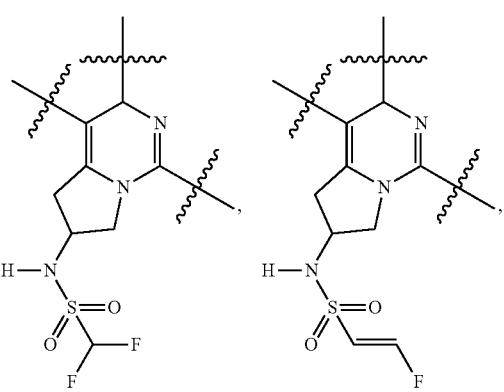
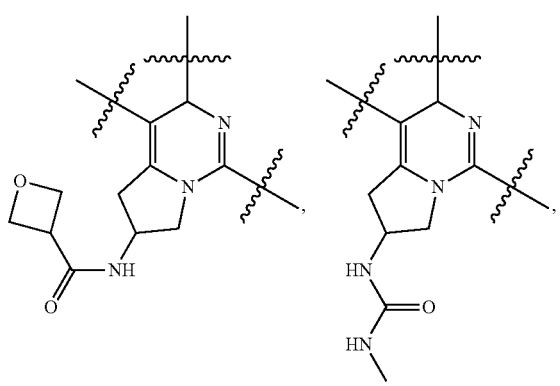
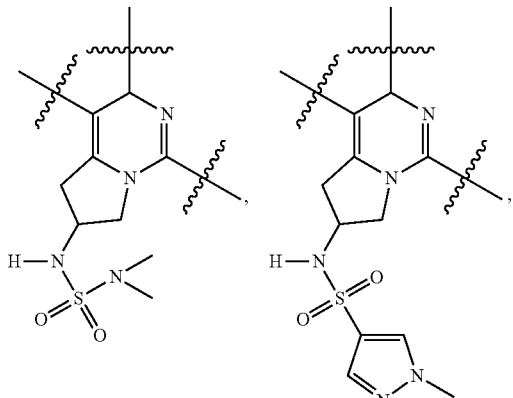
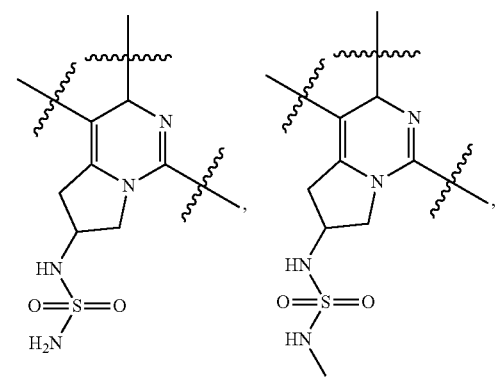
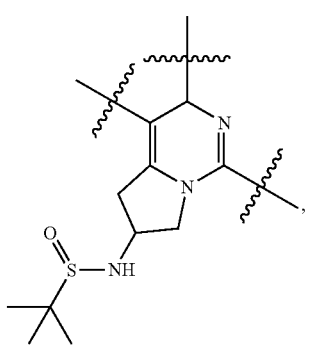

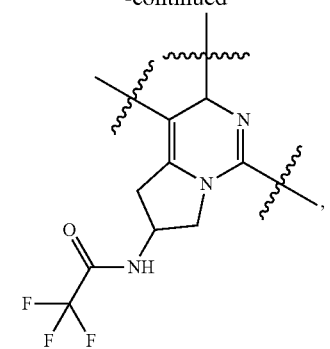
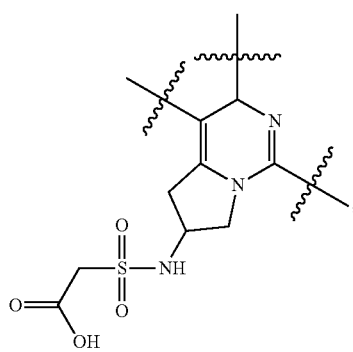
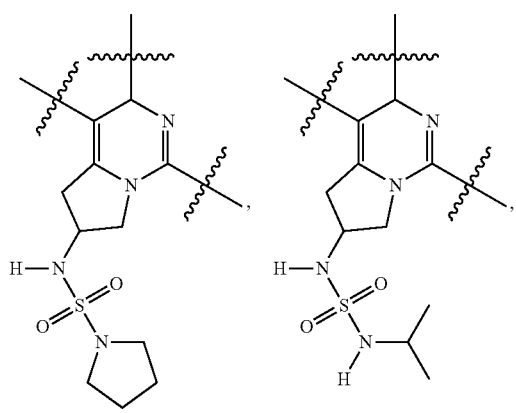
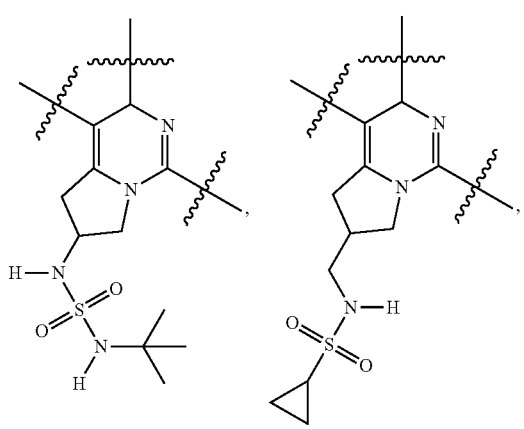
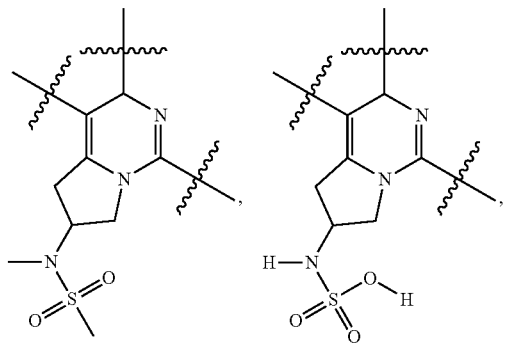
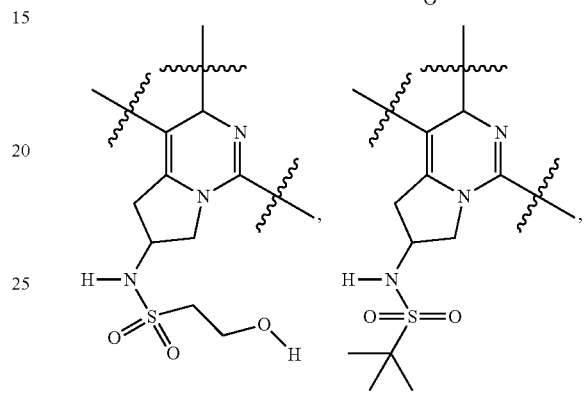
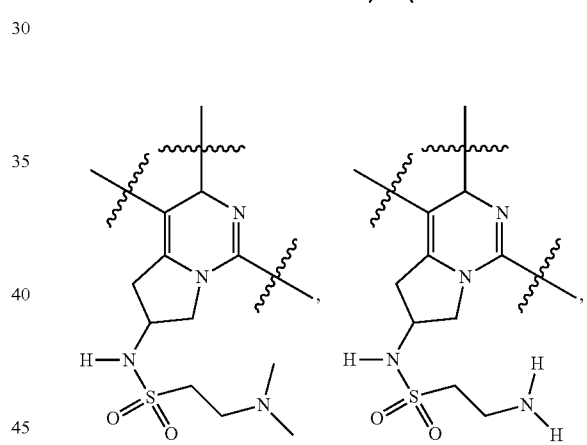
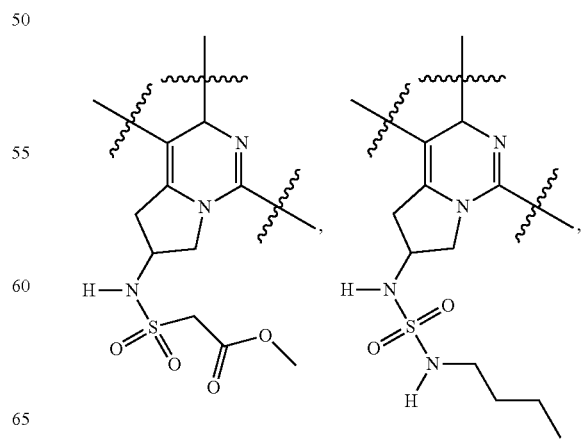

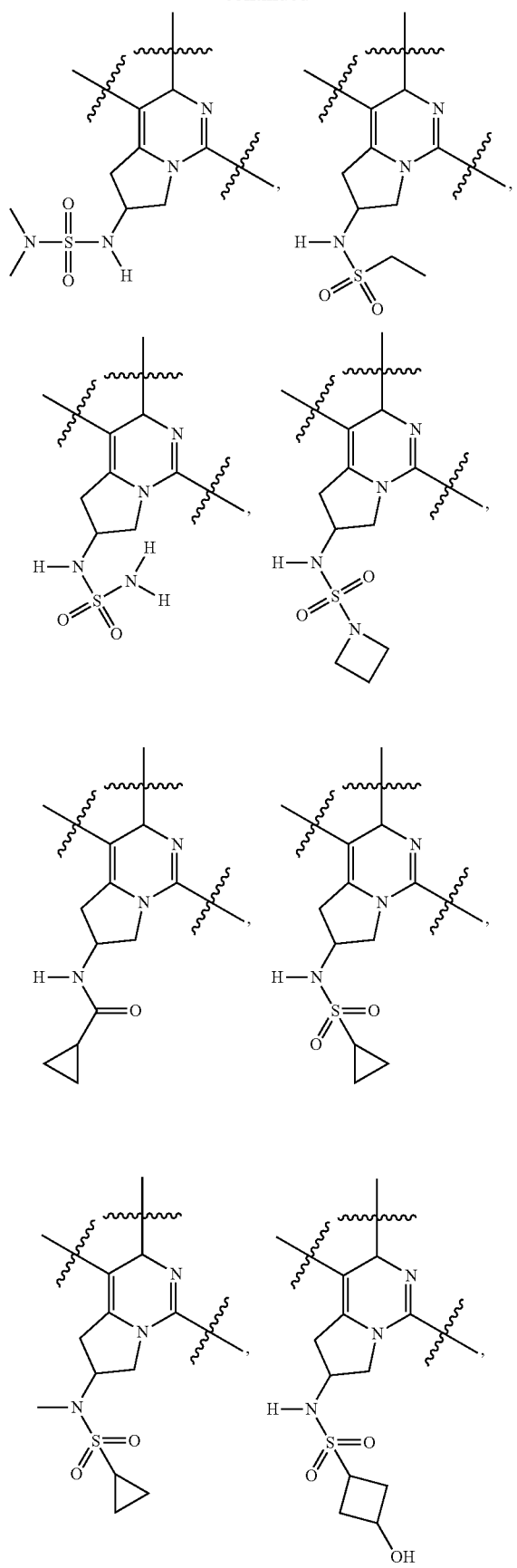
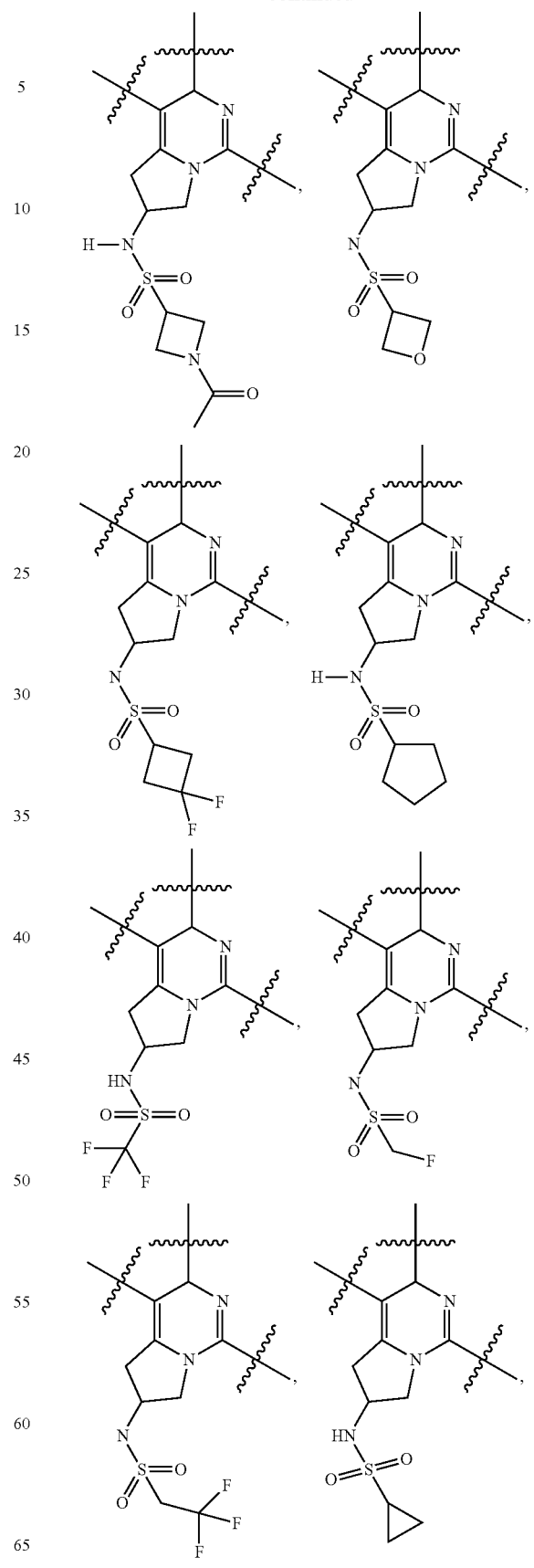

-continued
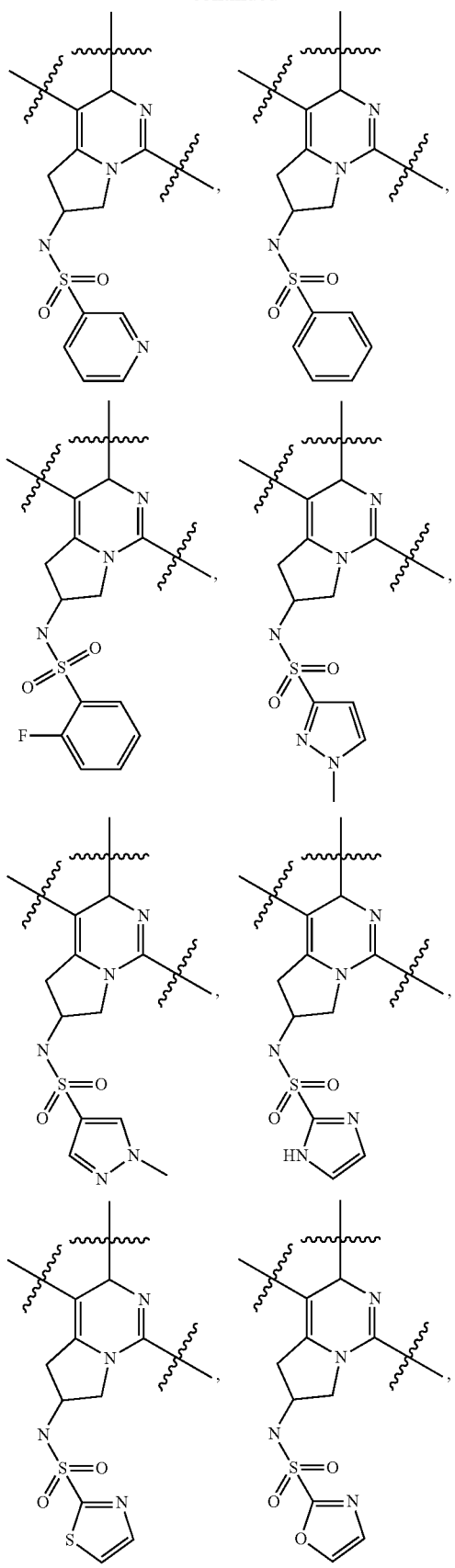
-continued
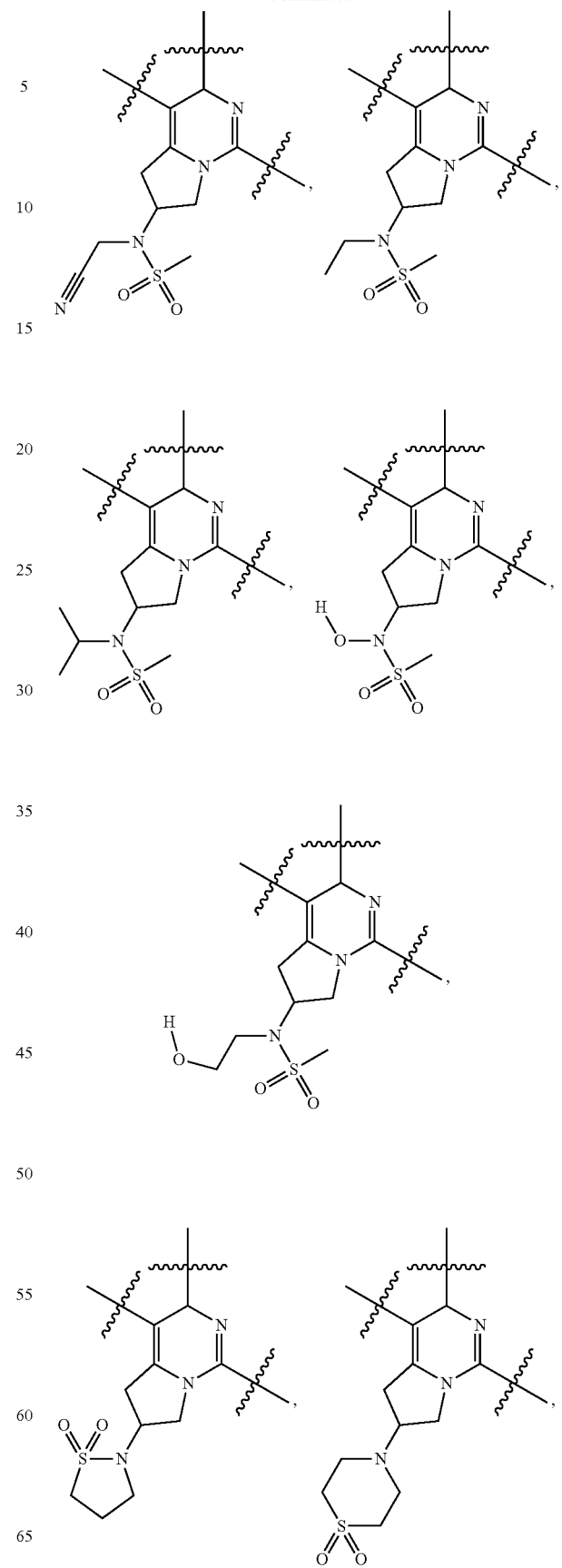

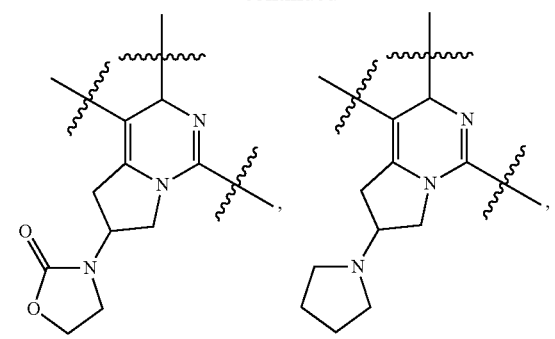
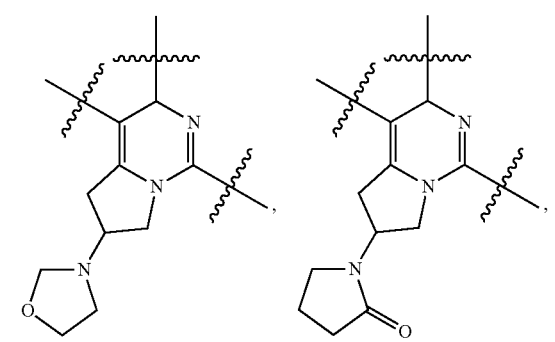
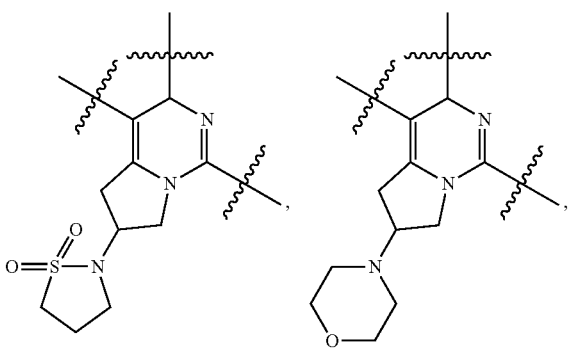
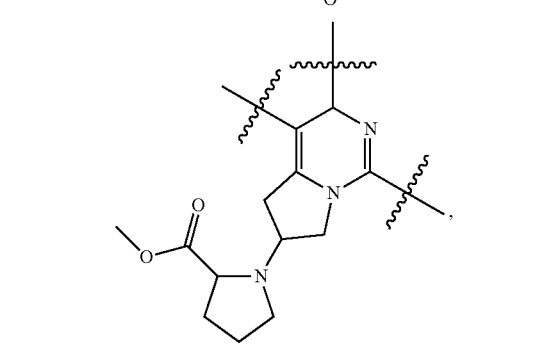
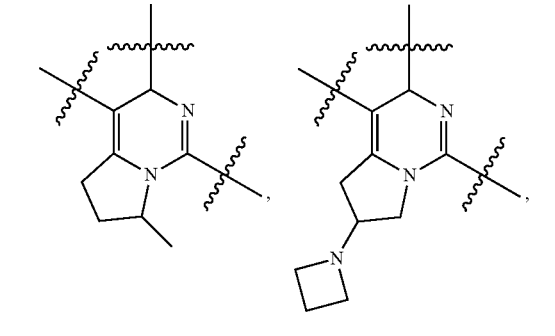
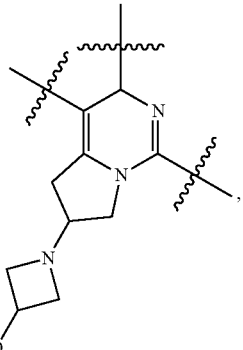
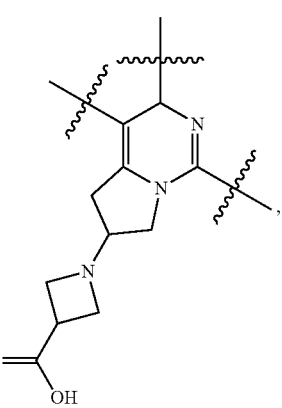
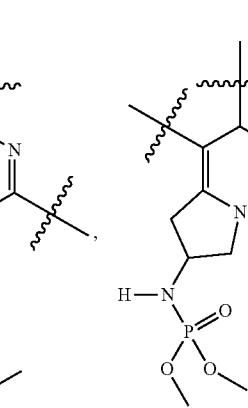
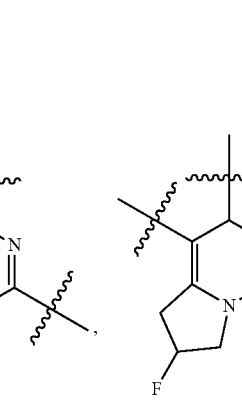

-continued
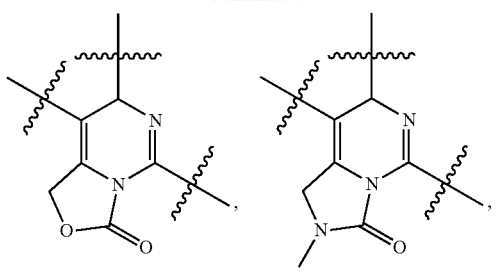
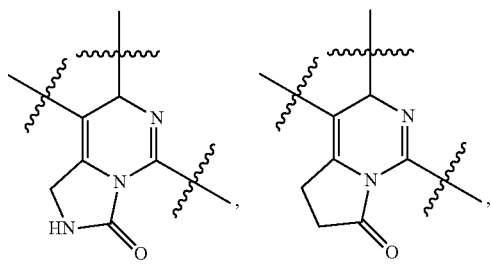
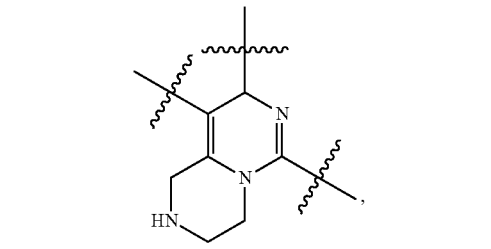
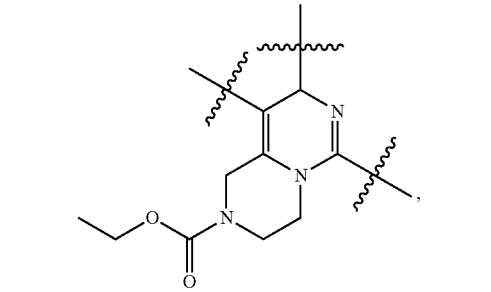
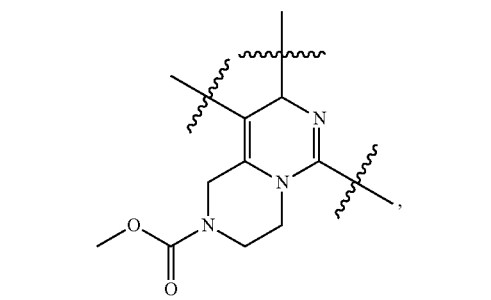

-continued
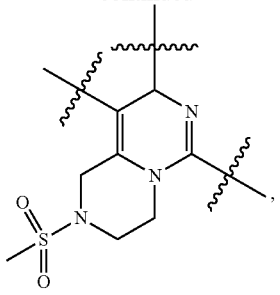
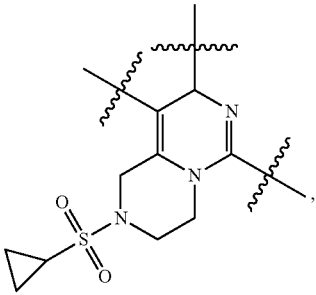
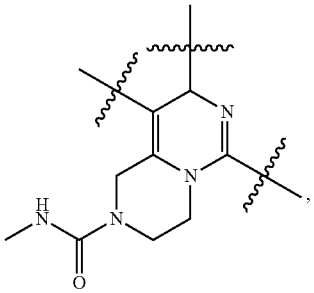
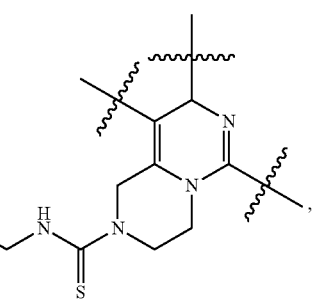
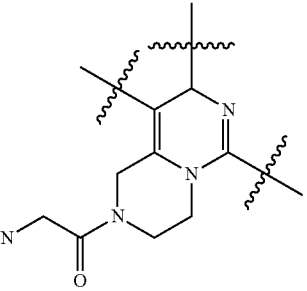

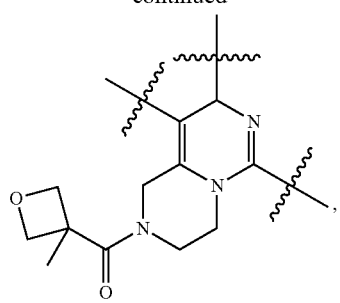,
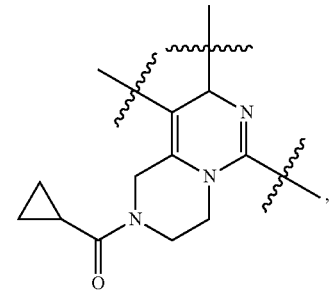,
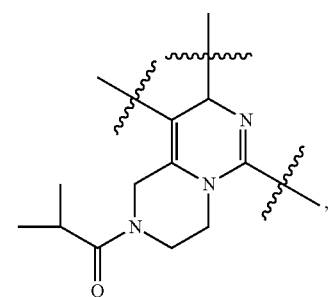,
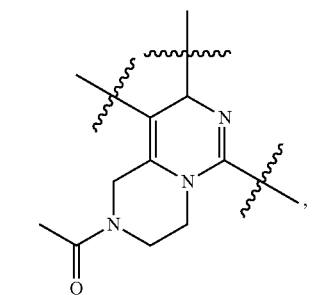,
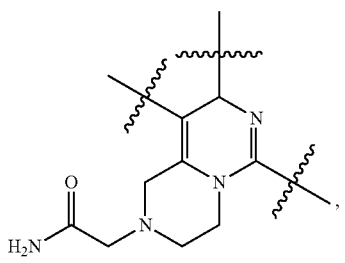,
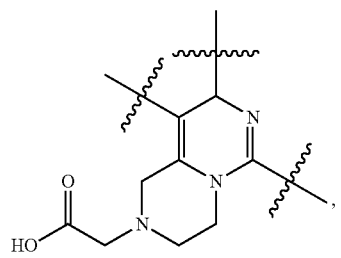,
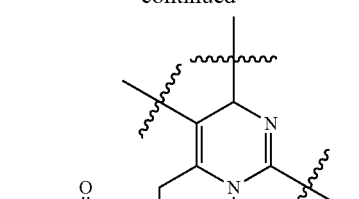,
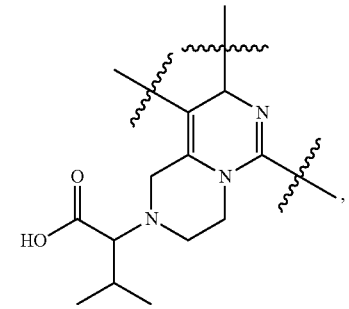,
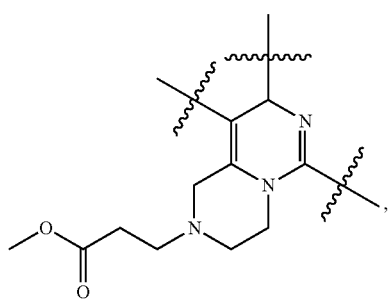,
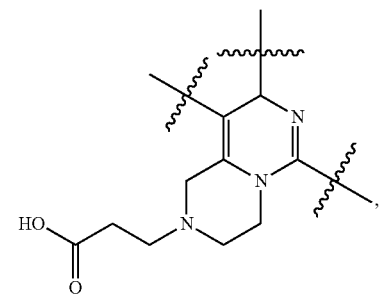,
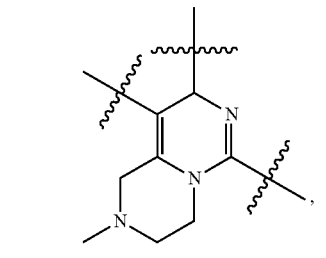,
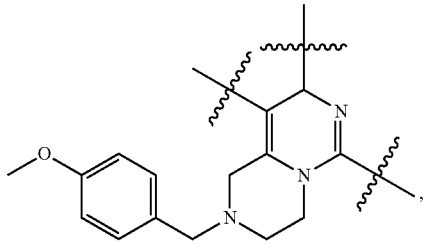, 35
-continued
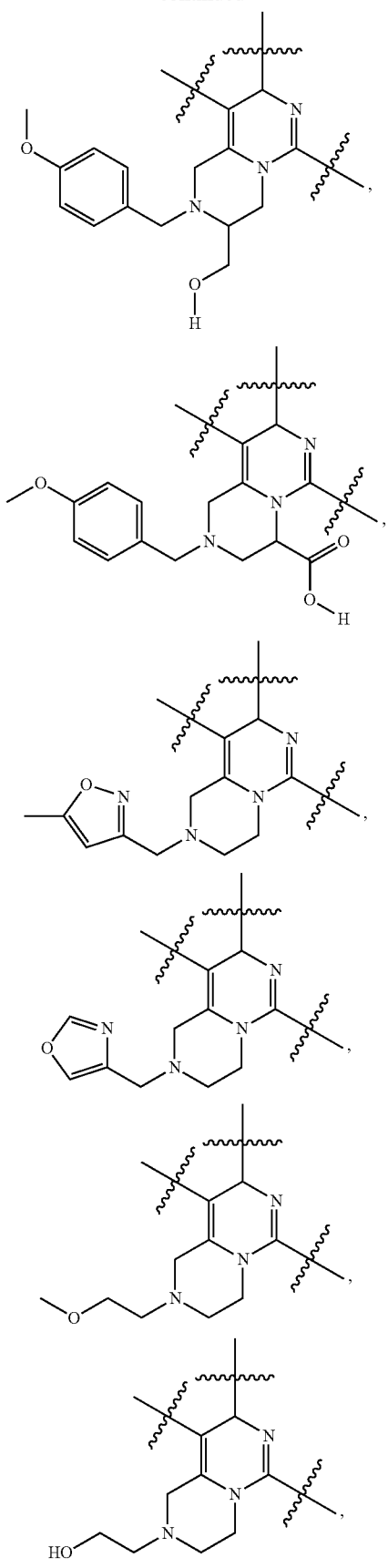
36
-continued
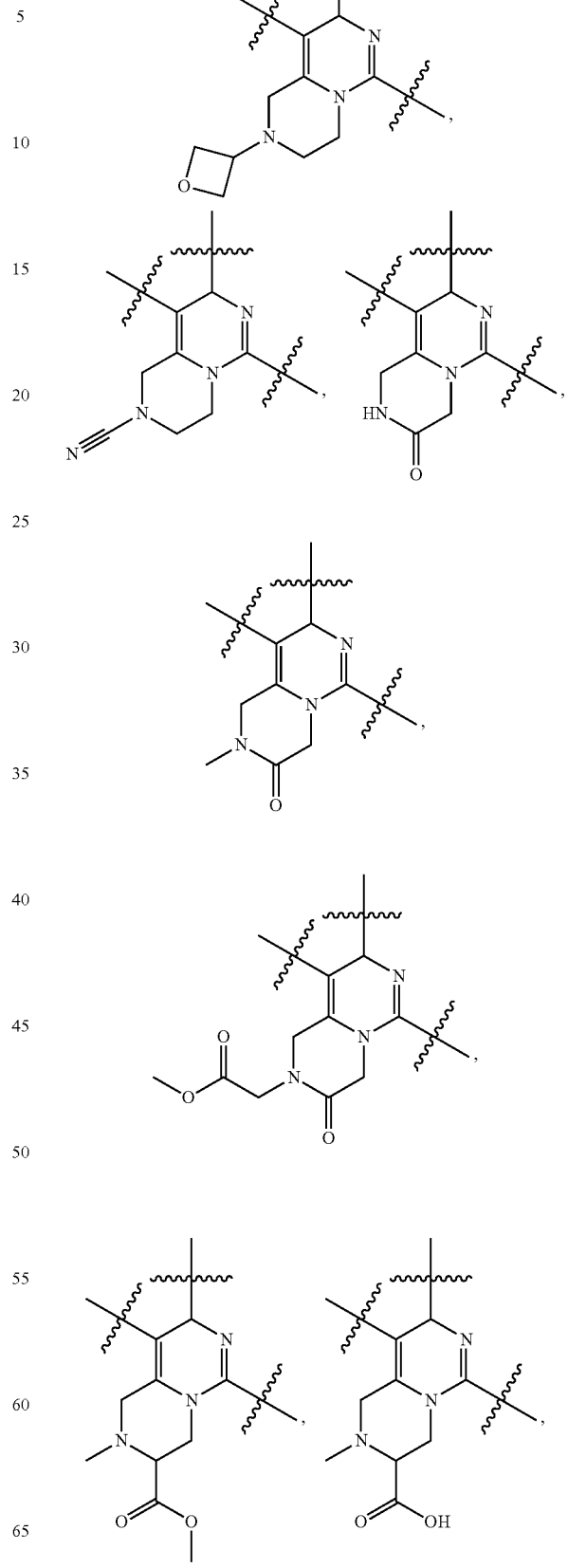

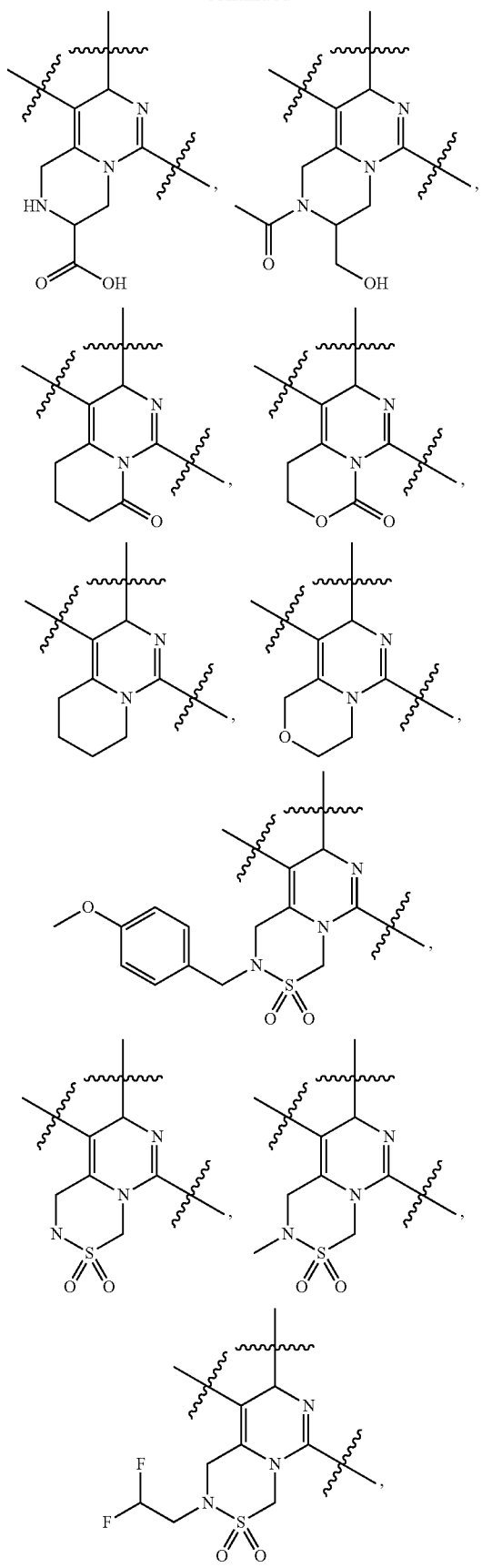
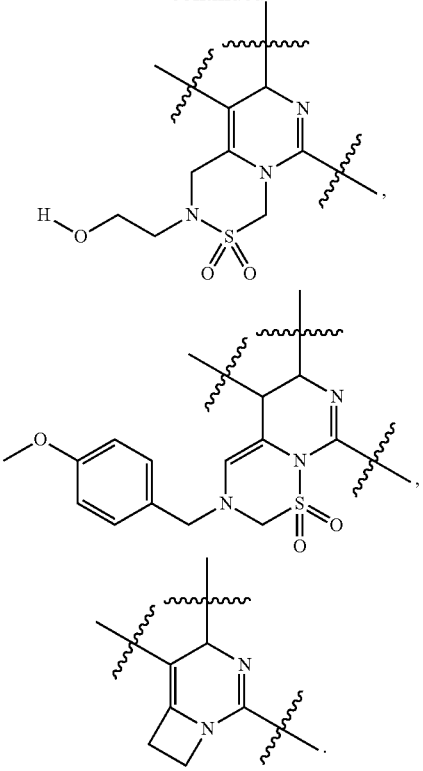
In some embodiments of the invention, the above described structural unit
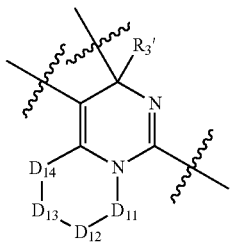
selected from:
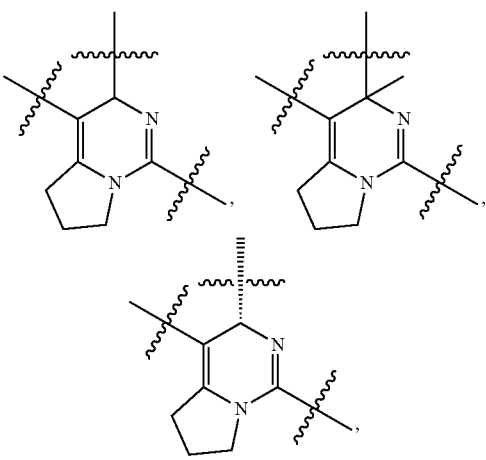

39
-continued
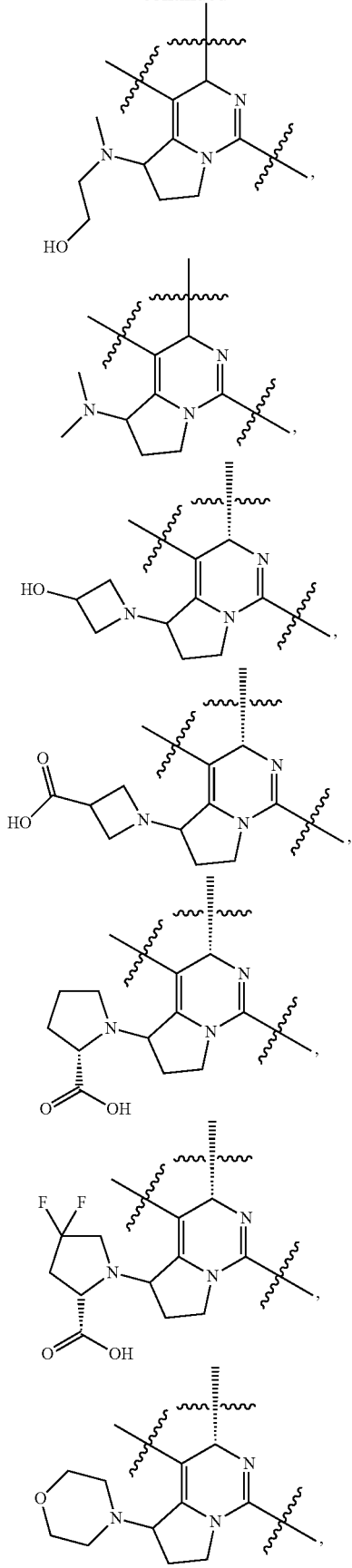
40
-continued
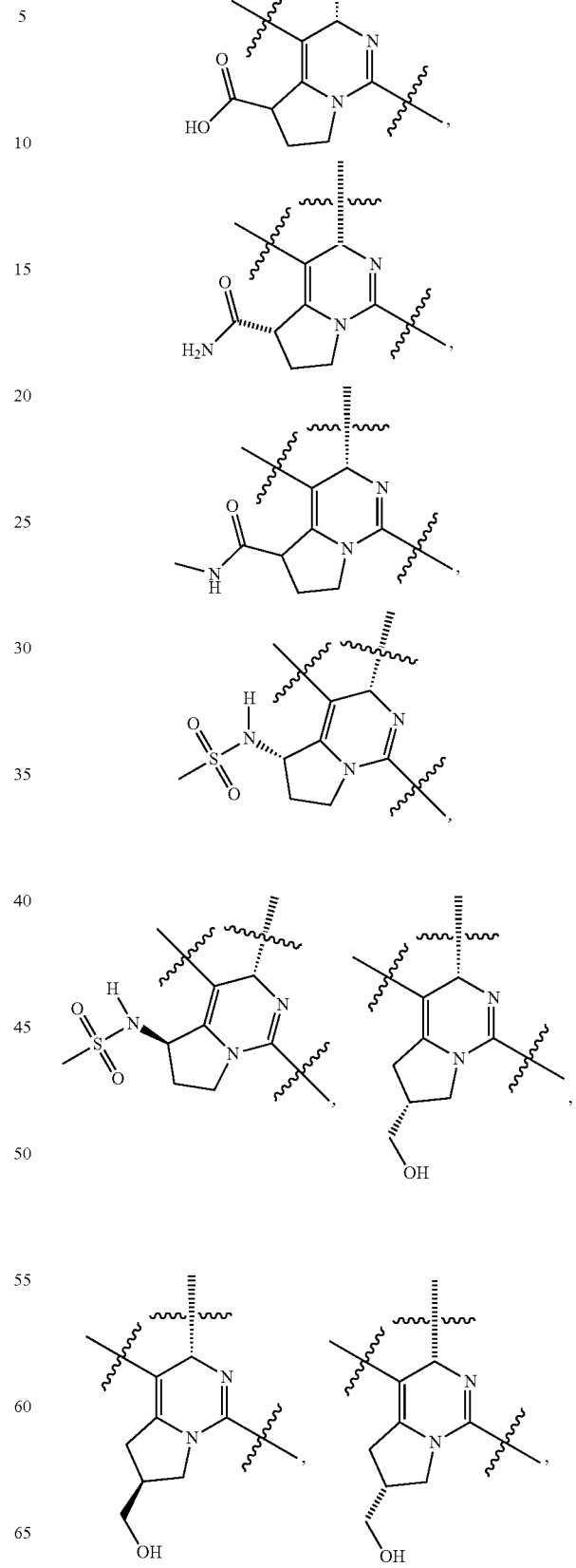

41
-continued
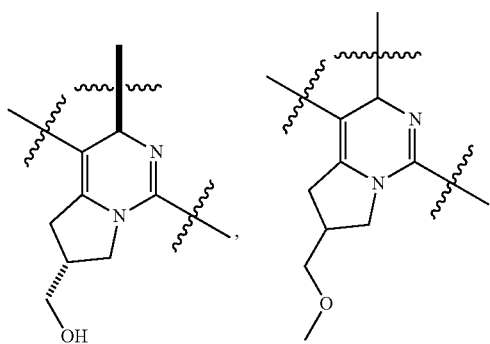
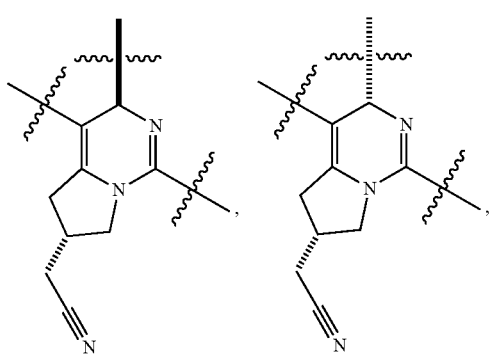
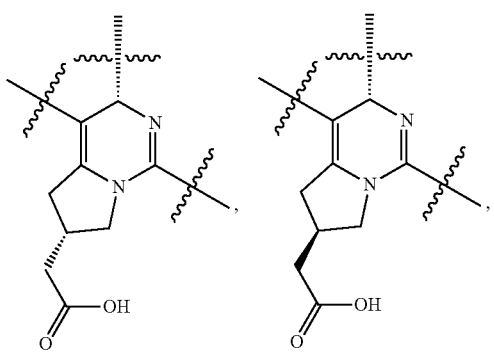
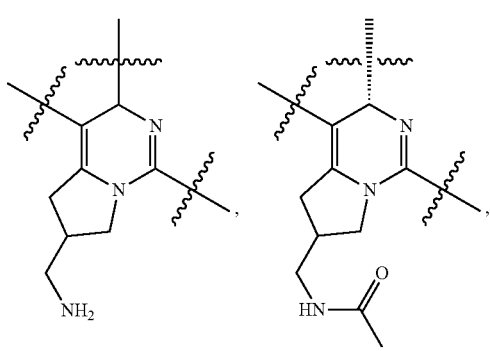
42
-continued
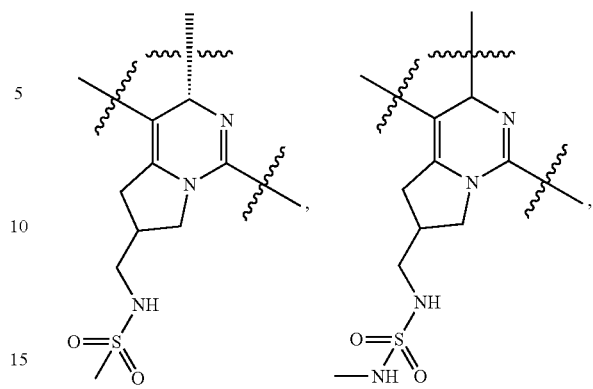
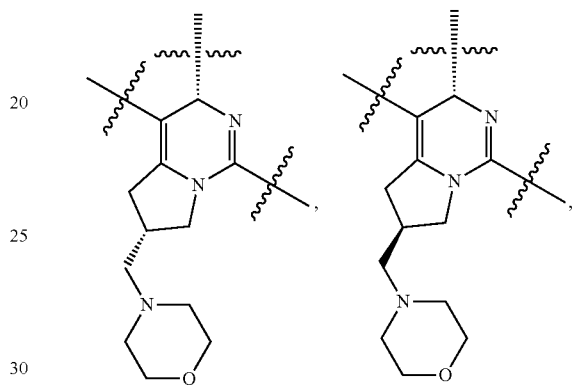
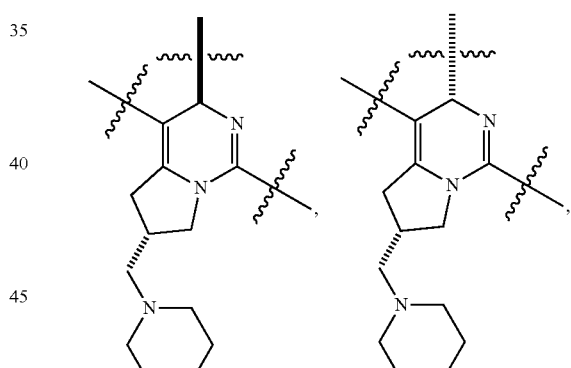
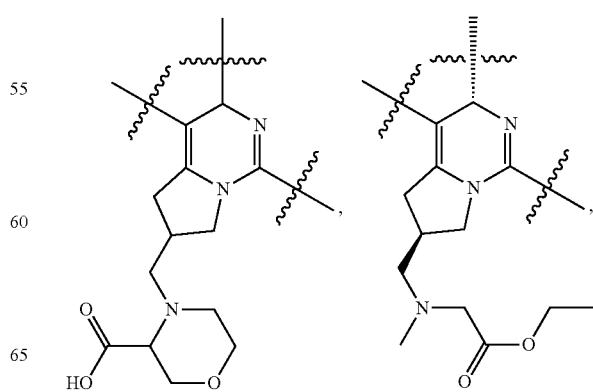

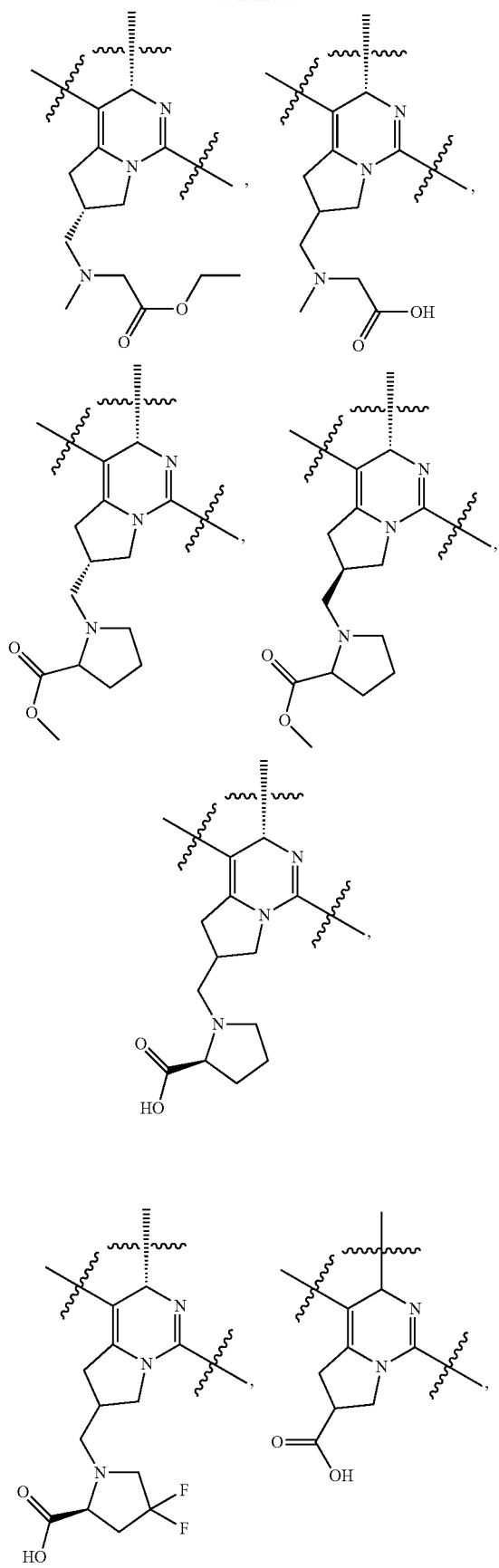
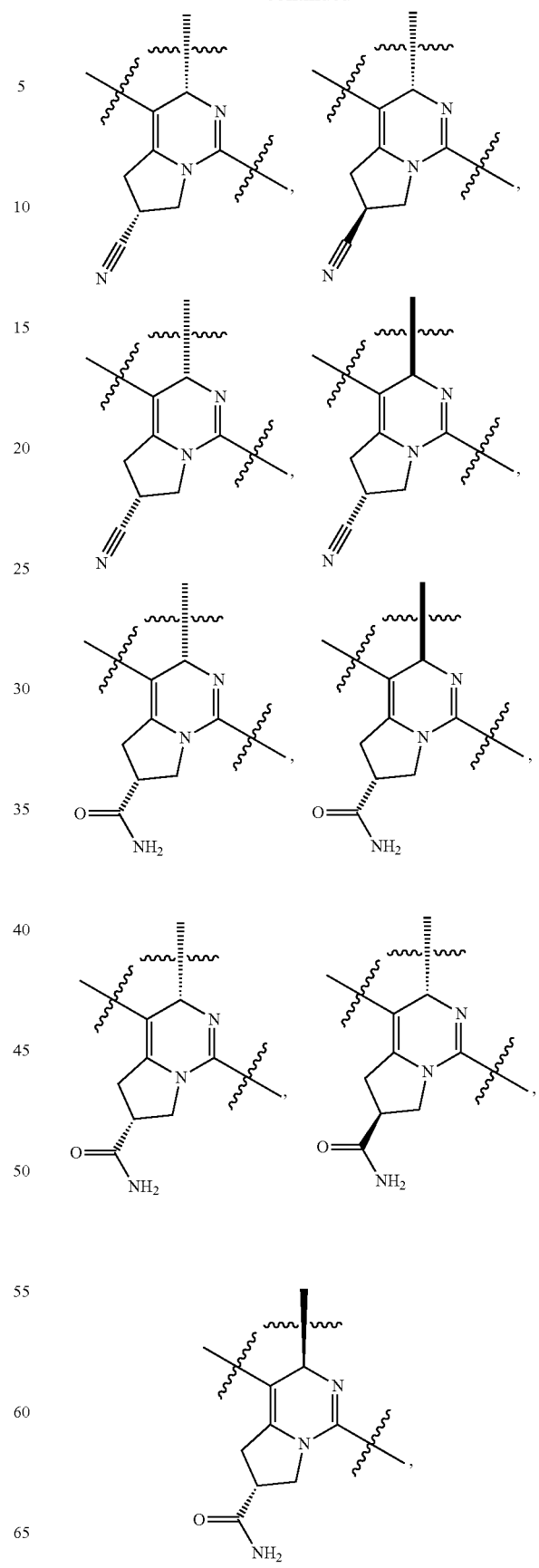

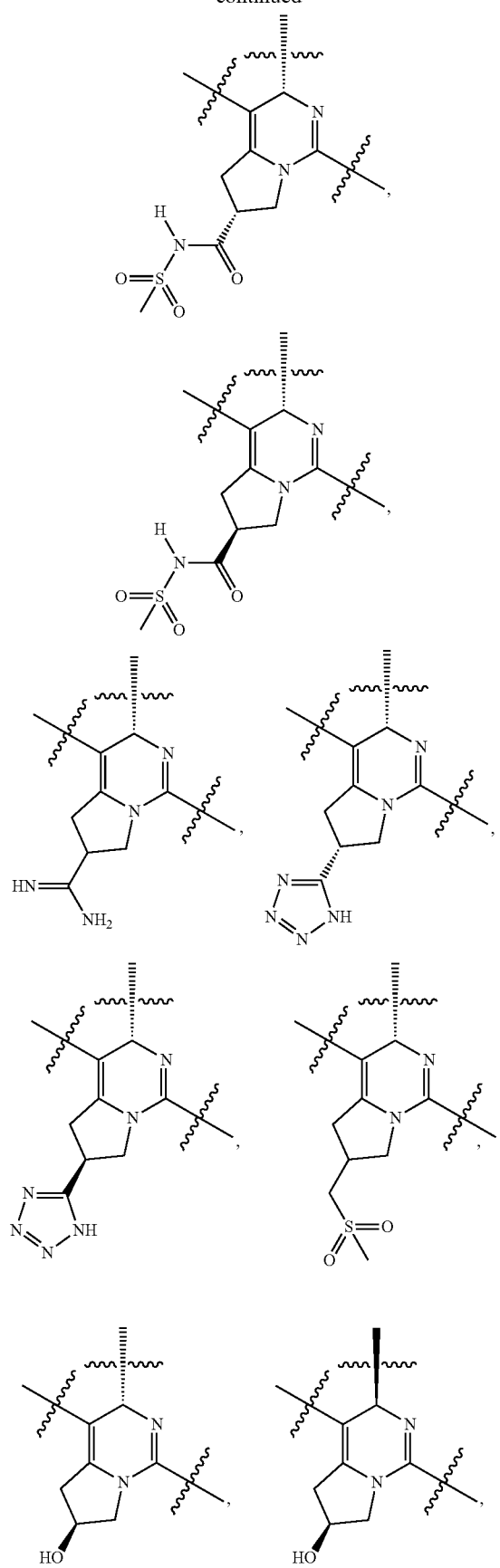
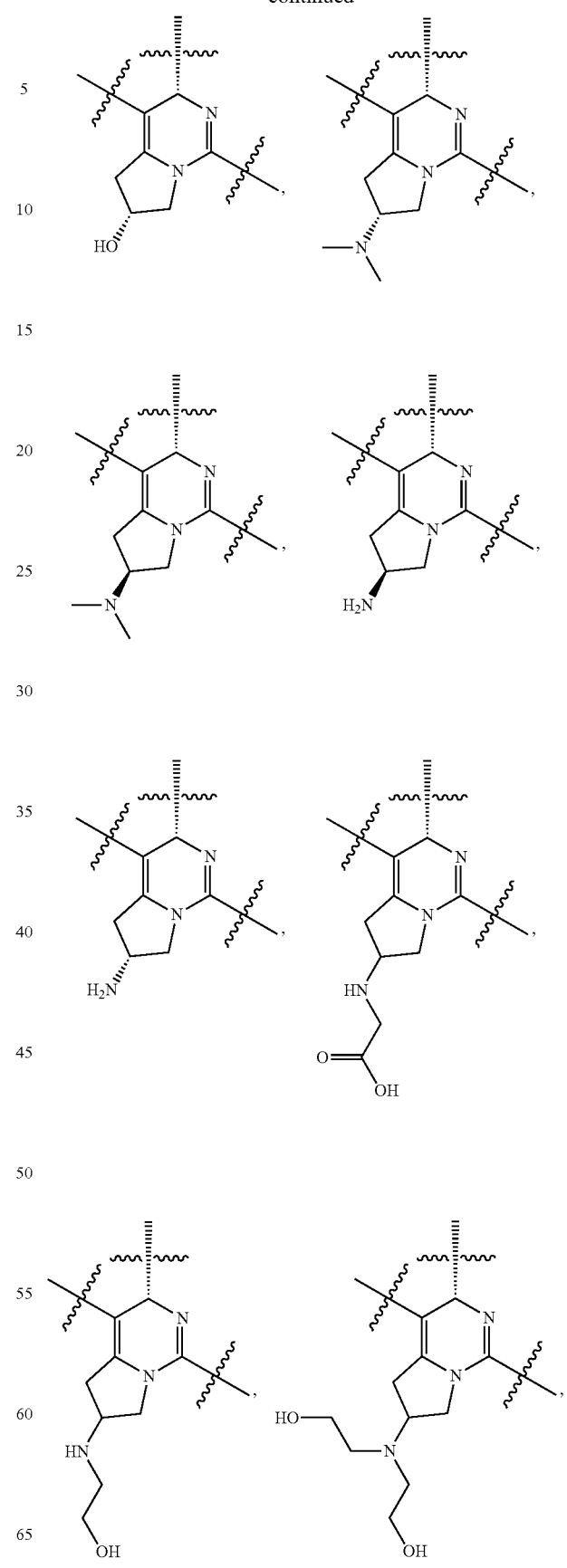

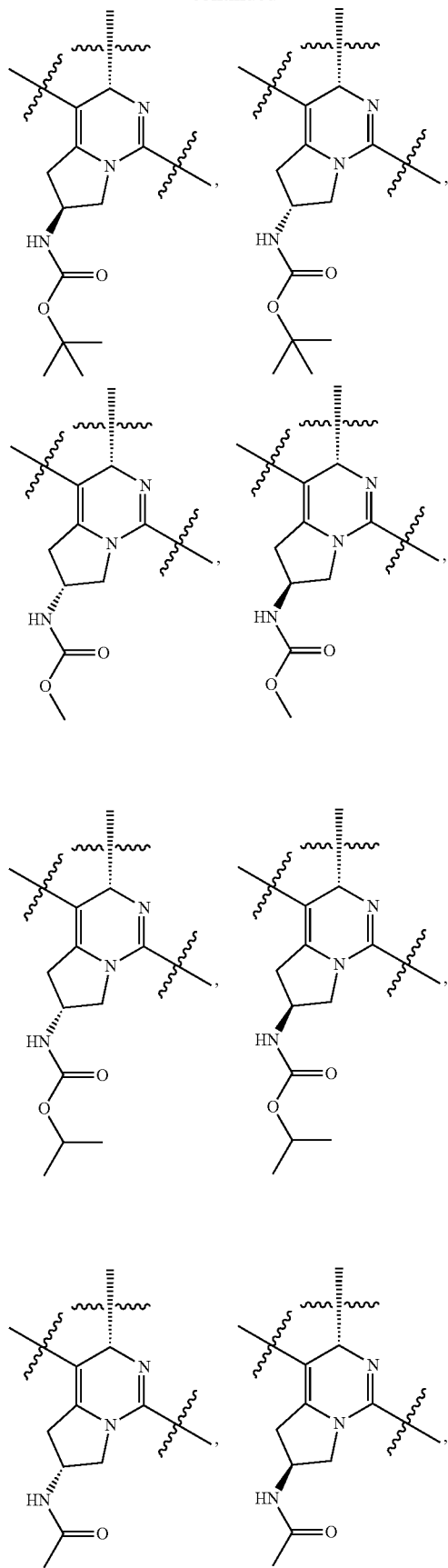
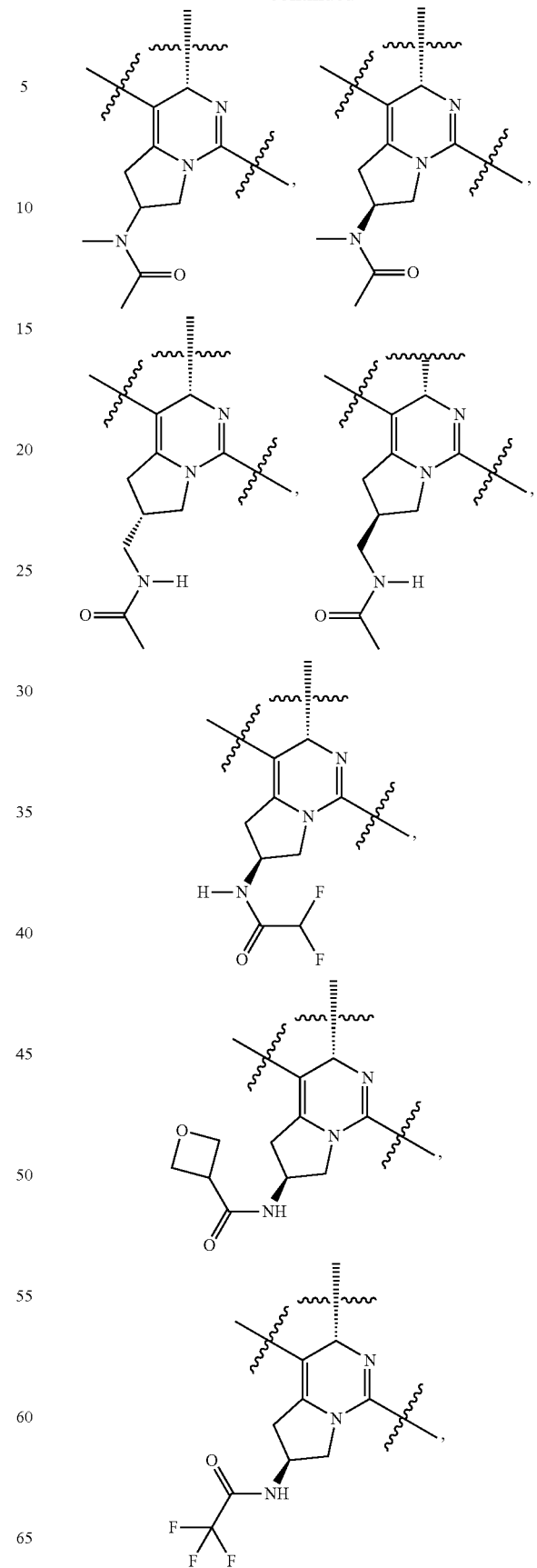

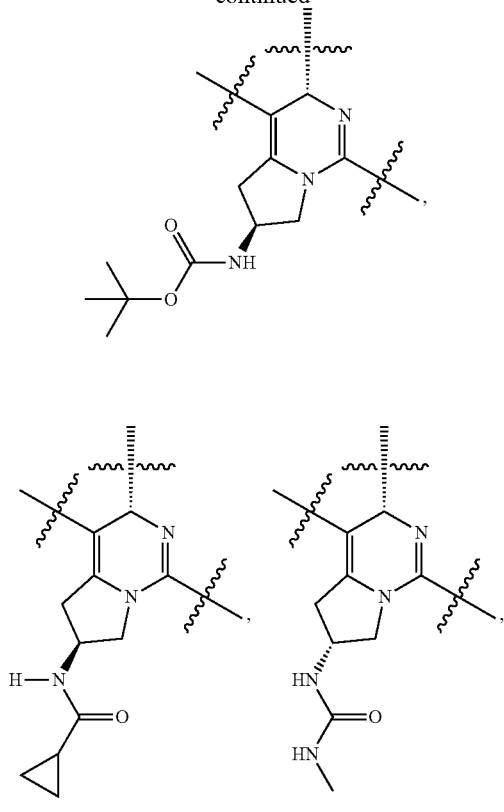
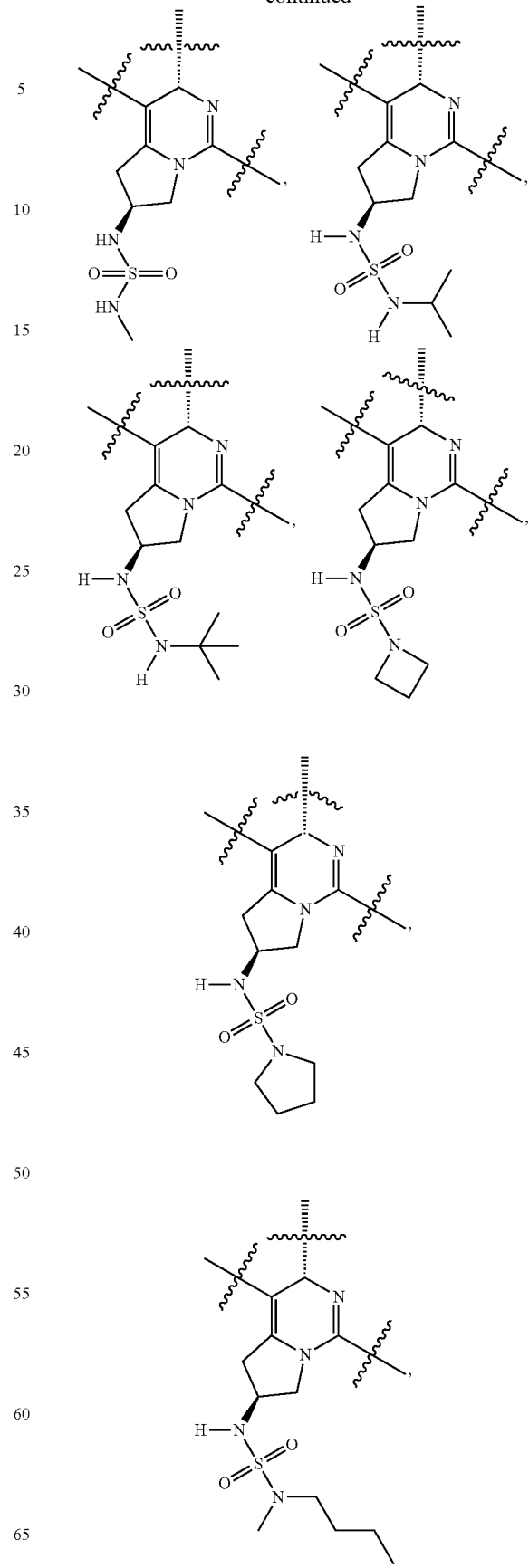

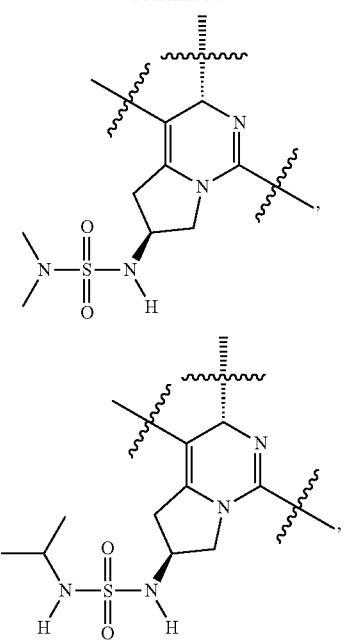
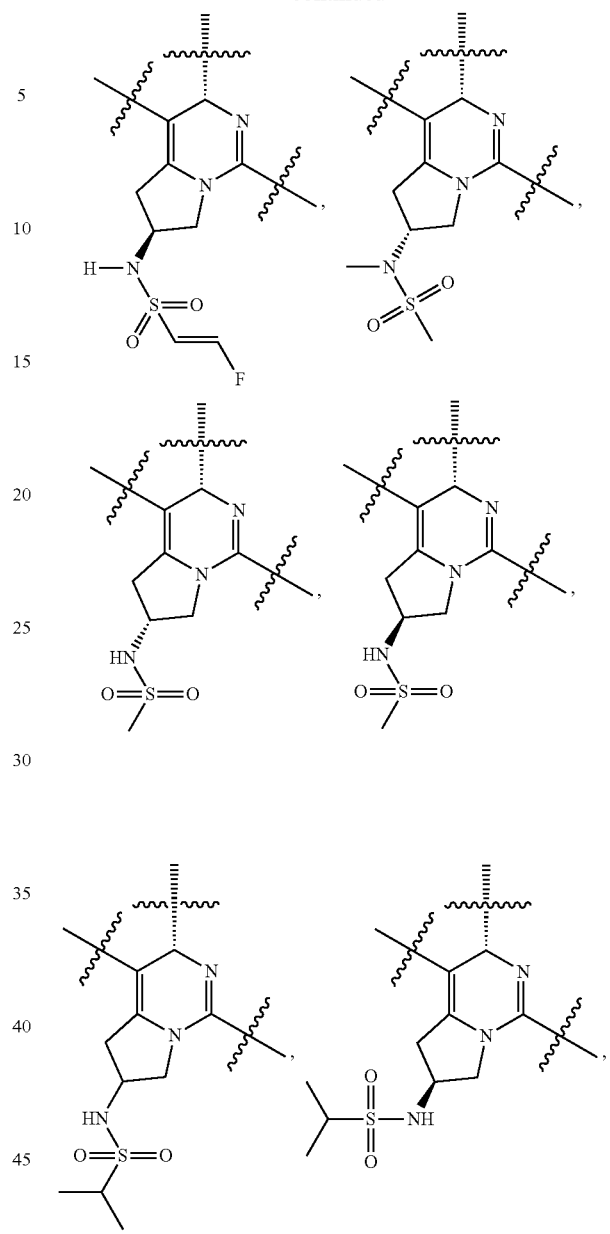
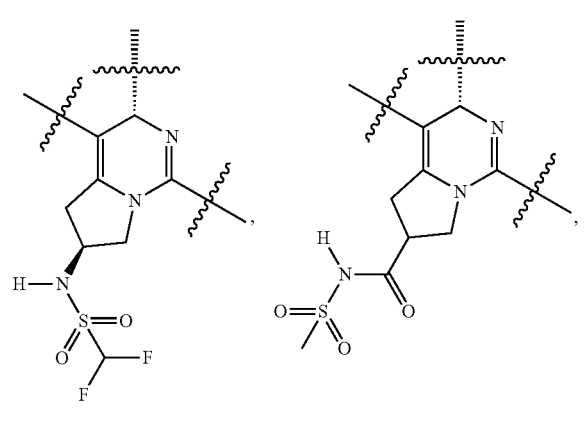

53
-continued
54
-continued
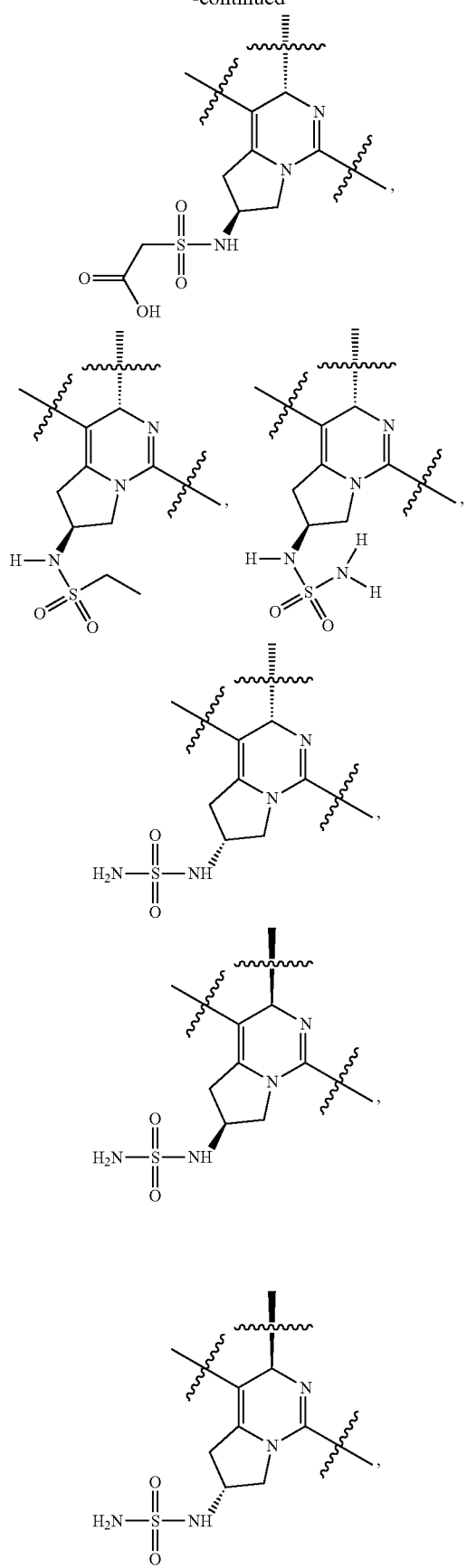
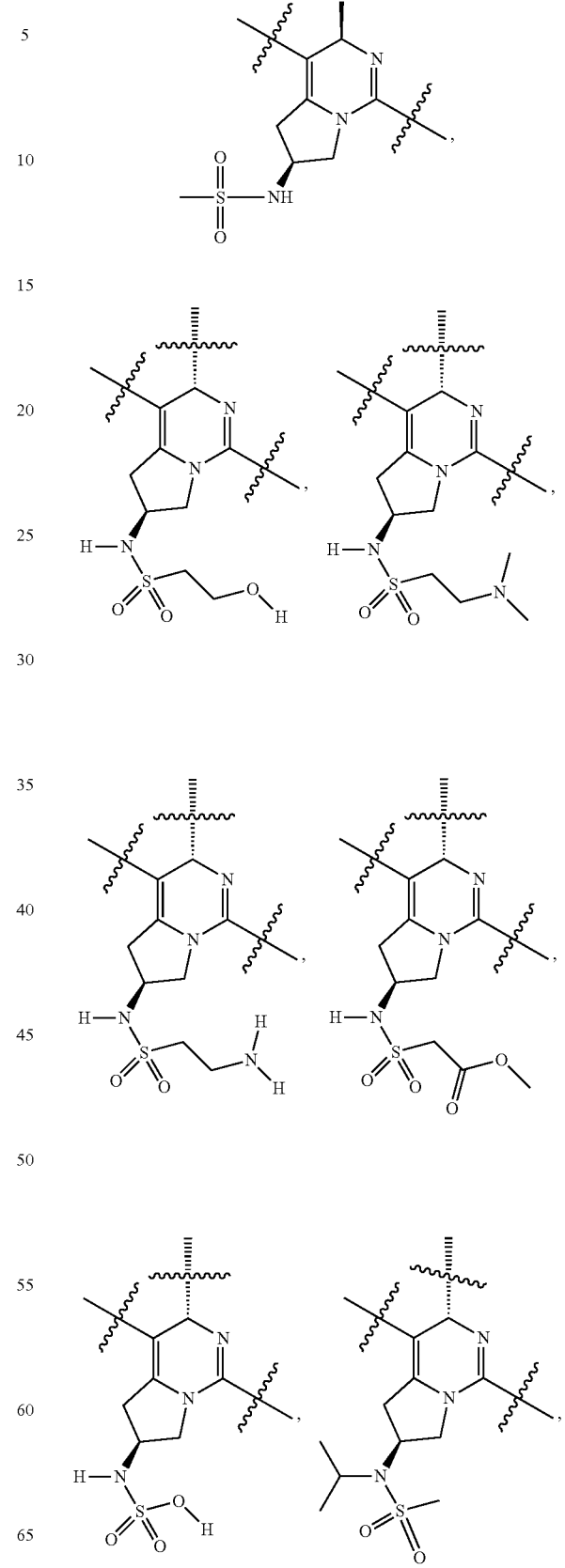

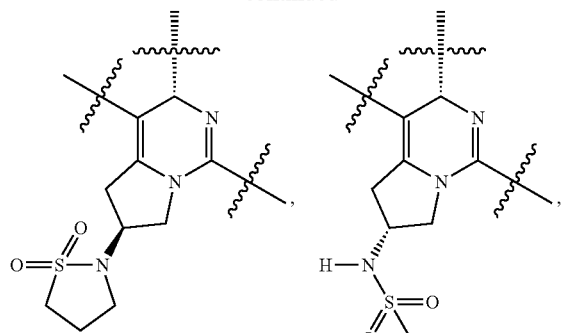
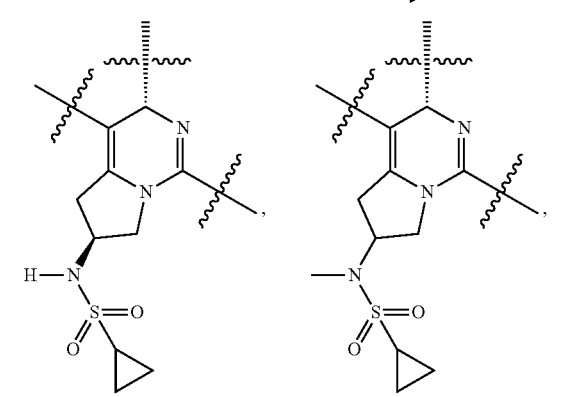
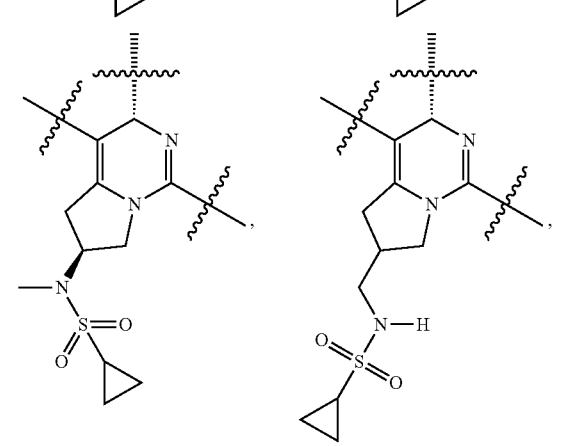
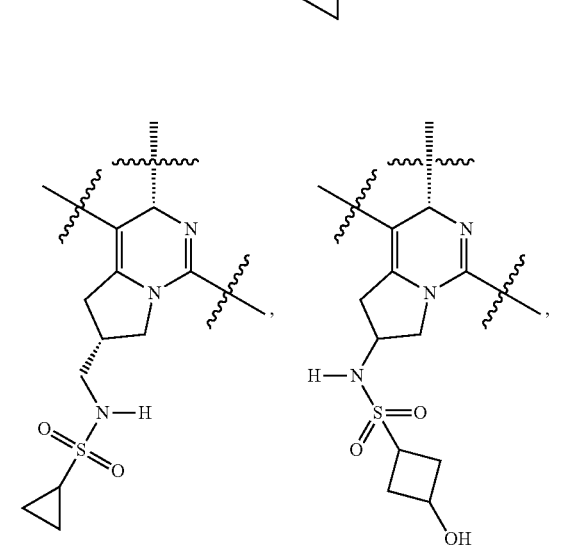
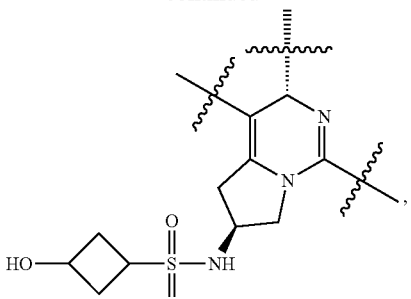
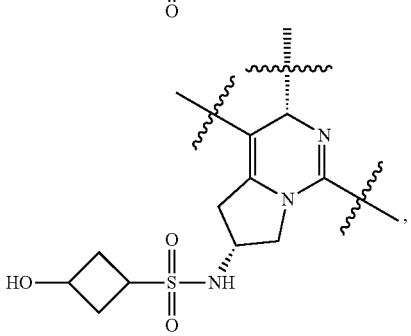

-continued
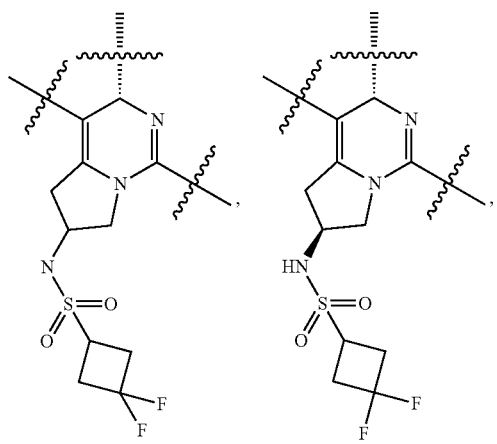
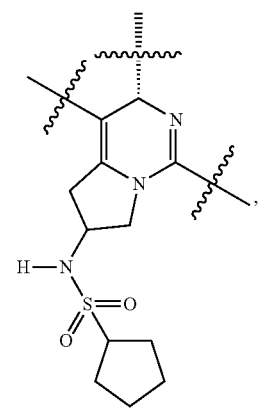
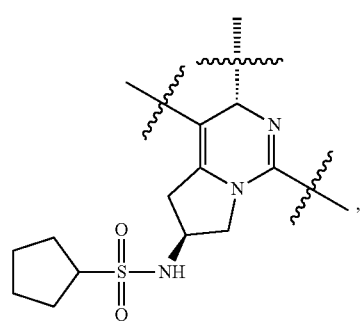
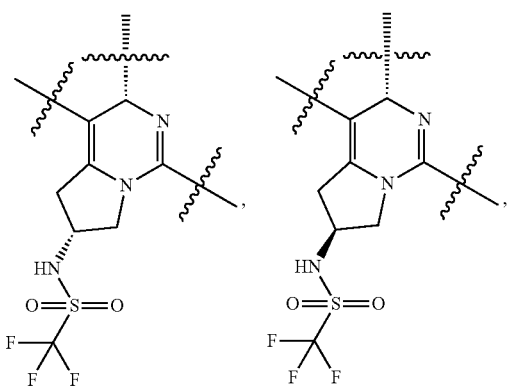
-continued
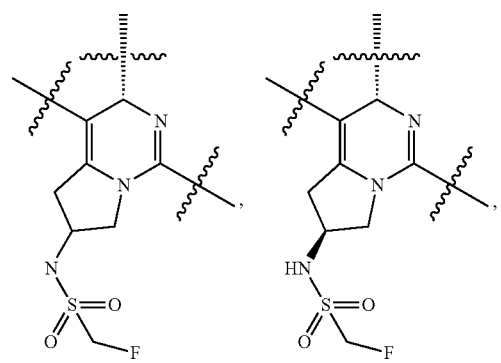
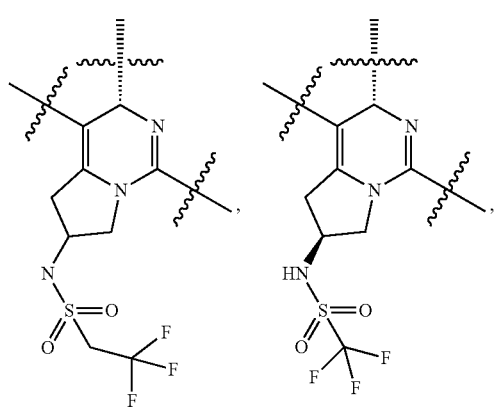
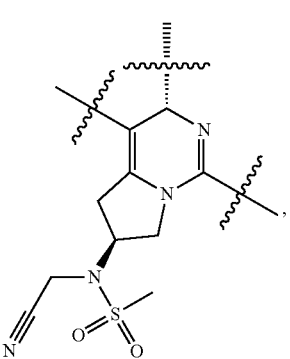
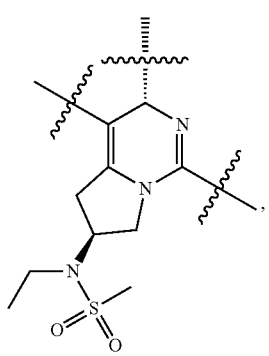

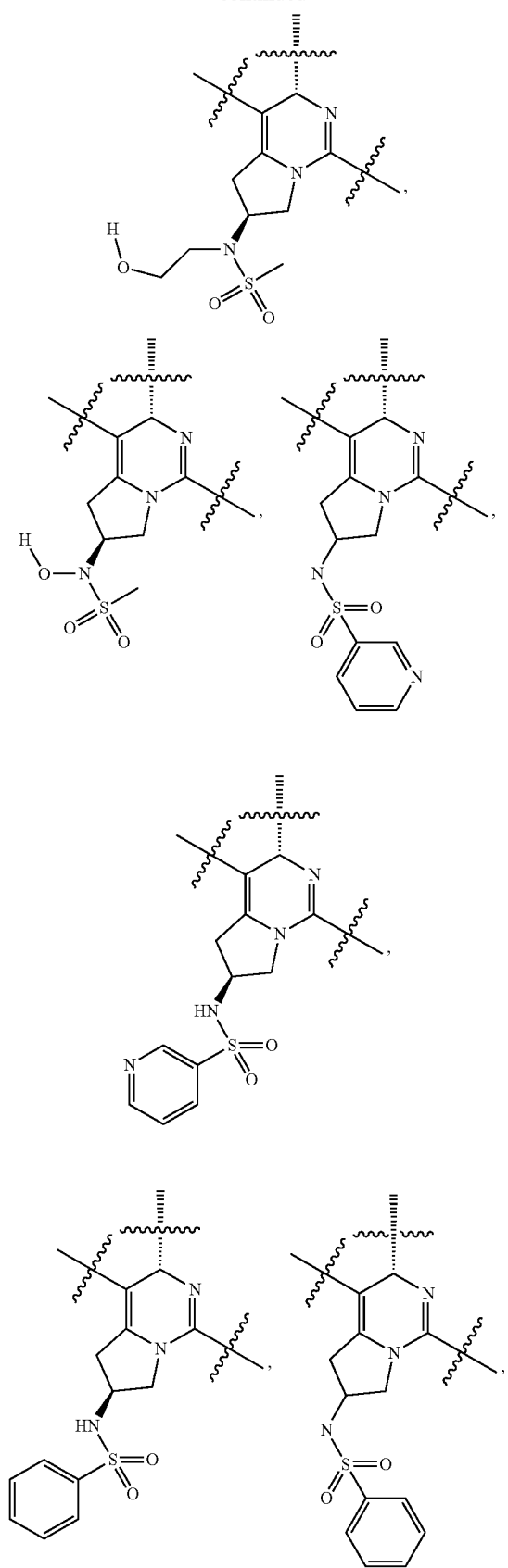
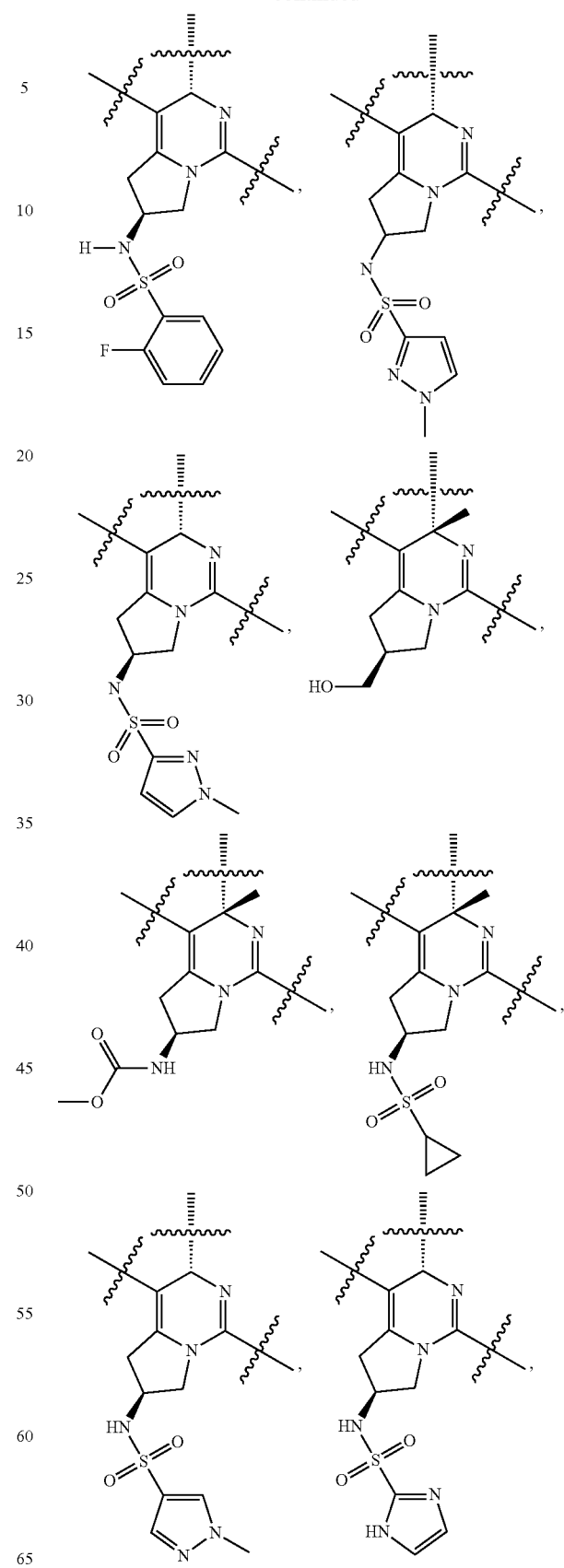

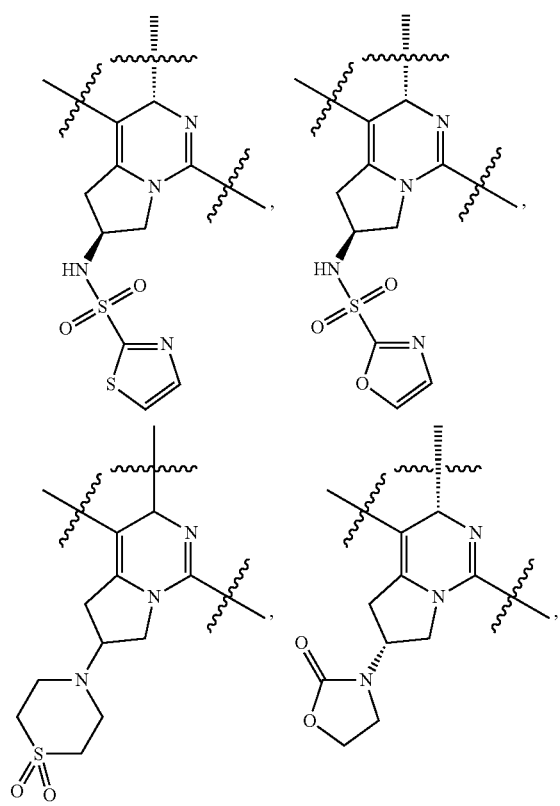
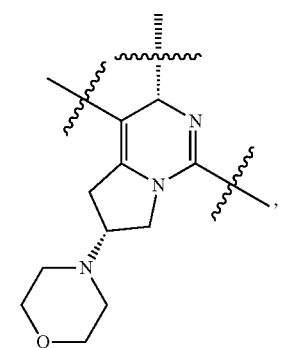
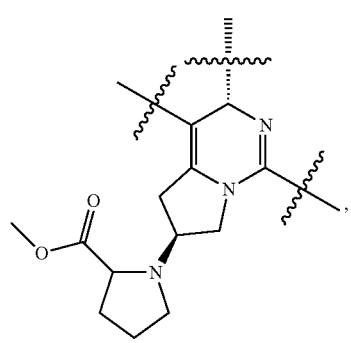
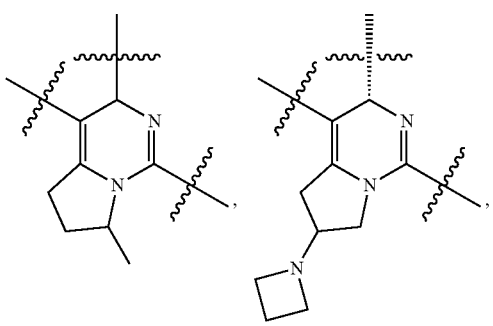
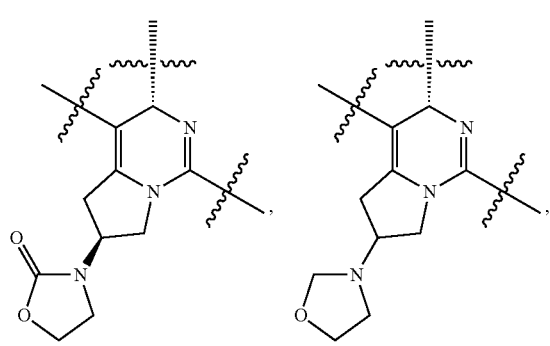
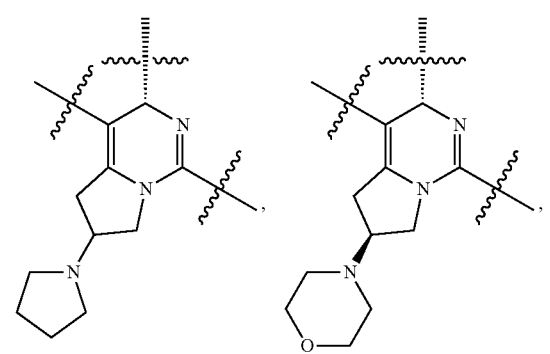
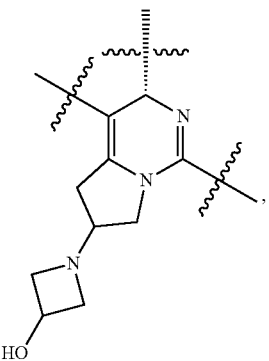

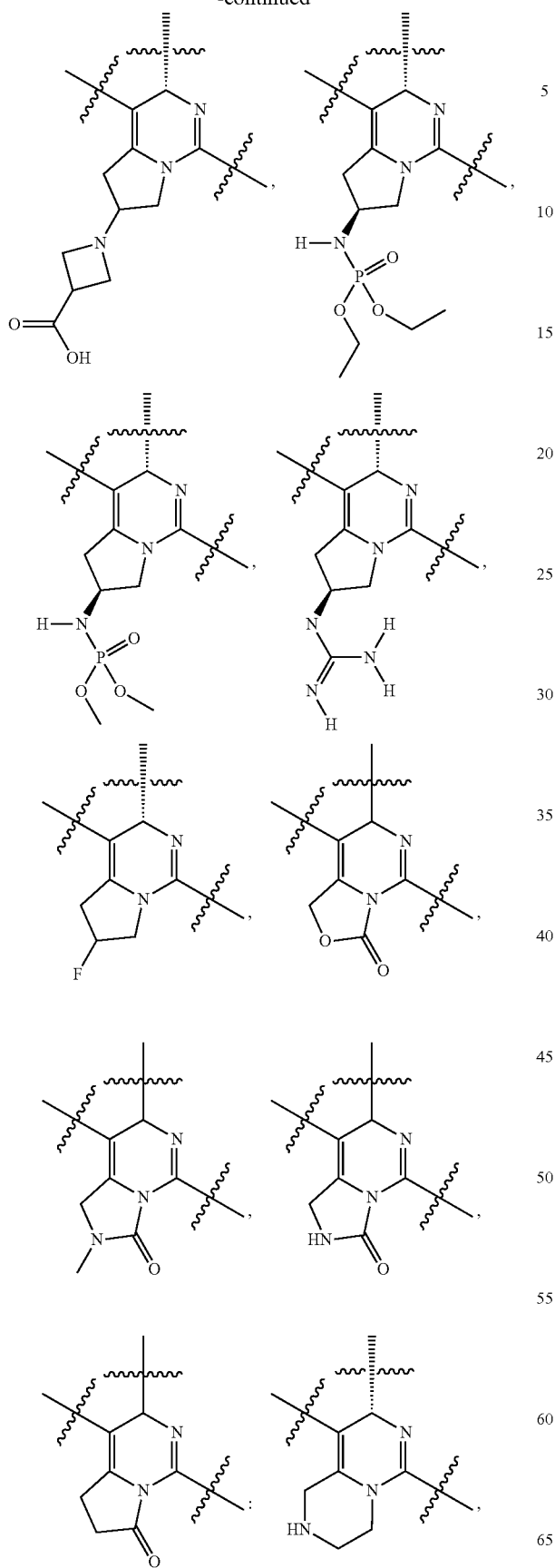
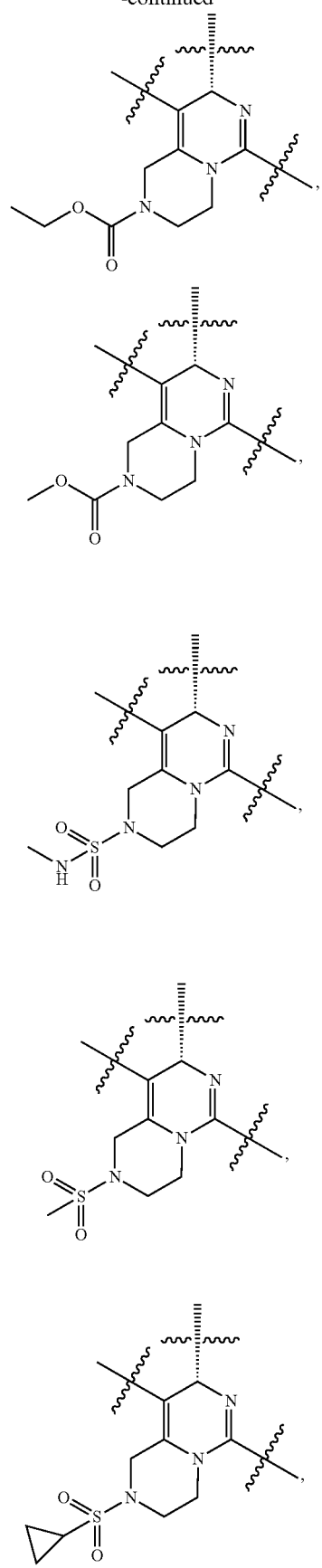

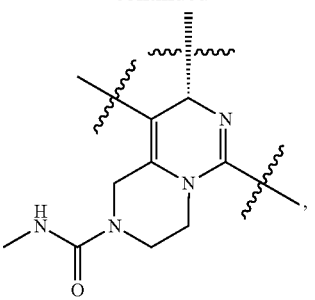
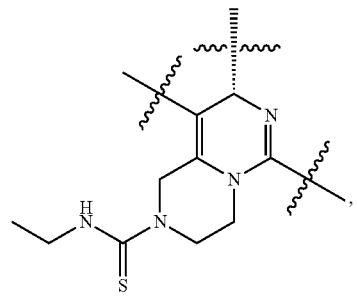
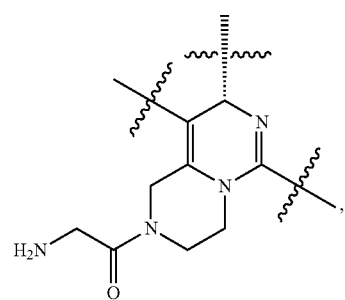
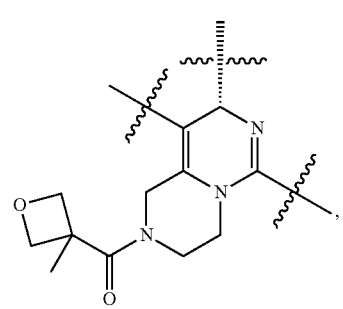
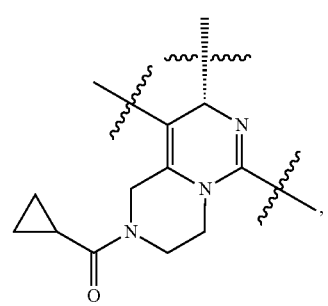
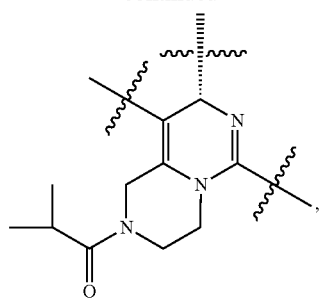
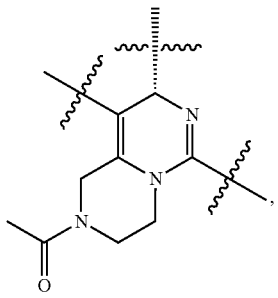
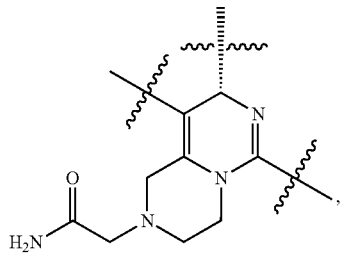
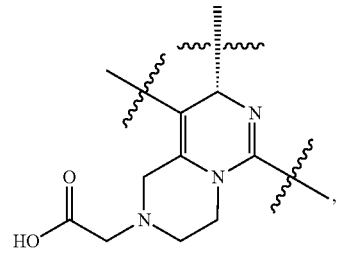
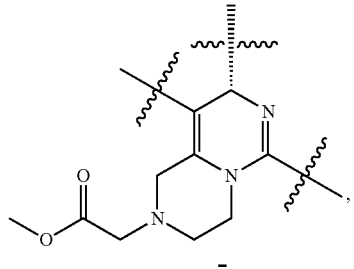
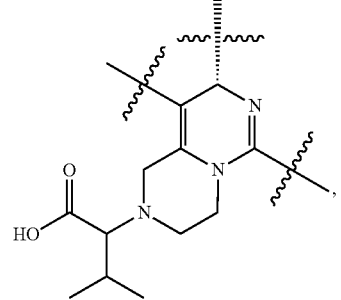

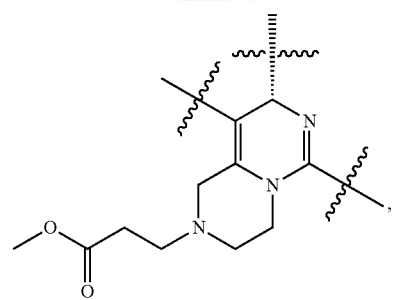
,
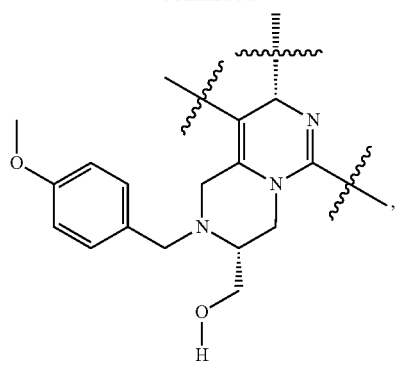
,
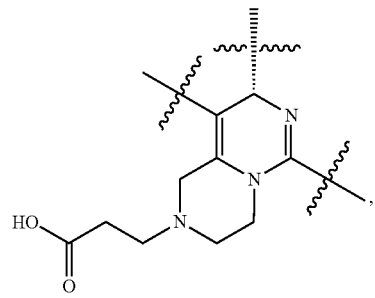
,
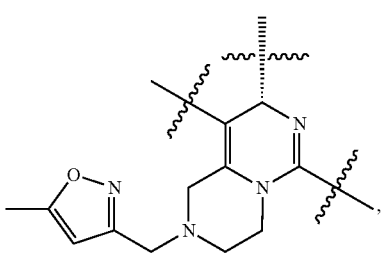
,
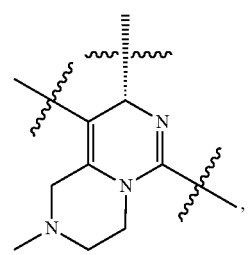
,
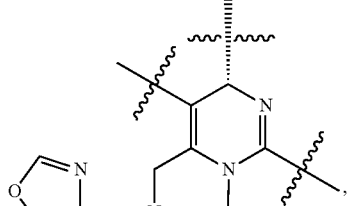
,
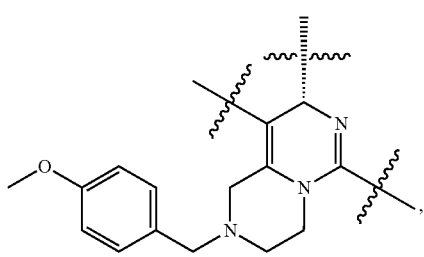
,
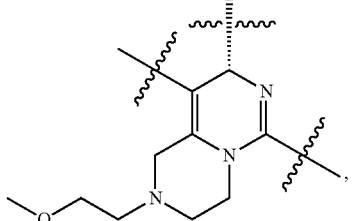
,
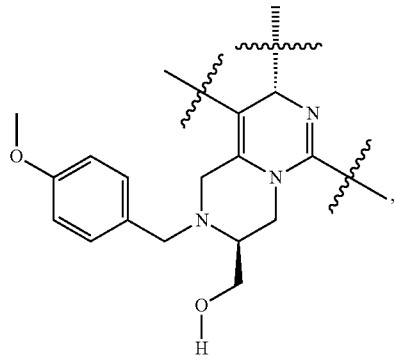
,
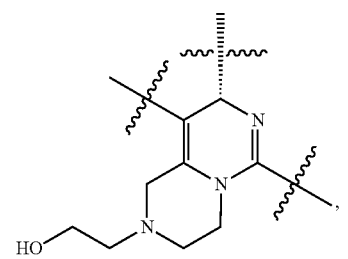
,
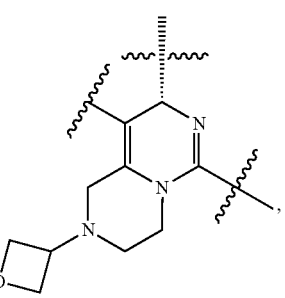
, 69
-continued
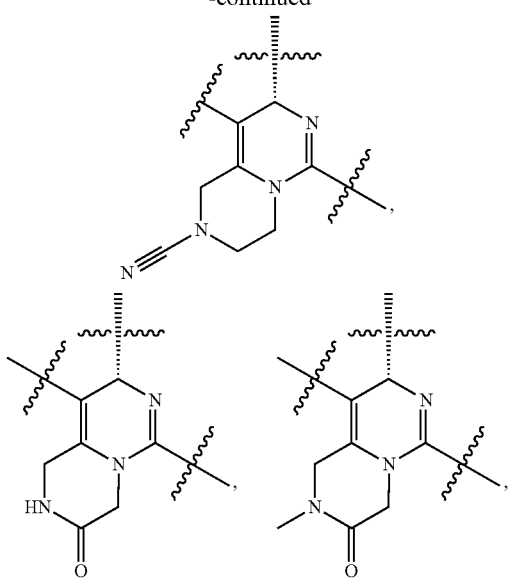
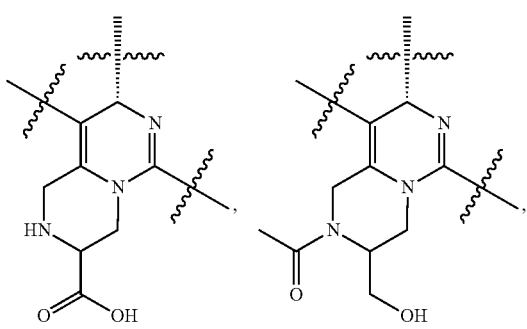
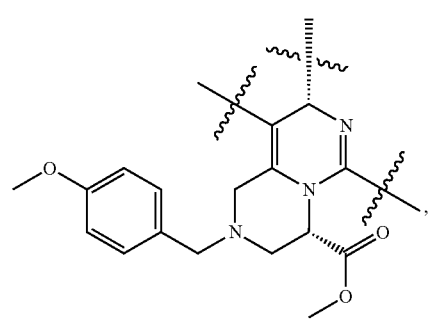
70
-continued
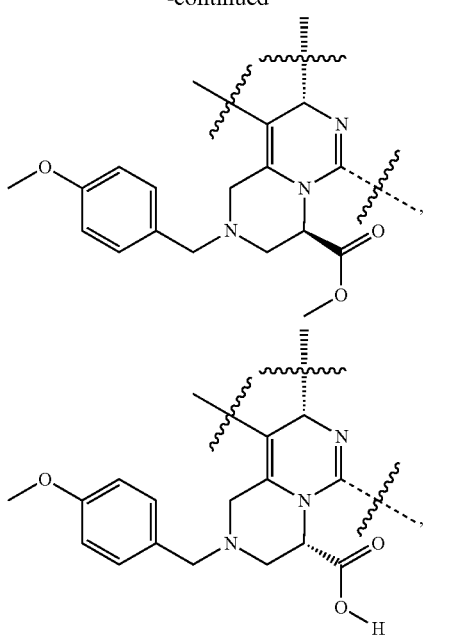
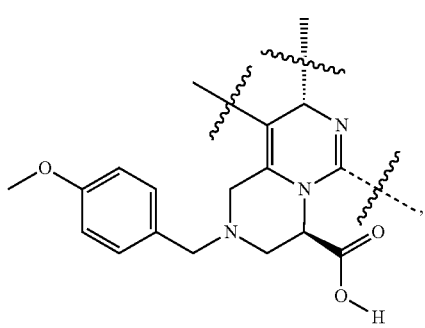
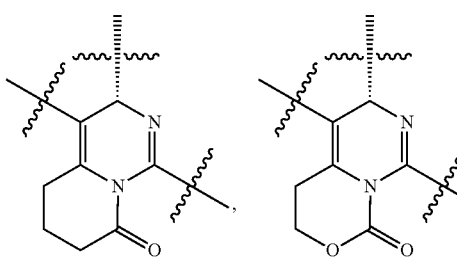
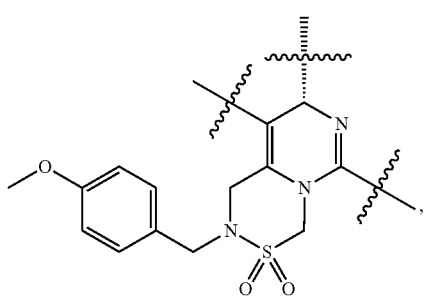

-continued

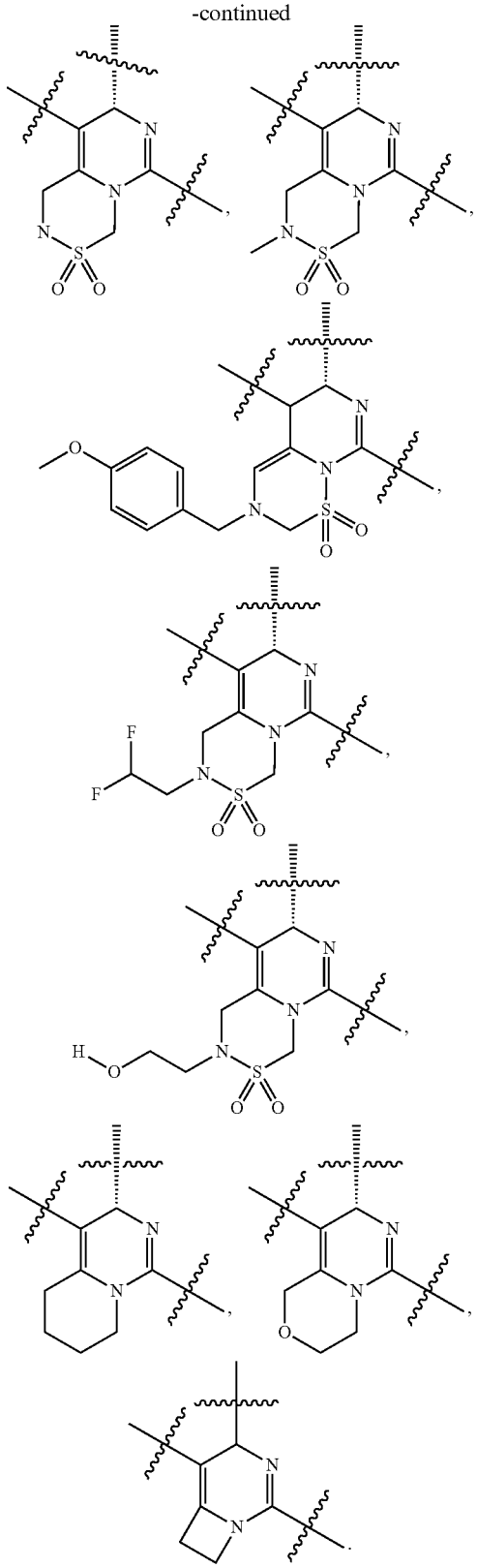

In some embodiments of the invention, the above described L and D$_{21}$ are selected from a single bond, —O—, —NH—; or R$_{21}$ is selected from C$_{1-4}$ alkyl, C$_{1-4}$ alkylamino, N,N-di(C$_{1-4}$ alkyl)amino, C$_{1-4}$ alkylamino-C$_{1-4}$ alkyl-, N,N-di(C$_{1-4}$ alkyl)amino-C$_{1-4}$ alkyl-, C$_{1-4}$ alkoxy, C$_{1-4}$ alkoxy-C$_{1-4}$ alkyl-, haloC$_{1-4}$ alkyl-, dihaloC$_{1-4}$alkyl-, aminooxy C$_{1-4}$ alkyl-, hydroxyl substituted C$_{1-4}$ alkyloxy-, hydroxyl substituted C$_{1-3}$ alkylamino-.

In some embodiments of the invention, the above described R$_{21}$ is selected from methyl, ethyl, n-propyl, isopropyl, methylamino, ethylamino, propylamino, dimethylamino, diethylamino, dipropylamino, methylaminoethyl, ethylaminoethyl, propylaminoethyl, dimethylaminoethyl, diethylaminomethyl, dimethylaminomethyl, diethylaminoethyl, methoxymethyl, methoxyethyl, methoxypropyl, ethoxymethyl, propoxymethyl, ethoxyethyl, propoxypropyl, fluoromethyl, fluoroethyl, fluoropropyl, difluoromethyl, difluoroethyl, difluoropropyl, aminooxymethyl, aminooxyethyl, aminooxypropyl, hydroxymethyloxy, hydroxyethyloxy, hydroxypropoxy.

In some embodiments of the invention, the above described structural unit

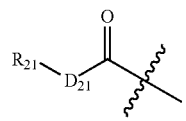

is selected from

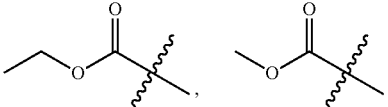

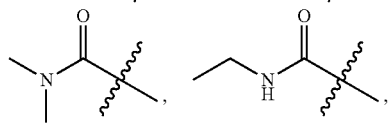

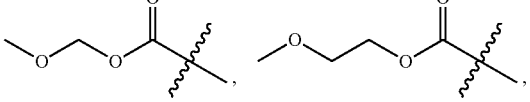

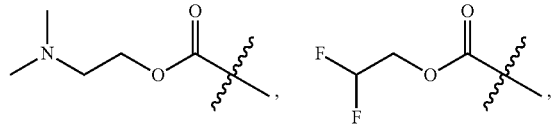

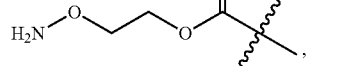

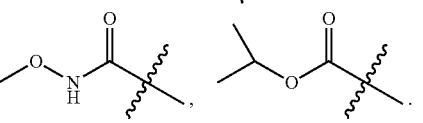

In some embodiments of the invention, the above described structural unit

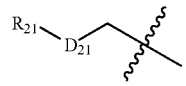

is selected from

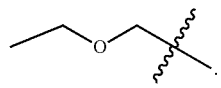

In some embodiments of the invention, the above described $R_3$ or $R_4$ is separately and independently selected from the following groups optionally substituted by 1, 2 or 3 $R_{001}$: phenyl, pyridyl, quinolinyl, isoquinolinyl, thiazolyl, thienyl, oxazolyl, isoxazolyl, pyrazolyl, isothiazole, furyl, pyrrolyl, pyrrolidinyl, 1, 3-dioxolanyl, 2-pyrazolinyl, pyrazolidinyl, imidazolyl, 1,2,3-azolyl, 1,2,3-triazolyl, 1,2,4-triazolyl, 1,3,4-thiadiazolyl, piperidyl, 1,4-dioxanyl, morpholinyl, piperazinyl, piperidyl, pyrimidinyl, pyrazinyl, 1,3,5-trithianyl, 1,3,5-triazinyl, indenyl, naphthyl, benzofuranyl, benzothienyl, indolyl, benzimidazolyl, benzothiazolyl, benzocyclopentyl, cyclopropyl;

or the structural unit

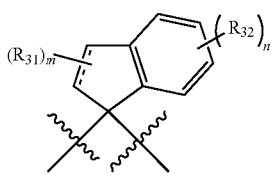

is selected from benzocyclopentyl, indenyl optionally substituted by 1, 2 or 3 $R_{001}$;

$R_{001}$ is as defined above.

In some embodiments of the invention, $R_3$ is selected from

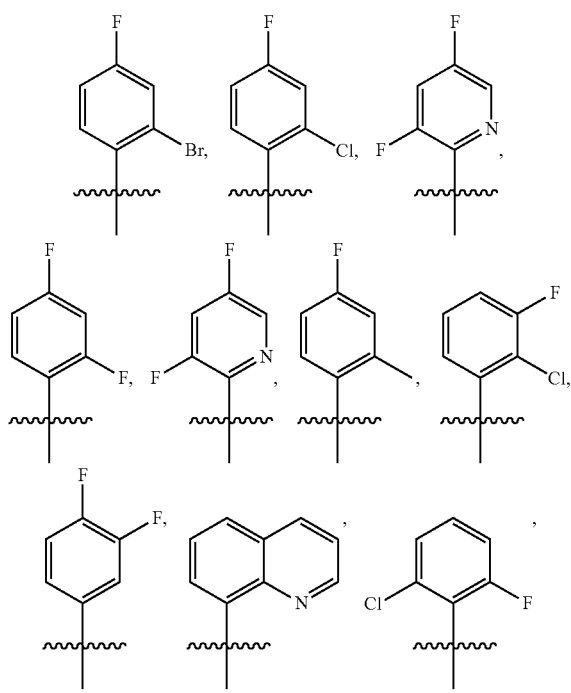

In some embodiments of the invention, $R_4$ is selected from

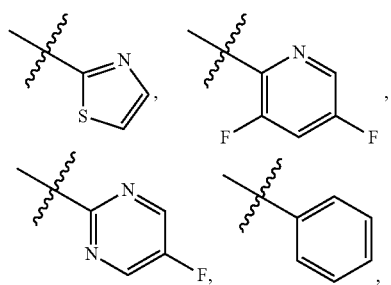

-continued
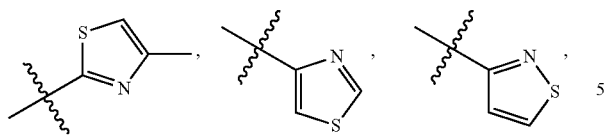

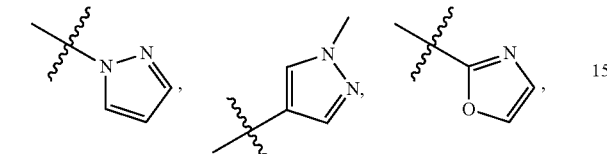
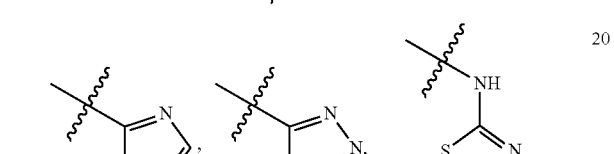
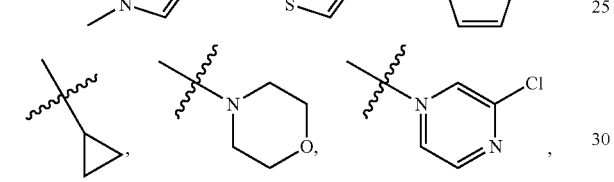

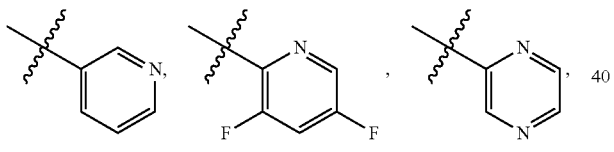
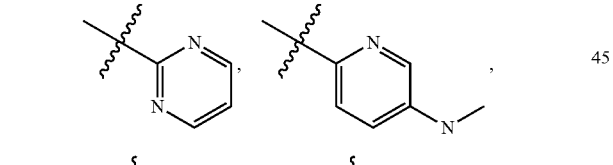
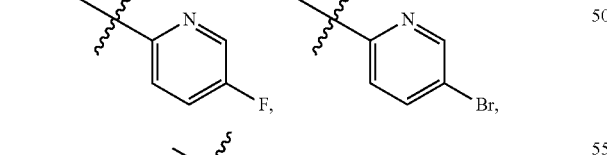
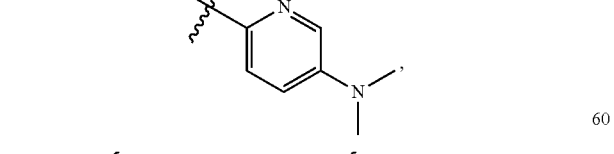
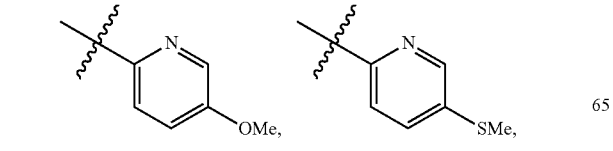
-continued
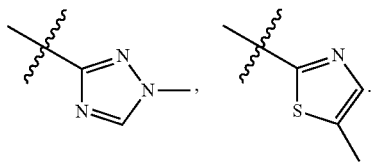
In some embodiments of the invention, the above described structural unit
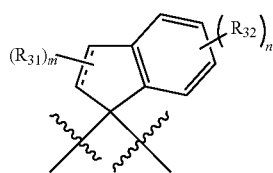
is selected from:
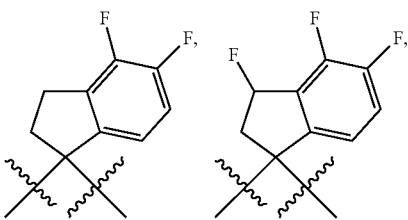
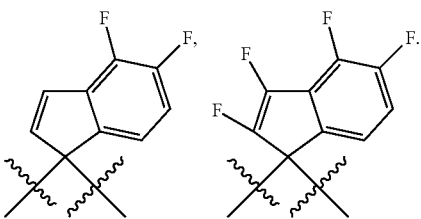
Particularly, the compound of the invention is selected from:
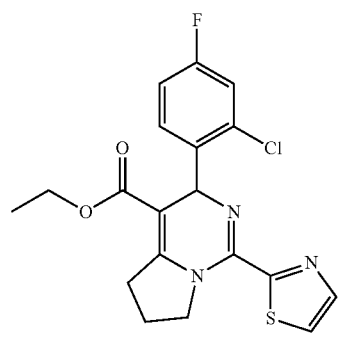
1

-continued
2
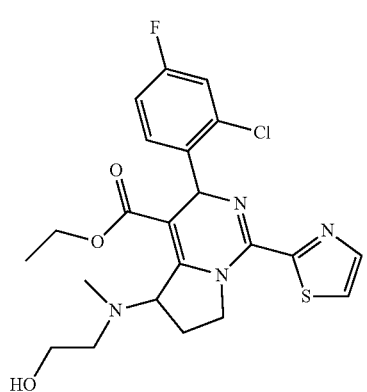
3
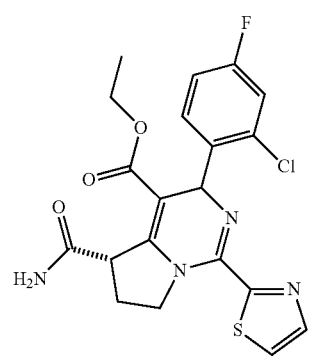
4
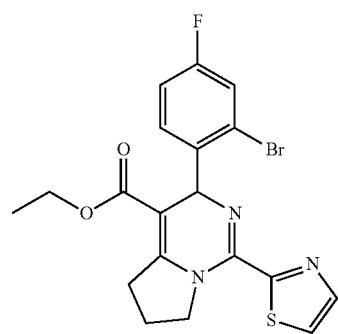
5
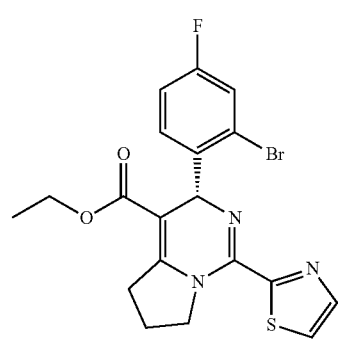
-continued
6
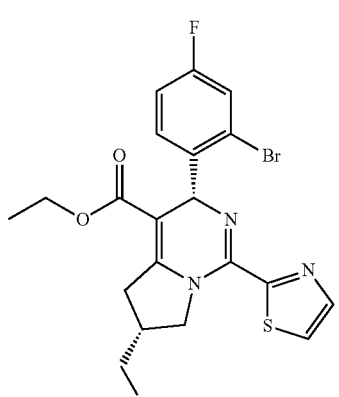
7
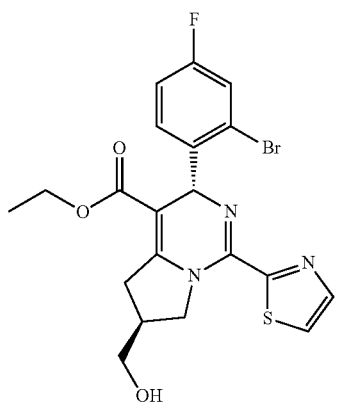
8
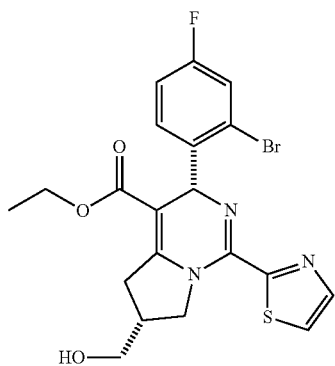
9
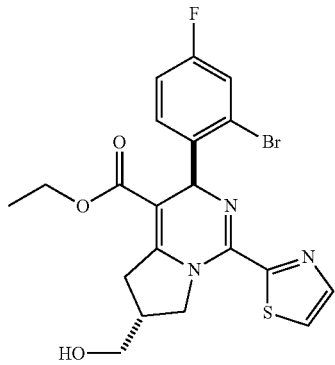

10
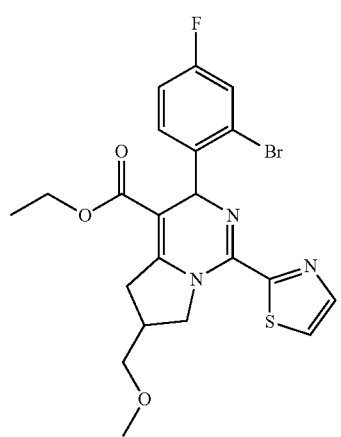
11
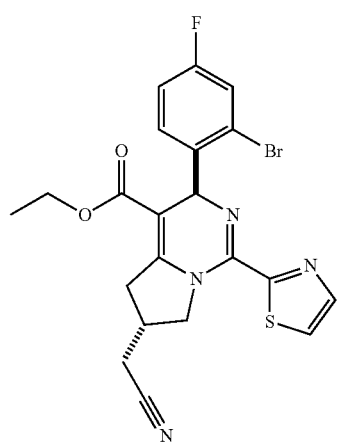
12
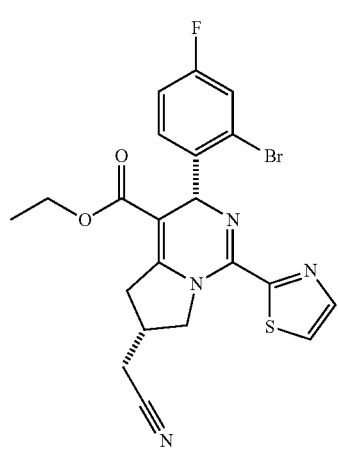
13
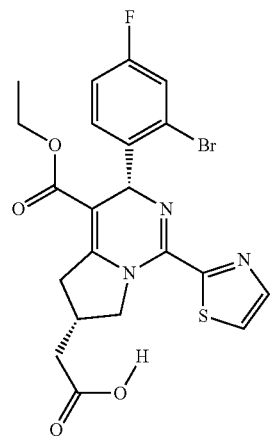
14
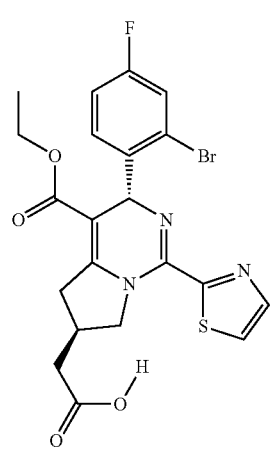
15
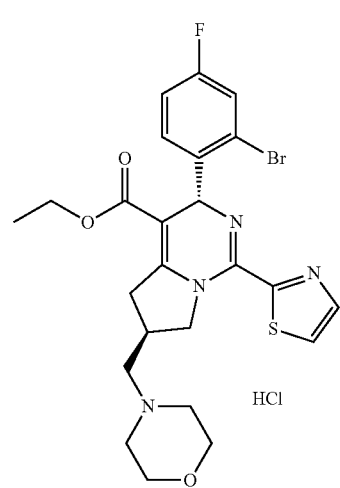
HCl

81
-continued
16
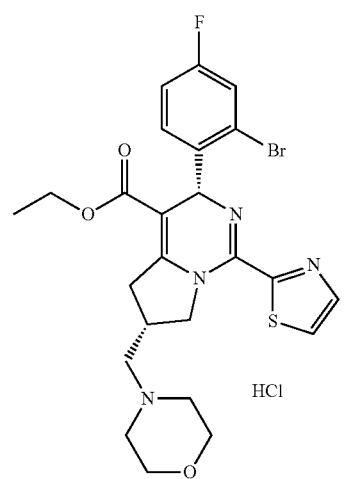
HCl
17
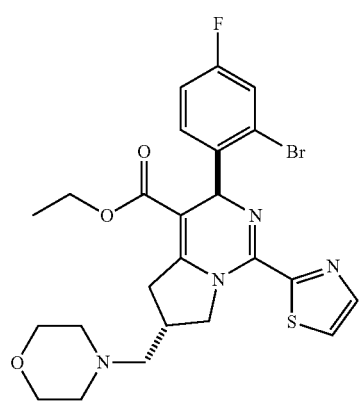
18
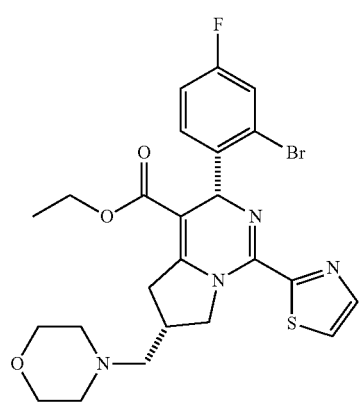
82
-continued
19
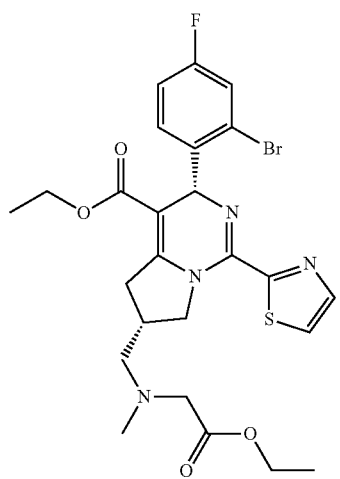
20
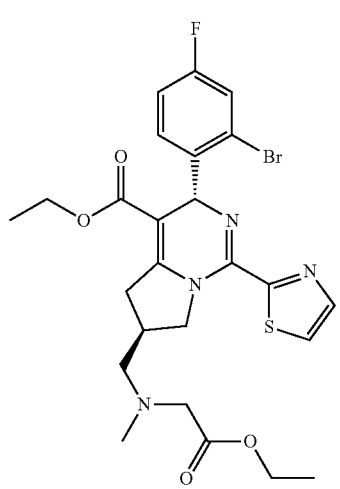
21
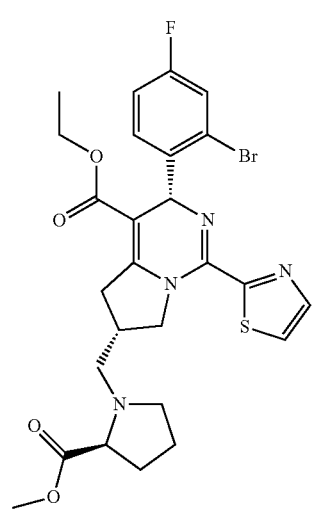

83
-continued
22
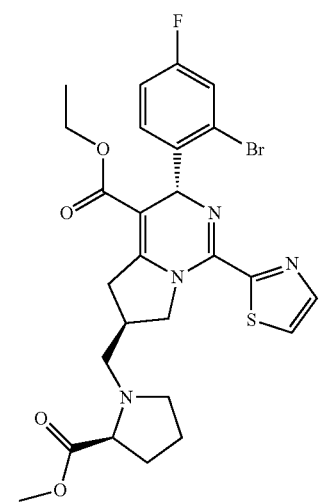
26
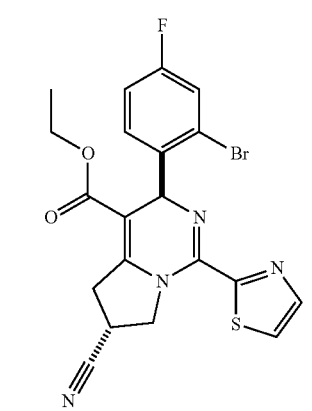
23
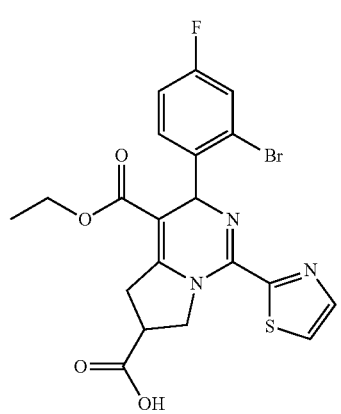
84
-continued
24
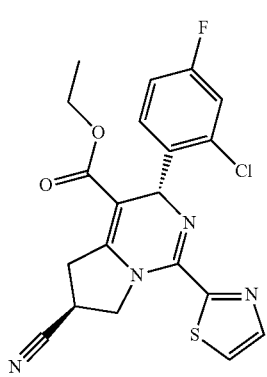
25
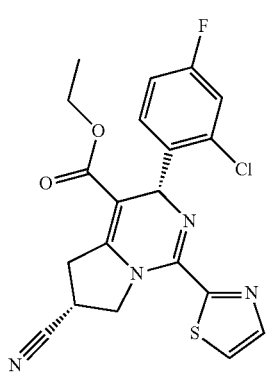
27
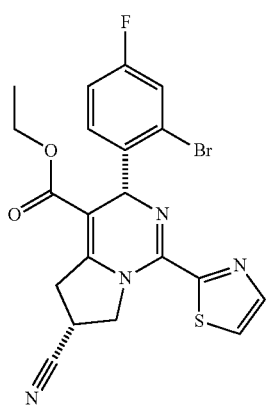
28
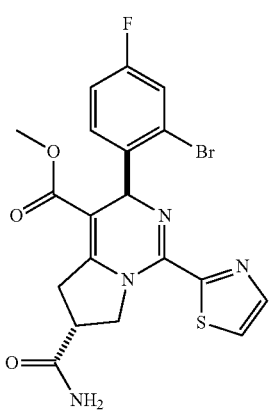

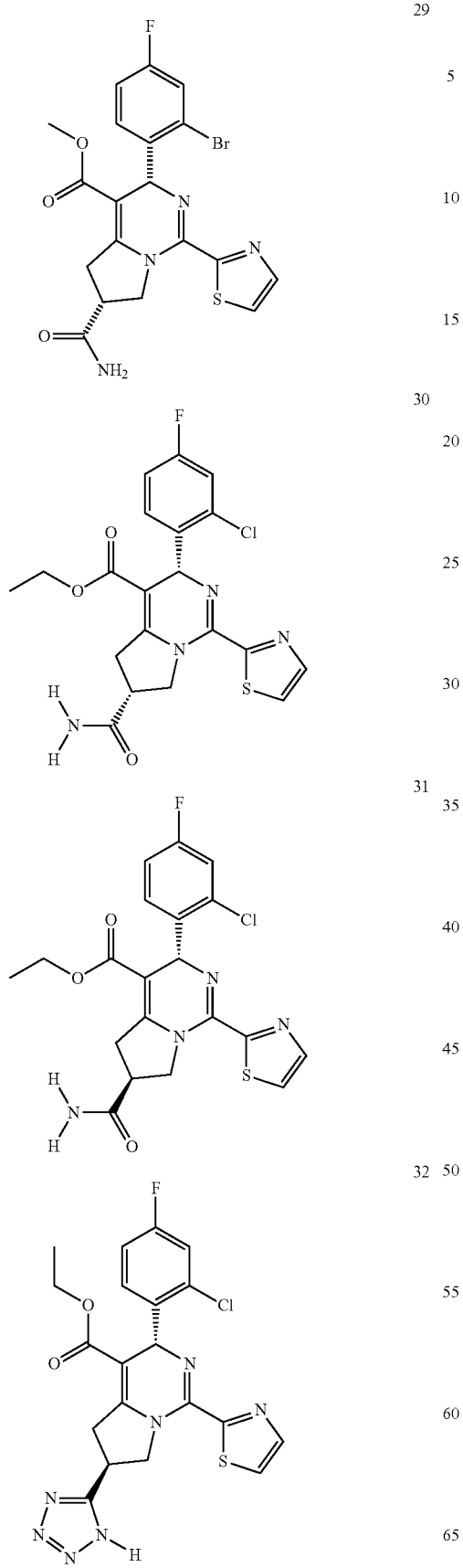
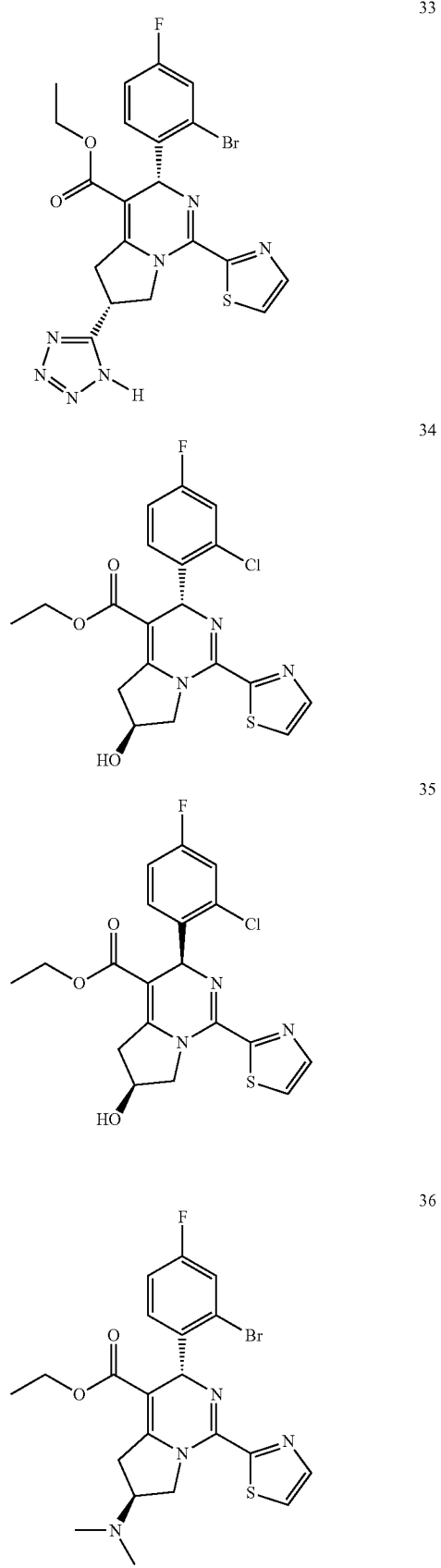

87
-continued
37
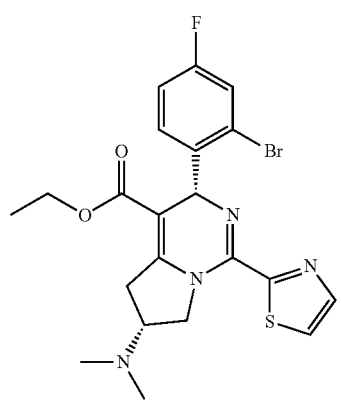
38
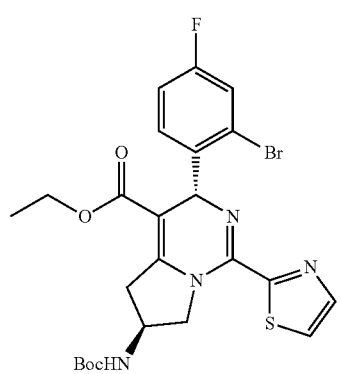
39
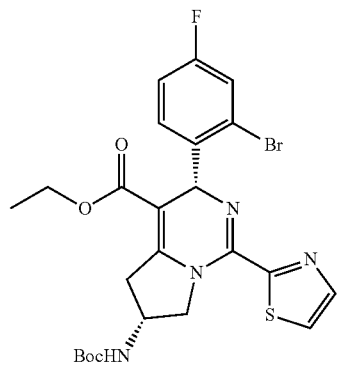
42
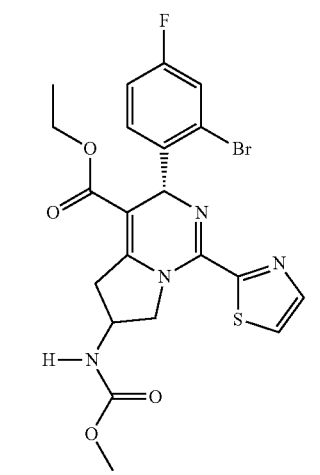
88
-continued
40
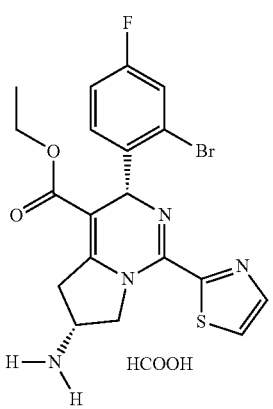
41
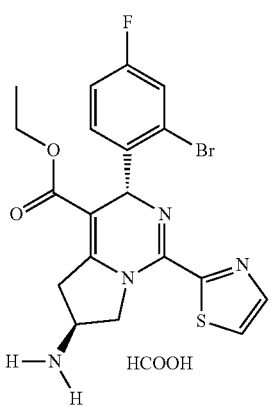
43
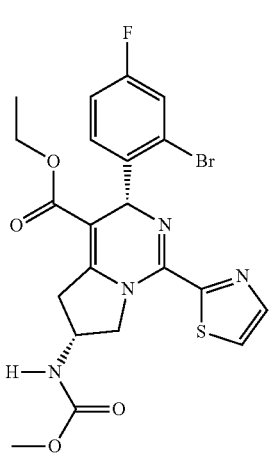

44
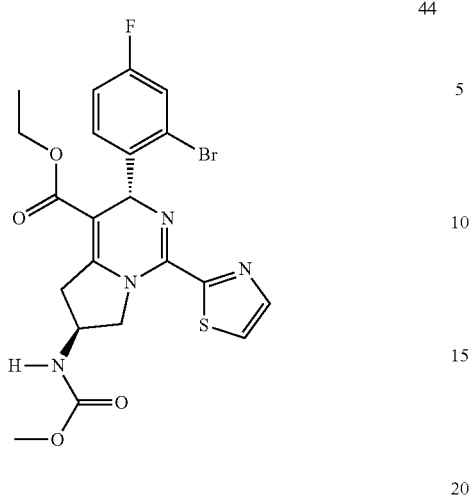
45
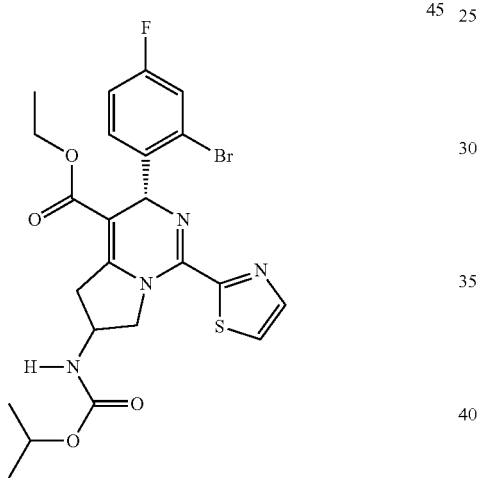
46
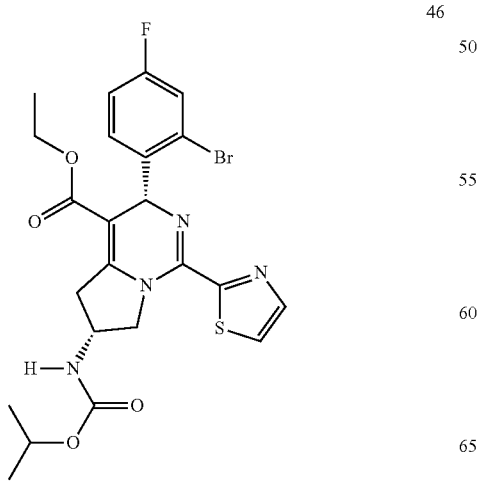
47
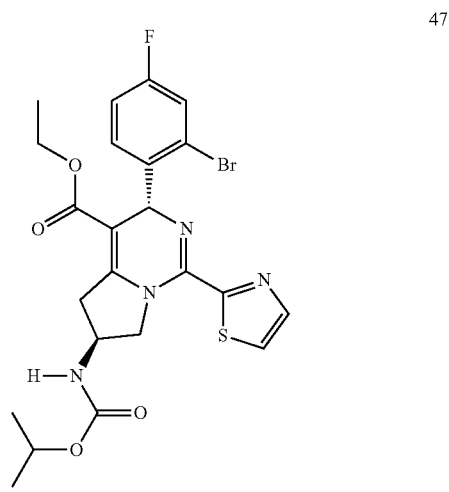
48
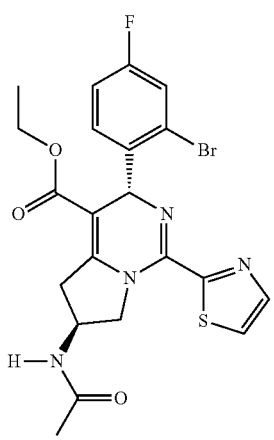
49
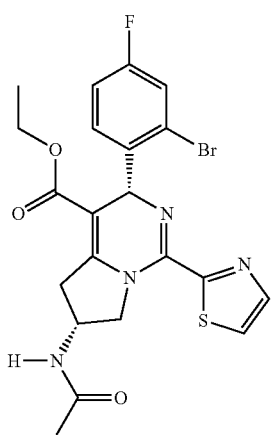

| 50 | 52 |
|---|---|
| 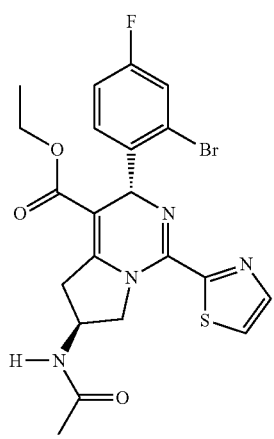 | 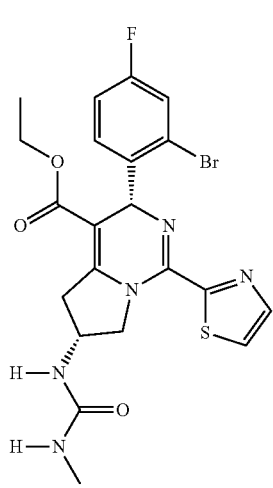 |
| 51 | 53 |
| 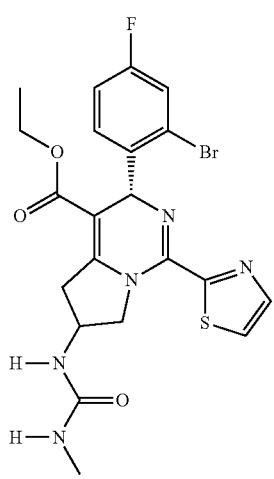 | 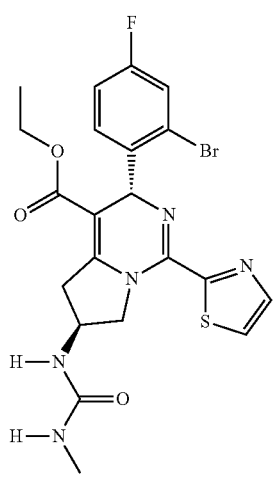 |
| 54 | 55 |
| 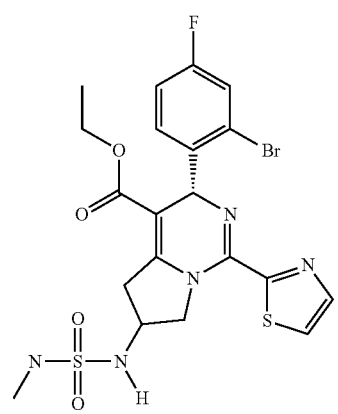 | 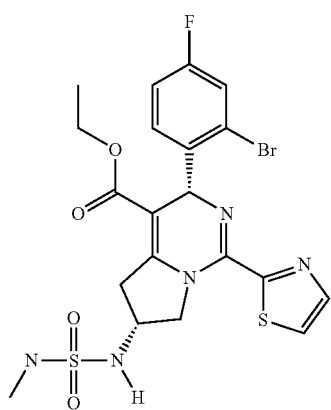 |

56
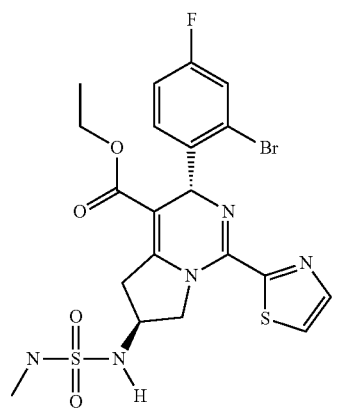
57
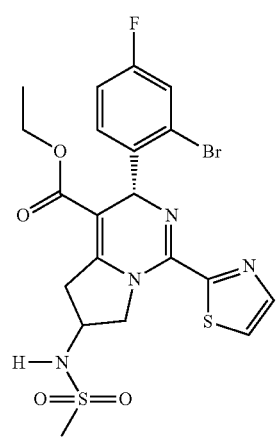
58
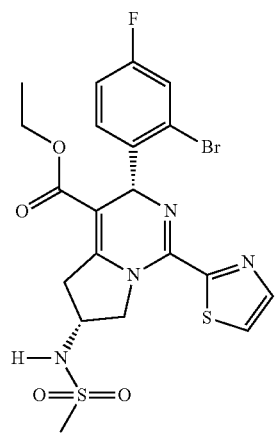
59
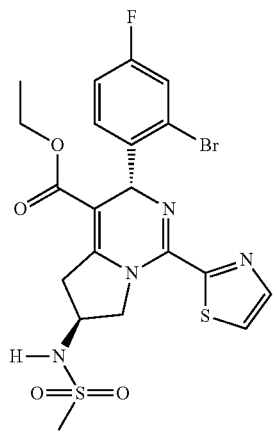
60
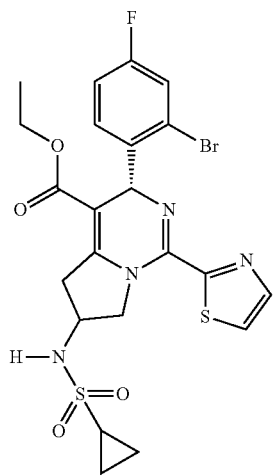
61
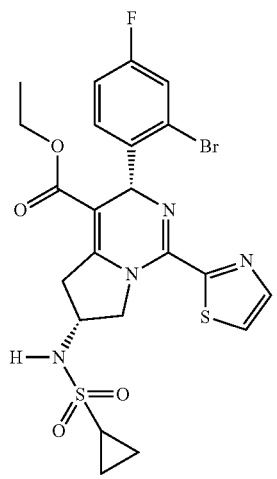

-continued
62
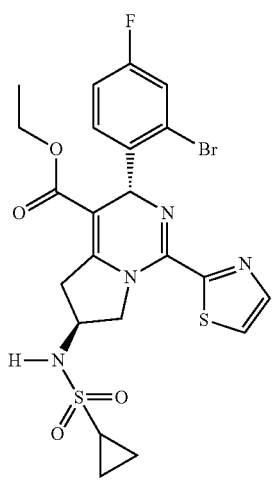
63
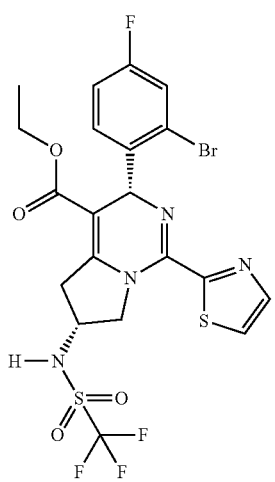
64
-continued
65
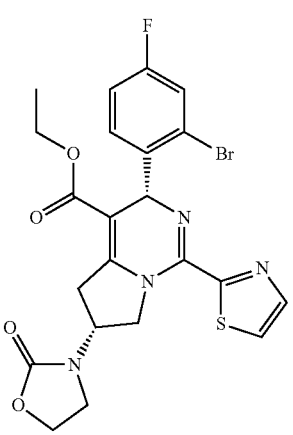
66
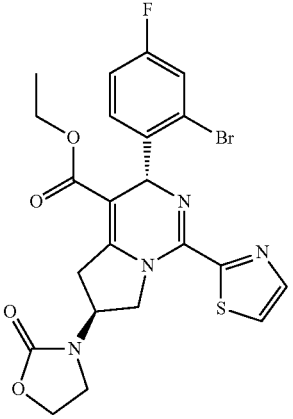
67
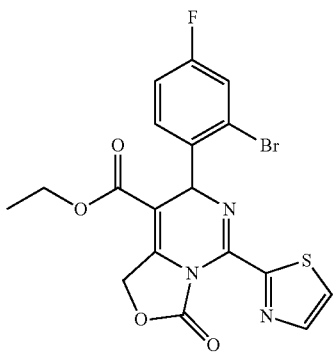
68
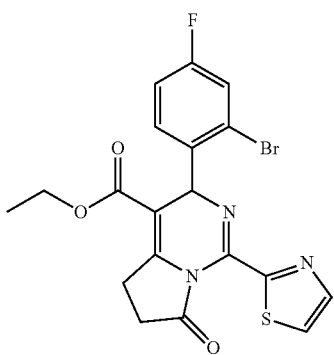

| 69 | 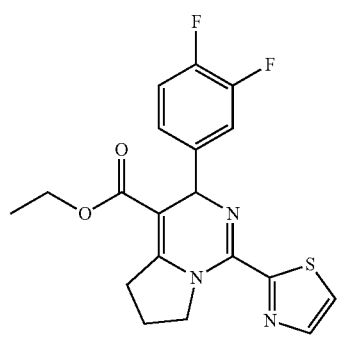 |
|---|---|
| 70 | 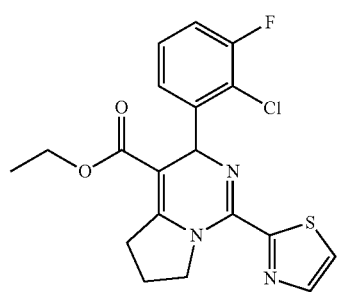 |
| 71 | 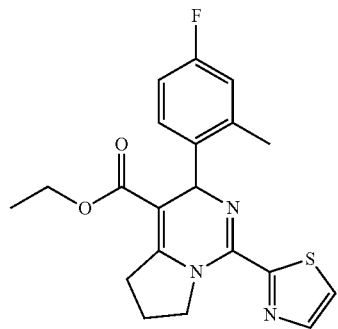 |
| 72 | 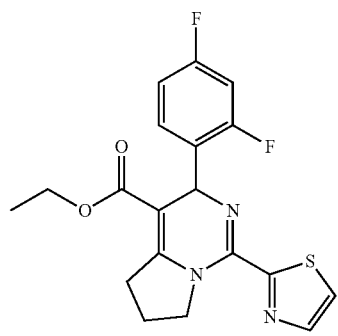 |
| 73 | 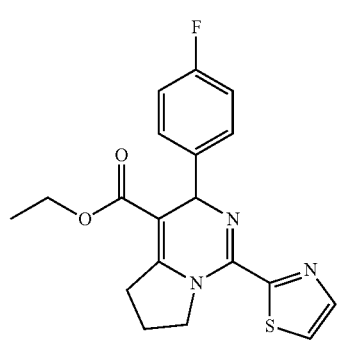 |
| 74 | 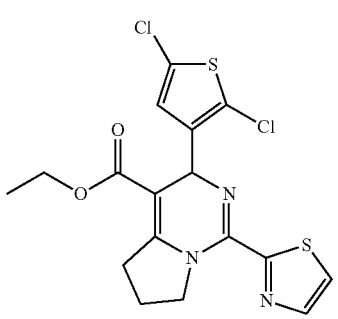 |
|---|---|
| 75 | 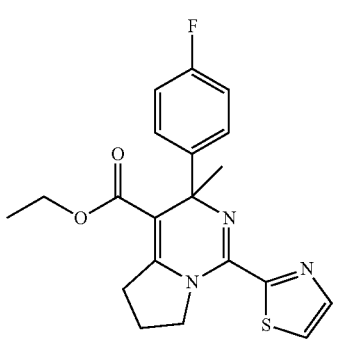 |
| 76 | 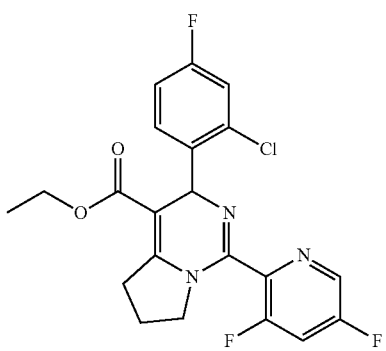 |
| 77 | 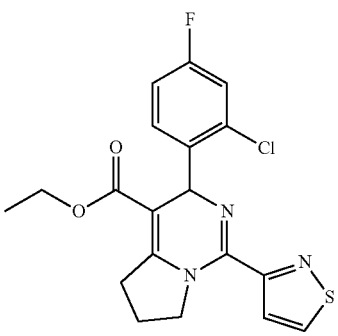 |

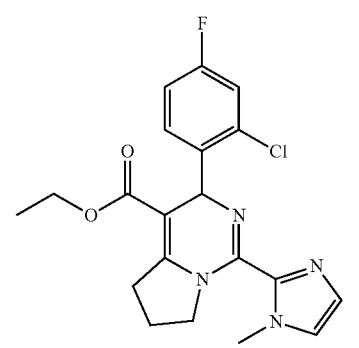
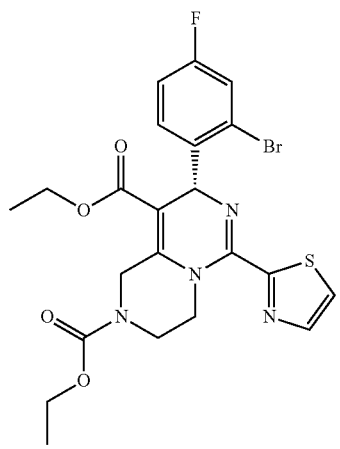
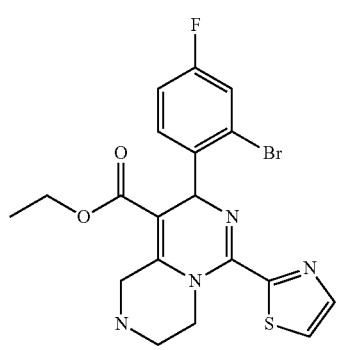
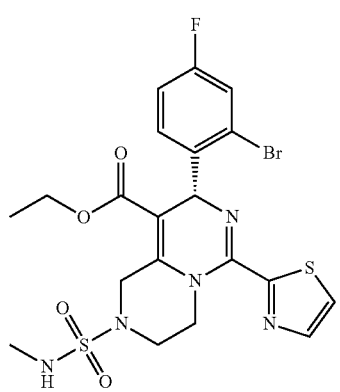
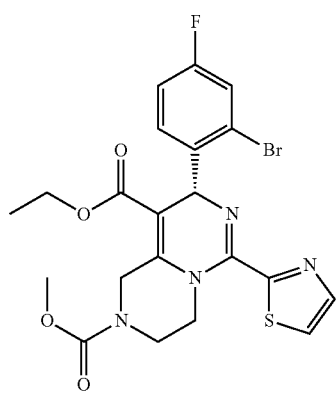

| 101 | 102 |
|---|---|
| 86 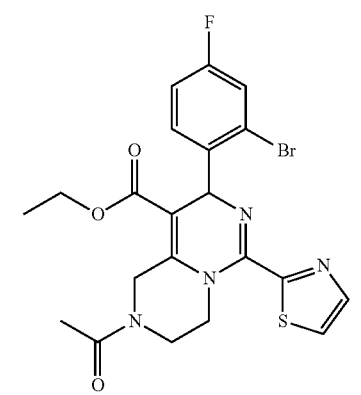 | 90 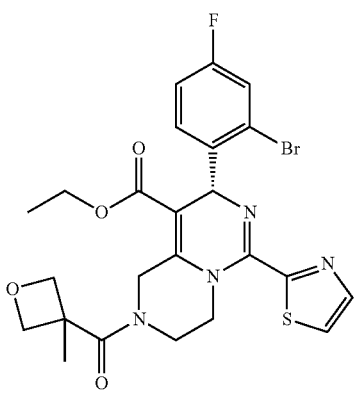 |
| 87 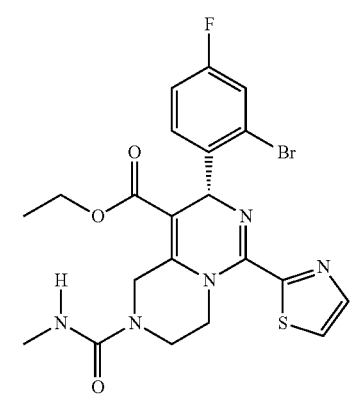 | 91 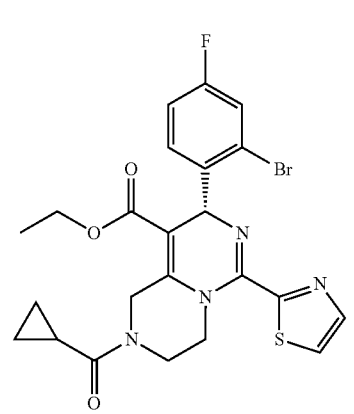 |
| 88 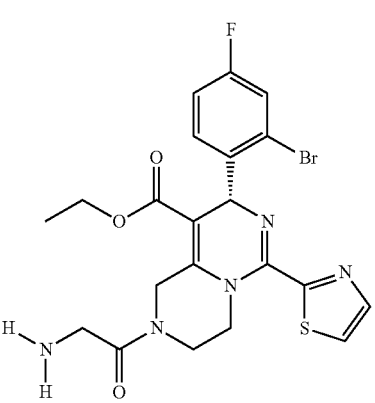 | 92 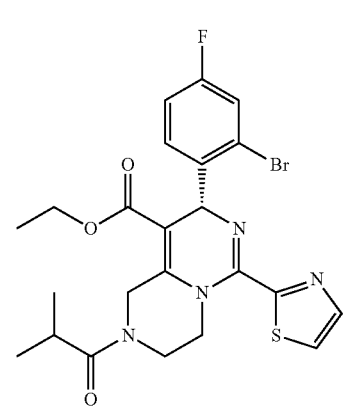 |
| 89 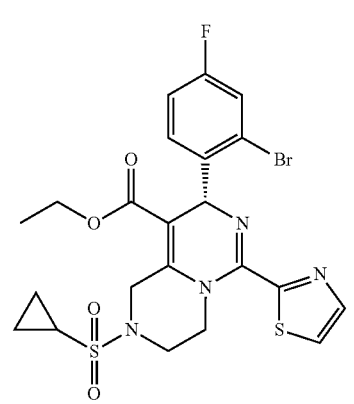 (left-bottom) | 93 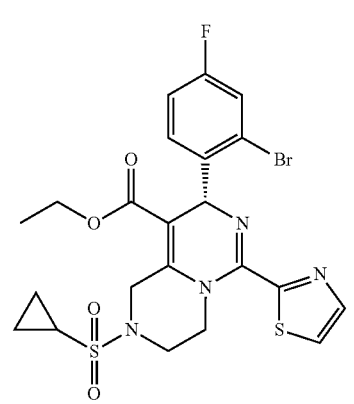 |

94
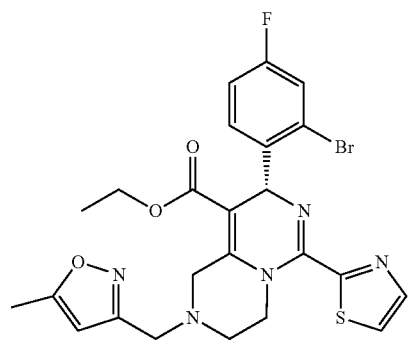
95
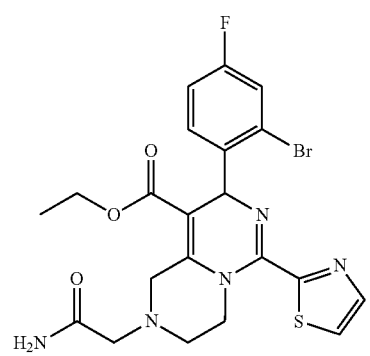
96
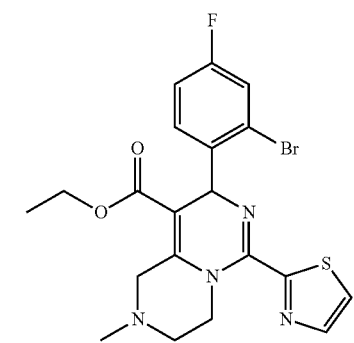
97
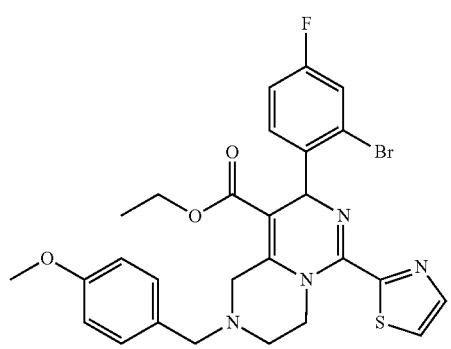
98
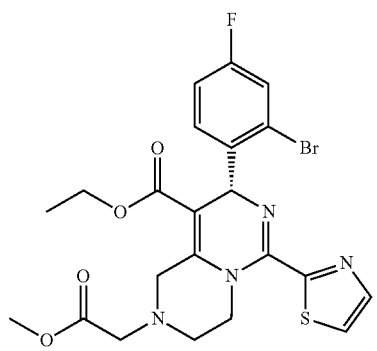
99
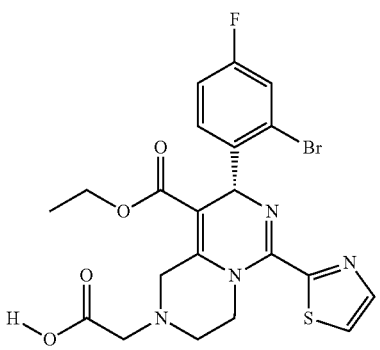
100
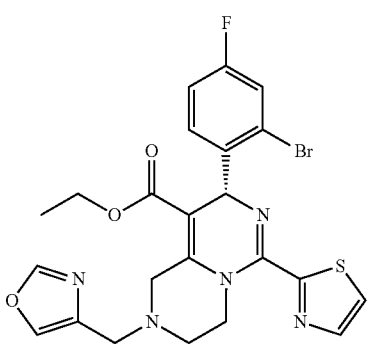
101
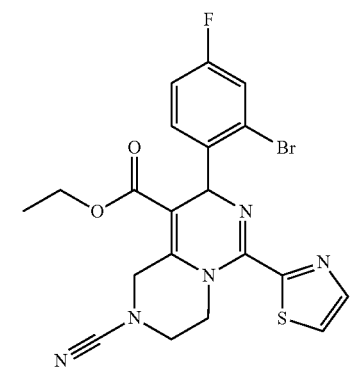

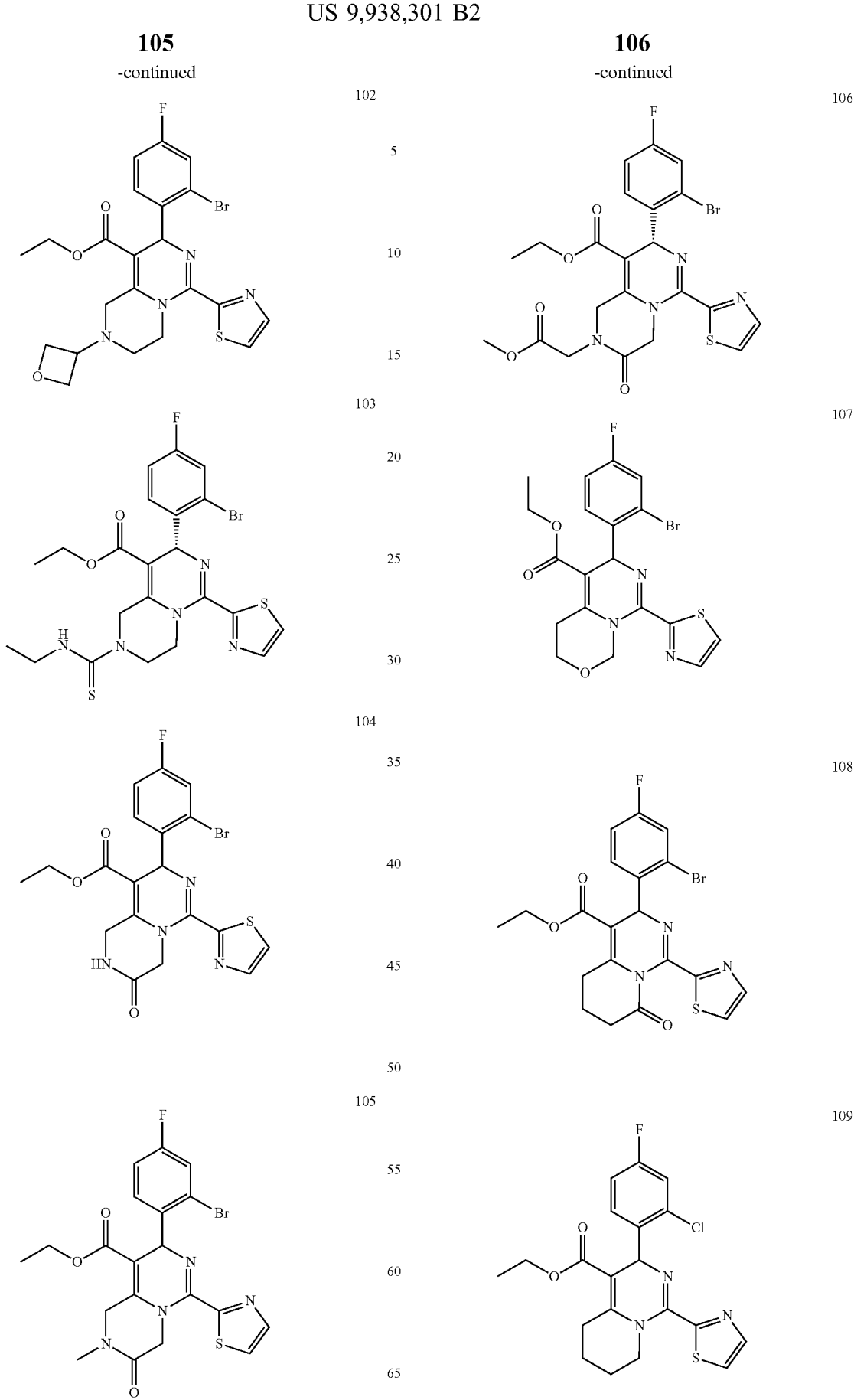

107
-continued
110
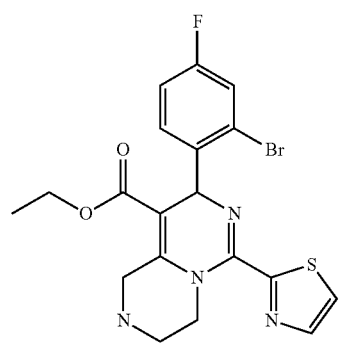
111
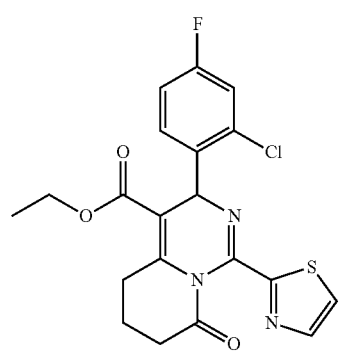
112
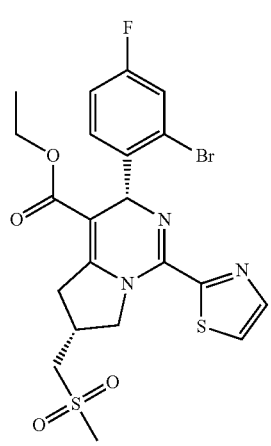
108
-continued
114
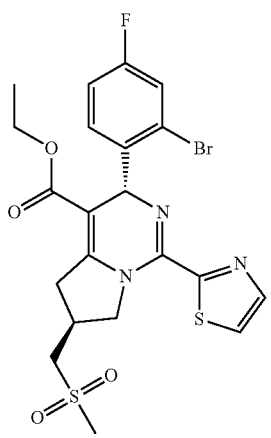
115
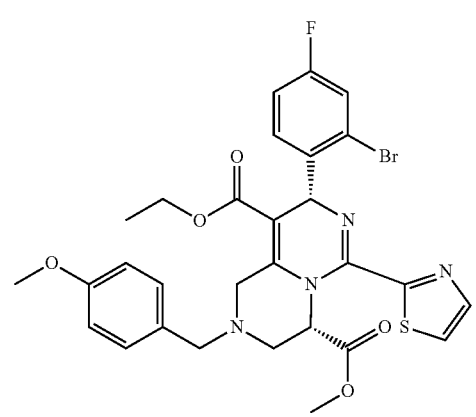
118
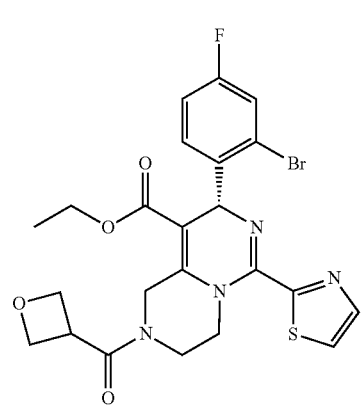
113

116
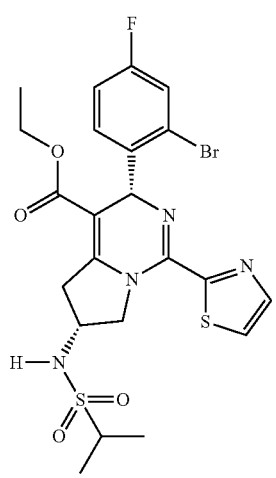
117
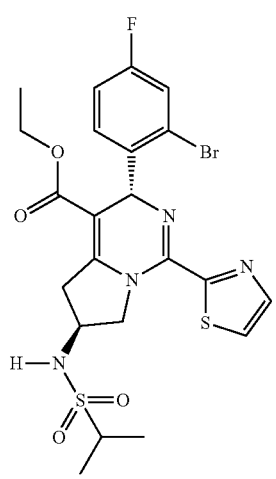
119
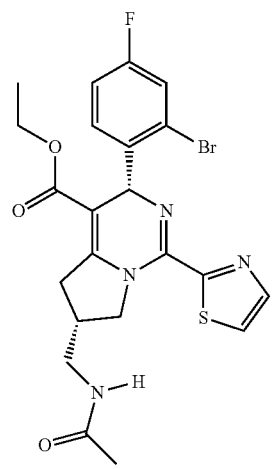
120
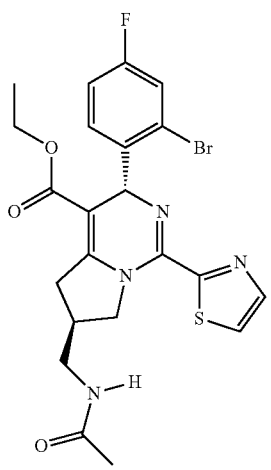
121
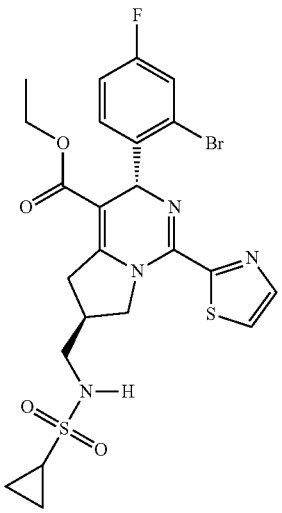
123
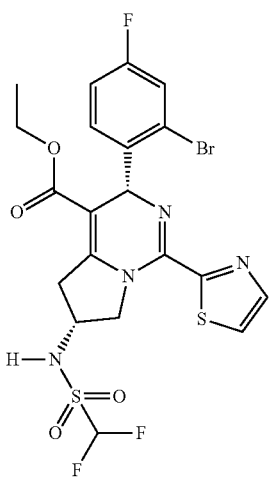

111
-continued
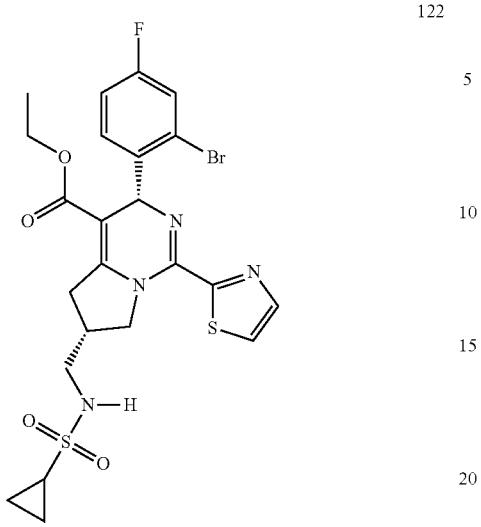
122
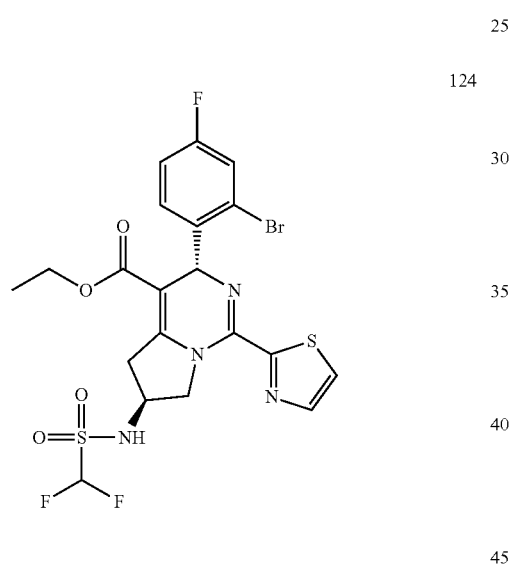
124
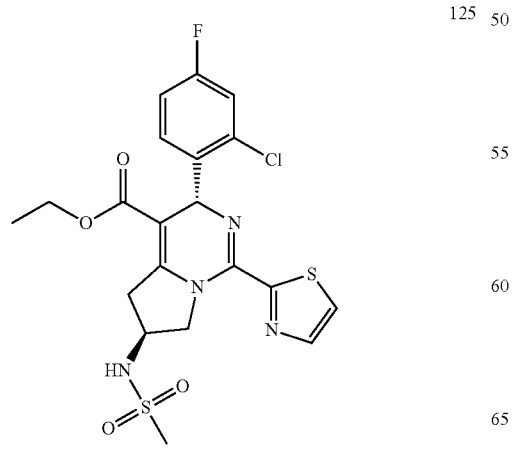
125
112
-continued
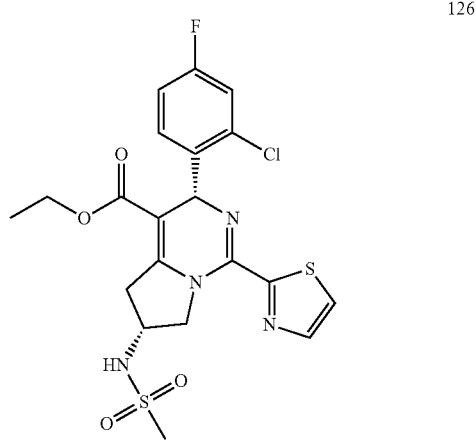
126
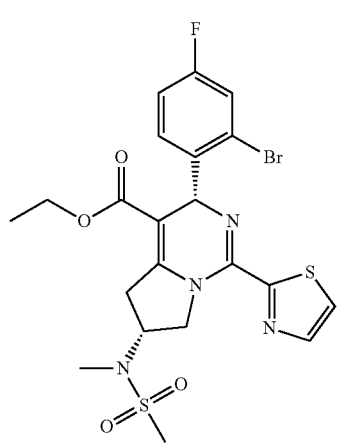
127
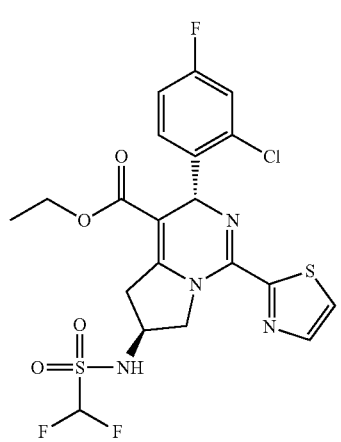
128

129
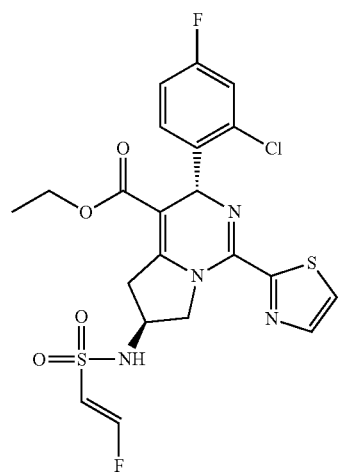
130
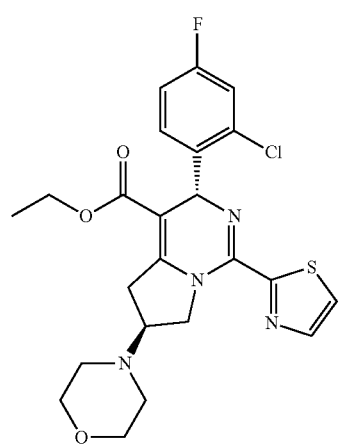
131
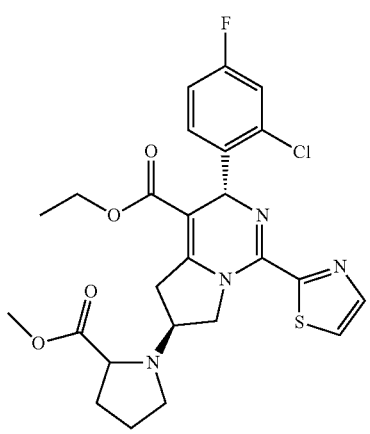
132
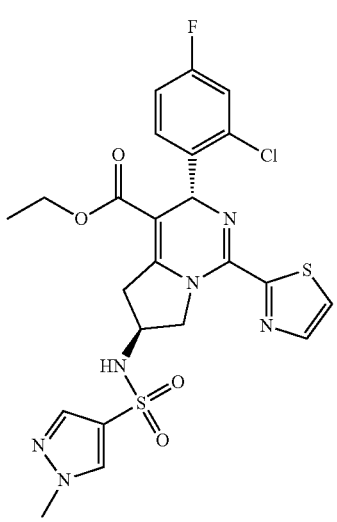
133
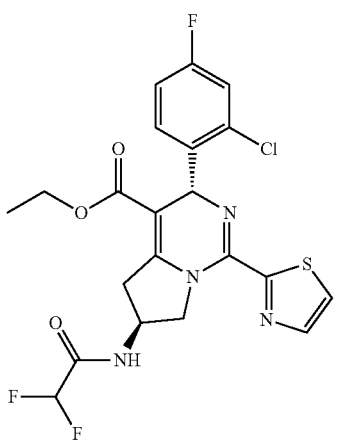
134
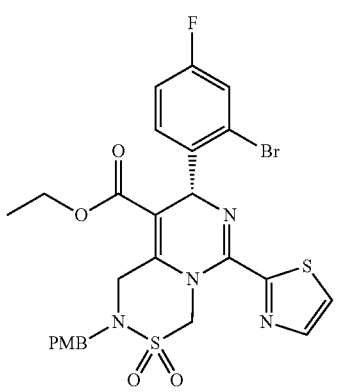

115
-continued
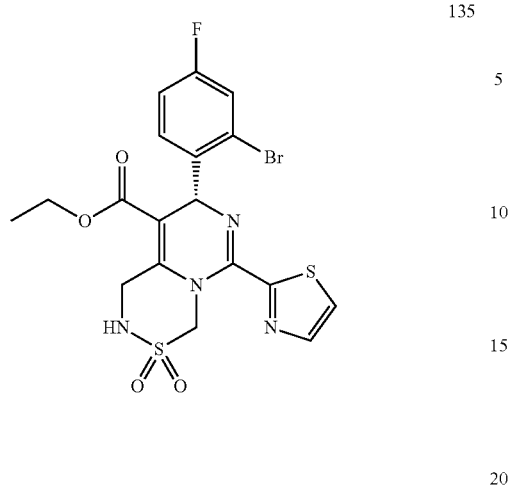
135
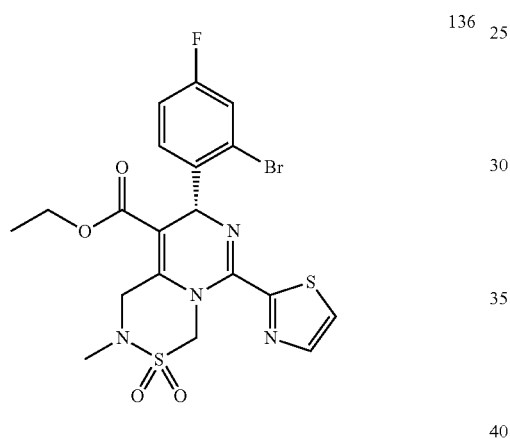
136
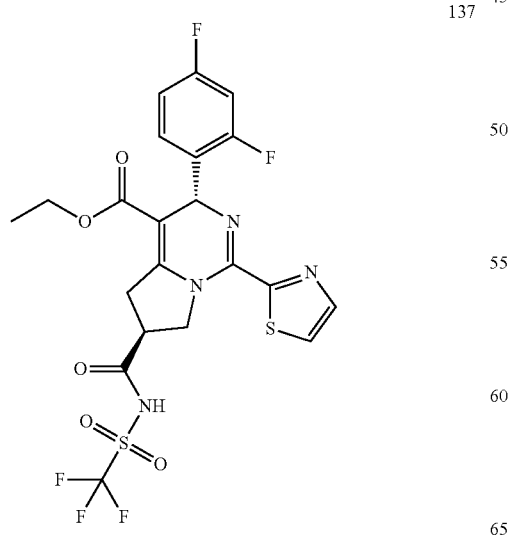
137
116
-continued
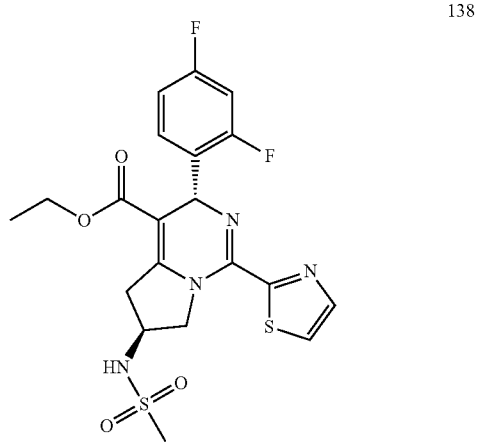
138
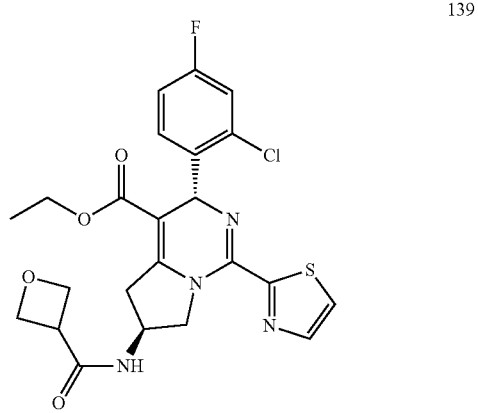
139
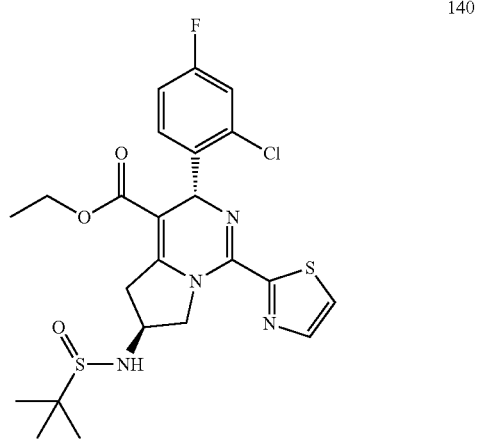
140

141 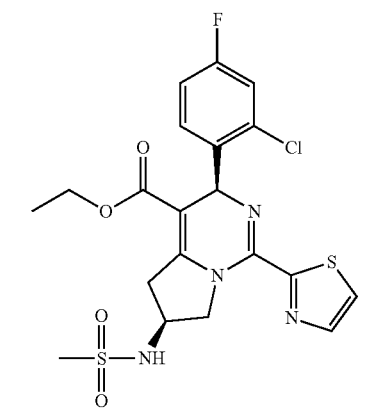
142 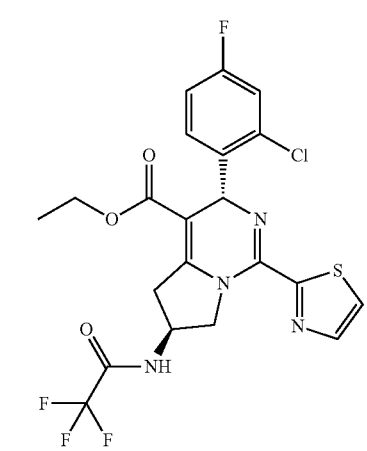
143 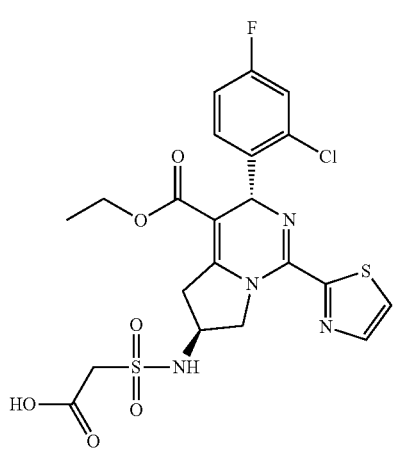
144 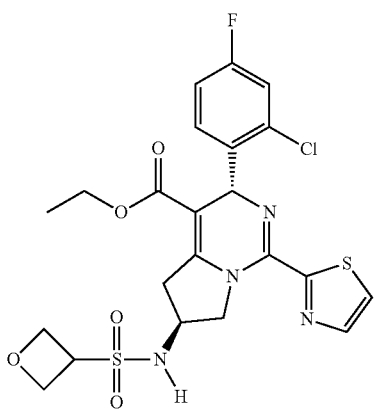
145 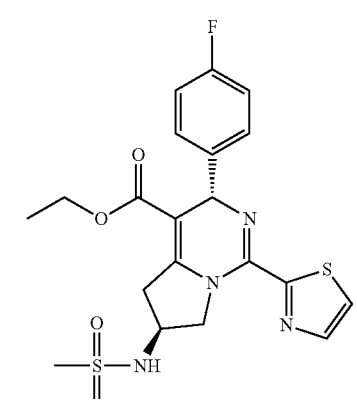
146
147

148 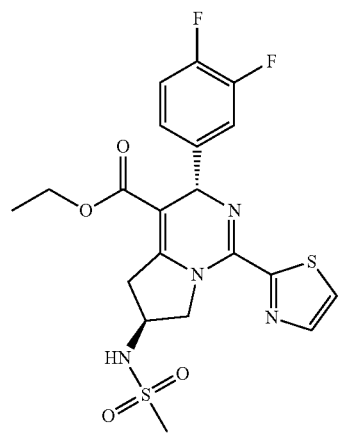
149 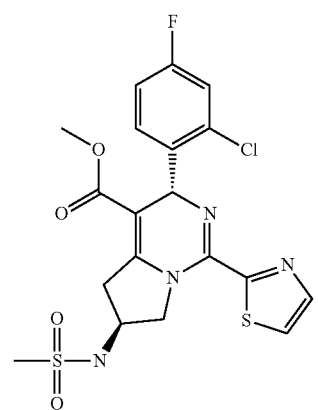
150 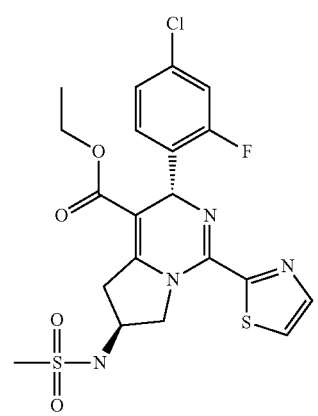
151 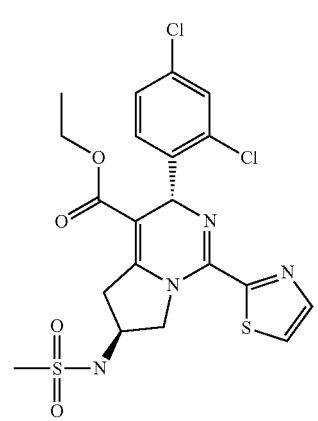
152 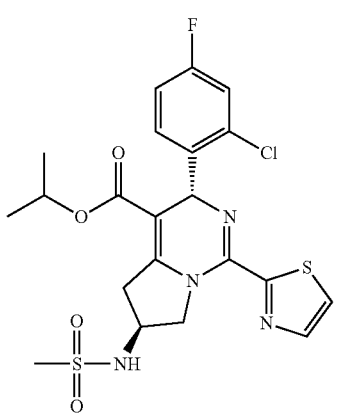
153 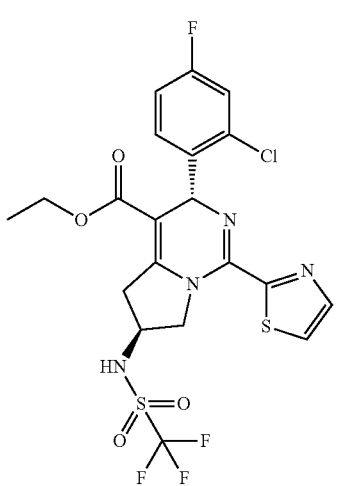
154 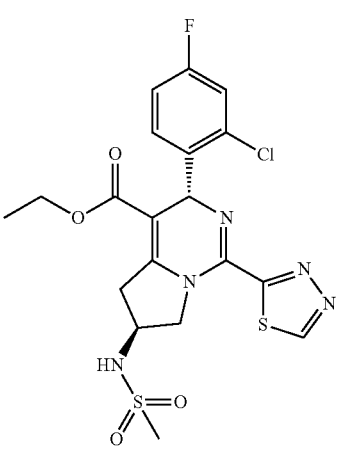

155 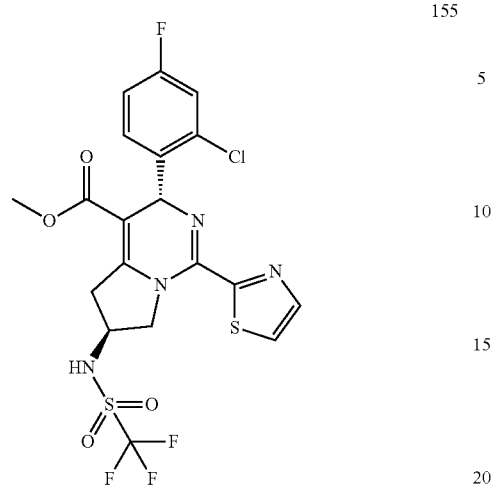
156 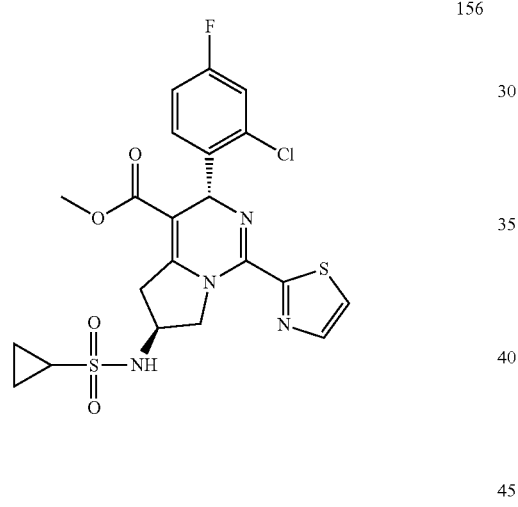
157 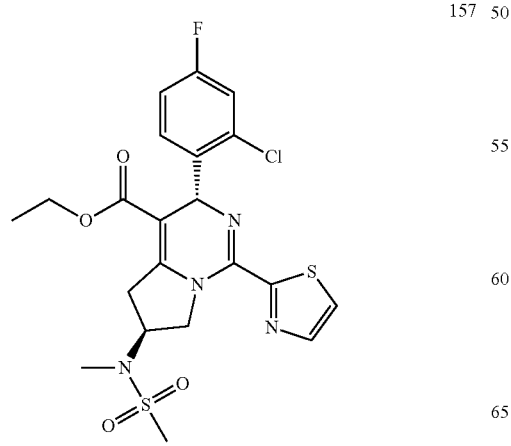
158 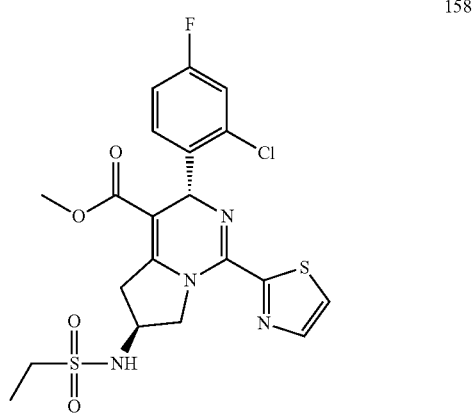
159 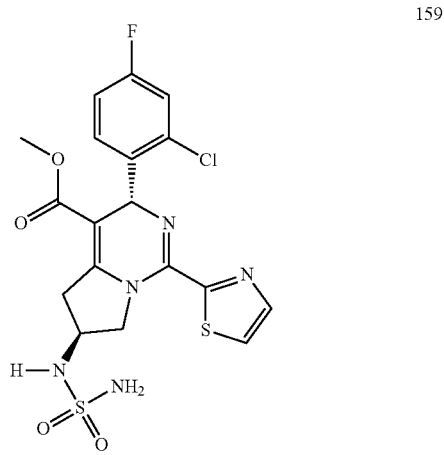
160 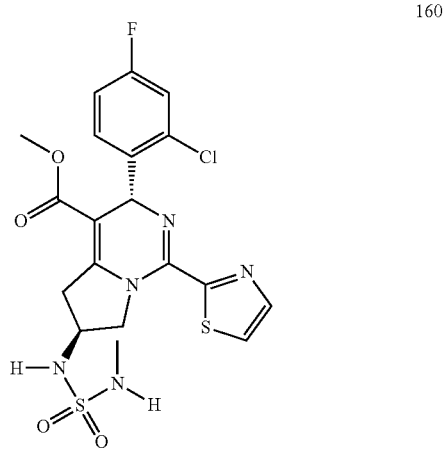

123
-continued
161
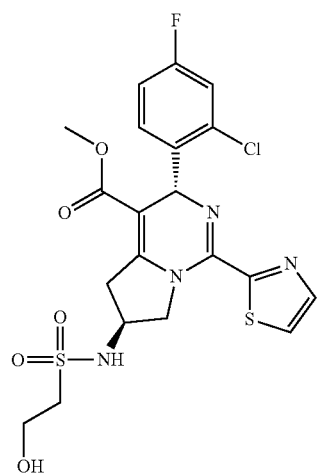
162
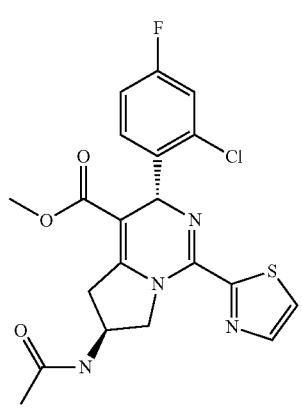
163
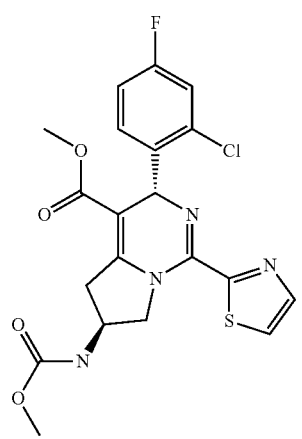
124
-continued
164
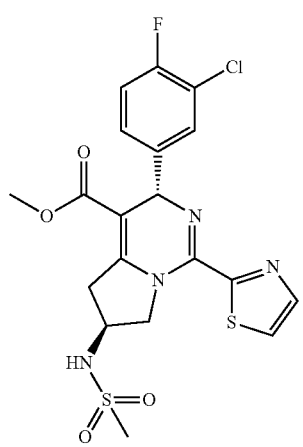
165
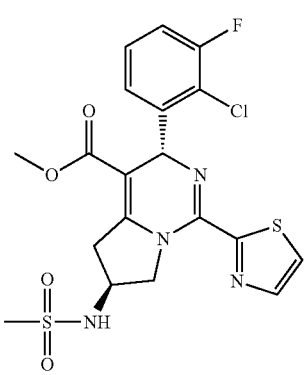
166
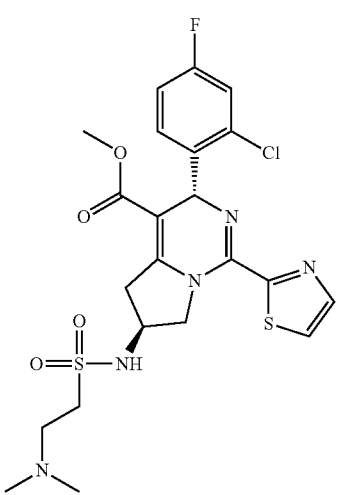

125
-continued
167
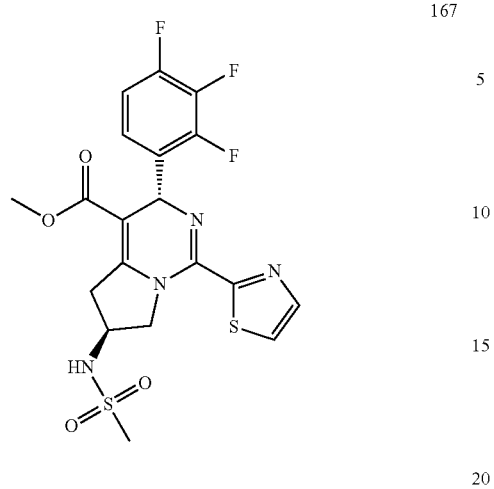
168
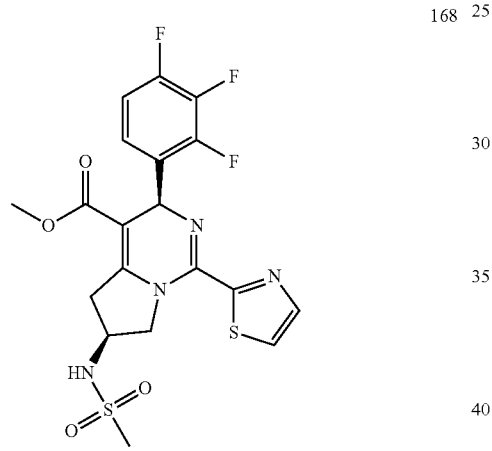
169
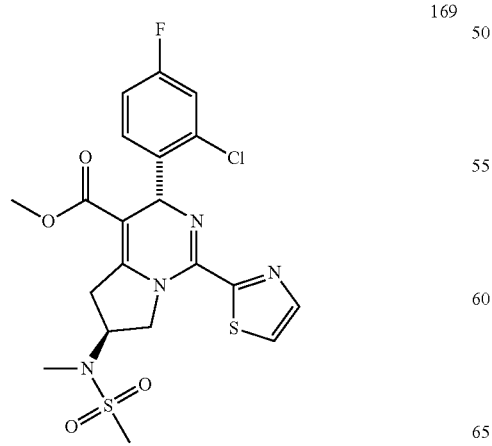
126
-continued
170
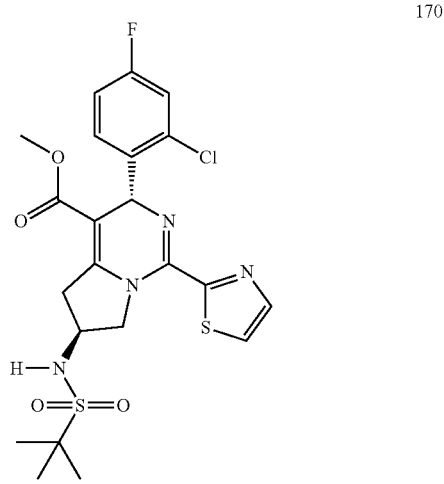
171
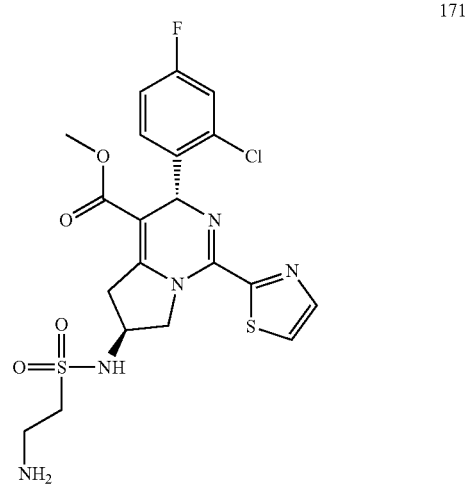
172
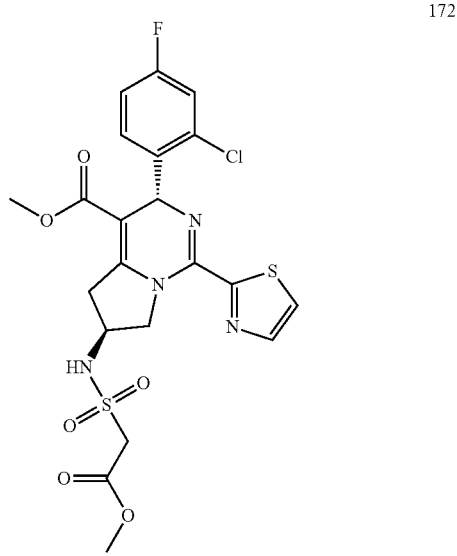

127
-continued
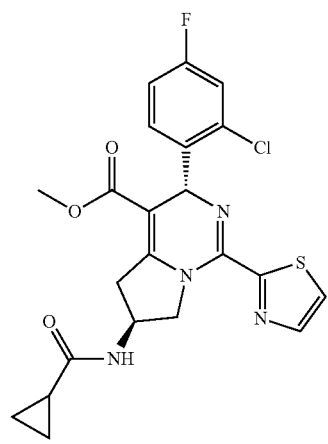
173
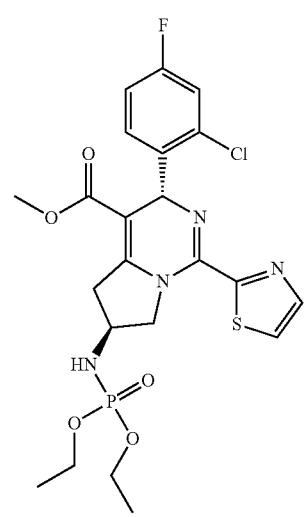
174
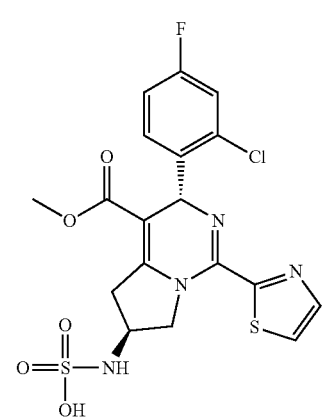
175
128
-continued
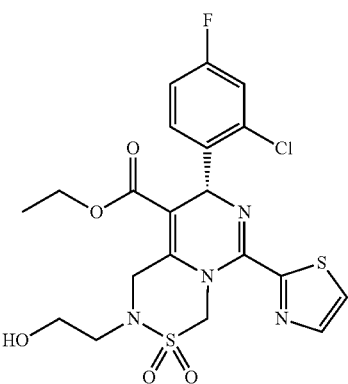
176
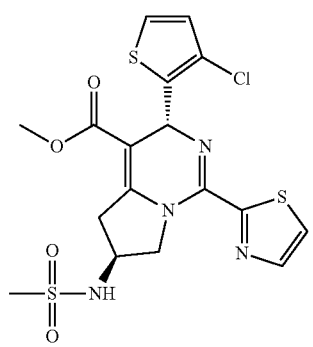
177
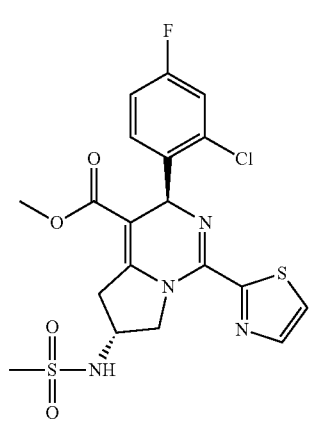
178
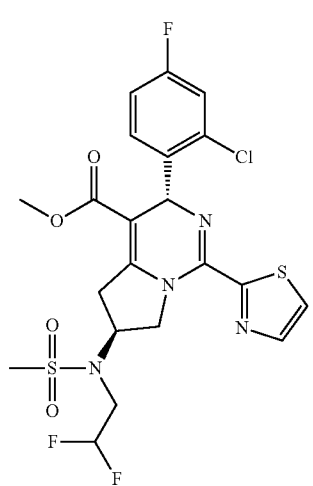
179

| 180 | 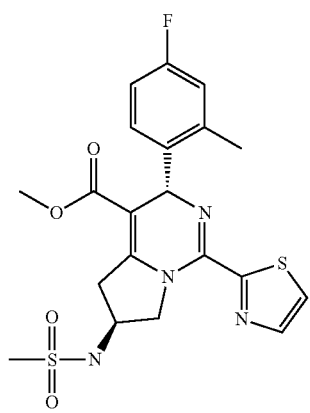 | 183 | 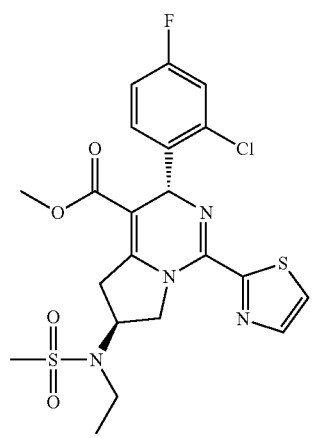 |
| --- | --- | --- | --- |
| 181 | 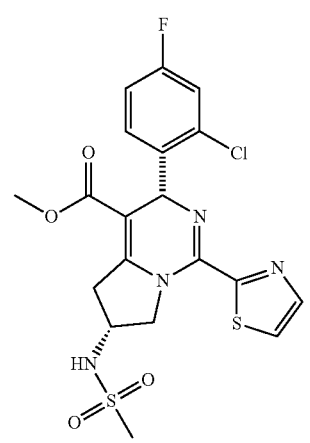 | 184 | 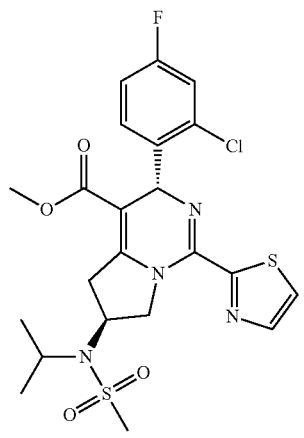 |
| 182 | 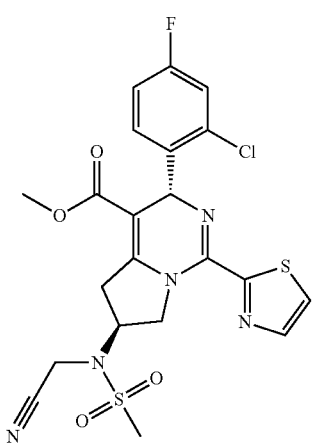 | 185 | 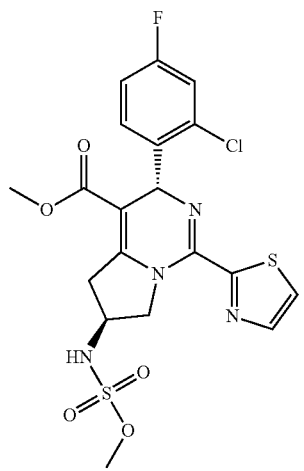 |

186
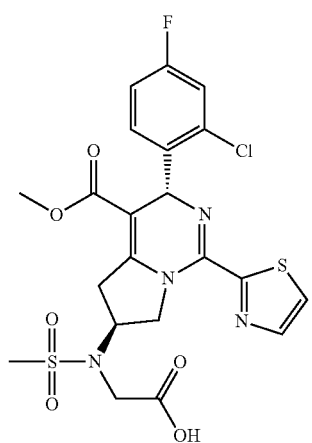
187
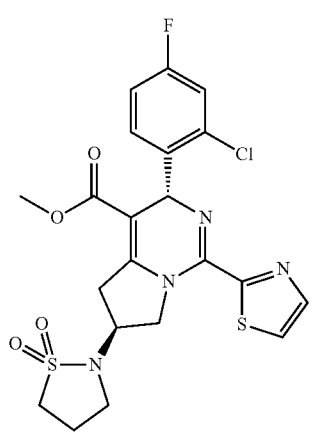
188
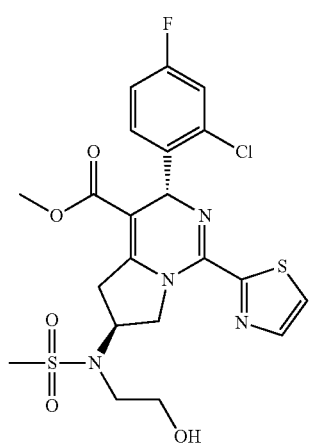
189
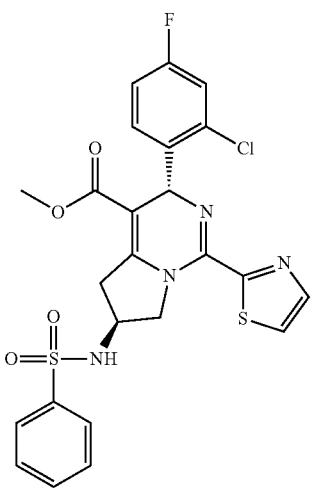
190
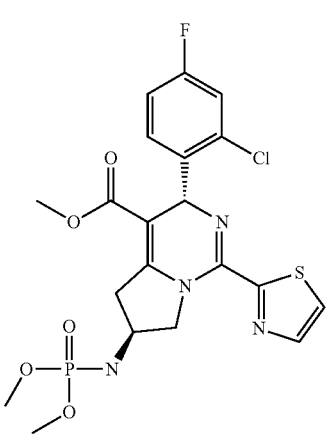
191
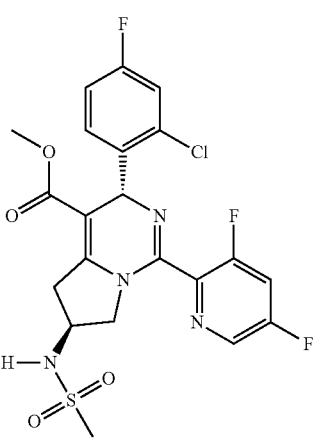

192
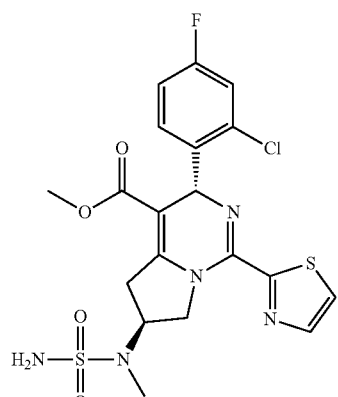
193
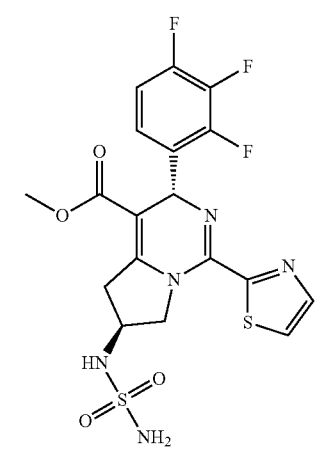
194
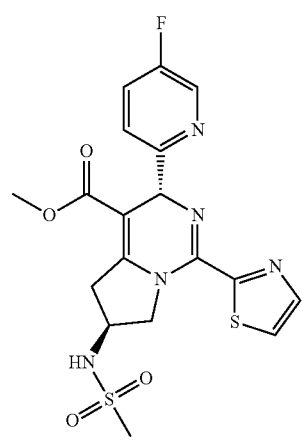
195
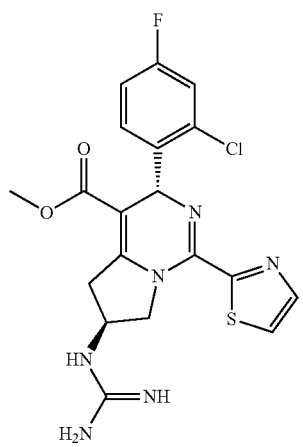
196
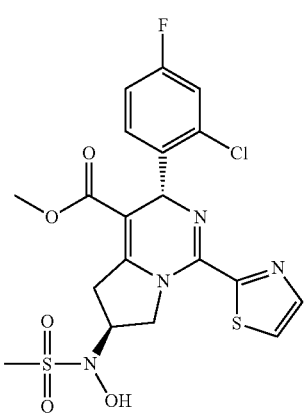
197
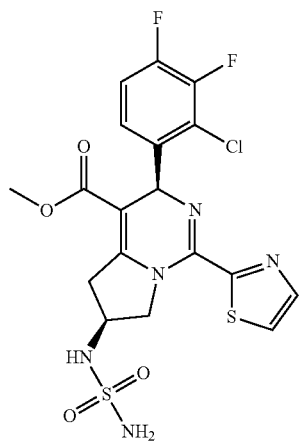

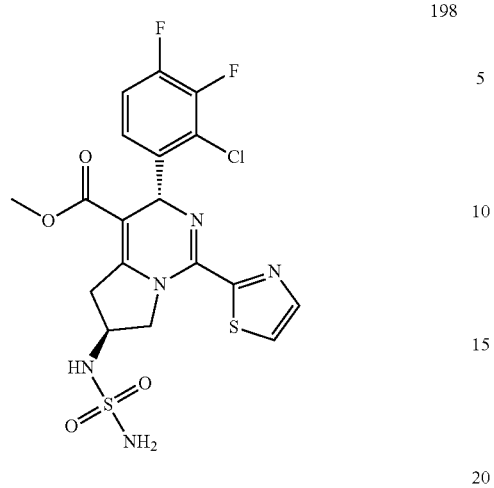
198
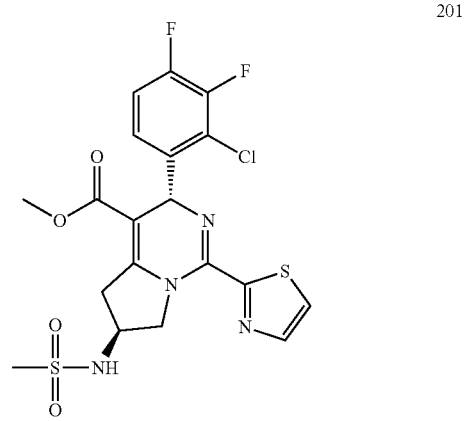
201
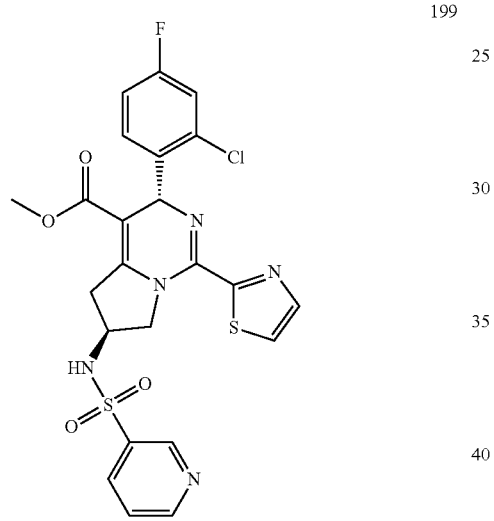
199
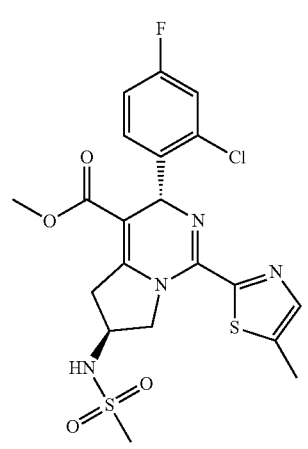
202
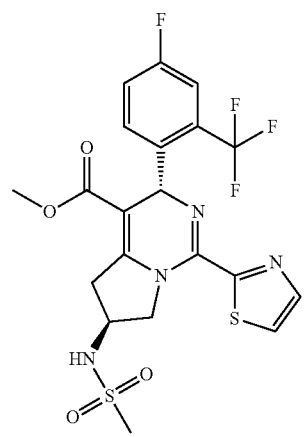
200
203

137
-continued
204
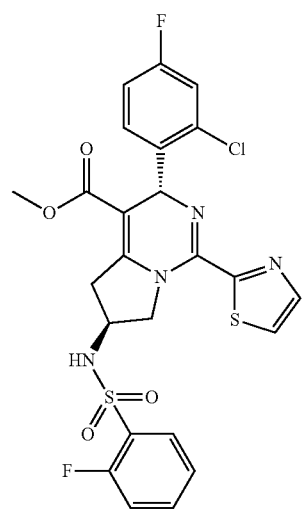
205
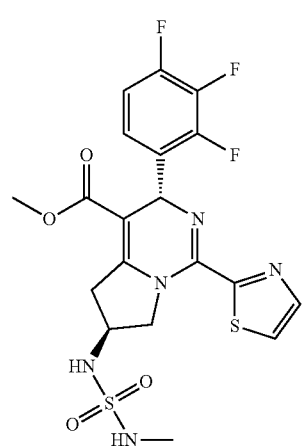
138
-continued
207
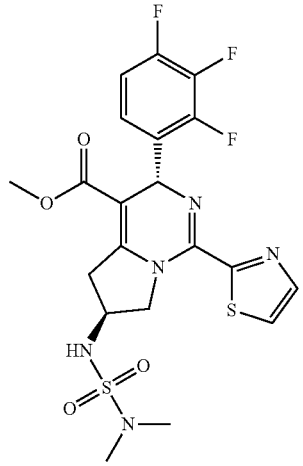
208
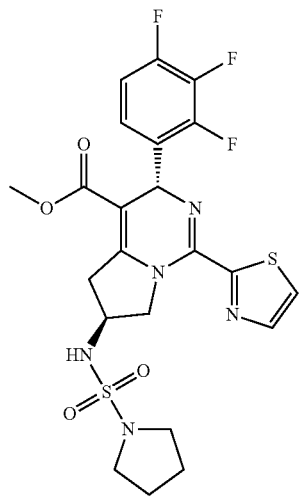
206
209
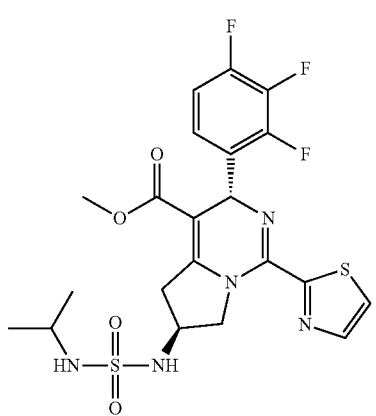

| 210 | 213 |
|---|---|
| 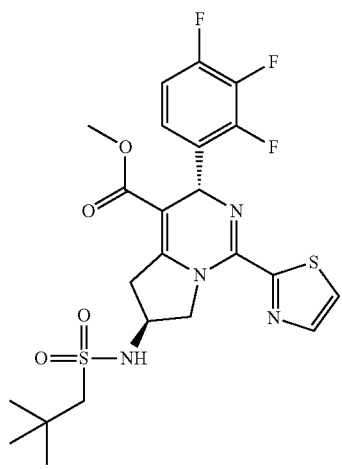 | 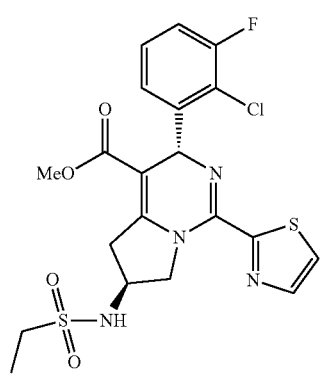 |
| 211 | 214 |
|---|---|
| 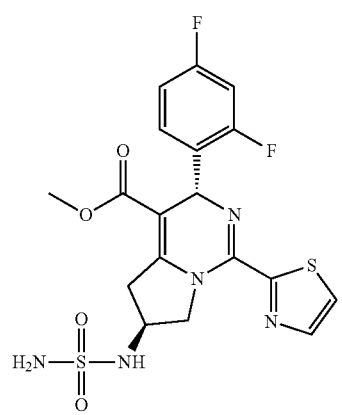 | 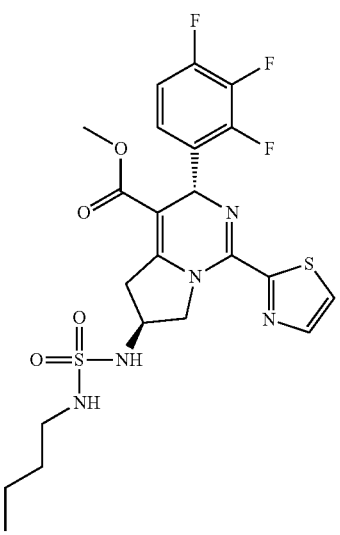 |
| 212 | 215 |
|---|---|
| 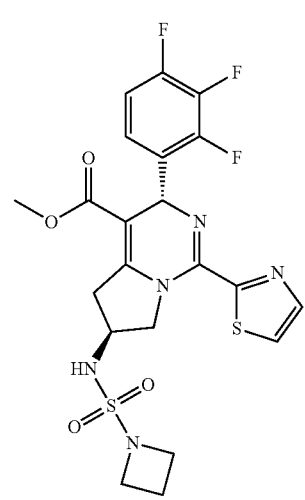 | 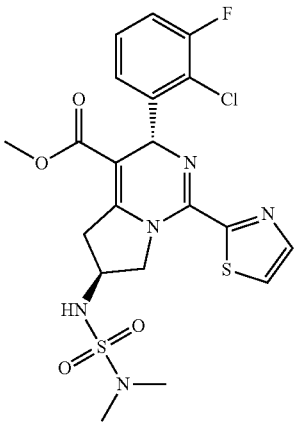 |

216 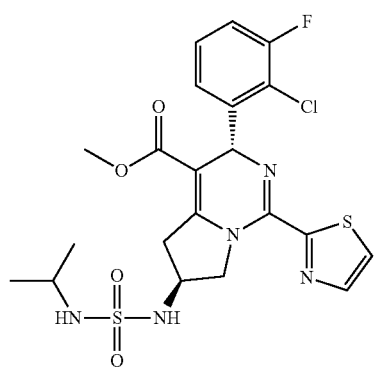
217 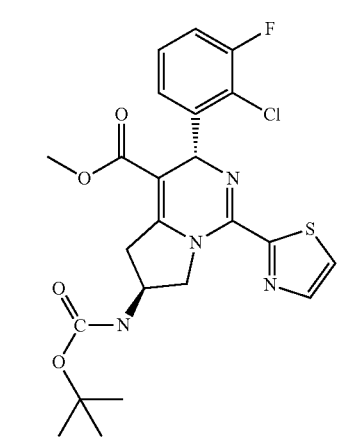
218 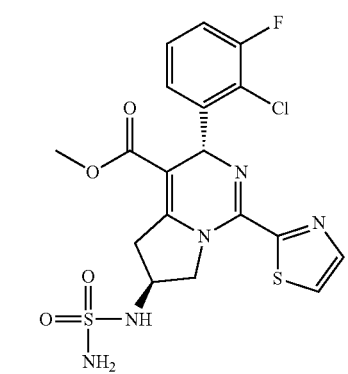
219 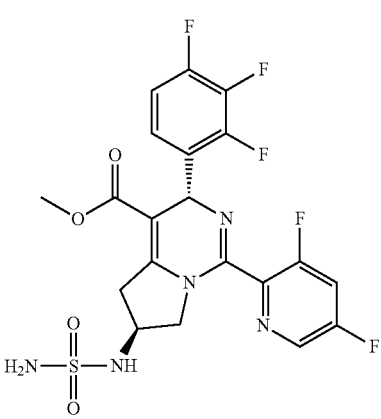
220 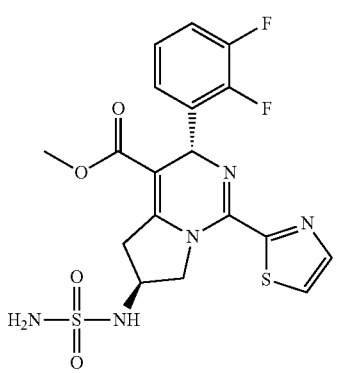
225 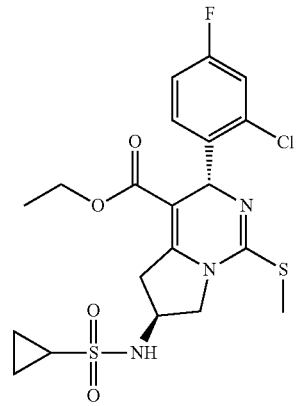
226 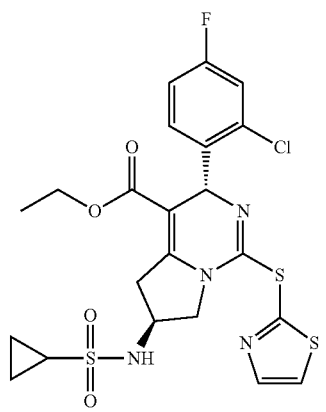
227 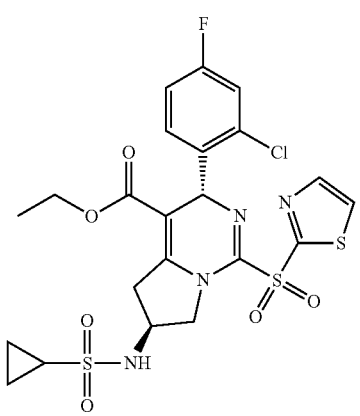

228
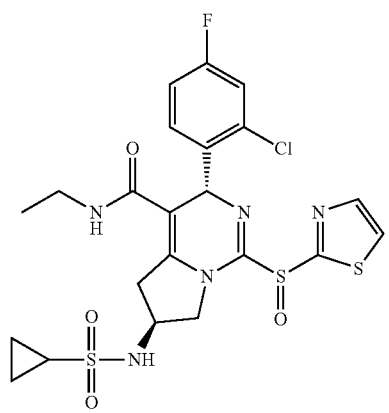
229
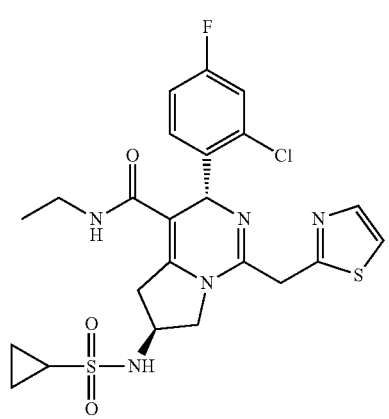
230
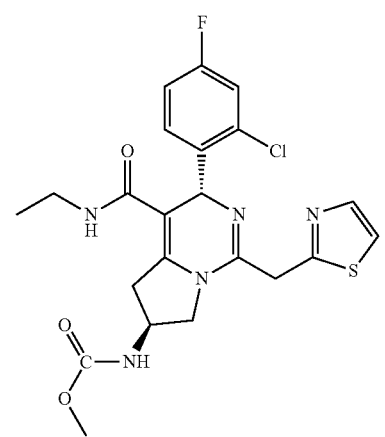
231
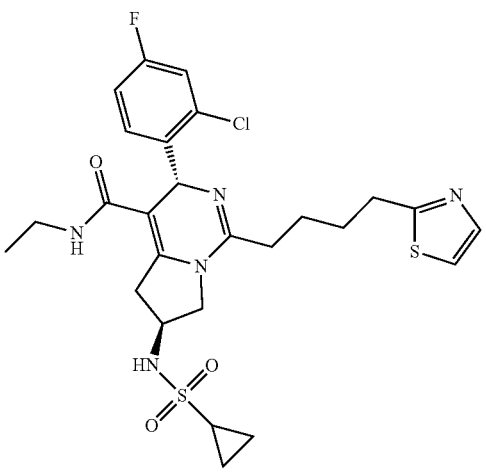
232
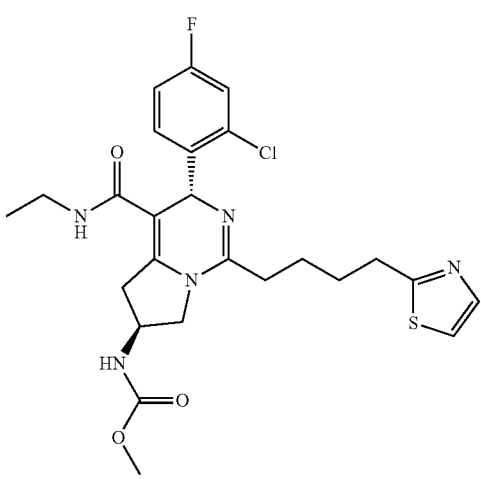
233
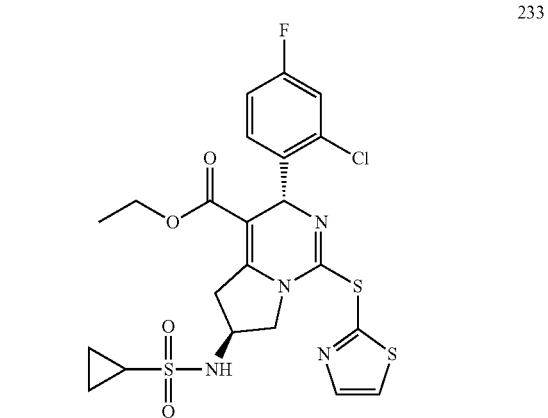

| 234 | 238 |
|---|---|
| 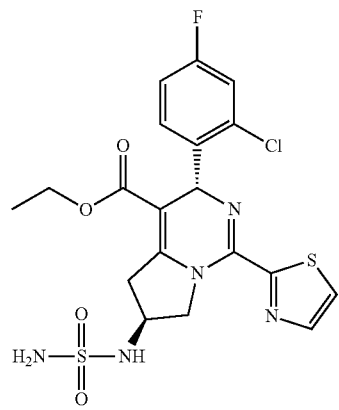 | 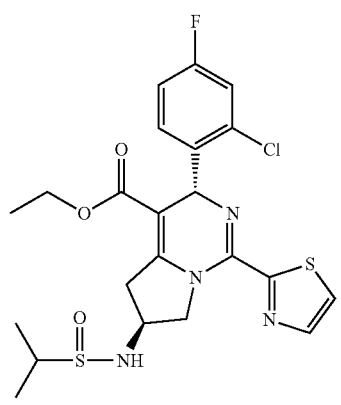 |
| 235 | 239 |
| 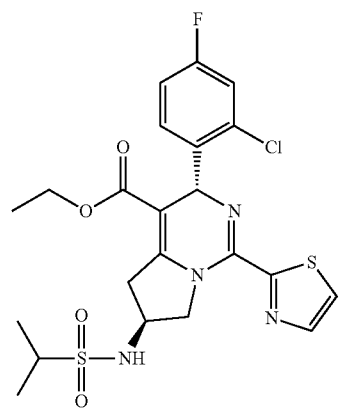 | 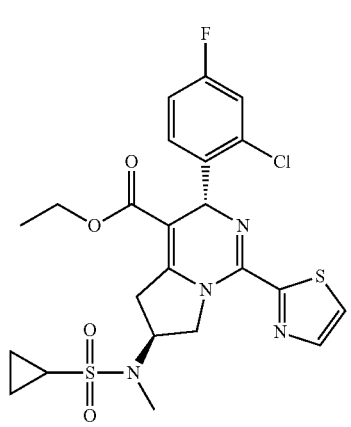 |
| 236 | 240 |
| 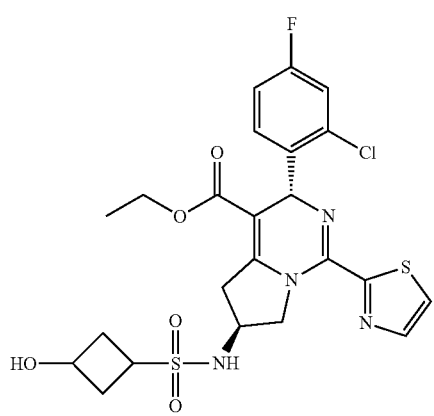 | 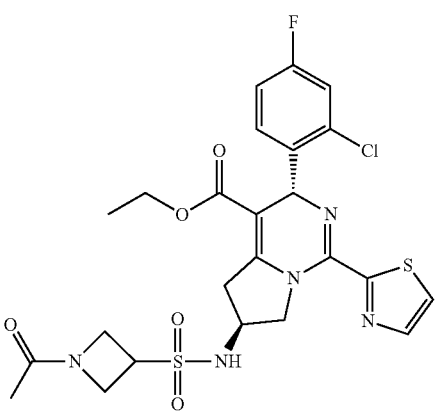 |
| 237 | 241 |
| 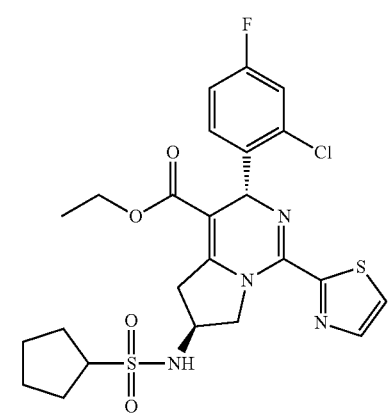 | 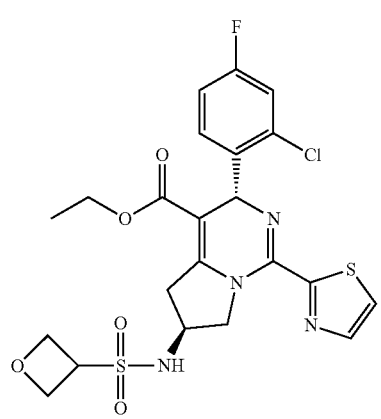 |

242 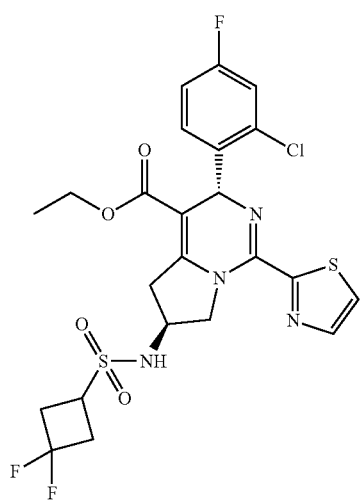
243 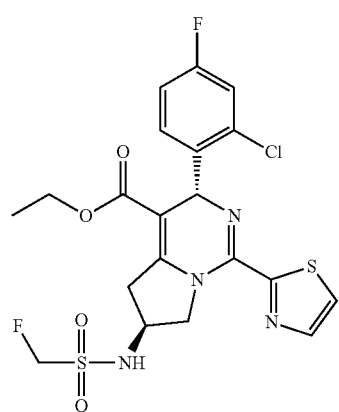
244 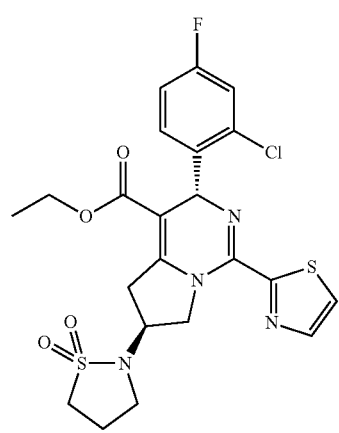
245 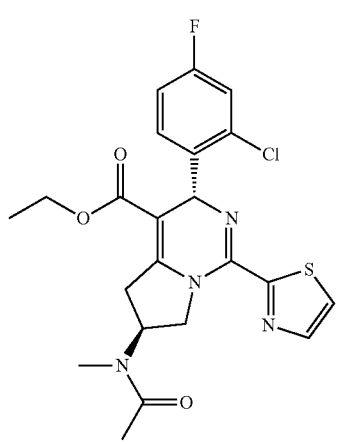
246 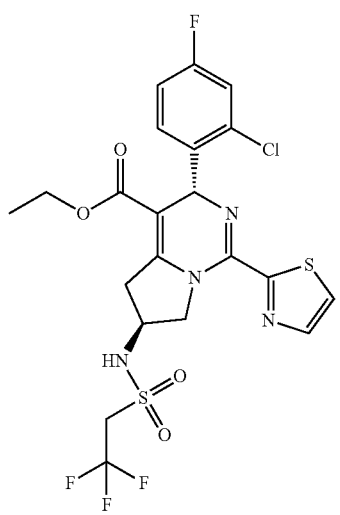
247 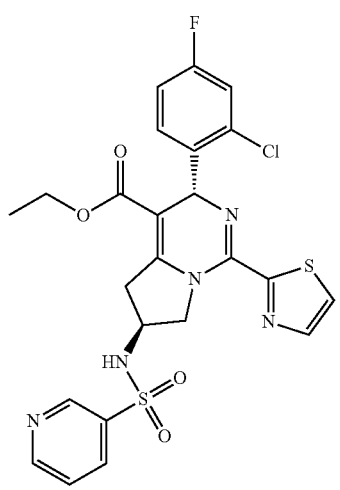

| 248 | 251 |
|---|---|
| 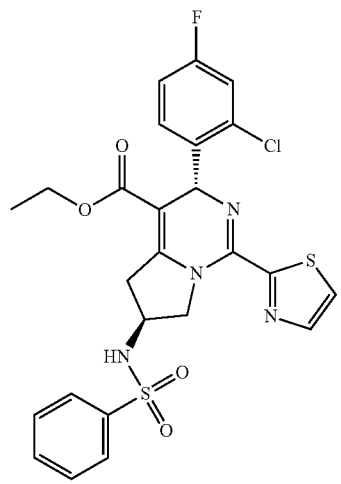 | 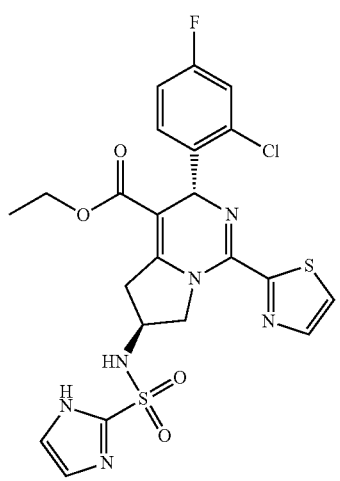 |
| 249 | 252 |
|---|---|
| 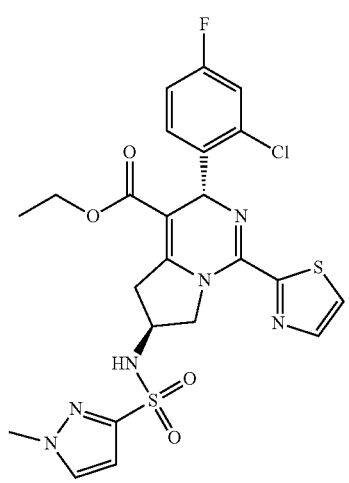 | 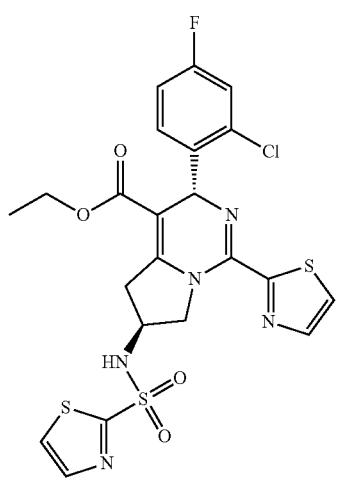 |
| 250 | 253 |
|---|---|
| 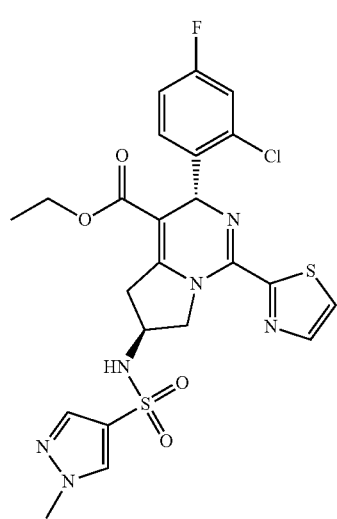 | 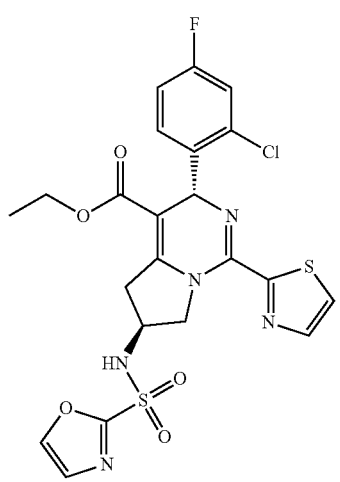 |

| 254 | 257 |
|---|---|
| 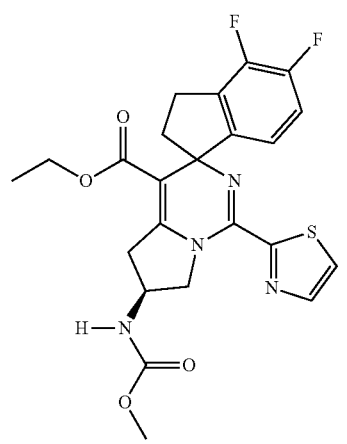 | 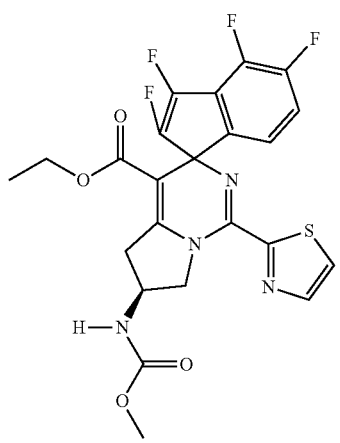 |
| 255 | 258 |
| 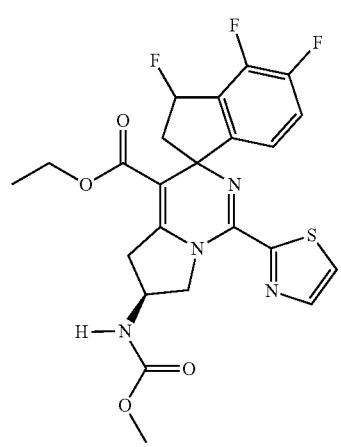 | 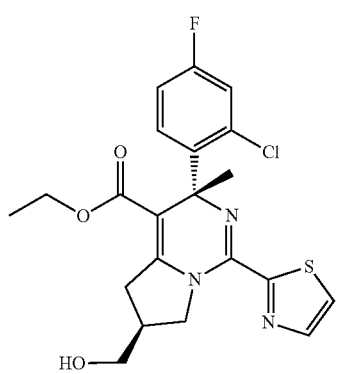 |
| 256 | 259 |
| 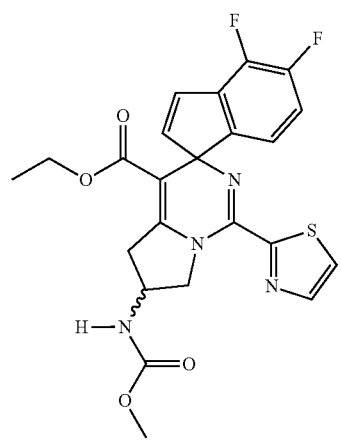 | 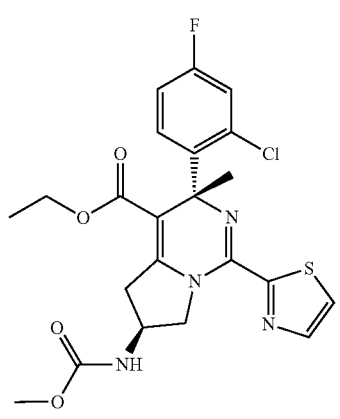 |

153
-continued
260
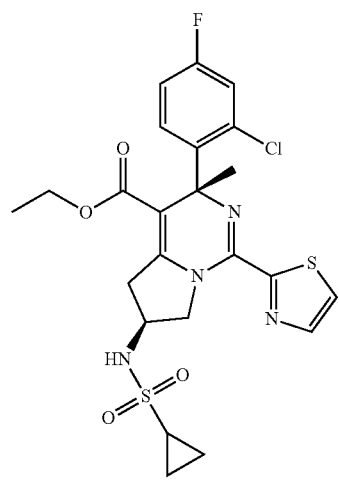
261
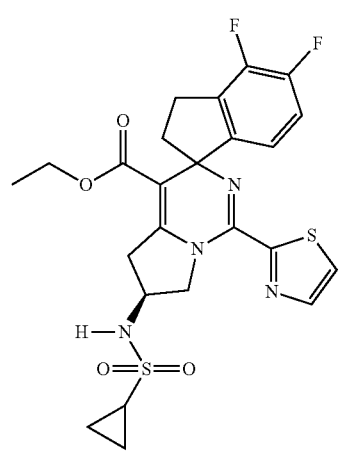
262
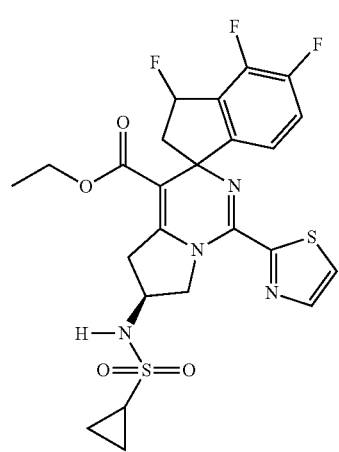
154
-continued
263
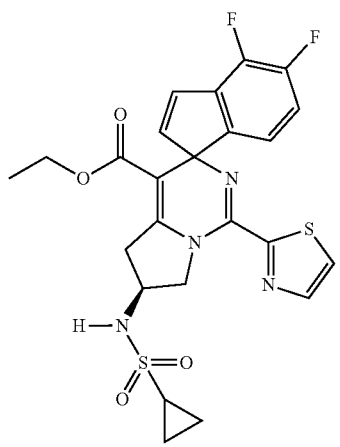
264
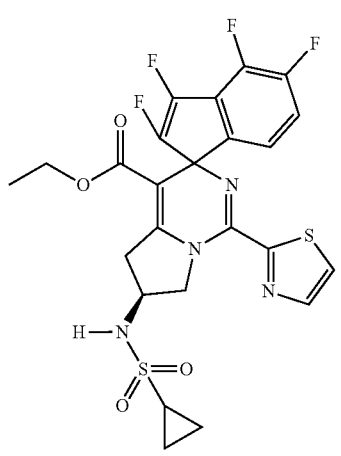
265
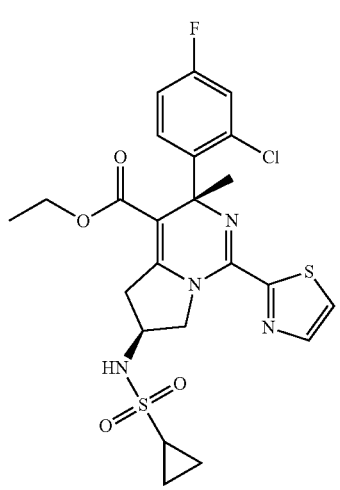

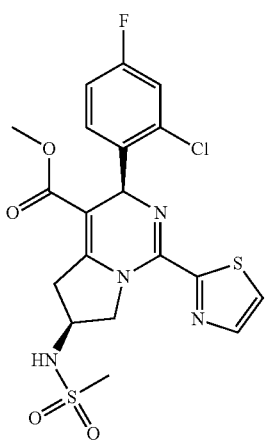

266

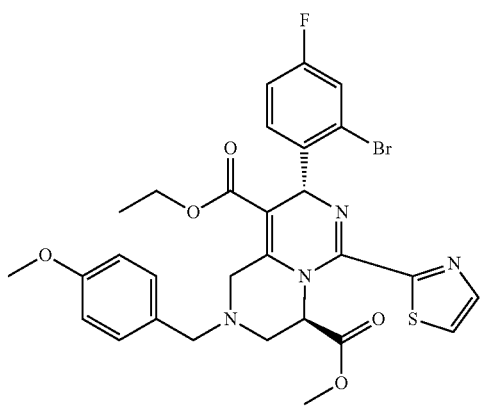

267

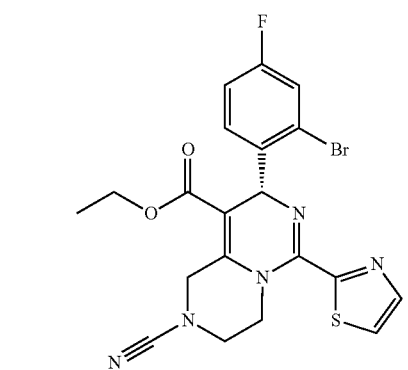

101a

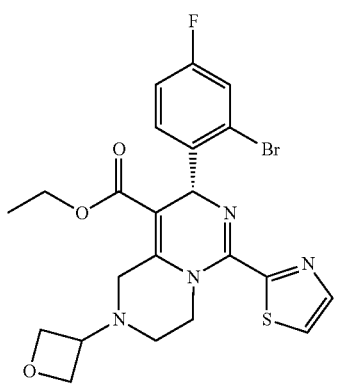

102a

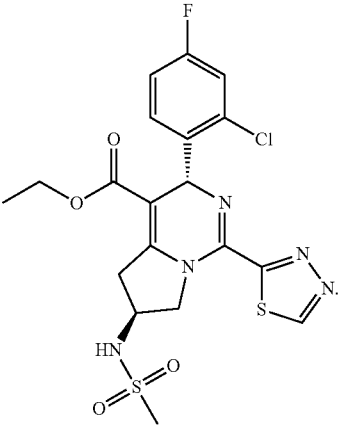

154a

Relevant Definition

Unless otherwise described, the following terms and phrases used herein are intended to have the following meanings. A specific term or phrase without being specifically defined should be understood by the plain meaning thereof rather than being regarded as uncertain or unclear. A brand name presented herein is intended to refer to a corresponding commercial product or the active component thereof.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

The $C_{1-12}$ alkyl or heteroalkyl, $C_{3-12}$ cyclic group or heterocyclic hydrocarbon group, $C_{1-12}$ alkyl or heteroalkyl substituted by a $C_{3-12}$ cyclic hydrocarbon group or heterocyclic hydrocarbon group includes but is not limited to:

$C_{1-12}$ alkyl, $C_{1-12}$ alkylamino, N,N-di($C_{1-12}$ alkyl)amino, $C_{1-12}$ alkoxy, $C_{1-12}$ alkylacyl, $C_{1-12}$ alkoxycarbonyl, $C_{1-12}$ alkylsulfonyl, $C_{1-12}$ alkylsulfinyl, $C_{3-12}$ cycloalkyl, $C_{3-12}$ cycloalkylamino, $C_{3-12}$ heterocycloalkylamino, $C_{3-12}$ cycloalkoxy, $C_{3-12}$ cycloalkylacyl, $C_{3-12}$ cycloalkoxycarbonyl, $C_{3-12}$ cycloalkylsulfonyl, $C_{3-12}$ cycloalkylsulfinyl, 5-12 membered aryl or heteraryl, 5-12 membered arylalkyl or heterarylalkyl;

methyl, ethyl, n-propyl, isopropyl, —CH$_2$C(CH$_3$)(CH$_3$)(OH), cyclopropyl, cyclobutyl, propylmethylene, cyclopropionyl, benzoxy, trifluoromethyl, aminomethyl, hydroxymethyl, methoxy, formyl, methoxycarbonyl, methylsulfonyl, methylsulfinyl, ethoxy, acetyl, ethylsulfonyl, ethoxycarbonyl, dimethylamino, diethylamino, dimethylaminocarbonyl, diethylaminocarbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN, —CH$_2$CH(OH)(CH$_3$)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$; and phenyl, thiazolyl, biphenyl, naphthyl, cyclopentyl, furyl, 3-pyrrolinyl, pyrrolidinyl, 1,3-dioxolanyl, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridyl, piperidyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothienyl, indolyl, benzimidazolyl, benzothiazolyl, purinyl, quinolyl, isoquinolyl, cinnolinyl or quinoxalinyl;

The term "pharmaceutically acceptable" as used herein is directed to those compounds, materials, compositions and/or formulations which are within the scope of reliable medical judgment, suitable for use in contact with human and animal tissues but without too much toxicity, irritation, allergic reactions or other problems or complications, and also commensurate with a reasonable benefit/risk ratio.

The term "pharmaceutically acceptable salt" refers to a salt of the compound of the invention which is prepared from the compound with specific substituents discovered by the invention and a relatively non-toxic acid or alkali. When the compound of the present invention contains a relatively acidic functional group, an alkali-addition salt can be obtained by contacting the compound in a neutral form with a sufficient amount of alkali in a pure solution or suitable inert solvent. The pharmaceutically acceptable alkali-addition salt includes the salt of sodium, potassium, calcium, ammonium, organic ammine or magnesium or the like. When the compound of the present invention contains a relatively alkaline functional group, an acid-addition salt can be obtained by contacting the compound in a neutral form with a sufficient amount of acid in a pure solution or suitable inert solvent. Examples of the pharmaceutically acceptable acid-addition salt include a salt of an inorganic acid, where the inorganic acid includes such as hydrochloric acid, hydrobromic acid, nitric acid, carbonic acid, bicarbonate, phosphoric acid, hydrogen phosphate, dihydrogen phosphate, sulfuric acid, bisulfate, hydriodic acid, phosphorous acid etc; and a salt of an organic acid, where the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes a salt of an amino acid (e.g. arginine etc.), and salts of organic acids such as glucuronic acid and the like (see Berge et al., "Pharmaceutical Salts," Journal of Pharmaceutical Science 66: 1-19 (1977)). Some specific compounds of the present invention contain both alkaline and acidic functional groups and thereby may be transformed to any of the alkali-addition or acid-addition salt.

Preferably, the neutral form of the compound is regenerated by contacting the salt with a base or an acid in a conventional manner and then separating the parent compound. The difference between the parent form of the compound and the various salt forms thereof lies in certain physical properties, such as solubility in a polar solvent.

The "pharmaceutically acceptable salt" used herein belongs to the derivatives of the compound of the present invention, wherein the parent compound is modified by salifying with an acid or an alkali. Examples of the pharmaceutically acceptable salt include but are not limited to: an inorganic acid or organic acid salt of an alkali such as amine, alkali metal or an organic salt of an acid radical such as carboxylic acid and so on. The pharmaceutically acceptable salt includes conventional non-toxic salts or quaternary ammonium salts of the parent compound, such as a salt formed by a non-toxic inorganic acid or organic acid.

The conventional non-toxic salt includes but is not limited to those salts derived from an inorganic acid and an organic acid, the inorganic acid or organic acid is selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinic acid, succinic acid, aminosulfonic acid, p-aminobenzenesulfonic acid, sulphuric acid, tannic acid, tartaric acid and p-toluene sulfonic acid.

The pharmaceutically acceptable salt of the present invention can be prepared by a conventional chemical method with a parent compound containing an acidic or alkaline group. Generally, the preparation method of such salts comprises in water or an organic solvent or a mixture of both, reacting these compounds which are in the form of free acids or alkalis with a stoichiometric amount of proper alkalis or acids. In general, a non-aqueous media such as ether, ethyl acetate, ethanol, isopropanol or acetonitrile and so on is preferred.

In addition to the salt form, the compound provided in the present invention also presents in a prodrug form. The prodrug of the compound described herein easily undergoes chemical changes under physiological conditions and thereby transforms to the compound of the present invention. Besides, the prodrug can be transformed to the compound of the present invention via chemical or biochemical method in vivo environment.

Certain compounds of the present invention may be present in a non-solvate or solvate form, including a hydrate form. In general, the solvate form is similar to the non-solvate form, both of which are included within the scope of the present invention. Some compounds of the present invention may exist in polycrystalline or amorphous form.

Some compounds of the present invention may contain an asymmetric carbon atom (optical center) or double bond. The racemic isomers, diastereomers, geometric isomers and single isomers are all included within the scope of the present invention.

The diagrammatic representations of the racemic isomer, the ambiscalemic and scalemic or the enantiopure compound herein are from Maehr, J. Chem. Ed. 1985, 62: 114-120. 1985, 62: 114-120. Unless otherwise indicated, the absolute configuration of a stereocenter is represented by wedge and dashed lines. When the compound described herein contains an olefinic double bond or other geometric asymmetric center, unless otherwise specified, E, Z geometric isomers are included. Similarly, all tautomeric forms are all included within the scope of the present invention.

The compound of the present invention may exist as a specific geometric or stereoisomeric isomer. The present invention is envisaged that all of this class of compounds, including cis- and trans-isomers, (−)- and (+)-enantiomers, (R)- and (S)-enantiomers, diastereomers, (D)-isomer, (L)-isomer, as well as racemic mixtures and other mixtures, such as enantiomers- or diastereoisomers-enriched mixtures, and all of these mixtures are within the scope of the present invention. Other asymmetric carbon atoms may exist in substituents such as an alkyl. All of these isomers and their mixtures are included within the scope of the present invention.

Optically active (R)- and (S)-isomers, and also (D)- and (L)-isomers can be prepared by asymmetric synthesis or chiral reagents or other conventional techniques. If desired, an enantiomer of a compound of the present invention may be prepared by asymmetric synthesis or derivatization action of chiral auxiliaries, in which the resultant diastereomer mixtures are isolated, and the auxiliary groups are cleaved to provide the pure desired enantiomer. Or, when a molecule contains an alkaline functional group (such as an amino) or an acidic functional group (such as a carboxyl), a diastereomeric salt is formed with an appropriate optical active acid or alkali, followed by diastereoisomeric resolution by fractional crystallization or chromatography method known in the art and subsequent recovery to obtain the pure enantiomer. In addition, the separation of an enantiomer and a diastereomer is usually accomplished by chromatography, where the chromatography employs a chiral stationary phase, optionally in combination with chemical derivatization method (e.g. generating a carbamate from an amine).

One or more atoms constituting the compound of the present invention may comprise an unnatural proportion of atomic isotopes. For example, the compound can be labeled by a radioactive isotope, such as tritium ($^3H$), iodine-125 ($^{125}I$) or C-14 ($^{14}C$). All the variations in the isotopic composition of the compound of the present invention, whether radioactive or not, are included within the scope of the present invention.

The term "a pharmaceutically acceptable carrier" refers to any formulation or carrier medium which is capable of delivering effective amount of the active substance of the present invention, without interfering with the biological activity of the active substance and without any toxic side-effects on a host or patient, and typical carrier medium includes water, oil, vegetables and minerals, cream base, lotion matrix, ointment matrix etc. These matrixes comprise a suspending agent, a viscosity increaser, a transdermal enhancer etc. Their formulations are well known to a person in cosmetic or topical drug art. Other information about the carrier can refer to Remington: The Science and Practice of Pharmacy, 21st Ed., Lippincott, Williams & Wilkins (2005), the content of which is incorporated herein by reference.

The term "excipient" usually refers to a carrier, diluent and/or medium required for preparing an effective pharmaceutical composition.

In terms of drug or pharmacological active agent, the term "effective amount" or "therapeutically effective amount" refers to a quantity of a drug or formulation sufficient to achieve desired effects without toxicity. For the oral formulation of the present invention, "an effective amount" of one active substance in the composition refers to the amount required to achieve desired effects in combination with another active substance in the composition. The determination of the effective amount varies from person to person, and depends on the age and the general condition of a recipient, also on the specific active substance. In an individual case, an appropriate effective amount can be determined by a person skilled in the art according to conventional tests.

The term "active ingredient," "therapeutic agent," "active substance" or "active agent" refers to a chemical entity, which can effectively treat a disorder, illness or disease of a target subject.

The term "substituted" refers to any one or more hydrogen atoms on a specific atom being optionally replaced by a substituent, including a deuterium and a variant of hydrogen, as long as the valence state of the specific atom is normal and the substituted compound is stable. When the substituent is a keto group (i.e. =O), it means that two hydrogen atoms are replaced. A substitution of keto group will not occur on an aryl. The term "optionally substituted" means that it may be substituted or not be substituted, unless otherwise specified, the type and number of substituents can be arbitrary under the premise of being chemically feasible.

When any parameter (e.g. R) occurs more than once in the composition or structure of the compound, its definition at each occurrence is independent. Therefore, for example, if a group is substituted by 0-2 of R, the group may optionally be substituted by at most two Rs, and R has an independent option at each occurrence. In addition, a combination of substituents and/or their variants is allowed only if such a combination will lead to a stable compound.

When a bond of a substituent can be crossly connected to two atoms of a ring, the substituent can be bonded to any atom of the ring. When the listed substituent is not specified through which atom it is connected to a general structural formula including the compound that is not specifically mentioned, the substituent can be bonded through any of its atoms. A combination of substituents and/or their variants is allowed only if such a combination will lead to a stable compound. For example, a structural unit

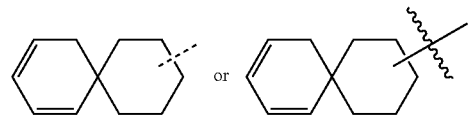

or represents that substitution may occur on any position of the cyclohexyl or cyclohexadiene.

The substituent of alkyl and heteroalkyl group is generally referred to as "alkyl substituent," which can be selected from, but not limited to, the group consisting of —R', —OR', =O, =NR', =N—OR', —NR'R", —SR', halogen, —SiR'R"R''', OC(O)R', —C(O)R', —CO$_2$R', —C(=O)NR'R", —OC(O)NR'R", —NR"C(O)R', NR'C(O)NR"R''', —NR"C(O)$_2$R', —NR''''—C(NR'R"R''')=NR'''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, and the number of the substituent is between 0 and (2m'+1), wherein m' is the total number of carbon atoms in the group. Each of R', R", R''', R'''' and R''''' is preferably and independently selected from H, substituted or unsubstituted heteroalkyl, substituted or unsubstituted aryl (e.g. an aryl substituted by 1-3 of halogen(s)), substituted or unsubstituted alkyl, alkoxy, thioalkoxy or arylalkyl. When the compound of the present invention includes more than one R groups, for example, each of the R groups is independently selected, as if each of R', R", R''', R'''' and R''''' groups is when it occurs more than once. When R' and R" are attached to the same nitrogen atom, they can form a 5-, 6-, or 7-membered ring together with the nitrogen atom. For example, —NR'R" is intended to include but not limited to 1-pyrrolidinyl and 4-morpholinyl. According to the above discussion on substituents, a person skilled in the art can understand that the term "alkyl" is intended to include a group formed by bonding a carbon atom to a non-hydrogen group, such as a haloalkyl (e.g. —CF$_3$, —CH$_2$CF$_3$) and an acyl (e.g. —C(O)CH$_3$, —C(O)CF$_3$, —C(O)CH$_2$OCH$_3$, etc.).

Similar to the substituent of the alkyl group, the substituent of aryl and heteroaryl group is generally referred to as "aryl substituent," selected from such as —R', —OR', —NR'R", —SR', -halogen, —SiR'R"R''', OC(O)R', —C(O)R', —CO$_2$R', —CONR'R", —OC(O)NR'R", —NR"C(O)R', NR'C(O)NR"R''', —NR"C(O)$_2$R', —NR''''—C(NR'R"R''') =NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$) alkoxy and fluoro(C$_1$-C$_4$)alkyl, etc., and the number of the substituent ranges from 0 to the total opening valence of the aromatic ring; wherein R', R", R'", R"" and R""' are independently and preferably selected from H, substituted or unsubstituted alkyl, substituted or unsubstituted heteroalkyl, substituted or unsubstituted aryl and substituted or unsubstituted heteroaryl. When the compound of the present invention includes more than one R groups, for example, each of the R groups is independently selected, as if each of R', R", R'", R"" and R""' groups is when it occurs more than once.

Two substituents attached to adjacent atoms of an aryl or heteroaryl ring can optionally be substituted by a substituent with a general formula of -T-C(O)—(CRR')q-U—, wherein T and U are independently selected from —NR—, —O—, CRR'— or a single bond, q is an integer from 0 to 3. As an alternative, two substituents attached to adjacent atoms of an aryl or heteroaryl ring can optionally be substituted by a substituent with a general formula of -A(CH$_2$)rB—, wherein the A and B are independently selected from —CRR'—, —O—, —NR—, —S—, —S(O)—, S(O)$_2$—, —S(O)$_2$NR'— or a single bond, r is an integer from 1 to 4. Optionally, a single bond of the new ring thus formed can be replaced by a double bond. As an alternative, two substituents attached to adjacent atoms of an aryl or heteroaryl ring can optionally be substituted by a substituent with a general formula of -A(CH$_2$)$_s$X(CH$_2$)$_d$B—, wherein s and d are separately and independently selected from an integer from 0 to 3, X is —O—, —NR', —S—, —S(O)—, —S(O)$_2$— or —S(O)$_2$NR'—. The substituents R, R', R" and R'" are separately, independently and preferably selected from hydrogen and substituted or unsubstituted (C$_1$-C$_6$) alkyl.

Unless otherwise specified, the term "halo" or "halogen" itself or as a part of another substituent refers to a fluorine, chlorine, bromine or iodine atom. In addition, the term "haloalkyl" is intended to include monohaloalkyl and polyhaloalkyl. For example, the term "halo(C$_1$-C$_4$)alkyl" is intended to include but not limited to trifluoromethyl, 2, 2, 2-trifluoroethyl, 4-chlorobutyl and 3-bromopropyl, etc.

Examples of haloalkyl include but are not limited to: trifluoromethyl, trichloromethyl, pentafluoroethyl, and pentachloroethyl. The "alkoxy" represents an alkyl group as described above with a specific number of carbon atoms which is connected by an oxygen bridge. The C$_{1-6}$ alkoxy includes C$_1$, C$_2$, C$_3$, C$_4$, C$_5$ and C$_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3-7 cycloalkyl includes C$_3$, C$_4$, C$_5$, C$_6$ and C$_7$ cycloalkyl. The "alkenyl" includes linear or branched hydrocarbon chain, wherein one or more than one C—C double bond presents at any stable position on the chain, such as a vinyl and a propenyl.

The term "halo" or "halogen" refers to fluorine, chlorine, bromine and iodine.

Unless otherwise specified, the term "hetero" refers to a heteroatom or a heteroatom group (i.e. a group containing a heteroatom), including atoms other than carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a joint ring, a spiro ring, a fused ring or a bridged ring. A number of the atoms on the ring is usually defined as the member of the ring, for example, "5- to 7-membered ring" refers to a ring looped with 5 to 7 atoms. Unless otherwise specified, the ring optionally contains 1-3 of heteroatoms. Therefore, "5- to 7-membered ring" includes, for example, phenyl, pyridine and piperidinyl; on the other hand, the term "5- to 7-membered heterocycloalkyl" includes pyridyl and piperidinyl, but does not include phenyl. The term "ring" also includes a ring system containing at least one ring, wherein each of the "rings" is independently in line with the above definition.

Unless otherwise specified, the term "heterocycle" or "heterocyclyl" refers to a stable monocyclic, bicyclic or tricyclic group containing a heteroatom or heteroatom group, which can be saturated, partially unsaturated or unsaturated (aromatic), and contains carbon atoms and 1, 2, 3 or 4 ring heteroatom(s) independently selected from the group consisting of N, O and S, wherein any of the above heterocycle can be fused to a benzene ring to form a bicyclic ring. Nitrogen and sulfur heteroatoms can be optionally oxidized (i.e., NO and S(O)$_p$). The nitrogen atom can be substituted or unsubstituted (i.e. N or NR, wherein R is H or other substituent defined herein). The heterocycle can be attached to a side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment, when the total number of S and O atoms contained in the heterocycle exceeds 1, these heteroatoms are not adjacent to each other. As another preferred embodiment, the total number of S and O atoms in the heterocycle is no more than 1. As used herein, the term "aromatic heterocyclyl" or "heteroaryl" refers to a stable aromatic ring of a 5-, 6-, 7-membered monocyclic or bicyclic or 7-, 8-, 9- or 10-membered bicyclic heterocyclyl, which contains carbon atoms and 1, 2, 3 or 4 ring heteroatoms independently selected from the group consisting of N, O and S. The nitrogen atom can be substituted or unsubstituted (i.e. N or NR, wherein R is H or other substituent defined herein). Nitrogen and sulfur heteroatoms can be optionally oxidized (i.e., NO and S(O)$_p$). It is worth noting that the total number of S and O atoms on the heteroaromatic ring is no more than 1. Bridge rings are also included in the definition of the heterocycle. When one or more than one atoms (i.e. C, O, N, or S) are connected to two nonadjacent carbon atoms or nitrogen atoms, a bridged ring is formed. The preferred bridge ring includes but is not limited to: one carbon atom, two carbon atoms, one nitrogen atom, two nitrogen atoms and one carbon-nitrogen group. It is worth noting that a bridge always converts a monocyclic ring into a tricyclic ring. In the bridge ring, the substituent on the ring can also locate on the bridge.

Examples of heterocyclic compound include but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, isoindolyl, isoindolinyl isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyl indyl, pyrimidyl, phenanthridinyl, phenanthrolinyl, phenazine, phenothiazine, benzoxanthinyl, phenoxazinyl, phthalazinyl, piperazinyl, piperidyl, piperidinonyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridoimidazole, pyridothiazole, pyridyl, pyrrolidinyl, pyrrolinyl, 2H-pyrrolyl, pyrrolyl, quinazolyl, quinolyl, 4H-quinolizinyl, quinoxalinyl, quinuclidinyl, tetrahydrofuryl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, triazinyl, 1,2,3-triazolyl, 1,2,4-triazolyl, 1,2,5-triazolyl, 1,3,4-triazolyl and xanthenyl. Fused and spiro cyclic compounds are also included.

Unless otherwise specified, the term "hydrocarbon group" or its specific concept (such as alkyl, alkenyl, alkynyl, phenyl, etc.) itself or as a part of another substituent represents a linear, branched or cyclic hydrocarbon group or a combination thereof, which can be fully saturated, mono- or poly-unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as $C_1$-$C_{10}$ representing 1 to 10 carbon atoms). The "hydrocarbon group" includes but is not limited to an aliphatic hydrocarbon group and aromatic hydrocarbon group, wherein the aliphatic hydrocarbon group includes linear and cyclic structures, specifically including but not limited to alkyl, alkenyl, alkynyl, and the aromatic hydrocarbon group includes but is not limited to 6- to 12-membered aromatic hydrocarbon group such as benzene, naphthalene and the like. In some embodiments, the term "alkyl" refers to a linear or branched group or their combination, which can be completely saturated, mono- or poly-unsaturated, can include divalent and polyvalent groups. Examples of saturated hydrocarbon group include but are not limited to a homologue or an isomer of a group such as methyl, ethyl, n-propyl, iso-propyl, n-butyl, tert-butyl, iso-butyl, sec-butyl, iso-butyl, cyclohexyl, (cyclohexyl)methyl, cyclopropylmethyl, and n-pentyl, n-hexyl, n-heptyl, n-octyl and the like. The unsaturated alkyl has one or more than one double or triple bond, examples of which include but are not limited to a vinyl, 2-propenyl, butenyl, crotyl, 2-isopentenyl, 2-butadienyl, 2,4-(pentadienyl), 3-(1,4-pentadienyl), acetenyl, 1- and 3-propynyl, 3-butynyl, and higher level homologues and isomers.

Unless otherwise specified, the term "heterohydrocarbon group" or its specific concepts (such as heteroalkyl, heteroalkenyl, heteroalkynyl, heteroaryl, etc.) itself or combined with another term refers to a stable linear, branched or cyclic hydrocarbon group or their combinations, which consists of a certain number of carbon atoms and at least one heteroatom. In some embodiments, the term "heteroalkyl" itself or combined with another term refers to a stable linear, branched hydrocarbon group or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. The heteroatom or heteroatom group can be located at any internal position of the heterohydrocarbon group (including the position where the hydrocarbon group is attached to the rest part of a molecule). Examples include but are not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$ and —CH═CH—N(CH$_3$)—CH$_3$. At most two heteroatoms may be consecutive, such as —CH$_2$—NH—OCH$_3$.

The terms "alkoxy," "alkylamino" and "alkylthio" (or thioalkoxy) belong to customary expressions, and refer to those alkyl groups which are attached to the rest of a molecule through an oxygen, an amino, or a sulfur atom, respectively.

Unless otherwise specified, the term "cyclohydrocarbon group," "heterocyclohydrocarbon group" or specific concepts thereof (such as aryl, heteroaryl, cycloalkyl, heterocycloalkyl, cycloalkenyl, heterocyclo alkenyl, cycloalkynyl, heterocycloalkynyl, etc.) itself or combined with other terms respectively refers to a cyclic "hydrocarbon group," "heterohydrocarbon group." In addition, in terms of heterohydrocarbon group or heterocyclohydrocarbon group (such as heteroalkyl, heterocycloalkyl), the heteroatoms can occupy the position where the heterocyclic ring is attached to the rest part of a molecule. Examples of the cycloalkyl include but are not limited to cyclopentyl, cyclohexyl, 1-cyclohexenyl, 3-cyclohexenyl, cycloheptyl etc.

Unrestricted examples of the heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent, and can be monocyclic or polycyclic (e.g., 1 to 3 rings, wherein at least one ring is aromatic). They are fused together or connected by a covalent linkage. The term "heteroaryl" refers to an aryl (or ring) containing 1 to 4 heteroatoms. In a typical embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of a molecule via a heteroatom. Unrestricted examples of the aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. A substituent of any one of the above aryl and heteroaryl ring system is selected from the acceptable substituents described herein.

For the sake of briefness, when used in combination with other terms (e.g. aryloxy, arylthio, arylalkyl), the aryl includes the aryl and heteroaryl ring as defined above. Therefore, the term "arylalkyl" is intended to include those groups in which an aryl is attached to an alkyl (e.g. benzyl, phenylethyl, pyridylmethyl, etc.), including those alkyls wherein a carbon atom (such as methylene) has been replaced by for example an oxygen atom, such as phenoxymethyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include: triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but is not limited to "amino protecting group," "hydroxy protecting group" or "mercapto protecting group". The term "amino protecting group" refers to a protecting group suitable for preventing side reactions occurring at the nitrogen position of an amino group. A representative amino protecting group includes but is not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzoxycarbonyl (Cbz) and 9-fluorenylmethoxycarbonyl (Fmoc); arylmethyl, such as benzyl (Bn), triphenylmethyl (Tr), 1,1-bis-(4'-methoxyphenyl)methyl; silyl, such as trimethylsilyl (TMS) and tert-butyldimethylsilyl (TBS), etc. The term "hydroxy protecting group" refers to a protecting group suitable for preventing side reactions of a hydroxy group. A representative hydroxy protecting group includes but is not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl; such as trimethylsilyl (TMS) and tert-butyldimethylsilyl (TBS), etc.

The compound of the present invention can be prepared through many synthetic methods well-known to a person skilled in the art, including the specific embodiments listed below and its combination with other chemical synthetic methods and equivalent alternatives known to a person skilled in the art, and the preferred embodiments include but are not limited to the examples of the present invention.

The solvents used in the invention may be commercially obtained.

The following abbreviations are used herein: aq represents water; HATU represents O-7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzoxycarbonyl, an amino protecting group; BOC represents tert-butoxycarbonyl, an amino protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluene sulfonic acid; NFSI represents N-fluorobenzenesulfonimide; NCS represents N-chlorosuccinimide; n-$Bu_4$NF represents tetrabutylammonium fluoride; iPrOH represents 2-propanol; NBS represents N-bromosuccinimide; AIBN represents 2,2'-azo bisisobutyronitrile; BTC represents triphosgene; mp represents melting point.

Compounds are named manually or by software ChemDraw®, and commercially available compounds are named according to catalogs of suppliers.

Target Compounds of Specific Examples and Conclusions of their Inhibitory Actions on HBV DNA:

Definition of bioactivity: A: $EC_{50} \leq 100$ nM; B: 100 nM<$EC_{50} \leq 500$ nM; C: 500 nM<$EC_{50} \leq 1000$ nM; D: 1000 nM<$EC_{50} \leq 5000$ nM;

Conclusion: the compound of the invention shows significantly inhibitory actions on HBV DNA.

A List of Target Compounds of Examples and their Inhibitory Actions on HBV DNA (Bioactivities the Same as Table 2)

| EXAMPLE | STRUCTURAL FORMULEA | STEREOCHEMISTRY | BIOACTIVITY |
|---|---|---|---|
| 1 | F | racemic | B |

-continued
| EXAMPLE | STRUCTURAL FORMULA | STEREOCHEMISTRY | BIOACTIVITY |
|---|---|---|---|
| 2 | 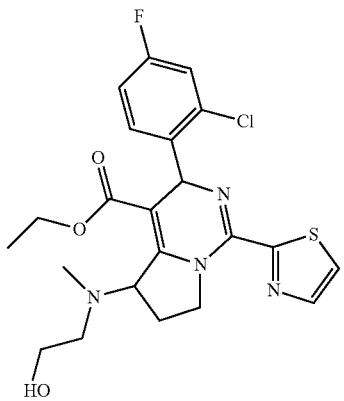 [SMILES: CCOC(=O)C1=C2C(N(C)CCO)CCN2C(c2nccs2)=NC1c1ccc(F)cc1Cl] | racemic | D |
| 3 | 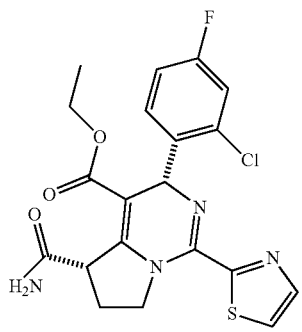 [SMILES: CCOC(=O)C1=C2[C@@H](C(N)=O)CCN2C(c2nccs2)=N[C@H]1c1ccc(F)cc1Cl] | cis-racemic | B |
| 4 | 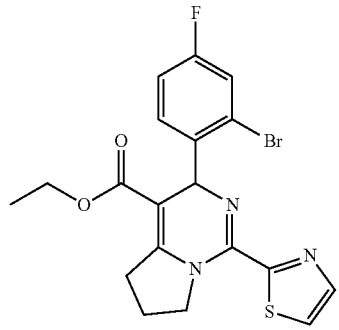 | racemic | B |
| 5 | 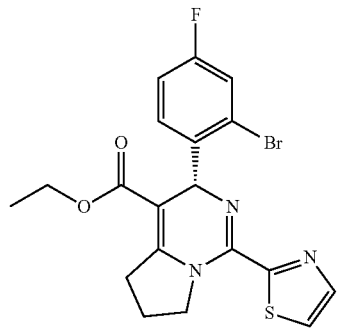 [SMILES: CCOC(=O)C1=C2CCCN2C(c2nccs2)=N[C@H]1c1ccc(F)cc1Br] | optically pure | B |

-continued
| EXAMPLE | STRUCTURAL FORMULA | STEREOCHEMISTRY | BIOACTIVITY |
|---|---|---|---|
| 6 | 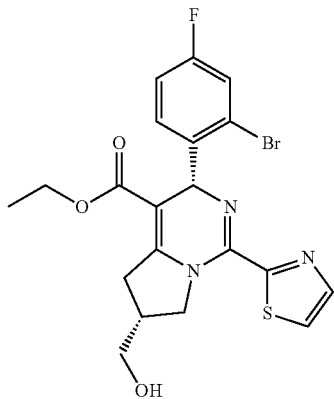 [SMILES: CCOC(=O)C1=C2C[C@@H](CO)CN2C(c2nccs2)=N[C@H]1c1ccc(F)cc1Br] | optically pure | A |
| 7 | 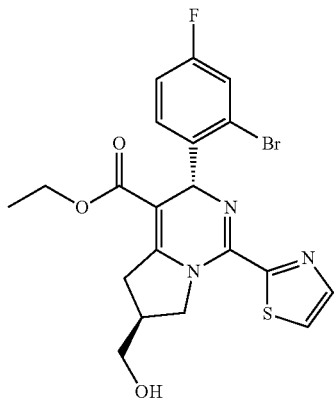 [SMILES: CCOC(=O)C1=C2C[C@H](CO)CN2C(c2nccs2)=N[C@H]1c1ccc(F)cc1Br] | optically pure | B |
| 8 | 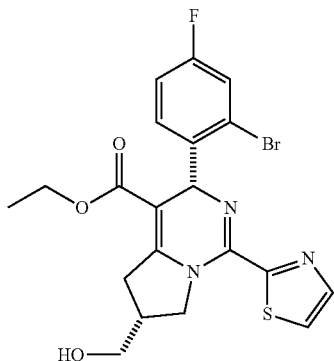 | cis-racemic | B |
| 9 | 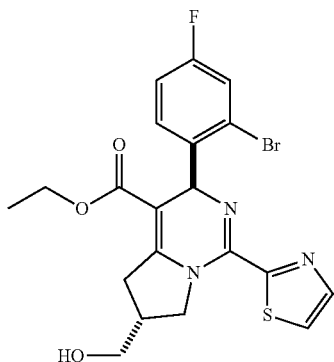 | trans-racemic | B |

| EXAMPLE | STRUCTURAL FORMULEA | STEREOCHEMISTRY | BIOACTIVITY |
| --- | --- | --- | --- |
| 10 | 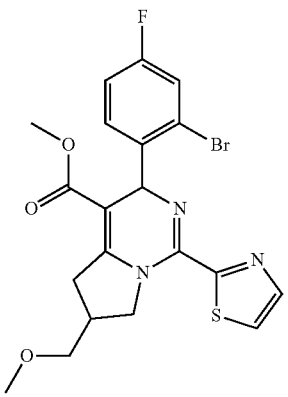 [SMILES: COCC1CC2=C(C(=O)OC)C(c3ccc(F)cc3Br)N=C(c3nccs3)N2C1] | racemic | D |
| 11 | 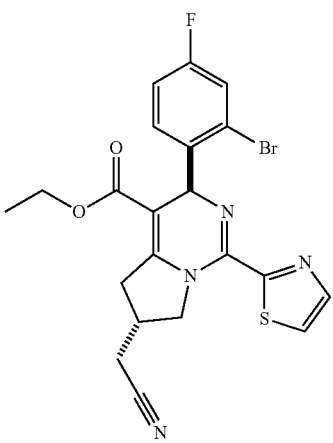 | trans-racemic | D |
| 12 | 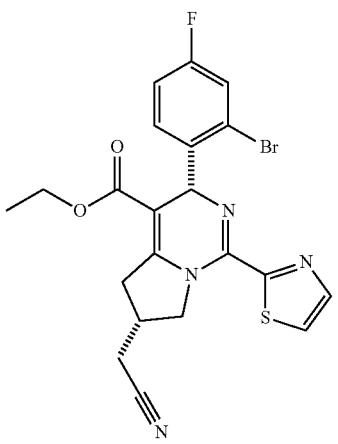 | cis-racemic | B |

-continued
| EXAMPLE | STRUCTURAL FORMULEA | STEREOCHEMISTRY | BIOACTIVITY |
|---|---|---|---|
| 13 | 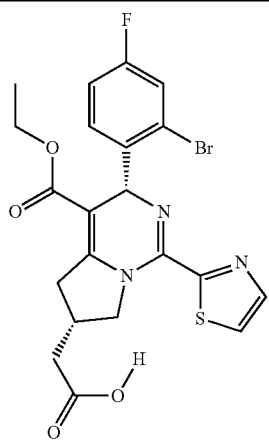 | optically pure | B |
| 14 | 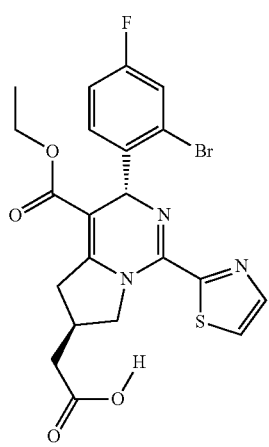 [SMILES: CCOC(=O)C1=C2C[C@H](CC(=O)O)CN2C(c2nccs2)=N[C@H]1c1ccc(F)cc1Br] | optically pure | C |
| 15 | 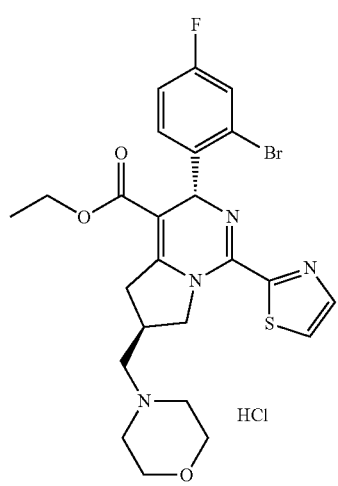 [SMILES: CCOC(=O)C1=C2C[C@H](CN3CCOCC3)CN2C(c2nccs2)=N[C@H]1c1ccc(F)cc1Br ; Cl] | optically pure | B |

-continued
| EXAMPLE | STRUCTURAL FORMULEA | STEREOCHEMISTRY | BIOACTIVITY |
| --- | --- | --- | --- |
| 16 | 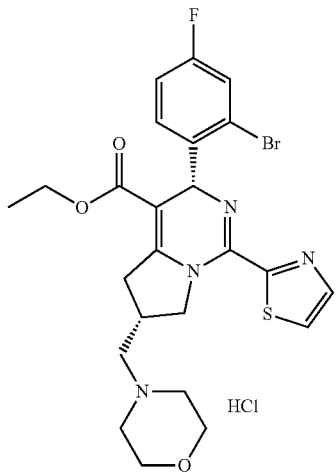 [SMILES: CCOC(=O)C1=C2C[C@@H](CN3CCOCC3)CN2C(c2nccs2)=N[C@H]1c1ccc(F)cc1Br ; Cl] HCl | optically pure | D |
| 17 | 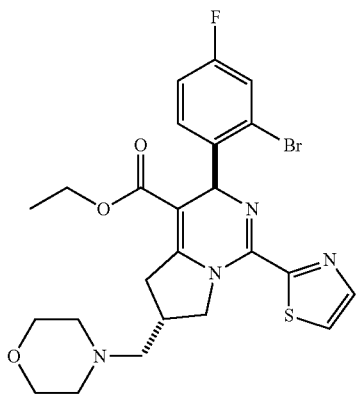 | trans-racemic | D |
| 18 | 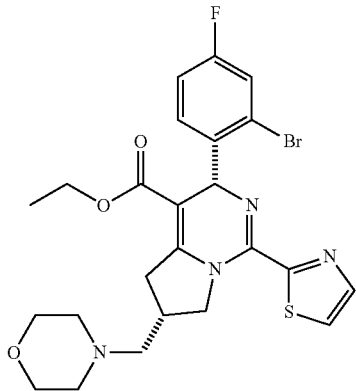 | cis-racemic | D |

-continued
| EXAMPLE | STRUCTURAL FORMULEA | STEREOCHEMISTRY | BIOACTIVITY |
|---|---|---|---|
| 19 | 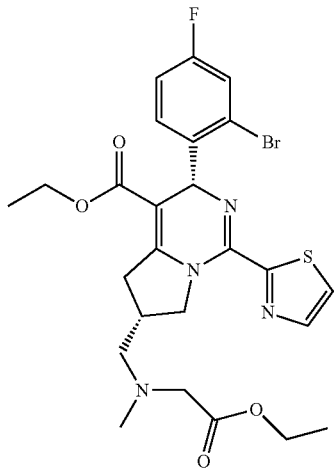 [SMILES: CCOC(=O)CN(C)C[C@@H]1CC2=C(C(=O)OCC)[C@H](c3ccc(F)cc3Br)N=C(c3nccs3)N2C1] | optically pure | D |
| 20 | 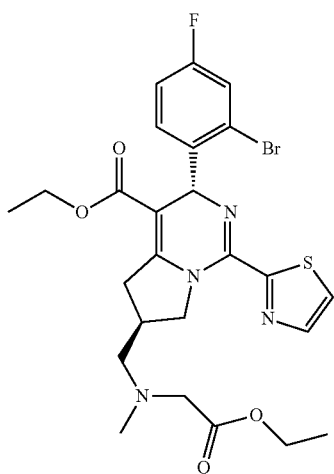 [SMILES: CCOC(=O)CN(C)C[C@H]1CC2=C(C(=O)OCC)[C@H](c3ccc(F)cc3Br)N=C(c3nccs3)N2C1] | optically pure | D |
| 21 | 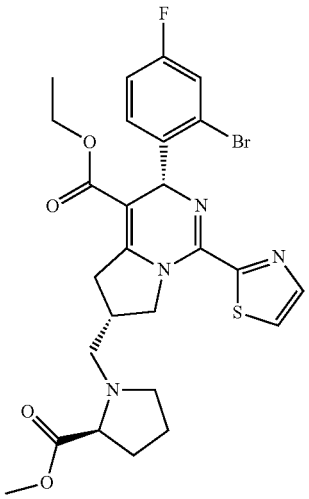 [SMILES: CCOC(=O)C1=C2C[C@@H](CN3CCC[C@H]3C(=O)OC)CN2C(c2nccs2)=N[C@H]1c1ccc(F)cc1Br] | optically pure | D |

-continued
| EXAMPLE | STRUCTURAL FORMULEA | STEREOCHEMISTRY | BIOACTIVITY |
|---|---|---|---|
| 22 | 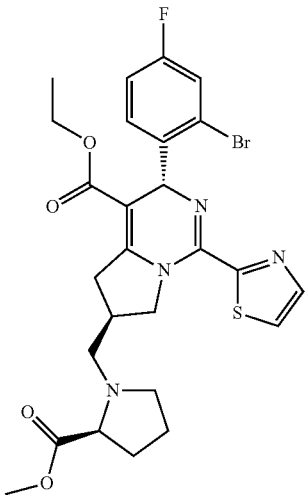 [SMILES: CCOC(=O)C1=C2C[C@H](CN3CCC[C@H]3C(=O)OC)CN2C(c2nccs2)=N[C@H]1c1ccc(F)cc1Br] | optically pure | D |
| 23 | 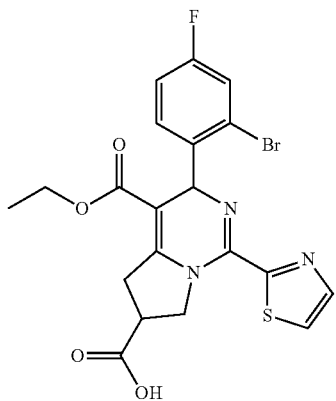 [SMILES: CCOC(=O)C1=C2CC(C(=O)O)CN2C(c2nccs2)=NC1c1ccc(F)cc1Br] | racemic | D |
| 24 | 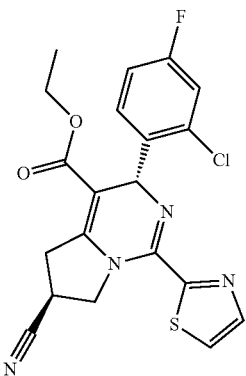 [SMILES: CCOC(=O)C1=C2C[C@H](C#N)CN2C(c2nccs2)=N[C@H]1c1ccc(F)cc1Cl] | optically pure | C |

-continued

| EXAMPLE | STRUCTURAL FORMULEA | STEREOCHEMISTRY | BIOACTIVITY |
|---|---|---|---|
| 25 | | optically pure | D |
| 26 | | trans-racemic | C |
| 27 | | cis-racemic | B |
| 28 | | trans-racemic | B |

| EXAMPLE | STRUCTURAL FORMULA | STEREOCHEMISTRY | BIOACTIVITY |
|---|---|---|---|
| 29 | 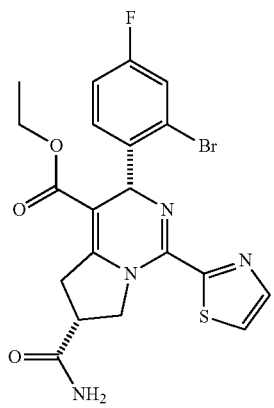 | cis-racemic | B |
| 30 | 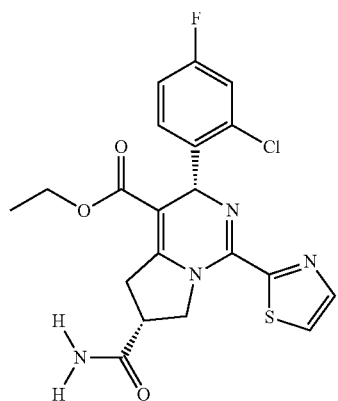 [SMILES: CCOC(=O)C1=C2C[C@@H](C(N)=O)CN2C(c2nccs2)=N[C@H]1c1ccc(F)cc1Cl] | optically pure | B |
| 31 | 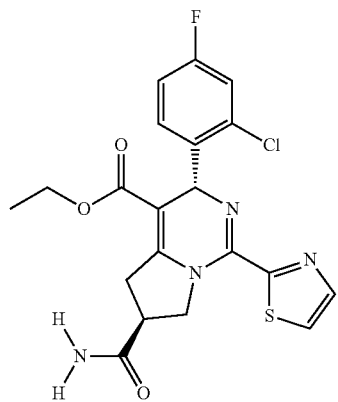 [SMILES: CCOC(=O)C1=C2C[C@H](C(N)=O)CN2C(c2nccs2)=N[C@H]1c1ccc(F)cc1Cl] | optically pure | B |

-continued

| EXAMPLE | STRUCTURAL FORMULEA | STEREOCHEMISTRY | BIOACTIVITY |
|---|---|---|---|
| 32 | | optically pure | D |
| 33 | | optically pure | D |
| 34 | | optically pure | B |
| 35 | | optically pure | D |

-continued
| EXAMPLE | STRUCTURAL FORMULEA | STEREOCHEMISTRY | BIOACTIVITY |
|---|---|---|---|
| 36 | 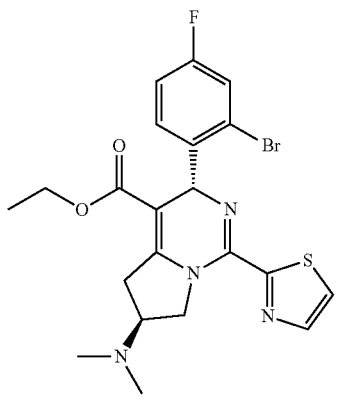 [SMILES: CCOC(=O)C1=C2C[C@H](N(C)C)CN2C(c2nccs2)=N[C@H]1c1ccc(F)cc1Br] | optically pure | C |
| 37 | 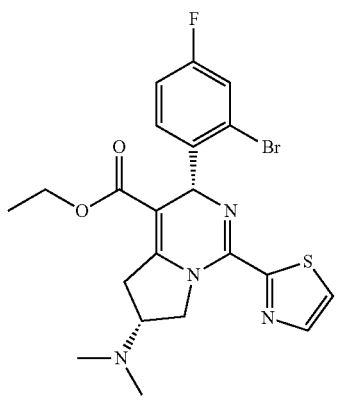 [SMILES: CCOC(=O)C1=C2C[C@@H](N(C)C)CN2C(c2nccs2)=N[C@H]1c1ccc(F)cc1Br] | optically pure | D |
| 38 | 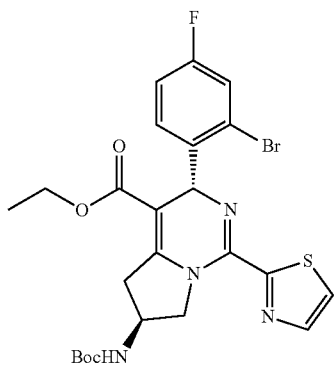 [SMILES: CCOC(=O)C1=C2C[C@H](NC(=O)OC(C)(C)C)CN2C(c2nccs2)=N[C@H]1c1ccc(F)cc1Br] | optically pure | A |
| 39 | 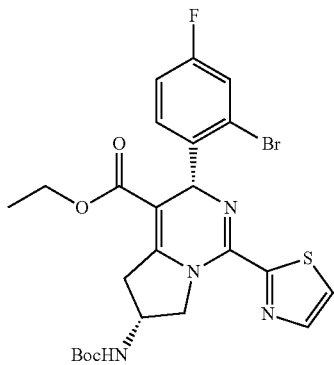 [SMILES: CCOC(=O)C1=C2C[C@@H](NC(=O)OC(C)(C)C)CN2C(c2nccs2)=N[C@H]1c1ccc(F)cc1Br] | optically pure | A |

-continued
| EXAMPLE | STRUCTURAL FORMULEA | STEREOCHEMISTRY | BIOACTIVITY |
| --- | --- | --- | --- |
| 40 | 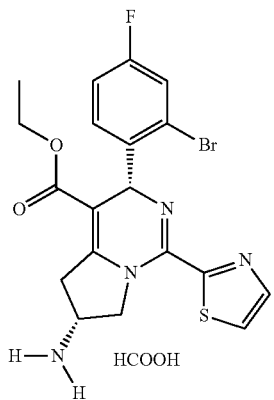 [SMILES: CCOC(=O)C1=C2C[C@@H](N)CN2C(c2nccs2)=N[C@H]1c1ccc(F)cc1Br ; "HCOOH"] HCOOH | optically pure | D |
| 41 | 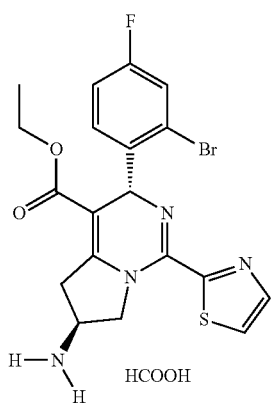 [SMILES: CCOC(=O)C1=C2C[C@H](N)CN2C(c2nccs2)=N[C@H]1c1ccc(F)cc1Br ; "HCOOH"] HCOOH | optically pure | D |
| 42 | 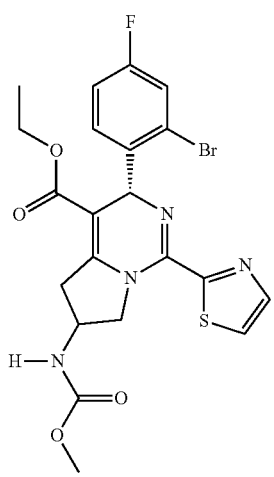 | racemic | A |

-continued
| EXAMPLE | STRUCTURAL FORMULEA | STEREOCHEMISTRY | BIOACTIVITY |
|---|---|---|---|
| 43 | 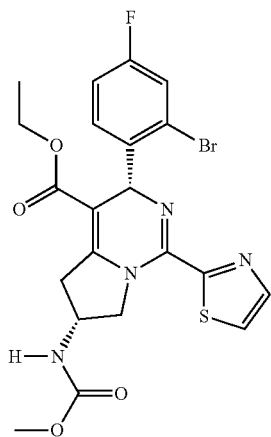 [SMILES: CCOC(=O)C1=C2C[C@@H](NC(=O)OC)CN2C(c2nccs2)=N[C@H]1c1ccc(F)cc1Br] | optically pure | B |
| 44 | 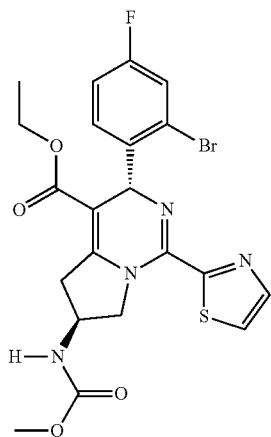 [SMILES: CCOC(=O)C1=C2C[C@H](NC(=O)OC)CN2C(c2nccs2)=N[C@H]1c1ccc(F)cc1Br] | optically pure | A |
| 45 | 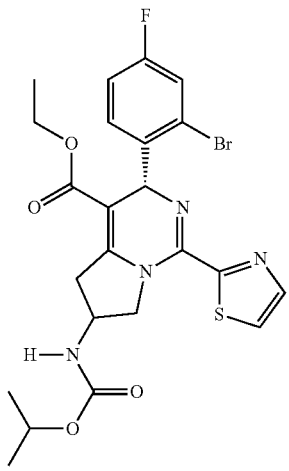 [SMILES: CCOC(=O)C1=C2CC(NC(=O)OC(C)C)CN2C(c2nccs2)=N[C@H]1c1ccc(F)cc1Br] | racemic | A |

-continued
| EXAMPLE | STRUCTURAL FORMULEA | STEREOCHEMISTRY | BIOACTIVITY |
|---|---|---|---|
| 46 | 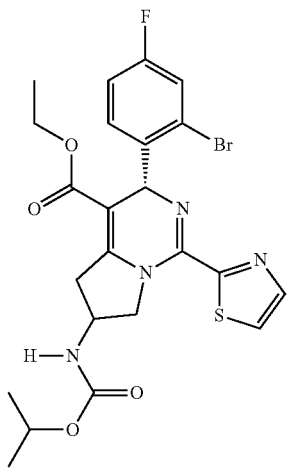 [SMILES: CCOC(=O)C1=C2CC(NC(=O)OC(C)C)CN2C(c2nccs2)=N[C@H]1c1ccc(F)cc1Br] | optically pure | B |
| 47 | 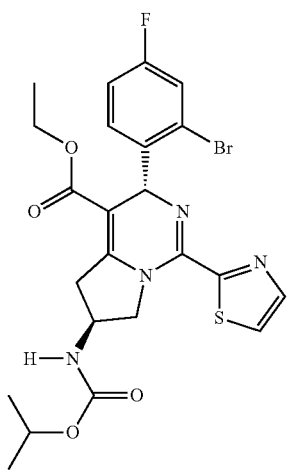 [SMILES: CCOC(=O)C1=C2C[C@H](NC(=O)OC(C)C)CN2C(c2nccs2)=N[C@H]1c1ccc(F)cc1Br] | optically pure | A |
| 48 | 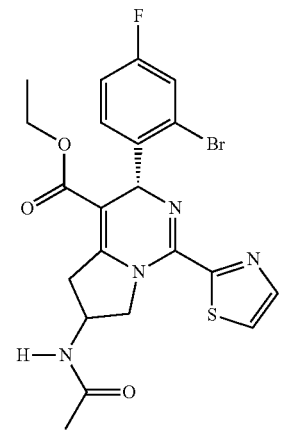 | racemic | B |

-continued
| EXAMPLE | STRUCTURAL FORMULEA | STEREOCHEMISTRY | BIOACTIVITY |
|---|---|---|---|
| 49 | 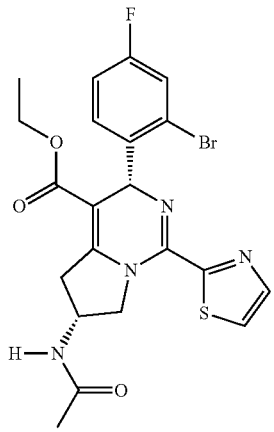 | optically pure | B |
| 50 | 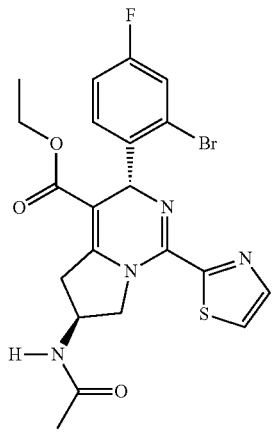 [SMILES: CCOC(=O)C1=C2C[C@H](NC(C)=O)CN2C(c2nccs2)=N[C@H]1c1ccc(F)cc1Br] | optically pure | D |
| 51 | 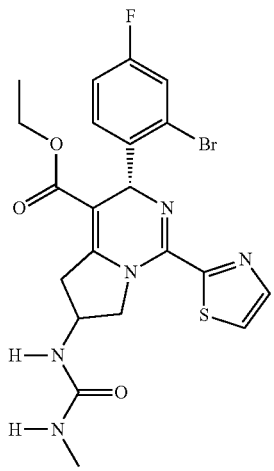 [SMILES: CCOC(=O)C1=C2CC(NC(=O)NC)CN2C(c2nccs2)=N[C@H]1c1ccc(F)cc1Br] | racemic | B |

-continued
| EXAMPLE | STRUCTURAL FORMULEA | STEREOCHEMISTRY | BIOACTIVITY |
|---|---|---|---|
| 52 | 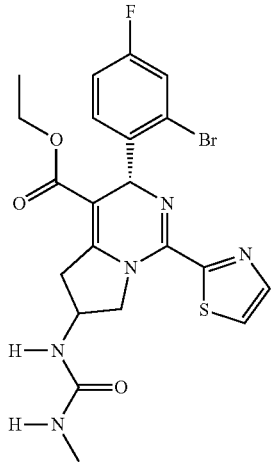 [SMILES: CCOC(=O)C1=C2CC(NC(=O)NC)CN2C(c2nccs2)=N[C@H]1c1ccc(F)cc1Br] | optically pure | C |
| 53 | 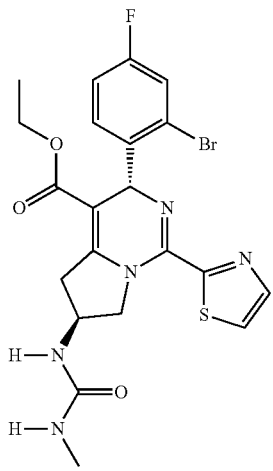 [SMILES: CCOC(=O)C1=C2C[C@H](NC(=O)NC)CN2C(c2nccs2)=N[C@H]1c1ccc(F)cc1Br] | optically pure | A |
| 54 | 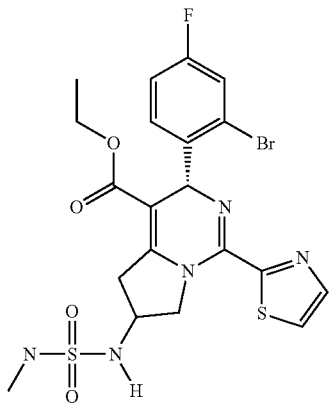 [SMILES: CCOC(=O)C1=C2CC(NS(=O)(=O)NC)CN2C(c2nccs2)=N[C@H]1c1ccc(F)cc1Br] | racemic | A |

| EXAMPLE | STRUCTURAL FORMULEA | STEREOCHEMISTRY | BIOACTIVITY |
|---|---|---|---|
| 55 | 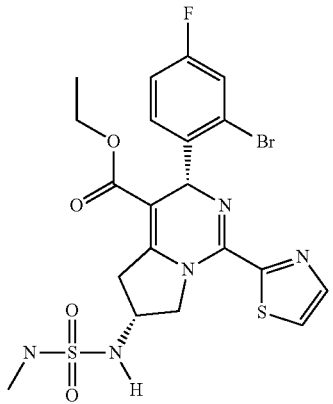 | optically pure | A |
| 56 | 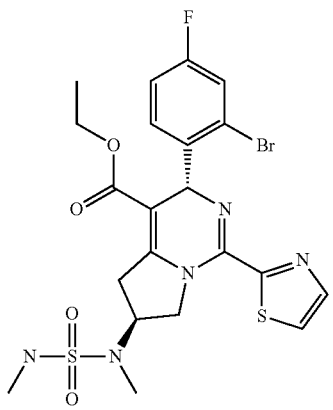 [SMILES: CCOC(=O)C1=C2C[C@H](N(C)S(=O)(=O)NC)CN2C(c2nccs2)=N[C@H]1c1ccc(F)cc1Br] | optically pure | A |
| 57 | 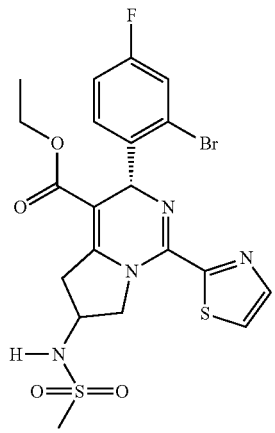 | racemic | A |

-continued
| EXAMPLE | STRUCTURAL FORMULEA | STEREOCHEMISTRY | BIOACTIVITY |
|---|---|---|---|
| 58 | 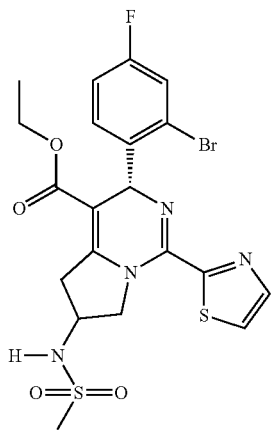 | optically pure | A |
| 59 | 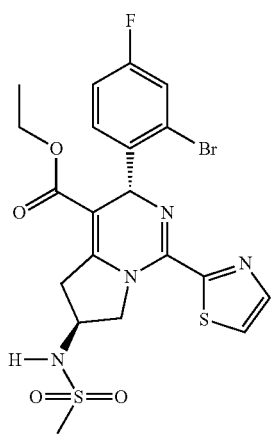 | optically pure | A |
| 60 | 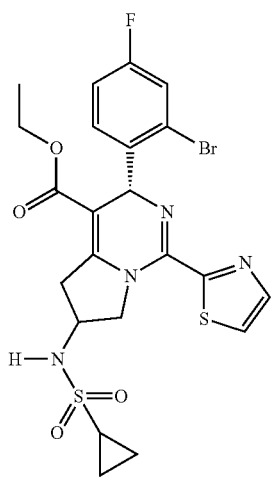 | racemic | A |

-continued
| EXAMPLE | STRUCTURAL FORMULEA | STEREOCHEMISTRY | BIOACTIVITY |
|---------|---------------------|-----------------|-------------|
| 61 | 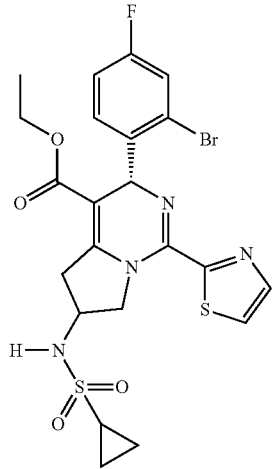 [SMILES: CCOC(=O)C1=C2CC(NS(=O)(=O)C3CC3)CN2C(c2nccs2)=N[C@H]1c1ccc(F)cc1Br] | optically pure | A |
| 62 | 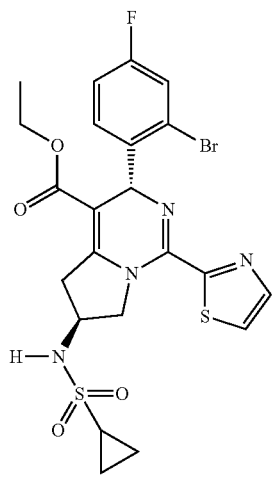 [SMILES: CCOC(=O)C1=C2C[C@H](NS(=O)(=O)C3CC3)CN2C(c2nccs2)=N[C@H]1c1ccc(F)cc1Br] | optically pure | A |
| 63 | 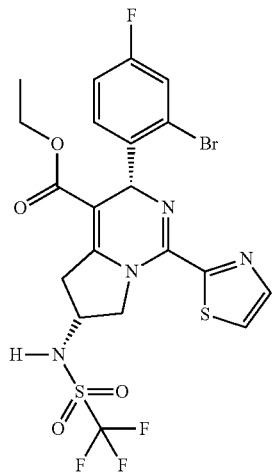 | optically pure | B |

-continued
| EXAMPLE | STRUCTURAL FORMULEA | STEREOCHEMISTRY | BIOACTIVITY |
|---|---|---|---|
| 64 | 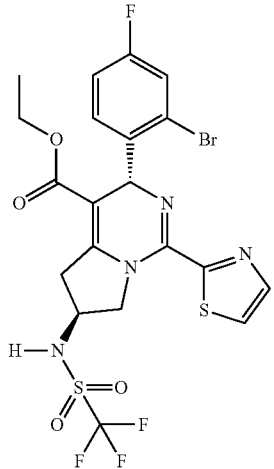 [SMILES: CCOC(=O)C1=C2C[C@H](NS(=O)(=O)C(F)(F)F)CN2C(c2nccs2)=N[C@H]1c1ccc(F)cc1Br] | optically pure | B |
| 65 | 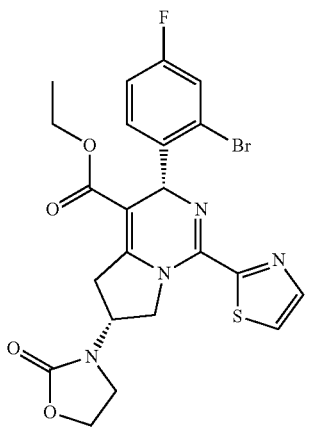 [SMILES: CCOC(=O)C1=C2C[C@@H](N3CCOC3=O)CN2C(c2nccs2)=N[C@H]1c1ccc(F)cc1Br] | optically pure | B |
| 66 | 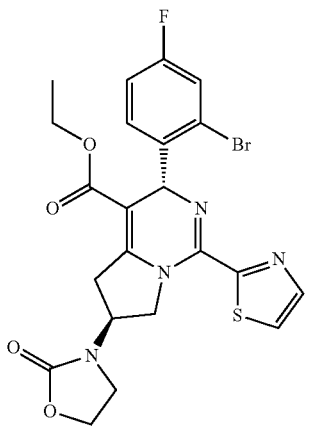 [SMILES: CCOC(=O)C1=C2C[C@H](N3CCOC3=O)CN2C(c2nccs2)=N[C@H]1c1ccc(F)cc1Br] | optically pure | B |

| EXAMPLE | STRUCTURAL FORMULEA | STEREOCHEMISTRY | BIOACTIVITY |
|---|---|---|---|
| 67 | 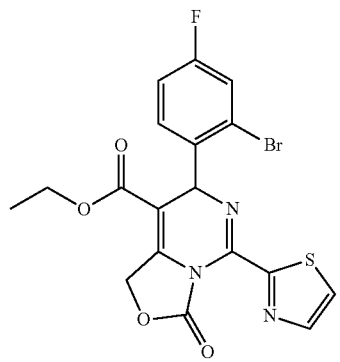 [SMILES: CCOC(=O)C1=C2COC(=O)N2C(c2nccs2)=NC1c1ccc(F)cc1Br] | racemic | B |
| 68 | 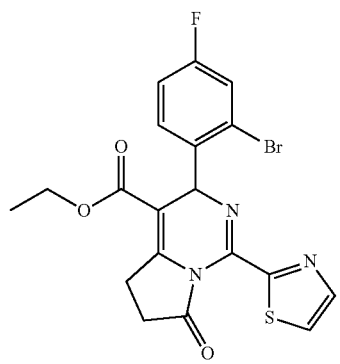 [SMILES: CCOC(=O)C1=C2CCC(=O)N2C(c2nccs2)=NC1c1ccc(F)cc1Br] | racemic | D |
| 69 | 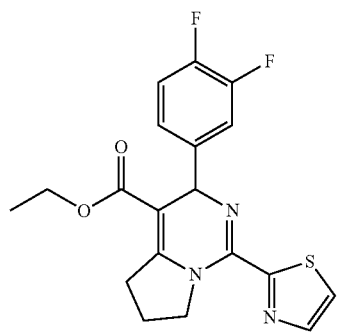 [SMILES: CCOC(=O)C1=C2CCCN2C(c2nccs2)=NC1c1ccc(F)c(F)c1] | racemic | B |
| 70 | 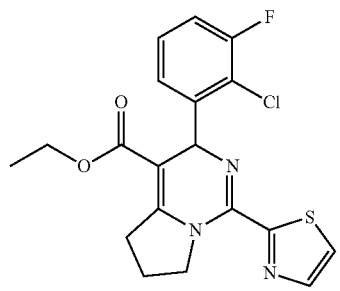 [SMILES: CCOC(=O)C1=C2CCCN2C(c2nccs2)=NC1c1cccc(F)c1Cl] | racemic | B |

-continued
| EXAMPLE | STRUCTURAL FORMULEA | STEREOCHEMISTRY | BIOACTIVITY |
|---|---|---|---|
| 71 | 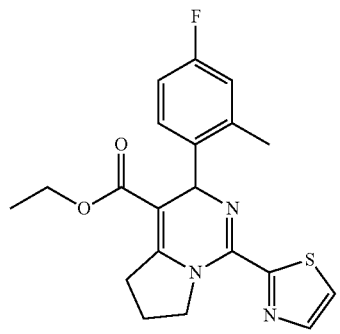 [SMILES: CCOC(=O)C1=C2CCCN2C(c2nccs2)=NC1c1ccc(F)cc1C] | racemic | B |
| 72 | 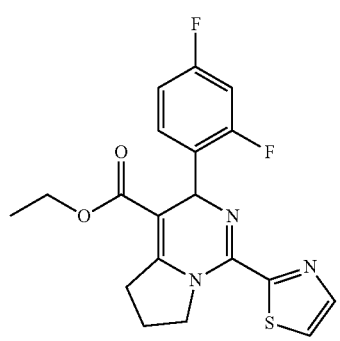 [SMILES: CCOC(=O)C1=C2CCCN2C(c2nccs2)=NC1c1ccc(F)cc1F] | racemic | C |
| 73 | 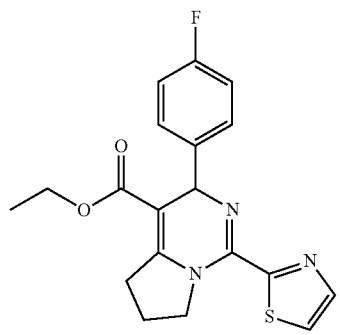 [SMILES: CCOC(=O)C1=C2CCCN2C(c2nccs2)=NC1c1ccc(F)cc1] | racemic | D |
| 74 | 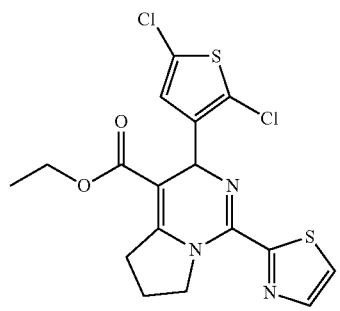 [SMILES: CCOC(=O)C1=C2CCCN2C(c2nccs2)=NC1c1cc(Cl)sc1Cl] | racemic | D |

-continued
| EXAMPLE | STRUCTURAL FORMULEA | STEREOCHEMISTRY | BIOACTIVITY |
|---|---|---|---|
| 75 | 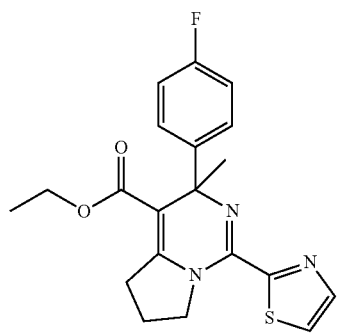 [SMILES: CCOC(=O)C1=C2CCCN2C(c2nccs2)=NC1(C)c1ccc(F)cc1] | racemic | D |
| 76 | 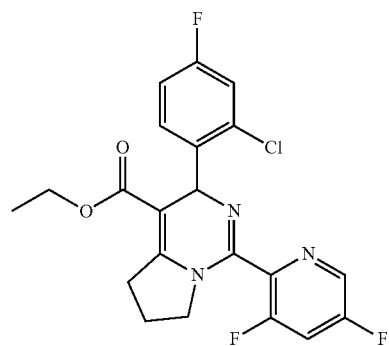 [SMILES: CCOC(=O)C1=C2CCCN2C(c2ncc(F)cc2F)=NC1c1ccc(F)cc1Cl] | racemic | D |
| 77 | 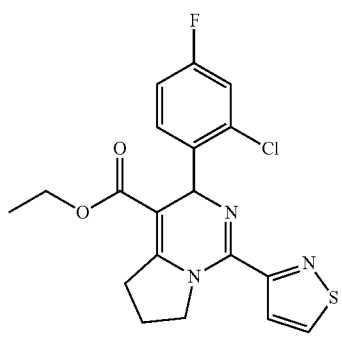 [SMILES: CCOC(=O)C1=C2CCCN2C(c2ccsn2)=NC1c1ccc(F)cc1Cl] | racemic | D |
| 78 | 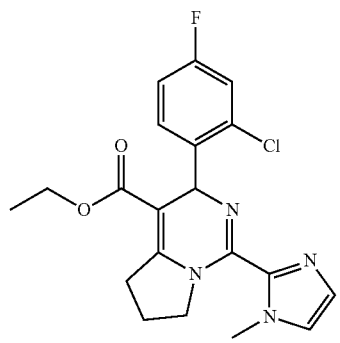 [SMILES: CCOC(=O)C1=C2CCCN2C(c2nccn2C)=NC1c1ccc(F)cc1Cl] | racemic | D |

-continued
| EXAMPLE | STRUCTURAL FORMULEA | STEREOCHEMISTRY | BIOACTIVITY |
|---|---|---|---|
| 79 | 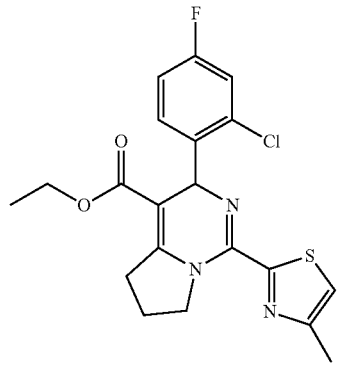 [SMILES: CCOC(=O)C1=C2CCCN2C(c2nc(C)cs2)=NC1c1ccc(F)cc1Cl] | racemic | D |
| 80 | 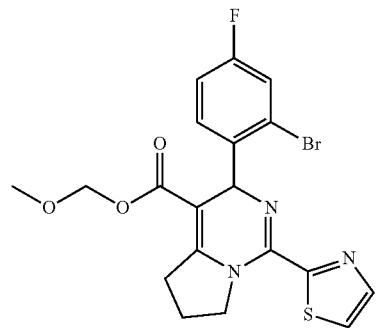 [SMILES: COCOC(=O)C1=C2CCCN2C(c2nccs2)=NC1c1ccc(F)cc1Br] | racemic | D |
| 81 | 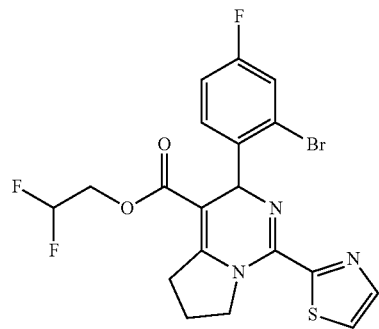 [SMILES: O=C(OCC(F)F)C1=C2CCCN2C(c2nccs2)=NC1c1ccc(F)cc1Br] | racemic | D |
| 82 | 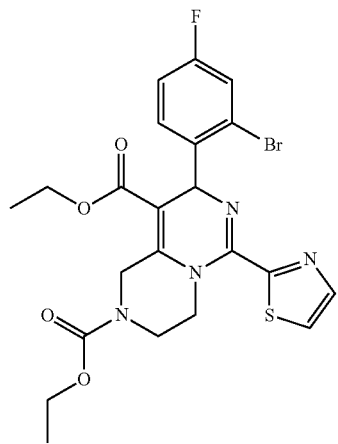 [SMILES: CCOC(=O)C1=C2CN(C(=O)OCC)CCN2C(c2nccs2)=NC1c1ccc(F)cc1Br] | optically pure | B |

-continued
| EXAMPLE | STRUCTURAL FORMULEA | STEREOCHEMISTRY | BIOACTIVITY |
|---------|---------------------|-----------------|-------------|
| 83 | 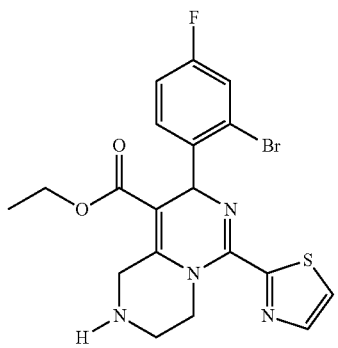 [SMILES: CCOC(=O)C1=C2CNCCN2C(c2nccs2)=NC1c1ccc(F)cc1Br] | racemic | D |
| 84 | 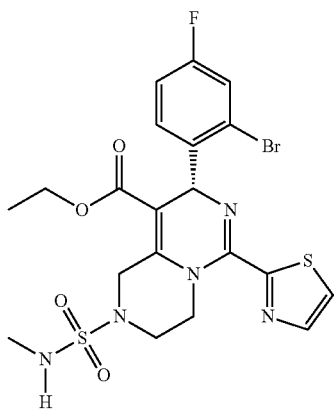 [SMILES: CCOC(=O)C1=C2CN(S(=O)(=O)NC)CCN2C(c2nccs2)=N[C@H]1c1ccc(F)cc1Br] | optically pure | B |
| 85 | 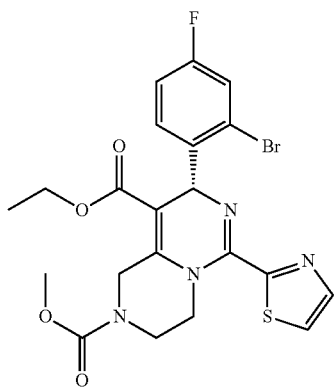 [SMILES: CCOC(=O)C1=C2CN(C(=O)OC)CCN2C(c2nccs2)=N[C@H]1c1ccc(F)cc1Br] | optically pure | B |
| 86 | 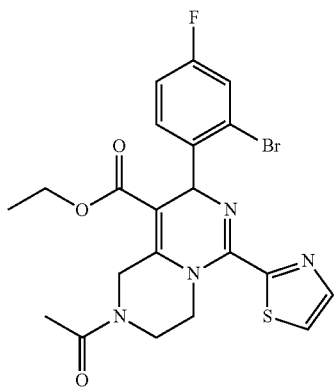 [SMILES: CCOC(=O)C1=C2CN(C(C)=O)CCN2C(c2nccs2)=NC1c1ccc(F)cc1Br] | racemic | C |

-continued
| EXAMPLE | STRUCTURAL FORMULEA | STEREOCHEMISTRY | BIOACTIVITY |
|---|---|---|---|
| 87 | 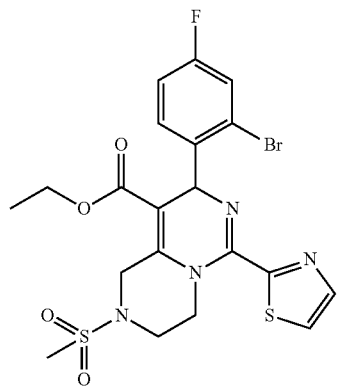 [SMILES: CCOC(=O)C1=C2CN(S(C)(=O)=O)CCN2C(c2nccs2)=NC1c1ccc(F)cc1Br] | racemic | C |
| 88 | 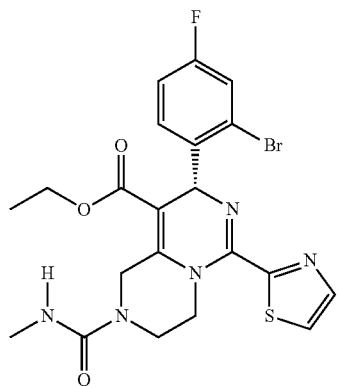 [SMILES: CCOC(=O)C1=C2CN(C(=O)NC)CCN2C(c2nccs2)=N[C@H]1c1ccc(F)cc1Br] | optically pure | C |
| 89 | 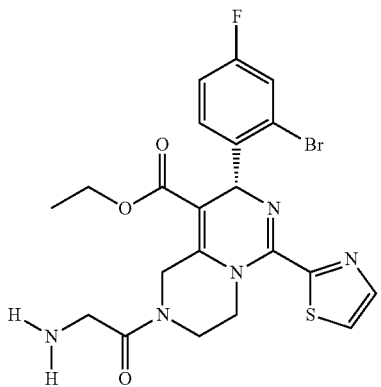 [SMILES: CCOC(=O)C1=C2CN(C(=O)CN)CCN2C(c2nccs2)=N[C@H]1c1ccc(F)cc1Br] | optically pure | D |
| 90 | 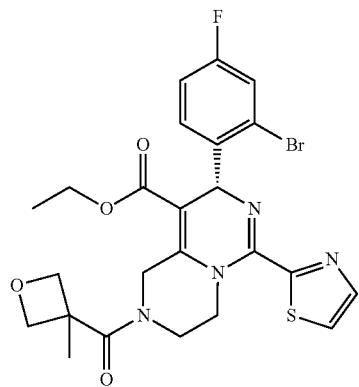 | optically pure | B |

-continued
| EXAMPLE | STRUCTURAL FORMULEA | STEREOCHEMISTRY | BIOACTIVITY |
|---|---|---|---|
| 91 | 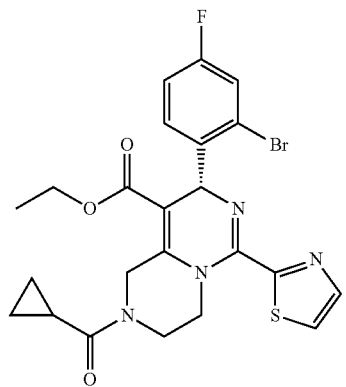 [SMILES: CCOC(=O)C1=C2CN(C(=O)C3CC3)CCN2C(c2nccs2)=N[C@H]1c1ccc(F)cc1Br] | optically pure | B |
| 92 | 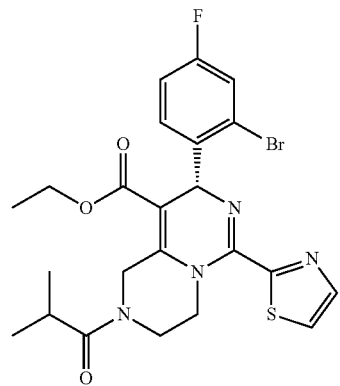 [SMILES: CCOC(=O)C1=C2CN(C(=O)C(C)C)CCN2C(c2nccs2)=N[C@H]1c1ccc(F)cc1Br] | optically pure | A |
| 93 | 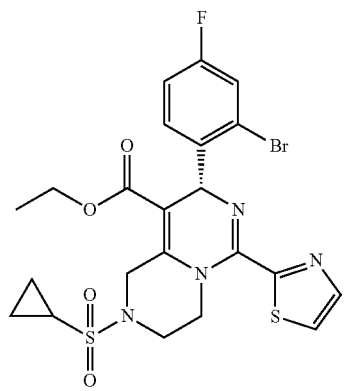 [SMILES: CCOC(=O)C1=C2CN(S(=O)(=O)C3CC3)CCN2C(c2nccs2)=N[C@H]1c1ccc(F)cc1Br] | optically pure | B |
| 94 | 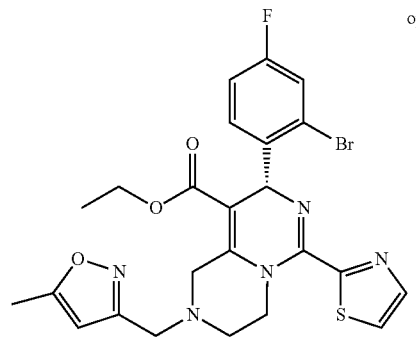 | optically pure | D |

| EXAMPLE | STRUCTURAL FORMULEA | STEREOCHEMISTRY | BIOACTIVITY |
|---|---|---|---|
| 95 | | racemic | B |
| 96 | | racemic | D |
| 97 | | racemic | D |
| 98 | | optically pure | D |

-continued
| EXAMPLE | STRUCTURAL FORMULEA | STEREOCHEMISTRY | BIOACTIVITY |
|---|---|---|---|
| 99 | 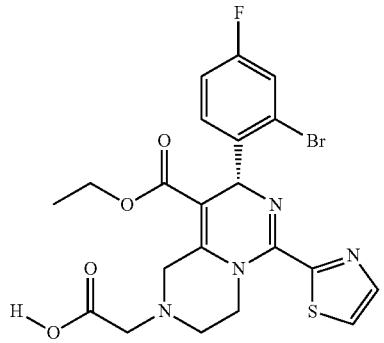 [SMILES: CCOC(=O)C1=C2CN(CC(=O)O)CCN2C(c2nccs2)=N[C@H]1c1ccc(F)cc1Br] | optically pure | D |
| 100 | 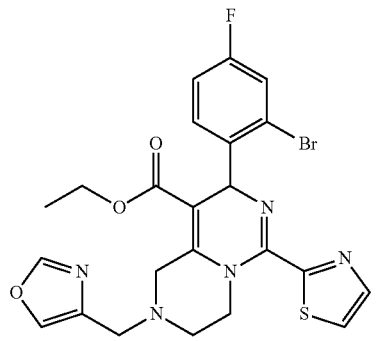 [SMILES: CCOC(=O)C1=C2CN(Cc3cocn3)CCN2C(c2nccs2)=NC1c1ccc(F)cc1Br] | optically pure | D |
| 101 | 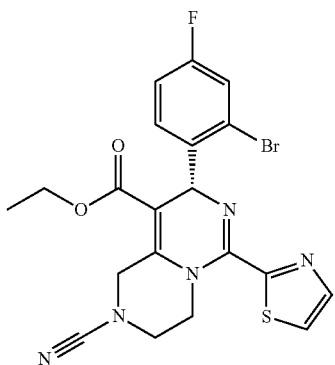 [SMILES: CCOC(=O)C1=C2CN(C#N)CCN2C(c2nccs2)=N[C@H]1c1ccc(F)cc1Br] | optically pure | C |
| 102 | 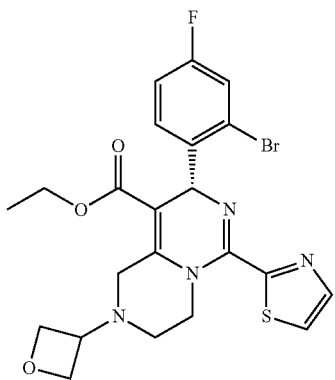 [SMILES: CCOC(=O)C1=C2CN(C3COC3)CCN2C(c2nccs2)=N[C@H]1c1ccc(F)cc1Br] | optically pure | C |

-continued
| EXAMPLE | STRUCTURAL FORMULEA | STEREOCHEMISTRY | BIOACTIVITY |
|---|---|---|---|
| 103 | 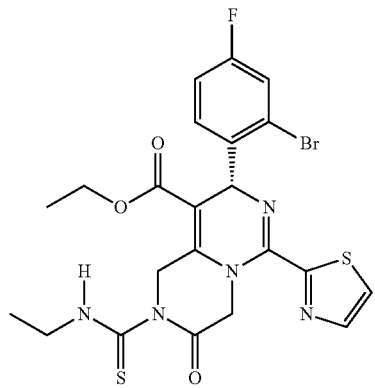 [SMILES: CCNC(=S)N1CC2=C(C(=O)OCC)[C@H](c3ccc(F)cc3Br)N=C(c3nccs3)N2CC1=O] | optically pure | B |
| 104 | 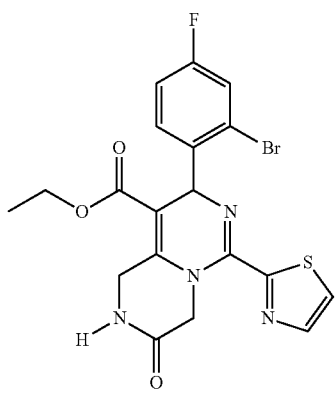 [SMILES: CCOC(=O)C1=C2CNC(=O)CN2C(c2nccs2)=NC1c1ccc(F)cc1Br] | racemic | D |
| 105 | 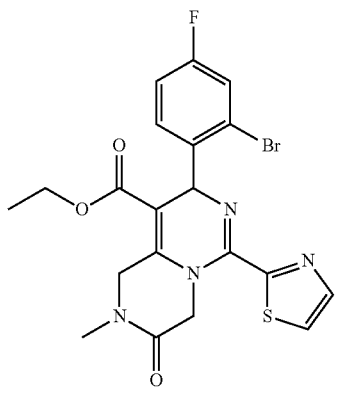 [SMILES: CCOC(=O)C1=C2CN(C)C(=O)CN2C(c2nccs2)=NC1c1ccc(F)cc1Br] | racemic | C |
| 106 | 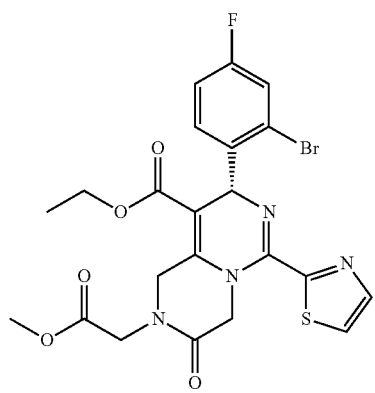 [SMILES: CCOC(=O)C1=C2CN(CC(=O)OC)C(=O)CN2C(c2nccs2)=N[C@H]1c1ccc(F)cc1Br] | optically pure | D |

-continued
| EXAMPLE | STRUCTURAL FORMULEA | STEREOCHEMISTRY | BIOACTIVITY |
|---|---|---|---|
| 107 | 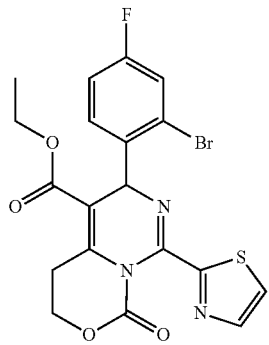 [SMILES: CCOC(=O)C1=C2CCOC(=O)N2C(c2nccs2)=NC1c1ccc(F)cc1Br] | racemic | B |
| 108 | 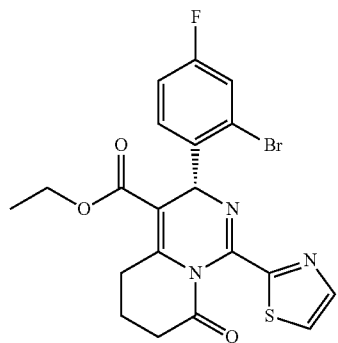 [SMILES: CCOC(=O)C1=C2CCCC(=O)N2C(c2nccs2)=N[C@H]1c1ccc(F)cc1Br] | racemic | D |
| 109 | 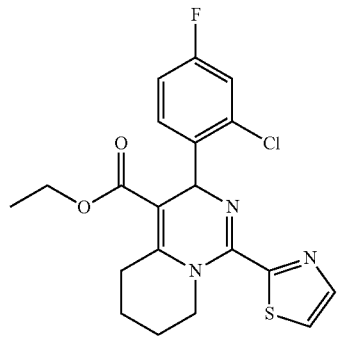 [SMILES: CCOC(=O)C1=C2CCCCN2C(c2nccs2)=NC1c1ccc(F)cc1Cl] | racemic | D |
| 110 | 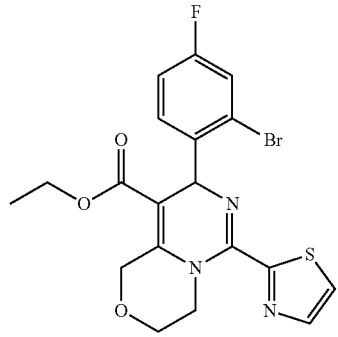 [SMILES: CCOC(=O)C1=C2COCCN2C(c2nccs2)=NC1c1ccc(F)cc1Br] | racemic | D |

| EXAMPLE | STRUCTURAL FORMULEA | STEREOCHEMISTRY | BIOACTIVITY |
|---|---|---|---|
| 111 | 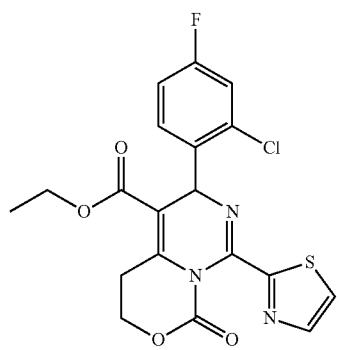 [SMILES: CCOC(=O)C1=C2CCOC(=O)N2C(c2nccs2)=NC1c1ccc(F)cc1Cl] | racemic | D |
| 112 | 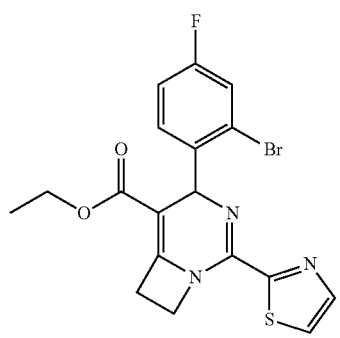 [SMILES: CCOC(=O)C1=C2CCN2C(c2nccs2)=NC1c1ccc(F)cc1Br] | racemic | D |
| 113 | 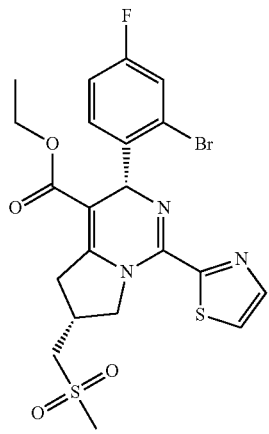 [SMILES: CCOC(=O)C1=C2C[C@@H](CS(C)(=O)=O)CN2C(c2nccs2)=N[C@H]1c1ccc(F)cc1Br] | optically pure | B |
| 114 | 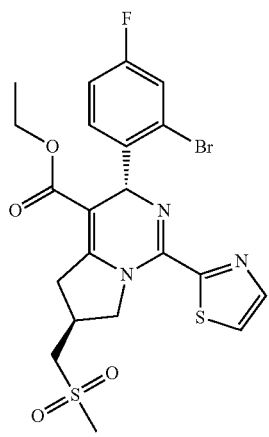 [SMILES: CCOC(=O)C1=C2C[C@H](CS(C)(=O)=O)CN2C(c2nccs2)=N[C@H]1c1ccc(F)cc1Br] | optically pure | B |

-continued
| EXAMPLE | STRUCTURAL FORMULEA | STEREOCHEMISTRY | BIOACTIVITY |
|---------|---------------------|-----------------|-------------|
| 115 | 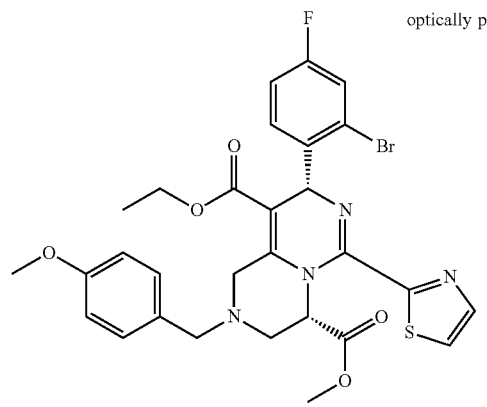 | optically pure | B |
| 116 | 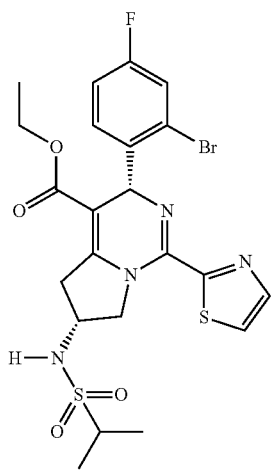 [SMILES: CCOC(=O)C1=C2C[C@@H](NS(=O)(=O)C(C)C)CN2C(c2nccs2)=N[C@H]1c1ccc(F)cc1Br] | optically pure | A |
| 117 | 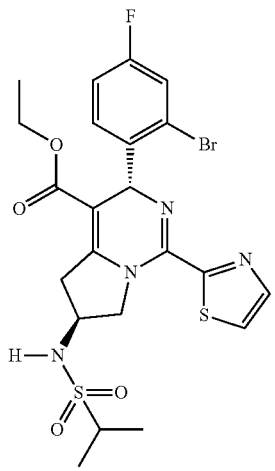 [SMILES: CCOC(=O)C1=C2C[C@H](NS(=O)(=O)C(C)C)CN2C(c2nccs2)=N[C@H]1c1ccc(F)cc1Br] | optically pure | A |

| EXAMPLE | STRUCTURAL FORMULEA | STEREOCHEMISTRY | BIOACTIVITY |
|---|---|---|---|
| 118 | 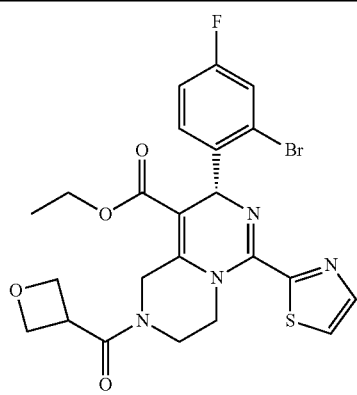 | optically pure | B |
| 119 | 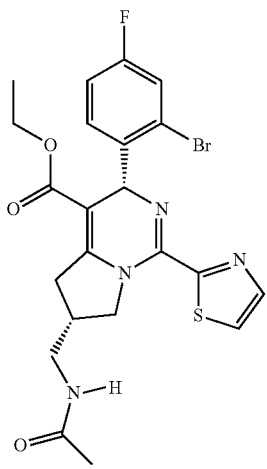 [SMILES: CCOC(=O)C1=C2C[C@@H](CNC(C)=O)CN2C(c2nccs2)=N[C@H]1c1ccc(F)cc1Br] | optically pure | A |
| 120 | 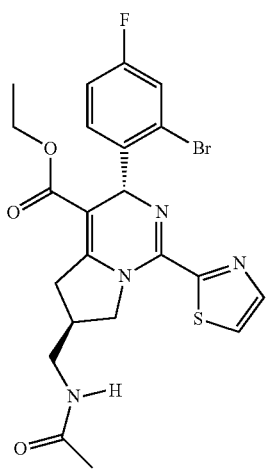 [SMILES: CCOC(=O)C1=C2C[C@H](CNC(C)=O)CN2C(c2nccs2)=N[C@H]1c1ccc(F)cc1Br] | optically pure | A |

| EXAMPLE | STRUCTURAL FORMULEA | STEREOCHEMISTRY | BIOACTIVITY |
|---|---|---|---|
| 121 | 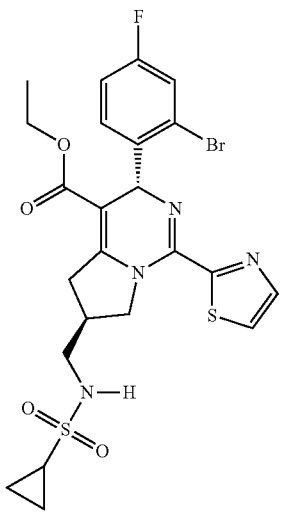 [SMILES: CCOC(=O)C1=C2C[C@H](CNS(=O)(=O)C3CC3)CN2C(c2nccs2)=N[C@H]1c1ccc(F)cc1Br] | optically pure | A |
| 122 | 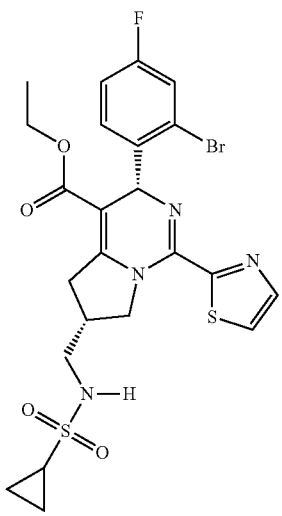 [SMILES: CCOC(=O)C1=C2C[C@@H](CNS(=O)(=O)C3CC3)CN2C(c2nccs2)=N[C@H]1c1ccc(F)cc1Br] | optically pure | D |
| 123 | 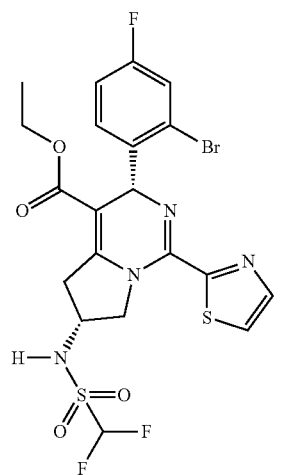 | optically pure | A |

| EXAMPLE | STRUCTURAL FORMULEA | STEREOCHEMISTRY | BIOACTIVITY |
|---|---|---|---|
| 124 | 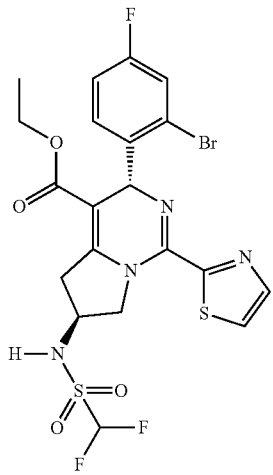 [SMILES: CCOC(=O)C1=C2C[C@H](NS(=O)(=O)C(F)F)CN2C(c2nccs2)=N[C@H]1c1ccc(F)cc1Br] | optically pure | A |
| 125 | 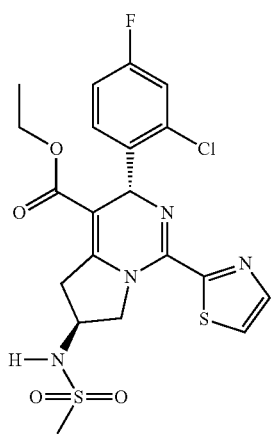 [SMILES: CCOC(=O)C1=C2C[C@H](NS(C)(=O)=O)CN2C(c2nccs2)=N[C@H]1c1ccc(F)cc1Cl] | optically pure | A |
| 126 | 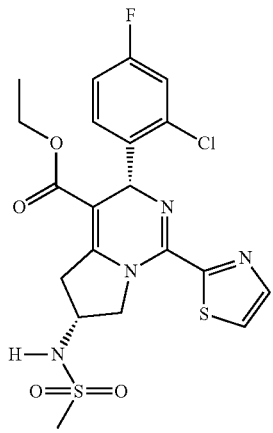 | optically pure | A |

| EXAMPLE | STRUCTURAL FORMULEA | STEREOCHEMISTRY | BIOACTIVITY |
|---|---|---|---|
| 127 | 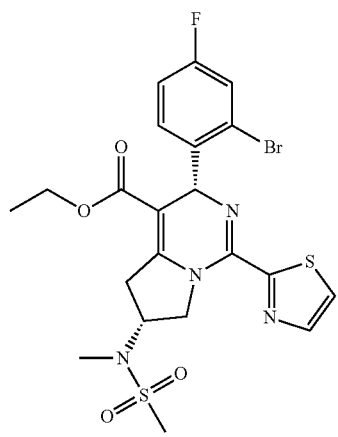 [SMILES: CCOC(=O)C1=C2C[C@@H](N(C)S(C)(=O)=O)CN2C(c2nccs2)=N[C@H]1c1ccc(F)cc1Br] | optically pure | A |
| 128 | 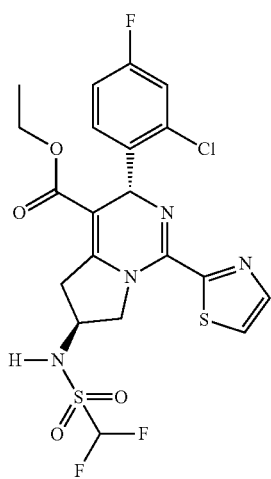 [SMILES: CCOC(=O)C1=C2C[C@H](NS(=O)(=O)C(F)F)CN2C(c2nccs2)=N[C@H]1c1ccc(F)cc1Cl] | optically pure | A |
| 129 | 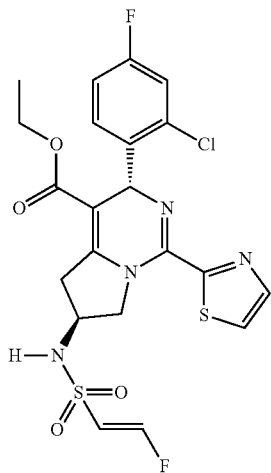 [SMILES: CCOC(=O)C1=C2C[C@H](NS(=O)(=O)/C=C/F)CN2C(c2nccs2)=N[C@H]1c1ccc(F)cc1Cl] | optically pure | A |

-continued
| EXAMPLE | STRUCTURAL FORMULEA | STEREOCHEMISTRY | BIOACTIVITY |
|---|---|---|---|
| 130 | 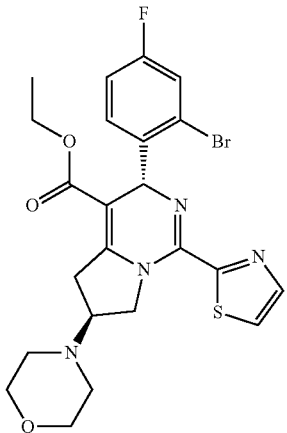 [SMILES: CCOC(=O)C1=C2C[C@H](N3CCOCC3)CN2C(c2nccs2)=N[C@H]1c1ccc(F)cc1Br] | optically pure | A |
| 131 | 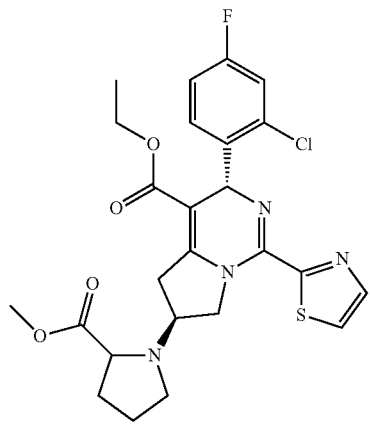 [SMILES: CCOC(=O)C1=C2C[C@H](N3CCCC3C(=O)OC)CN2C(c2nccs2)=N[C@H]1c1ccc(F)cc1Cl] | optically pure | D |
| 132 | 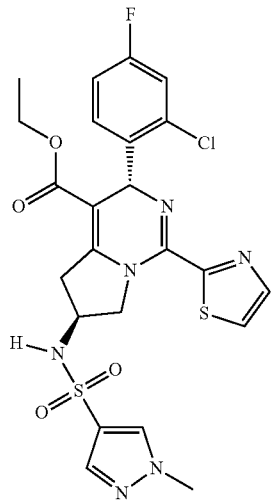 [SMILES: CCOC(=O)C1=C2C[C@H](NS(=O)(=O)c3cnn(C)c3)CN2C(c2nccs2)=N[C@H]1c1ccc(F)cc1Cl] | optically pure | A |

-continued

| EXAMPLE | STRUCTURAL FORMULEA | STEREOCHEMISTRY | BIOACTIVITY |
|---|---|---|---|
| 133 | | optically pure | B |
| 134 | | optically pure | D |
| 135 | | optically pure | c |
| 136 | | optically pure | C |

-continued
| EXAMPLE | STRUCTURAL FORMULEA | STEREOCHEMISTRY | BIOACTIVITY |
|---|---|---|---|
| 137 | 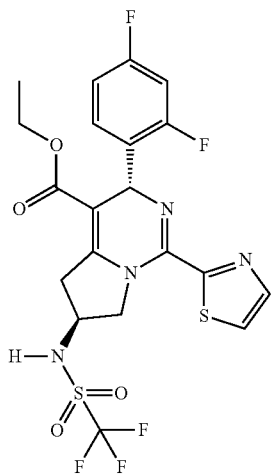 [SMILES: CCOC(=O)C1=C2C[C@H](NS(=O)(=O)C(F)(F)F)CN2C(c2nccs2)=N[C@H]1c1ccc(F)cc1F] | optically pure | D |
| 138 | 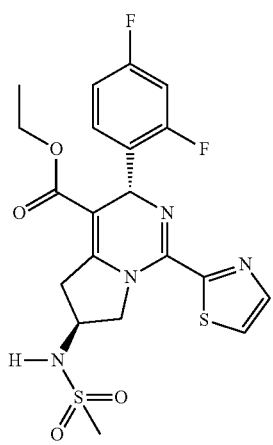 [SMILES: CCOC(=O)C1=C2C[C@H](NS(C)(=O)=O)CN2C(c2nccs2)=N[C@H]1c1ccc(F)cc1F] | optically pure | A |
| 139 | 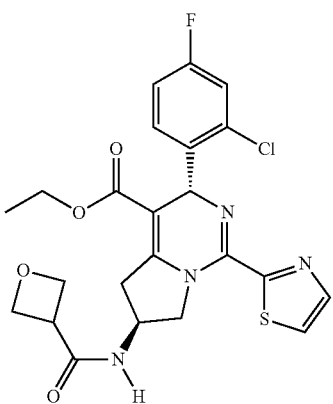 [SMILES: CCOC(=O)C1=C2C[C@H](NC(=O)C3COC3)CN2C(c2nccs2)=N[C@H]1c1ccc(F)cc1Cl] | optically pure | D |

-continued
| EXAMPLE | STRUCTURAL FORMULA | STEREOCHEMISTRY | BIOACTIVITY |
|---|---|---|---|
| 140 | 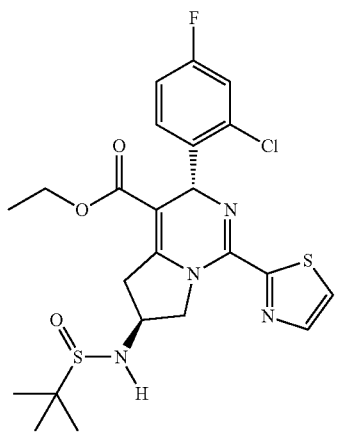 [SMILES: CCOC(=O)C1=C2C[C@H](NS(=O)C(C)(C)C)CN2C(c2nccs2)=N[C@H]1c1ccc(F)cc1Cl] | optically pure | C |
| 141 | 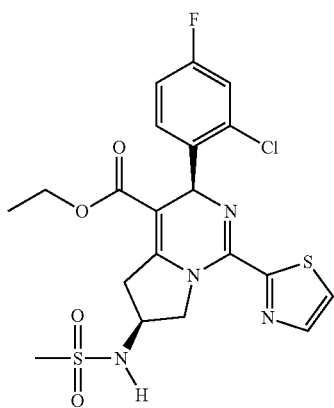 [SMILES: CCOC(=O)C1=C2C[C@H](NS(C)(=O)=O)CN2C(c2nccs2)=N[C@@H]1c1ccc(F)cc1Cl] | optically pure | C |
| 142 | 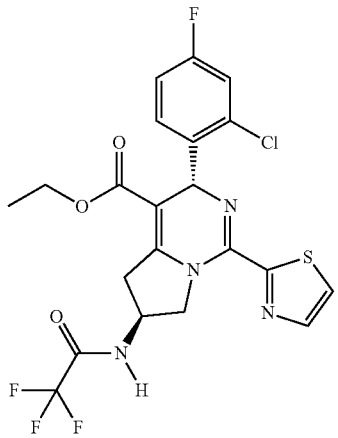 [SMILES: CCOC(=O)C1=C2C[C@H](NC(=O)C(F)(F)F)CN2C(c2nccs2)=N[C@H]1c1ccc(F)cc1Cl] | optically pure | B |

-continued
| EXAMPLE | STRUCTURAL FORMULEA | STEREOCHEMISTRY | BIOACTIVITY |
|---|---|---|---|
| 143 | 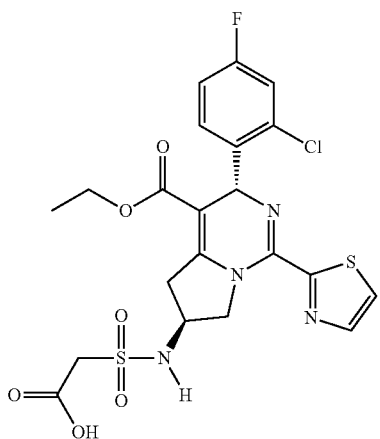 [SMILES: CCOC(=O)C1=C2C[C@H](NS(=O)(=O)CC(=O)O)CN2C(c2nccs2)=N[C@H]1c1ccc(F)cc1Cl] | optically pure | B |
| 144 | 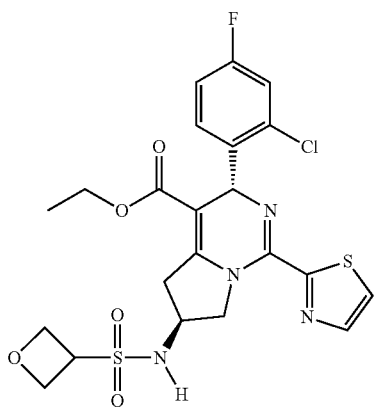 [SMILES: CCOC(=O)C1=C2C[C@H](NS(=O)(=O)C3COC3)CN2C(c2nccs2)=N[C@H]1c1ccc(F)cc1Cl] | optically pure | A |
| 145 | 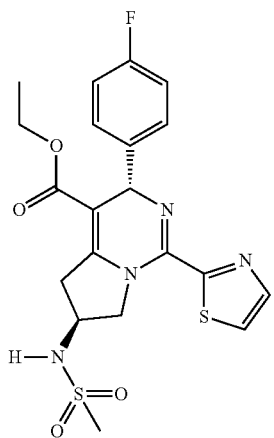 [SMILES: CCOC(=O)C1=C2C[C@H](NS(C)(=O)=O)CN2C(c2nccs2)=N[C@H]1c1ccc(F)cc1] | optically pure | C |

-continued
| EXAMPLE | STRUCTURAL FORMULEA | STEREOCHEMISTRY | BIOACTIVITY |
| --- | --- | --- | --- |
| 146 | 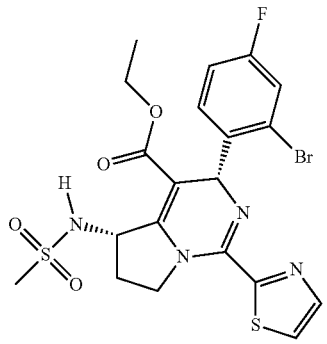 [SMILES: CCOC(=O)C1=C2[C@@H](NS(C)(=O)=O)CCN2C(c2nccs2)=N[C@H]1c1ccc(F)cc1Br] | optically pure | D |
| 147 | 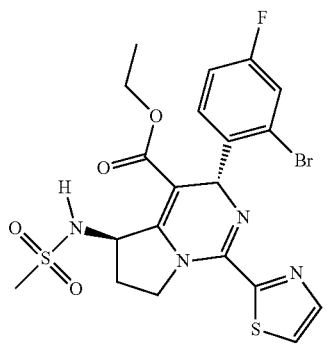 [SMILES: CCOC(=O)C1=C2[C@H](NS(C)(=O)=O)CCN2C(c2nccs2)=N[C@H]1c1ccc(F)cc1Br] | optically pure | D |
| 148 | 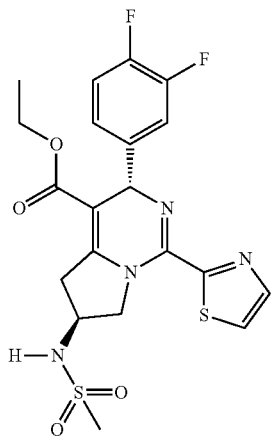 [SMILES: CCOC(=O)C1=C2C[C@H](NS(C)(=O)=O)CN2C(c2nccs2)=N[C@H]1c1ccc(F)c(F)c1] | optically pure | B |
| 149 | 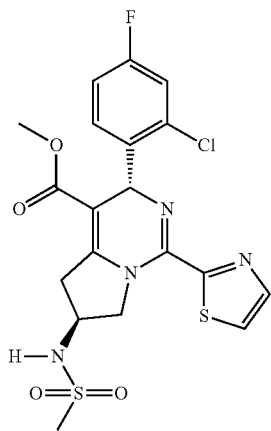 | optically pure | A |

-continued
| EXAMPLE | STRUCTURAL FORMULEA | STEREOCHEMISTRY | BIOACTIVITY |
|---|---|---|---|
| 150 | 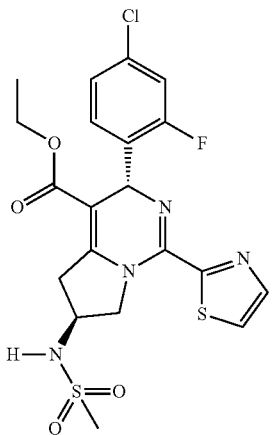 | optically pure | B |
| 151 | 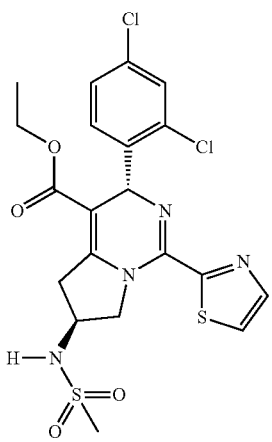 [SMILES: CCOC(=O)C1=C2C[C@H](NS(C)(=O)=O)CN2C(c2nccs2)=N[C@H]1c1ccc(Cl)cc1Cl] | optically pure | A |
| 152 | 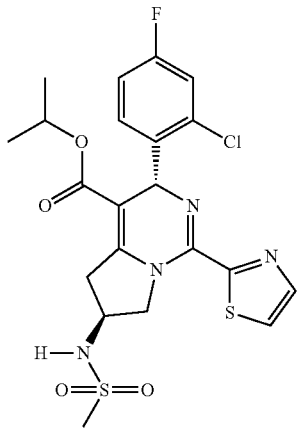 [SMILES: CC(C)OC(=O)C1=C2C[C@H](NS(C)(=O)=O)CN2C(c2nccs2)=N[C@H]1c1ccc(F)cc1Cl] | optically pure | B |

| EXAMPLE | STRUCTURAL FORMULEA | STEREOCHEMISTRY | BIOACTIVITY |
|---|---|---|---|
| 153 | 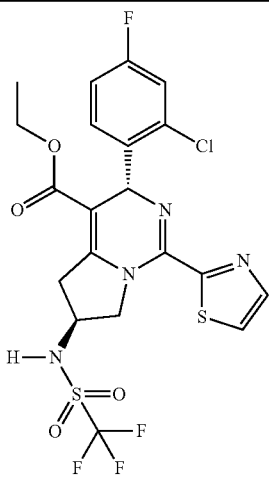 | optically pure | A |
| 154 | 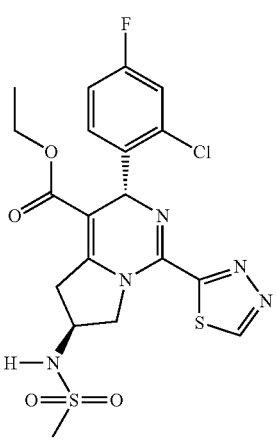 [SMILES: CCOC(=O)C1=C2C[C@H](NS(C)(=O)=O)CN2C(c2nncs2)=N[C@H]1c1ccc(F)cc1Cl] | optically pure | B |
| 155 | 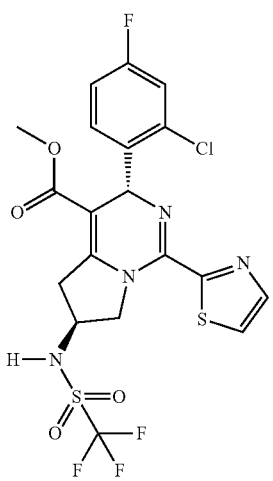 [SMILES: COC(=O)C1=C2C[C@H](NS(=O)(=O)C(F)(F)F)CN2C(c2nccs2)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 156 | 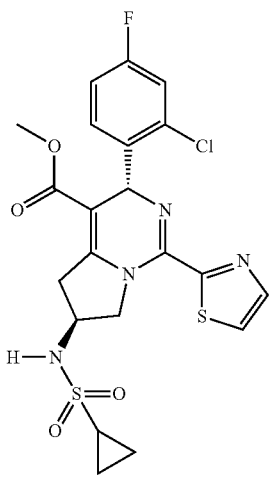 [SMILES: COC(=O)C1=C2C[C@H](NS(=O)(=O)C3CC3)CN2C(c2nccs2)=N[C@H]1c1ccc(F)cc1Cl] | optically pure | A |
| 157 | 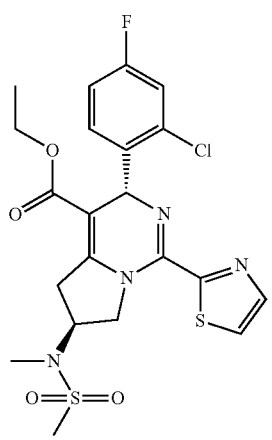 [SMILES: CCOC(=O)C1=C2C[C@H](N(C)S(C)(=O)=O)CN2C(c2nccs2)=N[C@H]1c1ccc(F)cc1Cl] | optically pure | A |
| 158 | 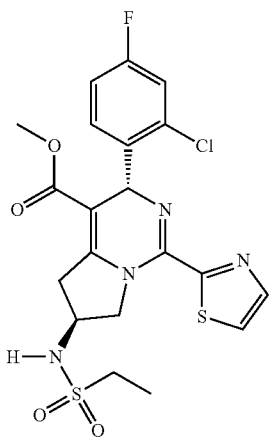 [SMILES: CCS(=O)(=O)N[C@H]1CC2=C(C(=O)OC)[C@H](c3ccc(F)cc3Cl)N=C(c3nccs3)N2C1] | optically pure | A |

| EXAMPLE | STRUCTURAL FORMULEA | STEREOCHEMISTRY | BIOACTIVITY |
|---|---|---|---|
| 159 | 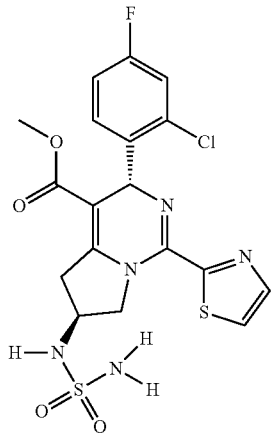 [SMILES: COC(=O)C1=C2C[C@H](NS(N)(=O)=O)CN2C(c2nccs2)=N[C@H]1c1ccc(F)cc1Cl] | optically pure | A |
| 160 | 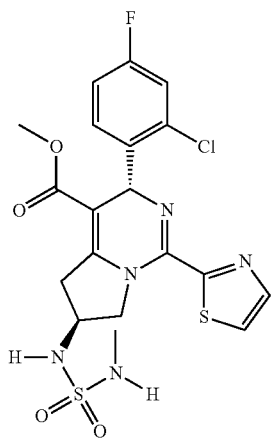 [SMILES: CNS(=O)(=O)N[C@H]1CC2=C(C(=O)OC)[C@H](c3ccc(F)cc3Cl)N=C(c3nccs3)N2C1] | optically pure | A |
| 161 | 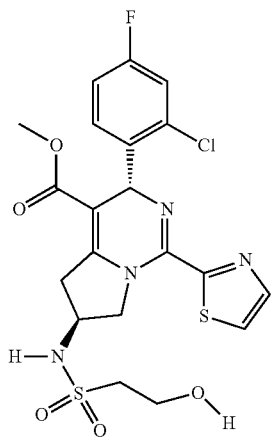 [SMILES: COC(=O)C1=C2C[C@H](NS(=O)(=O)CCO)CN2C(c2nccs2)=N[C@H]1c1ccc(F)cc1Cl] | optically pure | A |

-continued
| EXAMPLE | STRUCTURAL FORMULEA | STEREOCHEMISTRY | BIOACTIVITY |
|---|---|---|---|
| 162 | 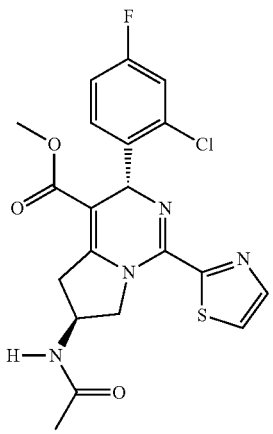 [SMILES: COC(=O)C1=C2C[C@H](NC(C)=O)CN2C(c2nccs2)=N[C@H]1c1ccc(F)cc1Cl] | optically pure | B |
| 163 | 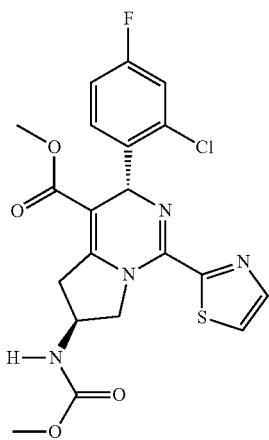 [SMILES: COC(=O)N[C@H]1CC2=C(C(=O)OC)[C@H](c3ccc(F)cc3Cl)N=C(c3nccs3)N2C1] | optically pure | A |
| 164 | 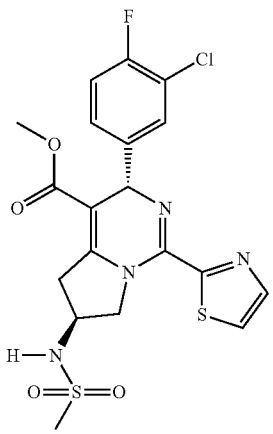 [SMILES: COC(=O)C1=C2C[C@H](NS(C)(=O)=O)CN2C(c2nccs2)=N[C@H]1c1ccc(F)c(Cl)c1] | optically pure | D |

| EXAMPLE | STRUCTURAL FORMULEA | STEREOCHEMISTRY | BIOACTIVITY |
|---|---|---|---|
| 165 | 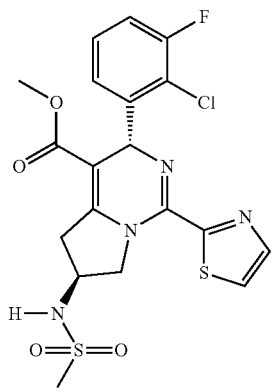 [SMILES: COC(=O)C1=C2C[C@H](NS(C)(=O)=O)CN2C(c2nccs2)=N[C@H]1c1cccc(F)c1Cl] | optically pure | A |
| 166 | 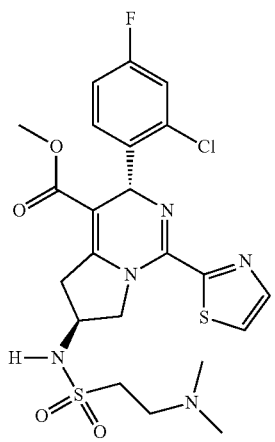 [SMILES: COC(=O)C1=C2C[C@H](NS(=O)(=O)CCN(C)C)CN2C(c2nccs2)=N[C@H]1c1ccc(F)cc1Cl] | optically pure | A |
| 167 | 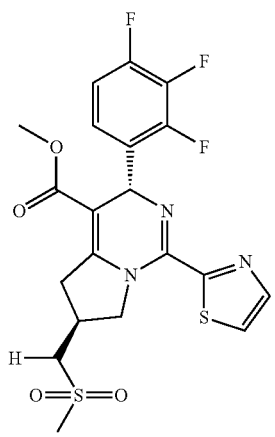 [SMILES: COC(=O)C1=C2C[C@H](CS(C)(=O)=O)CN2C(c2nccs2)=N[C@H]1c1ccc(F)c(F)c1F] | optically pure | A |

| EXAMPLE | STRUCTURAL FORMULEA | STEREOCHEMISTRY | BIOACTIVITY |
|---------|---------------------|-----------------|-------------|
| 168 | 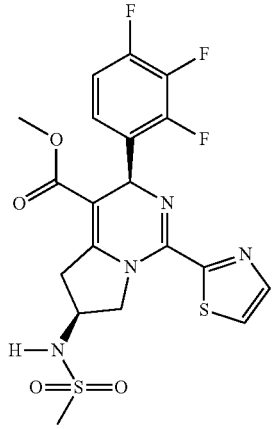 [SMILES: COC(=O)C1=C2C[C@H](NS(C)(=O)=O)CN2C(c2nccs2)=N[C@@H]1c1ccc(F)c(F)c1F] | optically pure | B |
| 169 | 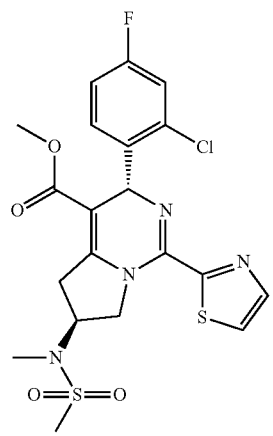 [SMILES: COC(=O)C1=C2C[C@H](N(C)S(C)(=O)=O)CN2C(c2nccs2)=N[C@H]1c1ccc(F)cc1Cl] | optically pure | A |
| 170 | 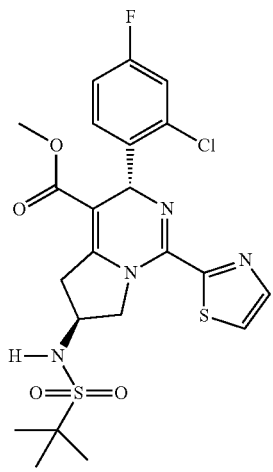 [SMILES: COC(=O)C1=C2C[C@H](NS(=O)(=O)C(C)(C)C)CN2C(c2nccs2)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 171 | 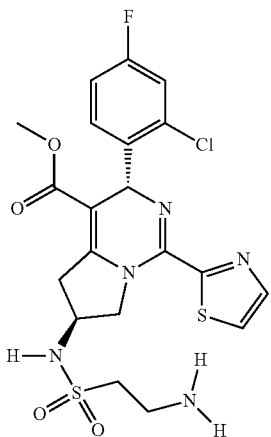 [SMILES: COC(=O)C1=C2C[C@H](NS(=O)(=O)CCN)CN2C(c2nccs2)=N[C@H]1c1ccc(F)cc1Cl] | optically pure | A |
| 172 | 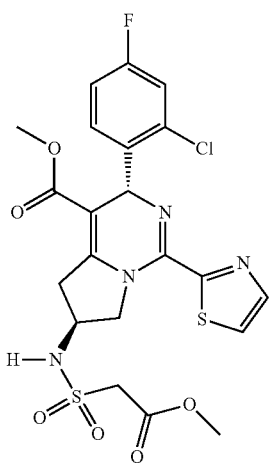 [SMILES: COC(=O)CS(=O)(=O)N[C@H]1CC2=C(C(=O)OC)[C@H](c3ccc(F)cc3Cl)N=C(c3nccs3)N2C1] | optically pure | A |
| 173 | 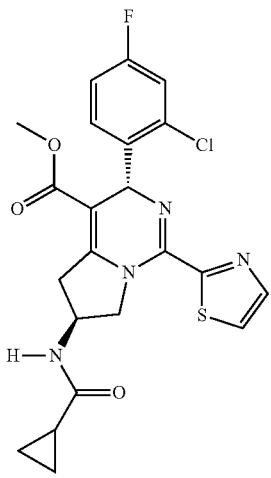 [SMILES: COC(=O)C1=C2C[C@H](NC(=O)C3CC3)CN2C(c2nccs2)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 174 | 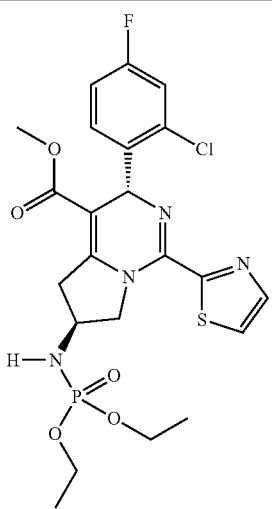 | optically pure | B |
| 175 | 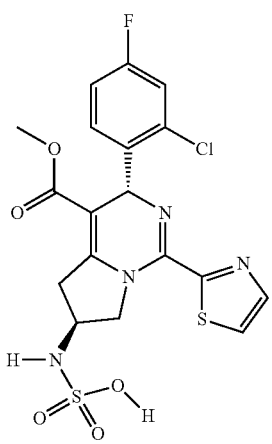 [SMILES: COC(=O)C1=C2C[C@H](NS(=O)(=O)O)CN2C(c2nccs2)=N[C@H]1c1ccc(F)cc1Cl] | optically pure | D |
| 176 | 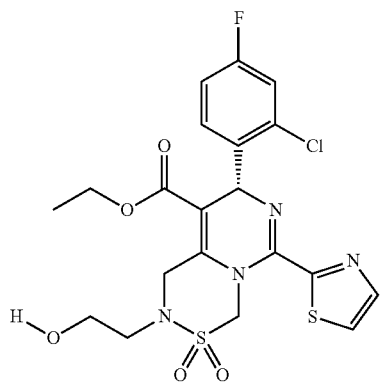 [SMILES: CCOC(=O)C1=C2CN(CCO)S(=O)(=O)CN2C(c2nccs2)=N[C@H]1c1ccc(F)cc1Cl] | optically pure | D |

| EXAMPLE | STRUCTURAL FORMULEA | STEREOCHEMISTRY | BIOACTIVITY |
|---------|---------------------|-----------------|-------------|
| 177 | 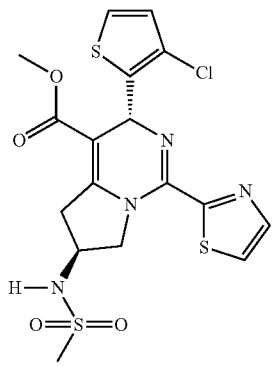 [SMILES: COC(=O)C1=C2C[C@H](NS(C)(=O)=O)CN2C(c2nccs2)=N[C@H]1c1sccc1Cl] | optically pure | A |
| 178 | 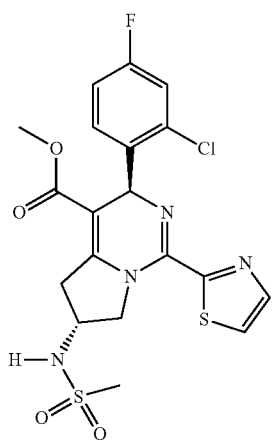 | optically pure | B |
| 179 | 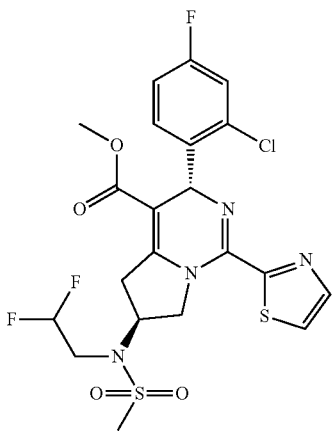 [SMILES: COC(=O)C1=C2C[C@H](N(CC(F)F)S(C)(=O)=O)CN2C(c2nccs2)=N[C@H]1c1ccc(F)cc1Cl] | optically pure | B |

| EXAMPLE | STRUCTURAL FORMULEA | STEREOCHEMISTRY | BIOACTIVITY |
|---------|---------------------|-----------------|-------------|
| 180 | 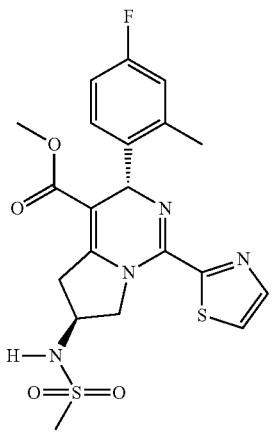 [SMILES: COC(=O)C1=C2C[C@H](NS(C)(=O)=O)CN2C(c2nccs2)=N[C@H]1c1ccc(F)cc1C] | optically pure | A |
| 181 | 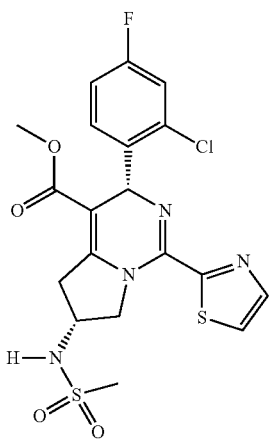 [SMILES: COC(=O)C1=C2C[C@@H](NS(C)(=O)=O)CN2C(c2nccs2)=N[C@H]1c1ccc(F)cc1Cl] | optically pure | A |
| 182 | 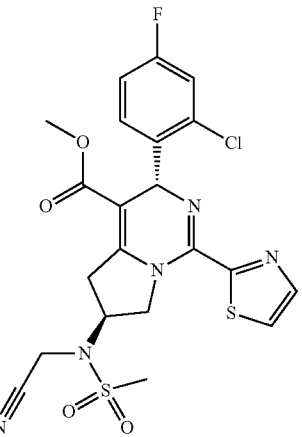 | optically pure | A |

-continued

| EXAMPLE | STRUCTURAL FORMULEA | STEREOCHEMISTRY | BIOACTIVITY |
|---------|---------------------|-----------------|-------------|
| 183 | | optically pure | A |
| 184 | | optically pure | B |
| 185 | | optically pure | A |

| EXAMPLE | STRUCTURAL FORMULEA | STEREOCHEMISTRY | BIOACTIVITY |
|---|---|---|---|
| 186 | 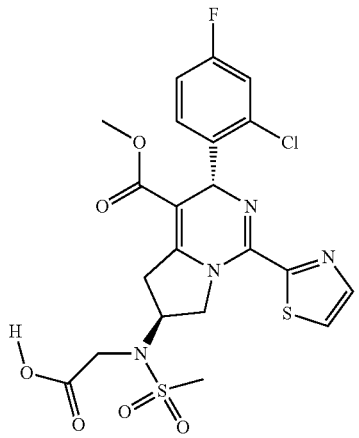 [SMILES: COC(=O)C1=C2C[C@H](N(CC(=O)O)S(C)(=O)=O)CN2C(c2nccs2)=N[C@H]1c1ccc(F)cc1Cl] | optically pure | D |
| 187 | 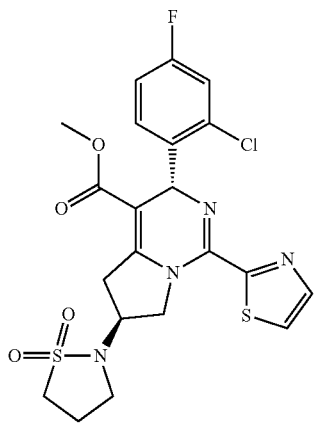 [SMILES: COC(=O)C1=C2C[C@H](N3CCCS3(=O)=O)CN2C(c2nccs2)=N[C@H]1c1ccc(F)cc1Cl] | optically pure | A |
| 188 | 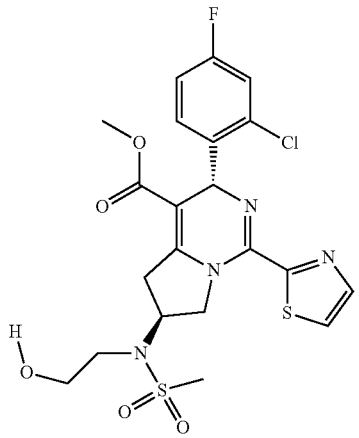 [SMILES: COC(=O)C1=C2C[C@H](N(CCO)S(C)(=O)=O)CN2C(c2nccs2)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 189 | 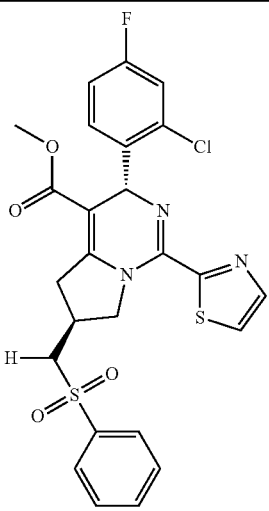 | optically pure | A |
| 190 | 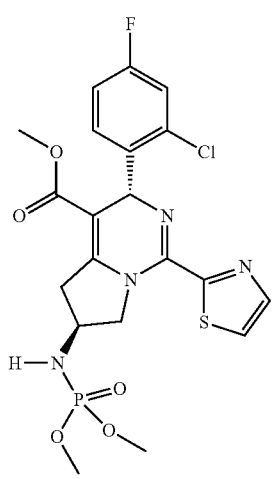 [SMILES: COC(=O)C1=C2C[C@H](NP(=O)(OC)OC)CN2C(c2nccs2)=N[C@H]1c1ccc(F)cc1Cl] | optically pure | B |
| 191 | 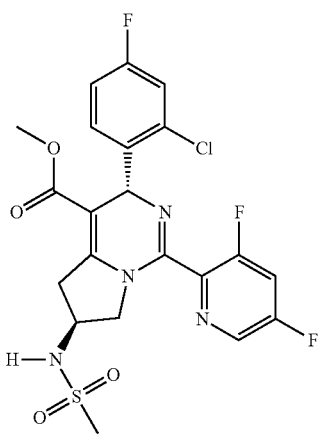 [SMILES: COC(=O)C1=C2C[C@H](NS(C)(=O)=O)CN2C(c2ncc(F)cc2F)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 192 | 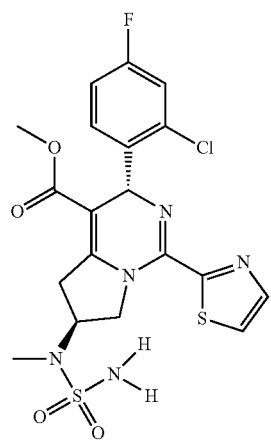 [SMILES: COC(=O)C1=C2C[C@H](N(C)S(N)(=O)=O)CN2C(c2nccs2)=N[C@H]1c1ccc(F)cc1Cl] | optically pure | A |
| 193 | 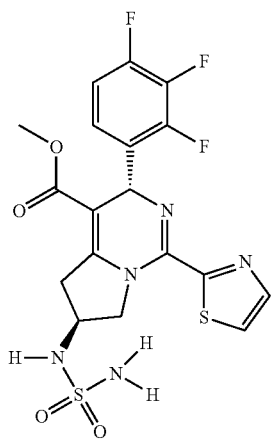 [SMILES: COC(=O)C1=C2C[C@H](NS(N)(=O)=O)CN2C(c2nccs2)=N[C@H]1c1ccc(F)c(F)c1F] | optically pure | A |
| 194 | 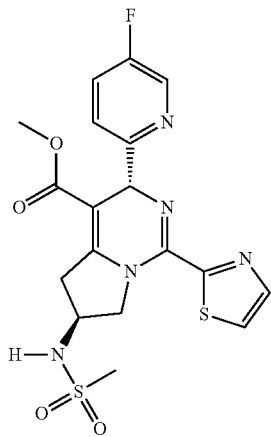 [SMILES: COC(=O)C1=C2C[C@H](NS(C)(=O)=O)CN2C(c2nccs2)=N[C@H]1c1ccc(F)cn1] | optically pure | D |

-continued

| EXAMPLE | STRUCTURAL FORMULA | STEREOCHEMISTRY | BIOACTIVITY |
|---|---|---|---|
| 195 | | optically pure | D |
| 196 | | optically pure | D |
| 197 | | optically pure | D |

US 9,938,301 B2
| EXAMPLE | STRUCTURAL FORMULEA | STEREOCHEMISTRY | BIOACTIVITY |
|---|---|---|---|
| 198 | 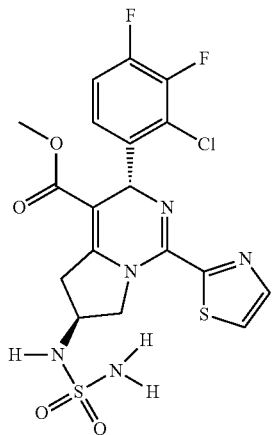 [SMILES: COC(=O)C1=C2C[C@H](NS(N)(=O)=O)CN2C(c2nccs2)=N[C@H]1c1ccc(F)c(F)c1Cl] | optically pure | A |
| 199 | 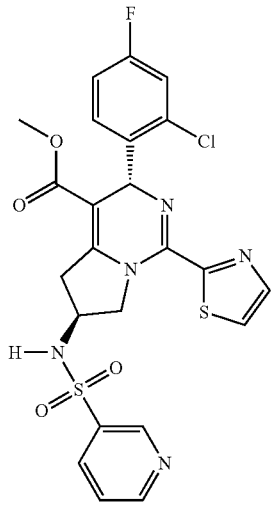 [SMILES: COC(=O)C1=C2C[C@H](NS(=O)(=O)c3cccnc3)CN2C(c2nccs2)=N[C@H]1c1ccc(F)cc1Cl] | optically pure | A |
| 200 | 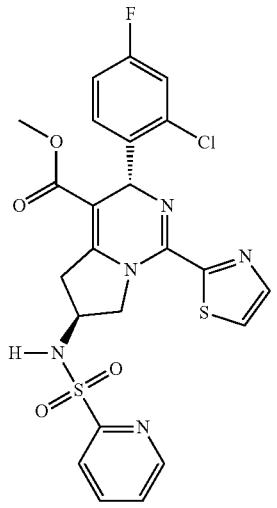 [SMILES: COC(=O)C1=C2C[C@H](NS(=O)(=O)c3ccccn3)CN2C(c2nccs2)=N[C@H]1c1ccc(F)cc1Cl] | optically pure | A |

| EXAMPLE | STRUCTURAL FORMULEA | STEREOCHEMISTRY | BIOACTIVITY |
|---|---|---|---|
| 201 | 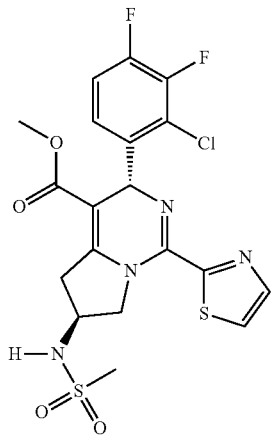 [SMILES: COC(=O)C1=C2C[C@H](NS(C)(=O)=O)CN2C(c2nccs2)=N[C@H]1c1ccc(F)c(F)c1Cl] | optically pure | A |
| 202 | 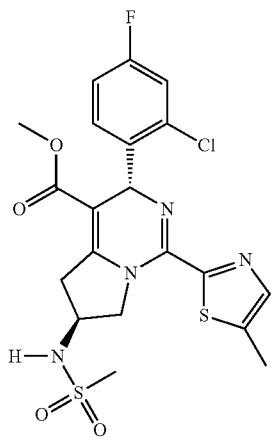 [SMILES: COC(=O)C1=C2C[C@H](NS(C)(=O)=O)CN2C(c2ncc(C)s2)=N[C@H]1c1ccc(F)cc1Cl] | optically pure | B |
| 203 | 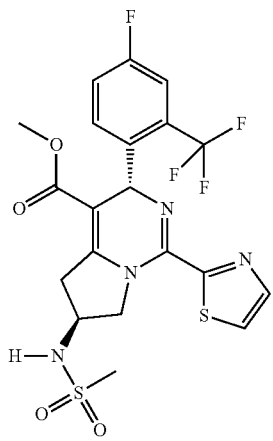 [SMILES: COC(=O)C1=C2C[C@H](NS(C)(=O)=O)CN2C(c2nccs2)=N[C@H]1c1ccc(F)cc1C(F)(F)F] | optically pure | B |

-continued
| EXAMPLE | STRUCTURAL FORMULEA | STEREOCHEMISTRY | BIOACTIVITY |
|---|---|---|---|
| 204 | 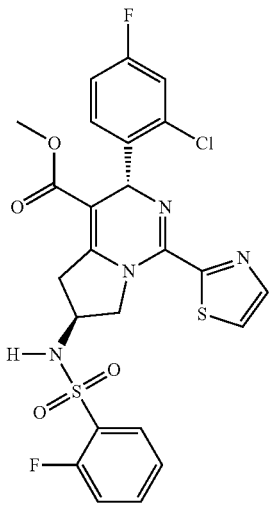 [SMILES: COC(=O)C1=C2C[C@H](NS(=O)(=O)c3ccccc3F)CN2C(c2nccs2)=N[C@H]1c1ccc(F)cc1Cl] | optically pure | A |
| 205 | 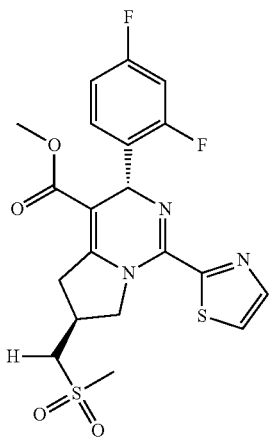 [SMILES: COC(=O)C1=C2C[C@H](CS(C)(=O)=O)CN2C(c2nccs2)=N[C@H]1c1ccc(F)cc1F] | optically pure | A |
| 206 | 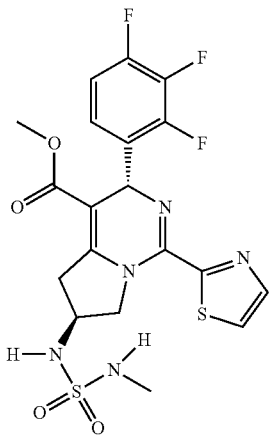 [SMILES: CNS(=O)(=O)N[C@H]1CC2=C(C(=O)OC)[C@H](c3ccc(F)c(F)c3F)N=C(c3nccs3)N2C1] | optically pure | A |

-continued

| EXAMPLE | STRUCTURAL FORMULEA | STEREOCHEMISTRY | BIOACTIVITY |
| --- | --- | --- | --- |
| 207 | (structure) | optically pure | A |
| 208 | (structure) | optically pure | A |
| 209 | (structure) | optically pure | A |

US 9,938,301 B2
-continued
| EXAMPLE | STRUCTURAL FORMULEA | STEREOCHEMISTRY | BIOACTIVITY |
|---|---|---|---|
| 210 | 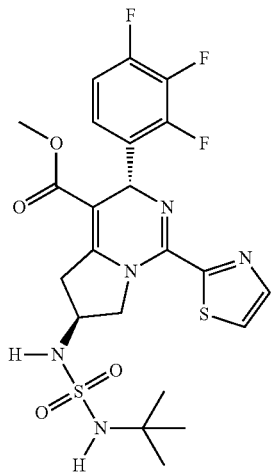 [SMILES: COC(=O)C1=C2C[C@H](NS(=O)(=O)NC(C)(C)C)CN2C(c2nccs2)=N[C@H]1c1ccc(F)c(F)c1F] | optically pure | A |
| 211 | 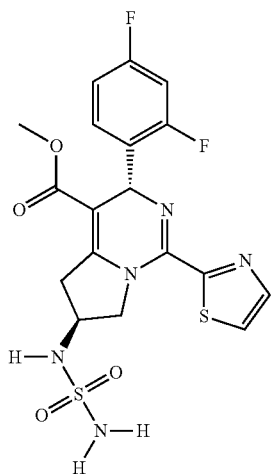 [SMILES: COC(=O)C1=C2C[C@H](NS(N)(=O)=O)CN2C(c2nccs2)=N[C@H]1c1ccc(F)cc1F] | optically pure | A |
| 212 | 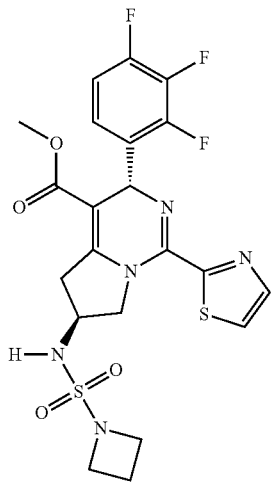 [SMILES: COC(=O)C1=C2C[C@H](NS(=O)(=O)N3CCC3)CN2C(c2nccs2)=N[C@H]1c1ccc(F)c(F)c1F] | optically pure | B |

| EXAMPLE | STRUCTURAL FORMULEA | STEREOCHEMISTRY | BIOACTIVITY |
|---|---|---|---|
| 213 | | optically pure | A |
| 214 | | optically pure | A |
| 215 | | optically pure | A |
| 216 | | optically pure | A |

| EXAMPLE | STRUCTURAL FORMULEA | STEREOCHEMISTRY | BIOACTIVITY |
|---|---|---|---|
| 217 | 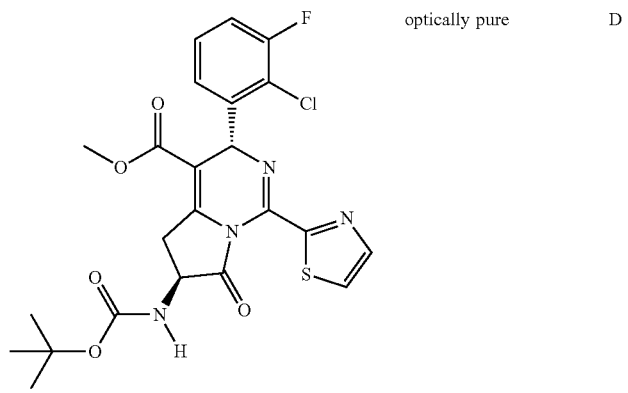 | optically pure | D |
| 218 | 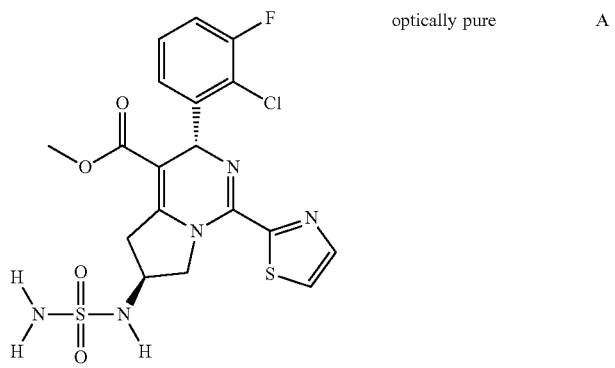 | optically pure | A |
| 219 | 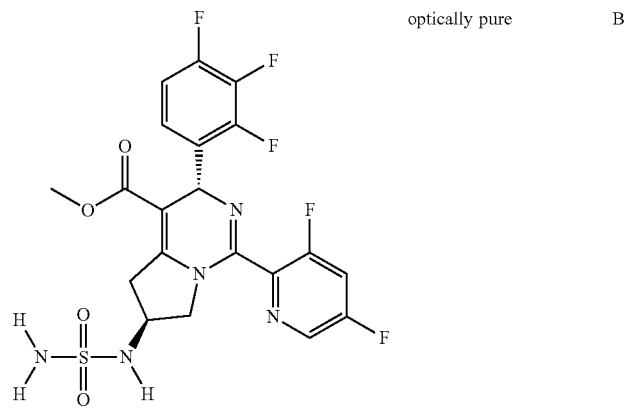 | optically pure | B |
| 220 | 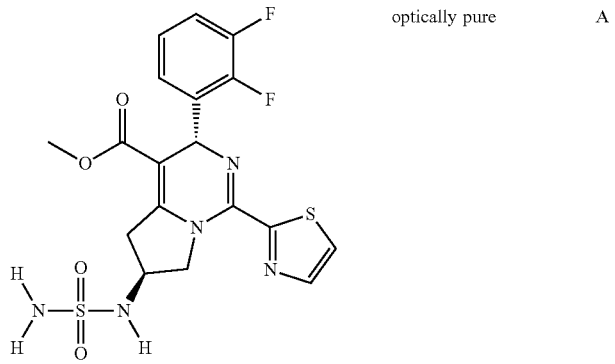 | optically pure | A |

EMBODIMENTS
The following examples were provided to describe the invention in more details, but the scope of the invention was not limited thereto.
Examples 1, 2
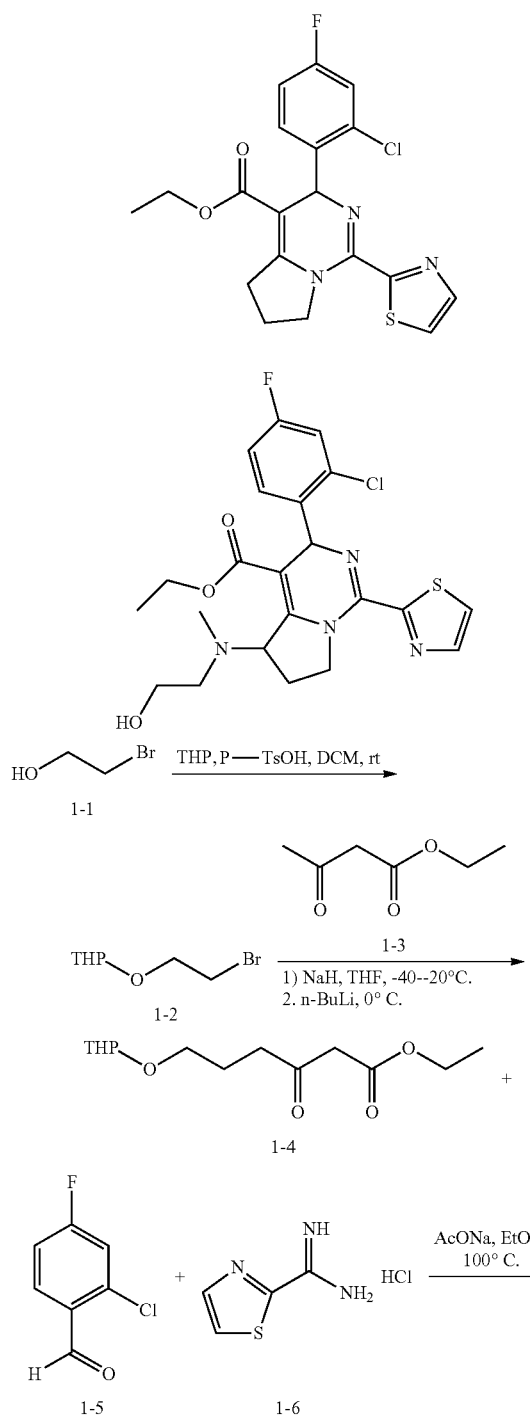
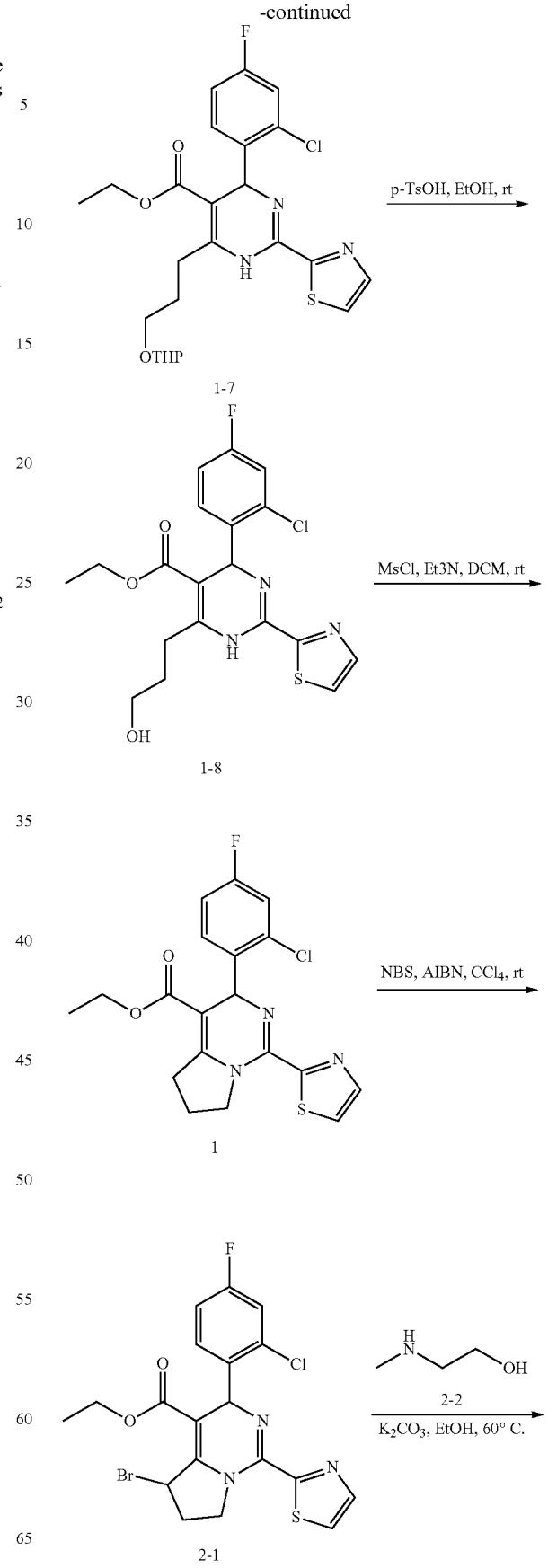

-continued

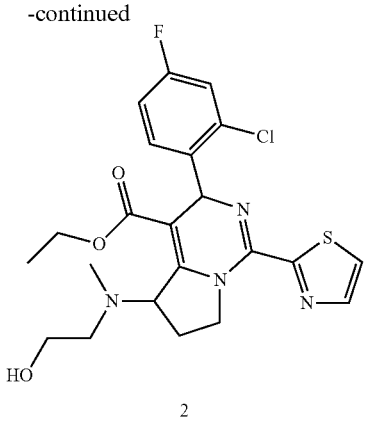

2

Step 1 (Synthesis of Compound 1-2)

Compound 1-1 (12.5 g, 100 mmol) was dissolved in methanol (30 mL), and THP (12.6 g, 150 mmol), p-TsOH (250 mg, 1.3 mmol) were added at room temperature, stirring at room temperature overnight. The reaction mixture was concentrated under reduced pressure and then purified by silica gel column chromatography with an eluent system (PE:EtOAc=30:1) to obtain the product 1-2, yield: 80%.

$^1$H NMR (400 MHz, CDCl$_3$) δ: 4.68 (t, J=3.6 Hz, 1H), 4.03 (td, J=6.4, 11.2 Hz, 1H), 3.90 (ddd, J=3.0, 8.4, 11.2 Hz, 1H), 3.73-3.82 (m, 1H), 3.45-3.58 (m, 3H), 1.80-1.91 (m, 1H), 1.70-1.79 (m, 1H), 1.51-1.63 (m, 4H).

Step 2 (Synthesis of Compound 1-4)

Sodium hydride (4.0 g, 100 mmol) was dissolved in anhydrous tetrahydrofuran (30 mL), and 1-3 (9.4 g, 72 mmol) was added at −40□, stirring at −20□ for 30 minutes. With the temperature being kept constant, n-butyllithium solution (40 mL, 2.5 N) was slowly added dropwise, after dropwise addition stirring at 0□ for 30 minutes. Compound 1-2 (10 g, 48 mmol) was dissolved in tetranolydrofuran (100 mL), and the solution was slowly added dropwise to the reaction mixture. The reaction mixture was stirred at 0□ for 2 hours, and the temperature was raised to room temperature stirring overnight. The reaction mixture was quenched with saturated ammonium chloride aqueous solution (1000 mL), and extracted with EtOAc (1000 mL×3).

The organic layer was washed with saturated saline solution (1000 mL×2). The organic phases were combined, dried over anhydrous sodium sulfate, and filtered. The filtrate was concentrated under reduced pressure, and purified by silica gel column chromatography with an eluent system (PE:EtOAc=20:1) to obtain 7.0 g product 1-4, yield: 56%.

$^1$H NMR (400 MHz, CDCl$_3$) δ: 4.50-4.61 (m, 1H), 4.20 (q, J=7.2 Hz, 2H), 3.69-3.89 (m, 2H), 3.32-3.57 (m, 4H), 2.58-2.75 (m, 2H), 1.91 (q, J=6.4 Hz, 2H), 1.75-1.84 (m, 1H), 1.63-1.75 (m, 2H), 1.51-1.57 (m, 3H), 1.23-1.33 (m, 3H).

Step 3 (Synthesis of Compound 1-7)

Compound 1-4 (4.3 g, 27 mmol) was dissolved in ethanol (20 mL), and compound 1-5 (7.0 g, 27 mmol), compound 1-6 (8.8 g, 54 mmol), sodium acetate (6.6 g, 81 mmol) were added. The temperature of the reaction mixture was slowly raised to reflux, and the reaction was stirred under reflux overnight. The reaction mixture was concentrated under reduced pressure and then extracted with EtOAc (500 mL×3). The organic layer was washed with saturated saline solution (1000 mL×2). The organic phases were combined, dried over anhydrous sodium sulfate, filtered. The filtrate was concentrated under reduced pressure, and purified by silica gel column chromatography with an eluent system (PE:EtOAc=10:1) to obtain 5.0 g product 1-7 (yellow solid), yield: 61%.

LCMS (ESI) m/z: 508.0 [M+H$^+$].

Step 4 (Synthesis of Compound 1-8)

Compound 1-7 (5.0 g, 10 mmol) was dissolved in ethanol (250 mL), and p-TsOH (5.5 g, 30 mmol) was added at room temperature, stirring at room temperature for 30 min. The reaction mixture was neutralized with saturated sodium bicarbonate aqueous solution (200 mL), extracted with EtOAc (500 mL×3). The organic phase was washed with water (300 mL×3), dried over anhydrous sodium sulfate, and filtered. The filtrate was concentrated under reduced pressure to obtain crude 5.5 g compound 1-8, yield: 85%.

LCMS(ESI) m/z: 423.9 [M+H$^+$].

Step 5 (Synthesis of Example 1)

Compound 1-8 (5.5 g, 13 mmol) was dissolved in anhydrous DCM (5 mL), and triethylamine (6.5 g, 65 mmol), methanesulfonyl chloride (7.4 g, 39 mmol) were added at 0□. After the addition, the mixture was raised to room temperature and stirred for 3 hours. The reaction mixture was poured into 300 mL water, and extracted with DCM (500 mL×3). The organic phases were combined, washed sequentially with water (50 mL×2), saturated sodium chloride solution (100 mL×2), dried over anhydrous sodium sulfate, filtered, and purified by silica gel column chromatography with an eluent system (PE:EtOAc=10:1) to obtain 2.0 g Example 1, yield: 47%.

NMR data of Example 1: $^1$H NMR (400 MHz, CDCl$_3$) δ: 7.81 (d, J=3.2 Hz, 1H), 7.37 (d, J=3.2 Hz, 1H), 7.28-7.32 (m, 1H), 7.12 (dd, J=2.4, 8.4 Hz, 1H), 6.92 (dt, J=2.4, 8.4 Hz, 1H), 6.19 (s, 1H), 4.20-4.45 (m, 2H), 4.01-4.11 (m, 2H), 3.40 (ddd, J=3.6, 8.4, 18.0 Hz, 1H), 3.06 (td, J=9.2, 18.0 Hz, 1H), 1.93-2.29 (m, 2H), 1.14 (t, J=7.2 Hz, 3H).

LCMS (ESI) m/z: 405.9 [M+H$^+$].

Step 6 (Synthesis of Compound 2-1)

Compound 1 (800 mg, 1.96 mmol) was dissolved in tetrachloromethane (20 mL), and at room temperature were added NBS (528 mg, 3.0 mmol) and AIBN (3.2 mg, 0.02 mmol). After the addition, the mixture was stirred at room temperature for 3 hours. The reaction mixture was concentrated under pressure, and purified by silica gel column chromatography with an eluent system (PE:EtOAc=10:1) to obtain 400 mg product 2-1, yield: 42%.

1H NMR (400 MHz, CDCl$_3$) δ: 7.77-7.88 (m, 1H), 7.34-7.48 (m, 2H), 7.08-7.18 (m, 1H), 6.87-7.00 (m, 1H), 6.17-6.25 (m, 1H), 6.00-6.08 (m, 1H), 4.99-5.12 (m, 1H), 4.19-4.32 (m, 1H), 4.02-4.17 (m, 2H), 2.37-2.47 (m, 2H), 1.08-1.18 (m, 3H).

Step 7 (Synthesis of Example 2)

Compound 2-1 (150 mg, 0.3 mmol) was dissolved in ethanol (5 mL), and at room temperature were added compound 2-2 (69 mg, 0.9 mmol), potassium carbonate (123 mg, 0.9 mmol). After the addition, the mixture was raised to 60□ and stirred for 3 hours. The reaction mixture was filtered. The filtrate was concentrated under reduced pressure, and extracted with DCM (50 mL×3). The organic phases were combined, sequentially washed with water (50 mL×2), saturated sodium chloride solution (100 mL×2), dried over anhydrous sodium sulfate, filtered, and purified by silica gel column chromatography with an eluent system (PE: EtOAc=10:1) to obtain 47 mg Example 2, yield: 33%.

NMR data of Example 2: $^1$H NMR (400 MHz, DMSO-$d_6$) δ: 7.81 (d, J=3.2 Hz, 1H), 7.38 (d, J=3.2 Hz, 1H), 7.26-7.31 (m, 1H), 7.13 (dd, J=2.4, 8.4 Hz, 1H), 6.93 (dt, J=2.4, 8.4 Hz, 1H), 6.29 (s, 1H), 4.92 (br. s., 1H), 4.38 (d, J=9.2 Hz, 2H), 4.04 (q, J=7.2 Hz, 2H), 3.54-3.79 (m, 2H), 3.28-3.35 (m, 1H), 2.52-2.58 (m, 2H), 2.74 (br. s., 1H), 2.31 (s., 3H), 2.01 (s, 1H), 1.02-1.12 (m, 3H).

LCMS (ESI) m/z: 479.0 [M+H$^+$].

Example 3

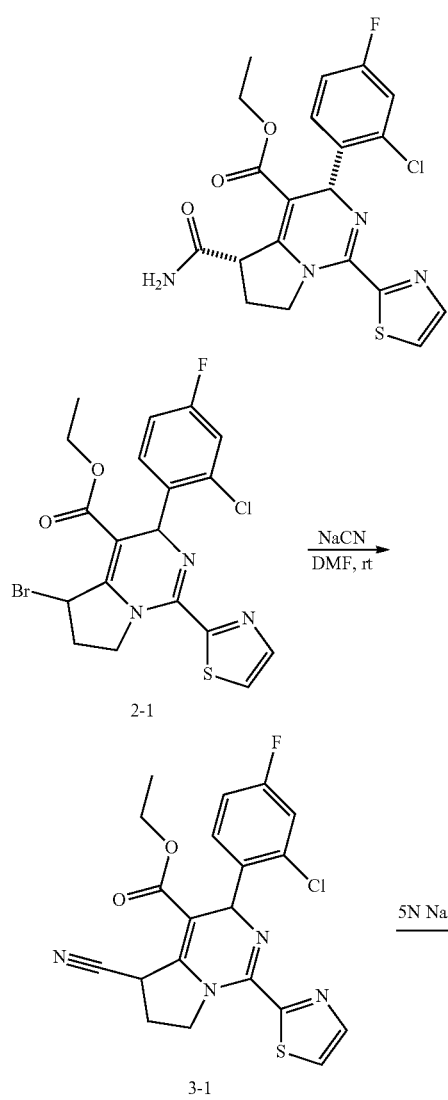

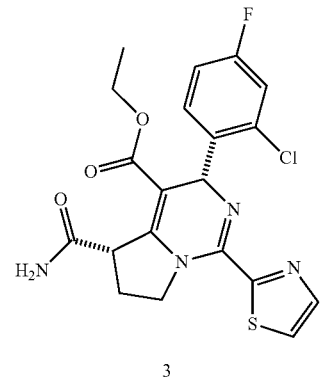

Step 1 (Synthesis of Compound 3-1)

Compound 2-1 (150 mg, 0.31 mmol) was dissolved in N,N-dimethylformamide (3 mL), and NaCN (54 mg, 2.2 mmol) was added, stirring at room temperature for 3 hours. The reaction mixture was extracted with EtOAc (10 mL×3). The organic phases were combined, sequentially washed with water (10 mL×2), saturated sodium chloride solution (10 mL×3), dried over anhydrous sodium sulfate, filtered, and purified by silica gel column chromatography with an eluent system (PE:EtOAc=10:1) to obtain 50 mg compound 3-1, yield: 37%.

LCMS (ESI) m/z: 430.9 [M+H$^+$].

Step 2 (Synthesis of Example 3)

Compound 3-1 (50 mg, 0.11 mmol) was dissolved in anhydrous ethanol (0.8 mL), and DMSO (0.2 mL), NaOH solution (0.1 mL, 5N), oxydol (0.1 mL) were added, stirring at room temperature for 3 hours. The reaction mixture was concentrated under reduced pressure and then extracted with DCM (30 mL×3). The organic phases were combined, sequentially washed with water (20 mL×2), saturated sodium chloride solution (20 mL×2), dried over anhydrous sodium sulfate, filtered, and purified by silica gel column chromatography with an eluent system (PE:EtOAc=10:1) to obtain 10 mg Example 3, yield: 19%.

NMR data of Example 3: $^1$H NMR (400 MHz, CDCl$_3$) δ: 7.83 (d, J=3.2 Hz, 1H), 7.45 (br. s., 1H), 7.38 (d, J=3.2 Hz, 1H), 7.30 (d, J=6.4 Hz, 1H), 7.16 (dd, J=2.4, 8.4 Hz, 1H), 6.95 (dt, J=2.4, 8.4 Hz, 1H), 6.21 (s, 1H), 5.34 (br. s., 1H), 4.61 (d, J=7.6 Hz, 1H), 4.51-4.59 (m, 1H), 4.34-4.44 (m, 1H), 4.00-4.17 (m, 2H), 2.72 (dd, J=6.0, 12.4 Hz, 1H), 2.09-2.23 (m, 1H), 1.12 (t, J=7.2 Hz, 3H).

LCMS (ESI) m/z: 449.1 [M+H$^+$].

Example 4

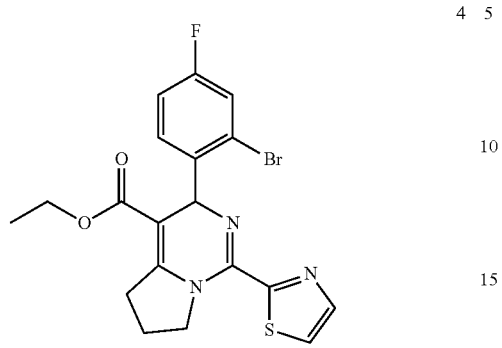

Example 4 was prepared according to the method as described in Example 1.

NMR data of Example 4: $^1$H NMR (400 MHz, CDCl$_3$) δ: 7.79 (d, J=3.2 Hz, 1H), 7.35 (d, J=3.2 Hz, 1H), 7.30 (dd, J=2.8, 8.4 Hz, 1H), 7.26 (d, J=6.4 Hz, 1H), 6.95 (dt, J=2.8, 8.4 Hz, 1H), 6.15 (s, 1H), 4.19-4.43 (m, 2H), 3.97-4.10 (m, 2H), 3.40 (ddd, J=3.6, 8.4, 18.0 Hz, 1H), 3.06 (td, J=9.2, 18.0 Hz, 1H), 1.97-2.21 (m, 2H), 1.13 (t, J=7.2 Hz, 3H).

LCMS (ESI) m/z: 449.9 [M+H$^+$].

Example 5

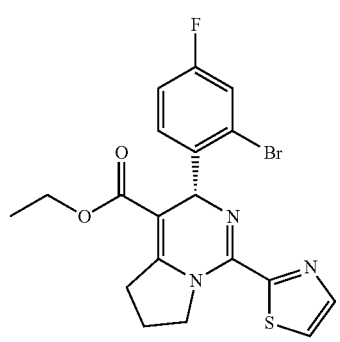

Example 5 was prepared according to the method as described in Example 1, and obtained by Prep-SFC separation.

NMR data of Example 5: $^1$H NMR (400 MHz, DMSO-d$_6$) δ: 7.79 (d, J=3.2 Hz, 1H), 7.35 (d, J=3.2 Hz, 1H), 7.30 (dd, J=2.8, 8.4 Hz, 1H), 7.26 (d, J=6.0 Hz, 1H), 6.95 (dt, J=2.8, 8.4 Hz, 1H), 6.15 (s, 1H), 4.19-4.43 (m, 2H), 3.97-4.10 (m, 2H), 3.40 (ddd, J=3.6, 8.4, 18.0 Hz, 1H), 3.06 (td, J=9.2, 18.4 Hz, 1H), 1.97-2.21 (m, 2H), 1.13 (t, J=7.2 Hz, 3H).

LCMS (ESI) m/z: 449.9 [M+H$^+$].

Examples 6, 7

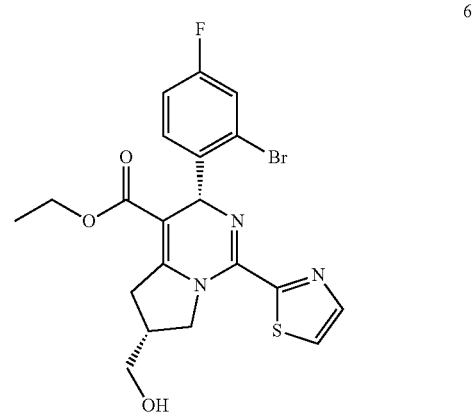

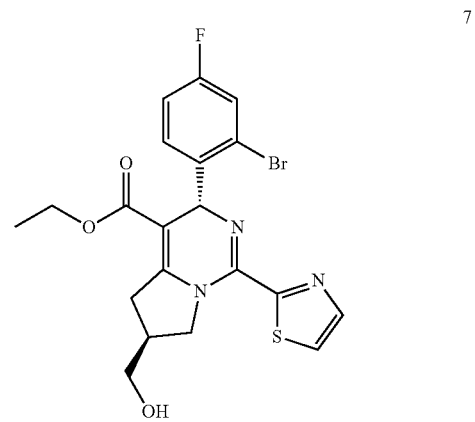

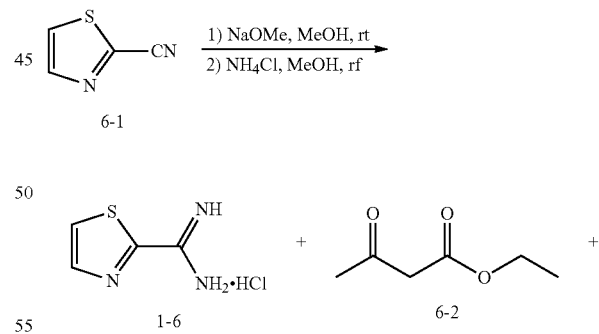

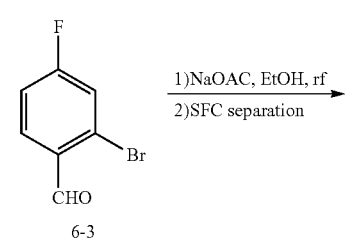

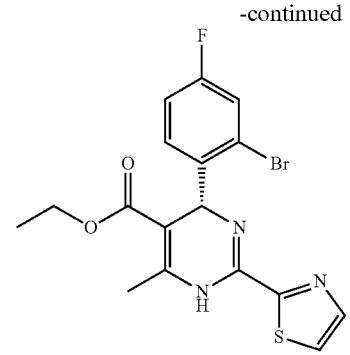

6-4

NBS, AIBN, CCl₄,
50° C.
→

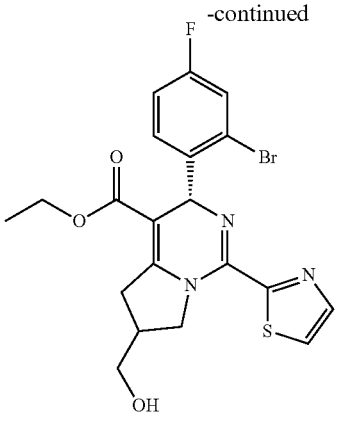

6-9

SFC separation →

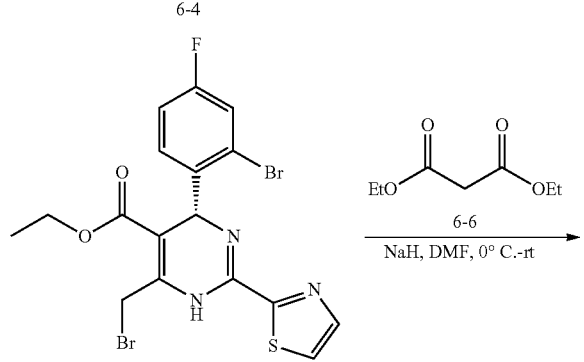

6-5

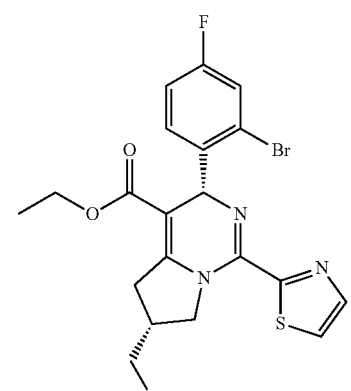

6

6-6

NaH, DMF, 0° C.-rt
→

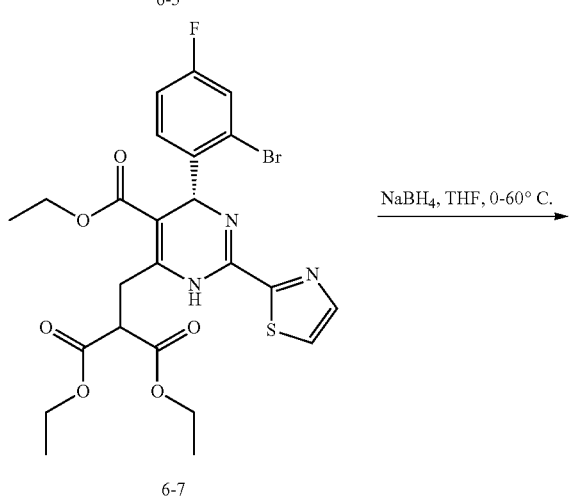

6-7

NaBH₄, THF, 0-60° C.
→

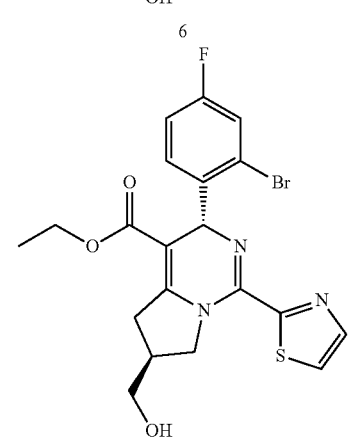

7

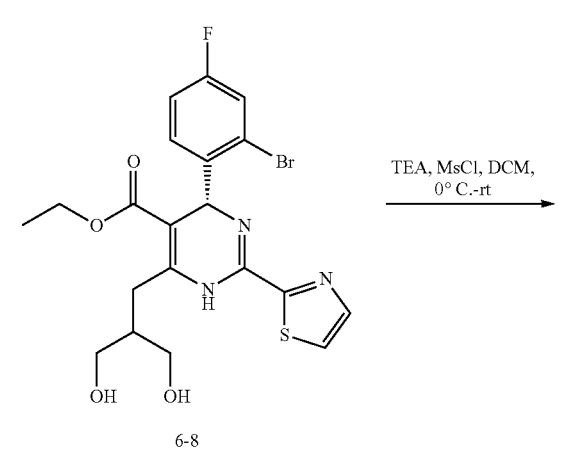

6-8

TEA, MsCl, DCM,
0° C.-rt
→

Step 1 (Synthesis of Compound 1-6)

Compound 6-1 (6.0 g, 54.5 mmol) was dissolved in methanol (20 mL), and at room temperature was added in portions sodium methoxide (2.9 g, 54.5 mmol), stirring at room temperature for 3 hours. Ammonium chloride (11.7 g, 218 mmol) was added in portions into the reaction mixture. After the addition, the temperature was slowly raised to reflux, and the reaction was stirred under reflux overnight. The reaction mixture was cooled to room temperature, and concentrated under reduced pressure to obtain product 1-6 as white solid, the product was used directly in the next reaction without purification, yield: 80%.

LCMS (ESI) m/z: 128.2 [M+H⁺].

Step 2 (Synthesis of Compound 6-4)

Compound 1-6 (2.0 g, 12.2 mmol) was dissolved in ethanol (50 mL), and compound 6-2 (0.98 mL, 9.8 mmol), compound 6-3 (2.0 g, 9.8 mmol), sodium acetate (1.0 g, 12.2 mmol) were added. The temperature of the reaction mixture was slowly raised to reflux, stirring under reflux overnight. The reaction mixture was concentrated under reduced pressure, and then EtOAc (100 mL) was added. The organic layer was washed with saturated saline solution (100 mL×2). The organic phases were combined, dried over anhydrous sodium sulfate, and filtered. The filtrate was concentrated under reduced pressure, and purified by silica gel column chromatography with an eluent system (PE:EtOAc=10:1) and separated by SFC to obtain compound 6-4 as yellow solid, yield: 40%.

$^1$H NMR (400 MHz, CDCl$_3$) δ: 9.88 (s, 1H), 7.95 (d, J=3.2 Hz, 1H), 7.86 (d, J=3.2 Hz, 1H), 7.53 (dd, J=2.4, 8.4 Hz, 1H), 7.34 (dd, J=6.4, 8.8 Hz, 1H), 7.22 (dt, J=2.4, 8.4 Hz, 1H), 5.95 (s, 1H), 3.92 (q, J=7.2 Hz, 2H), 2.45 (s, 3H), 1.06-0.97 (m, 3H).

LCMS (ESI) m/z: 425.8 [M+H$^+$].

Step 3 (Synthesis of Compound 6-5)

Compound 6-4 (2.08 g, 4.9 mmol) was dissolved in tetrachloromethane (30 mL), and NBS (920 mg, 5.2 mmol) and AIBN (81 mg, 0.49 mmol) were added at room temperature. After the addition, the mixture was raised to 50☐, and stirred until 6-4 completely reacted. The reaction mixture was cooled to room temperature, concentrated under pressure, and purified by silica gel column chromatography with an eluent system (PE:EtOAc=10:1) to obtain product 6-5 as yellow solid, yield: 64%.

1H NMR (400 MHz, CDCl3) δ: 7.83 (d, J=3.2 Hz, 1H), 7.52 (d, J=3.2 Hz, 2H), 7.39 (dd, J=6.0, 8.4 Hz, 1H), 7.31 (dd, J=2.4, 8.0 Hz, 1H), 7.01 (dt, J=2.4, 8.0 Hz, 1H), 6.06 (d, J=2.4 Hz, 1H), 4.92 (d, J=8.4 Hz, 1H), 4.58 (d, J=8.4 Hz, 1H), 4.10 (q, J=7.2 Hz, 2H), 1.14 (t, J=7.2 Hz, 3H).

Step 4 (Synthesis of Compound 6-7)

Compound 6-6 (1.27 g, 7.94 mmol) was dissolved in anhydrous N', N-dimethylformamide (100 mL), and sodium hydride (238 mg, 5.96 mmol) was added in portions at room temperature, stirring at room temperature for 15 minutes. Compound 6-5 (2.00 g, 3.97 mmol) was added and stirred at room temperature for 3 hours. The reaction mixture was quenched with saturated ammonium chloride aqueous solution (50 mL), and extracted with EtOAc (100 mL×3). The organic phase was washed with water (50 mL×3), dried over anhydrous sodium sulfate, and filtered. The filtrate was concentrated under reduced pressure, and purified by silica gel column chromatography with an eluent system (PE: EtOAc=10:1) to obtain 1.76 g compound 6-7, yield: 76%.

LCMS (ESI) m/z: 583.7 [M+H$^+$].

Step 5 (Synthesis of Compound 6-8)

Compound 6-7 (1.76 g, 3.02 mmol) was dissolved in anhydrous tetrahydrofuran (50 mL), and sodium borohydride (571 mg, 15.1 mmol) was slowly added at 0☐. After the addition, the temperature was raised to 60☐, and the reaction was undergoing at 60☐ for 18 hours. The reaction mixture was cooled to room temperature, and extracted with DCM (100 mL×3). The organic phase was washed with water (60 mL×3), dried over anhydrous sodium sulfate, and filtered. The filtrate was concentrated under reduced pressure, and purified by silica gel column chromatography with an eluent system (DCM:methanol=20:1) to obtain the product 780 mg compound 6-8, yield: 39%.

LC/MS (ESI) m/z: 521.7 [M+Na$^+$].

Step 6 (Synthesis of Compound 6-9)

Compound 6-8 (780 mg, 1.57 mmol) was dissolved in anhydrous DCM (40 mL), and at 0☐ were added triethylamine (318 mg, 3.14 mmol), methanesulfonyl chloride (270 mg, 2.36 mmol). The temperature remained, the mixture was stirred for 2 hours, and then raised to room temperature, stirred for 6 hours. The reaction mixture was poured into water (30 mL), and extracted with DCM (30 mL×3). The organic phases were combined, sequentially washed with water (10 mL×2), saturated sodium chloride solution (10 mL×2), dried over anhydrous sodium sulfate, filtered, and purified by silica gel column chromatography with an eluent system (PE:EtOAc=10:1) to obtain the product 340 mg compound 6-9, yield: 39%.

LCMS(ESI) m/z: 481.8 [M+H$^+$].

Step 7 (Synthesis of Compounds 6, 7)

Compound 6-9 (340 mg) was separated by preparative SFC to obtain chirally pure 47 mg Example 6, 34 mg Example 7.

NMR data of Example 6: $^1$H NMR (400 MHz, CDCl$_3$) δ: 7.81 (d, J=3.2 Hz, 1H), 7.38 (d, J=3.2 Hz, 1H), 7.32 (dd, J=2.8, 8.4 Hz, 1H), 7.29 (s, 1H), 6.96 (dt, J=2.8, 8.4 Hz, 1H), 6.16 (s, 1H), 4.45 (dd, J=7.2, 11.6 Hz, 1H), 4.31 (dd, J=3.2, 11.6 Hz, 1H), 4.01-4.11 (m, 2H), 3.73-3.80 (m, 1H), 3.64-3.72 (m, 1H), 3.23-3.29 (m, 2H), 2.68 (d, J=3.2 Hz, 1H), 1.67 (t, J=5.2 Hz, 1H), 1.15 (t, J=7.2 Hz, 3H).

LCMS (ESI) m/z: 481.8 [M+H$^+$].

NMR data of Example 7: $^1$H NMR (400 MHz, CDCl$_3$) δ: 7.81 (d, J=3.2 Hz, 1H), 7.38 (d, J=3.2 Hz, 1H), 7.33 (dd, J=2.8, 8.4 Hz, 1H), 7.25 (s, 1H), 6.97 (dt, J=2.4, 8.4 Hz, 1H), 6.16 (s, 1H), 4.43 (dd, J=7.6, 11.2 Hz, 1H), 4.23 (dd, J=7.6, 11.2 Hz, 1H), 4.00-4.10 (m, 2H), 3.78-3.86 (m, 1H), 3.72 (br. s., 1H), 3.47 (dd, J=8.0, 18.0 Hz, 1H), 2.95 (dd, J=8.4, 18.0 Hz, 1H), 2.63-2.74 (m, 1H), 1.83 (br. s., 1H), 1.15 (t, J=7.2 Hz, 3H).

LCMS (ESI) m/z: 481.8 [M+H$^+$].

Examples 8, 9

8

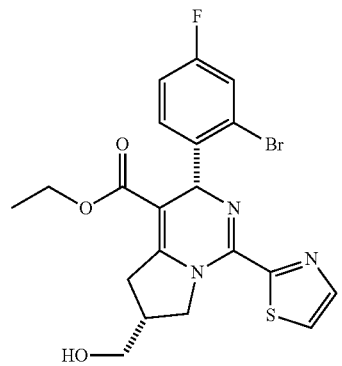

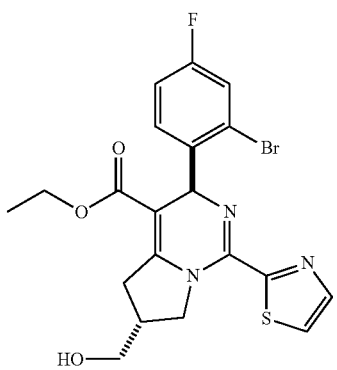

9

Examples 8, 9 were prepared according to the method as described in Examples 6, 7 and obtained by HPLC separation.

NMR data of Example 8: $^1$H NMR (400 MHz, CDCl$_3$) δ: 7.81 (d, J=3.0 Hz, 1H), 7.37 (d, J=3.0 Hz, 1H), 7.29-7.34 (m, 1H), 7.26 (br. s., 1H), 6.96 (dt, J=2.5, 8.2 Hz, 1H), 6.16 (s, 1H), 4.45 (dd, J=7.2, 11.5 Hz, 1H), 4.31 (dd, J=2., 11.5 Hz, 1H), 4.06 (q, J=6.6 Hz, 2H), 3.62-3.81 (m, 2H), 3.22-3.28 (m, 2H), 2.61-2.73 (m, 1H), 1.66 (t, J=5 Hz, 1H), 1.15 (t, J=7.2 Hz, 3H).

LCMS (ESI) m/z: 479.8 [M+H$^+$].

NMR data of Example 9: $^1$H NMR (400 MHz, CDCl$_3$) δ: 7.81 (d, J=3.0 Hz, 1H), 7.38 (d, J=3.2 Hz, 1H), 7.33 (dd, J=2.5, 8.2 Hz, 1H), 7.29 (br. s., 1H), 7.25 (s, 1H), 6.94-7.01 (m, 1H), 6.16 (s, 1H), 4.42 (dd, J=7.5, 11.0 Hz, 1H), 4.23 (dd, J=7.8, 11.29 Hz, 1H), 4.01-4.10 (m, 2H), 3.79-3.86 (m, 1H), 3.68-3.77 (m, 1H), 3.47 (dd, J=8.0, 18.08 Hz, 1H), 2.95 (dd, J=8.5, 18.0 Hz, 1H), 2.64-2.76 (m, 1H), 1.11-1.18 (m, 3H).

LCMS (ESI) m/z: 479.8 [M+H$^+$].

Example 10

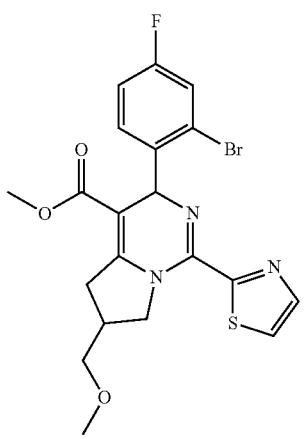

10

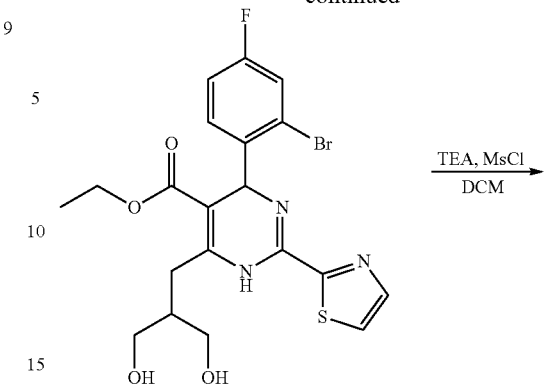

10-1

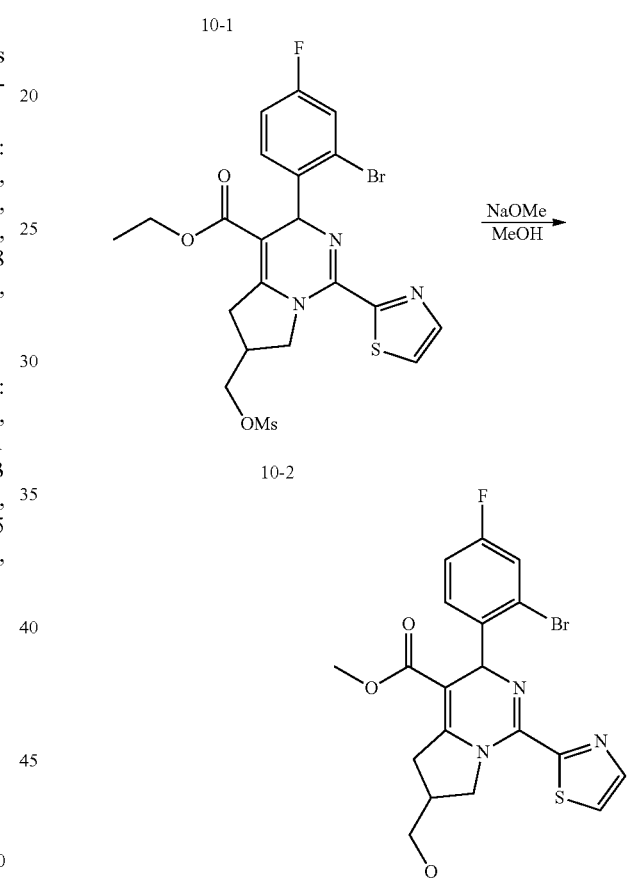

Step 1 (Synthesis of Compound 10-2)

Compound 10-1 (the same synthetic method as that of compound 6-8) (200 mg, 0.40 mmol) was dissolved in (5 mL) anhydrous DCM, and at room temperature were added triethylamine (406 mg, 4.01 mmol), methanesulfonyl chloride (460 mg, 4.01 mmol). The reaction mixture was stirred at room temperature overnight, and extracted with (50 mL×3) DCM. The organic phases were combined, sequentially washed with water (30 mL×2), saturated sodium chloride solution (30 mL×2), dried over anhydrous sodium sulfate, filtered, and concentrated under reduced pressure to obtain 150 mg compound 10-2.

LCMS (ESI) m/z: 557.6 [M+H$^+$].

Step 2 (Synthesis of Example 10)

Compound 10-2 (100 mg, 0.18 mmol) was dissolved in (3 mL) anhydrous methanol, and sodium methoxide (48 mg, 0.90 mmol) was added at room temperature. The reaction mixture was stirred under reflux overnight, concentrated under reduced pressure, and then extracted with (50 mL×3) DCM. The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=3:1) to obtain 6 mg Example 10, yield: 7%.

$^1$H NMR (400 MHz, CDCl$_3$) δ: 7.81 (d, J=3.0 Hz, 1H), 7.37 (d, J=3.0 Hz, 1H), 7.28-7.35 (m, 2H), 6.96 (dt, J=2.5, 8.2 Hz, 1H), 6.14 (s, 1H), 4.44-4.56 (m, 1H), 4.22 (dd, J=2.5, 11.5 Hz, 1H), 3.62 (s, 3H), 3.41-3.56 (m, 2H), 3.40 (s, 3H), 3.17-3.30 (m, 2H), 2.72 (br. s., 1H).

LCMS (ESI) m/z: 479.8 [M+H$^+$].

Examples 11, 12

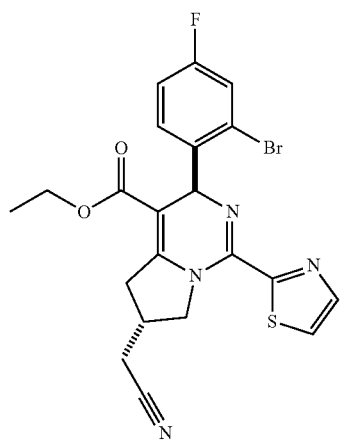

11

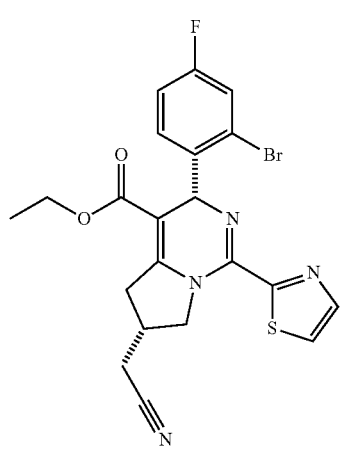

12

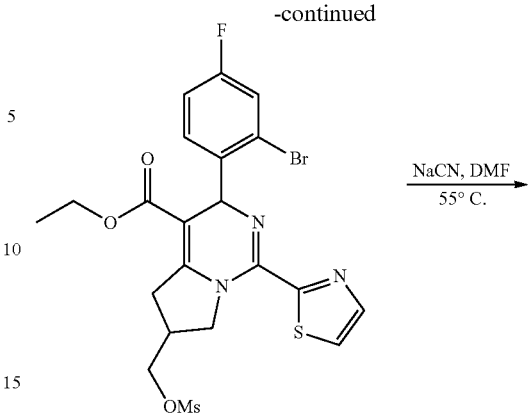

10-2

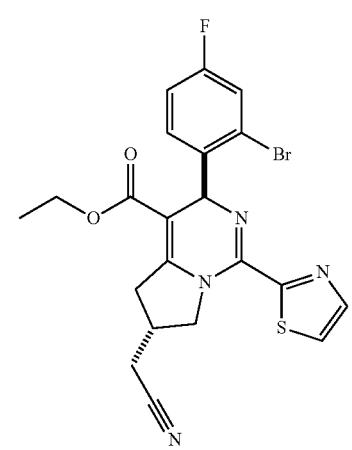

11

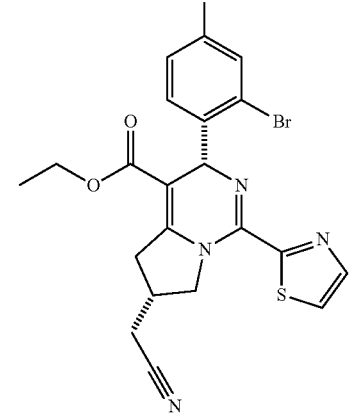

12

Compound 10-2 (30 mg, 0.05 mmol) was dissolved in (0.5 mL) anhydrous DMF, and NaCN (4.0 mg, 0.08 mmol) was added. The temperature was raised to 800, the reaction mixture was stirred at this temperature overnight and then extracted with (10 mL×3) EtOAc. The organic phases were combined, sequentially washed with water (10 mL×2), saturated sodium chloride solution (10 mL×3), dried over anhydrous sodium sulfate, filtered, and purified by silica gel column chromatography with an eluent system (PE: EtOAc=10:1) to obtain 12 mg Example 11, 8 mg Example 12, yield: 70%.

NMR data of Example 11: $^1$H NMR (400 MHz, CDCl$_3$) δ: 7.82 (d, J=3.0 Hz, 1H), 7.39 (d, J=3.0 Hz, 1H), 7.33 (dd, J=2.2, 8.2 Hz, 1H), 7.22-7.26 (m, 1H), 6.97 (dt, J=2.5, 8.2 Hz, 1H), 6.16 (s, 1H), 4.66 (dd, J=7.2, 11.2 Hz, 1H), 4.15 (dd, J=8.5, 11.0 Hz, 1H), 4.07 (dq, J=3.6, 7.0 Hz, 2H), 3.68 (dd, J=7.8, 17.8 Hz, 1H), 2.94 (dd, J=9.0, 17.6 Hz, 1H), 2.75-2.86 (m, 1H), 2.64 (d, J=6.4 Hz, 2H), 1.15 (t, J=7.2 Hz, 3H).

LCMS (ESI) m/z: 488.9 [M+H$^+$].

NMR data of Example 12: $^1$H NMR (400 MHz, CDCl$_3$) δ: 7.82 (d, J=3.6 Hz, 1H), 7.39 (d, J=3.0 Hz, 1H), 7.33 (dd, J=2.5, 8.0 Hz, 1H), 7.29 (br. s., 1H), 7.00 (dt, J=2.4, 8.2 Hz, 1H), 6.17 (s, 1H), 4.63 (dd, J=7.0, 11.6 Hz, 1H), 4.30 (dd, J=3.7, 11.8 Hz, 1H), 4.06 (q, J=7.0 Hz, 2H), 3.40-3.48 (m, 1H), 3.25 (dd, J=4.2, 18.3 Hz, 1H), 2.86 (d, J=3.6 Hz, 1H), 2.55-2.61 (m, 2H), 1.14 (t, J=7.0 Hz, 3H).

LCMS (ESI) m/z: 488.9 [M+H$^+$].

Examples 13, 14

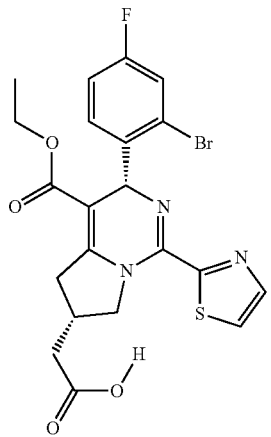

13

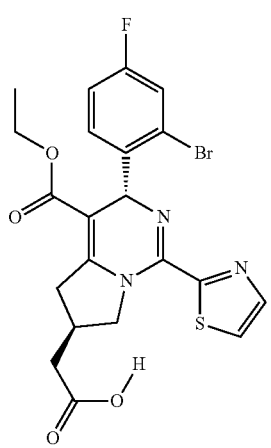

14

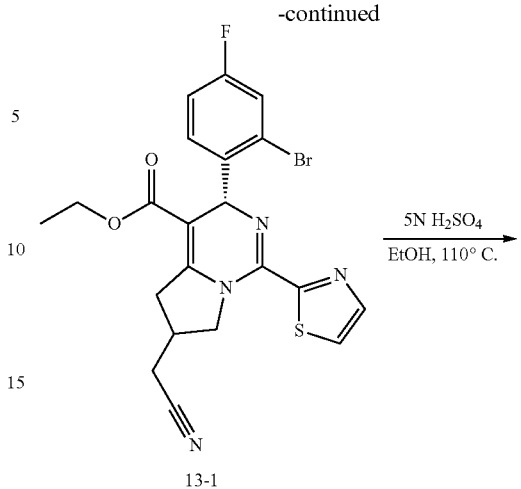

13-1

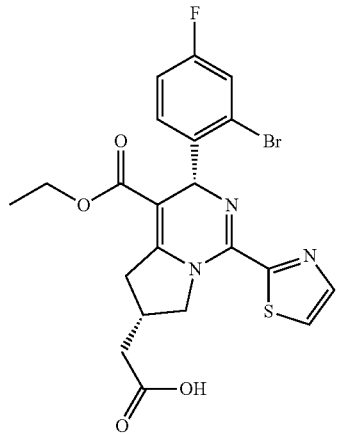

13

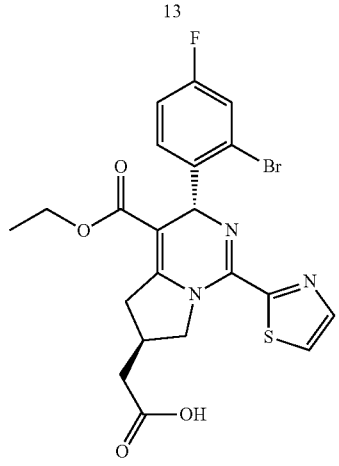

14

Compound 13-1 (the same synthetic method as that of 11, 12) (137 mg, 0.28 mmol) was dissolved in (3 mL) anhydrous ethanol, and 5N aq. sulfuric acid solution (2 mL) was added. The temperature was raised to 110□, the reaction mixture was stirred at this temperature for 3 hours, and then cooled to room temperature, neutralized with aq. sodium carbonate solution until pH=5, extracted with (10 mL×3) EtOAc. The organic phases were combined, sequentially washed with water (10 mL×2), saturated sodium chloride solution (10 mL×3), dried over anhydrous sodium sulfate, filtered, and purified by silica gel column chromatography with an eluent system (PE:EtOAc=10:1), and then separated by SFC to obtain 1 mg Example 13, 2 mg Example 14, yield: 2%.

NMR data of Example 13: $^1$H NMR (400 MHz, DMSO-d$_6$) δ: 7.94 (d, J=3.0 Hz, 1H), 7.85 (d, J=3.0 Hz, 1H), 7.53-7.57 (m, 1H), 7.31-7.38 (m, 1H), 7.26 (d, J=9.2 Hz, 1H), 5.98 (s, 1H), 4.41-4.48 (m, 1H), 3.98-4.03 (m, 1H), 3.94 (d, J=4.0 Hz, 2H), 3.26 (d, J=7.8 Hz, 2H), 2.92-3.02 (m, 2H), 1.94-2.04 (m, 1H), 1.04 (t, J=7.0 Hz, 3H).

LCMS (ESI) m/z: 508.0 [M+H$^+$].

NMR data of Example 14: $^1$H NMR (400 MHz, DMSO-d$_6$) δ: 7.93 (br. s., 1H), 7.85 (d, J=3.0 Hz, 1H), 7.55 (dd, J=2.4, 8.4 Hz, 1H), 7.40 (br. s., 1H), 7.22 (d, J=7.5 Hz, 1H), 5.96 (s, 1H), 4.53 (br. s., 1H), 3.95 (d, J=6.8 Hz, 2H), 3.78 (t, J=9.6 Hz, 1H), 3.50 (d, J=9.8 Hz, 2H), 2.68 (d, J=15.0 Hz, 2H), 1.93-2.03 (m, 1H), 1.05 (br. s., 3H).

LCMS (ESI) m/z: 508.0 [M+H$^+$].

Examples 15, 16

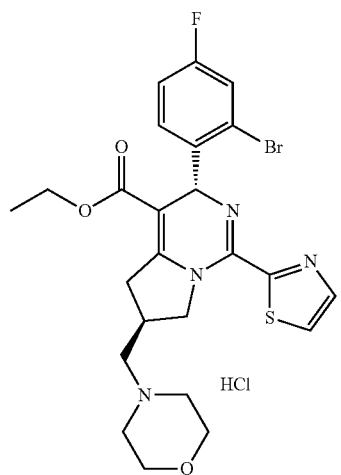

15

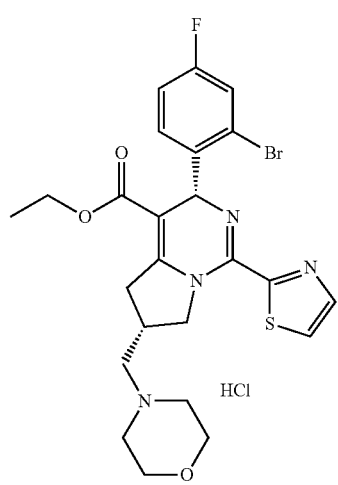

16

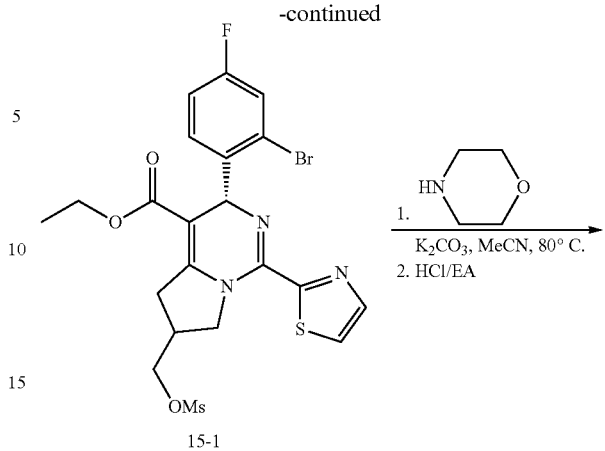

15-1

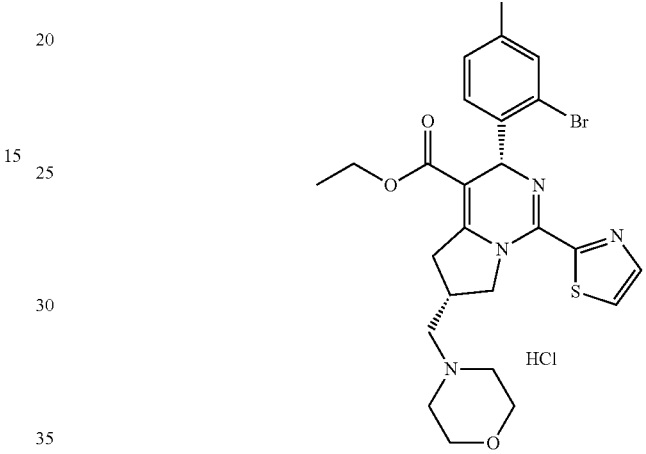

15

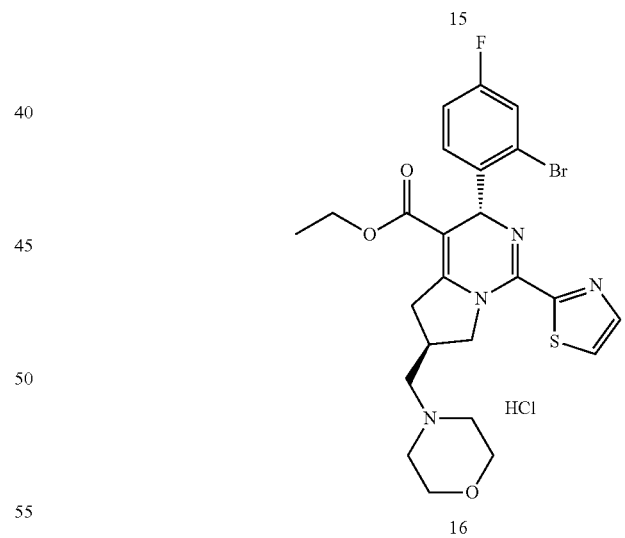

16

Compound 15-1 (the same synthetic method as that of compound 10-2) (80 mg, 0.14 mmol) was dissolved in (3 mL) acetonitrile, and potassium carbonate (39 mg, 0.29 mmol), morpholine (125 mg, 1.53 mmol) were added. The temperature was raised to 80□, the reaction mixture was stirred at this temperature overnight, and then extracted with EtOAc (30 mL×3). The organic phases were combined, sequentially washed with water (20 mL×2), saturated sodium chloride solution (20 mL×3), dried over anhydrous sodium sulfate, filtered, concentrated under reduced pressure and then separated by SFC to obtain 6 mg Example 15, 15 mg Example 16, yield: 35%.

Examples 15, 16 were separately dissolved in 1 mL EtOAc, and then 4 mL a solution of HCl in EtOAc was added respectively. The mixtures were stirred at 200 for 30 minutes, concentrated under reduced pressure, and lyophilized to provide Example 15, and Example 16 respectively.

NMR data of Example 15: $^1$H NMR (400 MHz, DMSO-$d_6$) δ: 10.94 (br. s., 1H), 7.91-8.02 (m, 2H), 7.57 (dd, J=2.4, 8.4 Hz, 1H), 7.47 (dd, J=6.2, 8.4 Hz, 1H), 7.20-7.31 (m, 1H), 6.00 (s, 1H), 4.57 (dd, J=7.4, 11.2 Hz, 1H), 4.18 (dd, J=5.2, 11.2 Hz, 2H), 3.91-4.03 (m, 5H), 3.78-3.91 (m, 3H), 3.31 (br. s., 2H), 2.93-3.19 (m, 4H), 1.06 (t, J=7.0 Hz, 3H).

LCMS (ESI) m/z: 549.1 [M+H$^+$].

NMR data of Example 16: $^1$H NMR (400 MHz, DMSO-$d_6$) δ: 11.19 (br. s., 1H), 7.89-7.98 (m, 2H), 7.57 (dd, J=2.5, 8.4 Hz, 1H), 7.45 (dd, J=6.5, 8.4 Hz, 1H), 7.22 (dt, J=2.5, 8.5 Hz, 1H), 5.97 (s, 1H), 4.64 (dd, J=7.8, 10.4 Hz, 1H), 4.14-4.32 (m, 1H), 3.93-4.03 (m, 4H), 3.82-3.92 (m, 3H), 3.66 (dd, J=7.5, 17.4 Hz, 2H), 3.33-3.37 (m, 2H), 2.96-3.15 (m, 3H), 2.84 (dd, J=10.2, 17.4 Hz, 1H), 1.08 (t, J=7.0 Hz, 3H).

LCMS (ESI) m/z: 549.1 [M+H$^+$].

Examples 17, 18

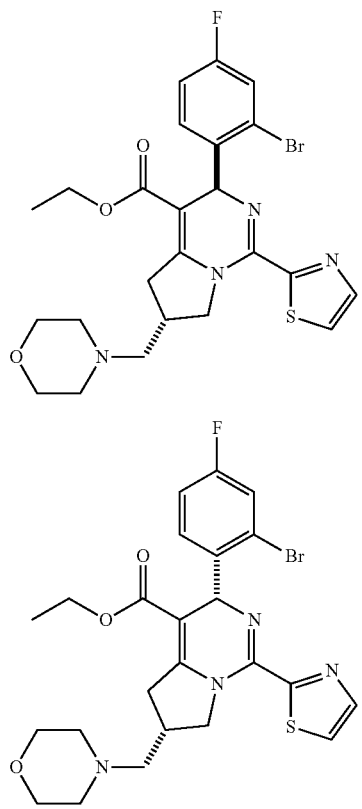

Examples 17, 18 were prepared according to the method as described in Examples 15, 16 and obtained by HPLC separation.

NMR data of Example 17: $^1$H NMR (400 MHz, DMSO-$d_6$) δ: 7.96 (d, J=3.6 Hz, 1H), 7.85 (d, J=3.0 Hz, 1H), 7.54 (d, J=6.0 Hz, 1H), 7.38-7.45 (m, 1H), 7.20 (t, J=8.2 Hz, 1H), 5.96 (s, 1H), 4.37-4.45 (m, 1H), 3.96 (q, J=7.0 Hz, 2H), 3.83-3.89 (m, 1H), 3.58 (br. s., 4H), 2.65-2.75 (m, 3H), 2.30-2.44 (m, 6H), 1.06 (t, J=7.0 Hz, 3H).

LCMS (ESI) m/z: 549.1 [M+H$^+$].

NMR data of Example 18: $^1$H NMR (400 MHz, DMSO-$d_6$) δ: 7.95 (d, J=3.0 Hz, 1H), 7.85 (d, J=3.0 Hz, 1H), 7.55 (d, J=6.4 Hz, 1H), 7.21-7.33 (m, 2H), 5.97 (s, 1H), 4.32 (dd, J=7.2, 10.8 Hz, 1H), 4.09 (d, J=8.0 Hz, 1H), 3.95 (q, J=7.0 Hz, 2H), 3.58 (br. s., 4H), 3.18 (dd, J=8.0, 18.0 Hz, 1H), 2.98-3.08 (m, 1H), 2.67 (br. s., 1H), 2.26-2.44 (m, 6H), 1.06 (t, J=7.0 Hz, 3H).

LCMS (ESI) m/z: 549.1 [M+H$^+$].

Examples 19, 20

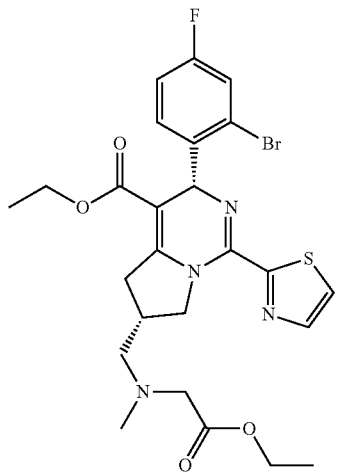

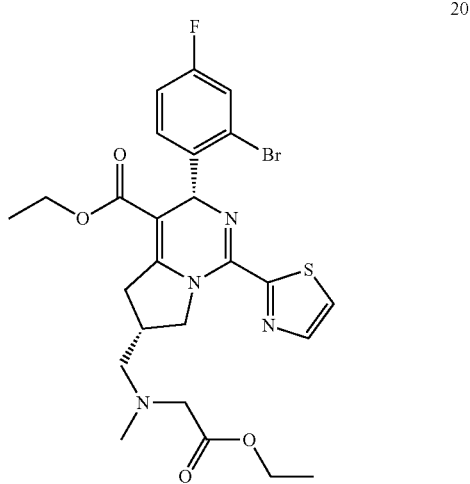

Examples 19, 20 were prepared according to the method as described in Examples 15, 16 and obtained by SFC separation.

NMR data of Example 19: $^1$H NMR (400 MHz, CDCl$_3$) δ: 7.82 (d, J=3.2 Hz, 1H), 7.36 (d, J=3.2 Hz, 1H), 7.32 (dd, J=2.4, 8.4 Hz, 1H), 7.23 (dd, J=6.4, 8.8 Hz, 1H), 6.97 (dt, J=2.4, 8.4 Hz, 1H), 6.15 (s, 1H), 4.46 (dd, J=6.4, 11.6 Hz, 1H), 4.20 (dd, J=2.8, 11.6 Hz, 1H), 4.14 (q, J=7.2 Hz, 2H), 4.06 (dq, J=1.6, 7.2 Hz, 2H), 3.26-3.40 (m, 2H), 3.17-3.24 (m, 2H), 2.54-2.75 (m, 3H), 2.45 (s, 3H), 1.24 (t, J=7.2 Hz, 3H), 1.15 (t, J=7.2 Hz, 3H).

LCMS (ESI) m/z: 580.9 [M+H$^+$].

NMR data of Example 20: $^1$H NMR (400 MHz, CDCl$_3$) δ 7.82 (d, J=3.2 Hz, 1H), 7.36 (d, J=3.2 Hz, 1H), 7.29-7.34 (m, 1H), 7.24-7.29 (m, 1H), 6.97 (dt, J=2.4, 8.4 Hz, 1H), 6.15 (s, 1H), 4.50 (dd, J=6.8, 11.6 Hz, 1H), 4.18 (q, J=7.2 Hz, 2H), 3.94-4.11 (m, 3H), 3.52 (dd, J=7.2, 17.6 Hz, 1H), 3.27-3.40 (m, 2H), 2.58-2.87 (m, 4H), 2.46 (s, 3H), 1.25 (t, J=7.2 Hz, 3H), 1.14 (t, J=7.2 Hz, 3H).

LCMS (ESI) m/z: 580.9 [M+H$^+$].

Examples 21, 22

NMR data of Example 22: $^1$H NMR (400 MHz, CDCl$_3$) δ 7.80 (d, J=3.2 Hz, 1H), 7.36 (d, J=3.2 Hz, 1H), 7.33 (dd, J=2.4, 8.4 Hz, 1H), 7.19-7.26 (m, 1H), 7.00 (dt, J=2.4, 8.4 Hz, 1H), 6.15 (s, 1H), 4.41 (dd, J=6.8, 11.6 Hz, 1H), 3.99-4.18 (m, 3H), 3.66 (s, 3H), 3.38-3.51 (m, 1H), 3.29 (dd, J=5.2, 8.4 Hz, 1H), 3.09-3.22 (m, 2H), 2.71-2.83 (m, 1H), 2.40-2.64 (m, 3H), 2.12 (d, J=4.4 Hz, 1H), 1.92-2.04 (m, 2H), 1.85 (d, J=7.6 Hz, 1H), 1.15 (t, J=7.2 Hz, 3H).

LCMS (ESI) m/z: 592.9 [M+H$^+$].

Example 23

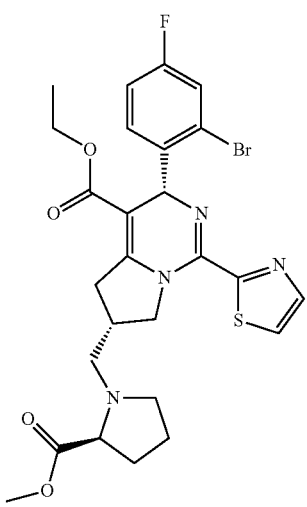

21

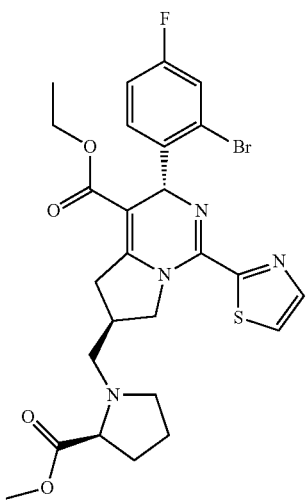

22

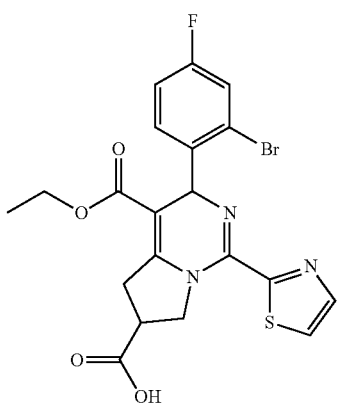

23

Examples 21, 22 were prepared according to the method as described in Examples 15, 16 and obtained by SFC separation.

NMR data of Example 21: $^1$H NMR (400 MHz, CDCl$_3$) δ 7.83 (d, J=3.2 Hz, 1H), 7.36 (d, J=3.2 Hz, 1H), 7.27-7.34 (m, 2H), 6.97 (dt, J=2.4, 8.4 Hz, 1H), 6.15 (s, 1H), 4.52 (dd, J=7.2, 11.2 Hz, 1H), 3.93-4.15 (m, 3H), 3.64-3.80 (m, 3H), 3.54 (dd, J=7.2, 17.6 Hz, 1H), 3.26 (dd, J=8.4, 14.0 Hz, 2H), 2.70-2.94 (m, 2H), 2.53-2.69 (m, 2H), 2.47 (q, J=7.6 Hz, 1H), 2.04-2.22 (m, 1H), 1.80-2.03 (m, 3H), 1.14 (t, J=7.2 Hz, 3H).

LCMS (ESI) m/z: 592.9 [M+H$^+$].

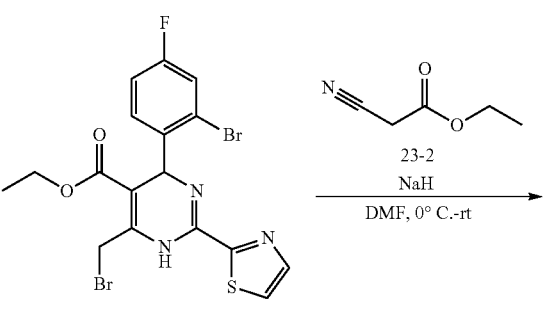

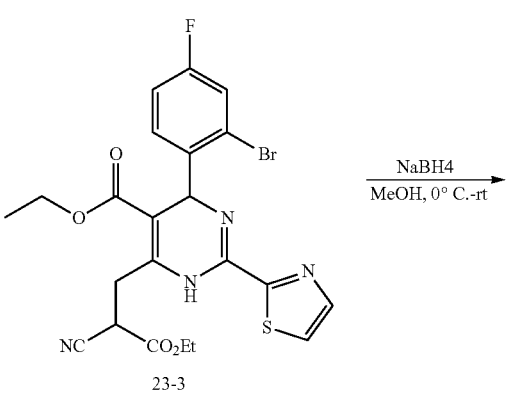

-continued

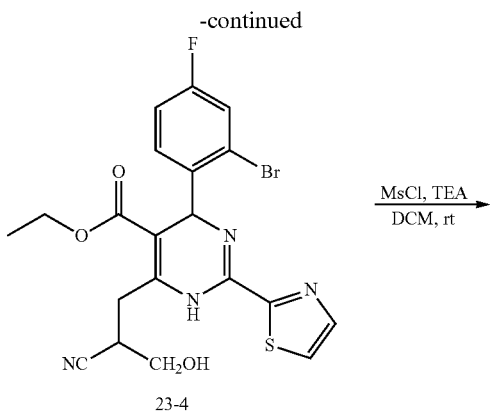

23-4

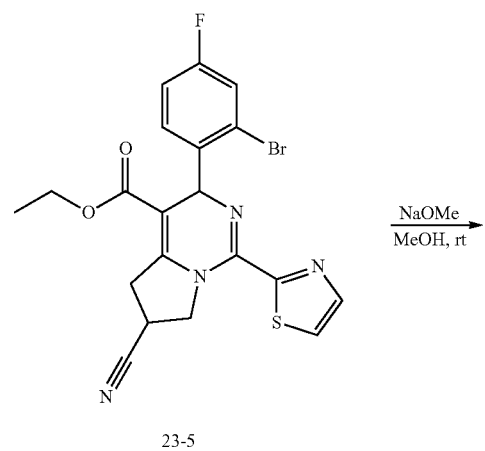

23-5

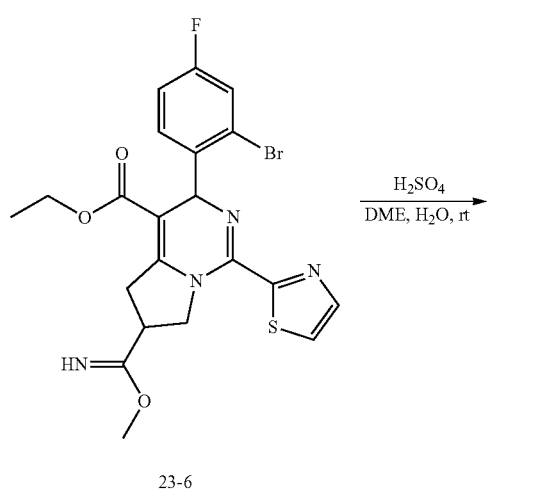

23-6

-continued

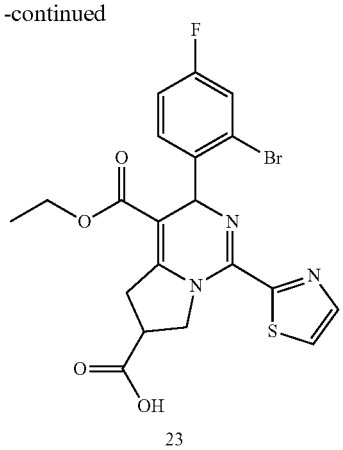

23

Step 1 (Synthesis of Compound 23-3)

Compound 23-2 (680 mg, 6 mmol) was dissolved in anhydrous N,N-dimethylformamide (50 mL), and sodium hydride (200 mg, 5 mmol) was slowly added at 0□, keeping the temperature and stirring for 30 minutes, then followed by adding compound 23-1 (the same synthetic method as that of compound 6-5) (2 g, 4 mmol). The mixture was stirred at room temperature for 2 hours, concentrated under reduced pressure and then extracted with DCM (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=10:1) to obtain the product 1.6 g compound 23-3, yield: 75%.

LCMS (ESI) m/z: 536.6 [M+H$^+$].

Step 2 (Synthesis of Compound 23-4)

Compound 23-3 (1.2 g, 2.24 mmol) was dissolved in anhydrous methanol (30 mL), and sodium borohydride (426 mg, 11.2 mmol) was slowly added at 0□, keeping the temperature and stirring for 30 minutes. The mixture was concentrated under reduced pressure and then extracted with DCM (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=10:1) to obtain the product 800 mg compound 23-4, yield: 74%.

LCMS (ESI) m/z: 494.7 [M+H$^+$].

Step 3 (Synthesis of Compound 23-5)

Compound 23-4 (800 mg, 1.6 mmol) was dissolved in anhydrous DCM (40 mL), and triethylamine (240 mg, 2.4 mmol), methanesulfonyl chloride (276 mg, 2.4 mmol) were slowly added at 0□. The temperature was raised to room temperature, the reaction mixture was stirred overnight, and then extracted with DCM (50 mL×3). The organic phases were combined, sequentially washed with water (30 mL×2), saturated sodium chloride solution (30 mL×2), dried over anhydrous sodium sulfate, filtered, and concentrated under reduced pressure to obtain 560 mg compound 23-5, yield: 74%.

LCMS (ESI) m/z: 476.7 [M+H$^+$].

Step 4 (Synthesis of Compound 23-6)

Compound 23-5 (180 mg, 0.38 mmol) was dissolved in anhydrous methanol (5 mL), and at room temperature was slowly added sodium methoxide (426 mg, 11.2 mmol). The mixture was stirred at room temperature under nitrogen atmosphere overnight, concentrated under reduced pressure and then extracted with DCM (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=10:1) to obtain 200 mg compound 23-6, yield: 90%.

LCMS (ESI) m/z: 509.0 [M+H⁺].

Step 5 (Synthesis of Example 23)

Compound 23-6 (200 mg, 0.39 mmol) was dissolved in ethylene glycol dimethyl ether (3 mL), and water (3 mL), sulfuric acid (0.3 mL) were added, the mixture was stirred at room temperature for 1 hours. Then the temperature was raised to 80□, the reaction underwent at this temperature for 6 hours. The reaction mixture was cooled to room temperature, concentrated under reduced pressure and then extracted with DCM (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=10:1) to obtain 6.6 mg Example 23, yield: 4%.

NMR data of Example 23: $^1$H NMR (400 MHz, MeOD-d$_4$) δ: 8.39-8.29 (m, 2H), 7.77 (dd, J=6.0, 8.4 Hz, 1H), 7.56 (dd, J=2.0, 8.0 Hz, 1H), 7.28 (t, J=6.8 Hz, 1H), 6.35 (s, 1H), 4.72-4.61 (m, 1H), 4.61-4.50 (m, 1H), 4.24-4.09 (m, 2H), 3.85-3.72 (m, 1H), 3.72-3.45 (m, 2H), 1.19 (t, J=7.2 Hz, 3H).

LCMS (ESI) m/z: 494.0 [M+H⁺].

Examples 24, 25

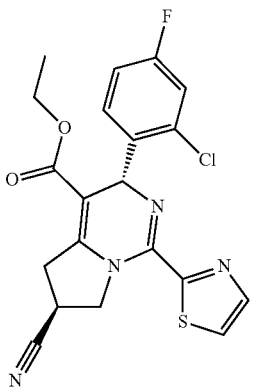

24

25

Examples 24, 25 were prepared according to the method of Example 23-5, and obtained by SFC separation.

NMR data of Example 24: $^1$H NMR (400 MHz, CDCl$_3$) δ: 7.86-7.80 (m, 1H), 7.40 (d, J=3.2 Hz, 1H), 7.23 (dd, J=6.0, 8.8 Hz, 1H), 7.13 (dd, J=2.4, 8.8 Hz, 1H), 6.91 (dt, J=2.8, 8.4 Hz, 1H), 6.18 (s, 1H), 4.83 (dd, J=7.6, 11.6 Hz, 1H), 4.56 (dd, J=8.4, 11.6 Hz, 1H), 4.06 (q, J=7.2 Hz, 2H), 3.80 (dd, J=7.6, 17.6 Hz, 1H), 3.50-3.27 (m, 2H), 1.21-1.08 (m, 3H).

LCMS (ESI) m/z: 431.0 [M+H⁺].

NMR data of Example 25: $^1$H NMR (400 MHz, CDCl$_3$) δ: 7.84 (d, J=3.2 Hz, 1H), 7.53 (d, J=3.2 Hz, 1H), 7.48-7.44 (m, 1H), 7.41 (dd, J=6.0, 8.8 Hz, 1H), 7.16-7.12 (m, 1H), 6.98 (dt, J=2.4, 8.4 Hz, 1H), 6.16-6.06 (m, 1H), 6.01 (s, 1H), 5.98 (s, 1H), 4.12-4.06 (m, 2H), 4.06-4.00 (m, 1H), 3.96-3.87 (m, 1H), 1.13 (t, J=7.2 Hz, 3H).

LCMS (ESI) m/z: 431.0 [M+H⁺].

Examples 26, 27

26

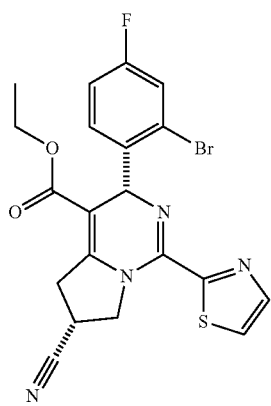
Examples 26, 27 were obtained from HPLC separation of 23-5.
NMR data of Example 26: $^1$H NMR (400 MHz, DMSO-$d_6$) δ: 7.98 (d, J=3.2 Hz, 1H), 7.89 (d, J=3.2 Hz, 1 H), 7.57 (dd, J=8.4, 2.4 Hz, 1H), 7.46 (dd, J=8.4, 6.4 Hz, 1H), 7.12-7.30 (m, 1H), 6.00 (s, 1H), 4.63-4.74 (m, 1H), 4.42-4.52 (m, 1H), 3.99 (q, J=7.2 Hz, 2H), 3.64-3.82 (m, 2H), 3.29-3.33 (m, 1H), 1.08 (t, J=7.2 Hz, 3H).
LCMS (ESI) m/z: 476.8 [M+H$^+$].
NMR data of Example 27: $^1$H NMR (400 MHz, DMSO-$d_6$) δ: 7.97 (d, J=3.2 Hz, 1H), 7.90 (d, J=3.2 Hz, 1H), 7.53-7.67 (m, 1H), 7.37-7.45 (m, 1H), 7.23 (t, J=8.4 Hz, 1H), 6.01 (s, 1H), 4.48-4.64 (m, 2H), 3.95-4.06 (m, 2H), 3.72-3.84 (m, 1H), 3.41-3.60 (m, 1H), 3.32-3.34 (m, 1H), 1.09 (t, J=7.2 Hz, 3H).
LCMS (ESI) m/z: 476.8 [M+H$^+$].
Examples 28, 29

-continued

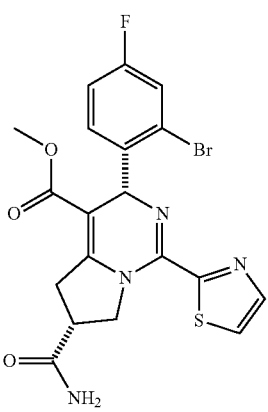
29

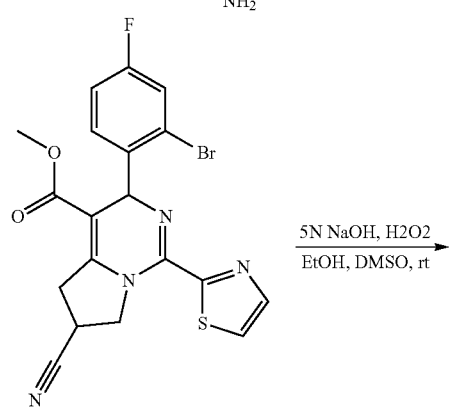

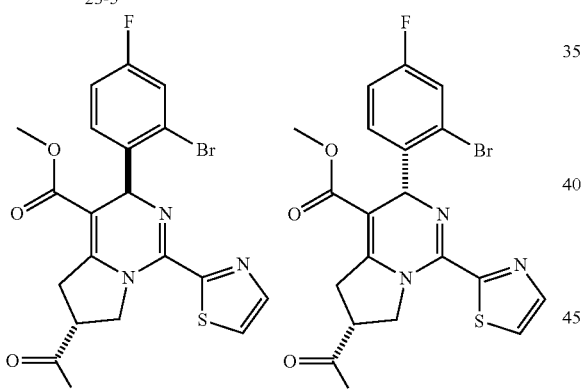

Compound 23-5 (80 mg, 0.16 mmol) was dissolved in anhydrous ethanol (1 mL), DMSO (0.1 mL), NaOH solution (0.05 mL, 5N), oxydol (0.06 mL) were added, stirring at room temperature for 3 hours. The reaction mixture was concentrated under reduced pressure and then extracted with DCM (30 mL×3). The organic phases were combined, sequentially washed with water (20 mL×2), saturated sodium chloride solution (20 mL×2), dried over anhydrous sodium sulfate, filtered, separated with preparative HPLC to obtain 15 mg Example 28, 11 mg Example 29, yield: 35%.

NMR data of Example 28: $^1$H NMR (400 MHz, CDCl$_3$) δ: 7.81 (d, J=3.2 Hz, 1H), 7.38 (d, J=3.2 Hz, 1H), 7.33 (dd, J=2.4, 8.4 Hz, 1H), 7.23-7.26 (m, 1H), 6.97 (dt, J=2.4, 8.4 Hz, 1H), 6.17 (s, 1H), 5.83 (br. s., 1H), 5.62 (br. s., 1H), 4.67 (dd, J=8.4, 11.2 Hz, 1H), 4.47 (dd, J=8.4, 11.2 Hz, 1H), 3.99-4.14 (m, 2H), 3.69 (dd, J=8.4, 18.0 Hz, 1H), 3.34-3.47 (m, 1H), 3.21 (q, J=8.4 Hz, 1H), 1.15 (t, J=7.2 Hz, 3H).

LCMS (ESI) m/z: 493.0 [M+H$^+$].

NMR data of Example 29: $^1$H NMR (400 MHz, CDCl$_3$) δ: 7.80 (d, J=3.2 Hz, 1H), 7.48 (dd, J=6.0, 8.4 Hz, 1H), 7.38 (d, J=3.6 Hz, 1H), 7.31 (dd, J=2.4, 8.4 Hz, 1H), 7.01 (dt, J=2.4, 8.4 Hz, 1H), 6.17 (s, 1H), 5.60 (br. s., 1H), 5.46 (br. s., 1H), 4.71 (dd, J=7.6, 11.6 Hz, 1H), 4.51 (dd, J=3.6, 11.6 Hz, 1H), 3.99-4.13 (m, 2H), 3.67 (dd, J=3.6, 18.0 Hz, 1H), 3.33-3.43 (m, 1H), 3.18 (tt, J=3.6, 8.0 Hz, 1H), 1.15 (t, J=7.2 Hz, 3H).

LCMS (ESI) m/z: 493.0 [M+H$^+$].

Examples 30, 31

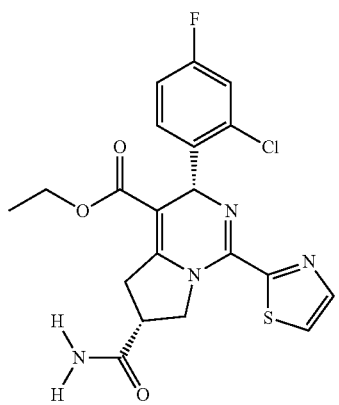

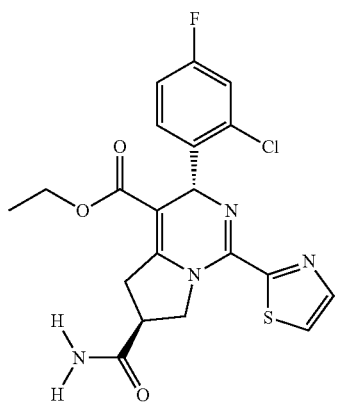

Examples 30, 31 were prepared according to the method as described in Examples 28, 29 and obtained by SFC separation.

NMR data of Example 31: $^1$H NMR (400 MHz, CDCl$_3$) δ: 7.83 (d, J=3.2 Hz, 1H), 7.41 (d, J=3.2 Hz, 1H), 7.29 (dd, J=6.0, 8.8 Hz, 1H), 7.12 (dd, J=2.4, 8.4 Hz, 1H), 6.92 (m, 1H), 6.19 (s, 1H), 5.97-5.59 (m, 2H), 4.65 (dd, J=8.4, 11.6 Hz, 1H), 4.47 (dd, J=8.4, 11.6 Hz, 1H), 4.13-3.98 (m, 2H), 3.67 (dd, J=8.4, 18.0 Hz, 1H), 3.45-3.33 (m, 1H), 3.21 (quin, J=8.4 Hz, 1H), 1.15 (t, J=7.2 Hz, 3H).

LCMS (ESI) m/z: 449.0 [M+H$^+$].

Example 32

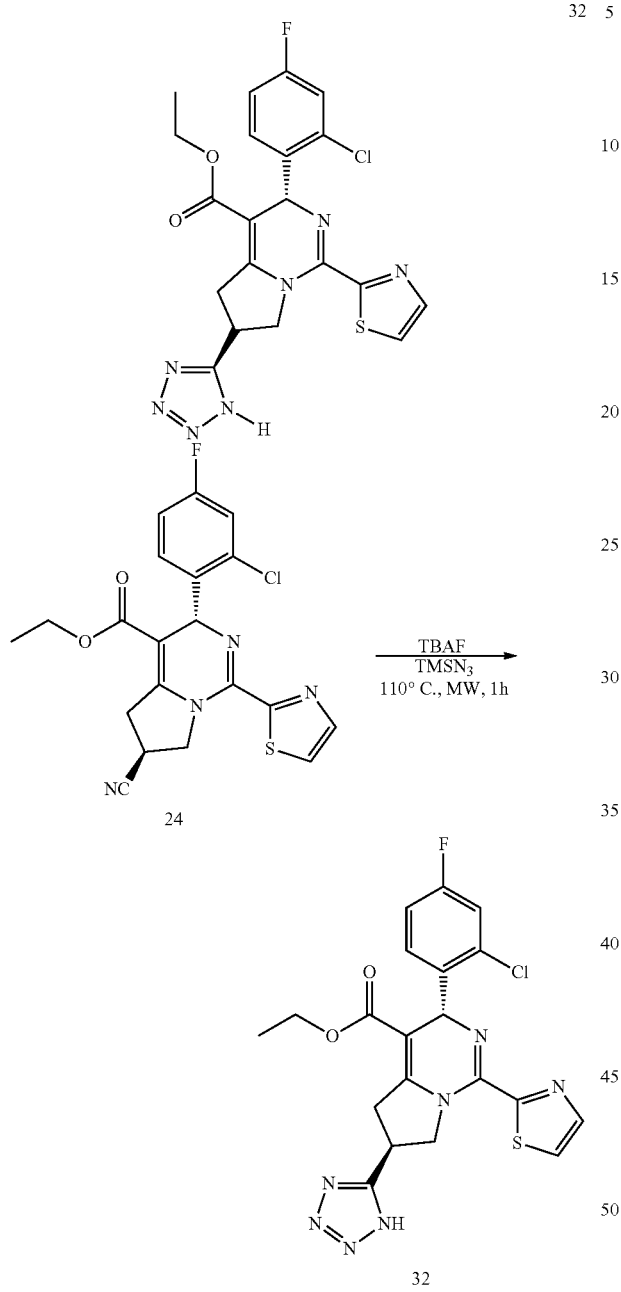

Compound 24 (50 mg, 0.11 mmol), TBAF (15 mg, 0.06 mmol), TMSN₃ (134 mg, 1.16 mmol) were added into a microwave tube, and allowed to react at 110□ under microwave for 1 hour. The reaction mixture was cooled to room temperature, followed by adding EtOAc (10 mL), 5% sodium carbonate aqueous solution (10 mL), and extracted with (10 mL×3) EtOAc. The organic phases were combined, sequentially washed with water (10 mL×2), saturated sodium chloride solution (10 mL×2), dried over anhydrous sodium sulfate, filtered. The filtrate was concentrated under reduced pressure and then separated by HPLC to obtain the product 16 mg Example 32, yield: 29%.

¹H NMR (400 MHz, MeOD-d4) δ: 8.08 (br. s., 1H), 7.93 (br. s., 1H), 7.65 (br. s., 1H), 7.15 (d, J=8.0 Hz, 1H), 7.08 (br. s., 1H), 6.25 (s, 1H), 4.80 (br. s., 1H), 4.68 (br. s., 1H), 4.33 (br. s., 1H), 4.07 (q, J=7.2 Hz, 2H), 4.01-3.84 (m, 1H), 3.31 (br. s., 1H), 1.13 (t, J=7.2 Hz, 3H).

LCMS (ESI) m/z: 474.1 [M+H⁺].

Example 33

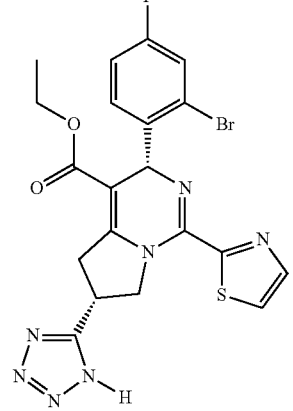

Example 33 was prepared according to the method as described in Example 32.

NMR data of Example 33: ¹H NMR (400 MHz, MeOD-d4) δ: 8.39-8.29 (m, 2H), 7.84 (dd, J=6.0, 8.4 Hz, 1H), 7.58 (dd, J=2.4, 8.4 Hz, 1H), 7.31 (dt, J=2.4, 8.4 Hz, 1H), 6.39 (s, 1H), 4.88-4.72 (m, 2H), 4.43-4.29 (m, 1H), 4.16 (dq, J=4.4, 7.2 Hz, 2H), 4.07 (dd, J=8.0, 18.0 Hz, 1H), 3.60 (dd, J=8.0, 18.0 Hz, 1H), 1.19 (t, J=7.2 Hz, 3H).

LCMS (ESI) m/z: 520.0 [M+H⁺].

Examples 34, 35

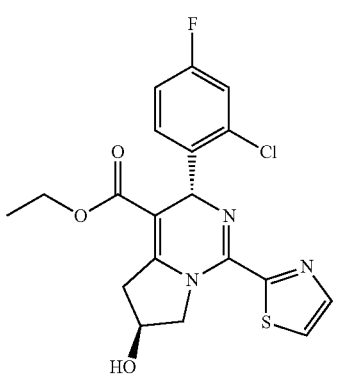

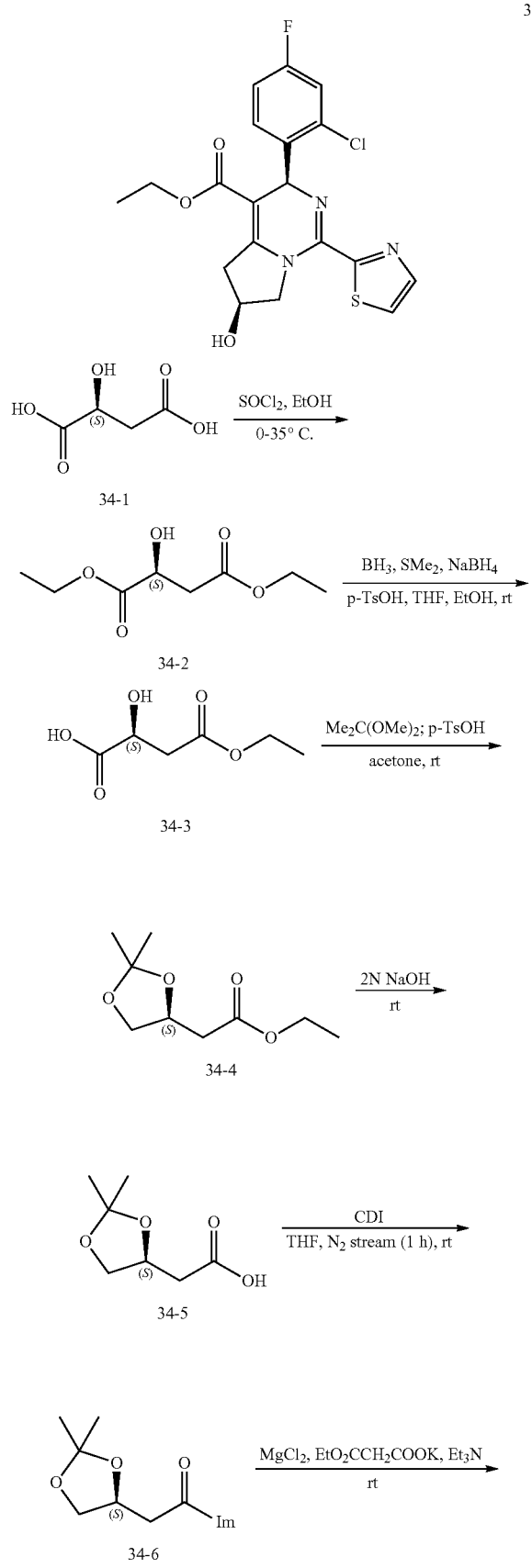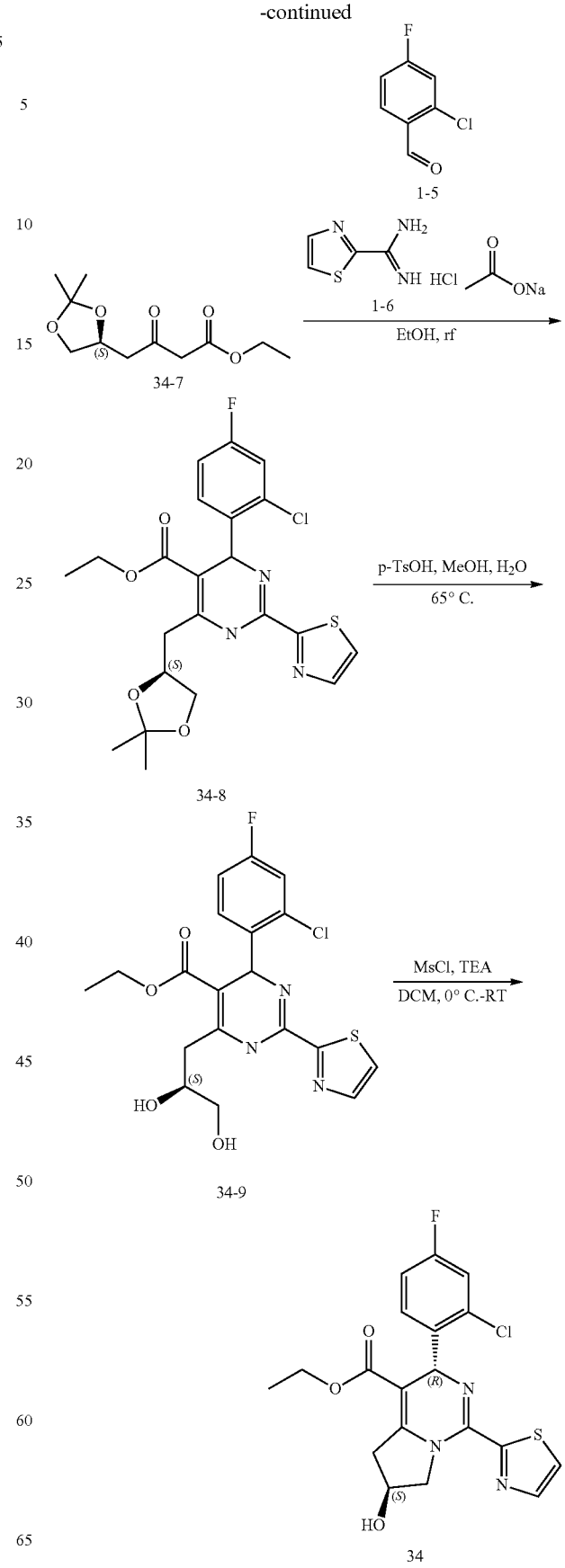

-continued

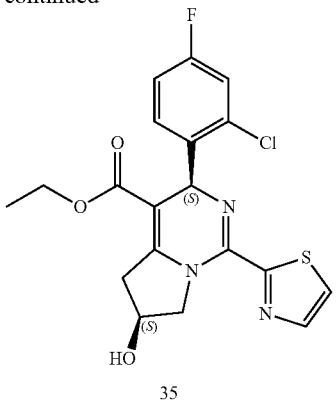

35

Step 1 (Synthesis of Compound 34-2)

Compound 34-1 (80 g, 600 mmol) was dissolved in anhydrous ethanol (500 mL), and thionyl chloride (100 mL, 1.5 mmol) was added at 0□, the mixture was stirred at 0□ for 20 minutes. Then the temperature was raised to room temperature, the reaction mixture was stirred overnight, concentrated under reduced pressure, and then extracted with EtOAc (1000 mL×3). The organic phases were combined, sequentially washed with water (500 mL×2), saturated sodium chloride solution (500 mL×2), dried over anhydrous sodium sulfate, filtered, and purified by silica gel column chromatography with an eluent system (PE:EtOAc=20:1) to obtain the product 113 g compound 34-2, yield: 99%.

$^1$H NMR (400 MHz, CDCl$_3$) δ: 4.47 (q, J=4.8 Hz, 1H), 4.26 (dq, J=2.4, 7.2 Hz, 2H), 4.16 (q, J=7.2 Hz, 2H), 3.28 (d, J=4.8 Hz, 1H), 2.72-2.89 (m, 2H), 1.20-1.34 (m, 6H).

Step 2 (Synthesis of Compound 34-3)

Compound 34-2 (30 g, 158 mmol) was dissolved in anhydrous tetrahydrofuran (400 mL), and at room temperature was slowly added dropwise a solution of borane in dimethyl sulfide (16.5 mL, 165 mmol).

The mixture was stirred at room temperature for 1 hour, cooled to 0□, sodium borohydride (300 mg, 8 mmol) was added, violently stirred for 30 minutes and then the temperature was raised to room temperature, stirred overnight. Anhydrous ethanol (80 mL), p-TsOH (450 mg, 4 mmol) were then added. The reaction mixture was stirred at room temperature for another half an hour. The reaction mixture was concentrated under reduced pressure, and purified by silica gel column chromatography with an eluent system (PE:EtOAc=1:1) to obtain the product 13.6 g compound 34-3, yield: 60%.

Step 3 (Synthesis of Compound 34-4)

Compound 34-3 (15 g, 100 mmol) was dissolved in acetone (200 mL), and at room temperature were slowly added dropwise 2,2-dimethoxypropane (21 g, 200 mmol) and p-TsOH (350 mg, 2 mmol). The mixture was stirred at room temperature overnight, and then concentrated under reduced pressure, purified by silica gel column chromatography with an eluent system (PE:EtOAc=10:1) to obtain the product 12 g compound 34-4, yield: 64%.

$^1$H NMR (400 MHz, CDCl$_3$) δ: 4.48 (q, J=6.4 Hz, 1H), 4.09-4.24 (m, 3H), 3.66 (dd, J=6.4, 8.4 Hz, 1H), 2.72 (dd, J=6.4, 15.6 Hz, 1H), 2.52 (dd, J=7.2, 15.6 Hz, 1H), 1.42 (s, 3H), 1.37 (s, 3H), 1.27 (t, J=7.2 Hz, 3H).

Step 4 (Synthesis of Compound 34-5)

Compound 34-4 (6.2 g, 32.9 mmol) was dissolved in 2N NaOH solution (33 mL) under an ice-water bath, and then the temperature was raised to room temperature. The reaction mixture was stirred for 3 hours and then extracted with DCM (50 mL×3). Water layers were retained, and to the water layers were added EtOAc (50 mL), 2N aq. NaHSO$_4$ solution (50 mL). The mixture was violently stirred for 15 minutes and extracted with EtOAc (100 mL×3). The organic phases were combined, sequentially washed with water (50 mL×2), saturated sodium chloride solution (50 mL×2), dried over anhydrous sodium sulfate, filtered, and concentrated under reduced pressure to obtain crude 4.2 g compound 34-5, yield: 79%.

$^1$H NMR (400 MHz, CDCl$_3$) δ: 4.49 (q, J=6.4 Hz, 1H), 4.18 (dd, J=6.0, 8.4 Hz, 1H), 3.68 (dd, J=6.4, 8.4 Hz, 1H), 2.70-2.80 (m, 1H), 2.54-2.64 (m, 1H), 1.44 (s, 3H), 1.37 (s, 3H).

Steps 5, 6 (Synthesis of Compound 34-7)

Compound 34-5 (1.0 g, 6.24 mmol) was dissolved in anhydrous tetrahydrofuran solution (17 mL) under an ice-water bath, and dicarbonyl imidazole (1.21 g, 7.49 mmol) was added. The reaction mixture was stirred at room temperature under nitrogen atmosphere for 4 hours, followed by adding MgCl$_2$ (594 mg, 6.24 mmol), monoethyl potassium malonate (2.12 g, 12.48 mmol), triethylamine (1.26 g, 12.49 mmol) under nitrogen atmosphere. After the addition, the reaction mixture was stirred at room temperature overnight, and then acidified with 1N HCl solution until pH=5, extracted with EtOAc (100 mL×3). The organic phases were combined, sequentially washed with water (50 mL×2), saturated sodium chloride solution (50 mL×2), dried over anhydrous sodium sulfate, filtered, and purified by silica gel column chromatography with an eluent system (PE:EtOAc=5:1) to obtain the product 336 mg compound 34-7, yield: 23%.

$^1$H NMR (400 MHz, CDCl$_3$) δ: 4.48 (q, J=6.4 Hz, 1H), 4.16-4.25 (m, 3H), 3.57 (dd, J=6.8, 8.4 Hz, 1H), 3.49 (s, 2H), 3.00 (dd, J=6.0, 17.2 Hz, 1H), 2.75 (dd, J=7.2, 17.2 Hz, 1H), 1.39-1.44 (m, 3H), 1.33-1.38 (m, 3H), 1.27-1.32 (m, 3H).

Step 7 (Synthesis of Compound 34-8)

Compound 34-7 (438 mg, 2.76 mmol) was dissolved in anhydrous ethanol solution (25 mL), and compound 1-5 (636 mg, 2.76 mmol), compound 1-6 (542 mg, 3.31 mmol), sodium acetate (566 mg, 6.91 mmol) were added. The reaction mixture was stirred under nitrogen atmosphere and reflux overnight and then concentrated under reduced pressure, extracted with EtOAc (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=3:1) to obtain the product 720 mg compound 34-8, yield: 54%.

$^1$H NMR (400 MHz, CDCl$_3$) δ: 8.77 (br. s., 1H), 7.82 (br. s., 1H), 7.37-7.48 (m, 2H), 7.13 (d, J=8.4 Hz, 1H), 6.94 (d, J=7.2 Hz, 1H), 6.22 (s, 1H), 4.42-4.56 (m, 1H), 4.19 (t, J=7.2

Hz, 1H), 3.98-4.08 (m, 2H), 3.78 (t, J=7.2 Hz, 1H), 3.61 (d, J=15.6 Hz, 1H), 3.04 (dd, J=7.6, 14.4 Hz, 1H), 1.47-1.57 (m, 3H), 1.38-1.44 (m, 3H), 1.13 (t, J=7.2 Hz, 3H).

LCMS (ESI) m/z: 480.0 [M+H⁺].

Step 8 (Synthesis of Compound 34-9)

Compound 34-8 (340 mg, 0.71 mmol) was dissolved in anhydrous methanol solution (7 mL), and p-TsOH (81 mg, 0.43 mmol), water (2 mL) were added. The reaction mixture was stirred under reflux overnight, and then concentrated under reduced pressure, extracted with EtOAc (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (DCM:methanol=20:1) to obtain 214 mg compound 34-9, yield: 69%.

¹H NMR (400 MHz, CDCl₃) δ: 7.80-7.90 (m, 1H), 7.56 (br. s., 1H), 7.42 (dd, J=6.4, 8.4 Hz, 1H), 7.16 (d, J=7.6 Hz, 1H), 6.90-7.05 (m, 1H), 6.08-6.25 (m, 1H), 4.66 (br. s., 1H), 4.17-4.29 (m, 1H), 4.07 (d, J=7.2 Hz, 2H), 3.71 (br. s., 2H), 3.30-3.53 (m, 1H), 2.88-3.26 (m, 2H), 1.15 (t, J=7.2 Hz, 3H).

LCMS (ESI) m/z: 440.0 [M+H⁺].

Step 9 (Synthesis of Examples 34, 35)

Compound 34-8 (199 mg, 0.45 mmol) was dissolved in anhydrous DCM (5 mL) solution, and at 00 were added triethylamine (69 mg, 0.68 mmol), methanesulfonyl chloride (52 mg, 0.45 mmol). The mixture was stirred at the same temperature for 1.5 hours. The temperature was raised to room temperature, and the mixture was stirred overnight, and then extracted with DCM (50 mL×3). The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=1:1) to obtain 3 mg Example 34, 10 mg Example 35, yield: 6.8%.

NMR data of Example 34: ¹H NMR (400 MHz, CDCl₃) δ: 7.82 (d, J=3.2 Hz, 1H), 7.38 (d, J=3.2 Hz, 1H), 7.28-7.32 (m, 1H), 7.12 (dd, J=2.4, 8.4 Hz, 1H), 6.92 (dt, J=2.4, 8.4 Hz, 1H), 6.21 (s, 1H), 4.59-4.72 (m, 2H), 4.29 (dd, J=4.4, 12.4 Hz, 1H), 4.04 (dt, J=5.2, 6.8 Hz, 2H), 3.38-3.50 (m, 1H), 3.25-3.37 (m, 1H), 1.12 (t, J=7.2 Hz, 3H).

LCMS (ESI) m/z: 422.0 [M+H⁺].

NMR data of Example 35: ¹H NMR (400 MHz, CDCl₃) δ: 7.81 (d, J=3.2 Hz, 1H), 7.34-7.43 (m, 2H), 7.13 (dd, J=2.8, 8.8 Hz, 1H), 6.92 (dt, J=2.4, 8.4 Hz, 1H), 6.21 (s, 1H), 4.70 (br. s., 1H), 4.34-4.49 (m, 2H), 4.00-4.14 (m, 2H), 3.56 (d, J=18.0 Hz, 1H), 3.14 (dd, J=5.3, 18.4 Hz, 1H), 1.17 (t, J=7.2 Hz, 3H).

LCMS (ESI) m/z: 422.0 [M+H⁺].

Examples 36, 37

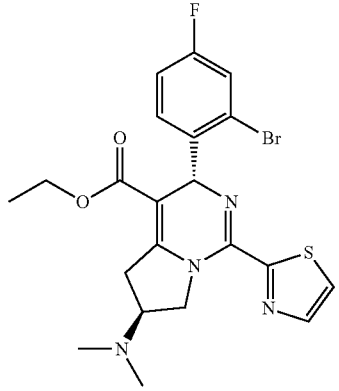

36

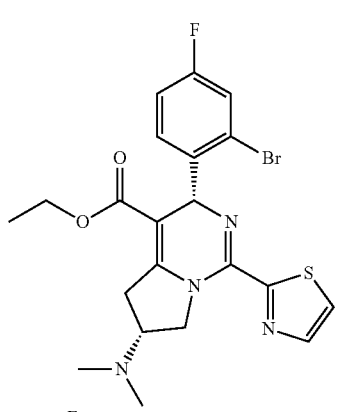

37

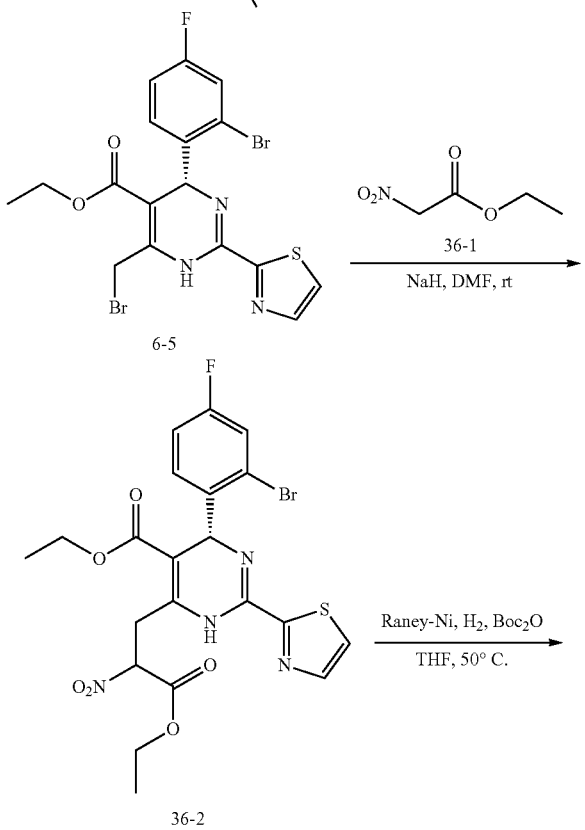

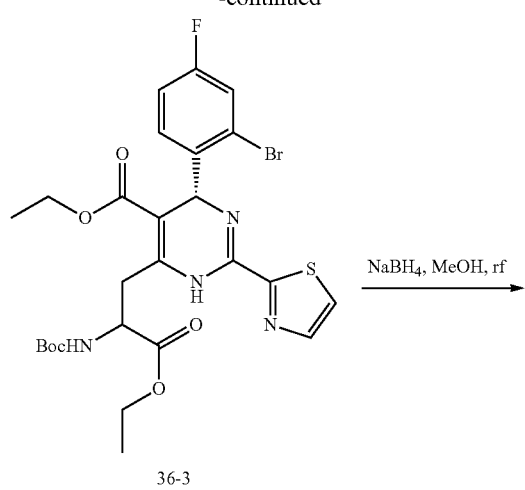

36-3

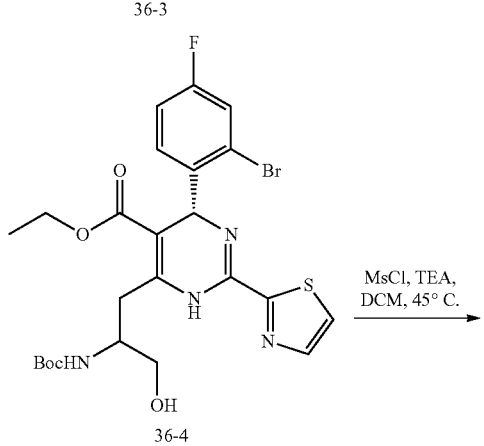

36-4

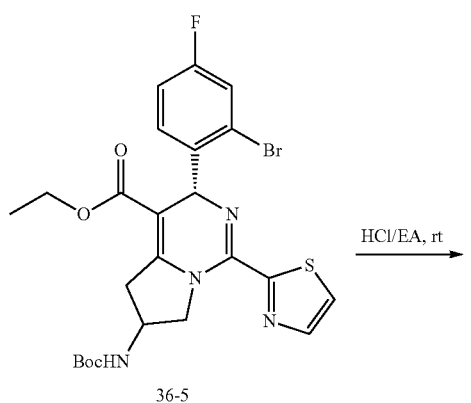

36-5

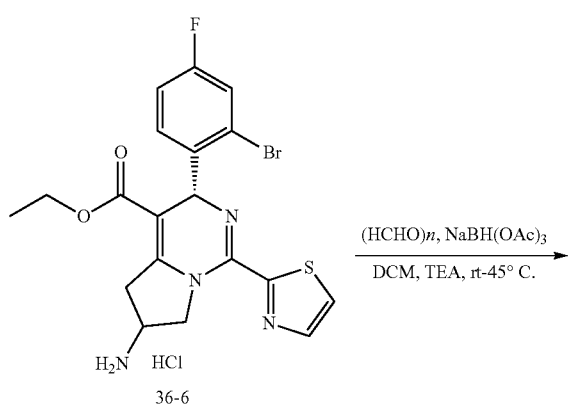

36-6

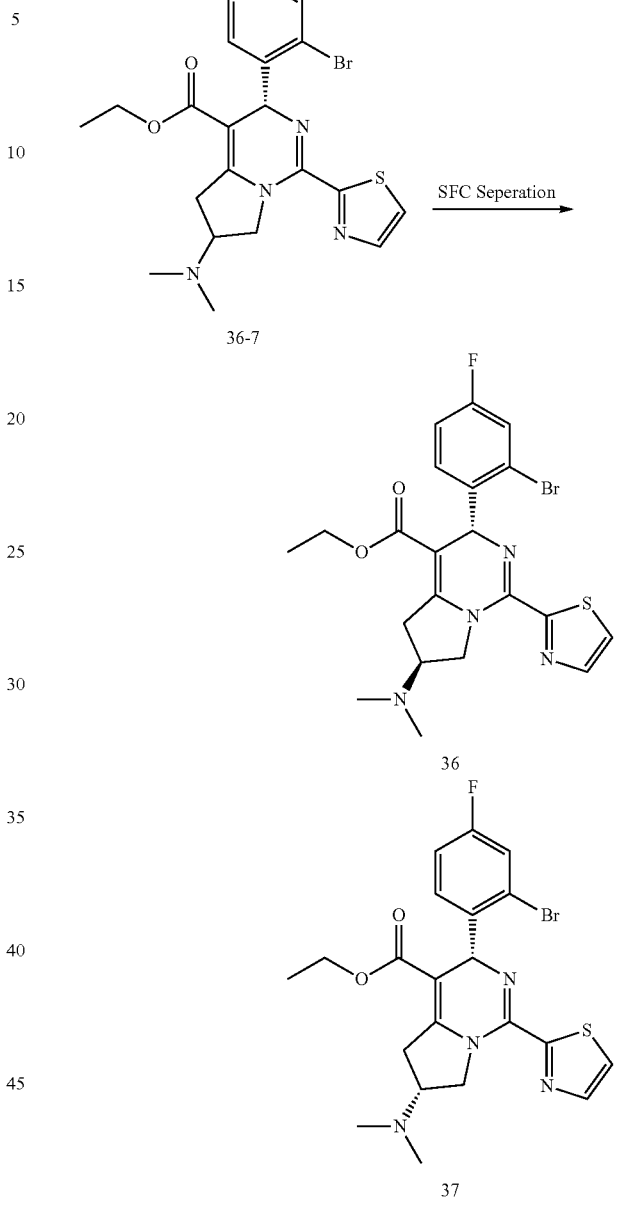

36-7

36

37

Step 1 (Synthesis of Compound 36-2)

Compound 36-1 (15.9 g, 119.2 mmol) was dissolved in anhydrous N',N-dimethylacetamide (300 mL), and at room temperature was added in portions sodium hydride (2.14 g, 89.4 mmol). The mixture was stirred under nitrogen atmosphere at room temperature for 2 hours. Then compound 6-5 (30.0 g, 59.6 mmol) was added to the reaction mixture, and after the addition, the mixture was stirred under nitrogen atmosphere at room temperature overnight. The reaction mixture was extracted with EtOAc (400 mL×3).

The organic phases were combined, sequentially washed with water (100 mL×2), saturated sodium chloride solution (100 mL×2), dried over anhydrous sodium sulfate, filtered, and purified by silica gel column chromatography with an eluent system (PE:EtOAc=20:1) to obtain 26 g compound 36-2, yield: 79%.

LCMS (ESI) m/z: 556.9 [M+H$^+$].

Step 2 (Synthesis of Compound 36-3)

Raney Ni (3.0 g) was dissolved in tetrahydrofuran (1000 mL), and at room temperature were added compound 36-2 (26 g, 46.8 mmol), (Boc)2O (30.6 g, 140 mmol). Under hydrogen atmosphere, the temperature was raised to 500 and the reaction mixture was stirred at this temperature for 4 hours, then filtered. The filtrate was concentrated under reduced pressure and extracted with EtOAc (500 mL×3).

The organic phases were combined, sequentially washed with water (200 mL×2), saturated sodium chloride solution (100 mL×2), dried over anhydrous sodium sulfate, filtered, and purified by silica gel column chromatography with an eluent system (PE:EtOAc=5:1) to obtain the product 20 g compound 36-3, yield: 70%

LCMS (ESI) m/z: 627.0 [M+H$^+$].

Step 3 (Synthesis of Compound 36-4)

Compound 36-3 (10 g, 16.0 mmol) was dissolved in anhydrous tetrahydrofuran (1000 mL), and at room temperature were added in portions sodium borohydride (600 mg, 16.0 mmol), methanol (1 mL). Under nitrogen atmosphere, the mixture was stirred at room temperature for 10 minutes. Then the temperature was raised to refluxing, and the reaction mixture was stirred under reflux for 6 hours, then cooled to room temperature, concentrated under reduced pressure. The residue was poured into ice water (1500 mL), stirred for 20 minutes, and extracted with EtOAc (400 mL×3). The organic phases were combined, sequentially washed with water (200 mL×2), saturated sodium chloride solution (100 mL×2), dried over anhydrous sodium sulfate, filtered, and purified by silica gel column chromatography with an eluent system (PE:EtOAc=5:1) to obtain 7.0 g compound 36-4, yield: 75%.

LCMS (ESI) m/z: 584.9 [M+H$^+$].

Step 4 (Synthesis of Compound 36-5)

Compound 36-4 (6.0 g, 10.3 mmol) was dissolved in anhydrous DCM (500 mL), and at room temperature were added dropwise triethylamine (1.56 g, 15.4 mmol), methanesulfonyl chloride (2.94 g, 15.4 mmol). After the addition, the temperature was raised to 45□, and the mixture was stirred under nitrogen atmosphere for 6 hours. The reaction mixture was cooled to room temperature, concentrated under reduced pressure and extracted with EtOAc (200 mL×3). The organic phases were combined, sequentially washed with water (100 mL×2), saturated sodium chloride solution (40 mL×2), dried over anhydrous sodium sulfate, filtered, and purified by silica gel column chromatography with an eluent system (PE:EtOAc=5:1) to obtain 3.0 g compound 36-5, yield: 52%.

LCMS (ESI) m/z: 567.1 [M+H$^+$].

Step 5 (Synthesis of Compound 36-6)

Compound 36-5 (3.0 g, 5.3 mmol) was dissolved in EtOAc (10 mL), and at room temperature was added dropwise HCl-EtOAc (50 mL). After the addition, the mixture was stirred under nitrogen atmosphere at room temperature overnight. The reaction mixture was concentrated under reduced pressure to obtain 2.4 g compound 36-6, which was used directly in the next reaction without purification, yield: 84%.

LCMS (ESI) m/z: 466.8 [M+H$^+$].

Step 6 (Synthesis of Compound 36-7)

Compound 36-6 (80 mg, 0.17 mmol) was dissolved in anhydrous DCM (5 mL), and at room temperature were added triethylamine (17 mg, 0.17 mmol), paraformaldehyde (26 mg, 0.86 mmol), sodium acetoxyborohydride (109 mg, 0.52 mmol). After the addition, the temperature was raised to 45□, and the mixture was stirred under nitrogen atmosphere overnight. The reaction mixture was cooled to room temperature, concentrated under reduced pressure. Then the residue was poured into ice water (15 mL), and extracted with EtOAc (20 mL×3). The organic phases were combined, sequentially washed with water (10 mL×2), saturated sodium chloride solution (10 mL×2), dried over anhydrous sodium sulfate, filtered, and purified by silica gel column chromatography with an eluent system (PE:EtOAc=3:1) to obtain 20 mg compound 36-7, yield: 24%.

LCMS (ESI) m/z: 492.9 [M+H$^+$].

Step 7 (Synthesis of Compounds 36, 37)

Compound 36-7 was separated by pre-SFC to obtain chirally pure Example 36 and Example 37.

NMR data of Example 36: $^1$H NMR (400 MHz, CDCl$_3$) δ: 7.81 (d, J=3.2 Hz, 1H), 7.37 (d, J=3.6 Hz, 1H), 7.30 (dd, J=2.4, 8.4 Hz, 1H), 7.24 (s, 1H), 6.95 (dt, J=2.4, 8.4 Hz, 1H), 6.15 (s, 1H), 4.69 (dd, J=6.8, 11.6 Hz, 1H), 4.11-4.05 (m, 1H), 4.05-3.99 (m, 2H), 3.48-3.37 (m, 1H), 3.22-3.09 (m, 2H), 2.33 (s, 6H), 1.15 (t, J=7.2 Hz, 3H).

LCMS (ESI) m/z: 493.2 [M+H$^+$].

NMR data of Example 37: $^1$H NMR (400 MHz, CDCl$_3$) δ: 7.81 (d, J=3.2 Hz, 1H), 7.36 (d, J=3.2 Hz, 1H), 7.31 (dd, J=2.4, 8.4 Hz, 1H), 7.26-7.23 (m, 1H), 6.96 (dt, J=2.4, 8.4 Hz, 1H), 6.14 (s, 1H), 4.55 (dd, J=6.4, 11.2 Hz, 1H), 4.14-4.06 (m, 1H), 4.05-3.97 (m, 2H), 3.63 (dd, J=6.4, 16.4 Hz, 1H), 3.05-2.89 (m, 2H), 2.34 (s, 6H), 1.14 (t, J=7.2 Hz, 3H).

LCMS (ESI) m/z: 465.1 [M+H$^+$].

Examples 38, 39

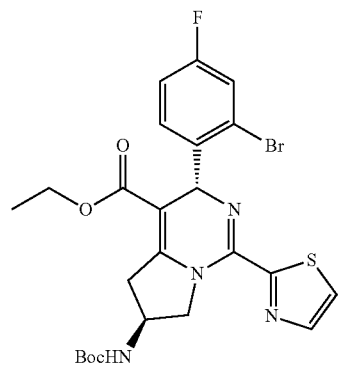

38

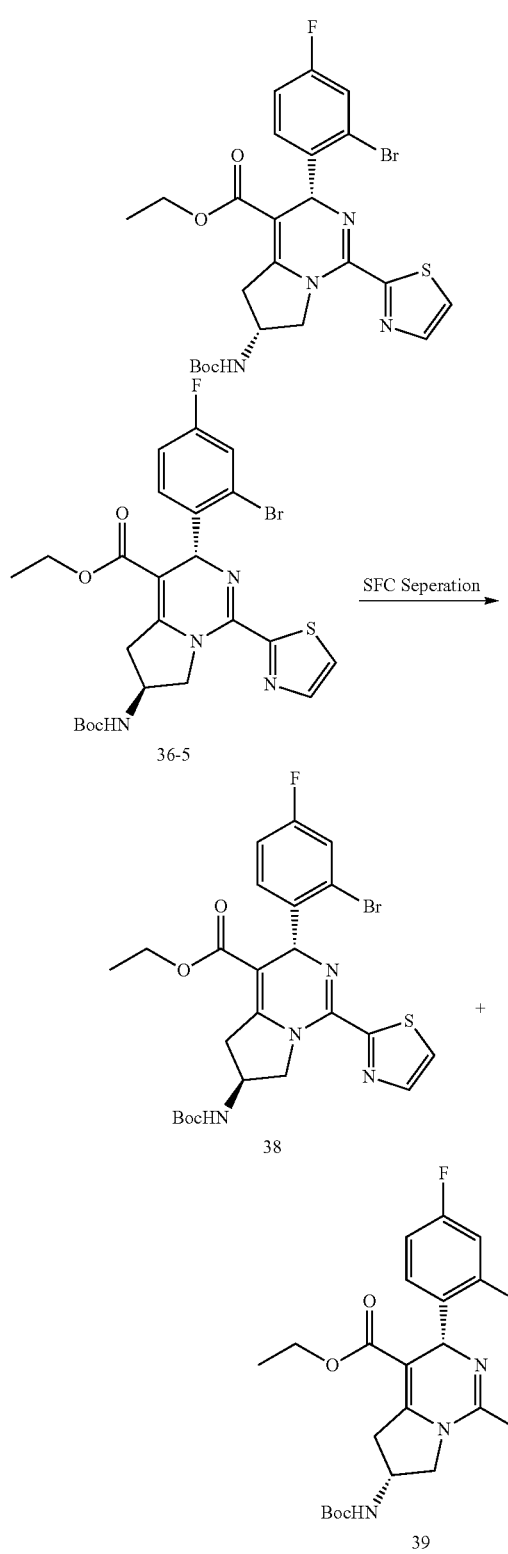
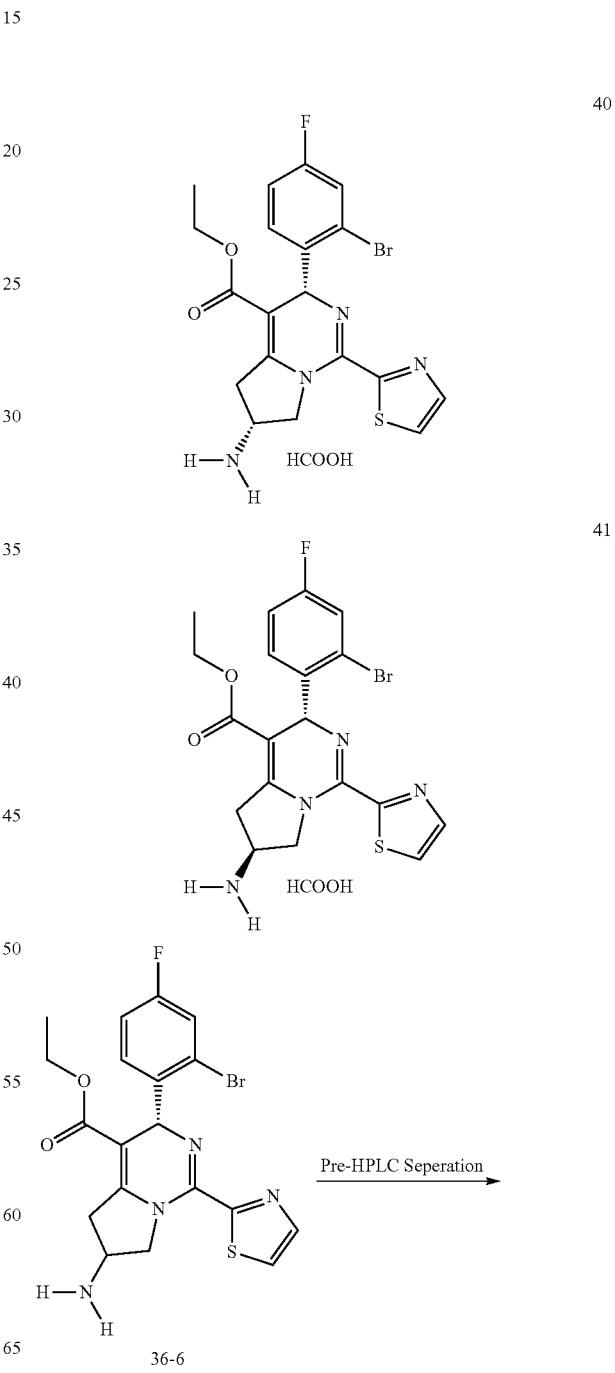
Compound 26-5 (30 mg) was separated by pre-SFC to obtain chirally pure Example 38, Example 39.
NMR data of Example 38: $^1$H NMR (400 MHz, CDCl$_3$) δ: 7.80 (d, J=3.2 Hz, 1H), 7.37 (d, J=3.2 Hz, 1H), 7.31 (dd, J=2.8, 8.4 Hz, 1H), 7.24-7.20 (m, 1H), 6.97 (dt, J=2.4, 8.4 Hz, 1H), 6.15 (s, 1H), 4.74 (br. s., 1H), 4.46 (d, J=10.0 Hz, 1H), 4.35-4.29 (m, 1H), 4.04 (q, J=7.2 Hz, 2H), 3.58 (dd, J=7.2, 18.4 Hz, 1H), 3.08 (dd, J=5.6, 17.6 Hz, 1H), 1.46 (s, 9H), 1.13 (t, J=7.2 Hz, 3H).
LCMS (ESI) m/z: 567.1 [M+H$^+$].
NMR data of Example 39: $^1$H NMR (400 MHz, CDCl$_3$) δ: 7.80 (d, J=3.6 Hz, 1H), 7.37 (d, J=3.2 Hz, 1H), 7.35-7.27 (m, 2H), 6.99 (dt, J=2.4, 8.4 Hz, 1H), 6.16 (s, 1H), 4.77 (br. s., 1H), 4.42 (s, 2H), 4.06 (q, J=7.2 Hz, 2H), 3.42-3.27 (m, 2H), 1.51-1.41 (m, 9H), 1.15 (t, J=7.2 Hz, 3H).
LCMS (ESI) m/z: 567.1 [M+H$^+$].
Examples 40, 41

345

-continued

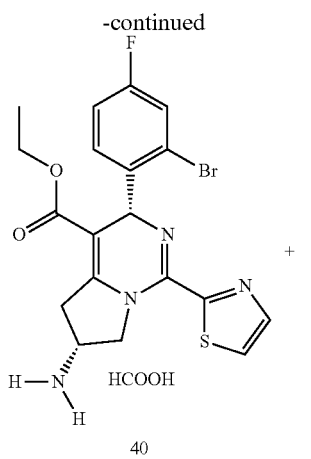

40

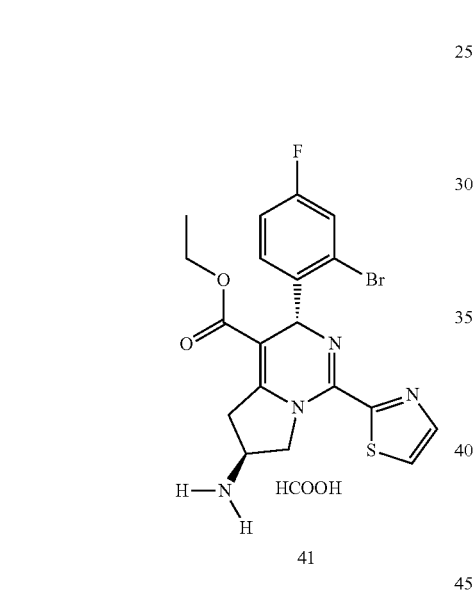

41

Compound 36-6 (500 mg) was separated by preparative chromatograph to obtain chirally pure compounds 115 mg Example 40, 130 mg Example 41.

NMR data of Example 40: $^1$H NMR (400 MHz, DMSO-$d_6$) δ: 7.96 (d, J=3.2 Hz, 1H), 7.87 (d, J=3.2 Hz, 1H), 7.55 (dd, J=2.4, 8.8 Hz, 1H), 7.42 (dd, J=6.4, 8.4 Hz, 1H), 7.22 (dt, J=2.4, 8.4 Hz, 1H), 6.00 (s, 1H), 4.33 (dd, J=6.3, 11.2 Hz, 1H), 4.18 (dd, J=4.4, 11.2 Hz, 1H), 4.01-3.91 (m, 2H), 3.3 (m, 1H), 3.03 (dd, J=5.2, 18.0 Hz, 2H), 1.06 (t, J=7.2 Hz, 3H).

LCMS (ESI) m/z: 465.1 [M+H$^+$].

NMR data of Example 41: $^1$H NMR (400 MHz, DMSO-$d_6$) δ: 7.97 (d, J=3.2 Hz, 1H), 7.89 (d, J=3.2 Hz, 1H), 7.66 (dd, J=6.4, 8.4 Hz, 1H), 7.57 (dd, J=2.4, 8.4 Hz, 1H), 7.23 (dt, J=2.4, 8.4 Hz, 1H), 6.06-5.99 (m, 1H), 4.56 (d, J=12.4 Hz, 1H), 4.33 (dd, J=6.4, 12.4 Hz, 1H), 4.05 (br. s., 1H), 4.00-3.89 (m, 2H), 3.3 (m, 2H), 1.06 (t, J=7.2 Hz, 3H).

LCMS (ESI) m/z: 465.1 [M+H$^+$].

346

Examples 42, 43, 44

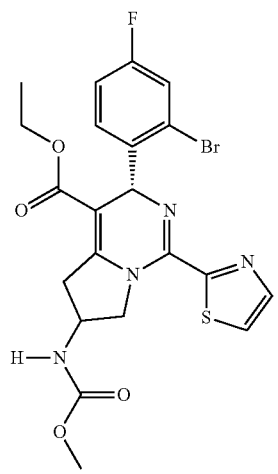

42

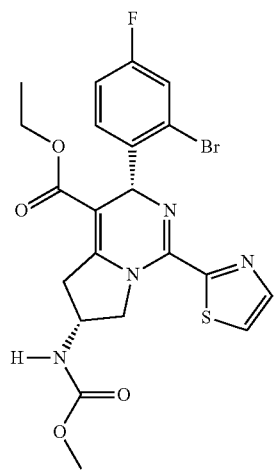

43

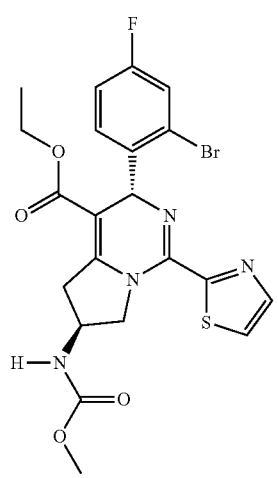

44

-continued

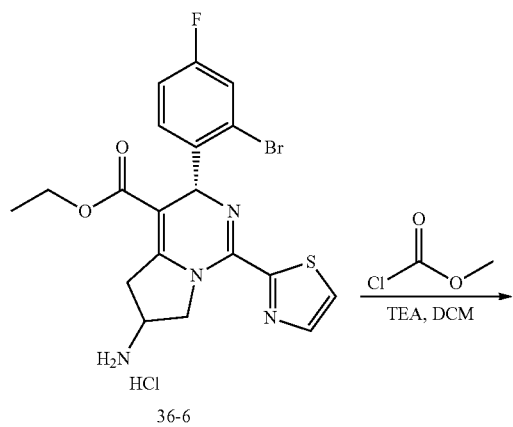

36-6

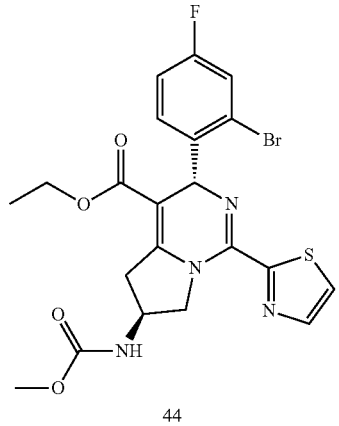

44

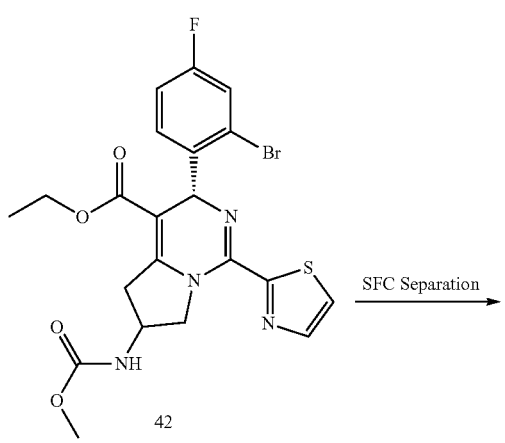

42

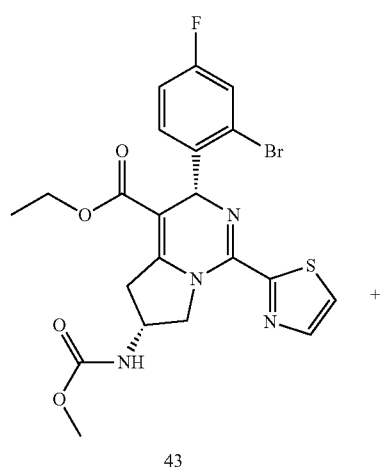

43

Step 1 (Synthesis of 42)

Example 36-6 (200 mg, 0.398 mmol) was dissolved in anhydrous DCM (5 mL), and at room temperature were added triethylamine (120.99 mg, 1.20 mmol), methyl chloroformate (113 mg, 1.2 mmol). After the addition, the mixture was fully stirred under nitrogen atmosphere for 3 hours. When TLC (PE:EtOAc=1:1) showed that the starting materials disappeared, the reaction mixture was poured into saturated sodium bicarbonate solution (15 mL), and extracted with DCM (20 mL×3). The organic phases were combined, sequentially washed with water (10 mL×2), saturated sodium chloride solution (10 mL×2), dried over anhydrous sodium sulfate, filtered, and purified by silica gel column chromatography with an eluent system (PE:EtOAc=100:1-3:1) to obtain 130 mg Example 42, yield: 62.23%.

NMR data of Example 42: $^1$H NMR (400 MHz, CDCl$_3$) δ: 7.82 (d, J=3.2 Hz, 1H), 7.40 (d, J=3.2 Hz, 1H), 7.35 (m, 1H), 7.27-7.24 (m, 1H), 7.05-6.97 (m, 1H), 6.18 (d, J=3.6 Hz, 1H), 4.95 (br. s., 1H), 4.55-4.40 (m, 2H), 4.15-4.01 (m, 1H), 3.73 (br. s., 3H), 3.66-3.58 (m, 1H), 3.47-3.28 (m, 1H), 3.13 (dd, J=5.6, 18.0 Hz, 1H), 1.16 (t, J=7.2 Hz, 3H).

LCMS (ESI) m/z: 523.0 [M+H$^+$].

Example 42 was separated by pre-SFC to obtain chirally pure Example 43 and Example 44.

NMR data of Example 43: $^1$H NMR (400 MHz, CDCl$_3$) δ: 7.80 (d, J=3.2 Hz, 1H), 7.37 (d, J=3.2 Hz, 1H), 7.33 (dd, J=2.4, 8.4 Hz, 1H), 7.29 (br. s., 1H), 7.25 (br. s., 1H), 6.16 (s, 1H), 4.97 (br. s., 1H), 4.45 (s, 2H), 4.42 (br. s., 1H), 4.06 (q, J=7.2 Hz, 2H), 3.71 (br. s., 3H), 3.49-3.38 (m, 1H), 3.35-3.22 (m, 1H), 1.15 (t, J=7.2 Hz, 3H).

LCMS (ESI) m/z: 523.0 [M+H$^+$].

NMR data of Example 44: $^1$H NMR (400 MHz, CDCl$_3$) δ: 7.80 (d, J=3.2 Hz, 1H), 7.37 (d, J=3.2 Hz, 1H), 7.32 (dd, J=2.4, 8.4 Hz, 1H), 7.26-7.21 (m, 1H), 6.98 (dt, J=2.4, 8.4 Hz, 1H), 6.15 (s, 1H), 5.03 (br. s., 1H), 4.55-4.42 (m, 2H), 4.33 (d, J=5.6 Hz, 1H), 4.04 (q, J=7.2 Hz, 2H), 3.70 (br. s., 3H), 3.61 (m, 1H), 3.11 (m, 1H), 1.13 (t, J=7.2 Hz, 3H).

LCMS (ESI) m/z: 523.0 [M+H$^+$].

Examples 45, 46, 47

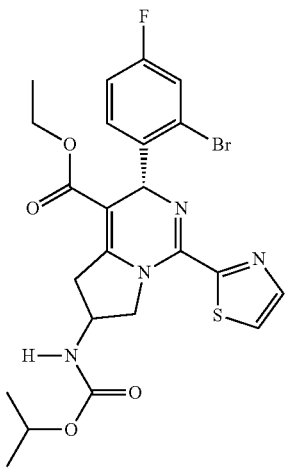
45

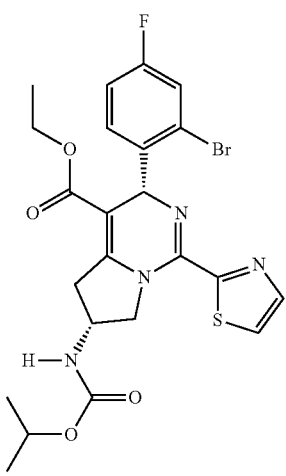
46

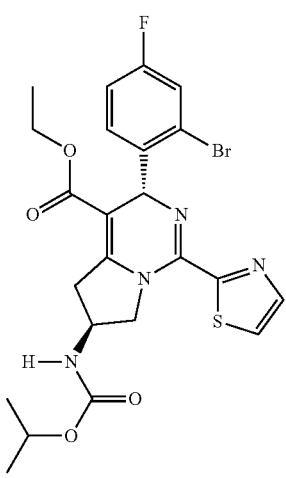
47

This Example was prepared according to the method as described in Examples 42, 43, 44.

NMR data of Example 45: $^1$H NMR (400 MHz, CDCl$_3$) δ: 7.81 (d, J=3.2 Hz, 1H), 7.38 (d, J=3.2 Hz, 1H), 7.34 (dd, J=2.4, 8.4 Hz, 1H), 7.30 (br. s., 1H), 7.04-6.94 (m, 1H), 6.17 (s, 1H), 4.95 (br. s., 1H), 4.84 (br. s., 1H), 4.45 (s, 3H), 4.06 (q, J=7.2 Hz, 2H), 3.48-3.25 (m, 2H), 1.26 (br. s., 6H), 1.16 (t, J=7.2 Hz, 3H).

LCMS (ESI) m/z: 551.1 [M+H$^+$].

NMR data of Example 46: $^1$H NMR (400 MHz, CDCl$_3$) δ: 7.81 (d, J=3.2 Hz, 1H), 7.38 (d, J=3.2 Hz, 1H), 7.34 (dd, J=2.4, 8.4 Hz, 1H), 7.30 (br. s., 1H), 7.04-6.94 (m, 1H), 6.17 (s, 1H), 4.95 (br. s., 1H), 4.84 (br. s., 1H), 4.45 (s, 3H), 4.06 (q, J=7.2 Hz, 2H), 3.48-3.25 (m, 2H), 1.26 (br. s., 6H), 1.16 (t, J=7.2 Hz, 3H).

LCMS (ESI) m/z: 551.1 [M+H$^+$].

NMR data of Example 47: $^1$H NMR (400 MHz, CDCl$_3$) δ: 7.80 (d, J=3.2 Hz, 1H), 7.37 (d, J=3.02 Hz, 1H), 7.32 (dd, J=2.4, 8.4 Hz, 1H), 7.26-7.22 (m, 1H), 6.98 (dt, J=2.4, 8.4 Hz, 1H), 6.16 (s, 1H), 4.94 (br. s., 1H), 4.82 (br. s., 1H), 4.57-4.45 (m, 2H), 4.39-4.26 (m, 1H), 4.05 (q, J=7.2 Hz, 2H), 3.61 (dd, J=7.2, 18.0 Hz, 1H), 3.10 (dd, J=6.0, 18.0 Hz, 1H), 1.26 (d, J=4.4 Hz, 6H), 1.13 (t, J=7.2 Hz, 3H).

LCMS (ESI) m/z: 551.1 [M+H$^+$].

Examples 48, 49, 50

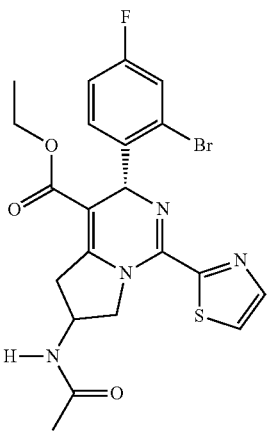
48

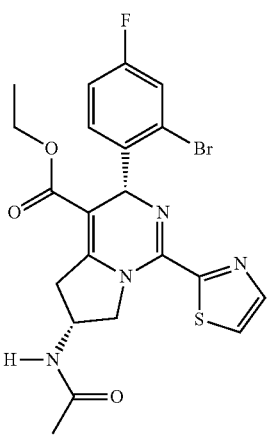
49

50

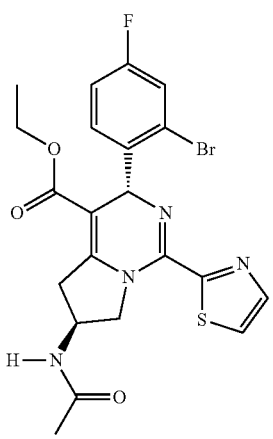

This Example was prepared according to the method as described in Examples 42, 43, 44.

NMR data of Example 48: $^1$H NMR (400 MHz, CDCl$_3$) δ: 7.82 (d, J=2.8 Hz, 1H), 7.42-7.38 (m, 1H), 7.38-7.31 (m, 1H), 7.30 (d, J=2.4 Hz, 1H), 7.27-7.22 (m, 1H), 7.04-6.96 (m, 1H), 6.19 (s, 1H), 5.83-5.70 (m, 1H), 4.77-4.62 (m, 1H), 4.52-4.38 (m, 1H), 4.07 (m, 1H), 3.64-3.57 (m, 1H), 3.45-3.31 (m, 1H), 3.16 (dd, J=5.6, 18.0 Hz, 1H), 2.05 (d, J=4.4 Hz, 3H), 1.16 (t, J=7.2 Hz, 3H).

LCMS (ESI) m/z: 507.1 [M+H$^+$].

NMR data of Example 49: $^1$H NMR (400 MHz, CDCl$_3$) δ: 7.79 (d, J=3.2 Hz, 1H), 7.37 (d, J=3.2 Hz, 1H), 7.32 (dd, J=2.4, 8.0 Hz, 1H), 7.26-7.20 (m, 1H), 6.98 (dt, J=2.4, 8.4 Hz, 1H), 6.16 (s, 1H), 5.95 (d, J=7.0 Hz, 1H), 4.76-4.63 (m, 1H), 4.48-4.40 (m, 2H), 4.04 (q, J=7.2 Hz, 2H), 3.56 (dd, J=7.2, 18.0 Hz, 1H), 3.16 (dd, J=5.6, 18.4 Hz, 1H), 2.00 (s, 3H), 1.13 (t, J=7.2 Hz, 3H).

LCMS (ESI) m/z: 507.1 [M+H$^+$].

NMR data of Example 50: $^1$H NMR (400 MHz, CDCl$_3$) δ: 7.80 (d, J=3.2 Hz, 1H), 7.38 (d, J=3.2 Hz, 1H), 7.36-7.27 (m, 2H), 6.97 (dt, J=2.4, 8.4 Hz, 1H), 6.17 (s, 1H), 5.78 (d, J=5.6 Hz, 1H), 4.69-4.59 (m, 1H), 4.49-4.36 (m, 2H), 4.06 (q, J=7.2 Hz, 2H), 3.45-3.27 (m, 2H), 2.10-1.99 (m, 3H), 1.15 (t, J=7.2 Hz, 3H).

LCMS (ESI) m/z: 507.1 [M+H$^+$].

Examples 51, 52, 53

51

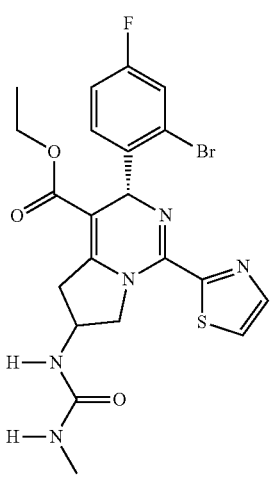

52

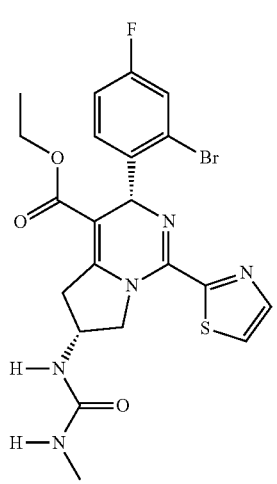

53

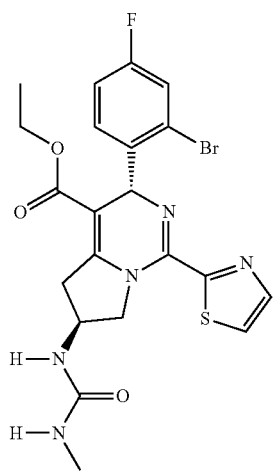

The Example was prepared according to the method as described in Examples 42, 43, 44.

NMR data of Example 51: $^1$H NMR (400 MHz, CDCl$_3$) δ: 7.80 (d, J=3.6 Hz, 1H), 7.37 (d, J=3.6 Hz, 1H), 7.31 (m, 2H), 6.94 (dt, J=2.4, 8.4 Hz, 1H), 6.16 (s, 1H), 4.62 (d, J=5.6 Hz, 1H), 4.51 (br. s., 1H), 4.47-4.38 (m, 3H), 4.05 (q, J=7.2 Hz, 2H), 3.42-3.34 (m, 1H), 3.34-3.25 (m, 1H), 2.79 (d, J=5.2 Hz, 3H), 1.15 (t, J=7.2 Hz, 3H).

LCMS (ESI) m/z: 522.0 [M+H$^+$].

NMR data of Example 52: $^1$H NMR (400 MHz, CDCl$_3$) δ: 7.80 (d, J=3.6 Hz, 1H), 7.37 (d, J=3.2 Hz, 1H), 7.31 (m, 2H), 6.94 (dt, J=2.4, 8.4 Hz, 1H), 6.16 (s, 1H), 4.62 (d, J=5.6 Hz, 1H), 4.51 (br. s., 1H), 4.47-4.38 (m, 3H), 4.05 (q, J=7.2 Hz, 2H), 3.42-3.34 (m, 1H), 3.34-3.25 (m, 1H), 2.79 (d, J=5.6 Hz, 3H), 1.15 (t, J=7.2 Hz, 3H).

LCMS (ESI) m/z: 522.0 [M+H$^+$].

NMR data of Example 53: $^1$H NMR (400 MHz, CDCl$_3$) δ: 7.79 (d, J=3.2 Hz, 1H), 7.36 (d, J=3.2 Hz, 1H), 7.32 (dd, J=2.4, 8.4 Hz, 1H), 7.26-7.22 (m, 1H), 6.99 (dt, J=2.4, 8.4 Hz, 1H), 6.14 (s, 1H), 4.76 (d, J=7.2 Hz, 1H), 4.65-4.53 (m, 1H), 4.49-4.41 (m, 1H), 4.41-4.31 (m, 2H), 4.04 (q, J=7.2 Hz, 2H), 3.55 (dd, J=7.2, 18.0 Hz, 1H), 3.12 (dd, J=5.6, 17.6 Hz, 1H), 2.77 (d, J=4.4 Hz, 3H), 1.13 (t, J=7.2 Hz, 3H).

LCMS (ESI) m/z: 522.0 [M+H$^+$].

Examples 54, 55, 56

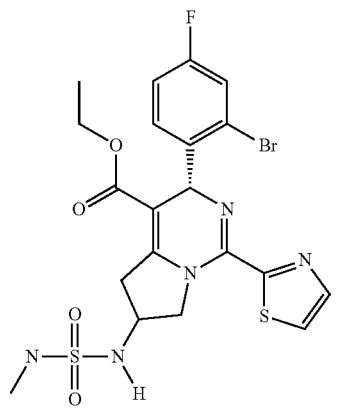

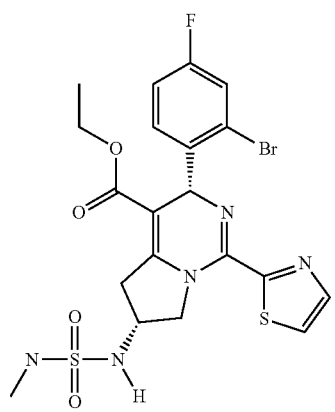

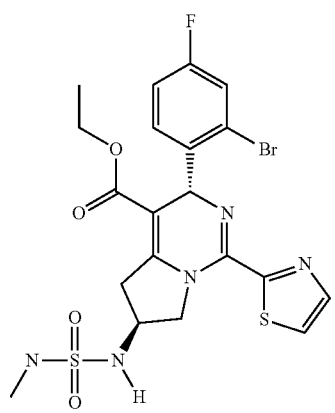

The Example was prepared according to the method as described in Examples 42, 43, 44.

NMR data of Example 54: $^1$H NMR (400 MHz, CDCl$_3$) δ: 7.81 (t, J=3.2 Hz, 1H), 7.39 (t, J=3.2 Hz, 1H), 7.33 (td, J=2.8, 8.4 Hz, 1H), 7.30-7.27 (m, 1H), 6.98 (dq, J=2.4, 8.0 Hz, 1H), 6.17 (s, 1H), 4.67-4.60 (m, 1H), 4.51 (d, J=6.0 Hz, 1H), 4.48-4.32 (m, 2H), 4.25-4.17 (m, 1H), 4.11-4.01 (m, 2H), 3.63-3.52 (m, 1H), 3.35-3.21 (m, 1H), 2.74 (dd, J=5.6, 8.8 Hz, 3H), 1.15 (t, J=7.2 Hz, 3H).

LCMS (ESI) m/z: 558.1 [M+H$^+$].

NMR data of Example 55: $^1$H NMR (400 MHz, CDCl$_3$) δ: 7.80 (d, J=3.2 Hz, 1H), 7.38 (d, J=3.6 Hz, 1H), 7.35-7.28 (m, 2H), 6.99 (dt, J=2.4, 8.4 Hz, 1H), 6.17 (s, 1H), 4.70-4.59 (m, 2H), 4.44-4.35 (m, 2H), 4.21 (br. s., 1H), 4.05 (m, 2H), 3.55 (d, J=18.0 Hz, 1H), 3.31 (dd, J=6.8, 18.0 Hz, 1H), 2.74 (d, J=3.2 Hz, 3H), 1.14 (t, J=7.2 Hz, 3H).

LCMS (ESI) m/z: 558.1 [M+H$^+$].

NMR data of Example 56: $^1$H NMR (400 MHz, CDCl$_3$) δ: 7.82 (d, J=3.2 Hz, 1H), 7.39 (d, J=3.2 Hz, 1H), 7.33 (dd, J=2.4, 8.4 Hz, 1H), 7.23 (dd, J=6.4, 8.8 Hz, 1H), 6.98 (dt, J=2.4, 8.34 Hz, 1H), 6.16 (s, 1H), 4.66-4.57 (m, 2H), 4.50 (d, J=5.6 Hz, 1H), 4.43 (dd, J=6.0, 12.0 Hz, 1H), 4.25-4.17 (m, 1H), 4.05 (q, J=7.2 Hz, 2H), 3.59 (dd, J=7.2, 18.0 Hz, 1H), 3.25 (dd, J=5.6, 18.0 Hz, 1H), 2.73 (d, J=5.6 Hz, 3H), 1.13 (t, J=7.2 Hz, 3H).

LCMS (ESI) m/z: 558.1 [M+H$^+$].

Examples 57, 58, 59

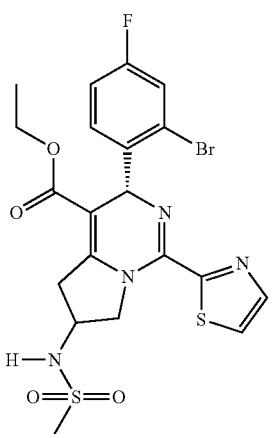

Examples 60, 61, 62

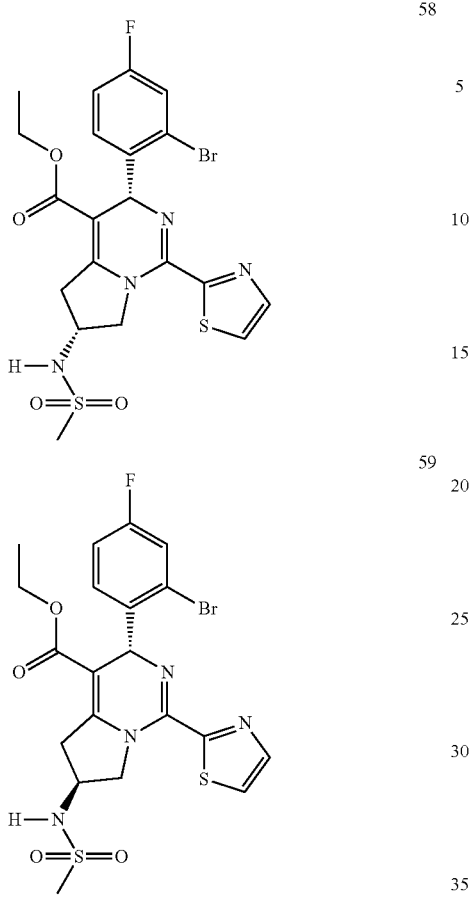

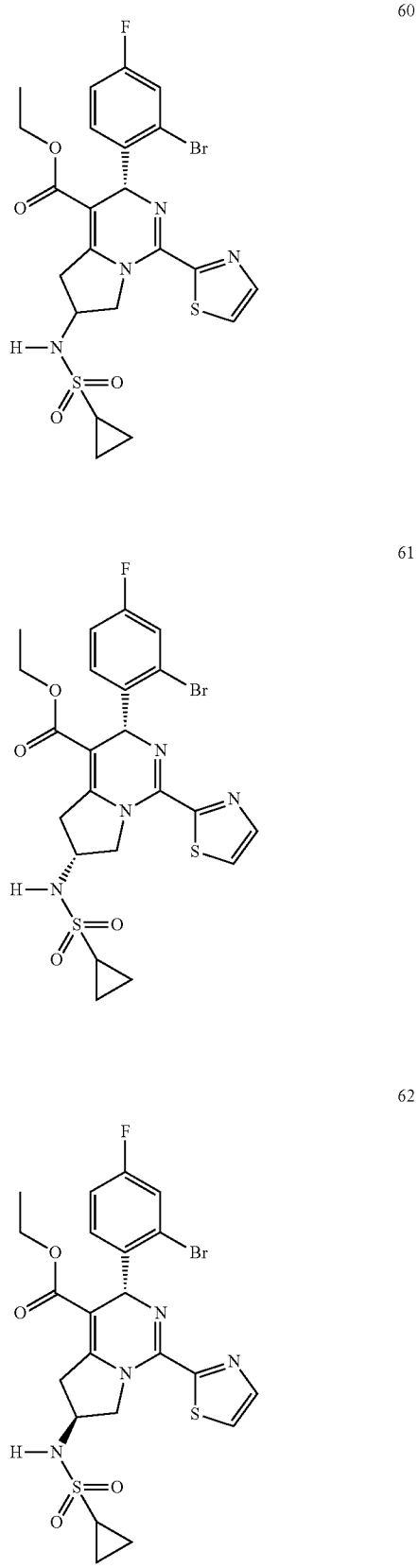

The Example was prepared according to the method as described in Examples 42, 43, 44.

NMR data of Example 57: $^1$H NMR (400 MHz, CDCl$_3$) δ: 7.81 (d, J=3.2 Hz, 1H), 7.38 (d, J=3.2 Hz, 1H), 7.33 (td, J=3.2, 8.4 Hz, 1H), 7.30-7.22 (m, 1H), 6.99 (dq, J=2.4, 8.4 Hz, 1H), 6.16 (d, J=4.8 Hz, 1H), 4.72-4.65 (m, 1H), 4.61-4.53 (m, 1H), 4.52-4.44 (m, 1H), 4.35-4.27 (m, 1H), 4.09-4.01 (m, 2H), 3.71-3.648 (m, 1H), 3.40-3.17 (m, 1H), 3.06 (d, J=2.4 Hz, 3H), 1.13 (q, J=6.8 Hz, 3H).

LCMS (ESI) m/z: 543.1 [M+H$^+$].

NMR data of Example 58: $^1$H NMR (400 MHz, CDCl$_3$) δ: 7.80 (d, J=3.6 Hz, 1H), 7.38 (d, J=3.2 Hz, 1H), 7.35-7.27 (m, 2H), 7.00 (dt, J=2.4, 8.4 Hz, 1H), 6.17 (s, 1H), 4.84 (d, J=5.6 Hz, 1H), 4.63-4.54 (m, 1H), 4.52-4.44 (m, 1H), 4.32 (d, J=2.4 Hz, 1H), 4.13-3.99 (m, 2H), 3.56-3.46 (m, 1H), 3.42-3.31 (m, 1H), 3.05 (s, 3H), 1.14 (t, J=7.2 Hz, 3H).

LCMS (ESI) m/z: 543.1 [M+H$^+$].

NMR data of Example 59: $^1$H NMR (400 MHz, CDCl$_3$) δ: 7.82 (d, J=3.2 Hz, 1H), 7.39 (d, J=3.2 Hz, 1H), 7.33 (dd, J=2.4, 8.4 Hz, 1H), 7.23 (dd, J=6.4, 8.8 Hz, 1H), 6.98 (dt, J=2.4, 8.4 Hz, 1H), 6.16 (s, 1H), 4.66-4.57 (m, 1H), 4.50 (d, J=5.6 Hz, 1H), 4.43 (dd, J=6.0, 12.0 Hz, 1H), 4.25-4.17 (m, 1H), 4.05 (q, J=7.2 Hz, 2H), 3.59 (dd, J=7.2, 18.0 Hz, 1H), 3.25 (dd, J=5.6, 18.0 Hz, 1H), 2.73 (d, J=5.6 Hz, 3H), 1.13 (t, J=7.2 Hz, 3H).

LCMS (ESI) m/z: 543.1 [M+H$^+$].

-continued

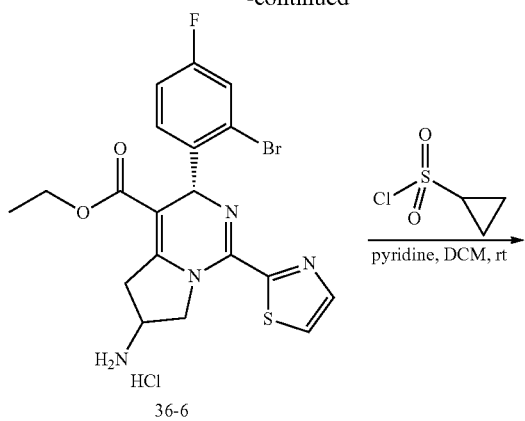

36-6

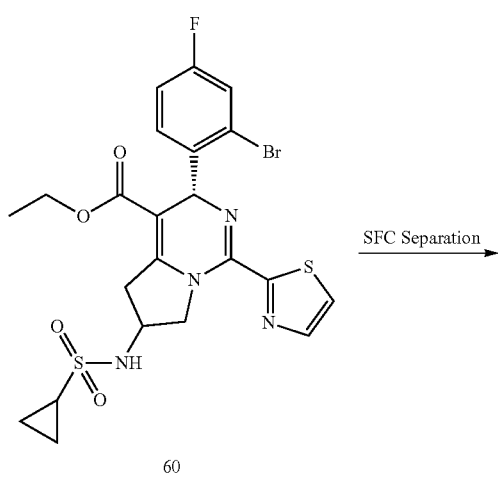

60

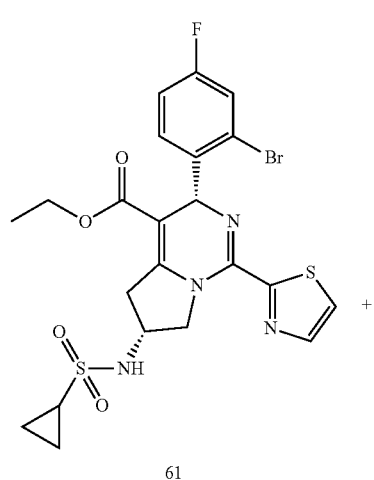

61

-continued

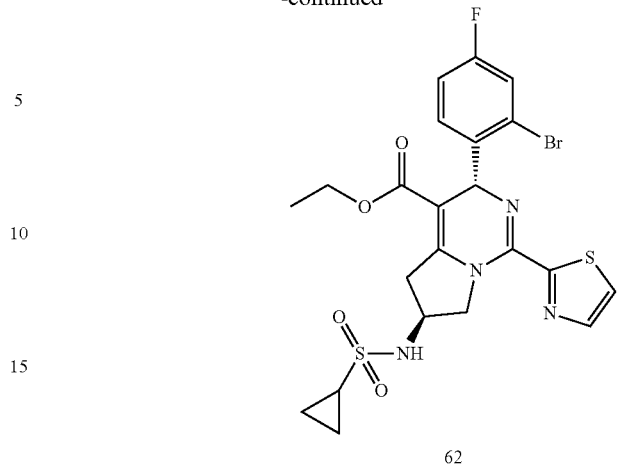

62

Example 36-6 (200 mg, 0.398 mmol) was dissolved in anhydrous pyridine (5 mL), and at room temperature was added cyclopropylsulfonyl chloride (56 mg, 0.477 mmol). After the addition, the mixture was fully stirred under nitrogen atmosphere for 2 hours, followed by a supplementary addition of cyclopropylsulfonyl chloride (56 mg, 0.477 mmol) and continued being stirred under nitrogen atmosphere for 2 hours. When TLC (PE:EtOAc; 1:1) showed that the starting materials disappeared, the reaction mixture was poured into saturated sodium bicarbonate solution (15 mL), and extracted with DCM (20 mL×3). The organic phases were combined, sequentially washed with water (10 mL×2), saturated sodium chloride solution (10 mL×2), dried over anhydrous sodium sulfate, filtered, and purified by silica gel column chromatography with an eluent system (PE:EtOAc=100:1-3:1) to obtain 140 mg diastereoisomers, yield: 62%.

NMR data of Example 60: $^1$H NMR (400 MHz, CDCl$_3$) δ: 7.81 (d, J=3.6 Hz, 1H), 7.39 (d, J=3.2 Hz, 1H), 7.36-7.31 (m, 1H), 7.31-7.27 (m, 1H), 7.01 (dt, J=2.4, 8.0 Hz, 1H), 6.17 (s, 1H), 4.63 (d, J=6.4 Hz, 1H), 4.62-4.56 (m, 1H), 4.54-4.45 (m, 1H), 4.39-4.29 (m, 1H), 4.12-4.00 (m, 2H), 3.59-3.49 (m, 1H), 3.43-3.32 (m, 1H), 2.57-2.42 (m, 1H), 1.29-1.20 (m, 2H), 1.15 (t, J=7.2 Hz, 3H), 1.07 (d, J=7.2 Hz, 2H).

LCMS (ESI) m/z: 569.1 [M+H$^+$].

The diastereoisomers were separated by pre-SFC to obtain chirally pure Example 61 and Example 62.

NMR data of Example 61: $^1$H NMR (400 MHz, CDCl$_3$) δ: 7.81 (d, J=3.6 Hz, 1H), 7.39 (d, J=3.2 Hz, 1H), 7.36-7.31 (m, 1H), 7.31-7.27 (m, 1H), 7.01 (dt, J=2.4, 8.0 Hz, 1H), 6.17 (s, 1H), 4.63 (d, J=6.0 Hz, 1H), 4.62-4.56 (m, 1H), 4.54-4.45 (m, 1H), 4.39-4.29 (m, 1H), 4.12-4.00 (m, 2H), 3.59-3.49 (m, 1H), 3.43-3.32 (m, 1H), 2.57-2.42 (m, 1H), 1.29-1.20 (m, 2H), 1.15 (t, J=7.2 Hz, 3H), 1.06-1.08 (m, 2H).

LCMS (ESI) m/z: 569.1 [M+H$^+$].

NMR data of Example 62: $^1$H NMR (400 MHz, CDCl$_3$) δ: 7.81 (d, J=3.2 Hz, 1H), 7.39 (d, J=3.2 Hz, 1H), 7.33 (dd, J=2.4, 8.4 Hz, 1H), 7.25-7.20 (m, 1H), 6.99 (dt, J=2.4, 8.4 Hz, 1H), 6.16 (s, 1H), 4.65-4.60 (m, 1H), 4.59-4.54 (m, 1H), 4.49-4.42 (m, 1H), 4.37-4.26 (m, 1H), 4.05 (q, J=7.2 Hz, 2H), 3.69 (dd, J=7.6, 18.1 Hz, 1H), 3.19 (dd, J=6.8, 17.6 Hz, 1H), 2.57-2.45 (m, 1H), 1.27-1.22 (m, 2H), 1.13 (t, J=7.2 Hz, 3H), 1.08 (d, J=3.2 Hz, 1H), 1.07-1.06 (m, 1H).

LCMS (ESI) m/z: 569.1 [M+H$^+$].

Examples 63, 64
Examples 65, 66
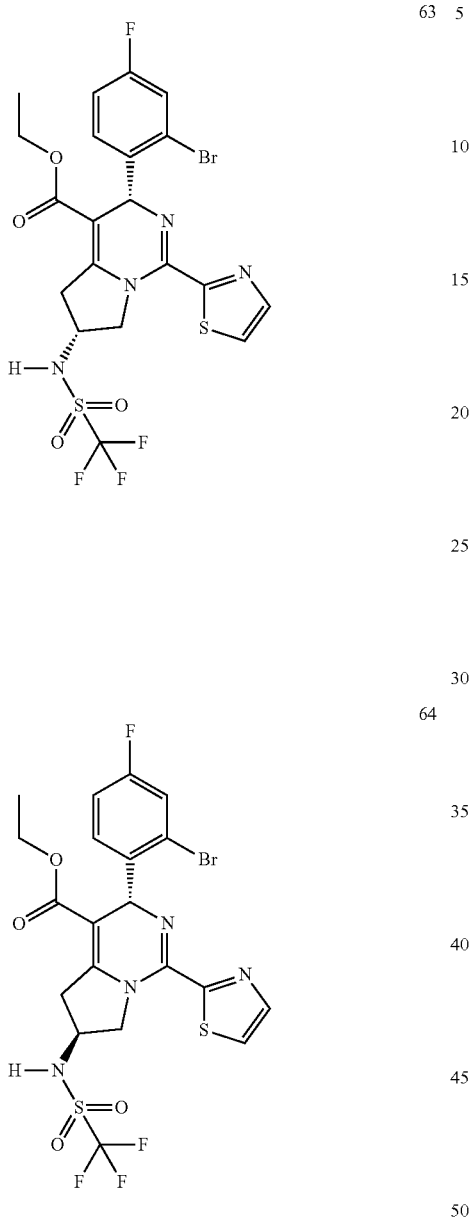
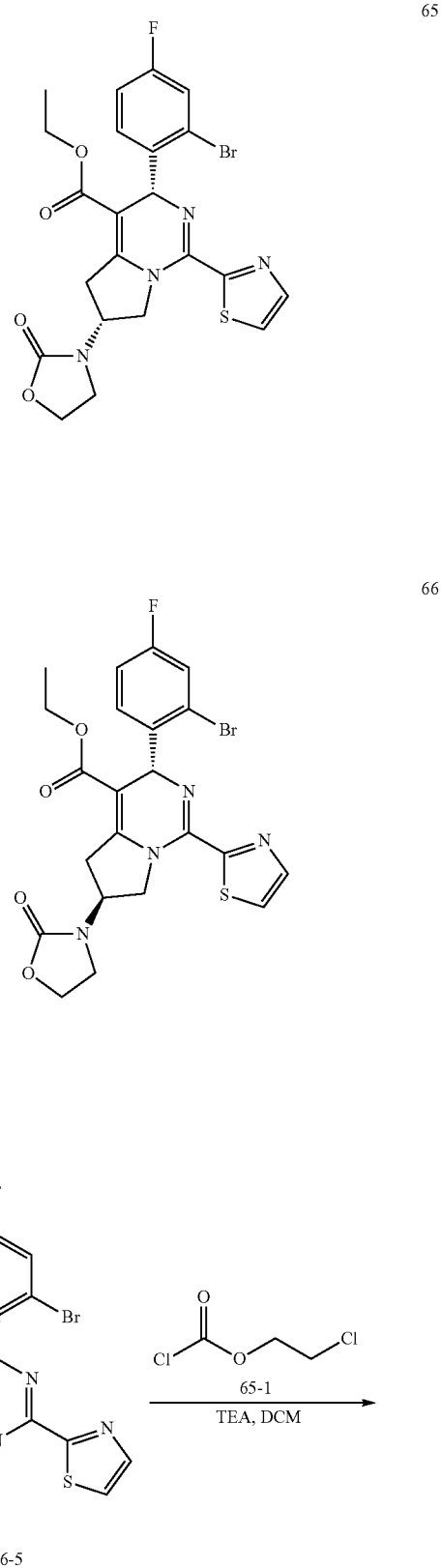
This Example was prepared according to the method as described in Examples 61, 62.
NMR data of Example 63: $^1$H NMR (400 MHz, DMSO-d6) δ: 7.96 (d, J=3.2 Hz, 1H), 7.86 (d, J=3.6 Hz, 1H), 7.55 (dd, J=2.4, 8.4 Hz, 1H), 7.44 (dd, J=6.0, 8.4 Hz, 1H), 7.22 (dt, J=2.4, 8.4 Hz, 1H), 5.98 (s, 1H), 4.42-4.39 (m, 1H), 4.00-3.95 (m, 2H), 3.48-3.38 (m, 3H), 2.94 (dd, J=7.6, 18.0 Hz, 1H), 1.06 (t, J=7.2 Hz, 3H).
LCMS (ESI) m/z: 599.0 [M+H$^+$].
NMR data of Example 64: $^1$H NMR (400 MHz, DMSO-d6) δ: 7.96 (d, J=3.0 Hz, 1H), 7.86 (d, J=3.6 Hz, 1H), 7.57 (dd, J=2.4, 8.4 Hz, 2H), 7.22 (dd, J=6.0, 8.4 Hz, 1H), 5.99 (s, 1H), 4.32-4.25 (m, 2H), 4.03-3.95 (m, 2H), 3.48-3.38 (m, 2H), 3.26 (s, 1H), 1.08 (t, J=7.2 Hz, 3H).
LCMS (ESI) m/z: 598.9 [M+H$^+$].

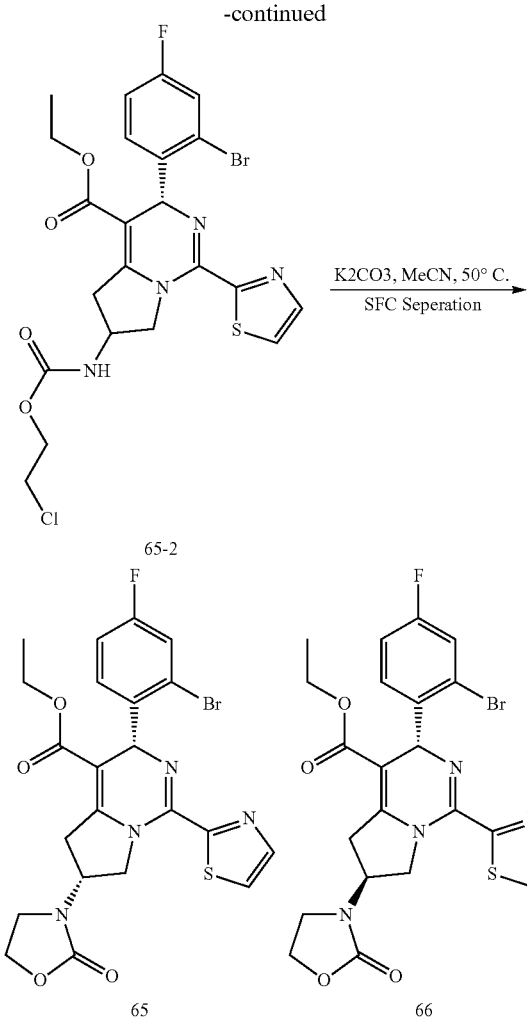

Step 1 (Synthesis of Compound 65-2)

Compound 36-5 (350 mg, 0.7 mmol) was dissolved in anhydrous DCM (15 mL), and at room temperature were added triethylamine (211 mg, 2.09 mmol), 65-1 (149 mg, 1.05 mmol). After the addition, the mixture was stirred at room temperature overnight, and then concentrated under reduced pressure, extracted with (30 mL×3) EtOAc. The organic phases were combined, sequentially washed with water (20 mL×2), saturated sodium chloride solution (20 mL×2), dried over anhydrous sodium sulfate, filtered. The filtrate was concentrated under reduced pressure and purified by silica gel column chromatography with an eluent system (PE:EtOAc=2:1) to obtain 220 mg compound 65-2, yield: 55%.

LCMS (ESI) m/z: 571.1 [M+H$^+$].

Step 2 (Synthesis of Examples 65, 66)

Compound 65-2 (200 mg, 0.35 mmol) was dissolved in acetonitrile (15 mL), and potassium carbonate (241 mg, 1.75 mmol) was added, the mixture was stirred under nitrogen atmosphere at 500 for 6 hours.

The reaction mixture was cooled, and then concentrated under reduced pressure, extracted with EtOAc (30 mL×3). The organic phases were combined, sequentially washed with water (20 mL×2), saturated sodium chloride solution (20 mL×2), dried over anhydrous sodium sulfate, and filtered. The filtrate was concentrated under reduced pressure and purified by silica gel column chromatography with an eluent system (PE:EtOAc=1:1), and separated by SFC to obtain 49 mg compound 65, 55 mg compound 66. Yield: 65%.

NMR data of Example 65: $^1$H NMR (400 MHz, CDCl$_3$) δ: 7.81 (d, J=3.2 Hz, 1H), 7.39 (d, J=3.6 Hz, 1H), 7.32 (dd, J=2.4, 8.4 Hz, 1H), 7.22 (dd, J=6.0, 8.4 Hz, 1H), 6.99 (dt, J=2.4, 8.4 Hz, 1H), 6.16 (s, 1H), 4.80-4.68 (m, 2H), 4.42-4.36 (m, 2H), 4.36-4.32 (m, 1H), 4.05 (q, J=7.0 Hz, 2H), 3.68-3.58 (m, 2H), 3.54 (dd, J=7.6, 18.0 Hz, 1H), 3.39-3.29 (m, 1H), 1.13 (t, J=7.2 Hz, 3H).

LCMS (ESI) m/z: 537.1 [M+H$^+$].

NMR data of Example 66: $^1$H NMR (400 MHz, CDCl$_3$) δ: 7.80 (d, J=3.2 Hz, 1H), 7.39 (d, J=3.0 Hz, 1H), 7.33 (dd, J=2.0, 8.4 Hz, 1H), 7.23 (dd, J=6.34, 8.4 Hz, 1H), 7.00-6.91 (m, 1H), 6.18 (s, 1H), 4.77-4.70 (m, 1H), 4.62 (d, J=12.4 Hz, 1H), 4.46 (dd, J=6.8, 12.4 Hz, 1H), 4.43-4.35 (m, 2H), 4.06 (q, J=7.0 Hz, 2H), 3.66 (t, J=7.8 Hz, 2H), 3.54-3.39 (m, 2H), 1.14 (t, J=7.0 Hz, 3H).

LCMS (ESI) m/z: 537.1 [M+H$^+$].

Example 67

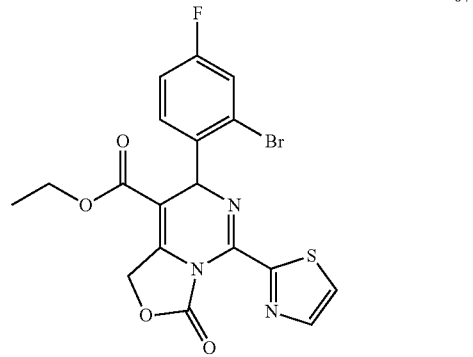

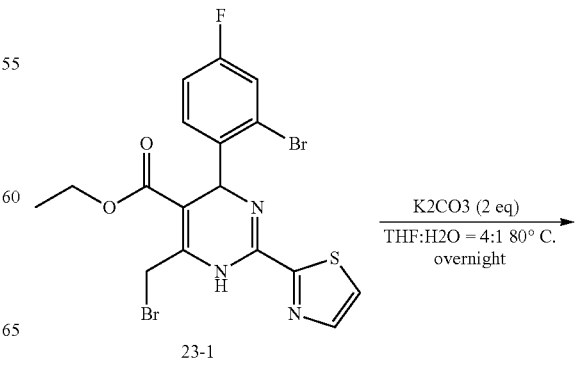

363

-continued

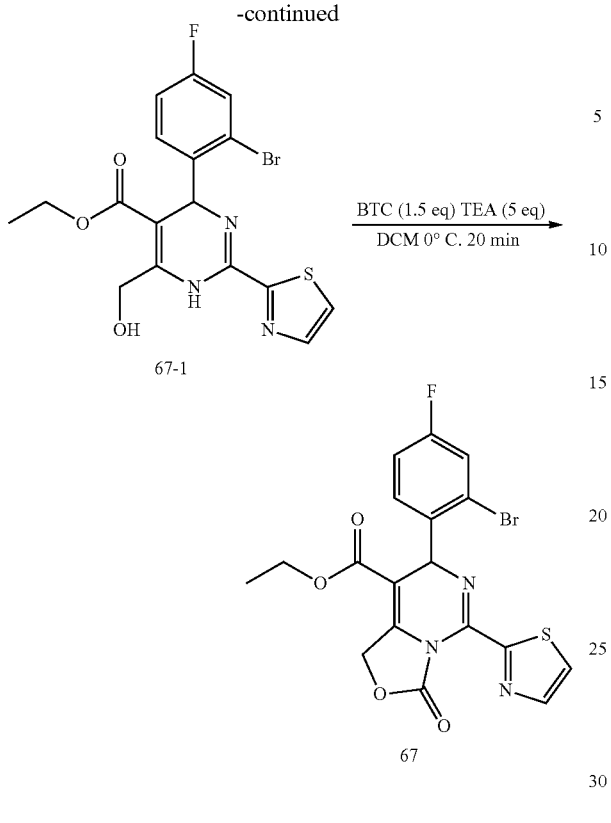

Step 1 (Synthesis of Compound 67-1)

Compound 23-1 (1.3 g, 2.6 mmol) was dissolved in tetrahydrofuran (40 mL) and water (10 mL), and potassium carbonate (717 mg, 5.2 mmol) was added. The reaction mixture was stirred at 80□ for 16 hours. The reaction mixture was concentrated under reduced pressure to obtain a crude product, to which were added 30 mL EtOAc and 20 mL water. The mixture was extracted with EtOAc (20 mL×2). The organic phases were combined, dried over anhydrous sodium sulfate, and filtered. The filtrate was concentrated under reduced pressure to obtain 400 mg compound 67-1. Yield: 35%.

LCMS (ESI) m/z: 439.8 [M+H⁺].

Step 2 (Synthesis of Example 67)

Compound 67-1 (210 mg, 0.48 mmol) was dissolved in anhydrous DCM (10 mL), and triethylamine (242 mg, 2.4 mmol), followed by triphosgene (210 mg, 0.72 mmol) were added. The mixture was stirred at 15□ for 30 minutes. The reaction mixture was quenched with 20 mL water, and extracted with DCM (20 mL×3). The organic layer was washed with saturated saline solution (30 mL×2). The organic phases were combined, dried over anhydrous sodium sulfate, and filtered. The filtrate was concentrated under reduced pressure, and purified by flash chromatography to obtain 80 mg Example 67. Yield: 24%.

NMR data of Example 67: ¹H NMR (400 MHz, DMSO-d6) δ: 7.92 (d, J=4.5 Hz, 2H), 7.73-7.83 (m, 1H), 7.63 (d, J=6.5 Hz, 1H), 7.32 (t, J=7.2 Hz, 1H), 6.12 (s, 1H), 5.45 (s, 2H), 3.92-4.12 (m, 2H), 1.08 (t, J=7.0 Hz, 3H).

LCMS (ESI) m/z: 466.0 [M+H⁺].

364

Example 68

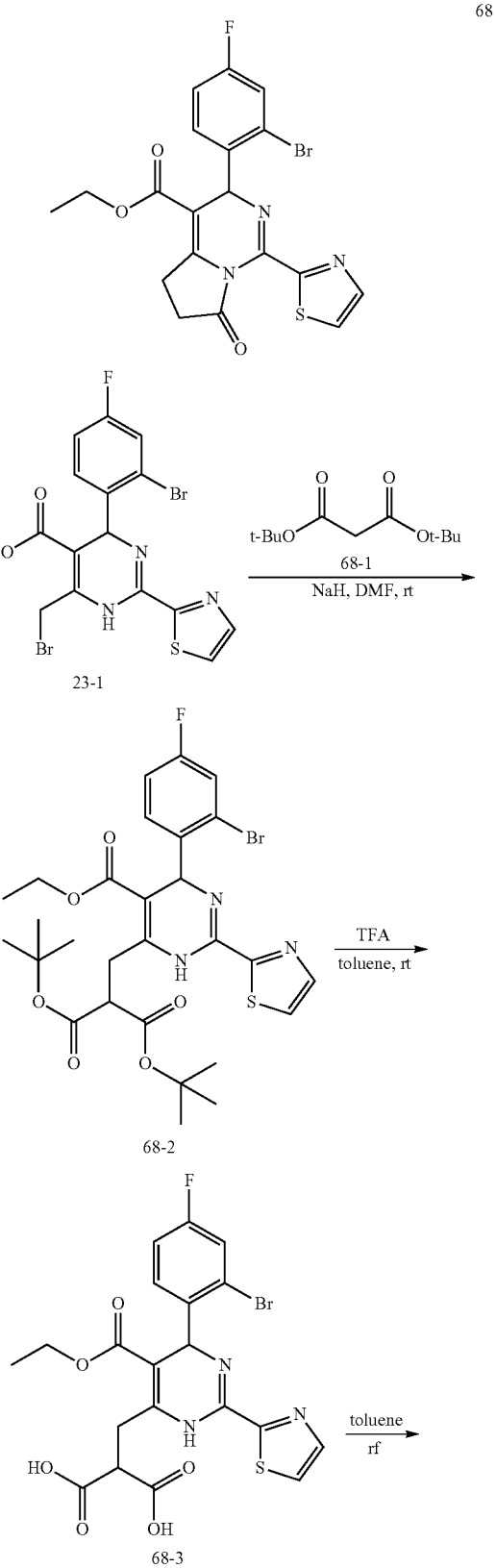

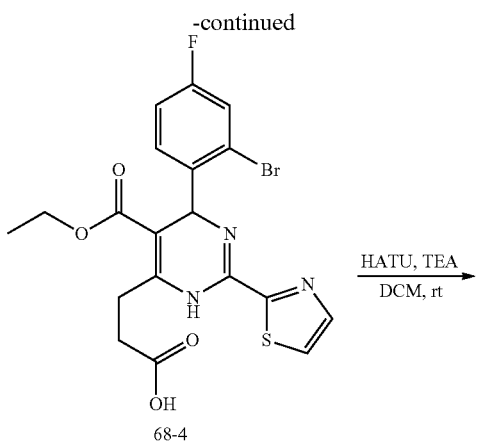

68-4

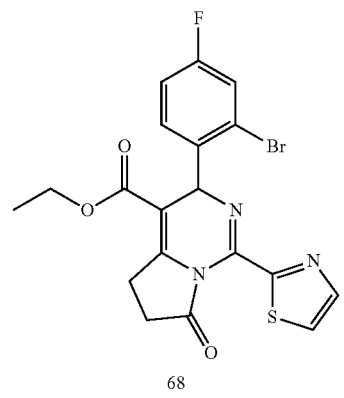

68

Step 1 (Synthesis of Compound 68-2)

Compound 23-1 (500 mg, 1 mmol) was dissolved in anhydrous N,N-dimethylformamide (10 mL), and 68-1 (216 mg, 1 mmol), sodium hydride (29 mg, 1.2 mmol) were added. After the addition, the mixture was stirred at room temperature overnight. The reaction mixture was concentrated under reduced pressure and then extracted with (200 mL×3) EtOAc. The organic layer was washed with saturated saline solution (200 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 120 mg product 68-2. Yield: 19%.

LCMS (ESI) m/z: 638.1 [M+H$^+$].

Step 2 (Synthesis of Compound 68-3)

Compound 68-2 (120 mg, 0.19 mmol) was dissolved in toluene (5 mL), and trifluoroacetic anhydride (21.9 mg, 0.23 mmol) was added. After the addition, the mixture was stirred at room temperature overnight. The reaction mixture was concentrated under reduced pressure and then extracted with (100 mL×3) DCM. The organic layer was washed with saturated saline solution (50 mL×2). The organic phases were combined, dried over anhydrous sodium sulfate, and filtered. The filtrate was concentrated under reduced pressure, and purified by silica gel column chromatography with an eluent system (PE:EtOAc=5:1) to obtain 100 mg crude product 68-3. Yield: 100%.

LCMS (ESI) m/z: 526.0 [M+H$^+$].

Step 3 (Synthesis of Compound 68-4)

Compound 68-3 (100 mg, 0.19 mmol) was dissolved in toluene (5 mL) and stirred under reflux overnight. The reaction mixture was concentrated under reduced pressure and then extracted with (100 mL×3) DCM. The organic layer was washed with saturated saline solution (50 mL×2). The organic phases were combined, dried over anhydrous sodium sulfate, and filtered. The filtrate was concentrated under reduced pressure to obtain 60 mg crude product 68-4. Yield: 66%.

LCMS (ESI) m/z: 482.0 [M+H$^+$].

Step 4 (Synthesis of Compound 68)

Compound 68-4 (60 mg, 0.13 mmol) was dissolved in anhydrous DCM (10 mL), and HATU (56 mg, 0.16 mmol), triethylamine (53 mg, 0.52 mmol) were added. After the addition, the mixture was stirred at room temperature for 3 hours. The reaction mixture was extracted with (100 mL×3) DCM. The organic layer was washed with saturated saline solution (50 mL×2). The organic phases were combined, dried over anhydrous sodium sulfate, and filtered. The filtrate was concentrated under reduced pressure, and purified by silica gel column chromatography with an eluent system (PE:EtOAc=5:1) to obtain 50 mg product 68.

Yield: 88%.

NMR data of Example 68: $^1$H NMR (400 MHz, ACETONITRILE-d$_3$) δ: 7.82 (d, J=3.0 Hz, 1H), 7.61 (d, J=3.3 Hz, 1H), 7.43-7.52 (m, 2H), 7.16 (dt, J=2.6, 8.4 Hz, 1H), 6.20 (s, 1H), 4.00-4.11 (m, 2H), 3.34-3.45 (m, 1H), 3.19-3.31 (m, 1H), 2.68 (t, J=7.8 Hz, 2H), 1.13 (t, J=7.2 Hz, 3H).

LCMS (ESI) m/z: 464.0 [M+H$^+$].

Example 69

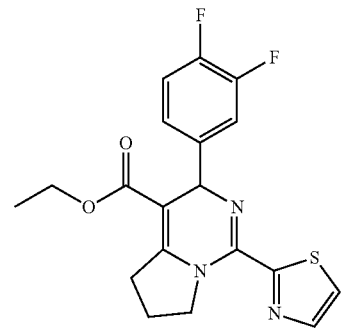

69

Example 69 was prepared according to the method as described in Example 1.

NMR data of Example 69: $^1$H NMR (400 MHz, CDCl$_3$) δ: 8.15 (s, 1H), 7.92 (br. s., 1H), 7.45 (br. s., 1H), 7.30-7.38 (m, 1H), 7.21 (d, J=8.0 Hz, 1H), 6.17 (s, 1H), 4.71 (br. s., 1H), 4.07-4.35 (m, 3H), 3.69 (d, J=11.80 Hz, 1H), 3.17 (br. s., 1H), 2.41 (br. s., 1H), 2.21 (br. s., 1H), 1.21 (t, J=7.0 Hz, 3H).

LCMS (ESI) m/z: 390.1 [M+H$^+$].

Example 70

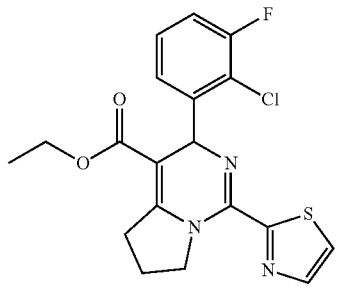

Example 70 was prepared according to the method as described in Example 1.

NMR data of Example 70: ¹H NMR (400 MHz, CDCl₃) δ: 7.94 (d, J=3.3 Hz, 1H), 7.85 (d, J=3.3 Hz, 1H), 7.39-7.21 (m, 3H), 6.06 (s, 1H), 4.34 (ddd, J=3.8, 7.7, 10.8 Hz, 1H), 4.21-4.11 (m, 1H), 4.01-3.91 (m, 2H), 3.31-3.22 (m, 1H), 3.00 (td, J=9.2, 17.9 Hz, 1H), 2.14-1.98 (m, 2H), 1.06 (t, J=7.2 Hz, 3H).

LCMS (ESI) m/z: 406.0 [M+H⁺].

Example 71

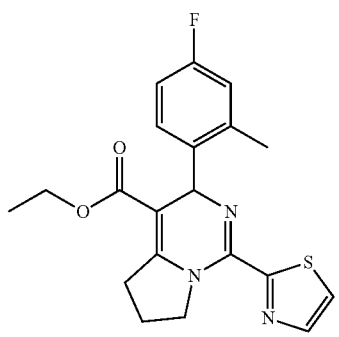

Example 71 was prepared according to the method as described in Example 1.
LCMS (ESI) m/z: 386.1 [M+H⁺].

Example 72

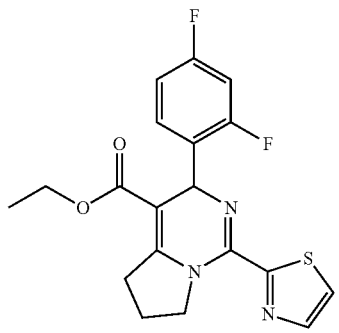

Example 72 was prepared according to the method as described in Example 1.

NMR data of Example 72: ¹H NMR (400 MHz, CDCl₃) δ: 7.84 (d, J=3.2 Hz, 1H), 7.39 (d, J=3.2 Hz, 1H), 7.28-7.33 (m, 1H), 6.73-6.84 (m, 2H), 6.02 (s, 1H), 4.39-4.43 (m, 1H), 4.22-4.32 (m, 1H), 4.05-4.11 (m, 2H), 3.31-3.37 (m, 1H), 3.00-3.04 (m, 1H), 2.09-2.21 (m, 1H), 1.97-2.09 (m, 1H), 1.18 (t, J=7.2 Hz, 3H).

LCMS (ESI) m/z: 390.0 [M+H⁺].

Example 73

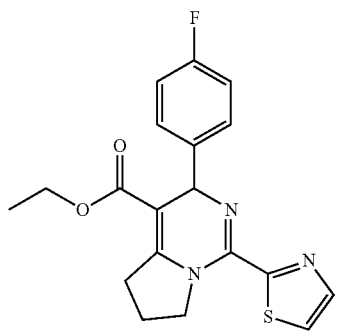

Example 73 was prepared according to the method as described in Example 1.

NMR data of Example 73: ¹H NMR (400 MHz, CDCl₃) δ: 7.86 (br. s., 1H), 7.39 (d, J=15.0 Hz, 3H), 6.99 (br. s., 2H), 5.83 (br. s., 1H), 4.05-4.50 (m, 4H), 3.34 (br. s., 1H), 2.99 (br. s., 1H), 1.89-2.27 (m, 2H), 1.25 (br. s., 3H).

LCMS (ESI) m/z: 372.0 [M+H⁺].

Example 74

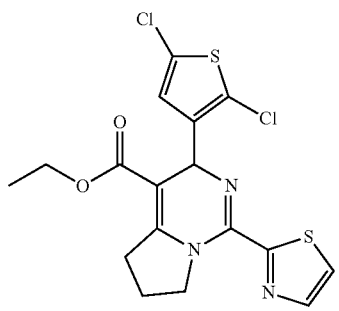

Example 74 was prepared according to the method as described in Example 1.

NMR data of Example 74: ¹H NMR (400 MHz, CDCl₃) δ: 7.85 (d, J=3.2 Hz, 1H), 7.41 (d, J=3.0 Hz, 1H), 6.68 (s, 1H), 5.89 (s, 1H), 4.45 (ddd, J=3.0, 8.2, 11.2 Hz, 1H), 4.20-4.30 (m, 1H), 4.07-4.18 (m, 2H), 3.34 (ddd, J=3.2, 8.4, 18.0 Hz, 1H), 2.98 (td, J=9.4, 18.3 Hz, 1H), 1.95-2.22 (m, 2H), 1.24 (t, J=7.0 Hz, 3H).

LCMS (ESI) m/z: 427.9 [M+H⁺].

Example 75
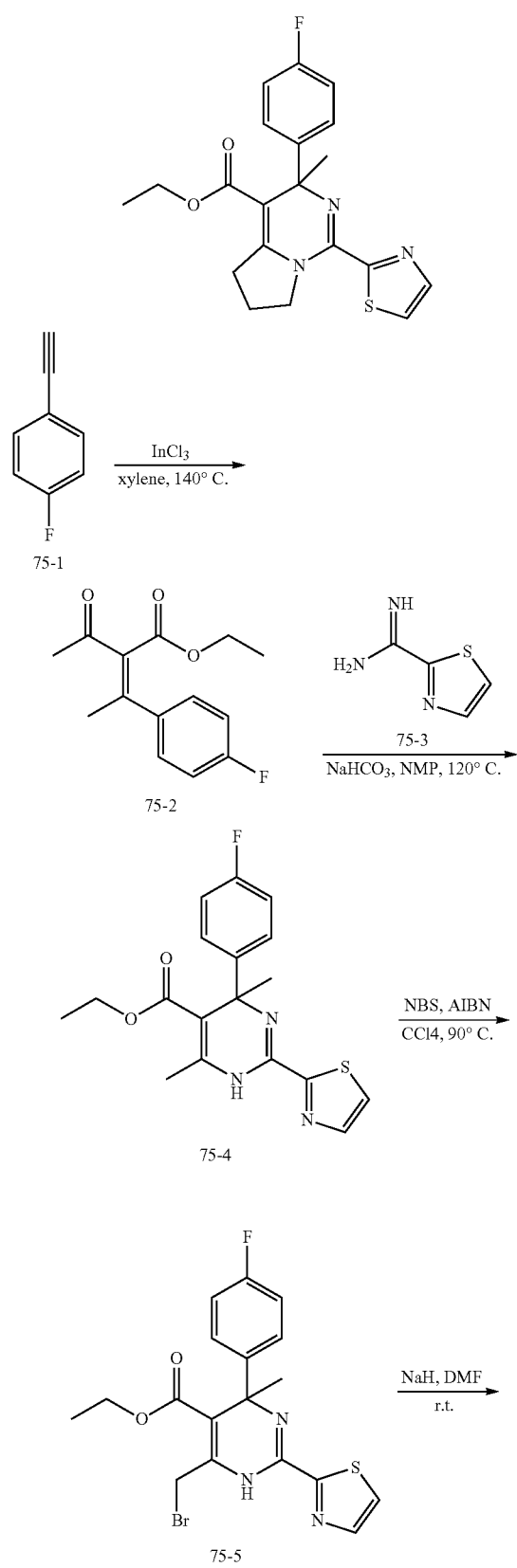
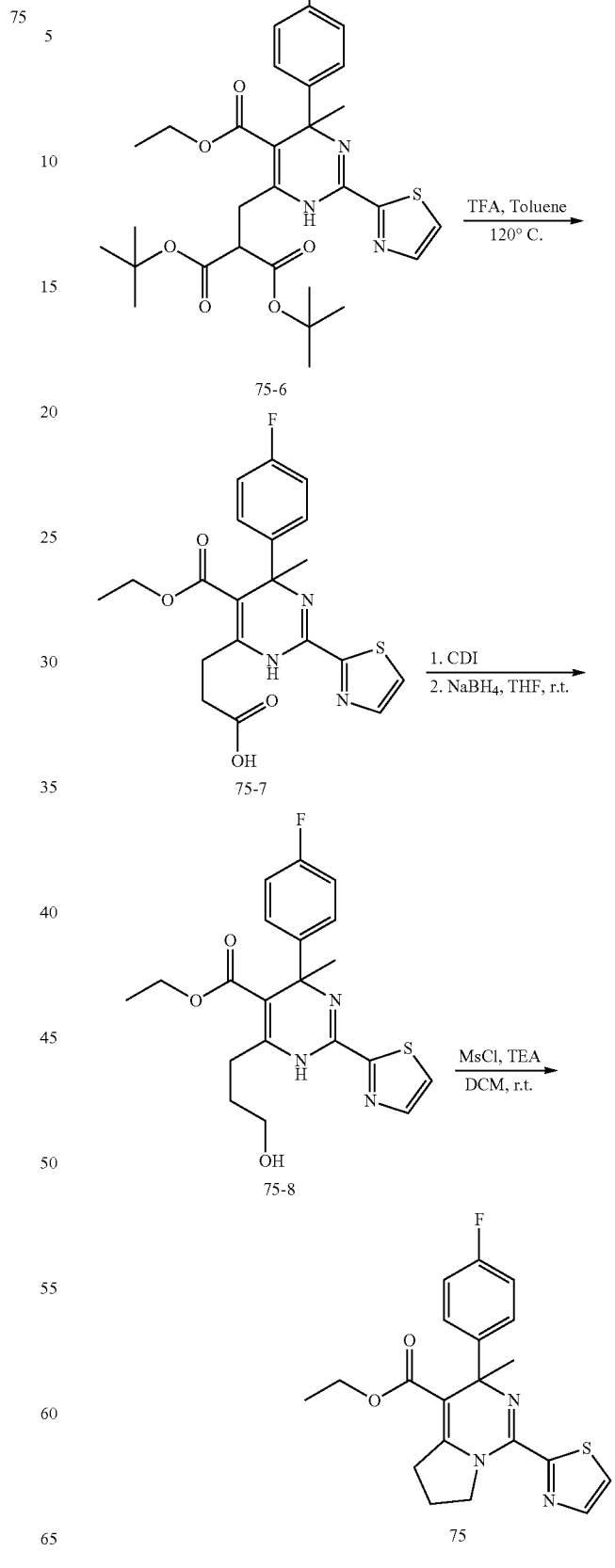

Step 1 (Synthesis of Compound 75-2)

Compound 75-1 (30 g, 250 mmol) was dissolved in (500 mL) xylene, and at room temperature was added indium trichloride (5.5 g, 25 mmol). After the addition, the mixture was stirred at 140□ overnight. The reaction mixture was concentrated under reduced pressure and extracted with DCM (500 mL×3). The organic phases were combined, sequentially washed with water (200 mL×2), saturated sodium chloride solution (200 mL×2), dried over anhydrous sodium sulfate, filtered, and purified by silica gel column chromatography with an eluent system (PE:EtOAc=10:1) to obtain 5.1 gram of a mixture of 75-2 including cis- and trans-configurations at a ratio of 3:2, yield: 8%.

NMR data of one configuration: $^1$H NMR (400 MHz, CDCl$_3$) δ: 7.22-7.19 (m, 2.4H), 7.09-7.05 (m, 2.4H), 3.80 (s, 3H), 2.41 (s, 3H), 1.90 (s, 3H).

NMR data of the other configuration: $^1$H NMR (400 MHz, CDCl$_3$) δ: 7.22-7.19 (m, 1.6H), 7.09-7.05 (m, 1.6H), 3.53 (s, 2H), 2.36 (s, 2H), 2.30 (s, 2H).

Step 2 (Synthesis of Compound 75-4)

Compound 75-3 (3.3 g, 20.4 mmol) was dissolved in (50 mL) N-methylpyrrolidone, and at room temperature was added sodium bicarbonate (4.97 g, 59.2 mmol). After the addition, the mixture was stirred at 12010 overnight, then cooled, and 75-2 (5.1 g, 20.4 mmol) was slowly added. After the addition, the reaction mixture was allowed to react under microwave at 120□ for 30 minutes. The reaction mixture was extracted with EtOAc (50 mL×3). The organic phases were combined, sequentially washed with water (20 mL×2), saturated sodium chloride solution (20 mL×3), dried over anhydrous sodium sulfate, filtered, and purified by silica gel column chromatography with an eluent system (PE: EtOAc=3:1) to obtain 3.1 g compound 75-4, yield: 42%.

$^1$H NMR (400 MHz, CDCl$_3$) δ: 7.95 (d, J=3.0 Hz, 1H), 7.72 (br. s., 1H), 7.56 (d, J=3.0 Hz, 1H), 7.46 (br. s., 2H), 7.01 (d, J=7.5 Hz, 2H), 3.94 (qdd, J=3.5, 7.0, 10.4 Hz, 2H), 2.32 (br. s., 3H), 1.93 (br. s., 3H), 1.02 (t, J=6.9 Hz, 3H).

Step 3 (Synthesis of Compound 75-5)

Compound 75-4 (3.1 g, 8.6 mmol) was dissolved in (50 mL) tetrachloromethane, and at room temperature were added NBS (1.84 g, 10.32 mmol), AIBN (141 mg, 0.86 mmol). After the addition, the mixture was stirred at 90□ for 1 hour. The reaction mixture was cooled and compound 75-2 (5.1 g, 20.4 mmol) was slowly added. After the addition, the reaction mixture was allowed to react under microwave at 120□ for 30 minutes. The reaction mixture was extracted with EtOAc (50 mL×3). The organic phases were combined, sequentially washed with water (20 mL×2), saturated sodium chloride solution (20 mL×3), dried over anhydrous sodium sulfate, filtered, and purified by silica gel column chromatography with an eluent system (PE:EtOAc=5:1) to obtain 900 mg compound 75-5, yield: 24%.

$^1$H NMR (400 MHz, CDCl$_3$) δ: 7.97 (d, J=3.0 Hz, 1H), 7.86 (br. s., 1H), 7.69 (d, J=3.0 Hz, 1H), 7.50-7.58 (m, 2H), 7.00-7.13 (m, 2H), 4.84 (s, 2H), 3.98 (q, J=7.0 Hz, 2H), 2.11 (s, 3H), 1.03 (t, J=7.2 Hz, 3H).

Step 4 (Synthesis of Compound 75-6)

Di-tert-Butyl malonate (285 mg, 1.32 mmol) was dissolved in 10 mL anhydrous N, N-dimethylformamide, and sodium hydride (53 mg, 1.32 mmol) was slowly added, the mixture was stirred at room temperature for 30 minutes. Compound 75-5 (480 mg, 1.1 mmol) was added to the reaction mixture, the mixture was stirred at room temperature overnight. The reaction mixture was extracted with EtOAc (50 mL×3). The organic phases were combined, sequentially washed with water (20 mL×2), saturated sodium chloride solution (20 mL×3), dried over anhydrous sodium sulfate, filtered, and purified by silica gel column chromatography with an eluent system (PE:EtOAc=5:1) to obtain 200 mg compound 75-6, yield: 32%.

$^1$H NMR (400 MHz, CDCl$_3$) δ: 7.84 (s., 1H), 7.53-7.63 (m, 1H), 7.34-7.53 (m, 2H), 7.01 (d, J=8.0 Hz, 2H), 3.94 (q, J=7.0 Hz, 2H), 3.74 (br. s., 1H), 3.01-3.31 (m, 3H), 1.86-2.04 (m, 3H), 1.41-1.54 (m, 18H), 1.02 (t, J=5.8 Hz, 3H).

LCMS (ESI) m/z: 574.1 [M+H$^+$].

Step 5 (Synthesis of Compound 75-7)

Compound 75-6 (200 mg, 0.35 mmol) was dissolved in (5 mL) toluene, and trifluoroacetic acid (798 mg, 7 mmol) was slowly added. The temperature was raised to 120□ and the mixture was stirred at this temperature for 1 hour. The reaction mixture was cooled to room temperature, concentrated under reduced pressure, and extracted with DCM (50 mL×3). The organic phases were combined, sequentially washed with water (20 mL×2) and saturated sodium chloride solution (20 mL×3), dried over anhydrous sodium sulfate, filtered, and concentrated under reduced pressure to obtain crude product 130 mg Example 75-7, yield: 86%.

LCMS (ESI) m/z: 418.1 [M+H$^+$].

Step 6 (Synthesis of Compound 75-8)

Compound 75-6 (130 mg, 0.31 mmol) was dissolved in 10 mL dry tetrahydrofuran, and at room temperature was added carbonyldiimidazole (147 mg, 0.91 mmol). The mixture was stirred at room temperature for 15 minutes, and then was added to a solution of sodium borohydride (118 mg, 3.1 mmol) in 10 mL methanol. After the addition, the reaction reacted at room temperature for 10 minutes. The reaction mixture was concentrated under reduced pressure and then extracted with DCM (30 mL×3). The organic phases were combined, sequentially washed with water (20 mL×2), saturated sodium chloride solution (20 mL×3), dried over anhydrous sodium sulfate, filtered, and purified by silica gel column chromatography with an eluent system (PE: EtOAc=3:1) to obtain 70 mg compound 75-8, yield: 56%.

LCMS (ESI) m/z: 403.9 [M+H$^+$].

Step 7 (Synthesis of Example 75)

Compound 75-8 (70 mg, 0.17 mmol) was dissolved in 10 mL dry DCM, and at room temperature triethylamine (35 mg, 0.34 mmol), methanesulfonyl chloride (29 mg, 0.25 mmol) were added. The mixture was stirred at room temperature for 30 minutes. The reaction mixture was extracted with DCM (30 mL×3). The organic phases were combined, sequentially washed with water (20 mL×2), saturated sodium chloride solution (20 mL×3), dried over anhydrous sodium sulfate, filtered, and purified by silica gel column chromatography with an eluent system (PE:EtOAc=3:1) to obtain 50 mg Example 75, yield: 76%.

NMR data of Example 75: $^1$H NMR (400 MHz, CDCl$_3$) δ: 7.84 (d, J=3.2 Hz, 1H), 7.46 (dd, J=5.5, 8.5 Hz, 2H), 7.38 (d, J=3.2 Hz, 1H), 6.99 (t, J=8.6 Hz, 2H), 4.21-4.39 (m, 2H), 3.98 (q, J=7.2 Hz, 2H), 3.12 (t, J=7.8 Hz, 2H), 2.06 (q, J=7.4 Hz, 2H), 1.94 (s, 3H), 1.06 (t, J=7.0 Hz, 3H).

LCMS (ESI) m/z: 386.5 [M+H$^+$].

Example 76

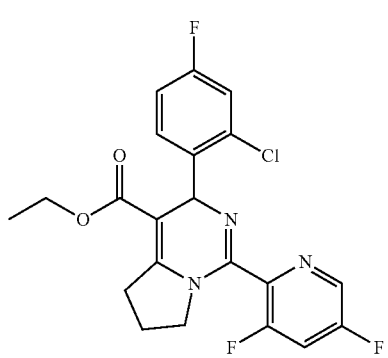

Example 76 was prepared according to the method as described in Example 1.

NMR data of Example 76: $^1$H NMR (400 MHz, DMSO-$d_6$) δ: 8.54 (d, J=2.0 Hz, 1H), 8.09 (dt, J=2.0, 9.2 Hz, 1H), 7.45 (dd, J=6.0, 8.4 Hz, 1H), 7.38 (dd, J=2.4, 8.4 Hz, 1H), 7.21 (dt, J=2.4, 8.4 Hz, 1H), 6.02 (s, 1H), 3.90-4.03 (m, 2H), 3.52-3.54 (m, 1H), 3.34-3.38 (m, 1H), 3.23-3.27 (m, 1H), 3.05-3.10 (m, 1H), 1.91-2.03 (m, 2H), 1.08 (t, J=7.2 Hz, 3H).

LCMS (ESI) m/z: 436.0[M+H$^+$].

Example 77

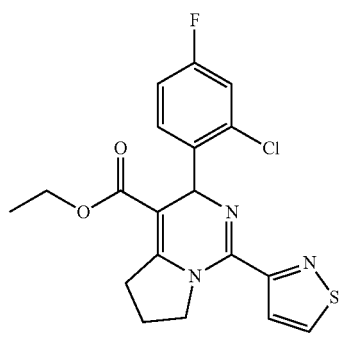

Example 77 was prepared according to the method as described in Example 1.

NMR data of Example 77: $^1$H NMR (400 MHz, CDCl$_3$) δ: 8.56 (d, J=5.0 Hz, 1H), 7.67 (br. s., 1H), 7.34 (dd, J=6.2, 8.2 Hz, 1H), 7.08-7.14 (m, 1H), 6.93 (dt, J=2.5, 8.2 Hz, 1H), 6.21 (s, 1H), 4.18-4.29 (m, 1H), 3.97-4.13 (m, 3H), 3.39 (ddd, J=4.0, 8.4, 18.2 Hz, 1H), 3.02-3.16 (m, 1H), 1.96-2.19 (m, 2H), 1.15 (t, J=7.2 Hz, 3H).

LCMS (ESI) m/z: 406.1[M+H$^+$].

Example 78

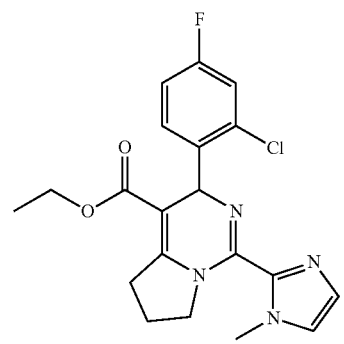

Example 78 was prepared according to the method as described in Example 1.

NMR data of Example 78: $^1$H NMR (400 MHz, CDCl$_3$) δ: 7.33-7.26 (m, 1H), 7.12 (d, J=7.0 Hz, 1H), 6.98 (br. s., 1H), 6.92 (t, J=7.4 Hz, 1H), 6.84 (s, 1H), 6.20 (s, 1H), 4.21 (d, J=8.5 Hz, 1H), 4.04 (q, J=6.9 Hz, 2H), 3.96 (br. s., 1H), 3.63 (br. s., 3H), 3.44-3.31 (m, 1H), 3.10 (td, J=8.9, 17.8 Hz, 1H), 2.15-1.91 (m, 2H), 1.13 (t, J=7.0 Hz, 3H).

LCMS (ESI) m/z: 403.1[M+H$^+$].

Example 79

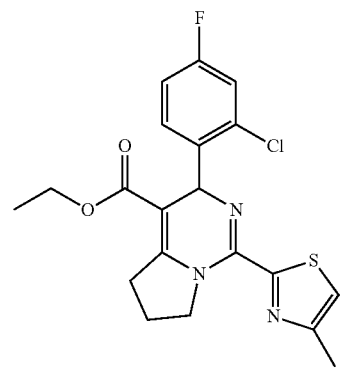

Example 79 was prepared according to the method as described in Example 1.

NMR data of Example 79: $^1$H NMR (400 MHz, CDCl3) δ: 7.29-7.33 (m, 1H), 7.13 (dd, J=2.5, 8.8 Hz, 1H), 6.87-6.98 (m, 2H), 6.19 (s, 1H), 4.40 (ddd, J=3.5, 8.0, 11.2 Hz, 1H), 4.19-4.31 (m, 1H), 4.07 (dq, J=1.6, 7.0 Hz, 2H), 3.34-3.47 (m, 1H), 3.08 (td, J=9.2, 18.2 Hz, 1H), 2.46 (s, 3H), 2.01-2.25 (m, 2H), 1.16 (t, J=7.2 Hz, 3H).

LCMS (ESI) m/z: 420.1[M+H$^+$].

Example 80

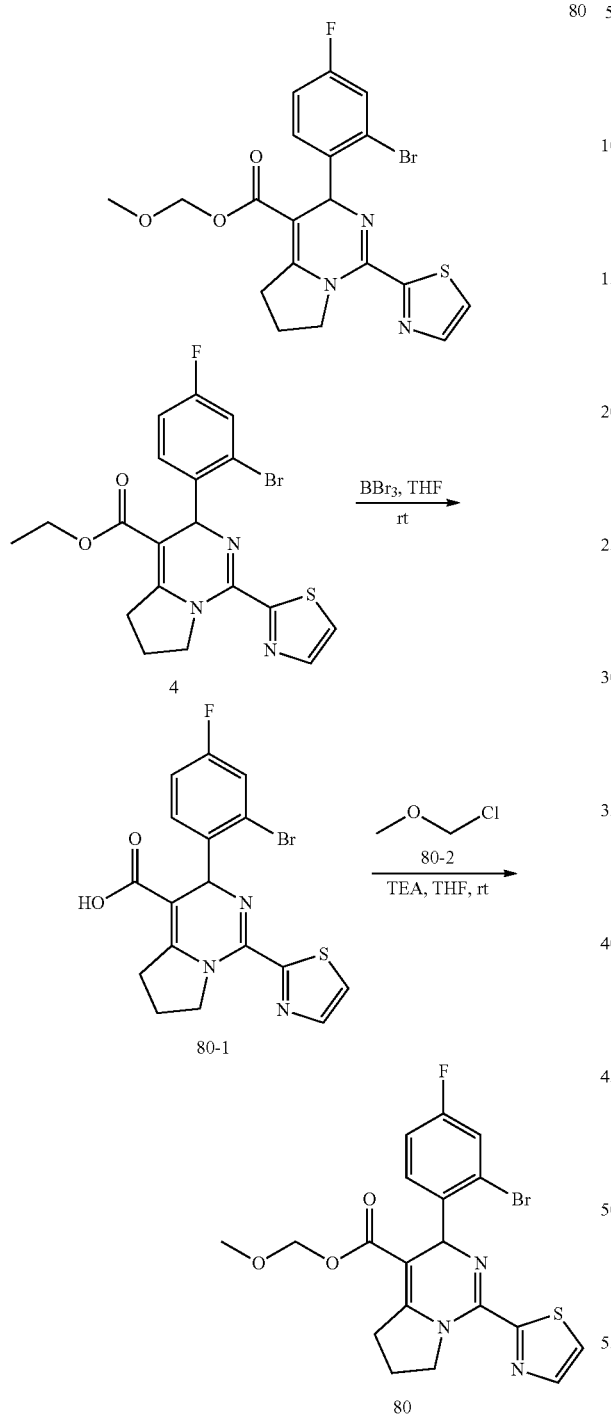

Step 1 (Synthesis of Compound 80-1)

Compound 4 (500 mg, 1.11 mmol) was dissolved in anhydrous tetrahydrofuran (10 mL), and 1 mL boron tribromide was slowly added. The mixture was stirred at room temperature for 1 hour, and then concentrated under reduced pressure, extracted with (50 mL×3) EtOAc. The organic phases were combined, sequentially washed with water (30 mL×2), saturated sodium chloride solution (30 mL×2), dried over anhydrous sodium sulfate, filtered, and purified by silica gel column chromatography with an eluent system (PE:EtOAc=5:1) to obtain 400 mg product compound 80-1, yield: 85%.

Step 2 (Synthesis of Example 80)

Compound 80-1 (50 mg, 0.12 mmol) was dissolved in anhydrous tetrahydrofuran (3 mL), and triethylamine (48 mg, 0.48 mmol), compound 80-2 (19 mg, 0.24 mmol) were slowly added. The mixture was stirred at room temperature for 2 hours, and then concentrated under reduced pressure, extracted with EtOAc (30 mL×3). The organic phases were combined, sequentially washed with water (20 mL×2), saturated sodium chloride solution (20 mL×2), dried over anhydrous sodium sulfate, filtered, and purified by silica gel column chromatography with an eluent system (PE:EtOAc=10:1) to obtain 400 mg product Example 80, yield: 61%.

NMR data of Example 80: $^1$H NMR (400 MHz, CDCl3) δ: 7.76 (d, J=3.2 Hz, 1H), 7.32 (d, J=3.2 Hz, 1H), 7.29-7.26 (m, 1H), 7.23 (dd, J=2.8, 8.8 Hz, 1H), 6.93 (dt, J=2.4, 8.2 Hz, 1H), 6.15 (s, 1H), 5.19 (d, J=6.0 Hz, 1H), 5.04 (d, J=6.0 Hz, 1H), 4.43-4.32 (m, 1H), 4.28-4.18 (m, 1H), 3.41 (ddd, J=3.6, 8.4, 18.0 Hz, 1H), 3.19 (s, 3H), 3.06 (td, J=9.3, 18.4 Hz, 1H), 2.20-2.08 (m, 1H), 2.06-1.93 (m, 1H).

LCMS (ESI) m/z: 466.0[M+H$^+$].

Example 81

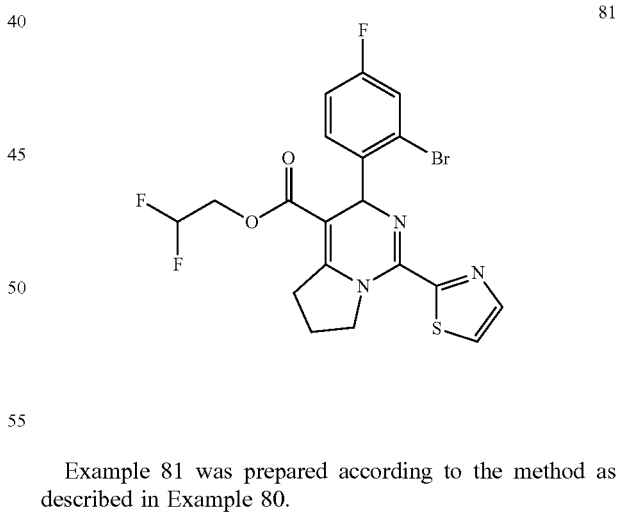

Example 81 was prepared according to the method as described in Example 80.

NMR data of Example 81: $^1$H NMR (400 MHz, CDCl3) δ: 7.81 (d, J=3.2 Hz, 1H), 7.37 (d, J=3.2 Hz, 1H), 7.32 (dd, J=2.6, 8.4 Hz, 1H), 7.28-7.24 (m, 1H), 6.97 (dt, J=2.6, 8.2 Hz, 1H), 6.19-6.14 (m, 1H), 5.99-5.66 (m, 1H), 4.47-4.38 (m, 1H), 4.34-4.25 (m, 1H), 4.20 (dt, J=4.0, 13.6 Hz, 2H), 3.39 (ddd, J=3.8, 8.5, 18.3 Hz, 1H), 3.08 (td, J=9.2, 18.3 Hz, 1H), 2.25-2.13 (m, 1H), 2.13-2.02 (m, 1H).

LCMS (ESI) m/z: 486.0[M+H$^+$].

Example 82
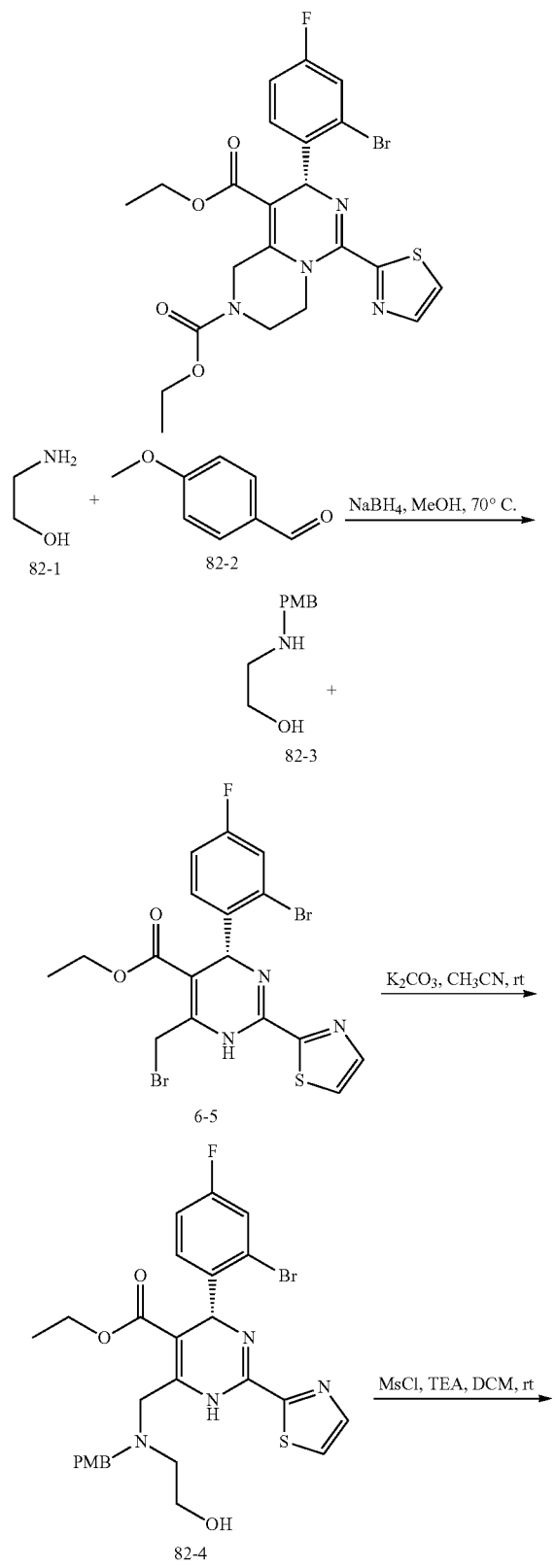
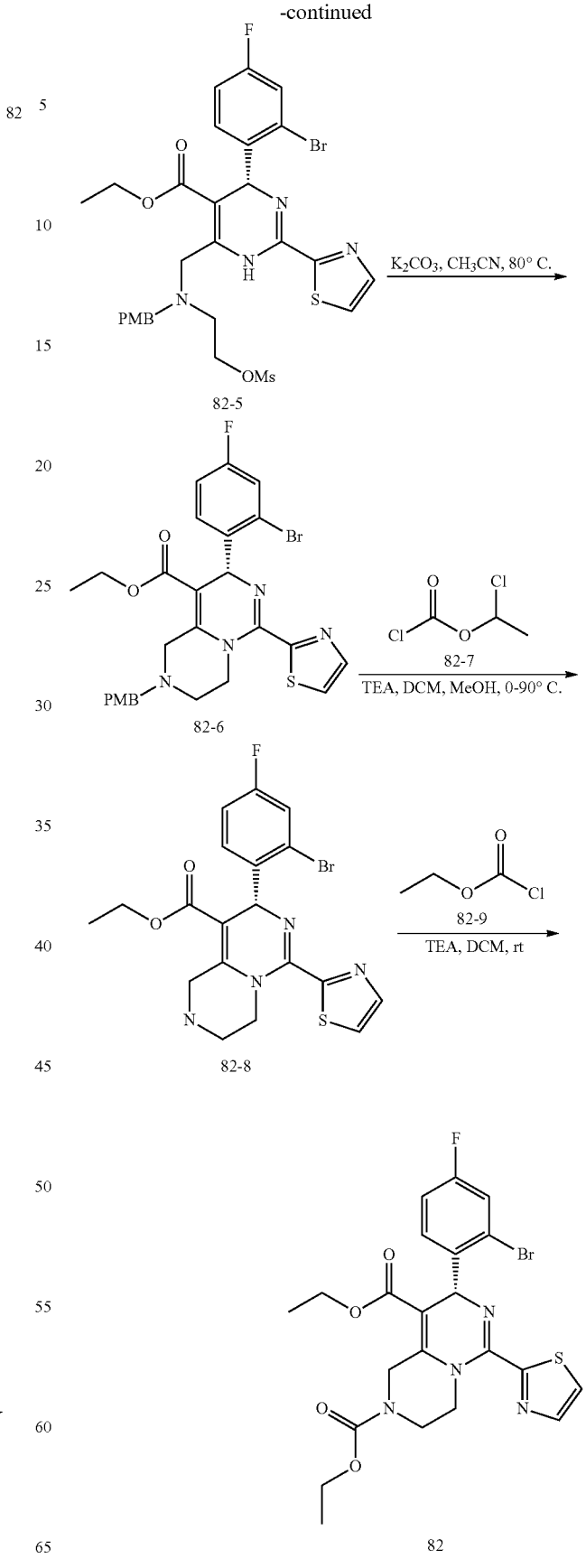

Step 1 (Synthesis of Compound 82-3)

Compound 82-1 (2.25 g, 36.9 mmol) was dissolved in methanol (30 mL), and at room temperature was added compound 82-2 (5.01 g, 36.9 mmol). The temperature was raised to 70□ and the mixture was stirred overnight. The reaction mixture was cooled to room temperature, and sodium borohydride (1.4 g, 36.9 mmol) was slowly added. After the addition, the temperature was raised to 70□ and the mixture was stirred for 2 hours. The reaction mixture was cooled to room temperature, and extracted with EtOAc (30 mL×3). The organic phases were combined, sequentially washed with water (50 mL×2), saturated sodium chloride solution (100 mL×3), dried over anhydrous sodium sulfate, filtered, and purified by silica gel column chromatography with an eluent system (PE:EtOAc=10:1) to obtain 6.0 g compound 82-3, yield: 90%.

$^1$H NMR (400 MHz, CDCl$_3$) δ: 7.24 (d, J=8.8 Hz, 2H), 6.88 (d, J=8.8 Hz, 2H), 3.81 (s, 3H), 3.75 (s, 2H), 3.65 (t, J=5.2 Hz, 2H), 2.79 (t, J=5.2 Hz, 2H), 2.34 (br, 2H).

Step 2 (Synthesis of Compound 82-4)

Compound 82-3 (1.0 g, 5.5 mmol) was dissolved in acetonitrile (30 mL), and at room temperature were added compound 6-5 (2.8 g, 5.5 mmol), potassium carbonate (1.5 g, 11 mmol). After the addition, the mixture was stirred at room temperature overnight. The reaction mixture was concentrated under pressure, and extracted with EtOAc (30 mL×3). The organic phases were combined, sequentially washed with water (50 mL×2) and saturated sodium chloride solution (100 mL×2), dried over anhydrous sodium sulfate, filtered, and purified by silica gel column chromatography with an eluent system (PE:EtOAc=10:1) to obtain 2.7 g compound 82-4, yield: 82%.

LCMS (ESI) m/z: 602.9 [M+H$^+$].

Step 3 (Synthesis of Compound 82-5)

Compound 82-4 (2.5 g, 4.2 mmol) was dissolved in anhydrous DCM (20 mL), and triethylamine (839 mg, 8.3 mmol), methanesulfonyl chloride (710 mg, 6.23 mmol) were added. After the addition, the mixture was stirred at room temperature for 3 hours. The reaction was extracted with (200 mL×3) DCM. The organic layer was washed with saturated saline solution (200 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 2.8 g product 82-5, yield: 99%.

LCMS (ESI) m/z: 681.0 [M+H$^+$].

Step 4 (Synthesis of Compound 82-6)

Compound 82-5 (2.8 g, 4.1 mmol) was dissolved in acetonitrile (30 mL), and at room temperature was added potassium carbonate (1.1 g, 8.2 mmol. After the addition, the reaction mixture was warmed to 800 and stirred overnight. The reaction mixture was concentrated under pressure, and extracted with EtOAc (30 mL×3). The organic phases were combined, sequentially washed with water (50 mL×2), saturated sodium chloride solution (100 mL×2), dried over anhydrous sodium sulfate, filtered, and purified by silica gel column chromatography with an eluent system (PE:EtOAc=10:1) to obtain 2.0 g compound 82-6, yield: 83%.

1H NMR (400 MHz, CDCl$_3$) δ: 7.93 (d, J=3.2 Hz, 1H), 7.84 (d, J=3.2 Hz, 1H), 7.58 (dd, J=2.4, 8.6 Hz, 1H), 7.30-7.38 (m, 1H), 7.27-7.30 (m, 1H), 7.25 (s, 2H), 6.91 (d, J=8.6 Hz, 2H), 5.94 (s, 1H), 4.53-4.62 (m, 1H), 4.10 (d, J=16.4 Hz, 1H), 3.91 (dqd, J=3.6, 7.01, 13.2 Hz, 2H), 3.70-3.75 (m, 4H), 3.60 (s, 2H), 3.45-3.53 (m, 1H), 2.68-2.79 (m, 2H), 0.98 (t, J=7.0 Hz, 3H).

LCMS (ESI) m/z: 585.0 [M+H$^+$].

Step 5 (Synthesis of Compound 82-8)

Compound 82-6 (420 mg, 0.7 mmol) was dissolved in anhydrous DCM (10 mL), and at 0□ were added triethylamine (145 mg, 1.43 mmol), compound 82-7 (205 mg, 1.43 mmol). The mixture was stirred at 0□ for 1.5 hours, and then concentrated under reduced pressure. 5 mL Methanol was added, the temperature was raised to 80□ and the mixture was stirred for 1 hour. The reaction mixture was concentrated under pressure, and extracted with EtOAc (30 mL×3). The organic phases were combined, sequentially washed with water (50 mL×2), saturated sodium chloride solution (50 mL×2), dried over anhydrous sodium sulfate, filtered, and purified by silica gel column chromatography with an eluent system (PE:EtOAc=10:1) to obtain 300 mg compound 82-8, yield: 90%. 1H NMR (400 MHz, CDCl$_3$) δ: 7.82 (d, J=3.0 Hz, 1H), 7.42-7.33 (m, 2H), 7.28 (d, J=6.4 Hz, 1H), 6.99 (dt, J=2.4, 8.4 Hz, 1H), 6.14 (s, 1H), 4.75-4.64 (m, 1H), 4.58-4.29 (m, 2H), 4.15-3.97 (m, 2H), 3.52-3.30 (m, 2H), 3.17-3.04 (m, 1H), 1.14 (t, J=7.0 Hz, 3H).

LCMS (ESI) m/z: 465.0 [M+H$^+$].

Step 6 (Synthesis of Example 82)

Compound 82-8 (100 mg, 0.2 mmol) was dissolved in anhydrous DCM (10 mL), and at room temperature were added triethylamine (22 mg, 0.2 mmol), compound 82-9 (23 mg, 0.2 mmol). After the addition, the mixture was stirred at room temperature for 1 hour. The reaction mixture was quenched by water, and extracted with (30 mL×3) DCM. The organic layer was washed with saturated saline solution (20 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 56 mg Example 82, yield: 49%.

NMR data of Example 82: $^1$H NMR (400 MHz, CDCl$_3$) δ: 7.6 (d, J=3.0 Hz, 1H), 7.41 (d, J=3.0 Hz, 1H), 7.35 (d, J=6.0 Hz, 1H), 7.13-7.19 (m, 1H), 6.96 (t, J=7.2 Hz, 1H), 6.14 (s, 1H), 5.23 (br. s., 1H), 4.95-5.12 (m, 1H), 4.69 (br. s., 1H), 4.20 (q, J=6.4 Hz, 2H), 4.03-4.15 (m, 2H), 3.92 (d, J=14.4 Hz, 2H), 3.55 (br. s., 1H), 1.30 (t, J=6.8 Hz, 3H), 1.17 (t, J=7.0 Hz, 3H).

LCMS (ESI) m/z: 537.2 [M+H$^+$].

Example 83

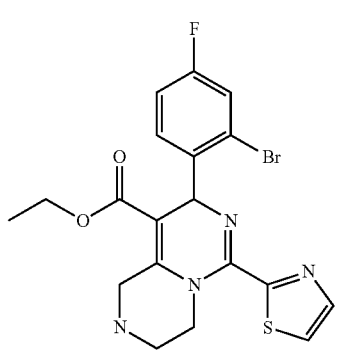

Example 83 was prepared according to the method as described in Example 82-8.

NMR data of Example 83: $^1$H NMR (400 MHz, CDCl$_3$) δ: 7.82 (d, J=3.0 Hz, 1H), 7.42-7.33 (m, 2H), 7.28 (d, J=6.4 Hz, 1H), 6.99 (dt, J=2.4, 8.4 Hz, 1H), 6.14 (s, 1H), 4.75-4.64 (m, 1H), 4.58-4.29 (m, 2H), 4.15-3.97 (m, 2H), 3.52-3.30 (m, 2H), 3.17-3.04 (m, 1H), 1.14 (t, J=7.0 Hz, 3H).

LCMS (ESI) m/z: 465.0 [M+H$^+$].

Example 84

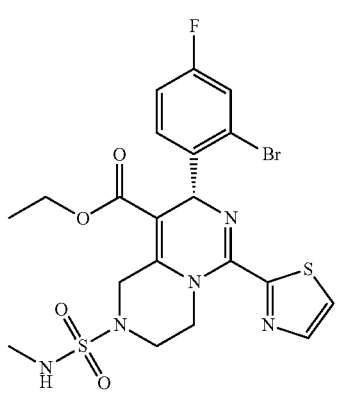

Example 84 was prepared according to the method as described in Example 82.

NMR data of Example 84: $^1$H NMR (400 MHz, CDCl$_3$) δ: 7.84 (d, J=3.0 Hz, 1H), 7.42 (d, J=3.0 Hz, 1H), 7.30-7.39 (m, 2H), 7.01 (dt, J=2.8, 8.0 Hz, 1H), 6.17 (s, 1H), 5.24 (d, J=16.6 Hz, 1H), 4.77-4.87 (m, 1H), 4.64 (d, J=16.6 Hz, 1H), 4.42 (d, J=5.0 Hz, 1H), 4.00-4.20 (m, 2H), 3.75-3.88 (m, 2H), 3.66-3.74 (m, 1H), 2.78 (d, J=5.6 Hz, 3H), 1.17 (t, J=7.0 Hz, 3H).

LCMS (ESI) m/z: 558.1 [M+H$^+$].

Example 85

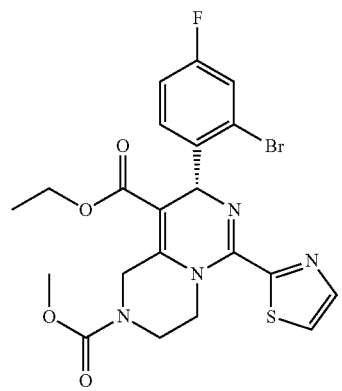

Example 85 was prepared according to the method as described in Example 82.

NMR data of Example 85: $^1$H NMR (400 MHz, CDCl$_3$) δ: 7.85 (d, J=3.2 Hz, 1H), 7.43 (d, J=3.2 Hz, 1H), 7.39 (dd, J=2.4, 8.4 Hz, 1H), 7.21 (dd, J=6.0, 8.4 Hz, 1H), 6.96-7.04 (m, 1H), 6.19 (s, 1H), 5.24-5.41 (m, 1H), 5.05 (d, J=19.2 Hz, 1H), 4.77 (br. s., 1H), 4.08-4.23 (m, 2H), 3.99 (br. s., 2H), 3.82 (s, 3H), 3.56-3.67 (m, 1H), 1.21 (t, J=6.4 Hz, 3H).

LCMS (ESI) m/z: 522.8 [M+H$^+$].

Example 86

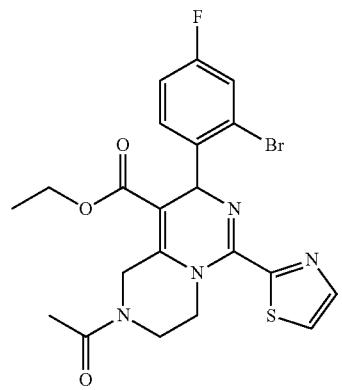

Example 86 was prepared according to the method as described in Example 82.

NMR data of Example 86: $^1$H NMR (400 MHz, CDCl$_3$) δ: 7.84 (d, J=3.2 Hz, 1H), 7.44 (d, J=3.2 Hz, 1H), 7.38 (dd, J=2.4, 8.0 Hz, 1H), 7.20 (dd, J=6.0, 8.8 Hz, 1H), 6.99 (dt, J=2.4, 8.4 Hz, 1H), 6.17 (s, 1H), 5.15-4.90 (m, 2H), 4.89-4.82 (m, 1H), 4.19-4.04 (m, 2H), 3.96-3.86 (m, 1H), 3.77-3.67 (m, 2H), 2.89 (s, 3H), 1.18 (t, J=7.2 Hz, 3H).

LCMS (ESI) m/z: 507.0 [M+H$^+$].

Example 87

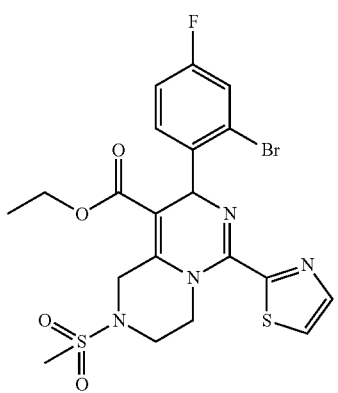

Example 87 was prepared according to the method as described in Example 82.

NMR data of Example 87: ¹H NMR (400 MHz, CDCl₃) δ: 7.84 (d, J=3.2 Hz, 1H), 7.44 (d, J=3.2 Hz, 1H), 7.38 (dd, J=2.8, 8.4 Hz, 1H), 7.20 (dd, J=6.0, 8.8 Hz, 1H), 6.99 (dt, J=2.8, 8.4 Hz, 1H), 6.17 (s, 1H), 5.14-4.90 (m, 2H), 4.90-4.82 (m, 1H), 4.20-4.04 (m, 2H), 3.96-3.85 (m, 1H), 3.76-3.66 (m, 2H), 2.89 (s, 3H), 1.18 (t, J=7.2 Hz, 3H).

LCMS (ESI) m/z: 543.0 [M+H⁺].

Example 88

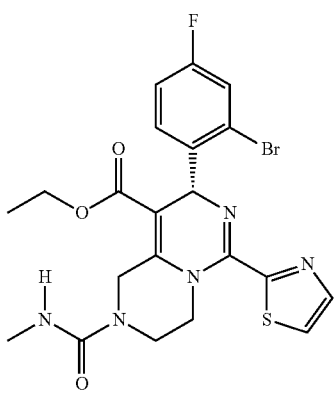

Example 88 was prepared according to the method as described in Example 82.

NMR data of Example 88: ¹H NMR (400 MHz, CDCl₃) δ: 7.84 (d, J=3.2 Hz, 1H), 7.42 (d, J=3.2 Hz, 1H), 7.38 (dd, J=2.5, 8.2 Hz, 1H), 7.20 (dd, J=6.0, 8.5 Hz, 1H), 7.00 (dt, J=2.5, 8.2 Hz, 1H), 6.18 (s, 1H), 4.99-5.20 (m, 2H), 4.88 (d, J=3.8 Hz, 1H), 4.70-4.82 (m, 1H), 3.93-4.23 (m, 4H), 3.54-3.66 (m, 1H), 2.89 (d, J=4.5 Hz, 3H), 1.19 (t, J=7.2 Hz, 3H).

LCMS (ESI) m/z: 544.0 [M+Na⁺].

Example 89

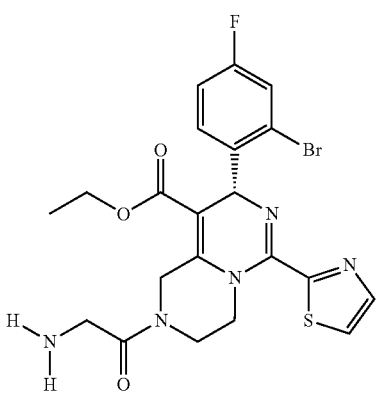

Example 89 was prepared according to the method as described in Example 82.

NMR data of Example 89: ¹H NMR (400 MHz, CDCl₃) δ: 7.85 (d, J=3.2 Hz, 1H), 7.43 (d, J=3.2 Hz, 1H), 7.39 (dd, J=2.4, 8.4 Hz, 1H), 7.22-7.14 (m, 1H), 7.05-6.95 (m, 1H), 6.22-6.17 (m, 1H), 5.39-5.07 (m, 2H), 5.04-4.77 (m, 2H), 4.22-3.95 (m, 4H), 3.80-3.50 (m, 4H), 1.20 (t, J=7.2 Hz, 3H).

LCMS (ESI) m/z: 522.0 [M+H⁺].

Example 90

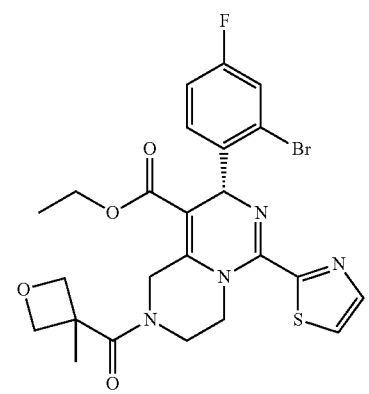

Example 90 was prepared according to the method as described in Example 82.

NMR data of Example 90: ¹H NMR (400 MHz, CDCl₃) δ: 7.83 (d, J=3.2 Hz, 1H), 7.41 (d, J=3.2 Hz, 1H), 7.36 (dd, J=2.4, 8.0 Hz, 1H), 7.14 (dd, J=6.0, 8.8 Hz, 1H), 6.98 (dt, J=2.4, 8.4 Hz, 1H), 6.18 (s, 1H), 5.02 (dd, J=2.8, 5.6 Hz, 2H), 4.97-4.77 (m, 3H), 4.48 (t, J=6.8 Hz, 2H), 4.16-3.96 (m, 4H), 3.76-3.67 (m, 1H), 1.72 (s, 3H), 1.20-1.08 (t, J=7.2 Hz, 3H).

LCMS (ESI) m/z: 563.1 [M+H⁺].

Example 91

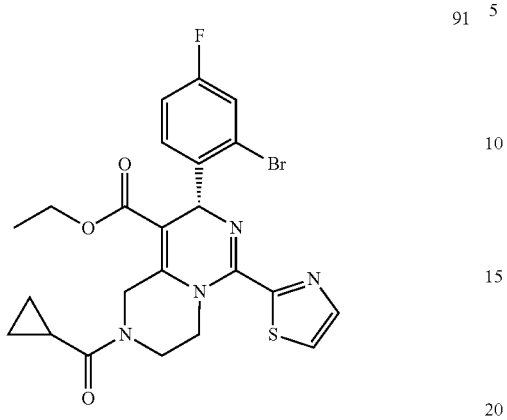

Example 91 was prepared according to the method as described in Example 82.

NMR data of Example 91: ¹H NMR (400 MHz, CDCl$_3$) δ: 7.82 (d, J=3.2 Hz, 1H), 7.40 (d, J=3.2 Hz, 1H), 7.37 (dd, J=2.4, 8.4 Hz, 1H), 7.19 (dd, J=6.0, 8.4 Hz, 1H), 6.99 (t, J=7.2 Hz, 1H), 6.22-6.14 (m, 1H), 5.78-5.23 (m, 2H), 4.95-4.70 (m, 1H), 4.27-3.99 (m, 4H), 3.73-3.40 (m, 1H), 2.04-1.83 (m, 1H), 1.23-1.11 (m, 3H), 1.11-0.99 (m, 2H), 0.86 (s, 2H).

LCMS (ESI) m/z: 533.1 [M+H⁺].

Example 92

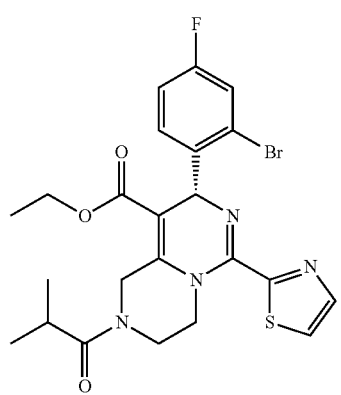

Example 92 was prepared according to the method as described in Example 82.

NMR data of Example 92: ¹H NMR (400 MHz, CDCl$_3$) δ: 7.83 (d, J=3.2 Hz, 1H), 7.40 (d, J=3.2 Hz, 1H), 7.39-7.34 (m, J=2.4, 8.4 Hz, 1H), 7.16 (dd, J=6.0, 8.4 Hz, 1H), 6.97 (dt, J=2.4, 8.4 Hz, 1H), 6.19 (s, 1H), 5.55-5.11 (m, 2H), 4.84-4.71 (m, 1H), 4.20-4.00 (m, 4H), 3.68-3.53 (m, 1H), 2.98 (td, J=6.8, 13.6 Hz, 1H), 1.23-1.12 (m, 9H).

LCMS (ESI) m/z: 535.1 [M+H⁺].

Example 93

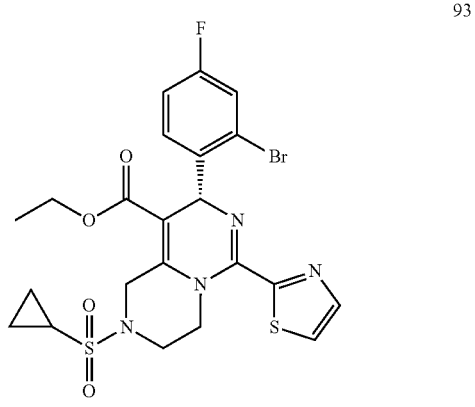 [SMILES: CCOC(=O)C1=C2CN(S(=O)(=O)C3CC3)CCN2C(c2nccs2)=N[C@H]1c1ccc(F)cc1Br]

Example 93 was prepared according to the method as described in Example 82.

NMR data of Example 93: ¹H NMR (400 MHz, CDCl$_3$) δ: 7.84 (d, J=3.2 Hz, 1H), 7.43 (d, J=3.2 Hz, 1H), 7.38 (dd, J=2.4, 8.4 Hz, 1H), 7.21 (dd, J=6.0, 8.8 Hz, 1H), 6.99 (dt, J=2.4, 8.4 Hz, 1H), 6.18 (s, 1H), 5.15-4.91 (m, 2H), 4.87 (td, J=4.4, 13.6 Hz, 1H), 4.20-4.06 (m, 2H), 4.01 (m, 1H), 3.75 (td, J=4.0, 12.0 Hz, 1H), 3.66 (m, 1H), 2.44-2.35 (m, 1H), 1.24-1.15 (m, 5H), 1.01-0.86 (m, 2H).

LCMS (ESI) m/z: 569.0 [M+H⁺].

Example 94

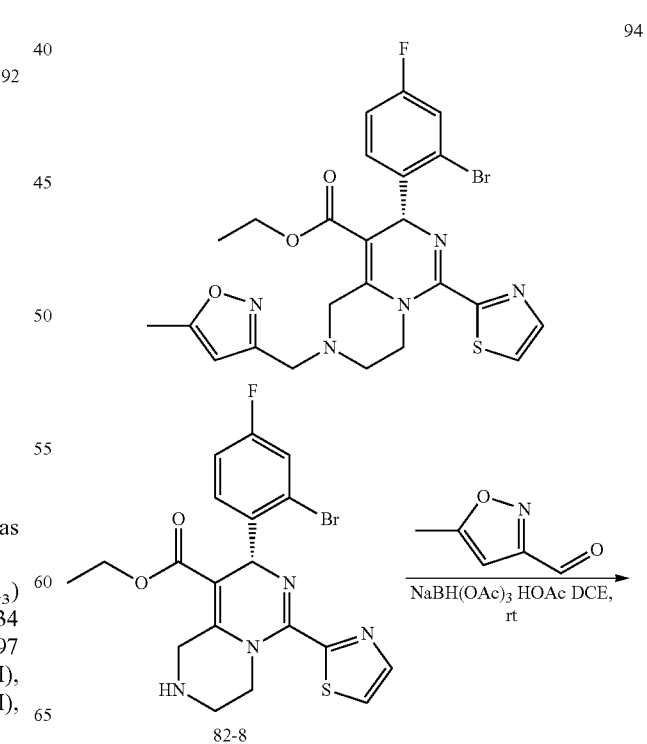

-continued

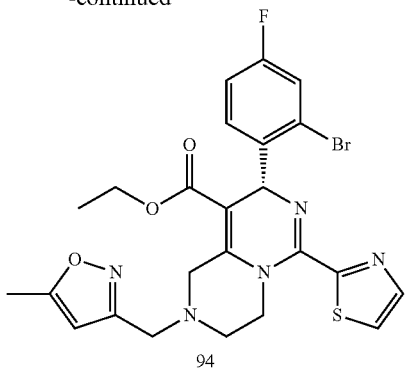

94

Compound 82-8 (93 mg, 0.2 mmol) was dissolved in DCM (10 mL), and a corresponding aldehyde (44 mg, 0.4 mmol), sodium acetoborohydride (127 mg, 0.6 mmol) and acetic acid (60 mg, 1 mmol) were added.

The reactants were stirred at room temperature for 20 minutes and then concentrated under reduced pressure to obtain crude, which was separated by preparative HPLC to obtain 10 mg Example 94, yield 10%.

NMR data of Example 94: $^1$H NMR (400 MHz, CDCl$_3$) δ: 7.96 (d, J=3.2 Hz, 1H), 7.87 (d, J=3.2 Hz, 1H), 7.60 (dd, J=8.4, 2.4 Hz, 1H), 7.24-7.39 (m, 2H), 5.96 (s, 1H), 4.56-4.65 (m, 1H), 4.43 (d, J=5.6 Hz, 1H), 4.19 (d, J=16.4 Hz, 1H), 3.96 (m, 2H), 3.84 (d, J=16.4 Hz, 1H), 3.74 (s, 2H), 3.48-3.57 (m, 1H), 2.77-2.89 (m, 2H), 2.40 (s, 3H), 1.04 (t, J=7.0 Hz, 3H).

LCMS (ESI) m/z: 560.1 [M+H$^+$].

Example 95

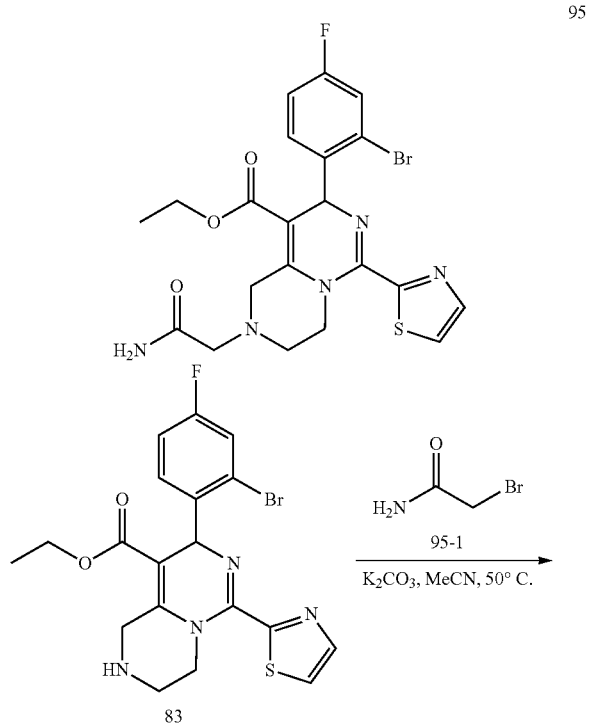

-continued

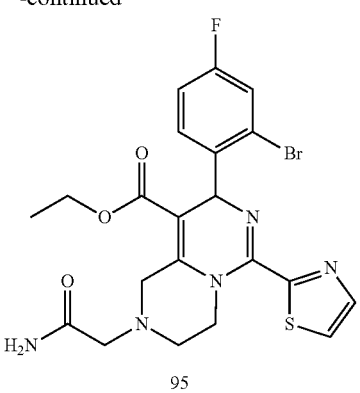

95

Compound 83 (50 mg, 0.11 mmol) was dissolved in acetonitrile (10 mL), and compound 95-1 (45 mg, 0.33 mmol), potassium carbonate (76 mg, 0.55 mmol) were added. After the addition, the temperature was raised to 500 and the mixture was stirred overnight. The reaction mixture was cooled, followed by suction filtration. The filtrate was concentrated under reduced pressure to obtain crude, which was separated by preparative HPLC to obtain 23 mg Example 95, yield 41%.

NMR data of Example 95: $^1$H NMR (400 MHz, CDCl$_3$) δ: 7.95 (d, J=3.2 Hz, 1H), 7.86 (d, J=3.2 Hz, 1H), 7.60 (dd, J=2.4, 8.4 Hz, 1H), 7.45-7.38 (m, 2H), 7.26 (dt, J=2.4, 8.4 Hz, 1H), 7.18 (br. s., 1H), 5.97 (s, 1H), 4.64-4.54 (m, 1H), 4.23 (d, J=16.6 Hz, 1H), 4.05-3.91 (m, 2H), 3.87 (d, J=16.8 Hz, 1H), 3.61-3.53 (m, 1H), 3.10 (s, 2H), 2.92-2.81 (m, 2H), 1.05 (t, J=7.2 Hz, 3H).

LCMS (ESI) m/z: 522.0 [M+H$^+$].

Example 96

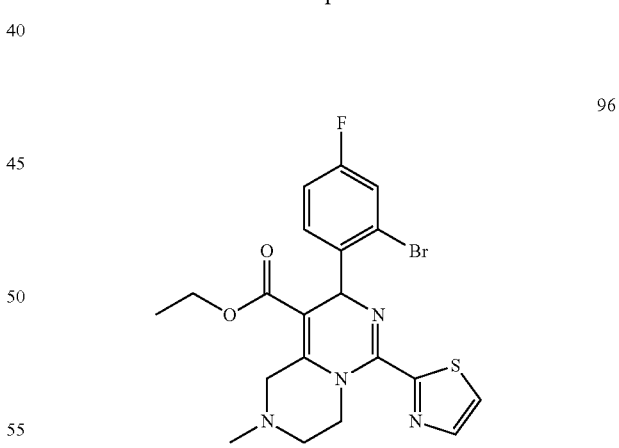

96

Example 96 was prepared according to the method as described in Example 95.

NMR data of Example 96: $^1$H NMR (400 MHz, CDCl$_3$) δ: 7.82 (br. s., 1H), 7.43-7.28 (m, 3H), 6.99 (br. s., 1H), 6.13 (br. s., 1H), 4.87 (d, J=11.2 Hz, 1H), 4.56 (d, J=15.6 Hz, 1H), 4.20-3.92 (m, 2H), 3.49 (d, J=15.6 Hz, 2H), 2.91-2.68 (m, 2H), 2.49 (br. s., 3H), 1.14 (t, J=6.4 Hz, 3H).

LCMS (ESI) m/z: 479.1 [M+H$^+$].

Example 97

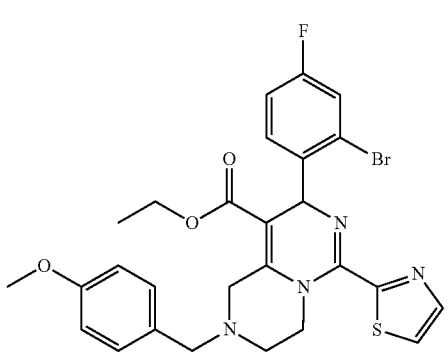

Example 97 was prepared according to the method as described in Example 95.

NMR data of Example 97: $^1$H NMR (400 MHz, CDCl$_3$) δ: 7.93 (d, J=3.2 Hz, 1H), 7.84 (d, J=3.2 Hz, 1H), 7.58 (dd, J=2.4, 8.4 Hz, 1H), 7.30-7.38 (m, 1H), 7.27-7.30 (m, 1H), 7.25 (s, 2H), 6.91 (d, J=8.4 Hz, 2H), 5.94 (s, 1H), 4.53-4.62 (m, 1H), 4.10 (d, J=16.4 Hz, 1H), 3.91 (m, 2H), 3.70-3.75 (m, 4H), 3.60 (s, 2H), 3.45-3.53 (m, 1H), 2.68-2.79 (m, 2H), 0.98 (t, J=7.0 Hz, 3H).

LCMS (ESI) m/z: 585.0 [M+H$^+$].

Example 98

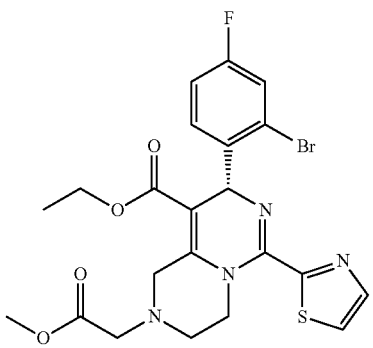

Example 98 was prepared according to the method as described in Example 95.

NMR data of Example 98: $^1$H NMR (400 MHz, CDCl$_3$) δ: 7.95 (d, J=3.2 Hz, 1H), 7.86 (d, J=3.2 Hz, 1H), 7.64-7.55 (m, 1H), 7.42-7.33 (m, 1H), 7.32-7.24 (m, 1H), 5.97 (s, 1H), 4.67-4.54 (m, 1H), 4.30 (d, J=16.6 Hz, 1H), 4.05-3.89 (m, 3H), 3.65 (s, 3H), 3.58-3.48 (m, 3H), 3.03-2.86 (m, 2H), 1.05 (t, J=7.2 Hz, 3H).

LCMS (ESI) m/z: 537.1 [M+H$^+$].

Example 99

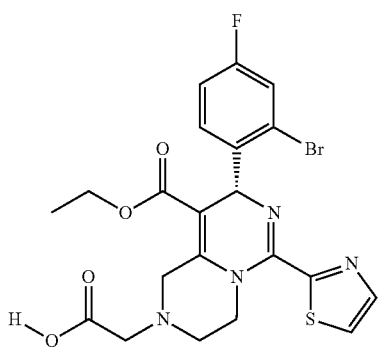

Example 99 was prepared according to the method as described in Example 95.

NMR data of Example 99: $^1$H NMR (400 MHz, CDCl$_3$) δ: 7.92 (br. s., 1H), 7.86 (br. s., 1H), 7.59 (d, J=7.2 Hz, 1H), 7.37 (br. s., 1H), 7.26 (br. s., 1H), 5.97 (s, 1H), 4.57 (br. s., 1H), 4.33-4.02 (m, 2H), 3.92 (br. s., 2H), 3.23-2.79 (m, 5H), 1.02 (br. s., 3H).

LCMS (ESI) m/z: 523.0 [M+H$^+$].

Example 100

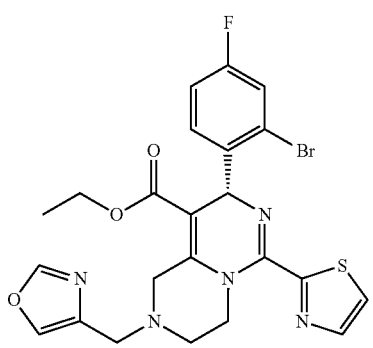

Example 100 was prepared according to the method as described in Example 94.

NMR data of Example 100: $^1$H NMR (400 MHz, DMSO-d$_6$) δ: 8.38 (s, 1H), 8.09 (s, 1H), 7.95 (d, J=3.2 Hz, 1H), 7.87 (d, J=3.2 Hz, 1H), 7.60 (dd, J=8.4, 2.4 Hz, 1H), 7.23-7.40 (m, 2H), 5.96 (s, 1H), 4.55-4.67 (m, 1H), 4.24 (d, J=16.4 Hz, 1H), 3.89-4.04 (m, 2H), 3.78 (d, J=16.4 Hz, 1H), 3.64 (s, 2H), 3.47-3.54 (m, 1H), 2.84 (t, J=5.6 Hz, 2H), 1.05 (t, J=7.2 Hz, 3H).

LCMS (ESI) m/z: 546.1 [M+H$^+$].

Example 101

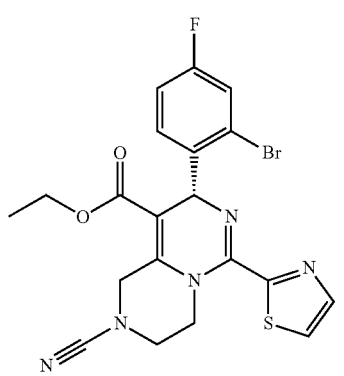

Example 101 was prepared according to the method as described in Example 95.

NMR data of Example 101: $^1$H NMR (400 MHz, CDCl$_3$) δ: 7.82 (d, J=3.2 Hz, 1H), 7.42 (d, J=3.2 Hz, 1H), 7.38 (dd, J=2.4, 8.4 Hz, 1H), 7.21 (dd, J=6.0, 8.8 Hz, 1H), 7.02 (dt, J=2.4, 8.4 Hz, 1H), 6.17 (s, 1H), 5.06-4.79 (m, 3H), 4.19-4.00 (m, 2H), 3.90-3.77 (m, 2H), 3.68-3.60 (m, 1H), 1.16 (t, J=7.2 Hz, 3H).

LCMS (ESI) m/z: 489.8 [M+H$^+$].

Example 102

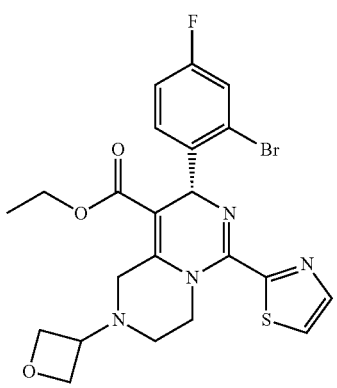

Example 102 was prepared according to the method as described in Example 94.

NMR data of Example 102: $^1$H NMR (400 MHz, CDCl$_3$) δ: 7.82 (d, J=3.2 Hz, 1H), 7.41-7.33 (m, 2H), 7.29 (dd, J=6.0, 8.8 Hz, 1H), 7.02 (dt, J=2.4, 8.4 Hz, 1H), 6.15 (s, 1H), 4.87 (td, J=4.4, 12.0 Hz, 1H), 4.77 (q, J=6.4 Hz, 2H), 4.69 (q, J=6.4 Hz, 2H), 4.39 (d, J=15.8 Hz, 1H), 4.15-4.04 (m, 1H), 3.99 (qd, J=7.2, 10.8 Hz, 1H), 3.72 (quin, J=6.2 Hz, 1H), 3.56 (d, J=16.0 Hz, 1H), 3.53-3.45 (m, 1H), 2.74 (t, J=5.6 Hz, 2H), 1.13 (t, J=7.2 Hz, 3H).

LCMS (ESI) m/z: 521.0 [M+H$^+$].

Example 103

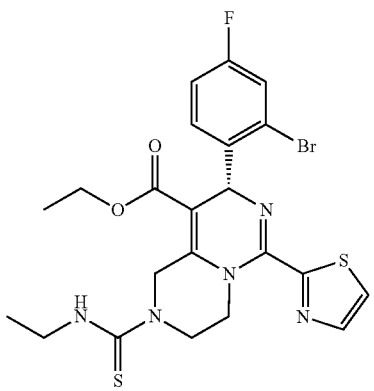

Example 103 was prepared according to the method as described in Example 95.

NMR data of Example 103: $^1$H NMR (400 MHz, CDCl$_3$) δ: 7.85 (d, J=3.2 Hz, 1H), 7.44 (d, J=3.2 Hz, 1H), 7.39 (dd, J=2.4, 8.4 Hz, 1H), 7.19 (dd, J=6.0, 8.4 Hz, 1H), 7.01 (dt, J=2.4, 8.4 Hz, 1H), 6.19 (s, 1H), 6.17 (br. s., 1H), 5.34-5.47 (m, 2H), 4.88 (m, 1H), 4.47 (ddd, J=4.4, 7.2, 12.0 Hz, 1H), 4.14-4.23 (m, 2H), 4.05-4.13 (m, 1H), 3.93 (ddd, J=4.4, 7.6, 12.0 Hz, 1H), 3.76 (quin, J=6.4 Hz, 2H), 1.27-1.32 (m, 3H), 1.20 (t, J=7.2 Hz, 3H).

LCMS (ESI) m/z: 551.8 [M+H$^+$].

Example 104

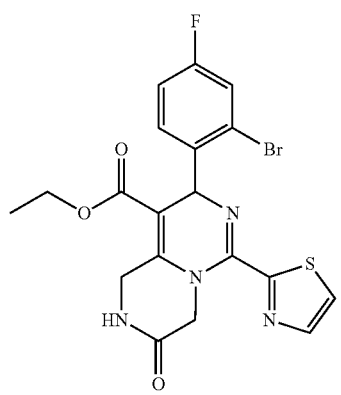

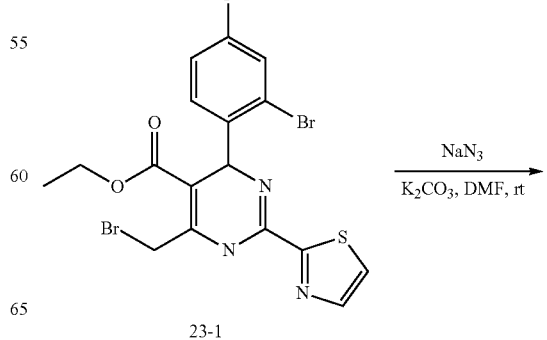

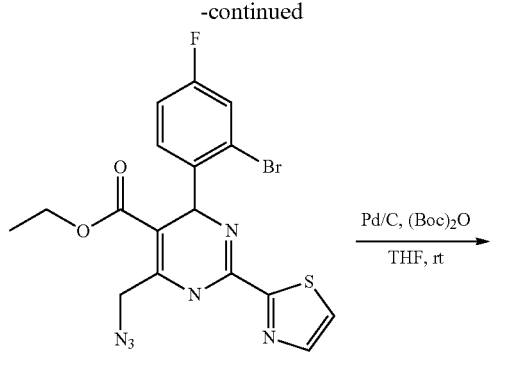

104-1

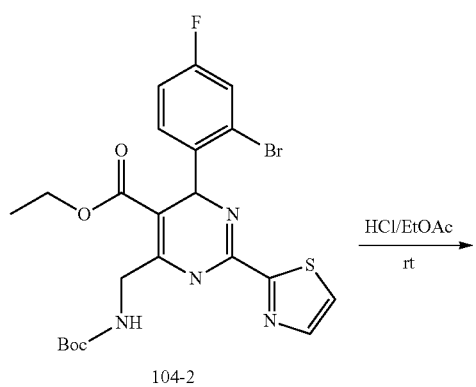

104-2

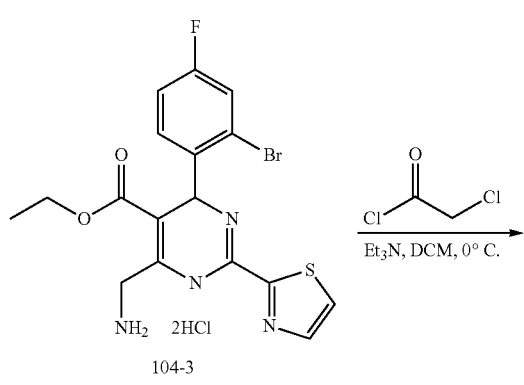

104-3

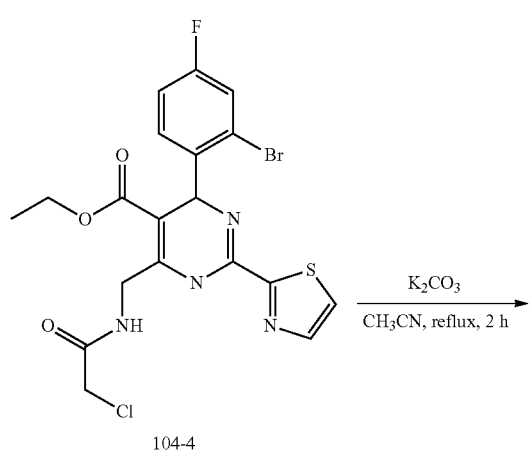

104-4

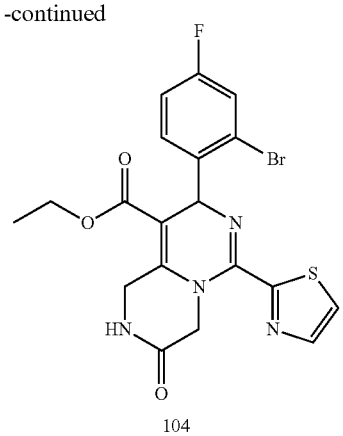

104

Step 1 (Synthesis of Example 104-1)

Compound 23-1 (1.0 g, 1.99 mmol) was dissolved in anhydrous N,N-dimethylformamide (100 mL), and at room temperature was added sodium azide (240 mg, 9.69 mmol). After the addition, the mixture was stirred under nitrogen atmosphere at room temperature for 1 hour. The reaction mixture was extracted with (300 mL×3) DCM. The organic layer was washed with saturated saline solution (200 mL×2). The organic phases were combined, dried over anhydrous sodium sulfate, and filtered. The filtrate was concentrated under reduced pressure to obtain 1.1 g Example 104-1, yield: 100%.

LCMS (ESI) m/z: 466.6 [M+H$^+$].

Step 2 (Synthesis of Example 104-2)

Pd/C (100 mg) was dissolved in 100 mL anhydrous tetrahydrofuran, and at room temperature were added 104-1 (1.1 g, 2.37 mmol), Boc$_2$O (618 mg, 2.84 mmol). After the addition, the mixture was stirred under hydrogen atmosphere (45 psi) at room temperature overnight. The reaction mixture was filtered.

The filtrate was concentrated under reduced pressure, and purified by silica gel column chromatography with an eluent system (PE:EtOAc=10:1) to obtain 760 mg Example 104-2, yield: 60%.

LCMS (ESI) m/z: 560.9 [M+Na$^+$].

Step 3 (Synthesis of Example 104-3)

104-2 (760 mg, 1.41 mmol) was dissolved in EtOAc (5 mL), and at room temperature was added a solution of HCl in EtOAc (10 mL), the mixture was stirred at room temperature for 1 hour. The reaction mixture was concentrated under reduced pressure, and washed with EtOAc, filtered to obtain 700 mg Example 104-3, yield: 97%.

LCMS (ESI) m/z: 462.7 [M+Na$^+$].

Step 4 (Synthesis of Example 104-4)

104-3 (700 mg, 1.4 mmol) was dissolved in anhydrous DCM (10 mL), and at 0□ triethylamine (470 mg, 4.6 mmol), chloroacetyl chloride (0.1 mL, 1.4 mmol) were added. After the addition, the temperature was raised to room temperature and the mixture was stirred for 1 hour. The reaction mixture was extracted with (100 mL×3) DCM. The organic layer was sequentially washed with water (100 mL×2), saturated saline solution (100 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 700 mg Example 104-4, yield: 97%.

LCMS (ESI) m/z: 538.7 [M+H⁺].

Step 5 (Synthesis of Example 104)

104-4 (110 mg, 0.21 mmol) was dissolved in acetonitrile (2 mL), and at room temperature was added potassium carbonate (59 mg, 0.42 mmol). After the addition, the temperature was raised to refluxing and the mixture was stirred overnight. The reaction mixture was cooled to room temperature, and filtered. The filtrate was concentrated under reduced pressure and then extracted with (30 mL×3) DCM. The organic layer was sequentially washed with water (30 mL×2), saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=5:1) to obtain 5 mg Example 104, yield: 5%.

NMR data of Example 104: ¹H NMR (400 MHz, CDCl₃) δ: 7.92 (d, J=3.2 Hz, 1H), 7.46 (d, J=3.2 Hz, 2H), 7.36 (dd, J=2.4, 8.4 Hz, 1H), 7.05-6.97 (m, 1H), 6.97-6.90 (m, 1H), 6.00 (d, J=16.8 Hz, 1H), 5.72 (s, 1H), 5.52 (d, J=4.4 Hz, 1H), 4.42 (d, J=16.8 Hz, 1H), 4.23 (dq, J=3.2, 7.1 Hz, 2H), 3.47 (d, J=1.6 Hz, 1H), 1.28 (t, J=7.2 Hz, 3H).

LCMS (ESI) m/z: 478.8 [M+H⁺].

Example 105

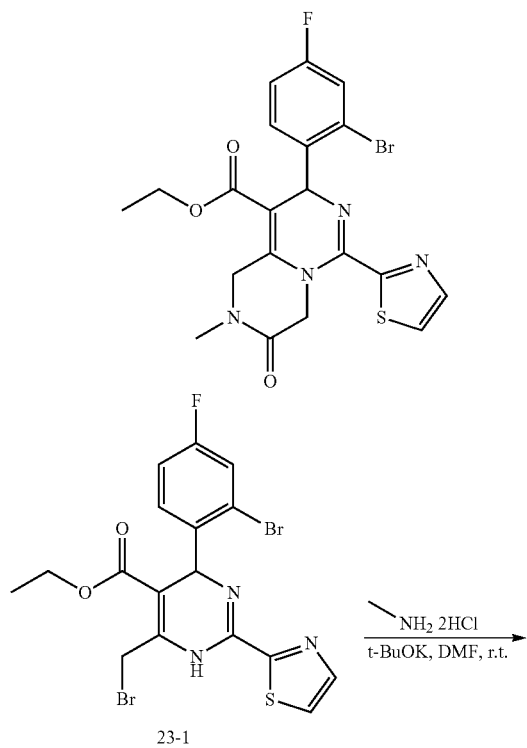

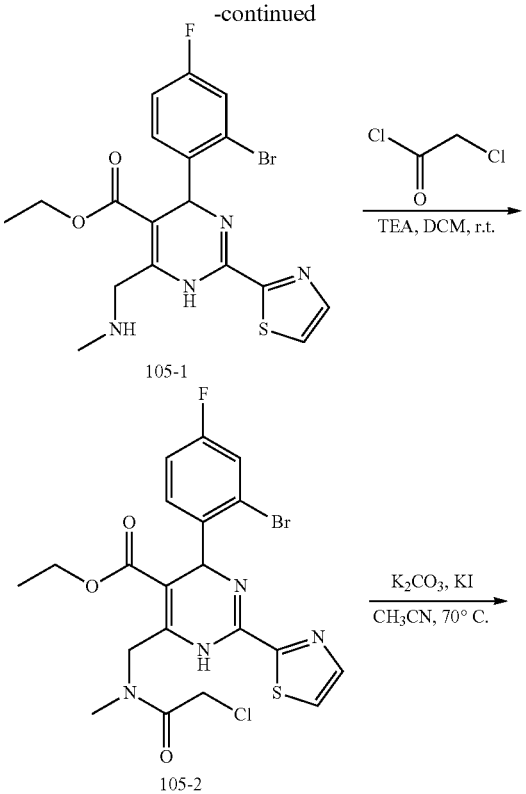

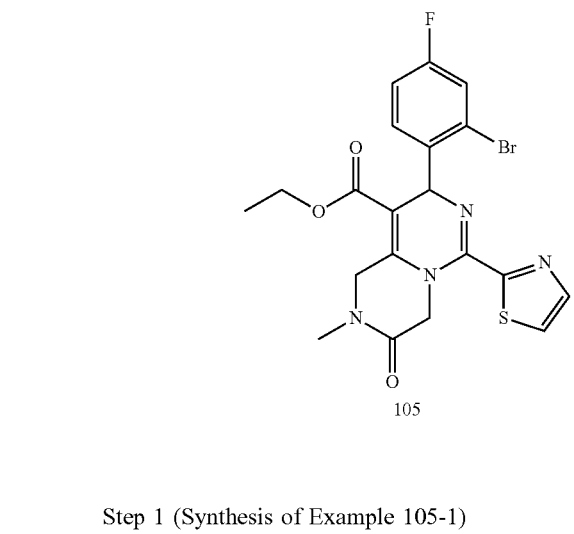

Step 1 (Synthesis of Example 105-1)

Compound 23-1 (300 mg, 0.6 mmol) was dissolved in anhydrous N,N-diformylacetamide (10 mL), and at room temperature were added methylamine hydrochloride (405 mg, 0.6 mmol), potassium tert-butoxide (334 mg, 2.98 mmol). After the addition, the mixture was stirred under nitrogen atmosphere at room temperature for 1 hour. The reaction mixture was poured into ice water, and extracted with EtOAc (100 mL×3). The organic layer was washed with saturated saline solution (50 mL×2). The organic phases were combined, dried over anhydrous sodium sulfate, and filtered. The filtrate was concentrated under reduced pressure, and purified by silica gel column chromatography with an eluent system (PE:EtOAc=5:1) to obtain 160 mg Example 105-1, yield: 59%.

LCMS (ESI) m/z: 452.9 [M+H⁺].

Steps 2, 3 (Synthesis of Example 105)

The steps 2, 3 of Example 105 were the same as that of Example 104.

NMR data of Example 105: ¹H NMR (400 MHz, CDCl₃) δ: 7.93 (d, J=3.2 Hz, 1H), 7.71 (d, J=3.2 Hz, 1H), 7.49-7.38 (m, 2H), 7.12 (dt, J=2.4, 8.4 Hz, 1H), 6.17 (s, 1H), 5.26 (d, J=16.0 Hz, 1H), 5.06 (d, J=4.0 Hz, 2H), 4.37 (d, J=16.0 Hz, 1H), 4.09 (dq, J=3.2, 7.2 Hz, 2H), 3.11 (s, 3H), 1.15 (t, J=7.2 Hz, 3H).

LCMS (ESI) m/z: 492.8 [M+H⁺].

Example 106

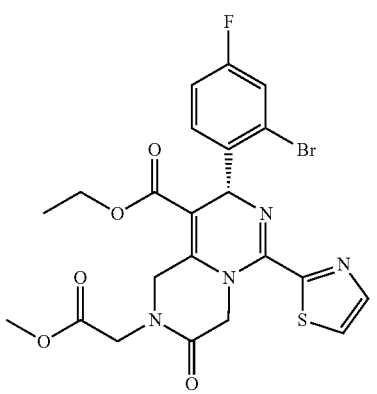

106

The Example was prepared according to the same method as that of Example 104.

NMR data of Example 106: ¹H NMR (400 MHz, MeOD-d₄) δ: 7.95 (d, J=3.2 Hz, 1H), 7.73 (d, J=3.2 Hz, 1H), 7.60 (dd, J=6.0, 8.8 Hz, 1H), 7.46 (dd, J=2.8, 8.4 Hz, 1H), 7.13 (dt, J=2.4, 8.4 Hz, 1H), 6.19 (s, 1H), 5.38-5.19 (m, 2H), 5.03 (d, J=16.8 Hz, 1H), 4.62-4.53 (m, 2H), 4.21 (d, J=17.6 Hz, 1H), 4.16-4.03 (m, 2H), 3.80 (s, 3H), 1.16 (t, J=7.2 Hz, 3H).

LCMS (ESI) m/z: 550.8 [M+H⁺].

Example 107

107

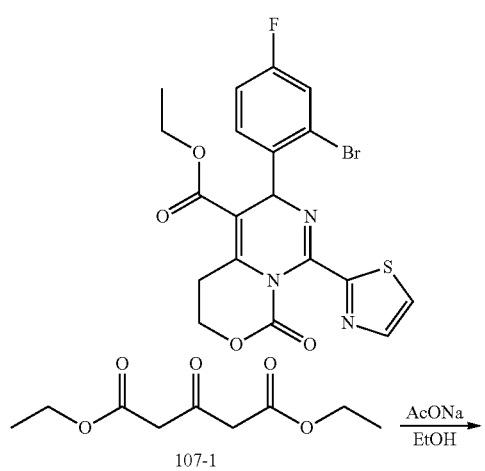

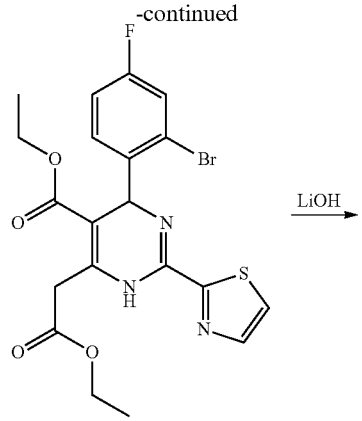

107-2

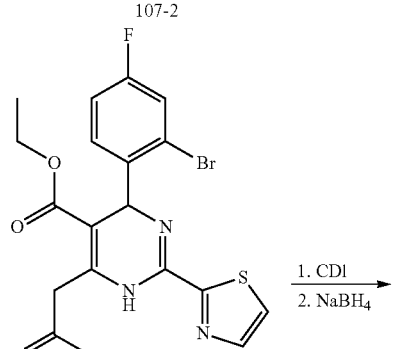

107-3

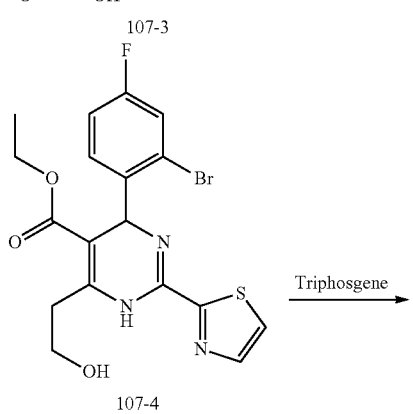

107-4

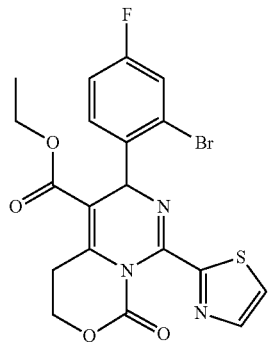

107

Step 1 (Synthesis of Compound 107-2)

Compound 107-1 (8.0 g, 39.6 mmol) was dissolved in anhydrous ethanol (200 mL), and 2-bromo-4-fluorobenzaldehyde (8.0 g, 39.6 mmol), thiazoledicarboxamidine hydrochloride (6.5 g, 39.6 mmol), sodium acetate (6.5 g, 79.2 mmol) were added. The reaction mixture was slowly warmed to reflux, and the reaction was stirred under reflux overnight. The reaction mixture was concentrated under reduced pressure and then extracted with (500 mL×3) EtOAc. The organic layer was washed with saturated saline solution (300 mL×2). The organic phases were combined, dried over anhydrous sodium sulfate, and filtered. The filtrate was concentrated under reduced pressure, and purified by silica gel column: chromatography with an eluent system (PE:EtOAc=10:1) to obtain 5.0 g product 107-2, yield: 25.5%.

LCMS (ESI) m/z: 496.0 [M+H].

Step 2 (Synthesis of Compound 107-3)

Compound 107-2 (5.0 g, 10.0 mmol) was dissolved in 80 mL tetrahydrofuran and 80 mL water, and LiOH (1.3 g, 30.2 mmol) was added. The reaction mixture was stirred at 15□ for 2 hours. The reaction mixture was concentrated under reduced pressure to obtain a crude product. To the crude product were added 100 mL tert-butyl methyl ether and water (50 mL), followed by slow addition of 1N HCl to adjust until pH=3 and extraction. The organic phases were combined, dried over anhydrous sodium sulfate, and filtered. The filtrate was concentrated under reduced pressure to obtain 3.0 g compound 107-3, yield: 37.9%.

$^1$H NMR (400 MHz, DMSO-d$_6$) δ: 10.13 (s, 1H), 7.85-7.96 (m, 2H), 7.60 (dd, J=6.4, 8.8 Hz, 1H), 7.52 (dd, J=2.4, 8.4 Hz, 1H), 7.18 (dt, J=2.4, 8.4 Hz, 1H), 5.96 (s, 1H), 3.88 (d, J=6.8 Hz, 2H), 0.99 (t, J=7.2 Hz, 3H).

Step 3 (Synthesis of Compound 107-4)

Compound 107-3 (3.0 g, 6.4 mmol) was dissolved in anhydrous DCM (60 mL), and carbonyldiimidazole (2.1 g, 12.8 mmol) was added. The mixture was stirred at 151 for 30 minutes, and then poured into sodium borohydride (4.9 g, 64 mmol) in methanol (30 mL), stirred for 15 minutes. The reaction mixture was diluted with water (50 mL) and DCM (100 mL), and extracted with DCM (50 mL×3). The organic layer was washed with saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=1:1) to obtain 1.0 g compound 107-4, yield: 34.4%.

$^1$H NMR (400 MHz, CDCl3) δ: 8.59 (br. s., 1H), 7.84 (d, J=2.4 Hz, 1H), 7.48-7.64 (m, 1H), 7.41 (dd, J=6.4, 8.8 Hz, 1H), 7.32 (dd, J=2.4, 8.0 Hz, 1H), 7.02 (d, J=5.6 Hz, 1H), 6.02-6.25 (m, 1H), 4.04 (d, J=7.2 Hz, 4H), 3.27-3.38 (m, 1H), 3.19 (br. s., 1H), 1.11 (t, J=7.2 Hz, 3H).

Step 4 (Synthesis of Example 107)

Compound 107-4 (200 mg, 0.44 mmol) was dissolved in anhydrous tetrahydrofuran (10 mL), and triphosgene (196 mg, 0.66 mmol) was added, the mixture was stirred at 150 for 10 minutes. To the reaction mixture was added potassium tert-butoxide (1.32 mL, 1.32 mmol, 1M in THF), the mixture was stirred for 60 minutes. The reaction mixture was diluted with water (20 mL) and DCM (10 mL), and extracted with DCM (20 mL×3). The organic layer was washed with saturated saline solution (30 mL×2). The organic phases were combined, dried over anhydrous sodium sulfate, and filtered. The filtrate was concentrated under reduced pressure, and purified with prep-silica gel plate to obtain crude product, which was further purified by preparative chromatograph to obtain 11 mg Example 107, yield: 5.2%.

NMR data of Example 107: $^1$H NMR (400 MHz, CDCl3) δ: 7.80-7.88 (m, 1H), 7.53 (d, J=3.2 Hz, 1H), 7.35-7.42 (m, 1H), 7.33 (dd, J=2.4, 8.0 Hz, 1H), 6.88-7.13 (m, 1H), 5.99-6.27 (s, 1H), 4.66-4.75 (m, 1H), 4.07 (q, J=7.0 Hz, 2H), 3.30-3.68 (m, 1H), 3.01-3.09 (m, 2H), 1.13 (t, J=7.0 Hz, 3H).

LCMS (ESI) m/z: 479.9 [M+H$^+$].

Example 108

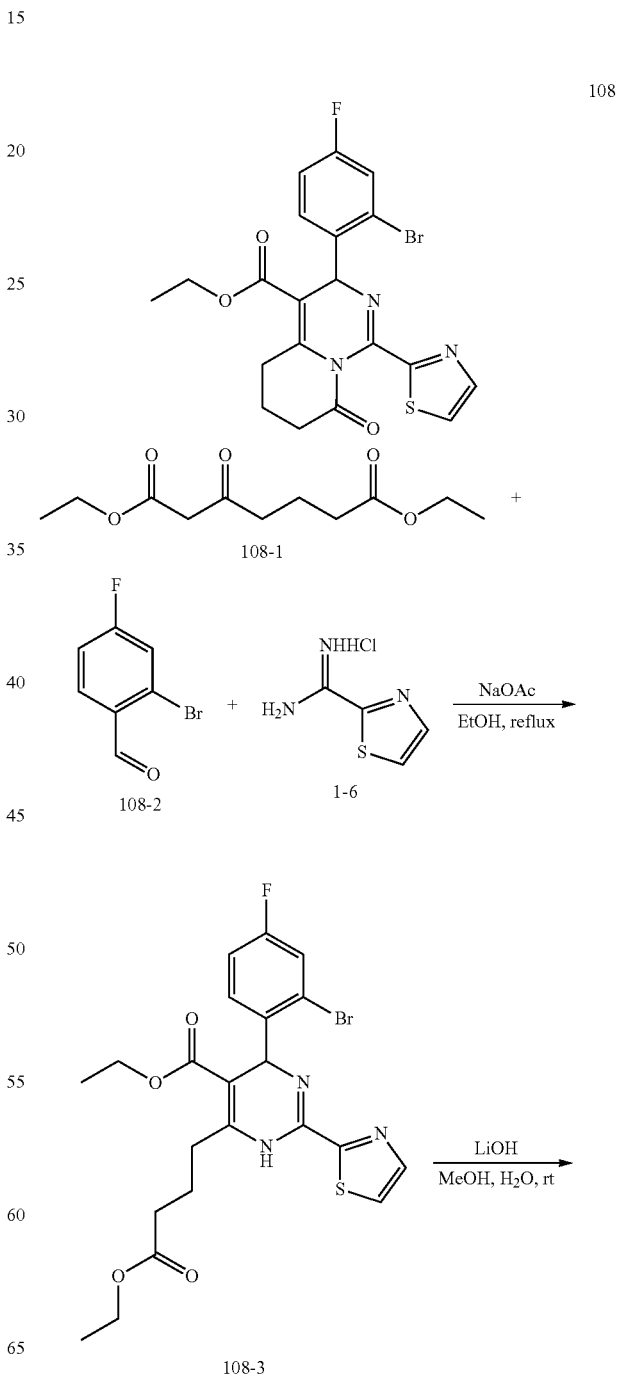

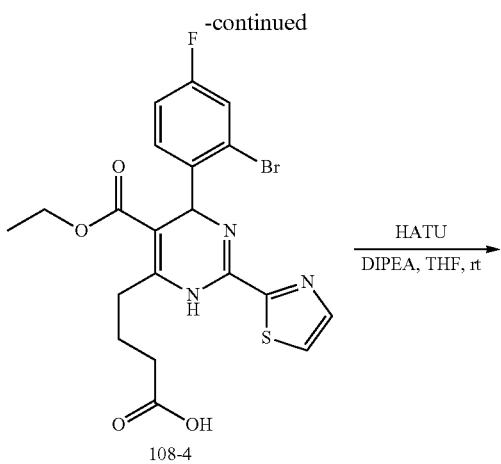

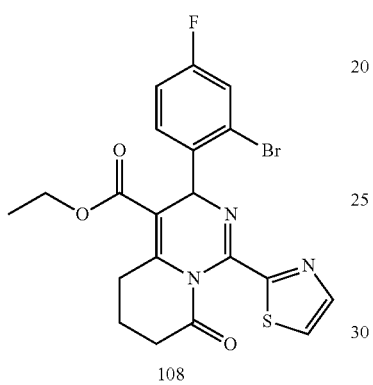

Step 1 (Synthesis of Compound 108-3)

Compound 108-1 (1.0 g, 4.3 mmol) was dissolved in anhydrous ethanol (30 mL), and 2-bromo-4-fluorobenzaldehyde (883 mg, 4.3 mmol), thiazoledicarboxamidine hydrochloride (709 mg, 4.3 mmol), sodium acetate (1.06 g, 12.9 mmol) were added. The reaction mixture was slowly warmed to reflux, and the reaction was stirred under reflux overnight. The reaction mixture was concentrated under reduced pressure and then extracted with (40 mL×3) EtOAc. The organic layer was washed with saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 600 mg product 108-3, yield: 27%.

LCMS (ESI) m/z: 524.0 [M+H$^+$].

Step 2 (Synthesis of Compound 108-4)

Compound 108-4 (600 mg, 1.1 mmol) was dissolved in methanol (8 mL) and water (8 mL), and LiOH (264 mg, 11 mmol) was added. The reaction mixture was stirred at 150 for 16 hours. With TLC (PE:EA; 5:1) showing completion of the reaction, the reaction mixture was concentrated under reduced pressure to obtain a crude product. To the crude product was added EtOAc (30 mL) and water (20 mL), followed by slow addition of 1N HCl to adjust until pH=1 and extraction with EtOAc (30 mL×3). The organic phases were combined, dried over anhydrous sodium sulfate, and filtered. The filtrate was concentrated under reduced pressure to obtain 400 mg compound 108-4, yield: 71%.

LCMS (ESI) m/z: 496 [M+H$^+$].

Step 3 (Synthesis of Example 108)

Compound 108-4 (270 mg, 0.54 mmol) was dissolved in anhydrous tetrahydrofuran (10 mL), and HATU (310 mg, 0.82 mmol), DIPEA (209 mg, 1.62 mmol) were added. The reaction mixture was stirred at 200 for 16 hours. When LC-MS showed completion of the reaction, the reaction mixture was concentrated under reduced pressure and then extracted with EtOAc (40 mL×3). The organic layer was washed with saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=10:1) to obtain 66 mg Example 108, yield: 26%.

NMR data of Example 108: $^1$H NMR (400 MHz, CDCl$_3$) δ: 7.78 (m, 1H), 7.37 (d, J=3.2 Hz, 2H), 7.04 (m, 1H), 6.95 (dd, J=2.4, 8.0 Hz, 1H), 6.30 (s, 1H), 4.20-4.08 (m, 2H), 3.40-3.34 (m, 2H), 2.87 (t, J=6.4 Hz, 1H), 2.56 (d, J=7.2 Hz, 1H), 2.22-2.08 (m, 2H), 1.18 (m, 3H).

LCMS (ESI) m/z: 478.0 [M+H$^+$].

Example 109

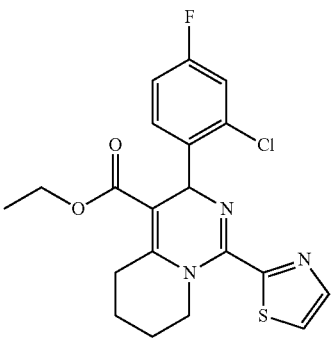

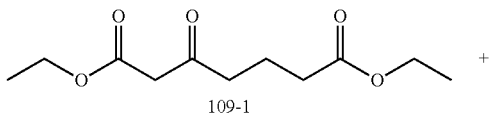

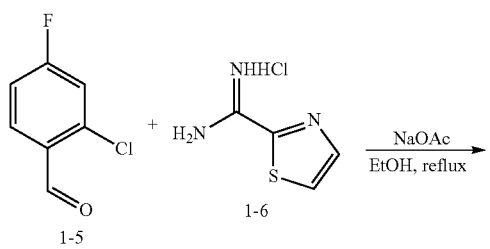

-continued

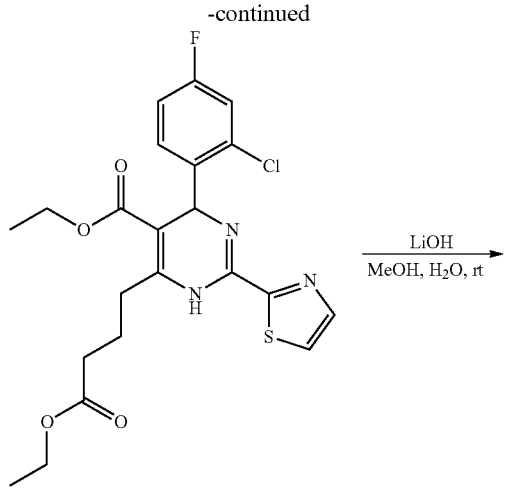

109-2

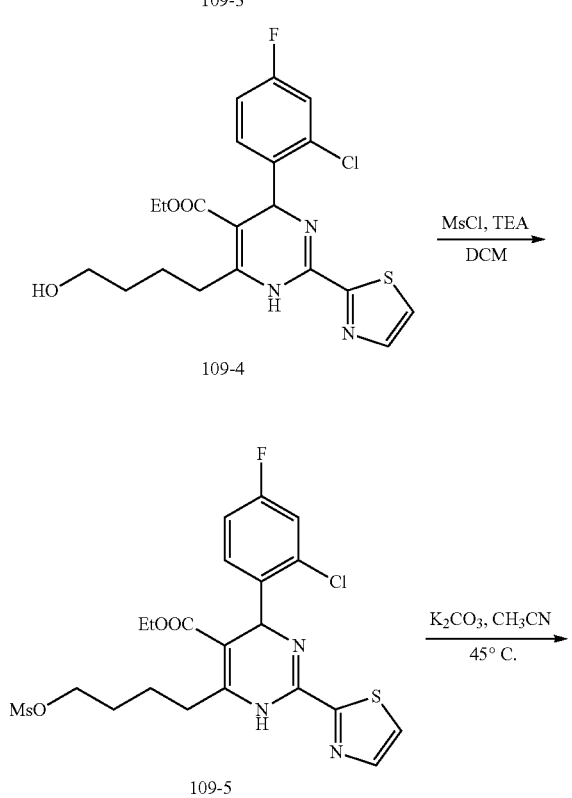

-continued

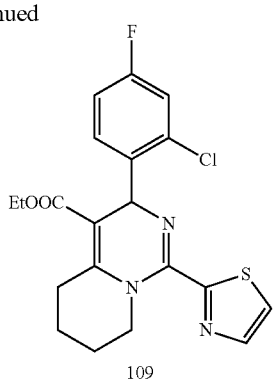

109

Step 1 (Synthesis of Compound 109-2)

Compound 109-1 (1.34 g, 5.8 mmol) was dissolved in anhydrous ethanol (30 mL), and 2-chloro-4-fluorobenzaldehyde (1.08 g, 5.8 mmol), thiazoledicarboxamidine hydrochloride (0.95 g, 5.8 mmol), sodium acetate (1.1 g, 17.4 mmol) were added. The reaction mixture was slowly warmed to reflux, and the reaction was stirred under reflux overnight. The reaction mixture was concentrated under reduced pressure and subsequently extracted with EtOAc (40 mL×3). The organic layer was washed with saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=5:1) to obtain 1.5 g compound 109-2, yield: 62%.

LCMS (ESI) m/z: 480.0 [M+H$^+$].

Step 2 (Synthesis of Compound 109-3)

Compound 109-2 (1.5 g, 3.1 mmol) was dissolved in tetrahydrofuran (20 mL) and water (20 mL), and LiOH (394 mg, 9.3 mmol) was added. The reaction mixture was stirred at 15□ for 16 hours. With TLC (PE:EA; 5:1) showing completion of the reaction, the reaction mixture was concentrated under reduced pressure to obtain a crude product. To the crude product were added EtOAc (30 mL) and water (20 mL), followed by slow addition of 1N HCl to adjust until pH=1 and extraction with EtOAc (3×30 mL). The organic phases were combined, dried over anhydrous sodium sulfate, and filtered. The filtrate was concentrated under reduced pressure to obtain 1.3 g compound 109-3, yield: 93%.

LCMS (ESI) m/z: 452.0 [M+H$^+$].

Step 3 (Synthesis of Compound 109-4)

Compound 109-3 (500 mg, 1.11 mmol) was dissolved in anhydrous DCM (20 mL), and carbonyldiimidazole (360 mg, 2.22 mmol) was added, the mixture was stirred at 15□ for 30 minutes. The reaction mixture was poured into sodium borohydride (360 mg, 2.22 mmol) in methanol (20 mL), and stirred for 15 minutes. The reaction mixture was diluted with water (50 mL) and DCM (100 mL), and extracted with DCM (50 mL×3). The organic layer was washed with saturated saline solution (30 mL×2). The organic phases were combined, dried over anhydrous sodium sulfate, and filtered. The filtrate was concentrated under reduced pressure, and purified by silica gel column chromatography with an eluent system (PE:EtOAc=3:1) to obtain 300 mg compound 109-4, yield: 61.7%.

LCMS (ESI) m/z: 437.9 [M+H⁺].

Step 4 (Synthesis of Compound 109-5)

Compound 109-4 (300 mg, 0.68 mmol) was dissolved in anhydrous DCM (10 mL), and at room temperature were added triethylamine (206 mg, 2.04 mmol), methanesulfonyl chloride (118 mg, 1.03 mmol). After the addition, the mixture was fully stirred under nitrogen atmosphere for 15 hours. When TLC (PE:EtOAc; 1:1) showed the starting materials disappeared, the reaction mixture was poured into saturated sodium bicarbonate solution (15 mL), and extracted with DCM (20 mL×3). The organic phases were combined, sequentially washed with water (10 mL×2), saturated sodium chloride solution (10 mL×2), dried over anhydrous sodium sulfate, filtered, and purified by flash chromatography with an eluent system (PE:EtOAc=100:1-5:1) to obtain 130 mg compound 109-5, yield: 36.8%.

LCMS m/z: 516.1 [M+H⁺].

Step 5 (Synthesis of Example 109)

Compound 109-5 (130 mg, 0.25 mmol) was dissolved in anhydrous acetonitrile (10 mL), and at room temperature was added potassium carbonate (69 mg, 0.5 mmol). After the addition, the mixture was fully stirred under nitrogen atmosphere at 45□ for 1 hour. When LC-MS showed completion of the reaction, the mixture was concentrated under vacuum, followed by adding water (10 mL) and being extracted with DCM (20 mL×3). The organic phases were combined, sequentially washed with water (10 mL×2), saturated sodium chloride solution (10 mL×2), dried over anhydrous sodium sulfate, filtered, and purified by preparative chromatograph to obtain 35 mg Example 109, yield: 33.2%.

NMR data of Example 109: ¹H NMR (400 MHz, MeOD-d₄) δ: 7.95 (d, J=3.2 Hz, 1H), 7.73 (d, J=3.2 Hz, 1H), 7.38 (dd, J=6.4, 8.8 Hz, 1H), 7.28 (dd, J=2.4, 8.4 Hz, 1H), 7.09 (dt, J=2.4, 8.4 Hz, 1H), 6.12 (s, 1H), 4.20-4.30 (m, 1H), 4.03-4.17 (m, 2H), 3.61 (td, J=6.0, 16.4 Hz, 1H), 3.44 (ddd, J=4.2, 8.0, 12.8 Hz, 1H), 3.00-3.13 (m, 1H), 2.04-2.17 (m, 1H), 1.93 (quin, J=6.8 Hz, 2H), 1.75-1.86 (m, 1H), 1.18 (t, J=7.2 Hz, 3H).

LCMS m/z: 420.0 [M+H⁺].

Example 110

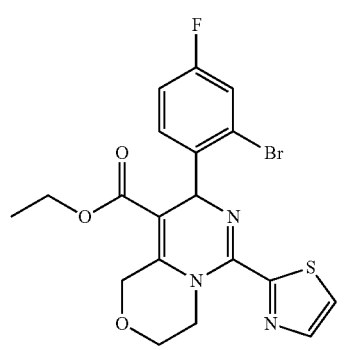

110

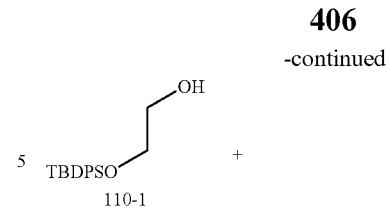

110-1

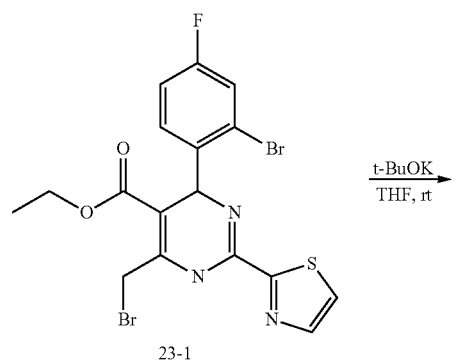

23-1

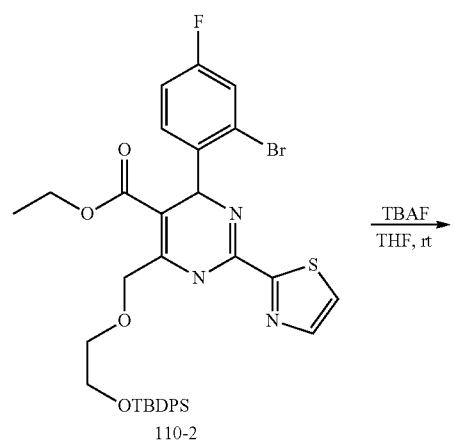

110-2

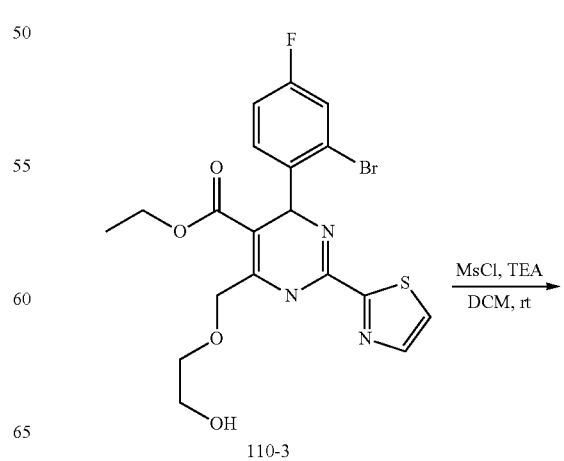

110-3

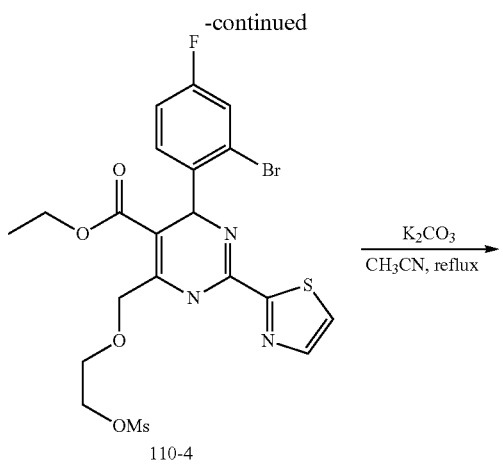

Step 1 (Synthesis of Compound 110-2)

Compound 110-1 (1.07 g, 3.57 mmol) was dissolved in anhydrous tetrahydrofuran (10 mL), and at room temperature was added potassium tert-butoxide (400 mg, 3.57 mmol). After the addition, the mixture was fully stirred under nitrogen atmosphere at 20□ for 0.5 hour, followed by adding Example 23-1 (600 mg, 1.19 mmol) and the mixture was fully stirred under nitrogen atmosphere at 200 for 16 hours. When LC-MS showed completion of the reaction, the mixture was concentrated under vacuum, followed by adding 10 mL water and being extracted with DCM (20 mL×3). The organic phases were combined, sequentially washed with water (10 mL×2), saturated sodium chloride solution (10 mL×2), dried over anhydrous sodium sulfate, filtered, and evaporated to dry by rotation to obtain 840 mg product, which was directly used in the next step without purification. Yield, 98%.

LCMS (ESI) m/z: 723.9 [M+H$^+$].

Step 2 (Synthesis of Compound 110-3)

Compound 110-2 (840 mg, 1.16 mmol) was dissolved in anhydrous tetrahydrofuran (10 mL), and at room temperature was added TBAF (10 mmol, 10 mL, 1M in THF). After the addition, the mixture was fully stirred under nitrogen atmosphere at 20□ for 16 hours. When LC-MS showed completion of the reaction, the mixture was concentrated under vacuum, followed by adding water (10 mL) and being extracted with DCM (20 mL×3). The organic phases were combined, sequentially washed with water (10 mL×2), saturated sodium chloride solution (10 mL×2), dried over anhydrous sodium sulfate, filtered, evaporated to dry by rotation, and purified by preparative chromatography (PE:EA=1:1) to obtain 300 mg compound 110-3, yield, 53%.

$^1$H NMR (400 MHz, CDCl$_3$) δ: 9.08 (br. s., 1H), 7.82 (d, J=3.2 Hz, 1H), 7.43 (d, J=3.2 Hz, 1H), 7.36-7.29 (m, 2H), 6.97 (dt, J=2.4, 8.4 Hz, 1H), 6.18 (s, 1H), 4.96 (d, J=2.0 Hz, 2H), 4.11-3.97 (m, 2H), 3.90 (br. s., 2H), 3.84-3.69 (m, 2H), 1.13 (t, J=7.2 Hz, 3H).

LCMS (ESI) m/z: 486.0 [M+H$^+$].

Step 3 (Synthesis of Compound 110-4)

Compound 110-3 (280 mg, 0.58 mmol) was dissolved in anhydrous DCM (10 mL), and at room temperature were added triethylamine (176 mg, 1.74 mmol), methanesulfonyl chloride (132 mg, 1.16 mmol). After the addition, the mixture was fully stirred under nitrogen atmosphere for 15 hours. When TLC (PE: EtOAc; 1:1) showed the starting materials disappeared, the reaction mixture was poured into saturated sodium bicarbonate (15 mL) solution, and extracted with DCM (20 mL×3). The organic phases were combined, sequentially washed with water (10 mL×2), saturated sodium chloride solution (10 mL×2), dried over anhydrous sodium sulfate, filtered, and purified by flash chromatography with an eluent system (PE:EtOAc=3:1) to obtain 150 mg compound 110-4, yield, 46%.

$^1$H NMR (400 MHz, CDCl$_3$) δ: 8.95 (br. s., 1H), 7.83 (d, J=3.2 Hz, 1H), 7.47 (d, J=3.2 Hz, 1H), 7.40-7.31 (m, 1H), 7.00 (dt, J=2.4, 8.4 Hz, 1H), 6.20 (s, 1H), 5.09-4.92 (m, 2H), 4.58-4.44 (m, 2H), 4.13-4.00 (m, 2H), 4.00-3.90 (m, 2H), 3.17 (s, 3H), 1.15 (t, J=7.2 Hz, 3H).

LCMS (ESI) m/z: 564.0 [M+H$^+$].

Step 4 (Synthesis of Example 110)

Compound 110-4 (140 mg, 0.24 mmol) was dissolved in anhydrous acetonitrile (5 mL), and at room temperature was added potassium carbonate (68 mg, 0.50 mmol). After the addition, the mixture was fully stirred under nitrogen atmosphere at 90□ for 16 hours. When LC-MS showed completion of the reaction, the mixture was concentrated under vacuum, followed by adding 10 mL water and being extracted with DCM (20 mL×3). The organic phases were combined, sequentially washed with water (10 mL×2), saturated sodium chloride solution (10 mL×2), dried over anhydrous sodium sulfate, filtered, and purified by preparative chromatography to obtain 64 mg Example 110. Yield, 52%.

NMR data of Example 110: $^1$H NMR (400 MHz, CDCl$_3$) δ: 7.82 (d, J=3.6 Hz, 1H), 7.42-7.34 (m, 2H), 7.31-7.27 (m, 1H), 7.01 (dt, J=2.4, 8.4 Hz, 1H), 6.14 (s, 1H), 5.29 (d, J=16.8 Hz, 1H), 5.00 (d, J=16.8 Hz, 1H), 4.80 (ddd, J=4.0, 6.8, 12.4 Hz, 1H), 4.15-4.05 (m, 2H), 4.04-3.97 (m, 1H), 3.96-3.86 (m, 1H), 3.64 (ddd, J=3.6, 6.8, 12.4 Hz, 1H), 1.14 (t, J=7.2 Hz, 3H).

LCMS (ESI) m/z: 467.9 [M+1].

Example 111

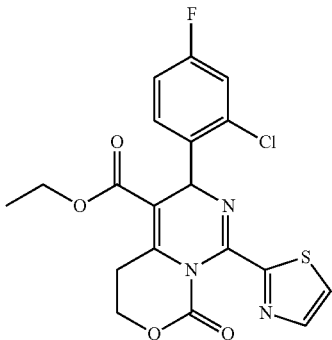

111

The Example was prepared according to the method as described in Example 107.

NMR data of Example 111: $^1$H NMR (400 MHz, CDCl3) δ: 7.85 (d, J=3.2 Hz, 1H), 7.44 (d, J=3.2 Hz, 1H), 7.16-7.25 (m, 2H), 6.98 (dt, J=2.2, 8.0 Hz, 1H), 6.39 (s, 1H), 4.55-4.72 (m, 2H), 4.11-4.22 (m, 2H), 3.83 (d, J=19.58 Hz, 1H), 3.32-3.43 (m, 1H), 1.22 (t, J=7.15 Hz, 3H).

LCMS (ESI) m/z: 436.0 [M+H$^+$].

Example 112

112

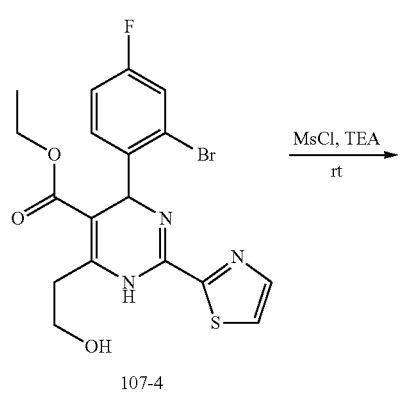

107-4

MsCl, TEA
rt

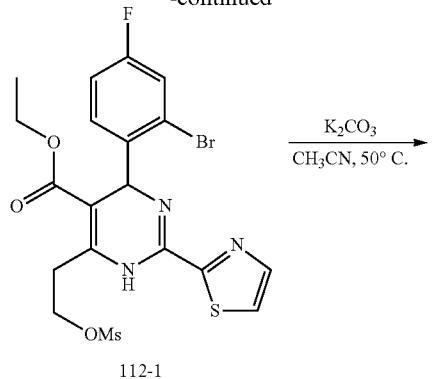

112-1

K$_2$CO$_3$
CH$_3$CN, 50° C.

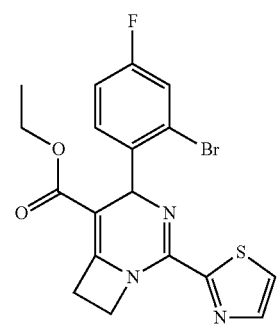

112

Step 1 (Synthesis of Compound 112-1)

Compound 107-4 (150 mg, 0.33 mmol) was dissolved in anhydrous DCM (10 mL), and at room temperature were added triethylamine (101 mg, 1.0 mmol), methanesulfonyl chloride (56 mg, 0.5 mmol), the mixture was stirred at room temperature overnight. The reaction mixture was concentrated under reduced pressure and then extracted with DCM (20 mL×3). The organic phases were combined, sequentially washed with water (20 mL×2), saturated sodium chloride solution (20 mL×2), dried over anhydrous sodium sulfate, filtered, and purified by silica gel column chromatography with an eluent system (PE:EtOAc=10:1) to obtain 120 mg compound 112-1, yield: 68%.

$^1$H NMR (400 MHz, CDCl3) δ: 7.80-7.88 (m, 1H), 7.53 (d, J=3.01 Hz, 1H), 7.35-7.42 (m, 1H), 7.33 (dd, J=2.52, 8.03 Hz, 1H), 6.88-7.13 (m, 1H), 6.0 (s, 1H), 4.66-4.75 (m, 1H), 4.07 (q, J=7.04 Hz, 2H), 3.30-3.68 (m, 1H), 3.01-3.09 (m, 3H), 1.99-2.06 (m, 2H), 1.13 (t, J=7.04 Hz, 3H).

Step 2 (Synthesis of Example 112)

Compound 112-1 (100 mg, 0.19 mmol) was dissolved in acetonitrile (3 mL), and at room temperature was added potassium carbonate (52 mg, 0.38 mmol). The temperature was raised to 45□ and the mixture was stirred at the temperature for 1 hour. The reaction mixture was concentrated under reduced pressure and then extracted with DCM (20 mL×3). The organic phases were combined, sequentially washed with water (20 mL×2), saturated sodium chloride solution (20 mL×2), dried over anhydrous sodium sulfate, filtered, and purified by silica gel column chromatography with an eluent system (PE:EtOAc=2:1) to obtain 28 mg Example 112. Yield: 34%.

NMR data of Example 112: $^1$H NMR (400 MHz, CDCl3) δ: 7.84 (d, J=3.2 Hz, 1H), 7.36-7.44 (m, 2H), 7.31 (dd, J=2.4, 8.4 Hz, 1H), 6.97 (dt, J=2.4, 8.4 Hz, 1H), 6.17 (s, 1H), 4.61-4.77 (m, 2H), 4.11 (ttd, J=3.60, 7.2, 10.4 Hz, 2H), 3.37-3.58 (m, 2H), 1.22 (t, J=7.2 Hz, 3H).
LCMS (ESI) m/z: 435.8 [M+H⁺].
Examples 113, 114
113
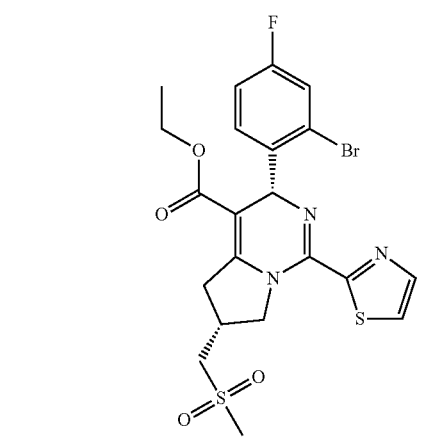
114
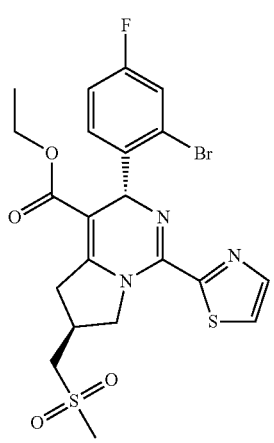
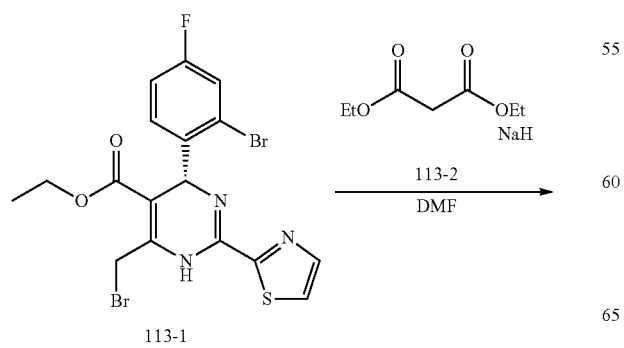
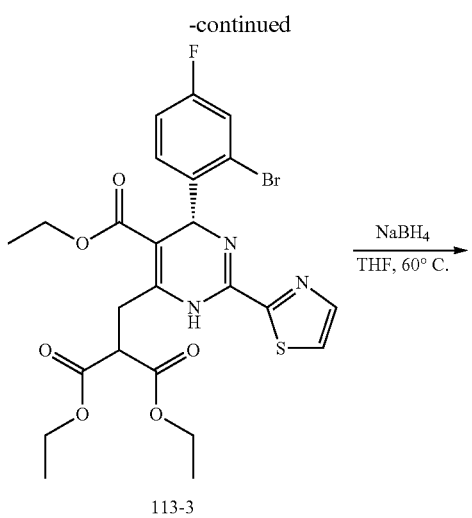
113-3
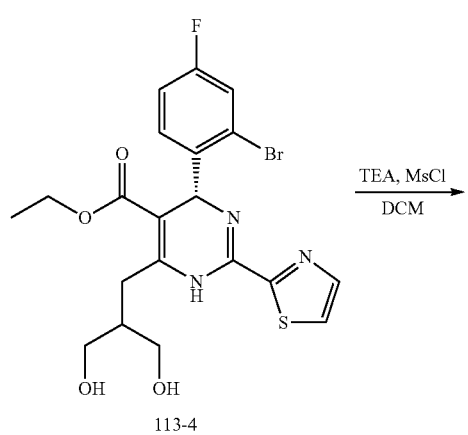
113-4
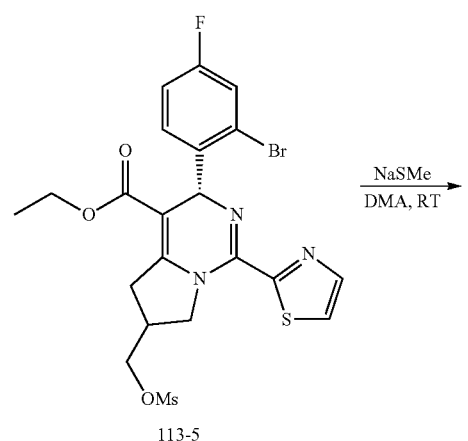
113-5

-continued

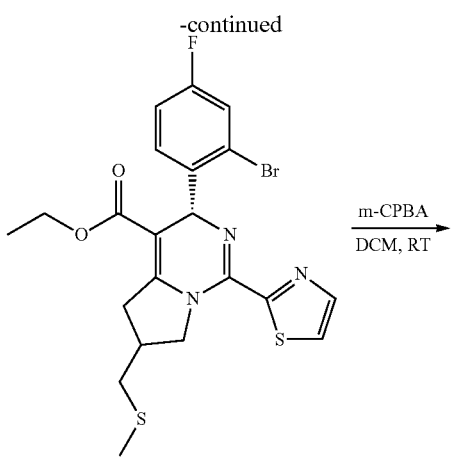

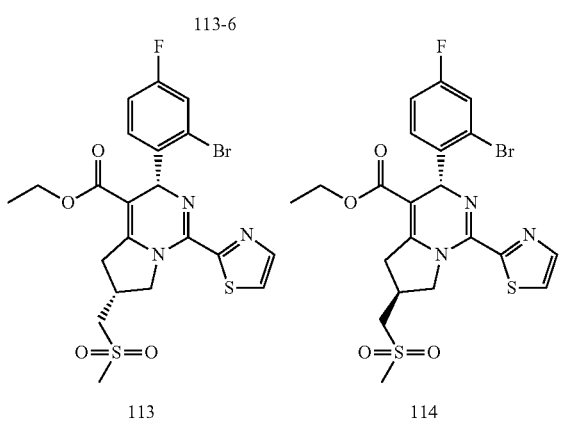

Step 1 (Synthesis of 113-3)

Compound 113-2 (1.27 g, 7.94 mmol) was dissolved in anhydrous DMF (100 mL), and at 0° C. was added in portions NaH (238.2 mg, 5.96 mmol, 1.5 eq.), the mixture was stirred at this temperature for 15 minutes. Subsequently, to the reaction mixture was added 113-1 (2.0 g, 3.97 mmol, 1.0 eq.), and the reaction mixture was warmed to 16° C., and continued stirring for 3 hours. The reaction mixture was quenched with saturated ammonium chloride solution, extracted with EtOAc (300 mL) for 3 times, and washed with water (150 mL) for 3 times. The organic phases were dried over anhydrous sodium sulfate, filtered, and concentrated under reduced pressure. The residue was purified by a silica gel column with an eluent solution of PE:EtOAc=3:1, to obtain the product 1.76 g, yield: 76%.

LCMS (ESI) m/z: 583.7 [M+H$^+$].

Step 2 (Synthesis of 113-4)

Compound 113-3 (1.76 g, 3.02 mmol, 1.0 eq.) was dissolved in anhydrous THF (50 mL), and at 0° C. was added in portions sodium borohydride (571 mg, 15.1 mmol, 5.0 eq.). After the addition, the reaction mixture was warmed to 60° C., and the mixture was stirred for 18 hours. The reaction mixture was cooled to room temperature, quenched with water (50 mL), and extracted with DCM (100 mL) for 3 times. The organic phases were dried over anhydrous sodium sulfate, filtered, and concentrated under reduced pressure. The residue was purified by a silica gel column with an eluent solution of DCM:methanol=20:1, to obtain 780 mg product, yield: 39%.

LCMS (ESI) m/z: 521.7 [M+Na$^+$].

Step 3 (Synthesis of 113-5)

Compound 113-4 (2.70 g, 5.42 mmol, 1.0 eq.) was dissolved in anhydrous DCM (100 mL), and at 15° C. were sequentially added triethylamine (1.65 g, 16.26 mmol, 3.0 eq.), methanesulfonyl chloride (7.67 g, 66.96 mmol, 12.35 eq.). After the addition, and the mixture was stirred for 18 hours. The reaction mixture was quenched with water (100 mL), and extracted with DCM (200 mL) for 3 times. The organic phases were dried over anhydrous sodium sulfate, filtered, and concentrated under reduced pressure. The residue was purified by a silica gel column with an eluent solution of DCM:methanol=20:1, to obtain 1.4 g product, yield: 46%.

LCMS (ESI) m/z: 582.0 [M+Na$^+$].

Step 4 (Synthesis of 113-6)

Compound 113-5 (200 mg, 358.14 umol, 1.0 eq.) was dissolved in anhydrous DMA (8 mL), and at 20° C. was added sodium thiomethoxide (30 mg, 429.77 umol, 1.2 eq.). After the addition, the mixture was stirred for 3 hours. The reaction mixture was quenched with water (10 mL), and extracted with EtOAc (50 mL) for 3 times. The organic phases were dried over anhydrous sodium sulfate, filtered, and concentrated under reduced pressure. The residue was purified by a silica gel column with an eluent solution of PE:EtOAc=3:1, to obtain 160 mg product, yield: 88%.

LCMS (ESI) m/z: 512.0 [M+H$^+$].

Step 5 (Synthesis of 113, 114)

Compound 113-6 (160 mg, 313 μmol, 1.0 eq.) was dissolved in anhydrous DCM (10 mL), and at 20° C. was added m-chloroperbenzoic acid (81 mg, 470 μmol, 1.5 eq.). After the addition, the mixture was stirred for 3 hours, followed by supplementary addition of m-chloroperbenzoic acid (27 mg, 156 μmol, 0.5 eq.) and continued stirring for 3 hours. The reaction mixture was quenched with 1M potassium carbonate (10 mL), and extracted with DCM (20 mL) for 3 times. The organic phases were dried over anhydrous sodium sulfate, filtered, and concentrated under reduced pressure. The residue was separated by a chiral column to respectively obtain 50 mg Example 113, yield: 29%, 23 mg Example 114, yield: 13%.

NMR data of Example 113: $^1$H NMR (400 MHz, CDCl3) δ: 7.82 (d, J=3.0 Hz, 1H), 7.38 (d, J=3.0 Hz, 1H), 7.33 (dd, J=2.4, 8.4 Hz, 1H), 7.22 (dd, J=6.0, 8.4 Hz, 1H), 6.99 (dt, J=2.4, 8.0 Hz, 1H), 6.17 (s, 1H), 4.76 (dd, J=7.0, 12.0 Hz, 1H), 4.31 (dd, J=5.2, 11.80 Hz, 1H), 4.05 (q, J=7.0 Hz, 2H), 3.57 (dd, J=8.0, 18.0 Hz, 1H), 3.17-3.25 (m, 3H), 3.05-3.15 (m, 1H), 3.02 (s, 3H), 1.13 (t, J=7.0 Hz, 3H).

LCMS (ESI) m/z: 544.1 [M+H$^+$].

NMR data of Example 114: $^1$H NMR (400 MHz, CDCl3) δ: 7.82 (d, J=3.01 Hz, 1H), 7.38 (d, J=3.0 Hz, 1H), 7.34 (dd, J=2.4, 8.0 Hz, 1H), 7.22-7.26 (m, 1H), 6.99 (dt, J=2.4, 8.2 Hz, 1H), 6.16 (s, 1H), 4.78 (dd, J=7.6, 11.6 Hz, 1H), 4.13 (d, J=10.0 Hz, 1H), 4.02-4.10 (m, 2H), 3.83 (dd, J=7.6, 17.6 Hz, 1H), 3.23-3.35 (m, 2H), 3.05-3.13 (m, 1H), 3.04 (s, 3H), 2.88 (dd, J=10.2, 17.2 Hz, 1H), 1.16 (t, J=7.0 Hz, 3H).

LCMS (ESI) m/z: 544.0 [M+H$^+$].

Example 115

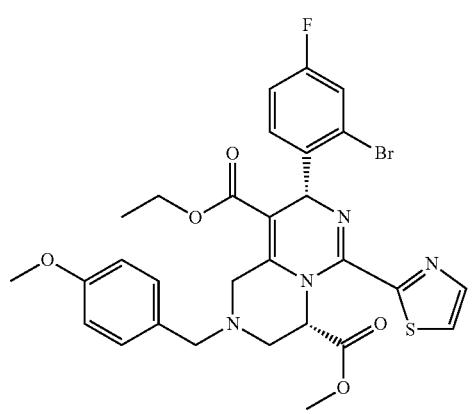

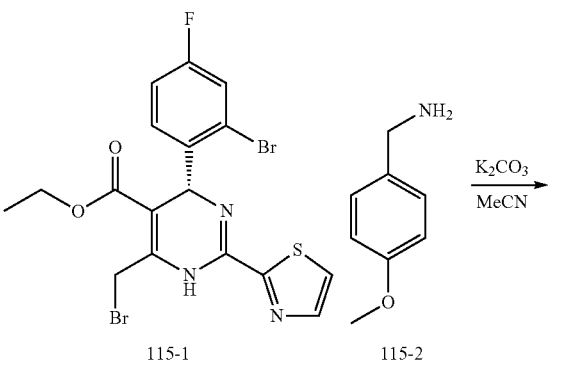

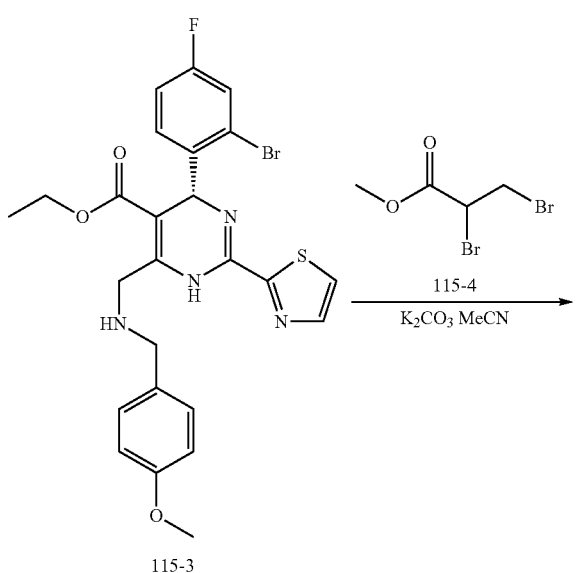

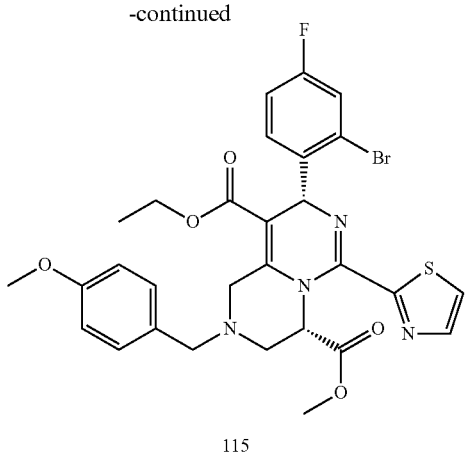

Step 1 (Synthesis of 115-3)

Compound 115-1 (1.51 g, 3.0 mmol, 1.0 eq.), 115-2 (4.12 g, 30 mmol, 10.0 eq.) were dissolved in acetonitrile (10 mL), and under nitrogen atmosphere at 20° C. was added potassium carbonate (4.15 g, 30 mmol, 10 eq.). After the addition, the mixture was stirred for 6 hours. The reaction mixture was concentrated. The residue was added to an ice-water mixture (w/w, 10 mL), stirred for 20 minutes. The aqueous phase was extracted with EtOAc (20 mL) for 3 times. The organic phases were dried over anhydrous sodium sulfate, filtered, and concentrated under reduced pressure. The residue was purified by a silica gel column to obtain 1.2 g product, yield: 71%.

LCMS (ESI) m/z: 561.1 [M+H$^+$].

Step 2 (Synthesis of 115)

Compound 115-3 (168 mg, 300.2 μmol 1.0 eq.), 115-4 (74 mg, 300.3 μmol 1.0 eq.) were dissolved in acetonitrile (5 mL), and under nitrogen atmosphere at 28° C. was added potassium carbonate (83 mg, 600.58 umol, 2 eq.). After the addition, the mixture was stirred for 48 hours. The reaction mixture was concentrated. The residue was added into an ice-water mixture (w/w, 10 mL), stirred for 20 minutes. The aqueous phase was extracted with EtOAc (20 mL) for 3 times. The organic phases were dried over anhydrous sodium sulfate, filtered, and concentrated under reduced pressure. The residue was purified by a silica gel column, to obtain 50 mg product.

NMR data of Example 115: $^1$H NMR (400 MHz, CDCl3) δ 7.91 (dd, J=6.2, 8.6 Hz, 1H), 7.74 (d, J=3.0 Hz, 1H), 7.33-7.39 (m, 2H), 7.26 (d, J=8.6 Hz, 2H), 7.12 (dt, J=2.6, 8.4 Hz, 1H), 6.90 (d, J=8.4 Hz, 2H), 6.34 (t, J=3.8 Hz, 1H), 6.19 (s, 1H), 4.80 (d, J=16.6 Hz, 1H), 3.91-4.14 (m, 2H), 3.77-3.87 (m, 4H), 3.44-3.59 (m, 5H), 3.25 (dd, J=2.4, 11.8 Hz, 1H), 2.77 (dd, J=4.2, 11.8 Hz, 1H), 1.11 (t, J=7.0 Hz, 3H).

LCMS (ESI) m/z: 644.5 [M+H$^+$].

Examples 116, 117

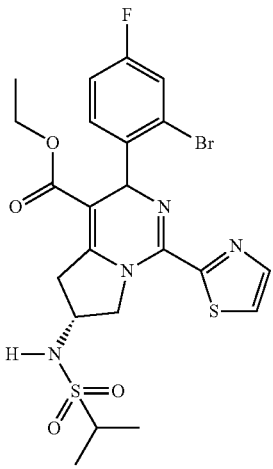

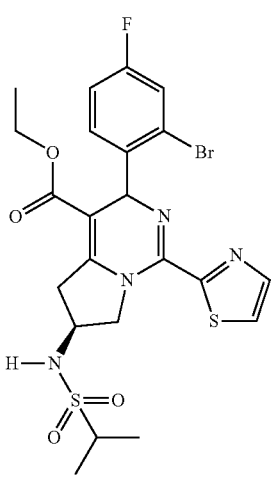

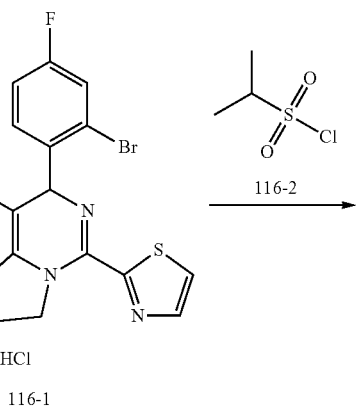

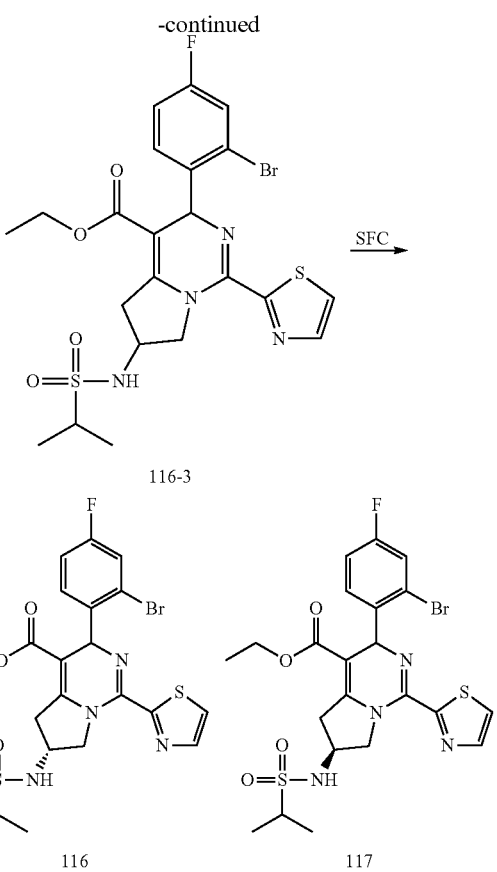

116-3

116    117

Step 1 (Synthesis of 116-3)

Compound 116-1 (150 mg, 322.34 μmol, 1.0 eq.) was dissolved in anhydrous DCM (10 mL), and at 20° C. were sequentially added DBU (147 mg, 967.02 μmol, 3.0 eq.), 116-2 (92 mg, 644.68 μmol, 2.0 eq.). After the addition, the mixture was stirred for 6 hours. With TLC showing completion of the reaction, the reaction mixture was quenched with water (10 mL), and extracted with DCM (20 mL) for 3 times. The organic phases were dried over anhydrous sodium sulfate, filtered, and concentrated under reduced pressure. The residue was purified by a silica gel column with an eluent solution of PE:EtOAc=100:1-1:1, to obtain 87 mg product, yield: 27%.

Step 2 (Synthesis of 116, 117)

Compound 116-3 (87 mg, 0.15 mmol) was chirally separated to obtain compounds 116 (8 mg), 117 (12 mg).

NMR data of Example 116: $^1$H NMR (400 MHz, CDCl3) δ: 7.80 (d, J=3.0 Hz, 1H), 7.37 (d, J=3.0 Hz, 1H), 7.35-7.27 (m, 2H), 6.99 (dt, J=2.3, 8.2 Hz, 1H), 6.16 (s, 1H), 4.54 (d, J=8.5 Hz, 2H), 4.50-4.44 (m, 1H), 4.31 (d, J=2.5 Hz, 1H), 4.10-4.01 (m, 2H), 3.52-3.43 (m, 1H), 3.41-3.31 (m, 1H), 3.20 (td, J=6.8, 13.6 Hz, 1H), 1.39 (d, J=6.8 Hz, 6H), 1.14 (t, J=7.2 Hz, 3H).

LCMS (ESI) m/z: 572.4 [M+H$^+$].

NMR data of Example 117: $^1$H NMR (400 MHz, CDCl3) δ·7.81 (br. s., 1H), 7.38 (br. s., 1H), 7.32 (d, J=7.3 Hz, 1H), 7.22 (br. s., 1H), 6.98 (br. s., 1H), 6.14 (br. s., 1H), 4.56 (d, J=6.8 Hz, 2H), 4.37 (d, J=11.0 Hz, 1H), 4.28 (d, J=6.3 Hz, 1H), 4.04 (d, J=6.8 Hz, 2H), 3.68 (dd, J=6.5, 17.6 Hz, 1H), 3.31-3.11 (m, 2H), 1.41 (d, J=5.5 Hz, 6H), 1.12 (br. s., 3H). LCMS (ESI) m/z: 572.4 [M+H⁺].

Example 118

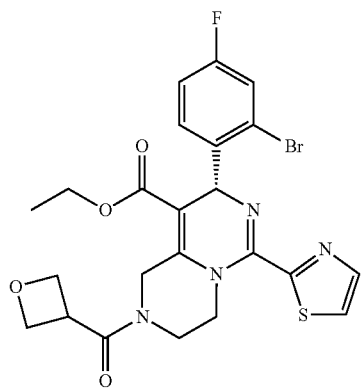

118

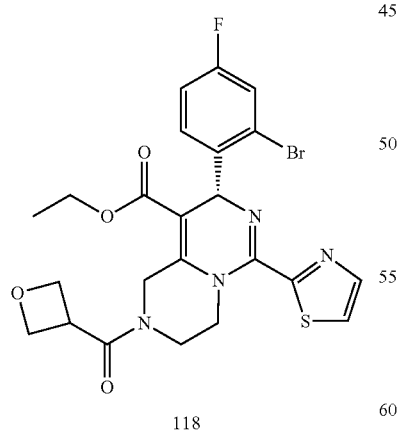

118

Step 1 (Synthesis of 118)

Compound 118-1 (80 mg, 171.9 μmol, 1.0 eq.), 118-2 (35 mg, 343.8 μmol, 2.0 eq.) were dissolved in anhydrous DMF (2 mL), and at 20° C. were sequentially added HATU (130 mg, 343.8 umol, 2.0 eq.), TEA (87 mg, 859.6 umol, 5.0 eq.). After the addition, the mixture was stirred for 2 hours. With TLC showing completion of the reaction, the reaction mixture was quenched with water (10 mL), and extracted with DCM (20 mL) for 3 times. The organic phases were dried over anhydrous sodium sulfate, filtered, and concentrated under reduced pressure. The residue was purified by instrumental separation (aqueous ammonia system), to obtain 22 mg Example 118 as yellow solid, yield: 23%.

NMR data of Example 118: ¹H NMR (400 MHz, CDCl₃) δ: 7.83 (d, J=3.3 Hz, 1H), 7.44-7.40 (m, 1H), 7.37 (dd, J=2.5, 8.3 Hz, 1H), 7.12 (dd, J=6.0, 8.8 Hz, 1H), 6.98 (dt, J=2.5, 8.3 Hz, 1H), 6.19-6.16 (m, 1H), 5.12 (d, J=16.1 Hz, 1H), 5.01-4.79 (m, 6H), 4.25-4.01 (m, 5H), 3.74-3.62 (m, 1H), 1.23-1.12 (m, 3H).

LCMS (ESI) m/z: 551.1 [M+H⁺].

Examples 119, 120

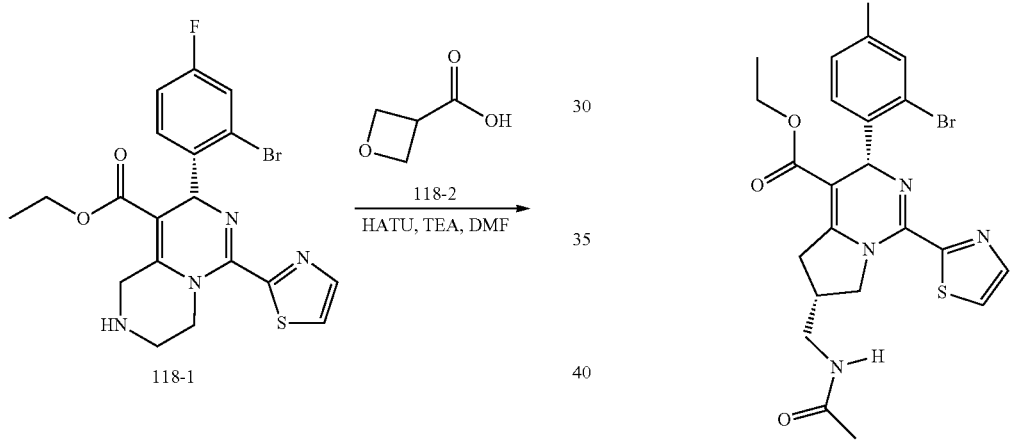

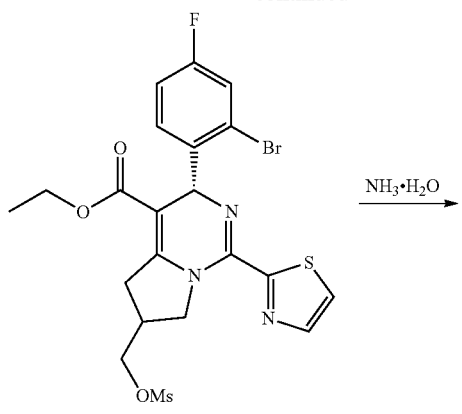

119-1

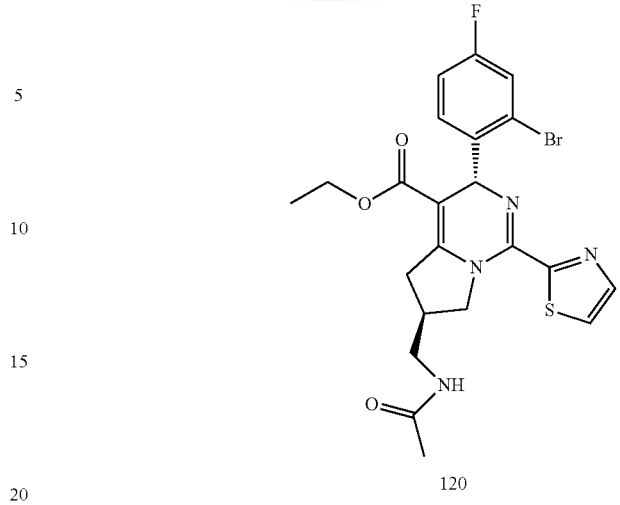

120

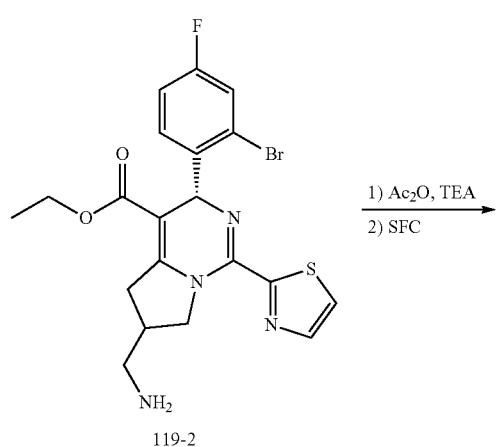

119-2

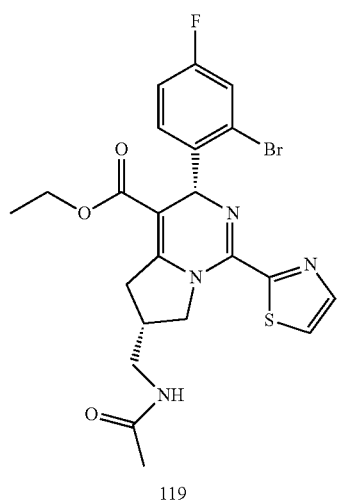

119

Step 1 (Synthesis of 119-2)

Compound 119-1 (100 mg, 179.1 μmol, 1.0 eq.) was dissolved in acetonitrile (4 mL), and $NH_3 \cdot H_2O$ (1 mL), sodium iodide (5 mg, 35.8 μmol, 0.2 Eq.) were sequentially added. After the addition, the mixture reacted at 110° C. in a sealed tube for 5 hours. With detection showing completion of the reaction, the mixture was cooled to room temperature, and concentrated under reduced pressure to obtain 60 mg crude product, and the crude product was directly used in the next reaction.

Step 2 (Synthesis of 119, 120)

Compound 119-1 (60 mg, 125.2 μmol, 1.0 eq.) was dissolved in anhydrous DCM (3 mL), and at 20° C. were sequentially added TEA (126 mg, 1.25 mmol, 10 eq.), $Ac_2O$ (127 mg, 1.25 mmol, 10 eq.). After the addition, the mixture was stirred for 3 hours. With TLC showing completion of the reaction, the reaction mixture was quenched with water (10 mL), and extracted with DCM (20 mL) for 3 times. The organic phases were dried over anhydrous sodium sulfate, filtered, and concentrated under reduced pressure. The residue was purified by instrumental separation to obtain Example 119 (10 mg), Example 120 (44 mg).

NMR data of Example 119: $^1H$ NMR (400 MHz, DMSO-$d_6$) δ: 7.81 (d, J=3.2 Hz, 1H), 7.38 (d, J=3.2 Hz, 1H), 7.33 (dd, J=2.4, 8.0 Hz, 1H), 7.29 (s, 1H), 7.25 (s, 1H), 7.00 (dt, J=2.4, 8.0 Hz, 1H), 6.16 (s, 1H), 5.77 (br. s., 1H), 4.43 (dd, J=7.2, 11.6 Hz, 1H), 4.15 (dd, J=3.2, 11.6 Hz, 1H), 3.98-4.11 (m, 2H), 3.34 (t, J=6.8 Hz, 2H), 3.09-3.29 (m, 1H), 2.72 (dt, J=3.6, 7.2 Hz, 1H), 2.03 (s, 3H), 1.14 (t, J=6.8 Hz, 3H).

LCMS (ESI) m/z: 522.0 [M+H$^+$].

NMR data of Example 120: $^1H$ NMR (400 MHz, DMSO-$d_6$) δ: 7.82 (d, J=3.2 Hz, 1H), 7.39 (d, J=3.2 Hz, 1H), 7.33 (dd, J=2.4, 8.0 Hz, 1H), 7.24 (dd, J=6.4, 8.8 Hz, 1H), 6.97 (dt, J=2.4, 8.0 Hz, 1H), 6.15 (s, 1H), 5.82 (br. s., 1H), 4.41 (dd, J=7.2, 11.2 Hz, 1H), 3.96-4.20 (m, 3H), 3.52 (dd, J=7.6, 18.0 Hz, 1H), 3.42 (t, J=6.8 Hz, 2H), 2.80-2.92 (m, 1H), 2.69-2.79 (m, 1H), 2.03 (s, 3H), 1.15 (t, J=7.2 Hz, 3H).

LCMS (ESI) m/z: 522.0 [M+H$^+$].

423
Examples 121, 122

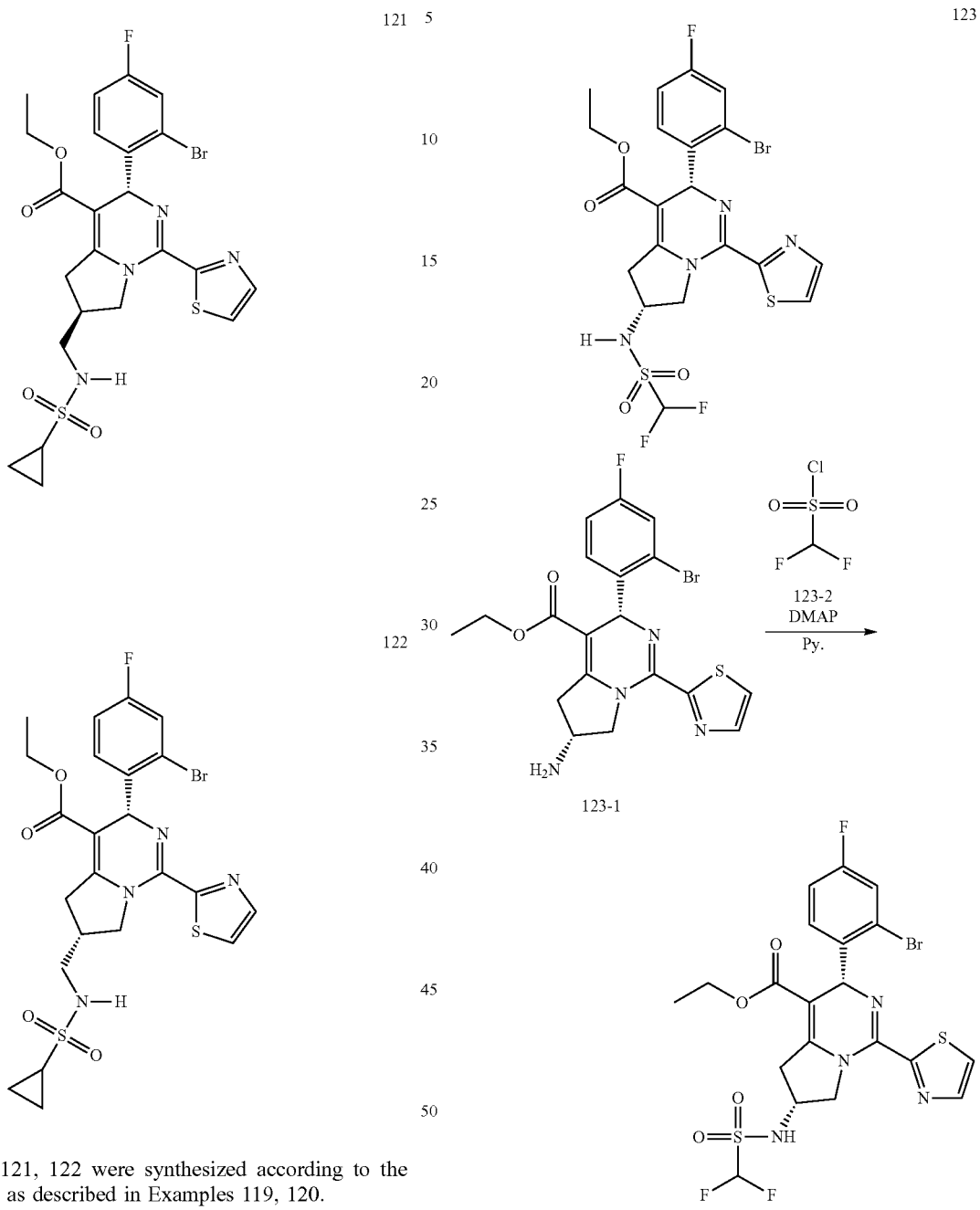

Examples 121, 122 were synthesized according to the same method as described in Examples 119, 120.

The mass-to-charge ratio of Example 121: LCMS (ESI) m/z: 583.1 [M+H$^+$].

NMR data of Example 122: $^1$H NMR (400 MHz, DMSO-d$_6$) δ: 07.82 (d, J=3.2 Hz, 1H), 7.39 (d, J=3.2 Hz, 1H), 7.33 (dd, J=2.4, 8.4 Hz, 1H), 7.24 (dd, J=6.0, 8.4 Hz, 1H), 6.98 (dt, J=2.4, 8.4 Hz, 1H), 6.16 (s, 1H), 4.73 (t, J=6.4 Hz, 1H), 4.42 (dd, J=7.2, 11.2 Hz, 1H), 4.24 (dd, J=7.6, 11.6 Hz, 1H), 4.06 (dq, J=4.0, 7.2 Hz, 2H), 3.52 (dd, J=7.6, 18.0 Hz, 1H), 3.33-3.43 (m, 1H), 3.21-3.32 (m, 1H), 2.92 (dd, J=8.0, 18.0 Hz, 1H), 2.74 (quin, J=7.2 Hz, 1H), 2.38-2.52 (m, 1H), 1.20 (d, J=3.6 Hz, 2H), 1.15 (t, J=7.2 Hz, 3H), 0.96-1.09 (m, 2H).

LCMS (ESI) m/z: 582.9 [M+H$^+$].

424
Example 123

Step 1 (Synthesis of 123)

Compound 123-1 (20 mg, 42.98 μmol, 1.0 eq.) was dissolved in anhydrous pyridine (0.5 mL), and at 20° C. were sequentially added DMAP (10.5 mg, 85.96 μmol, 2.0 eq.), 123-2 (9.7 mg, 64.5 μmol, 1.5 eq.). After the addition, the mixture was stirred for 0.5 hour. With TLC showing completion of the reaction, the reaction mixture was quenched with water (5 mL), and extracted with EtOAc (10 mL) for 3 times. The organic phases were dried over anhydrous sodium sulfate, filtered, and concentrated under reduced pressure. The residue was purified by a preparative plate, to obtain 2.8 mg product, yield: 11%.

NMR data of Example 123: $^1$H NMR (400 MHz, CDCl3) δ: 7.83 (d, J=3.51 Hz, 1H), 7.40 (d, J=3.01 Hz, 1H), 7.34 (dd, J=2.51, 8.03 Hz, 1H), 7.29 (br. s., 1H), 6.99 (dt, J=2.51, 8.03 Hz, 1H), 6.18 (s, 1H), 6.11-6.40 (m, 1H), 5.31 (br. s., 1H), 4.59-4.71 (m, 1H), 4.43-4.53 (m, 2H), 4.03-4.12 (m, 2H), 3.59 (d, J=19.07 Hz, 1H), 3.40 (dd, J=6.53, 18.57 Hz, 1H), 1.16 (t, J=7.03 Hz, 3H).

LCMS (ESI) m/z: 581.0 [M+H$^+$].

Examples 124, 125, 126, 128, 129, 130, 132, 137, 138, 140, 141, 144, 145, 148, 149, 150, 151, 153, 154, 155, 156, 158, 159, 160, 162, 163, 164, 165, 167, 168, 170, 172, 173, 174, 175 were synthesized according to the same method as described in Example 123.

Example 124

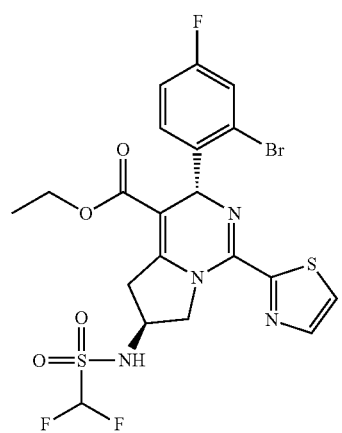

124

NMR data of Example 124: $^1$H NMR (400 MHz, CDCl3) δ: 7.83 (d, J=3.6 Hz, 1H), 7.41 (d, J=3.6 Hz, 1H), 7.33 (dd, J=2.6, 8.4 Hz, 1H), 7.23 (dd, J=6.0, 8.4 Hz, 1H), 6.99 (dt, J=2.6, 8.4 Hz, 1H), 6.15 (s, 1H), 6.11-6.42 (m, 1H), 5.70 (br. s., 1H), 4.53-4.62 (m, 1H), 4.39-4.53 (m, 2H), 4.00-4.10 (m, 2H), 3.69 (dd, J=7.2, 18.2 Hz, 1H), 3.27 (dd, J=6.0, 18.2 Hz, 1H), 1.13 (t, J=7.2 Hz, 3H).

LCMS (ESI) m/z: 581.0 [M+H$^+$].

Example 125

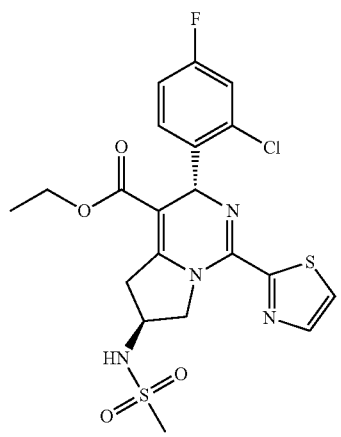

125

NMR data of Example 125: 1H NMR (400 MHz, CDCl3) δ: 7.84 (d, J=3.2 Hz, 1H), 7.41 (d, J=3.0 Hz, 1H), 7.24-7.28 (m, 1H), 7.15 (dd, J=2.6, 8.4 Hz, 1H), 6.96 (dt, J=2.6, 8.4 Hz, 1H), 6.19 (s, 1H), 4.76 (d, J=7.6 Hz, 1H), 4.47-4.60 (m, 2H), 4.32 (sxt, J=6.8 Hz, 1H), 4.07 (q, J=7.0 Hz, 2H), 3.68 (dd, J=7.2, 18.0 Hz, 1H), 3.19 (dd, J=6.4, 18.0 Hz, 1H), 3.09 (s, 3H), 1.15 (t, J=7.2 Hz, 3H).

LCMS (ESI) m/z: 499.2 [M+H$^+$].

Example 126

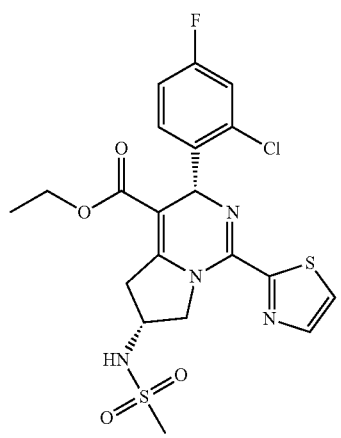

126

NMR data of Example 126: 1H NMR (400 MHz, CDCl3) δ: 7.84 (d, J=3.0 Hz, 1H), 7.41 (d, J=3.2 Hz, 1H), 7.33 (dd, J=6.2, 8.6 Hz, 1H), 7.16 (dd, J=2.6, 8.6 Hz, 1H), 6.98 (dt, J=2.6, 8.2 Hz, 1H), 6.20 (s, 1H), 4.72 (d, J=6.2 Hz, 1H), 4.57-4.65 (m, 1H), 4.45-4.54 (m, 1H), 4.29-4.40 (m, 1H), 4.08 (q, J=7.2 Hz, 2H), 3.47-3.56 (m, 1H), 3.32-3.43 (m, 1H), 3.08 (s, 3H), 1.17 (t, J=7.2 Hz, 3H).

LCMS (ESI) m/z: 521.2 [M+Na$^+$].

Example 127

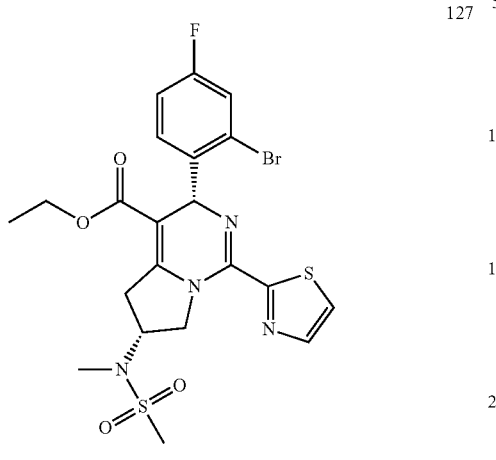

Example 127 was synthesized according to the same method as described in Example 123.

NMR data of Example 127: $^1$H NMR (400 MHz, CDCl$_3$-d$_6$) δ: 7.97 (d, J=2.5 Hz, 1H), 7.65 (br. s., 1H), 7.43-7.37 (m, 1H), 7.34 (dd, J=2.4, 8.2 Hz, 1H), 7.05-6.95 (m, 1H), 6.29 (s, 1H), 4.82 (br. s., 2H), 4.41 (d, J=8.8 Hz, 1H), 4.08 (q, J=7.2 Hz, 2H), 3.59-3.43 (m, 2H), 2.93 (d, J=4.5 Hz, 6H), 1.15 (t, J=7.2 Hz, 3H) LCMS (ESI) m/z: 559.0 [M+H$^+$].

Example 128

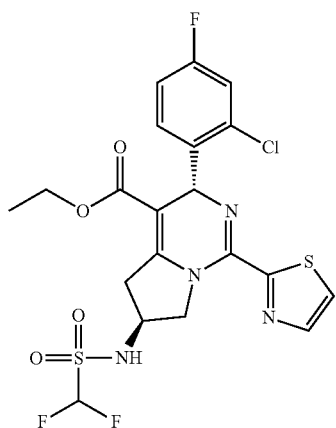

NMR data of Example 128: $^1$H NMR (400 MHz, DMSO-d$_6$) δ: ☐ 7.85 (d, J=3.2 Hz, 1H), 7.42 (d, J=3.2 Hz, 1H), 7.23-7.28 (m, 1H), 7.15 (dd, J=2.6, 8.6 Hz, 1H), 6.96 (dt, J=2.6, 8.2 Hz, 1H), 6.18 (s, 1H), 6.12-6.43 (m, 1H), 4.39-4.64 (m, 3H), 4.01-4.12 (m, 2H), 3.70 (dd, J=7.2, 18.2 Hz, 1H), 3.28 (dd, J=6.2, 18.2 Hz, 1H), 1.15 (t, J=7.2 Hz, 3H).

LCMS (ESI) m/z: 535.1 [M+H$^+$].

Example 129

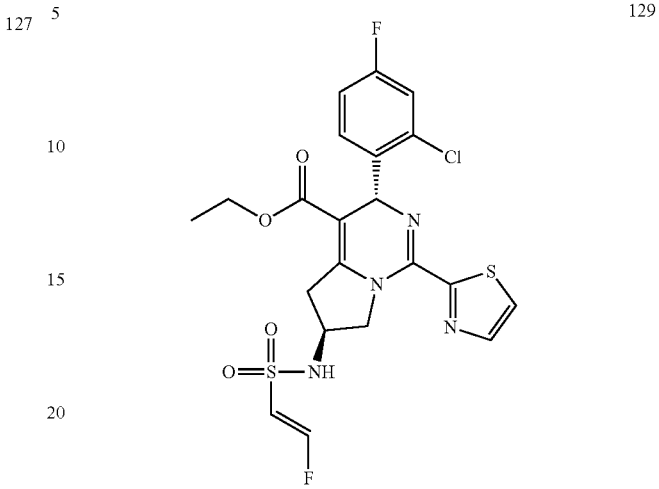

NMR data of Example 129: $^1$H NMR (400 MHz, CDCl3) δ: 7.82 (d, J=3.2 Hz, 1H), 7.45 (dd, J=8.8, 12.8 Hz, 1H), 7.41 (d, J=3.0 Hz, 1H), 7.25 (dd, J=6.0, 8.6 Hz, 1H), 7.16 (dd, J=2.6, 8.6 Hz, 1H), 6.96 (dt, J=2.6, 8.2 Hz, 1H), 6.15 (s, 2H), 5.19 (br. s., 1H), 4.82 (d, J=11.6 Hz, 1H), 4.29-4.42 (m, 1H), 3.93-4.16 (m, 3H), 3.37-3.56 (m, 2H), 1.15 (t, J=7.2 Hz, 3H).

LCMS (ESI) m/z: 529.1 [M+H$^+$].

Example 130

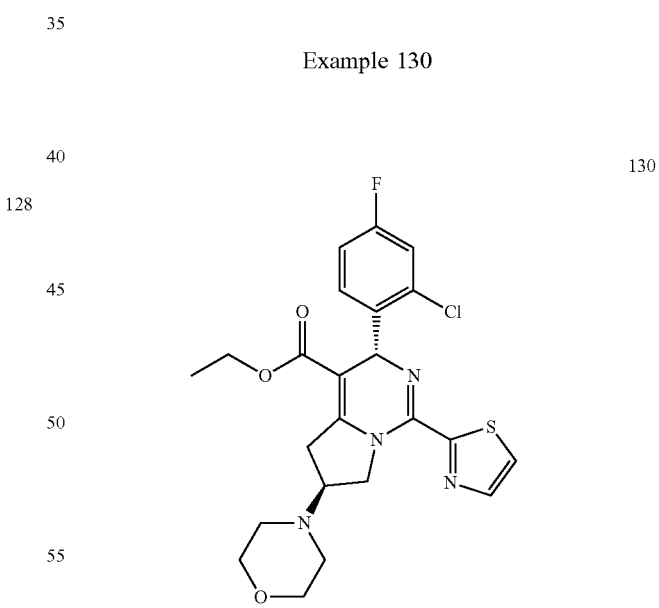

NMR data of Example 130: $^1$H NMR (400 MHz, CDCl3) δ: 7.83 (br. s., 1H), 7.40 (br. s., 1H), 7.33 (dd, J=2.6, 8.6 Hz, 1H), 7.25 (d, J=6.0 Hz, 1H), 6.98 (dt, J=2.6, 8.2 Hz, 1H), 6.15 (s, 1H), 4.57 (dd, J=7.0, 11.0 Hz, 1H), 3.97-4.18 (m, 3H), 3.77 (t, J=4.6 Hz, 4H), 3.66 (dd, J=7.2, 17.2 Hz, 1H), 3.15 (quin, J=7.9 Hz, 1H), 2.96 (dd, J=9.2, 17.2 Hz, 1H), 2.42-2.68 (m, 4H), 1.14 (t, J=7.2 Hz, 3H).

LCMS (ESI) m/z: 491.0 [M+H$^+$].

Example 131

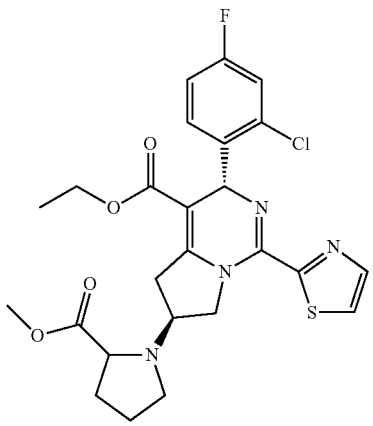

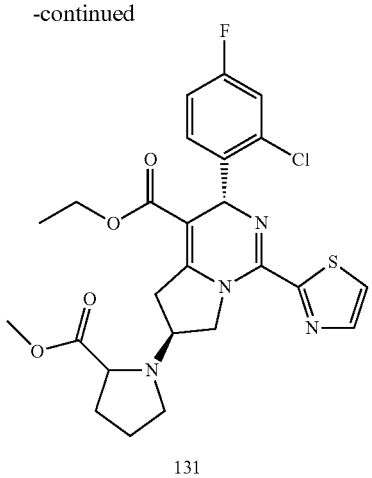

131

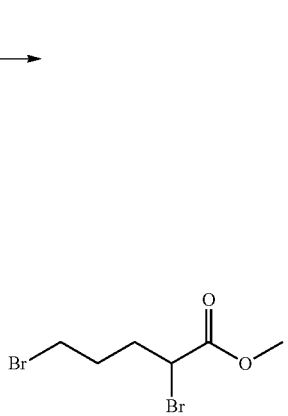

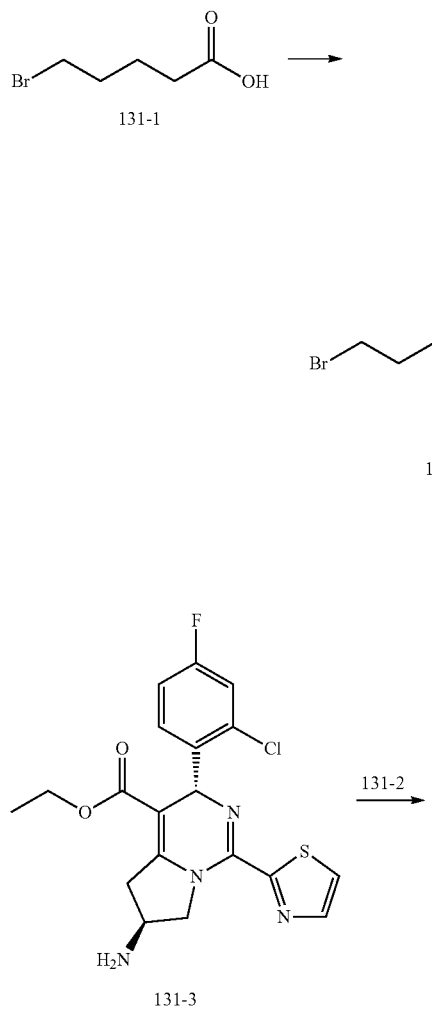

Step 1 (Synthesis of 131-2)

In a dry three-necked flask, compound 131-1 (18.00 g, 99.43 mmol, 1.0 eq.) was dissolved in thionyl chloride (59.15 g, 497.15 mmol, 5.0 eq.), and the mixture was warmed to 80° C., stirred for 1 hour, and then cooled to 50° C. $Br_2$ (31.78 g, 198.8 mmol, 2.0 eq.) was added into the reaction mixture, at 50° C. was stirred the mixture for 40 hours. The reaction mixture was cooled to 30° C., and anhydrous methanol (40 mL) was carefully added, then the mixture was heated up 50° C. and continued stirring for 1 hour. The reaction mixture was cooled to 25° C., and concentrated under reduced pressure. The residue was dissolved with EtOAc, and washed with saturated sodium sulfite. The organic phase was washed with saturated brine, dried over anhydrous sodium sulfate, filtered, and concentrated under reduced pressure to obtain 20 g crude product as yellow oil. The crude product was directly used in the next reaction.

$^1$H NMR (400 MHz, CDCl3) δ: 4.28 (q, J=6.0 Hz, 2H), 3.80 (s, 3H), 3.43 (t, J=6.0 Hz, 2H), 1.95-2.26 (m, 3H)

Step 2 (Synthesis of 131)

Compound 131-3 (80 mg, 190.1 μmol, 1.0 eq.) was dissolved in acetonitrile (2 mL), and at 0° C. were slowly and sequentially added 131-2 (52.1 mg, 190.1 μmol, 1.0 eq.), potassium carbonate (138 mg, 998.4 μmol, 5.25 eq.). After the addition, the reaction mixture was swept with nitrogen for 3 times, warmed to 85° C., and stirred for 24 hours. With TLC showing completion of the reaction, the reaction mixture was cooled to room temperature, filtered, and concentrated under reduced pressure. The residue was purified by instrumental separation (HCl system) to obtain the target product.

NMR data of Example 131: $^1$H NMR (400 MHz, DMSO-$d_6$) δ: 8.30 (s, 2H), 7.82 (dd, J=5.90, 8.66 Hz, 1H), 7.36 (dd, J=1.25, 8.53 Hz, 1H), 7.23 (dt, J=2.26, 8.28 Hz, 1H), 6.39 (d, J=10.79 Hz, 1H), 4.91-5.02 (m, 1H), 4.64-4.82 (m, 3H), 4.12-4.20 (m, 2H), 3.87-4.00 (m, 3H), 3.84 (s, 2H), 3.69-3.81 (m, 1H), 3.53 (dd, J=8.66, 17.94 Hz, 1H), 2.63 (dd, J=8.28, 13.05 Hz, 1H), 2.21-2.41 (m, 2H), 2.06-2.17 (m, 1H), 1.16 (dt, J=4.77, 7.03 Hz, 3H).

LCMS (ESI) m/z: 533.1 [M+H$^+$].

Example 132

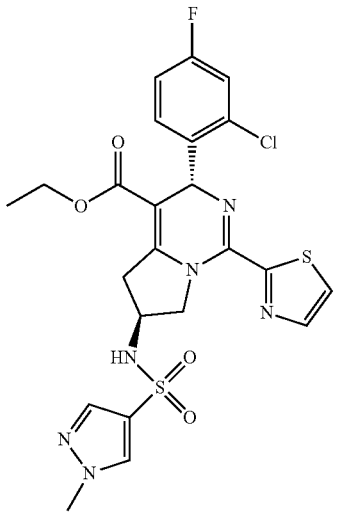

NMR data of Example 132: ¹H NMR (400 MHz, DMSO-d6) δ: 8.30 (s, 1H), 8.00 (br. s., 1H), 7.94 (d, J=3.2 Hz, 1H), 7.86 (d, J=3.0 Hz, 1H), 7.36-7.50 (m, 2H) 7.79 (s, 1H), 7.15 (td, J=8.4, 2.6 Hz, 1H), 6.00 (s, 1H), 4.36 (dd, J=11.2, 6.8 Hz, 1H), 4.09-4.21 (m, 1H), 3.86-4.04 (m, 7H), 3.02 (dd, J=17.8, 6.2 Hz, 1H), 1.04 (t, J=7.0 Hz, 3H).

LCMS (ESI) m/z: 565.1 [M+H⁺].

Example 133

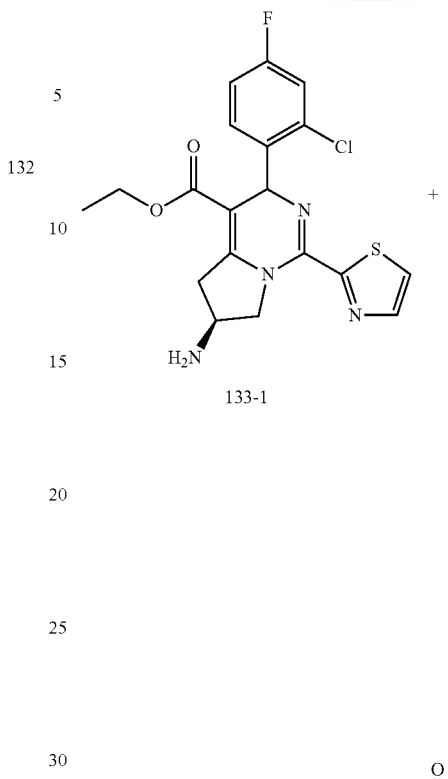

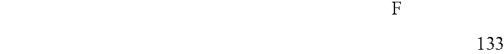

Compound 133-2 (13.69 mg, 142.56 μmol, 1.2 eq.) was dissolved in DCM (2 mL), and at 28° C. was slowly added CDI (38.53 mg, 237.60 μmol, 2.0 eq.). The mixture was stirred for 10 minutes. To the reaction mixture was added a solution of 133-1 (50 mg, 118.80 μmol, 1.0 eq.) in DCM (1 mL). The reaction mixture was further stirred for 20 minutes. With TLC showing completion of the reaction, the reaction mixture was concentrated under reduced pressure. The residue was purified by instrumental separation (formic acid system) and the target product Example 133 (12 mg, yield: 20%) may be obtained.

NMR data of Example 133: ¹H NMR (400 MHz, CDCl3) δ: 7.84 (d, J=3.26 Hz, 1H), 7.42 (d, J=3.01 Hz, 1H), 7.30 (d, J=12.00 Hz, 1H), 7.15 (dd, J=2.51, 8.53 Hz, 1H), 6.96 (dt, J=2.64, 8.22 Hz, 1H), 6.77 (d, J=6.53 Hz, 1H), 6.21 (s, 1H), 5.95 (t, J=52.0 Hz 1H), 4.71-4.82 (m, 1H), 4.54 (d, J=5.77 Hz, 2H), 4.07 (q, J=7.19 Hz, 2H), 3.66 (dd, J=7.53, 18.32 Hz, 1H), 3.26 (dd, J=5.77, 18.32 Hz, 1H), 1.15 (t, J=7.15 Hz, 3H) LCMS (ESI) m/z: 499.2 [M+H⁺].

Examples 139, 142 were synthesized according to the same method as described in Example 133.

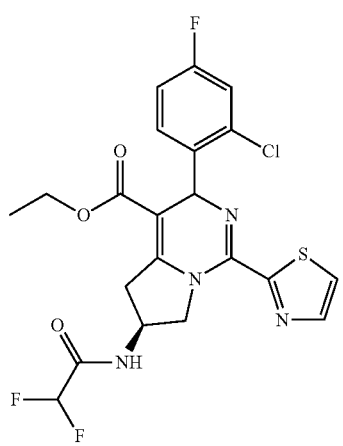

Examples 134, 135, 136
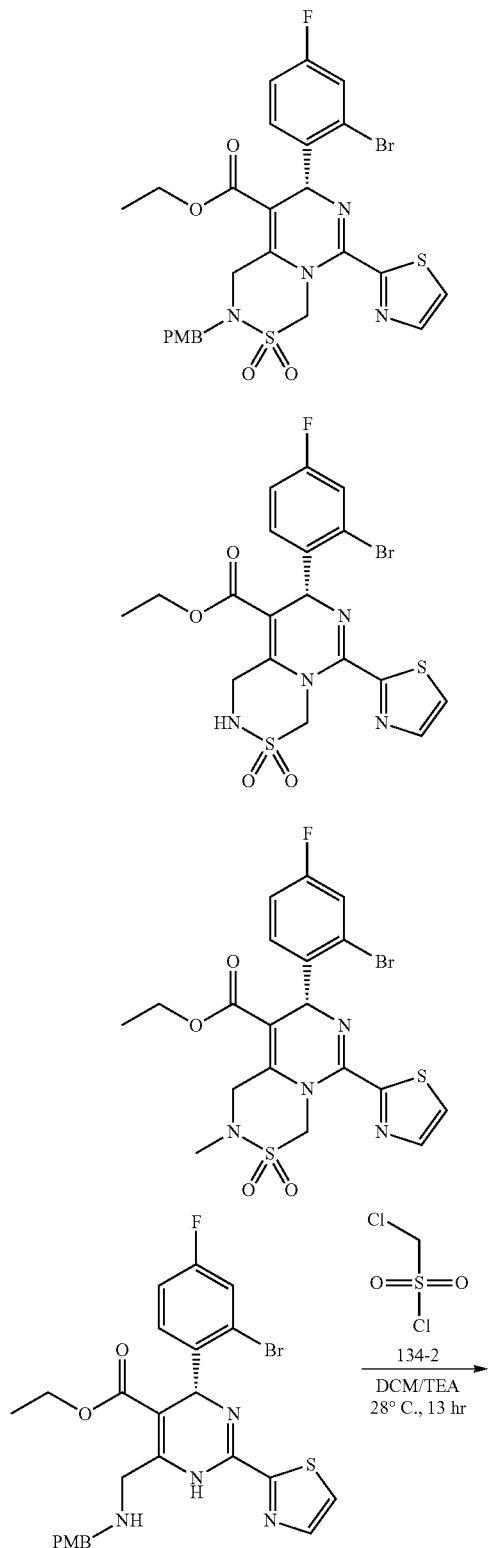
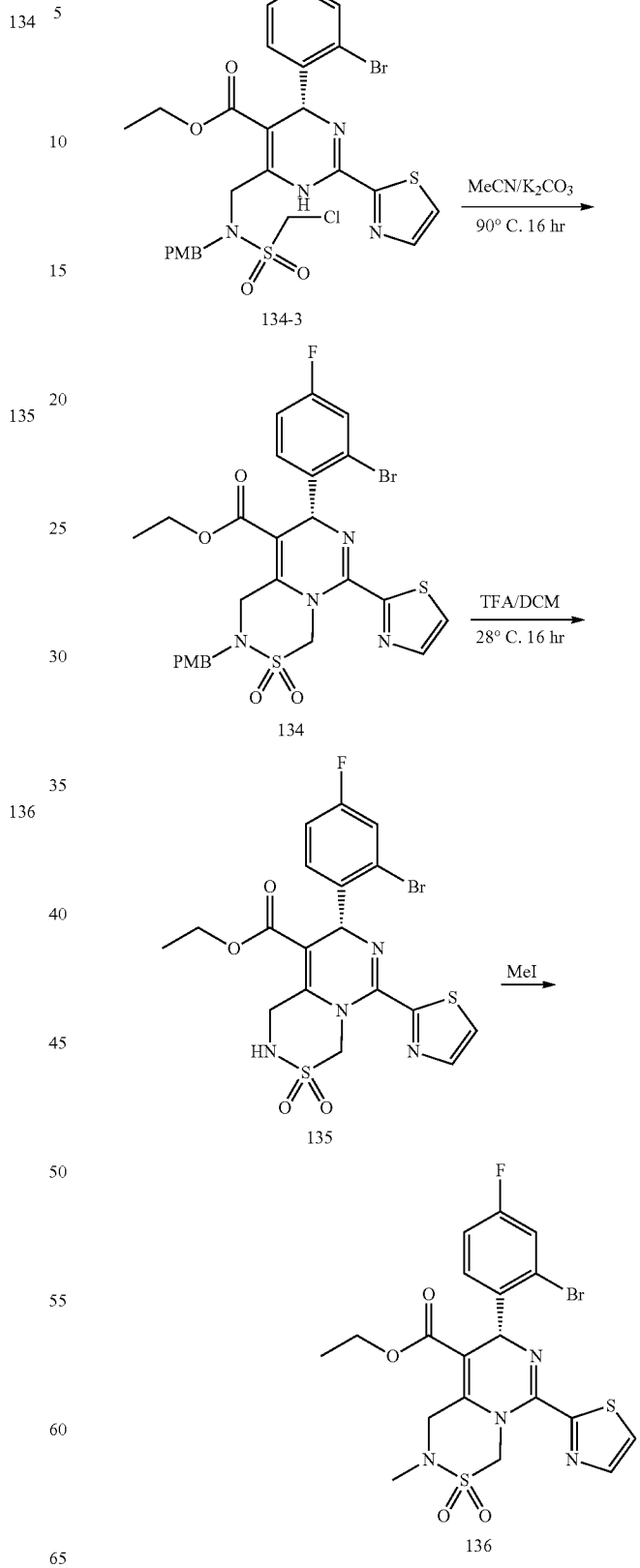

Step 1 (Synthesis of 134-3)

Compound 134-1 (700 mg, 1.25 mmol, 1.0 eq.), TEA (379 mg, 3.75 mmol, 3.0 eq.) were dissolved in anhydrous DCM (15 mL), and at 28° C. was slowly added 134-2 (372 mg, 2.5 mmol, 2 eq.). After the addition, the reaction mixture was swept with nitrogen for 3 times, stirred for 30 minutes. With TLC showing completion of the reaction, the reaction mixture was washed with water (10 mL), and then extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=50:1-3:1, to obtain 680 mg yellow solid, yield: 81%.

LCMS (ESI) m/z: 672.8[M+H$^+$].

Step 2 (Synthesis of Example 134)

Compound 134-3 (680 mg, 1.01 mmol, 1.0 eq.) was dissolved in acetonitrile (10 mL), and at 28° C. was slowly added potassium carbonate (700 mg, 5.07 mmol, 5 eq.). After the addition, the reaction mixture was swept with nitrogent for 3 times, and then warmed to 90° C., and stirred for 16 hours. With TLC showing completion of the reaction, the reaction mixture was cooled to room temperature, and filtered. The filtrate was concentrated. The residue was washed with water (10 mL), and then extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=30:1-4:1, to obtain 522 mg yellow solid, yield: 81%.

MS data of Example 134: LCMS (ESI) m/z: 659.1[M+H$^+$].

Step 3 (Synthesis of Example 135)

Compound 134 (522 mg, 824.2 μmol, 1.0 eq.) was dissolved in anhydrous DCM (5 mL), and at 28° C. was slowly added TFA (4.8 g, 42.1 mmol, 51 eq.). After the addition, the reaction mixture was swept with nitrogen for 3 times, and stirred for 72 hours at this temperature. With LCMS showing completion of the reaction, the reaction mixture was cooled to room temperature, and concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 105 mg yellow solid, yield: 20%.

NMR data of Example 135: $^1$H NMR (400 MHz, CDCl3) •δ: •7.90 (d, J=2.76 Hz, 1H), 7.45 (d, J=2.51 Hz, 1H), 7.40 (d, J=7.78 Hz, 1H), 7.18-7.26 (m, 1H), 7.05 (d, J=13.55 Hz, 2H), 6.24 (s, 1H), 5.48 (dd, J=4.27, 18.32 Hz, 1H), 4.86 (d, J=14.31 Hz, 1H), 4.76 (dd, J=4.39, 10.67 Hz, 1H), 4.49 (dd, J=11.17, 18.20 Hz, 1H), 4.05-4.20 (m, 2H), 1.18 (t, J=7.03 Hz, 3H)

LCMS (ESI) m/z: 517.0 [M+H$^+$].

Step 4 (Synthesis of 136)

Compound 135 (170 mg, 329.8 μmol, 1.0 eq.), potassium carbonate (136.8 mg, 989.5 μmol, 5 eq.) were dissolved in anhydrous DMF (10 mL), and at 28° C. was slowly added iodomethane (234 mg, 1.65 mmol, 5.0 eq). After the addition, the reaction mixture was with swept with nitrogen for 3 times, and stirred for 30 minutes at this temperature. With LCMS showing completion of the reaction, the reaction mixture was filtered. The filtrate was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 120 mg Example 136 as yellow solid, yield: 98%.

NMR data of Example 136: $^1$H NMR (400 MHz, CDCl3) •δ: •7.91 (d, J=3.26 Hz, 1H), 7.45 (d, J=3.26 Hz, 1H), 7.40 (dd, J=2.51, 8.28 Hz, 1H), 7.23-7.28 (m, 1H), 7.04 (dt, J=2.51, 8.16 Hz, 1H), 6.98 (d, J=14.05 Hz, 1H), 6.25 (s, 1H), 5.32 (d, J=17.57 Hz, 1H), 4.92 (d, J=14.05 Hz, 1H), 4.76 (d, J=17.57 Hz, 1H), 4.01-4.25 (m, 2H), 2.97 (s, 3H), 1.19 (t, J=7.15 Hz, 3H).

LCMS (ESI) m/z: 531.1[M+H$^+$].

Example 137

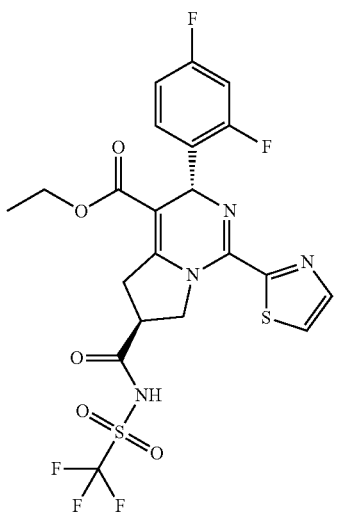

NMR data of Example 137: $^1$H NMR (400 MHz, CDCl$_3$) δ: 7.86 (d, J=3.2 Hz, 1H), 7.43 (d, J=3.2 Hz, 1H), 7.32-7.40 (m, 1H), 6.77-6.88 (m, 2H), 5.94 (s, 1H), 4.63-4.70 (m, 1H), 4.43-4.51 (m, 2H), 4.10 (q, J=7.0 Hz, 2H), 3.48-3.56 (m, 1H), 3.25-3.34 (m, 1H), 1.20 (t, J=7.0 Hz, 3H).

LCMS (ESI) m/z: 565.2 [M+H$^+$].

Example 138

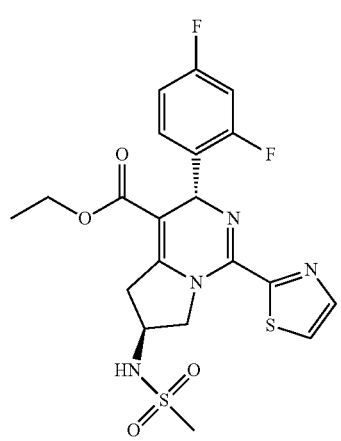

NMR data of Example 138: ¹H NMR (400 MHz, CDCl$_3$) δ: 8.09 (br. s., 1H), 7.92 (br. s., 1H), 7.71 (br. s., 1H), 6.80 (d, J=8.8 Hz, 2H), 6.50 (br. s., 1H), 6.15 (br. s., 1H), 4.79 (br. s., 1H), 4.31-4.67 (m, 2H), 4.15 (d, J=6.2 Hz, 2H), 3.72 (d, J=14.6 Hz, 1H), 3.42 (br. s., 1H), 3.02 (br. s., 3H), 1.15-1.28 (m, 3H).

LCMS (ESI) m/z: 483.1 [M+H⁺].

Example 139

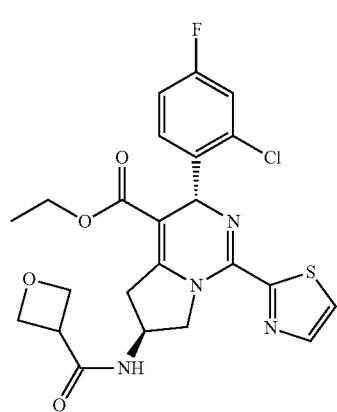

NMR data of Example 139: ¹H NMR (400 MHz, CDCl3) δ: □ 7.86 (d, J=3.26 Hz, 1H), 7.42 (d, J=3.01 Hz, 1H), 7.32 (d, J=12.00 Hz, 1H), 7.17 (dd, J=2.51, 8.53 Hz, 1H), 6.96 (dt, J=2.64, 8.22 Hz, 1H), 6.77 (d, J=6.53 Hz, 1H), 6.21 (s, 1H), 5.09 (d, J=5.80 Hz 2H), 4.84 (d, J=5.80 Hz 2H), 4.71-4.82 (m, 1H), 4.55 (d, J=5.77 Hz, 2H), 4.09 (q, J=7.19 Hz, 2H), 3.66 (m, 18.32 Hz, 2H), 3.28 (dd, J=5.77, 18.32 Hz, 1H), 1.17 (t, J=7.15 Hz, 3H)

LCMS (ESI) m/z: 505.2 [M+H⁺].

Example 140

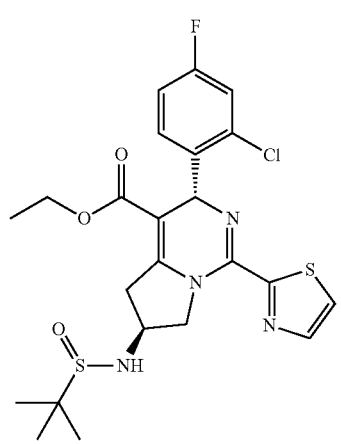

NMR data of Example 140: ¹H NMR (400 MHz, CDCl3) δ: 8.14 (s, 1H), 8.02 (s, 1H), 7.60 (s, 1H), 7.13 (d, J=7.6 Hz, 1H), 7.02 (s, 1H), 6.31 (s, 1H), 4.95 (s, 1H), 4.68 (s, 1H), 4.46 (s, 1H), 4.15-4.06 (m, 2H), 3.98-3.93 (m, 1H), 3.67 (s, 2H), 1.21 (s, 12H).

LCMS (ESI) m/z: 525.3 [M+H⁺].

Example 141

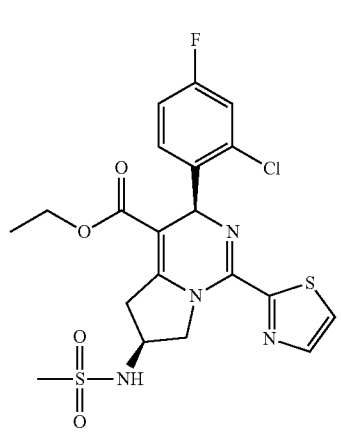

NMR data of Example 141: ¹H NMR (400 MHz, CDCl3) δ: 7.99 (s, 1H), 7.77-7.70 (m, 2H), 7.10-7.08 (d, J=8.0 Hz, 1H), 6.95 (s, 1H), 6.84 (s, 1H), 6.28 (s, 1H), 4.66-4.60 (m, 2H), 4.35 (s, 1H), 4.12-4.10 (m, 1H), 3.75-3.71 (m, 1H), 3.40 (s, 1H), 3.02 (s, 3H), 1.20-1.17 (s, 3H).

LCMS (ESI) m/z: 499.2 [M+H¹].

Example 142

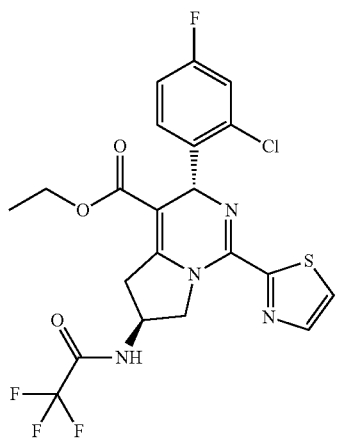

142

NMR data of Example 142: ¹H NMR (400 MHz, CDCl3) δ=8.98 (s, 1H), 8.01 (s, 1H), 7.73 (d, 1H), 7.41 (s, 1H), 7.16 (d, J=7.6, 1H), 7.01 (s, 1H), 6.27 (s, 1H), 4.86-4.79 (m, 2H), 4.46 (s, 1H), 4.14 (m, 2H), 3.58 (s, 2H), 1.20-1.14 (m, 3H).

LCMS m/z: 517.1 [M+1].

Example 143

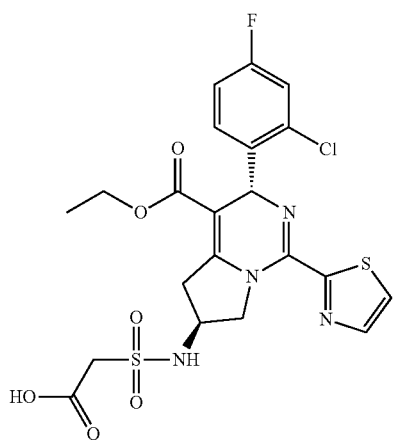

143

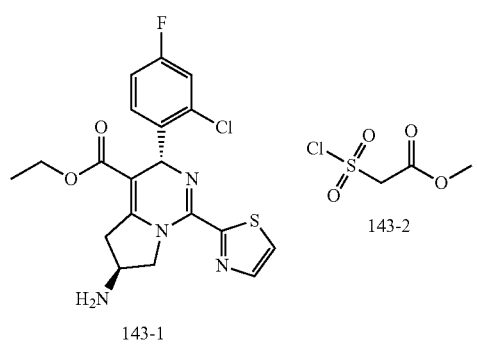

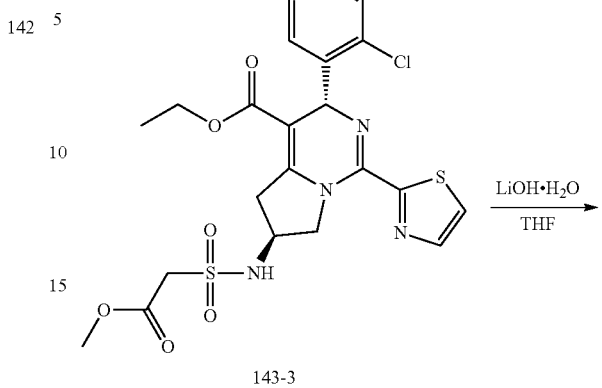

143-3

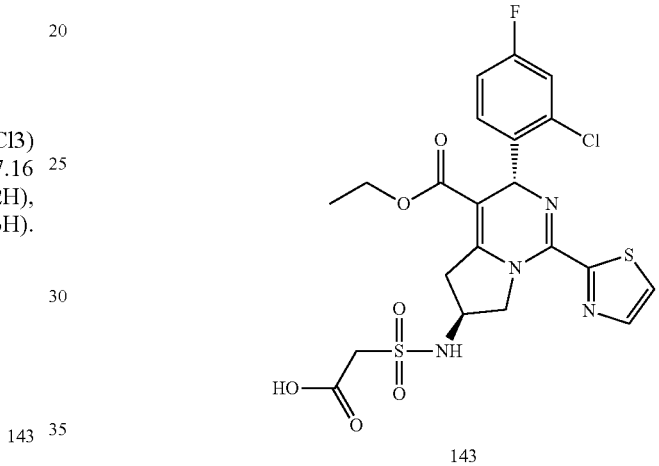

143

Step 1 Synthesis of (143-3)

Compound 143-1 (80 mg, 190.1 μmol, 1.0 eq.), TEA (57.70 mg, 570.2 μmol, 3.0 eq.) were dissolved in anhydrous DCM (3 mL), and at 25° C. was slowly added 143-2 (65.6 mg, 380.1 μmol, 2.0 eq.). After the addition, the reaction mixture was swept with nitrogen for 3 times, and stirred for 16 hours at this temperature. With LCMS showing completion of the reaction, the reaction mixture was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 25 mg yellow solid, yield: 24%.

LCMS (ESI) m/z: 556.8 [M+H⁺].

Step 2 Synthesis of (Example 143)

Compound 143-3 (25 mg, 44.9 μmol, 1.0 eq.), lithium hydroxide monohydrate (18 mg, 448.8 μmol, 10 eq.) were successively dissolved in a mixed solution of THF (1 mL) and H₂O (1 mL), at 25° C. was stirred the mixture for 1 hour. With LCMS showing completion of the reaction, the reaction mixture was concentrated. The residue was adjusted with diluted HCl to pH=1, washed with water (10 mL), and extracted with DCM (20 mL) for 3 times. The organic phases were washed with saturated brine, dried over anhydrous sodium sulfate, filtered, and concentrated under reduced pressure. The residue was purified by instrumental separation (HCl system), to obtain 19 mg yellow solid, yield: 80%.

MS data of Example 143: LCMS (ESI) m/z: 543.1 [M+H⁺].

Example 144

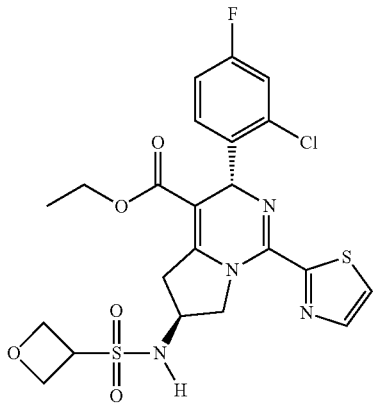

Example 144 was synthesized according to the same method as described in Example 123.

NMR data of Example 144: ¹H NMR (400 MHz, CDCl3-d) δ: 7.84 (d, J=3.01 Hz, 1H), 7.41 (d, J=3.01 Hz, 1H), 7.21-7.25 (m, 1H), 7.13 (dd, J=2.26, 8.78 Hz, 1H), 6.94 (dt, J=2.51, 8.28 Hz, 1H), 6.17 (s, 1H), 5.06 (d, J=8.03 Hz, 1H), 4.87-4.95 (m, 4H), 4.44-4.57 (m, 3H), 4.27-4.37 (m, 1H), 4.05 (q, J=7.03 Hz, 2H), 3.63 (dd, J=7.03, 18.07 Hz, 1H), 3.18 (dd, J=6.02, 18.07 Hz, 1H), 1.13 (t, J=7.03 Hz, 3H).

LCMS (ESI) m/z: 541.3 [M+H⁺].

Example 145

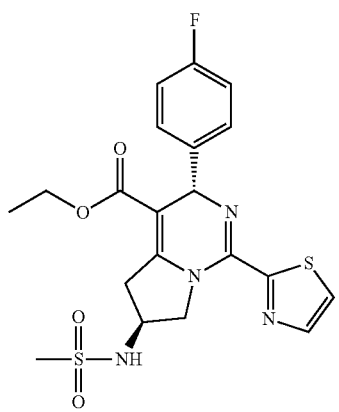

Example 145 was synthesized according to the same method as described in Example 123.

NMR data of Example 145: ¹H NMR (400 MHz, CDCl3) δ: 7.87 (d, J=3.2 Hz, 1H), 7.44 (d, J=3.2 Hz, 1H), 7.37 (dd, J=5.6, 8.4 Hz, 2H), 7.02 (t, J=8.4 Hz, 2H), 5.84 (s, 1H), 4.65-4.46 (m, 3H), 4.34 (d, J=5.2 Hz, 1H), 4.17 (q, J=6.8 Hz, 2H), 3.49-3.40 (m, 1H), 3.36-3.27 (m, 1H), 3.04 (s, 3H), 1.26 (t, J=7.2 Hz, 3H).

LCMS (ESI) m/z: 465.2 [M+H⁺].

Example 146

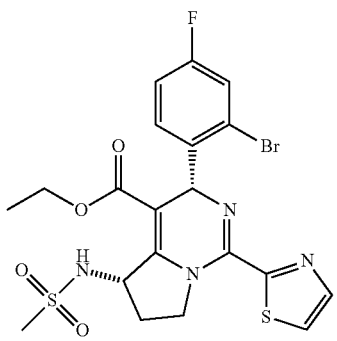

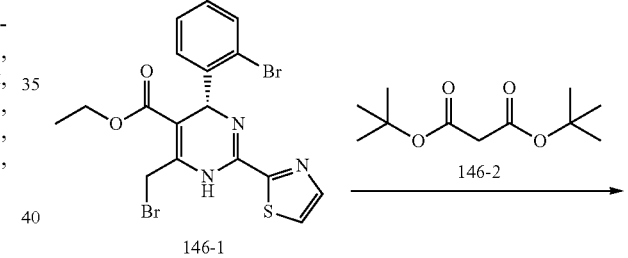

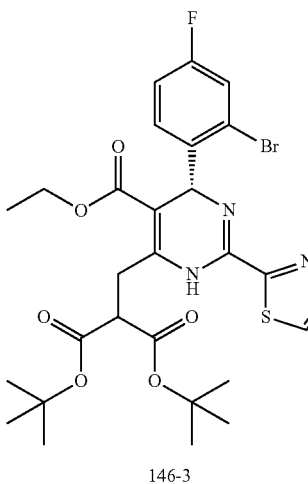

443
-continued
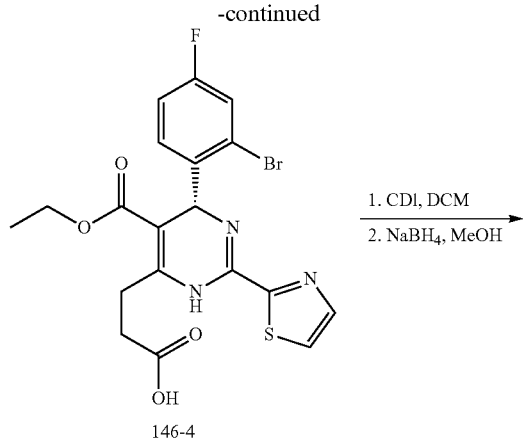
146-4
1. CDl, DCM
2. NaBH4, MeOH
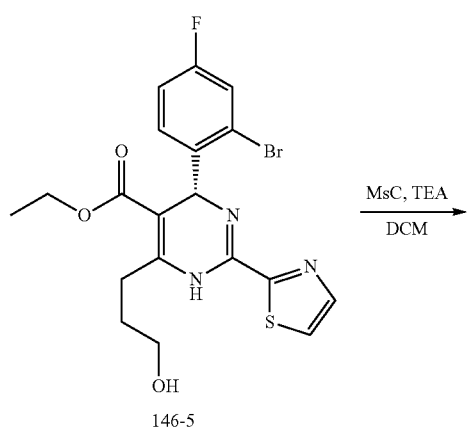
146-5
MsC, TEA
DCM
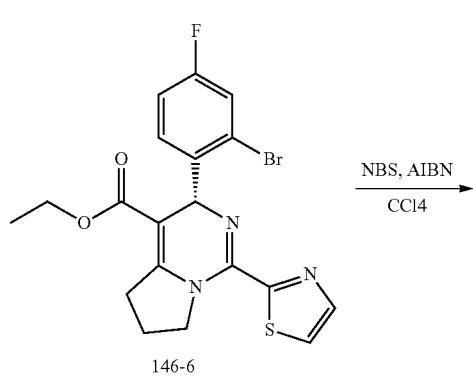
146-6
NBS, AIBN
CCl4
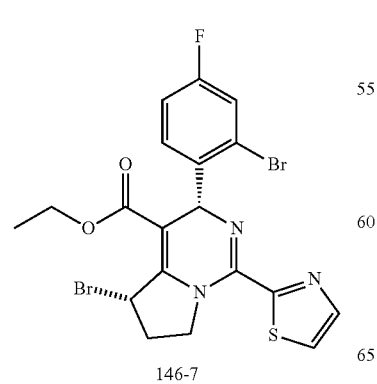
146-7
444
-continued
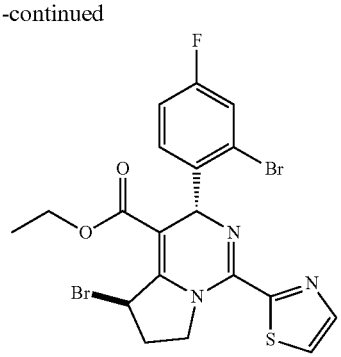
146-8
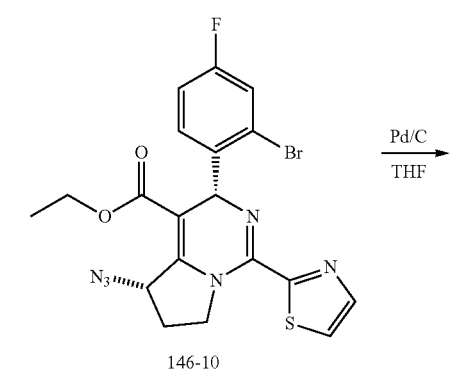
146-9
NaN3
DMSO
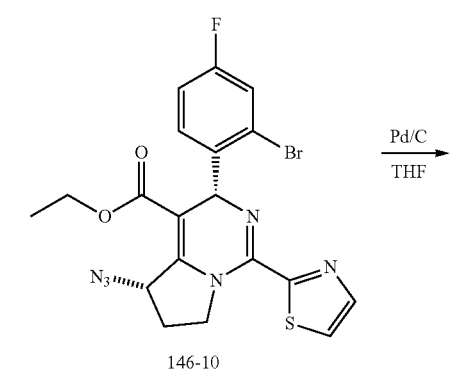
146-10
Pd/C
THF
146-11
MsCl, TEA
DCM

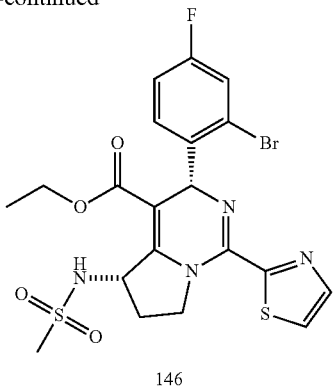

146

Step 1 Synthesis of (146-3)

Compound 146-2 (1.29 g, 5.96 mmol, 1.2 eq.) was dissolved in anhydrous THF (300 mL), and at 25° C. was added in portions NaH (238.4 mg, 5.96 mmol, 1.2 eq., 60% content). After the addition, the mixture was stirred for 30 minutes. To the reaction mixture was added 146-1 (2.50 g, 4.97 mmol, 1.0 eq.), the mixture continued stirring for 3 hours. With TLC showing completion of the reaction, the reaction mixture was quenched with water (10 mL), and extracted with EtOAc (100 mL) for 3 times. The organic phases were dried over anhydrous sodium sulfate, filtered, and concentrated under reduced pressure. The residue was purified by a silica gel column with an eluent solution of PE:EtOAc=5:1, to obtain 2.2 g product, yield: 68%.

LCMS (ESI) m/z: 640.1 [M+H$^+$].

Step 2 Synthesis of (146-4)

Compound 146-3 (2.2 g, 3.45 mmol, 1.0 eq.) was dissolved in anhydrous toluene (30 mL), and at 25° C. was added TFA (7.8 g, 69.0 mmol, 20.0 eq.). After the addition, the reaction mixture was warmed to 120° C., stirred for 5 hours. With TLC showing completion of the reaction, the reaction mixture was cooled to room temperature, concentrated under reduced pressure, washed with water (50 mL), and extracted with EtOAc (100 mL) for 3 times. The organic phases were dried over anhydrous sodium sulfate, filtered, and concentrated under reduced pressure to obtain 2.0 g crude product.

LCMS (ESI) m/z: 483.3 [M+H$^+$].

Step 3 Synthesis of (146-5)

Compound 146-4 (2.0 g, 4.1 mmol, 1.0 eq.) was dissolved in anhydrous DCM (30 mL), and at 28° C. was added carbonyldiimidazole (1.35 g, 8.3 mmol, 2.0 eq.). After the addition, the reaction mixture was swept with nitrogen for 3 times, and stirred for 30 minutes at this temperature. With TLC showing completion of the reaction, the reaction mixture was added dropwise into a solution of sodium borohydride (1.57 g, 41.5 mmol, 10.0 eq.) in methanol (30 mL), and continued stirring for 30 minutes. With TLC showing completion of the reaction, the reaction mixture was quenched with diluted HCl, dissolved in EtOAc, washed with water (100 mL), and then extracted with EtOAc (50 mL) for 3 times. The organic phases were washed with saturated brine, dried over anhydrous sodium sulfate, filtered, and concentrated under reduced pressure. The residue was purified by column chromatograph with an eluent system of PE:EtOAc=5:1, to obtain 1.04 g product as yellow oil.

LCMS (ESI) m/z: 492.0 [M+Na$^+$].

Step 4 Synthesis of (146-6)

Compound 146-5 (1.04 g, 2.22 mmol, 1.0 eq.) was dissolved in anhydrous DCM (30 mL), and at 28° C. were sequentially added TEA (673.9 mg, 6.6 mmol, 3.0 eq.), methanesulfonyl chloride (780 mg, 6.8 mmol, 3.1 eq.). After the addition, the reaction mixture was stirred at this temperature for 3 hours. With TLC showing completion of the reaction, the reaction mixture was washed with water, and extracted with DCM (50 mL) for 3 times. The organic phases were washed with saturated brine, dried over anhydrous sodium sulfate, filtered, and concentrated under reduced pressure. The residue was purified by column chromatograph with an eluent system of PE:EtOAc=5:1, to obtain 570 mg product, yield: 56%.

LCMS (ESI) m/z: 451.0 [M+Na$^+$].

Step 5 Synthesis of (146-7)

Compound 146-6 (468.3 mg, 1.04 mmol, 1.0 eq.) was dissolved in tetrachloromethane (5 mL), and at 23° C. were sequentially added NBS (277.6 mg, 1.56 mmol, 1.5 eq.), AIBN (8.5 mg, 52. μmol, 0.05 eq.).

After the addition, the reaction mixture was stirred at this temperature for 2.5 hours. With TLC showing completion of the reaction, the reaction mixture was washed with water, and extracted with DCM (10 mL) for 3 times. The organic phases were washed with saturated brine, dried over anhydrous sodium sulfate, filtered, and concentrated under reduced pressure. The residue was purified by column chromatograph with an eluent system of PE:EtOAc=5:1, to obtain 140 mg product 146-7, yield: 21% and 150 mg 146-8, yield: 26%.

LCMS (ESI) m/z: 529.6 [M+H$^+$].

Step 6 Synthesis of (146-9)

Compound 146-7 (120 mg, 226.7 μmol, 1.0 eq.) was dissolved in DMSO (3 mL), and at 23° C. was added sodium azide (10 mg, 153.8 μmol, 0.68 eq.). After the addition, the reaction mixture was stirred at this temperature for 18 hours. With TLC showing completion of the reaction, the reaction mixture was washed with water, and the suspension was filtered. The brown solid was washed with water, and dried to obtain 110 mg crude product.

LCMS (ESI) m/z: 491.2 [M+H$^+$].

Step 7 Synthesis of (146-10)

Compound 146-9 (110 mg, 223.8 μmol, 1.0 eq.) was dissolved in ethanol (3 mL), and at 25° C. was added Pd/C (11. mg, 223.8 umol, 1.0 eq.). After the addition, the reaction mixture was stirred under hydrogen atmosphere (15 psi) for 16 hours. With TLC showing completion of the reaction, the reaction mixture was filtered. The filtrate was concentrated to obtain 100 mg crude product.

LCMS (ESI) m/z: 466.9 [M+H$^+$].

Step 8 Synthesis of (Example 146)

Compound 146-10 (100 mg, 214.9 μmol, 1.0 eq.) was dissolved in DCM (3 mL), and at 23° C. were sequentially added TEA (108.7 mg, 1.1 mmol, 5.0 eq.) and methanesulfonyl chloride (73.8 mg, 644.7 umol, 3.0 eq). After the addition, the reaction mixture was stirred at this temperature for 1 hour. With TLC showing completion of the reaction, the reaction mixture was washed with water, and then extracted with DCM (50 mL) for 3 times. The organic phases was washed with saturated brine, dried over anhydrous sodium sulfate, filtered, and concentrated under reduced pressure. The residue was purified by a preparative separation column to obtain 6.7 mg product as white solid, yield: 6%.

NMR data of Example 146: $^1$H NMR (400 MHz, CDCl$_3$) δ: 7.84 (d, J=3.0 Hz, 1H), 7.40 (d, J=3.0 Hz, 1H), 7.35 (dd, J=2.4, 8.4 Hz, 1H), 7.23 (dd, J=6.4, 8.8 Hz, 1H), 6.99 (dt, J=2.4, 8.4 Hz, 1H), 6.16 (s, 1H), 5.22 (dd, J=2.0, 5.6 Hz, 1H), 4.78 (br. s., 1H), 4.54 (dd, J=8.4, 11.2 Hz, 1H), 4.38 (dt, J=5.6, 11.2 Hz, 1H), 3.99-4.16 (m, 2H), 3.19 (s, 3H), 2.84 (dd, J=5.6, 14.0 Hz, 1H), 2.12-2.25 (m, 1H), 1.14 (t, J=7.0 Hz, 3H).

LCMS (ESI) m/z: 545.0 [M+H$^+$].

Example 147

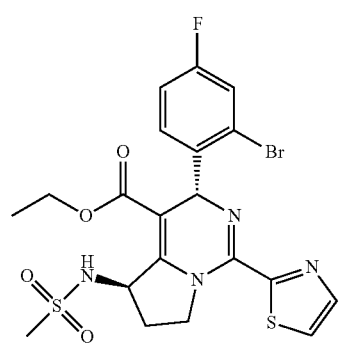

NMR data of Example 147: $^1$H NMR (400 MHz, CDCl$_3$) δ: 8.13 (br. s., 1H), 7.93 (br. s., 1H), 7.83 (br. s., 1H), 7.35 (d, J=6.4 Hz, 1H), 7.10 (br. s., 1H), 6.41 (br. s., 1H), 5.98 (br. s., 1H), 5.24 (br. s., 1H), 4.94 (br. s., 1H), 4.46 (br. s., 1H), 4.14 (d, J=7.0 Hz, 2H), 3.16 (s, 3H), 2.77 (br. s., 1H), 2.33 (br. s., 1H), 1.17 (t, J=6.8 Hz, 3H).

LCMS (ESI) m/z: 545.0 [M+H$^+$].

Example 148

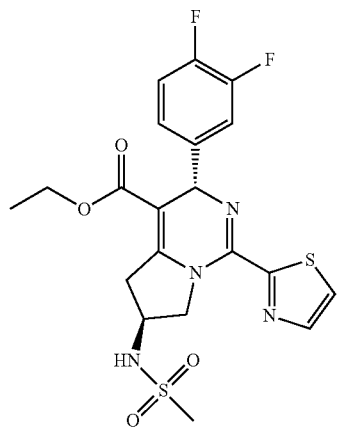

NMR data of Example 148: $^1$H NMR (400 MHz, MeOD) δ: 8.20 (d, J=17.6 Hz, 2H), 7.43-7.52 (m, 1H), 7.28-7.38 (m, 2H), 5.83 (br. s., 1H), 4.58 (br. s., 1H), 4.36-4.45 (m, 2H), 4.14-4.24 (m, 2H), 3.76 (dd, J=6.8, 17.8 Hz, 1H), 3.24 (dd, J=7.2, 17.8 Hz, 1H), 3.07 (s, 3H), 1.24 (t, J=7.2 Hz, 3H).

LCMS (ESI) m/z: 483.0 [M+H$^+$].

Example 149

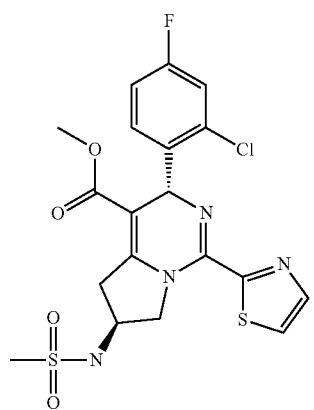

NMR data of Example 149: $^1$H NMR (400 MHz, CDCl3) δ: 7.82 (d, J=3.2 Hz, 1H), 7.40 (d, J=3.2 Hz, 1H), 7.23 (dd, J=6.4, 8.4 Hz, 1H), 7.14 (dd, J=2.4, 8.4 Hz, 1H), 6.93 (dt, J=2.4, 8.0 Hz, 1H), 6.16 (s, 1H), 4.81 (d, J=7.2 Hz, 1H), 4.60-4.45 (m, 2H), 4.37-4.24 (m, 1H), 3.67 (dd, J=7.2, 18.0 Hz, 1H), 3.61 (s, 3H), 3.16 (dd, J=6.4, 18.0 Hz, 1H), 3.07 (s, 3H).

LCMS (ESI) m/z: 485.2 [M+H$^+$].

Example 150

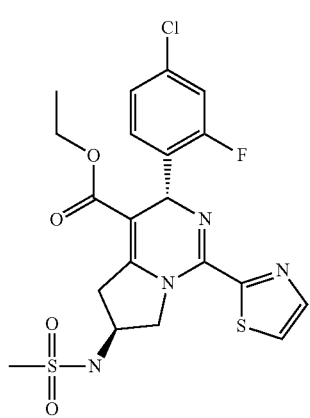

NMR data of Example 150: $^1$H NMR (400 MHz, DMSO-d6) δ: 7.98 (d, J=3.0 Hz, 1H), 7.88 (d, J=3.0 Hz, 1H), 7.63 (br. s., 1H), 7.36-7.46 (m, 2H), 7.24 (d, J=8.2 Hz, 1H), 5.88 (s, 1H), 4.44-4.54 (m, 1H), 4.20 (d, J=7.2 Hz, 2H), 3.93-4.05 (m, 2H), 3.48 (dd, J=17.4, 6.6 Hz, 1H), 3.01 (s, 4H), 1.09 (t, J=7.2 Hz, 3H).

LCMS (ESI) m/z: 499.2 [M+H$^+$].

Example 151

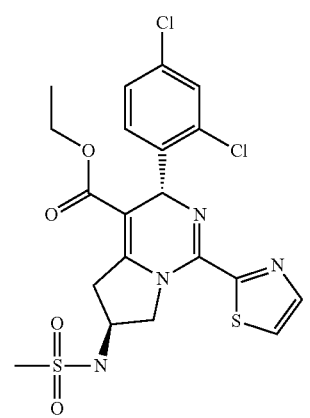

NMR data of Example 151: $^1$H NMR (400 MHz, DMSO-d$_6$) δ: 7.82 (d, J=3.2 Hz, 1H), 7.40 (dd, J=2.6, 5.0 Hz, 2H), 7.13-7.25 (m, 2H), 6.17 (s, 1H), 4.39-4.67 (m, 2H), 4.30 (t, J=6.6 Hz, 1H), 4.05 (q, J=7.0 Hz, 2H), 3.66 (dd, J=7.2, 18.0 Hz, 1H), 3.18 (dd, J=6.6, 18.0 Hz, 1H), 3.07 (s, 3H), 1.14 (t, J=7.2 Hz, 3H).

LCMS (ESI) m/z: 515.1 [M+H$^+$].

Example 152

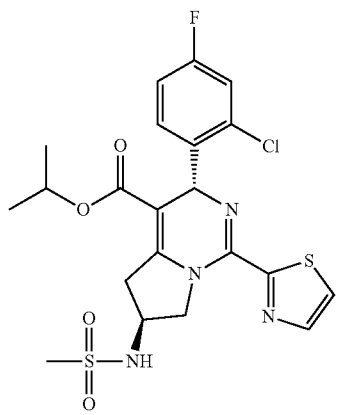

NMR data of Example 152: $^1$H NMR (400 MHz, CDCl3) δ: 7.82 (d, J=3.2 Hz, 1H), 7.39 (d, J=3.2 Hz, 1H), 7.29-7.26 (m, 1H), 7.13 (dd, J=2.4, 8.8 Hz, 1H), 6.94 (dt, J=2.4, 8.8 Hz, 1H), 6.17 (s, 1H), 4.91 (quin, J=6.4 Hz, 1H), 4.73 (d, J=7.6 Hz, 1H), 4.60-4.43 (m, 2H), 4.38-4.24 (m, 1H), 3.65 (dd, J=7.2, 17.6 Hz, 1H), 3.17 (dd, J=6.4, 18.0 Hz, 1H), 3.07 (s, 3H), 1.20 (d, J=6.4 Hz, 3H), 0.96 (d, J=6.0 Hz, 3H).

LCMS (ESI) m/z: 513.1 [M+H$^+$].

Example 153

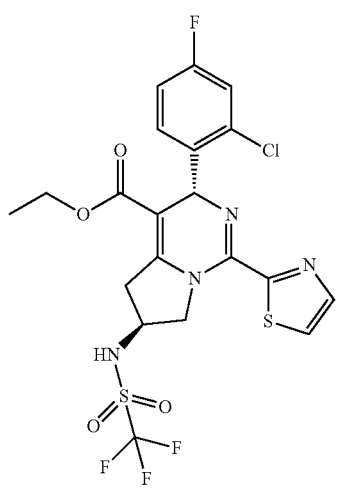

NMR data of Example 153: $^1$H NMR (400 MHz, DMSO-d$_6$) δ: 10.14 (br. s., 1H), 7.97 (d, J=3.0 Hz, 1H), 7.87 (d, J=3.0 Hz, 1H), 7.53 (dd, J=6.4, 8.6 Hz, 1H), 7.40 (dd, J=2.6, 8.8 Hz, 1H), 7.15 (dt, J=2.6, 8.4 Hz, 1H), 6.02 (s, 1H), 4.24-4.60 (m, 3H), 3.82-4.09 (m, 2H), 3.54 (dd, J=7.2, 17.8 Hz, 1H), 3.15 (dd, J=5.6, 17.8 Hz, 1H), 1.05 (t, J=7.2 Hz, 3H).

LCMS (ESI) m/z: 553.1 [M+H$^+$].

Example 154

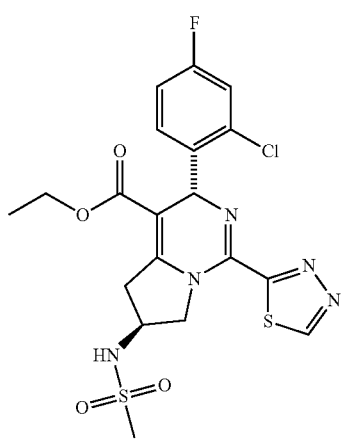

NMR data of Example 154: ¹H NMR (400 MHz, CDCl₃) δ: 9.11 (s, 1H), 7.22-7.26 (m, 1H), 7.14 (dd, J=2.4, 8.4 Hz, 1H), 6.92-7.00 (m, 1H), 6.19 (s, 1H), 5.35 (br. s., 1H), 4.65 (dd, J=6.6, 11.2 Hz, 1H), 4.45 (dd, J=6.6, 11.2 Hz, 1H), 4.30-4.39 (m, 1H), 4.06 (q, J=7.2 Hz, 2H), 3.72 (dd, J=7.2, 18.0 Hz, 1H), 3.19 (dd, J=7.2, 18.0 Hz, 1H), 3.08 (s, 3H), 1.14 (t, J=7.2 Hz, 3H).

LCMS (ESI) m/z: 500.1 [M+H⁺].

Example 155

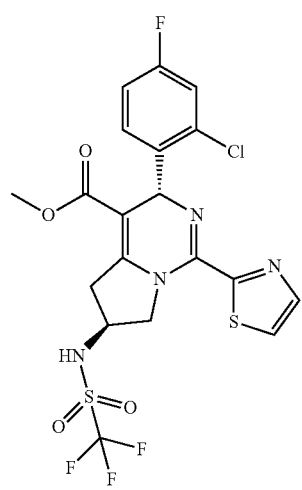

NMR data of Example 155: ¹H NMR (400 MHz, CDCl₃) δ: 7.84 (d, J=3.0 Hz, 1H), 7.42 (d, J=3.0 Hz, 1H), 7.22 (dd, J=6.0, 8.4 Hz, 1H), 7.14 (dd, J=2.6, 8.4 Hz, 1H), 6.95 (dt, J=2.6, 8.4 Hz, 1H), 6.14 (s, 1H), 4.49-4.60 (m, 2H), 4.42 (quin, J=6.6 Hz, 1H), 3.67 (dd, J=7.6, 18.6 Hz, 1H), 3.61 (s, 3H), 3.30 (dd, J=6.2, 18.4 Hz, 1H).

LCMS (ESI) m/z: 539.3 [M+H⁺].

Example 156

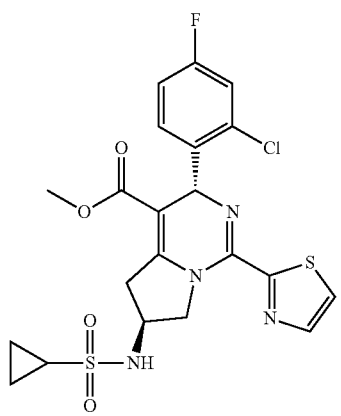

NMR data of Example 156: ¹H NMR (400 MHz, CDCl3) δ: 7.83 (d, J=3.2 Hz, 1H), 7.41 (d, J=3.2 Hz, 1H), 7.26 (dd, J=6.0, 8.8 Hz, 1H), 7.16 (dd, J=2.4, 8.4 Hz, 1H), 6.95 (dt, J=2.4, 8.4 Hz, 1H), 6.18 (s, 1H), 4.67 (d, J=7.2 Hz, 1H), 4.63-4.55 (m, 1H), 4.53-4.44 (m, 1H), 4.38-4.26 (m, 1H), 3.70 (dd, J=7.2, 18.0 Hz, 1H), 3.63 (s, 3H), 3.20 (dd, J=6.8, 18.0 Hz, 1H), 2.62-2.46 (m, 1H), 1.32-1.21 (m, 2H), 1.16-1.04 (m, 2H) LCMS (ESI) m/z: 511.2 [M+H⁺].

Example 157

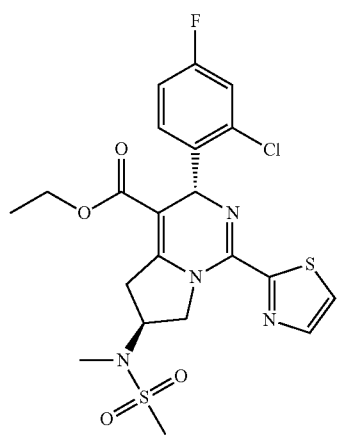

453
-continued

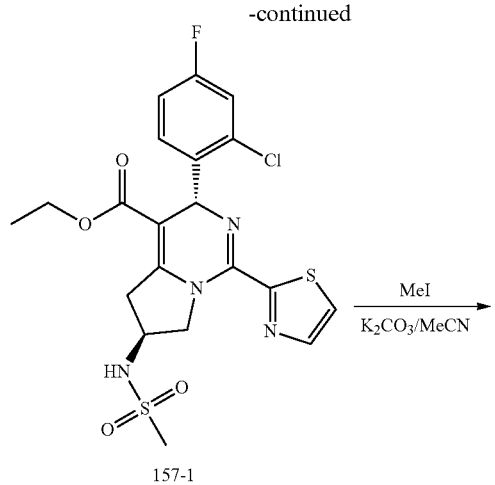

157-1

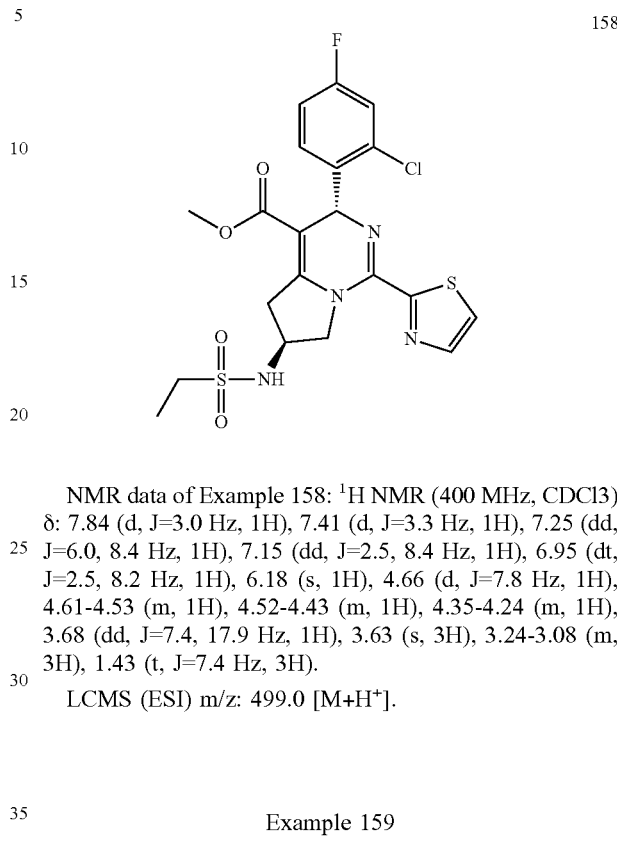

454
Example 158

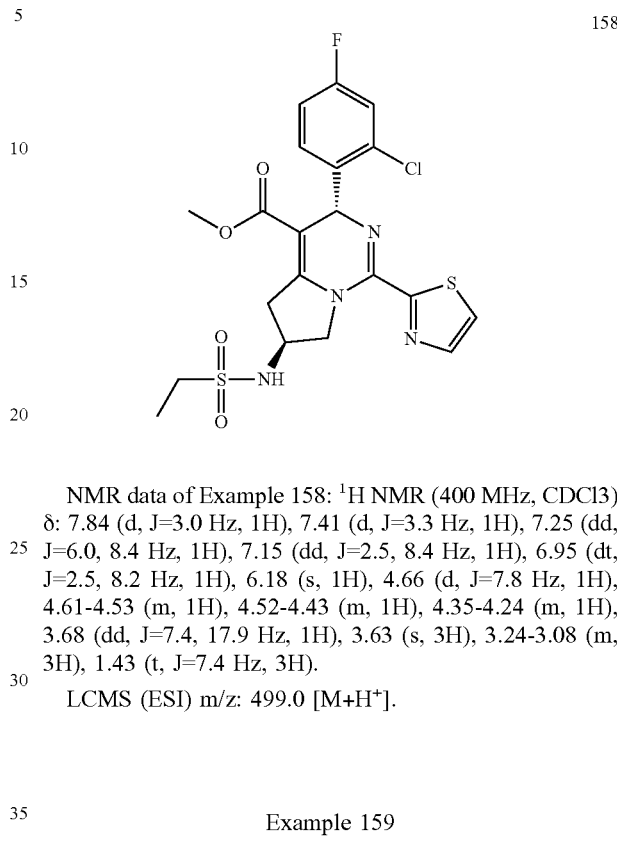

158

NMR data of Example 158: ¹H NMR (400 MHz, CDCl3) δ: 7.84 (d, J=3.0 Hz, 1H), 7.41 (d, J=3.3 Hz, 1H), 7.25 (dd, J=6.0, 8.4 Hz, 1H), 7.15 (dd, J=2.5, 8.4 Hz, 1H), 6.95 (dt, J=2.5, 8.2 Hz, 1H), 6.18 (s, 1H), 4.66 (d, J=7.8 Hz, 1H), 4.61-4.53 (m, 1H), 4.52-4.43 (m, 1H), 4.35-4.24 (m, 1H), 3.68 (dd, J=7.4, 17.9 Hz, 1H), 3.63 (s, 3H), 3.24-3.08 (m, 3H), 1.43 (t, J=7.4 Hz, 3H).

LCMS (ESI) m/z: 499.0 [M+H⁺].

Example 159

Compound 157-1 (100 mg, 200.4 μmol, 1.0 eq.), potassium carbonate (83.1 mg, 601.2 μmol, 3 eq.) were dissolved in anhydrous acetonitrile (5 mL), and at 28° C. was slowly added iodomethane (730 mg, 5.1 mmol, 25.6 eq.). After the addition, the reaction mixture was swept with nitrogen for 3 times, and stirred for 16 hours at this temperature. With LCMS showing completion of the reaction, the reaction mixture was filtered. The filtrate was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 50 mg yellow solid, yield: 49%.

NMR data of Example 157: ¹H NMR (400 MHz, CDCl3) δ 7.83 (d, J=3.6 Hz, 1H), 7.42 (d, J=3.6 Hz, 1H), 7.26 (d, J=6.02 Hz, 1H), 7.15 (dd, J=2.51, 8.53 Hz, 1H), 6.96 (dt, J=2.51, 8.28 Hz, 1H), 6.18 (s, 1H), 4.82 (d, J=6.53 Hz, 1H), 4.54-4.59 (m, 1H), 4.43-4.60 (m, 1H), 4.05 (q, J=7.11 Hz, 2H), 3.53 (dd, J=7.28, 18.07 Hz, 1H), 3.32 (dd, J=6.53, 18.07 Hz, 1H), 2.93 (s, 3H), 2.90 (s, 3H) 1.13 (t, J=7.03 Hz, 3H).

LCMS (ESI) m/z: 513.1 [M+H⁺].

Examples 169, 182, 183, 184, 186, 188, 192 were synthesized according to the same method as Example 157.

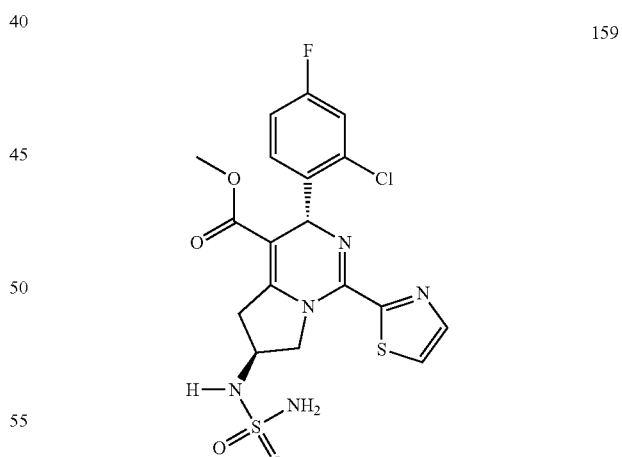

159

NMR data of Example 159: ¹H NMR (400 MHz, CDCl₃) δ: 7.82 (d, J=3.2 Hz, 1H), 7.39 (d, J=3.0 Hz, 1H), 7.24 (dd, J=6.2, 8.4 Hz, 1H), 7.14 (dd, J=2.4, 8.4 Hz, 1H), 6.93 (dt, J=2.4, 8.4 Hz, 1H), 6.16 (s, 1H), 5.18 (d, J=6.8 Hz, 1H), 5.06 (s, 2H), 4.62 (dd, J=5.6, 11.8 Hz, 1H), 4.44 (dd, J=6.4, 11.6 Hz, 1H), 4.23-4.34 (m, 1H), 3.64 (d, J=7.2 Hz, 1H), 3.60 (s, 3H), 3.26 (dd, J=6.0, 18.2 Hz, 1H).

LCMS (ESI) m/z: 486.1 [M+H⁺].

Example 160
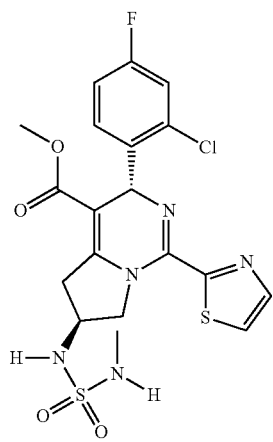
455
NMR data of Example 160: ¹H NMR (400 MHz, CDCl₃) δ: 7.82 (d, J=3.0 Hz, 1H), 7.40 (d, J=3.0 Hz, 1H), 7.24 (dd, J=6.4, 8.8 Hz, 1H), 7.14 (dd, J=2.4, 8.4 Hz, 1H), 6.93 (dt, J=2.4, 8.4 Hz, 1H), 6.17 (s, 1H), 4.67 (d, J=7.0 Hz, 1H), 4.62 (dd, J=5.6, 12.0 Hz, 1H), 4.53 (q, J=5.0 Hz, 1H), 4.44 (dd, J=6.0, 12.0 Hz, 1H), 4.20 (sxt, J=6.4 Hz, 1H), 3.61 (s, 3H), 3.57 (d, J=7.0 Hz, 1H), 3.23 (dd, J=6.0, 18.0 Hz, 1H), 2.74 (d, J=5.0 Hz, 3H).
LCMS (ESI) m/z: 500.2 [M+H⁺].
Examples 161, 166
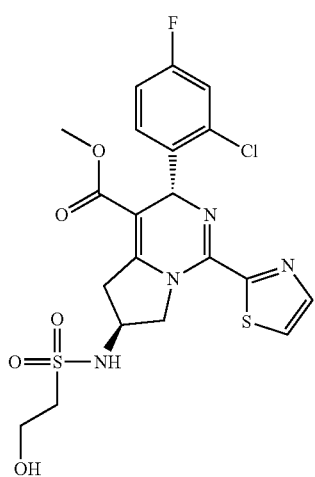
161
-continued
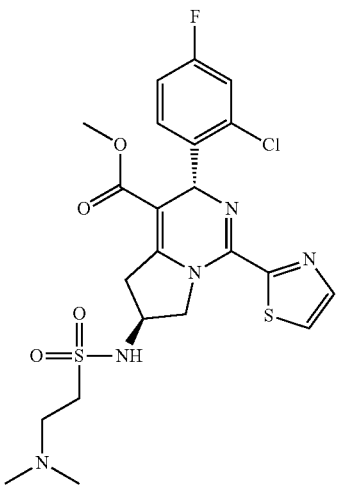
166
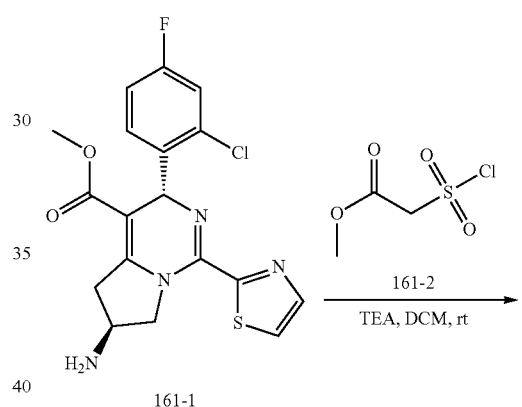
161-1, 161-2, TEA, DCM, rt
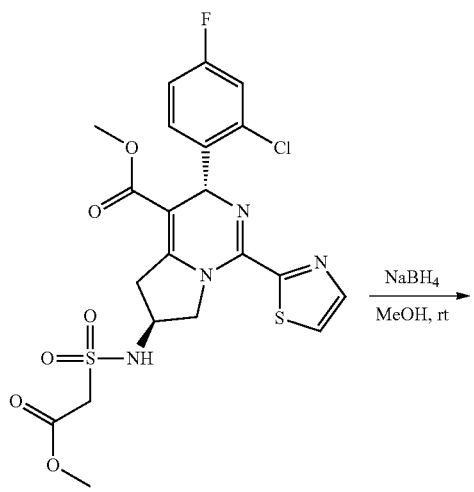
161-3
NaBH₄
MeOH, rt

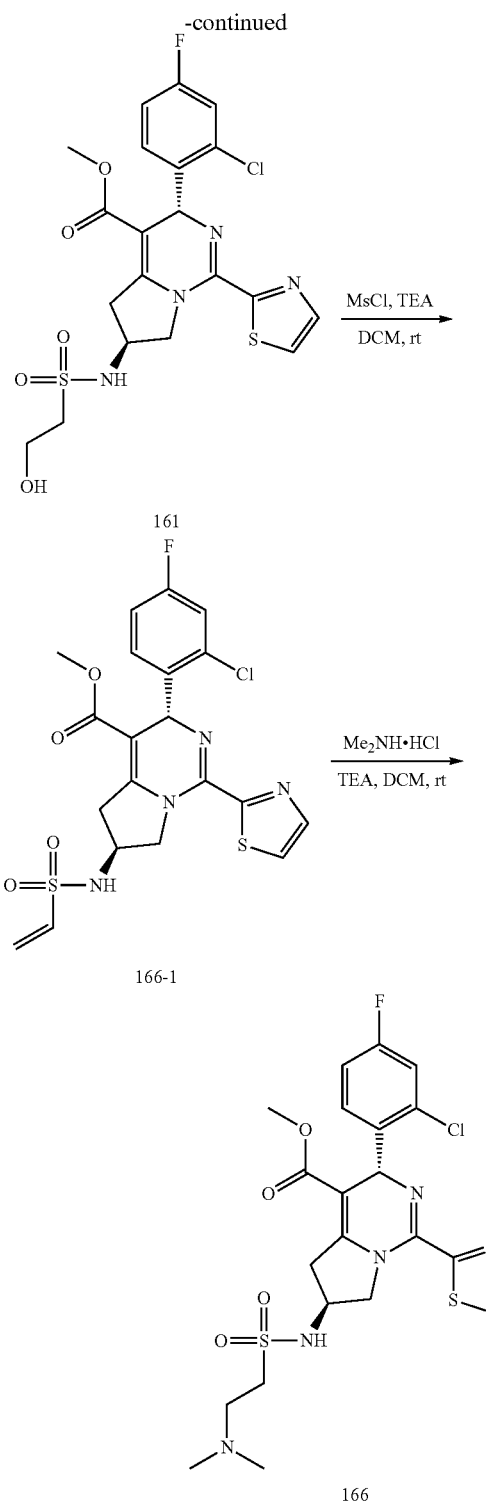

tion of the reaction, the reaction mixture was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=5:1-2:1, to obtain 22 mg white solid, yield: 33%.

LCMS (ESI) m/z: 543.1 [M+H$^+$]

Step 2 Synthesis of (161)

Compound 161-3 (22 mg, 40.5 μmol, 1.0 eq.) was dissolved in anhydrous methanol (2 mL), and at 25° C. was slowly added sodium borohydride (7.6 mg, 202.58 μmol, 5.0 eq.). After the addition, the reaction mixture was swept with nitrogen for 3 times, and stirred for 2 hours at this temperature. With TLC showing completion of the reaction, the reaction mixture was concentrated. The residue was washed with water (10 mL), and extracted with DCM (10 mL) for 3 times. The organic phases were washed with saturated brine, dried over anhydrous sodium sulfate, filtered, and concentrated under reduced pressure. The residue was purified by column chromatograph with an eluent system of PE:EtOAc=1:1-1:5, to obtain 6 mg white solid, yield: 29%.

NMR data of Example 161: $^1$H NMR (400 MHz, CDCl3) δ: 7.82 (d, J=3.2 Hz, 1H), 7.40 (d, J=3.2 Hz, 1H), 7.23 (dd, J=6.0, 8.4 Hz, 1H), 7.14 (dd, J=2.4, 8.4 Hz, 1H), 6.94 (dt, J=2., 8.4 Hz, 1H), 6.15 (s, 1H), 5.07 (d, J=7.6 Hz, 1H), 4.50 (d, J=6.0 Hz, 2H), 4.38-4.25 (m, 1H), 4.12 (br. s., 2H), 3.69-3.62 (m, 1H), 3.61 (s, 3H), 3.42-3.29 (m, 2H), 3.22 (dd, J=6.4, 18.0 Hz, 1H), 2.80 (br. s., 1H)

LCMS (ESI) m/z: 515.2 [M+H$^+$]

Step 3 Synthesis of (166-1)

Compound 161-3 (30 mg, 58.2 μmol, 1.0 eq.), TEA (17.68 mg, 174.75 mmol, 3.0 eq.) were dissolved in anhydrous DCM (2 mL), and at 25° C. was slowly added methanesulfonyl chloride (13 mg, 116.5 μmol, 2.0 eq.). After the addition, the reaction mixture was swept with nitrogen for 3 times, and stirred for 1 hour at this temperature. With TLC showing completion of the reaction, the reaction mixture was washed with water (10 mL), and extracted with DCM (20 mL) for 3 times. The organic phases were washed with saturated brine, dried over anhydrous sodium sulfate, filtered, and concentrated under reduced pressure. The residue was purified by TLC to obtain 9 mg white solid, yield: 31%.

$^1$H NMR (400 MHz, CDCl3) δ 7.82 (d, J=3.6 Hz, 1H), 7.39 (d, J=3.6 Hz, 1H), 7.22 (dd, J=6.0, 8.4 Hz, 1H), 7.13 (dd, J=2.4, 8.4 Hz, 1H), 6.93 (dt, J=2.4, 8.4 Hz, 1H), 6.60 (dd, J=10.0, 16.4 Hz, 1H), 6.34 (d, J=16.4 Hz, 1H), 6.15 (s, 1H), 6.01 (d, J=10.0 Hz, 1H), 4.96 (d, J=7.6 Hz, 1H), 4.58-4.48 (m, 1H), 4.47-4.36 (m, 1H), 4.21-4.08 (m, 1H), 3.68-3.56 (m, 4H), 3.21-3.11 (m, 1H)

LCMS (ESI) m/z: 497.1 [M+H$^+$]

Step 4 Synthesis of (166)

Compound dimethylamine hydrochloride (8.16 mg, 181.10 μmol, 10 eq.) was dissolved in anhydrous THF (2 mL), and at 25° C. was slowly added TEA (18.33 mg, 181.1 μmol). After the addition, the reaction mixture was stirred for 5 minutes at this temperature. Thereafter, to the reaction mixture was added 166-1 (9 mg, 18.1 μmol, 1.0 eq), the mixture continued stirring for 15 hours. With TLC showing completion of the reaction, the reaction mixture was filtered.

Step 1 Synthesis of (161-3)

Compound 161-1 (50 mg, 122.9 μmol, 1.0 eq.), TEA (49.7 mg, 491.56 μmol, 4.0 eq.) were dissolved in anhydrous DCM (1 mL), and at 25° C. was slowly added 161-2 (42.3 mg, 245.8 μmol, 2.0 eq.). After the addition, the reaction mixture was swept with nitrogen for 3 times, and stirred for 2 hours at this temperature. With LCMS showing comple- The filtrate was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by TLC to obtain 4 mg white solid, yield: 41%.

NMR data of Example 166: $^1$H NMR (400 MHz, CDCl3) δ 7.82 (d, J=3.6 Hz, 1H), 7.38 (d, J=3.2 Hz, 1H), 7.26-7.20 (m, 1H), 7.13 (dd, J=2.4, 8.4 Hz, 1H), 6.93 (dt, J=2.4, 8.4 Hz, 1H), 6.16 (s, 1H), 4.57 (dd, J=6.4, 11.6 Hz, 1H), 4.43 (dd, J=6.0, 11.6 Hz, 1H), 4.36-4.25 (m, 1H), 3.68 (dd, J=7.2, 17.6 Hz, 1H), 3.61 (s, 3H), 3.30 (d, J=6.0 Hz, 2H), 3.16 (dd, J=7.2, 18.2 Hz, 1H), 3.08-2.97 (m, 1H), 2.96-2.85 (m, 1H), 2.41 (s, 6H)

LCMS (ESI) m/z: 542.2 [M+H$^+$]

Example 162

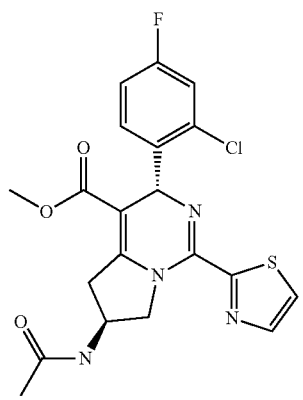

162

NMR data of Example 162: $^1$H NMR (400 MHz, CDCl$_3$) δ: 7.82 (d, J=3.2 Hz, 1H), 7.40 (d, J=3.2 Hz, 1H), 7.28-7.23 (m, 1H), 7.15 (dd, J=2.4, 8.4 Hz, 1H), 6.95 (dt, J=2.4, 8.4 Hz, 1H), 6.18 (s, 1H), 5.92 (d, J=6.8 Hz, 1H), 4.81-4.65 (m, 1H), 4.46 (d, J=5.8 Hz, 2H), 3.62 (s, 3H), 3.62-3.53 (m, 1H), 3.16 (dd, J=5.8, 18.1 Hz, 1H), 2.03 (s, 3H)

LCMS m/z: 449.1 [M+H$^+$].

Example 163

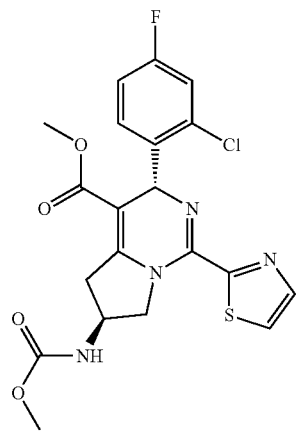

163

NMR data of Example 163: $^1$H NMR (400 MHz, CDCl3) δ: 7.81 (d, J=3.2 Hz, 1H), 7.38 (d, J=3.2 Hz, 1H), 7.26-7.21 (m, 1H), 7.13 (dd, J=2.4, 8.4 Hz, 1H), 6.93 (dt, J=2.4, 8.4 Hz, 1H), 6.16 (s, 1H), 5.01 (br. s., 1H), 4.54-4.43 (m, 2H), 4.36 (d, J=5.2 Hz, 1H), 3.70 (br. s., 3H), 3.64-3.56 (m, 4H), 3.10 (dd, J=5.6, 17.6 Hz, 1H).

LCMS m/z: 465.1 [M+H$^+$].

Example 164

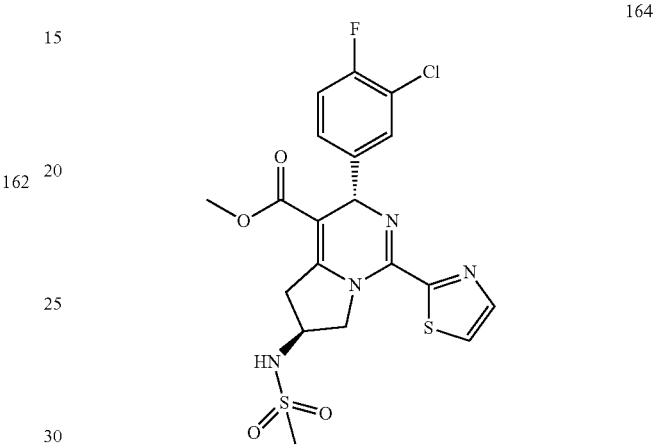

164

NMR data of Example 164: $^1$H NMR (400 MHz, MeOD-$d_4$) δ: 8.30 (dd, J=2.4, 10.54 Hz, 2H), 7.71 (d, J=6.4 Hz, 1H), 7.54 (br. s., 1H), 7.32 (t, J=8.4 Hz, 1H), 5.87 (s, 1H), 4.61 (d, J=3.6 Hz, 1H), 4.27-4.51 (m, 2H), 3.74-3.87 (m, 1H), 3.73 (s, 3H), 3.26 (dd, J=5.6, 18.2 Hz, 1H), 3.07 (s, 3H)

LCMS (ESI) m/z: 485.2 [M+H$^+$].

Example 165

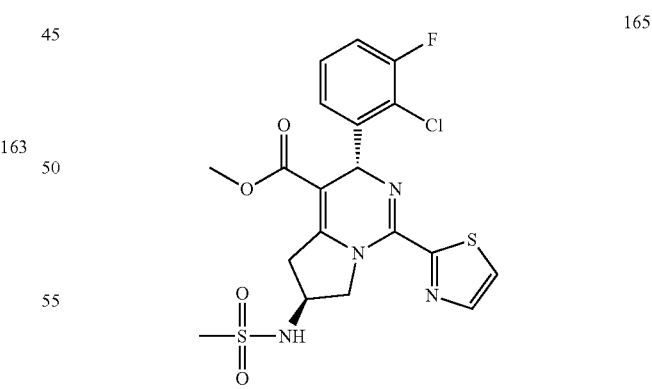

165

NMR data of Example 165: $^1$H NMR (400 MHz, CDCl3) δ: 7.82 (d, J=3.2 Hz, 1H), 7.40 (d, J=3.2 Hz, 1H), 7.22-7.15 (m, 1H), 7.11-7.01 (m, 2H), 6.23 (s, 1H), 4.80 (d, J=7.2 Hz, 1H), 4.61-4.45 (m, 2H), 4.38-4.25 (m, 1H), 3.68 (dd, J=7.2, 18.0 Hz, 1H), 3.61 (s, 3H), 3.17 (dd, J=7.2, 18.0 Hz, 1H), 3.08 (s, 3H).

LCMS (ESI) m/z: 485.2 [M+H$^+$].

Example 167

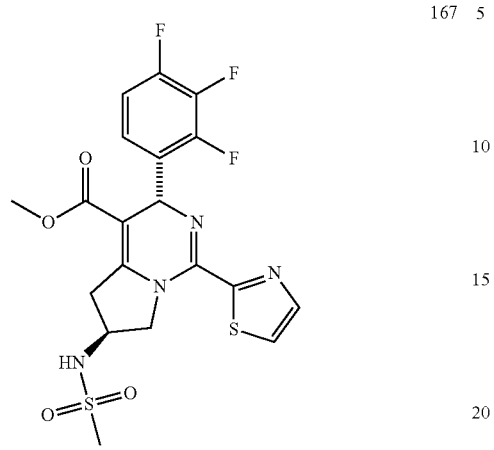

NMR data of Example 167: ¹H NMR (400 MHz, CDCl₃) δ: 7.85 (d, J=3.0 Hz, 1H), 7.42 (d, J=3.2 Hz, 1H), 6.98-7.06 (m, 1H), 6.87-6.95 (m, 1H), 5.98 (s, 1H), 4.92 (d, J=7.6 Hz, 1H), 4.48-4.60 (m, 2H), 4.28 (sxt, J=6.8 Hz, 1H), 3.64 (s, 3H), 3.55-3.62 (m, 1H), 3.13 (dd, J=6.8, 18.0 Hz, 1H), 3.07 (s, 3H).

LCMS (ESI) m/z: 487.2 [M+H⁺].

Example 168

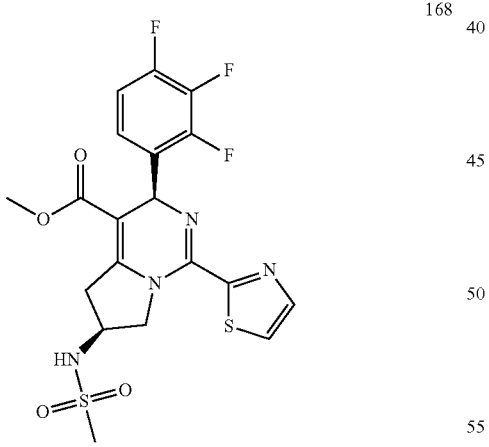

NMR data of Example 168: ¹H NMR (400 MHz, CDCl₃) δ: 8.05 (br. s., 1H), 7.81 (br. s., 1H), 7.42 (br. s., 1H), 6.93 (q, J=7.8 Hz, 1H), 6.13 (s, 1H), 6.06 (br. s., 1H), 4.74 (d, J=8.0 Hz, 1H), 4.60 (d, J=12.4 Hz, 1H), 4.40 (br. s., 1H), 3.71 (s, 3H), 3.64 (br. s., 1H), 3.36 (dd, J=5.6, 18.2 Hz, 1H), 3.03 (s, 3H).

LCMS (ESI) m/z: 487.2 [M+H⁺].

Example 169

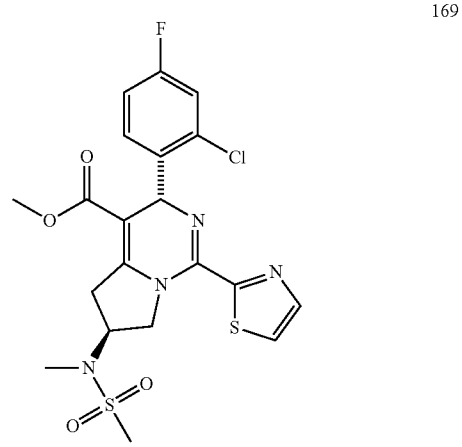

NMR data of Example 169: ¹H NMR (400 MHz, CDCl3) δ: 7.83 (d, J=3.26 Hz, 1H), 7.40 (d, J=3.01 Hz, 1H), 7.24 (dd, J=6.02, 8.53 Hz, 1H), 7.15 (dd, J=2.51, 8.53 Hz, 1H), 6.95 (dt, J=2.51, 8.16 Hz, 1H), 6.17 (s, 1H), 4.84 (quin, J=7.40 Hz, 1H), 4.59 (dd, J=6.53, 12.05 Hz, 1H), 4.43 (dd, J=7.65, 11.92 Hz, 1H), 3.62 (s, 3H), 3.54 (dd, J=8.28, 18.32 Hz, 1H), 3.29 (dd, J=7.28, 18.32 Hz, 1H), 2.92 (d, J=12.80 Hz, 6H)

LCMS (ESI) m/z: 499.1 [M+H⁺]

Example 170

NMR data of Example 170: ¹H NMR (400 MHz, CDCl3) δ: 7.84 (d, J=3.0 Hz, 1H), 7.40 (d, J=3.0 Hz, 1H), 7.26 (dd, J=8.4, 6.40 Hz, 1H), 7.15 (dd, J=8.4, 2.26 Hz, 1H), 6.92-6.99 (m, 1H), 6.18 (s, 1H), 4.64 (d, J=5.8 Hz, 1H), 4.22-4.40 (m, 3H), 3.70-3.79 (m, 1H), 3.63 (s, 3H), 3.06-3.15 (m, 1H), 1.46 (s, 9H).

LCMS (ESI) m/z: 527.1 [M+H⁺].

Example 171

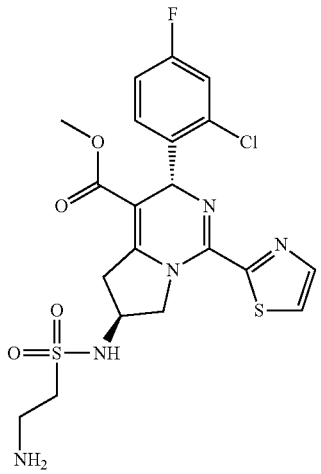

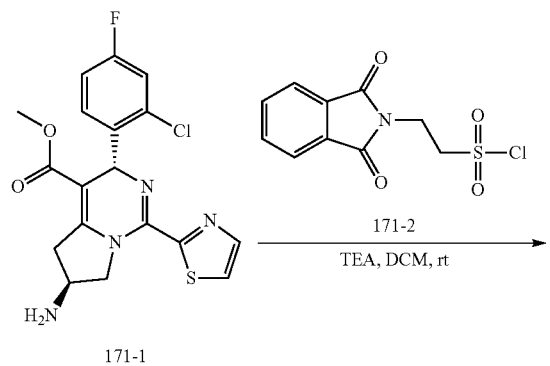

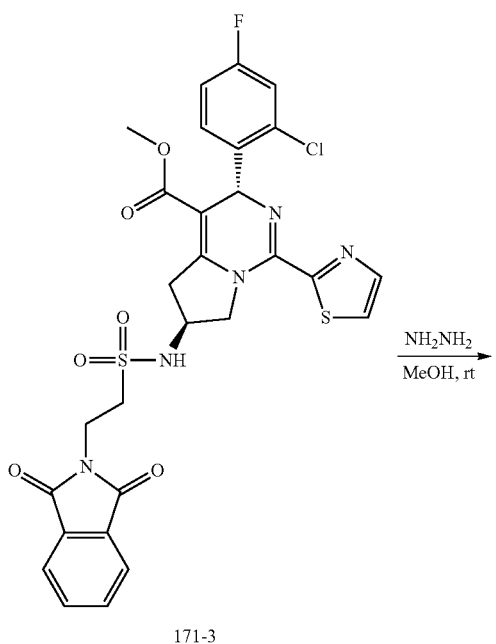

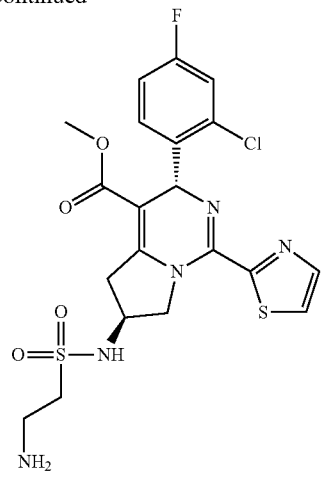

Step 1 Synthesis of (171-3)

Compound 171-1 (100 mg, 245.7 μmol, 1.0 eq.), TEA (74.6 mg, 737.3 μmol, 3.0 eq.) were dissolved in anhydrous DCM (2 mL), and at 25° C. was added 171-2 (100 mg, 368.6 μmol, 1.5 eq.). After the addition, the reaction mixture was swept with nitrogen for 3 times, and stirred for 2 hours at this temperature. With TLC showing completion of the reaction, the reaction mixture was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 44 mg white solid, yield: 25%.

LCMS (ESI) m/z: 665.9 [M+Na$^+$]

Step 2 Synthesis of (171)

Compound 171-3 (20 mg, 31.05 μmol, 1.0 eq.) was dissolved in methanol (2 mL), and at 25° C. was added N$_2$H$_4$·H$_2$O (15.5 mg, 310.5 μmol, 10.0 eq). After the addition, the reaction mixture was stirred for 2 hours at this temperature. With TLC showing completion of the reaction, the reaction mixture was concentrated. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by instrumental separation (aq. ammonia system) to obtain 10 mg white solid, yield: 58%.

NMR data of Example 171: $^1$H NMR (400 MHz, CDCl3) δ•: 7.82 (d, J=3.2 Hz, 1H), 7.39 (d, J=3.2 Hz, 1H), 7.25-7.20 (m, 1H), 7.13 (d, J=6.4 Hz, 1H), 6.99-6.88 (m, 1H), 6.15 (s, 1H), 4.50 (br. s., 2H), 4.30 (t, J=6.4 Hz, 1H), 3.71-3.54 (m, 4H), 3.35-3.13 (m, 5H)

LCMS (ESI) m/z: 514.1 [M+H$^+$]

Example 172

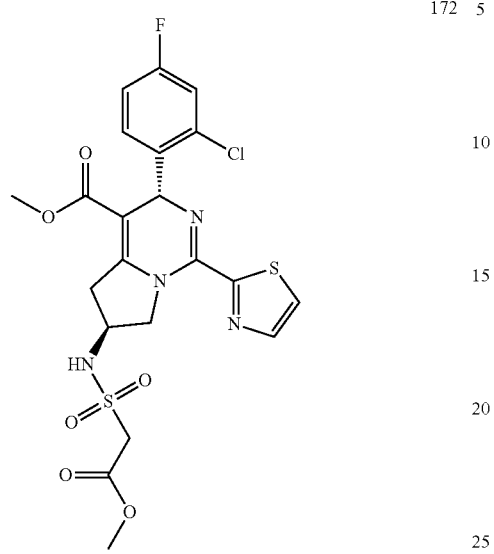

NMR data of Example 172: $^1$H NMR (400 MHz, CDCl3) δ: 7.82 (d, J=3.0 Hz, 1H), 7.39 (d, J=3.2 Hz, 1H), 7.24 (dd, J=6.4, 8.4 Hz, 1H), 7.14 (dd, J=2.4, 8.4 Hz, 1H), 6.94 (dt, J=2.4, 8.4 Hz, 1H), 6.16 (s, 1H), 5.43 (d, J=6.4 Hz, 1H), 4.53-4.62 (m, 1H), 4.44-4.52 (m, 1H), 4.29-4.41 (m, 1H), 4.13 (d, J=2.4 Hz, 2H), 3.82 (s, 3H), 3.68 (dd, J=7.2, 18.07 Hz, 1H), 3.61 (s, 3H), 3.22 (dd, J=6.8, 18.0 Hz, 1H).

LCMS (ESI) m/z: 543.1 [M+H$^+$].

Example 173

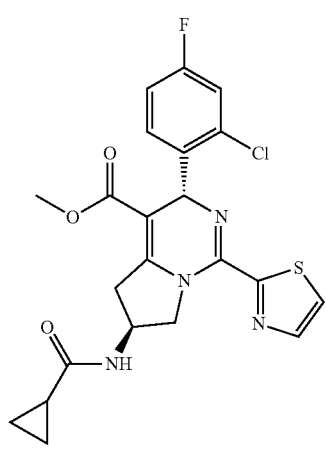

NMR data of Example 173: $^1$H NMR (400 MHz, CDCl3) δ: 7.81 (d, J=3.2 Hz, 1H), 7.39 (d, J=3.2 Hz, 1H), 7.23-7.28 (m, 1H), 7.15 (dd, J=8.6, 2.4 Hz, 1H), 6.95 (td, J=8.2, 2.4 Hz, 1H), 6.19 (s, 1H), 6.13 (d, J=7.2 Hz, 1H), 4.68-4.81 (m, 1H), 4.46 (d, J=5.6 Hz, 2H), 3.61-3.64 (m, 3H), 3.54-3.61 (m, 1H), 3.19 (dd, J=18.2, 6.0 Hz, 1H), 1.30-1.43 (m, 1H), 1.02 (br. s., 2H), 0.78 (dd, J=7.6, 3.2 Hz, 2H).

LCMS (ESI) m/z: 474.9 [M+H$^+$].

Example 174

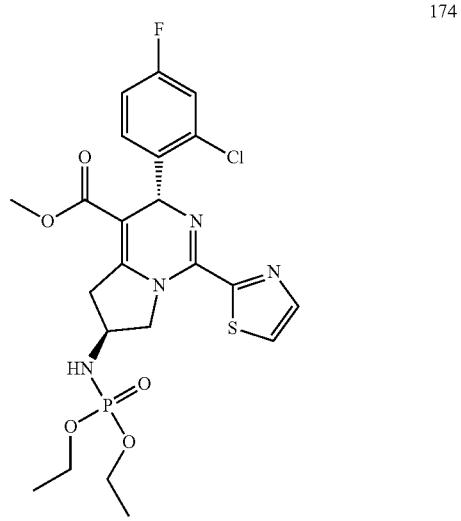 [SMILES: CCOP(=O)(N[C@H]1CC2=C(C(=O)OC)[C@H](c3ccc(F)cc3Cl)N=C(c3nccs3)N2C1)OCC]

NMR data of Example 174: $^1$H NMR (400 MHz, CDCl3) δ: 7.81 (d, J=3.6 Hz, 1H), 7.39 (d, J=3.0 Hz, 1H), 7.24 (dd, J=6.2, 8.8 Hz, 1H), 7.13 (dd, J=2.4, 8.6 Hz, 1H), 6.93 (dt, J=2.4, 8.4 Hz, 1H), 6.16 (s, 1H), 4.54 (dd, J=7.0, 11.6 Hz, 1H), 4.21 (dd, J=7.0, 11.6 Hz, 1H), 4.05-4.17 (m, 4H), 3.96-4.05 (m, 1H), 3.62-3.69 (m, 1H), 3.61 (s, 3H), 2.93-3.05 (m, 2H), 1.36 (dt, J=2.0, 7.0 Hz, 6H).

LCMS (ESI) m/z: 543.1 [M+H$^+$].

Example 175

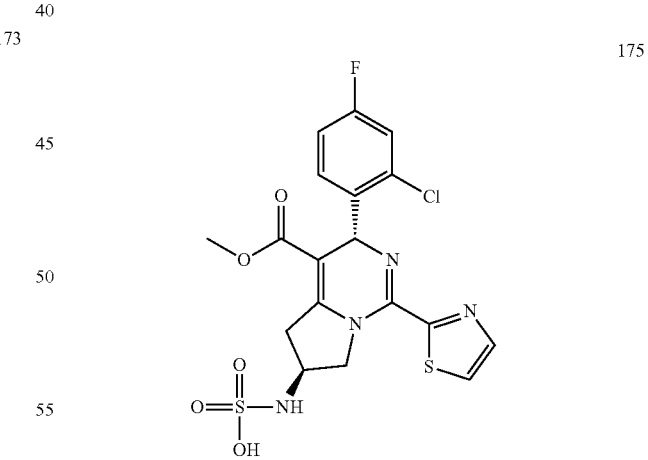

NMR data of Example 175: $^1$H NMR (400 MHz, MeOD-d$_4$) δ: 7.91 (d, J=3.2 Hz, 1H), 7.69 (d, J=3.0 Hz, 1H), 7.44 (dd, J=6.2, 8.6 Hz, 1H), 7.21 (dd, J=2.4, 8.8 Hz, 1H), 7.06 (dt, J=2.4, 8.4 Hz, 1H), 6.12 (s, 1H), 4.50 (dd, J=6.8, 11.6 Hz, 1H), 4.28 (dd, J=6.8, 11.2 Hz, 1H), 4.14 (quin, J=7.2 Hz, 1H), 3.62-3.72 (m, 1H), 3.61 (s, 3H), 3.14 (dd, J=7.2, 17.8 Hz, 1H), LCMS (ESI) m/z: 487.1 [M+H$^+$].

Example 176
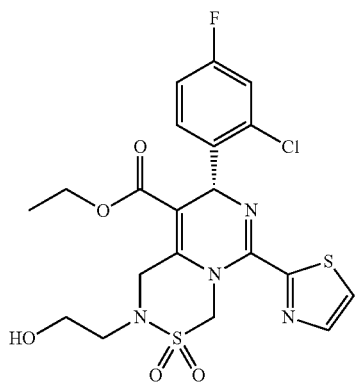
176
Example 176 was synthesized according to the same method as described in Example 136.
NMR data of Example 176: 1H NMR (400 MHz, CDCl3) δ: □ 7.92 (d, J=3.26 Hz, 1H), 7.45-7.56 (m, 2H), 7.17 (dd, J=2.38, 8.16 Hz, 1H), 6.96-7.09 (m, 2H), 5.91 (s, 1H), 5.34 (s, 1H), 4.50 (d, J=13.30 Hz, 1H), 4.24 (tdd, J=3.64, 7.15, 10.67 Hz, 2H), 3.70-3.84 (m, 2H), 3.59-3.68 (m, 1H), 3.43-3.53 (m, 1H), 3.38 (s, 1H), 1.32 (br. s., 3H).
LCMS (ESI) m/z: 515.1[M+H+].
Example 177
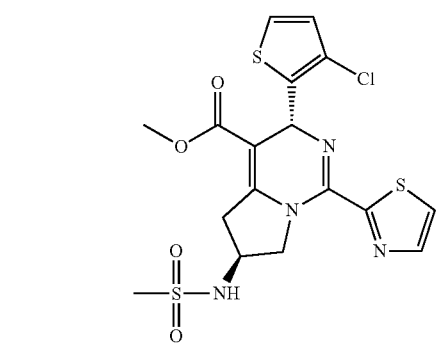
177
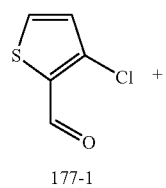
177-1
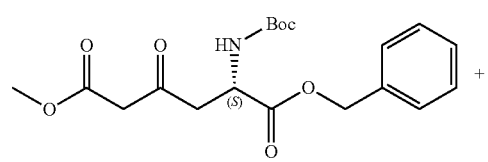
177-2
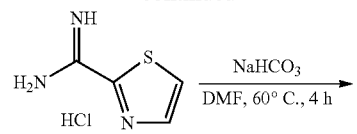
177-3
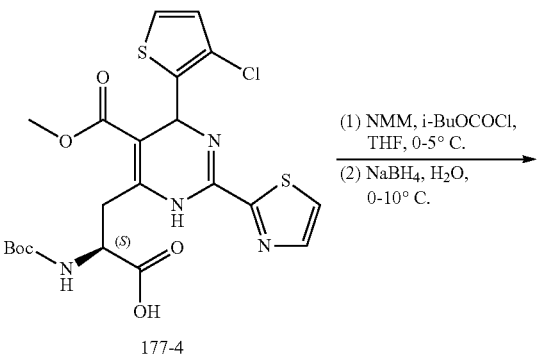
177-4
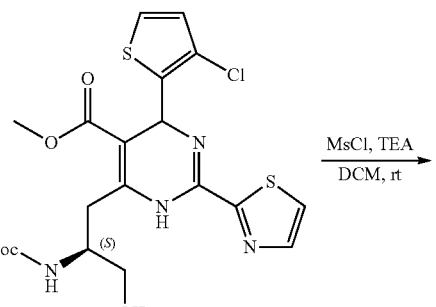
177-5
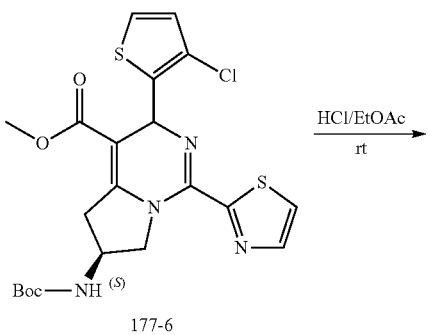
177-6
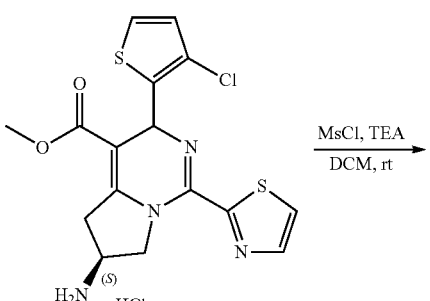
177-7

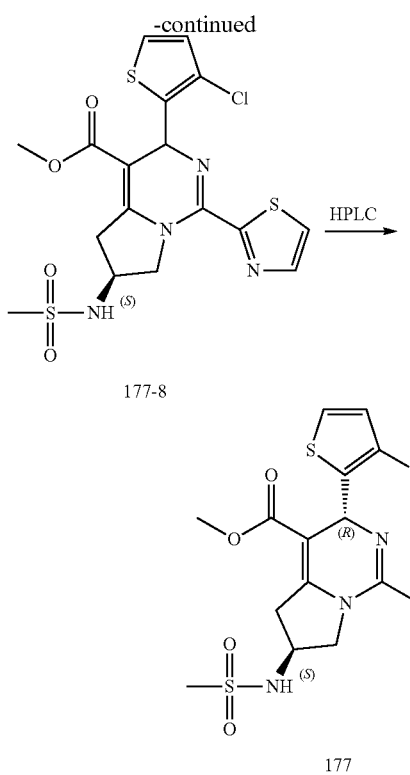

Step 1 (Synthesis of 177-4)

Compound 177-1 (3.86 g, 26.36 mmol, 1.0 eq.), 177-2 (10.0 g, 26.36 mmol, 1.0 eq.), 177-3 (4.31 g, 26.36 mmol, 1.0 eq.) were dissolved in anhydrous DMF (100 mL), and at 20° C. was added NaHCO₃ (8.86 g, 105.44 mmol, 4.00 eq). After the addition, the reaction mixture was swept with nitrogen for 3 times, the mixture was warmed to 60° C., and stirred for 4 hours. The reaction mixture was cooled to room temperature, and filtered. The filtrate was concentrated under reduced pressure. The residue was dissolved in EtOAc, washed with water (100 mL), and then extracted with EtOAc (100 mL) for 3 times.

The organic phases were washed with saturated brine, dried over anhydrous sodium sulfate, filtered, and concentrated under reduced pressure. The residue was purified by column chromatograph with an eluent system of DCM/MeOH=20/1, 10/1, to obtain 11 g product as yellow oil, yield: 66%.

LCMS (ESI) m/z: 527.1 [M+H⁺].

Step 2 (Synthesis of 177-5)

Compound 177-4 (10.0 g, 18.97 mmol, 1.0 eq.), NMM (2.49 g, 24.66 mmol, 1.30 eq) were dissolved in anhydrous THF (50 mL), and at 0° C. was slowly added isobutyl chloroformate (3.11 g, 22.76 mmol, 1.2 eq.).

After the addition, the reaction mixture was swept with nitrogen for 3 times, and stirred for 30 minutes at 0° C. With TLC showing completion of the reaction, the reaction mixture was filtered. The filtrate was slowly added dropwise to an aqueous NaBH₄ (1.4 g, 37.94 mmol, 2.0 eq.) solution (50 mL) at 0° C. The reaction mixture continued stirring for 1 hour. With TLC showing completion of the reaction, the reaction mixture was quenched with diluted HCl, dissolved in EtOAc, washed with water (100 mL), and then extracted with EtOAc (100 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 6.6 g product as yellow solid, yield: 64%.

LCMS (ESI) m/z: 513.1 [M+H⁺].

Step 3 (Synthesis of 177-6)

Compound 177-5 (6.60 g, 12.86 mmol, 1.0 eq.), TEA (2.60 g, 25.72 mmol, 2.0 eq.) were dissolved in anhydrous DCM (50 mL), and at 0° C. was slowly added methanesulfonyl chloride (1.92 g, 16.76 mmol, 1.3 eq.). After the addition, the reaction mixture was swept with nitrogen for 3 times, and then warmed to 27° C., stirred for 15 hours. With TLC showing completion of the reaction, the reaction mixture was washed with water (100 mL), and then extracted with DCM (100 mL) for 3 times. The organic phases were washed with saturated brine, dried over anhydrous sodium sulfate, filtered, and concentrated under reduced pressure. The residue was purified by column chromatograph with an eluent system of PE:EtOAc=10:1-3:1, to obtain 5.6 g product as yellow solid, yield: 87%.

LCMS (ESI) m/z: 495.2 [M+H⁺].

Step 4 (Synthesis of 177-7)

Compound 177-6 (5.60 g, 11.31 mmol, 1.0 eq.) was dissolved in anhydrous DCM (10 mL), and at 0° C. was slowly added into a solution of HCl/EtOAc (20 mL). After the addition, the reaction mixture was stirred for 1 hour. With TLC showing completion of the reaction, the reaction mixture was concentrated under reduced pressure to obtain 4.7 g yellow solid, yield: 92%. The crude product was directly used in the next reaction.

LCMS (ESI) m/z: 394.9 [M+H⁺].

Step 5 (Synthesis of 177-8)

Compound 177-7 (500 mg, 1.16 mmol, 1.0 eq.), TEA (234 mg, 2.32 mmol, 2.0 eq.) were dissolved in anhydrous DCM (5 mL), and at 0° C. was slowly added methanesulfonyl chloride (199 mg, 1.7 mmol, 1.5 eq.). After the addition, the reaction mixture was swept with nitrogen for 3 times, and then warmed to 27° C., stirred for 4 hours. With TLC showing completion of the reaction, the reaction mixture was washed with water (10 mL), and then extracted with DCM (10 mL) for 3 times. The organic phases was washed with saturated brine, dried over anhydrous sodium sulfate, filtered, and concentrated under reduced pressure. The residue was purified by column chromatograph with an eluent system of PE:EtOAc=10:1-3:1, to obtain the product as 300 mg yellow solid, yield: 52%.

LCMS (ESI) m/z: 473.0 [M+H⁺].

Step 6 (Synthesis of 177)

Compound 177-8 (300 mg, 634.26 mmol) was separated by a preparative separation column (formic acid system) to obtain optically pure 57 mg Example 177 as white solid, de value: 88%.

NMR data of Example 177: ¹H NMR (400 MHz, CDCl3) δ: 7.85 (d, J=3.2 Hz, 1H), 7.43 (d, J=3.2 Hz, 1H), 7.12 (d, J=5.2 Hz, 1H), 6.87 (d, J=5.2 Hz, 1H), 6.14 (s, 1H), 4.89 (d, J=7.6 Hz, 1H), 4.66-4.56 (m, 1H), 4.53-4.43 (m, 1H), 4.36-4.25 (m, 1H), 3.72-3.68 (m, 3H), 3.63 (dd, J=7.2, 17.6 Hz, 1H), 3.16-3.09 (m, 1H), 3.07 (s, 3H).

LCMS (ESI) m/z: 473.0 [M+H⁺].

Examples 152, 178, 179, 180, 181, 185, 187, 189, 190, 191, 193, 194, 197, 198, 199, 200, 201, 202, 203, 204, 205, 206, 207, 208, 209, 210, 211, 212, 213, 214, 215, 216, 217, 218, 219, 220, 223, 224, 225, 226 were synthesized according to the same method as described in Example 177.

Example 178

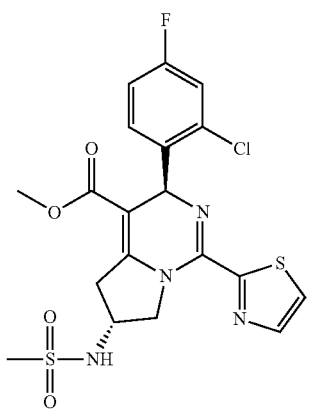

NMR data of Example 178: ¹H NMR (400 MHz, CDCl3) δ: 7.82 (d, J=3.2 Hz, 1H), 7.40 (d, J=3.2 Hz, 1H), 7.23 (dd, J=6.4, 8.8 Hz, 1H), 7.14 (dd, J=2.4, 8.4 Hz, 1H), 6.93 (dt, J=245, 8.4 Hz, 1H), 6.16 (s, 1H), 4.85 (d, J=7.6 Hz, 1H), 4.52 (dq, J=6.4, 11.6 Hz, 2H), 4.37-4.22 (m, 1H), 3.67 (dd, J=7.2, 18.0 Hz, 1H), 3.61 (s, 3H), 3.17 (dd, J=7.2, 18.0 Hz, 1H), 3.10-3.04 (m, 3H).

LCMS (ESI) m/z: 485.1 [M+H⁺].

Example 179

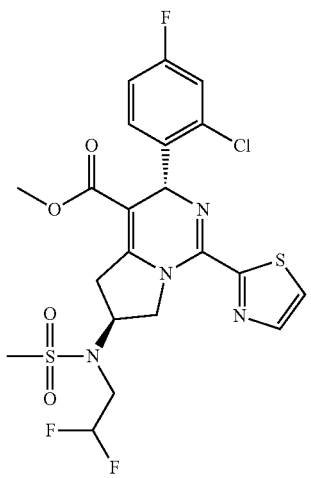

NMR data of Example 179: ¹H NMR (400 MHz, CDCl3) δ: 7.82 (d, J=3.2 Hz, 1H), 7.39 (d, J=3.2 Hz, 1H), 7.22-7.25 (m, 1H), 7.14 (dd, J=8.53, 2.4 Hz, 1H), 6.95 (td, J=8.2, 2.4 Hz, 1H), 6.17 (s, 1H), 5.83-6.08 (m, 1H), 4.55-4.71 (m, 2H), 4.32-4.47 (m, 1H), 3.53-3.72 (m, 6H), 3.20-3.32 (m, 1H), 3.04 (s, 3H).

LCMS (ESI) m/z: 549.1 [M+H⁺].

Example 180

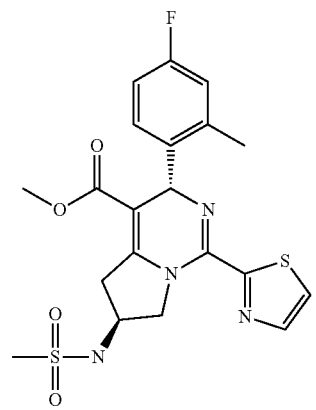

NMR data of Example 180: ¹H NMR (400 MHz, CDCl3) δ: 2.64 (s, 3H) 3.08 (s, 3H) 3.15 (dd, J=17.82, 7.2 Hz, 1H) 3.62 (s, 3H) 3.73 (dd, J=17.8, 7.28 Hz, 1H) 4.24-4.39 (m, 1H) 4.47-4.55 (m, 2H) 4.83 (d, J=7.6 Hz, 1H) 5.93 (s, 1H) 6.77-6.84 (m, 1H) 6.90 (dd, J=10.0, 2.51 Hz, 1H) 7.06 (dd, J=8.2, 5.77 Hz, 1H) 7.37 (d, J=3.6 Hz, 1H) 7.79 (d, J=3.0 Hz, 1H)

LCMS (ESI) m/z: 465.1 [M+H⁺].

Example 181

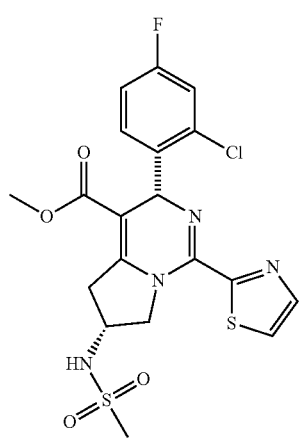

NMR data of Example 181: ¹H NMR (400 MHz, CDCl3) δ: 7.82 (d, J=3.6 Hz, 1H), 7.40 (d, J=3.2 Hz, 1H), 7.30 (dd, J=6.2, 8.8 Hz, 1H), 7.15 (dd, J=2.6, 8.8 Hz, 1H), 6.96 (dt, J=2.8, 8.4 Hz, 1H), 6.17 (s, 1H), 4.71 (d, J=6.4 Hz, 1H), 4.56-4.62 (m, 1H), 4.47-4.53 (m, 1H), 4.29-4.37 (m, 1H), 3.63 (s, 3H), 3.47-3.54 (m, 1H), 3.32-3.41 (m, 1H), 3.06 (s, 3H).

LCMS (ESI) m/z: 485.0 [M+H⁺].

Example 182

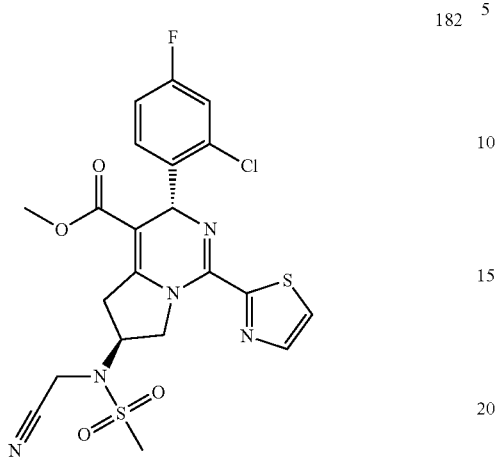

NMR data of Example 182: $^1$H NMR (400 MHz, CDCl3) δ: 7.85 (d, J=3.01 Hz, 1H), 7.43 (d, J=3.26 Hz, 1H), 7.24-7.28 (m, 1H), 7.17 (dd, J=2.26, 8.53 Hz, 1H), 6.97 (dt, J=2.51, 8.16 Hz, 1H), 6.21 (s, 1H), 4.67-4.81 (m, 2H), 4.54-4.63 (m, 1H), 4.27-4.42 (m, 2H), 3.71 (dd, J=7.65, 18.45 Hz, 1H), 3.64 (s, 3H), 3.46 (dd, J=6.90, 18.45 Hz, 1H), 3.17 (s, 3H)

LCMS (ESI) m/z: 524.1 [M+H$^+$]

Example 184

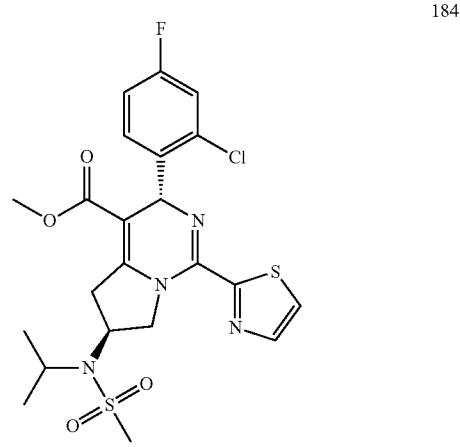 [SMILES: COC(=O)C1=C2C[C@H](N(C(C)C)S(C)(=O)=O)CN2C(c2nccs2)=N[C@H]1c1ccc(F)cc1Cl]

NMR data of Example 184: 1H NMR (400 MHz, CDCl3) δ: 7.81 (d, J=3.6 Hz, 1H), 7.37 (d, J=3.6 Hz, 1H), 7.29 (d, J=6.0 Hz, 1H), 7.14 (dd, J=8.6, 2.51 Hz, 1H), 6.94 (td, J=8.2, 2.51 Hz, 1H), 6.16 (s, 1H), 4.63 (dd, J=10.8, 8.28 Hz, 1H), 4.37-4.50 (m, 1H), 4.21 (t, J=9.0 Hz, 1H), 3.61 (s, 3H), 3.93-4.02 (m, 1H), 3.48-3.59 (m, 2H), 2.98 (s, 3H), 1.38 (d, J=6.4 Hz, 6H)

LCMS (ESI) m/z: 527.2 [M+H$^+$]

Example 183

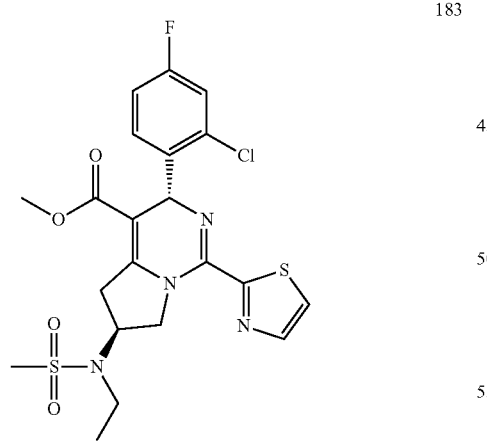

NMR data of Example 183: $^1$H NMR (400 MHz, DMSO-d6) δ: 7.98 (d, J=3.51 Hz, 1H), 7.88 (d, J=3.51 Hz, 1H), 7.51 (dd, J=8.53, 6.02 Hz, 1H), 7.43 (dd, J=8.53, 2.51 Hz, 1H), 7.18 (td, J=8.53, 2.51 Hz, 1H), 6.01 (s, 1H), 4.62-4.72 (m, 1H), 4.48-4.55 (m, 1H), 4.14-4.22 (m, 1H), 3.50-3.61 (m, 4H), 3.30 (d, J=5.52 Hz, 2H), 3.01-3.18 (m, 4H), 1.15 (t, J=7.03 Hz, 3H)

LCMS (ESI) m/z: 513.1 [M+H$^+$]

Example 185

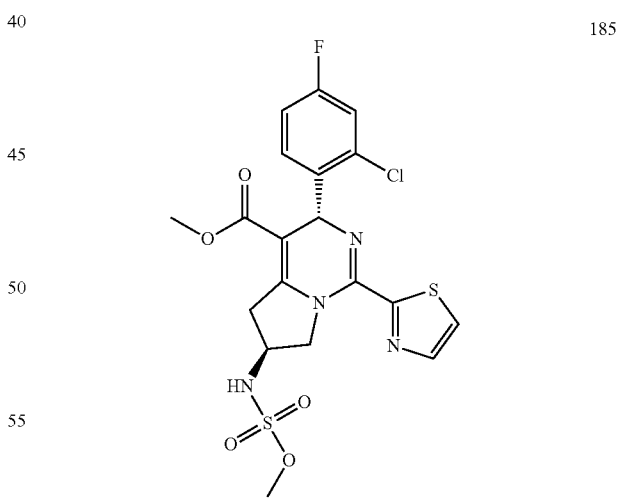

NMR data of Example 185: $^1$H NMR (400 MHz, CDCl3) δ: 7.83 (d, J=3.2 Hz, 1H), 7.40 (d, J=3.2 Hz, 1H), 7.19-7.24 (m, 1H), 7.14 (dd, J=3.2, 8.4 Hz, 1H), 6.94 (t, J=8.4 Hz, 1H), 6.17 (s, 1H), 4.64 (dd, J=5.2, 11.6 Hz, 1H), 4.42-4.53 (m, 1H), 4.28 (d, J=6.4 Hz, 1H), 3.88 (s, 3H), 3.57-3.63 (m, 4H), 3.22-3.33 (m, 1H).

LCMS (ESI) m/z: 501.1 [M+H$^+$].

Example 186

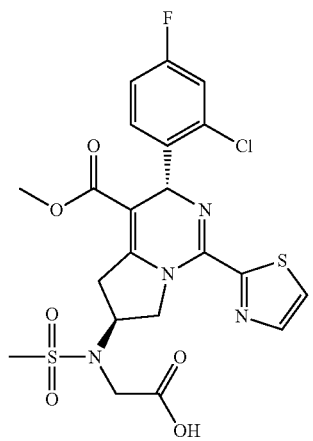

NMR data of Example 186: ¹H NMR (400 MHz, CDCl3) δ: 7.83 (br. s., 1H), 7.42 (d, J=2.76 Hz, 1H), 7.21-7.26 (m, 1H), 7.14 (dd, J=2.13, 8.41 Hz, 1H), 6.94 (t, J=7.15 Hz, 1H), 6.15 (s, 1H), 4.65-4.75 (m, 1H), 4.46-4.52 (m, 1H), 4.42 (br. s., 1H), 4.02-4.26 (m, 2H), 3.63 (d, J=7.78 Hz, 1H), 3.58 (br. s., 3H), 3.24 (dd, J=6.90, 17.94 Hz, 1H), 3.12 (s, 3H)

LCMS (ESI) m/z: 543.0 [M+H⁺]

Example 187

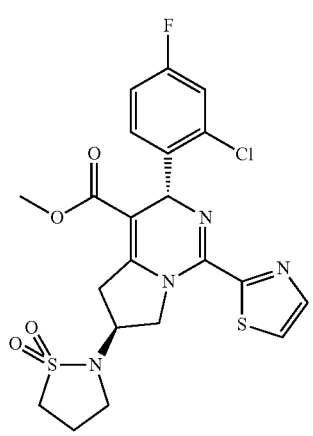

NMR data of Example 187: ¹H NMR (400 MHz, CDCl3) δ: □ 8.15 (br. s., 1H), 7.89 (br. s., 1H), 7.57 (t, J=6.4 Hz, 1H), 7.17 (d, J=7.0 Hz, 1H), 7.04 (t, J=6.8 Hz, 1H), 6.34 (br. s., 1H), 5.03 (br. s., 1H), 4.34 (br. s., 2H), 3.69 (s, 3H), 3.64 (br. s., 1H), 3.30-3.53 (m, 3H), 3.24 (t, J=7.0 Hz, 2H), 2.46 (br. s., 2H).

LCMS (ESI) m/z: 511.0 [M+H⁺].

Example 188

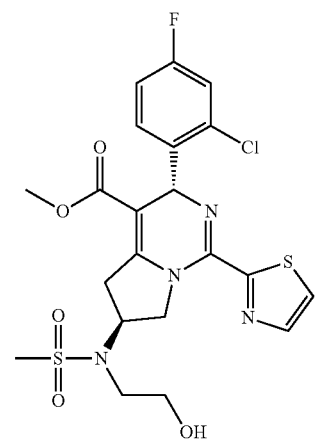

NMR data of Example 188: ¹H NMR (400 MHz, CDCl3) δ: 7.84 (d, J=3.26 Hz, 1H), 7.42 (d, J=3.26 Hz, 1H), 7.26 (dd, J=6.40, 8.66 Hz, 1H), 7.16 (dd, J=2.38, 8.66 Hz, 1H), 6.97 (dt, J=2.51, 8.16 Hz, 1H), 6.18 (s, 1H), 4.75 (quin, J=7.47 Hz, 1H), 4.54 (dd, J=2.38, 7.40 Hz, 2H), 3.86 (d, J=4.77 Hz, 2H), 3.67 (d, J=8.28 Hz, 1H), 3.63 (s, 3H), 3.39-3.51 (m, 2H), 3.34 (dd, J=8.03, 18.32 Hz, 1H), 3.05 (s, 3H)

LCMS (ESI) m/z: 529.1 [M+H⁺]

Example 189

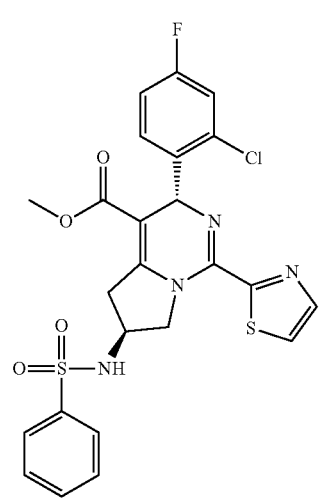

NMR data of Example 189: ¹H NMR (400 MHz, CDCl₃) δ: 7.92 (d, J=7.0 Hz, 2H), 7.76 (d, J=3.0 Hz, 1H), 7.51-7.67 (m, 3H), 7.37 (d, J=3.0 Hz, 1H), 7.19 (dd, J=6.4, 8.8 Hz, 1H), 7.11 (dd, J=2.4, 8.4 Hz, 1H), 6.90 (dt, J=2.4, 8.4 Hz, 1H), 6.12 (s, 1H), 5.12 (d, J=7.0 Hz, 1H), 4.35-4.50 (m, 1H), 4.22-4.34 (m, 1H), 4.11 (sxt, J=6.8 Hz, 1H), 3.56 (s, 3H), 3.45 (dd, J=7.6, 18.0 Hz, 1H), 3.03 (dd, J=6.8, 18.0 Hz, 1H).

LCMS (ESI) m/z: 547.1 [M+H⁺].

Example 190

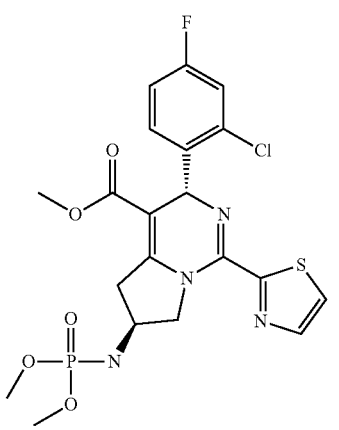

NMR data of Example 190: ¹H NMR (400 MHz, CDCl3) δ: 7.84 (d, J=3.0 Hz, 1H), 7.41 (d, J=3.0 Hz, 1H), 7.25 (dd, J=8.6, 6.4 Hz, 1H), 7.15 (dd, J=8.4, 2.4 Hz, 1H), 6.94 (td, J=8.4, 2.4 Hz, 1H), 6.17 (s, 1H), 4.54 (dd, J=11.6, 6.8 Hz, 1H), 4.25 (dd, J=11.2, 7.0 Hz, 1H), 3.96-4.12 (m, 1H), 3.78 (dd, J=11.6, 3.2 Hz, 6H), 3.65-3.71 (m, 1H), 3.63 (s, 3H), 2.90-3.09 (m, 2H).

LCMS (ESI) m/z: 515.0 [M+H⁺].

Example 191

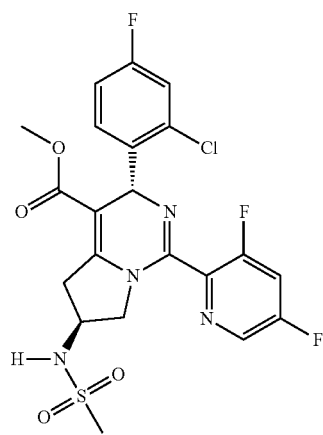

NMR data of Example 191: 1H NMR (400 MHz, CHLOROFORM-d) δ: 8.34 (d, J=2.5 Hz, 1H), 7.34 (dd, J=6.3, 8.8 Hz, 1H), 7.31-7.27 (m, 1H), 7.12 (dd, J=2.5, 8.5 Hz, 1H), 6.97 (dt, J=2.5, 8.3 Hz, 1H), 6.22 (s, 1H), 5.02 (br. s., 1H), 4.30-4.18 (m, 1H), 3.87 (dd, J=6.3, 10.8 Hz, 1H), 3.64-3.58 (m, 4H), 3.58-3.53 (m, 1H), 3.25 (dd, J=5.8, 18.3 Hz, 1H), 3.02 (s, 3H)

LCMS (ESI) m/z: 515.1 [M+H⁺].

Example 192

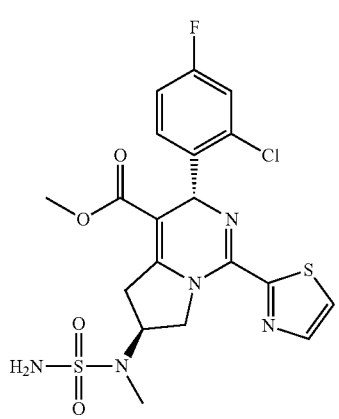

NMR data of Example 192: 1H NMR (400 MHz, CDCl3) δ: 7.82 (d, J=3.52 Hz, 1H), 7.40 (d, J=3.01 Hz, 1H), 7.24 (dd, J=8.53, 6.02 Hz, 1H), 7.14 (dd, J=8.53, 2.51 Hz, 1H), 6.94 (td, J=8.28, 2.51 Hz, 1H), 6.17 (s, 1H), 4.79 (dt, J=14.18, 7.22 Hz, 1H), 4.65 (dd, J=12.05, 6.02 Hz, 1H), 4.59 (s, 2H), 4.41 (dd, J=12.05, 7.53 Hz, 1H), 3.62 (s, 3H), 3.54 (dd, J=18.32, 8.28 Hz, 1H), 3.32-3.39 (m, 1H), 2.87 (s, 3H)

LCMS (ESI) m/z: 500.0 [M+H⁺]

Example 193

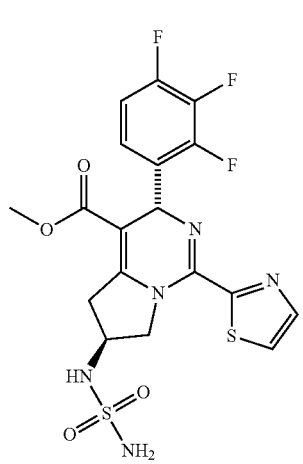

NMR data of Example 193: ¹H NMR (400 MHz, CDCl3) δ: 7.85 (d, J=3.0 Hz, 1H), 7.43 (d, J=3.0 Hz, 1H), 6.98-7.06 (m, 1H), 6.87-6.96 (m, 1H), 5.98 (s, 1H), 4.99 (d, J=7.0 Hz, 1H), 4.96 (s, 2H), 4.69 (dd, J=5.2, 11.6 Hz, 1H), 4.45 (dd, J=6.0, 12.0 Hz, 1H), 4.23-4.33 (m, 1H), 3.64 (s, 3H), 3.55 (dd, J=7.0, 18.0 Hz, 1H), 3.22 (dd, J=5.6, 18.4 Hz, 1H);

LCMS (ESI) m/z: 488.2 [M+H⁺].

Example 194

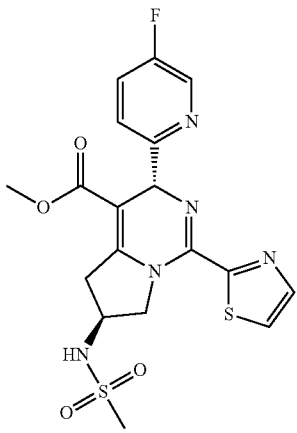

194

NMR data of Example 194: ¹H NMR (400 MHz, CDCl3) δ: 8.37 (d, J=2.4 Hz, 1H), 7.84 (d, J=3.0 Hz, 1H), 7.39-7.42 (m, 1H), 7.31-7.38 (m, 1H), 5.90 (s, 1H), 4.87 (d, J=7.2 Hz, 1H), 4.47-4.58 (m, 2H), 4.28 (qd, J=6.8, 13.6 Hz, 1H), 3.66 (s, 3H), 3.57-3.64 (m, 1H), 3.08-3.16 (m, 1H), 3.07 (s, 3H). LCMS (ESI) m/z: 452.0 [M+H⁺].

Example 195

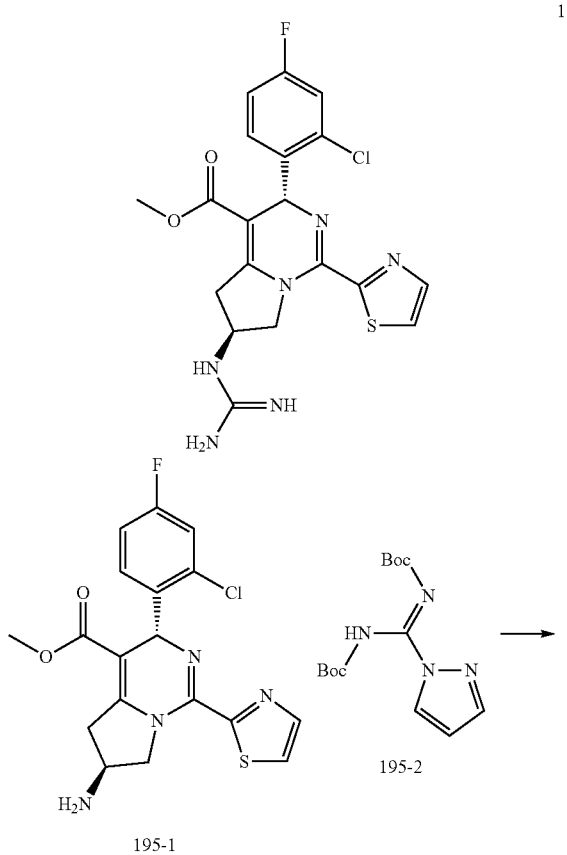

195

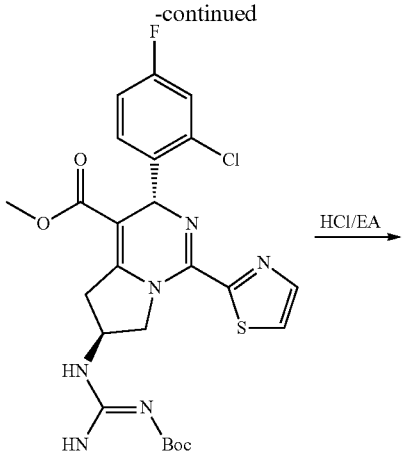

195-3

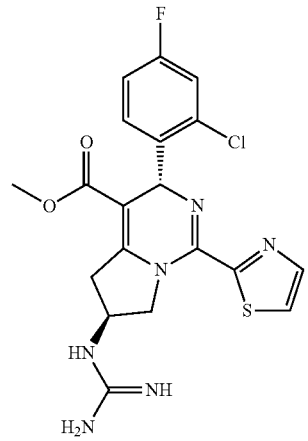

195

Step 1 Synthesis of (195-3)

Compound 195-1 (100 mg, 245.7 μmol, 1.0 eq.) was dissolved in anhydrous DCM (3 mL), and at 25° C. was added 195-2 (76.2 mg, 245.8 μmol, 1.0 eq). After the addition, the reaction mixture was stirred for 16 hours at this temperature. With TLC showing completion of the reaction, the reaction mixture was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=30:1-10:1 to obtain 130 mg white solid, yield: 79%.

LCMS (ESI) m/z: 649.2 [M+H⁺]

Step 2 Synthesis of (195)

Compound 195-3 (130 mg, 200.2 μmol, 1.0 eq.) was dissolved in anhydrous EtOAc (1 mL), and at 25° C. was added HCl/EtOAc (730 mg, 20. mmol, 99.87 eq.). After the addition, the reaction mixture was stirred for 16 hours at this temperature. With LCMS showing completion of the reaction, the reaction mixture was concentrated under reduced pressure to obtain 80 mg yellow solid, yield: 82%.

NMR data of Example 195: ¹H NMR (400 MHz, METHANOL-d4 ••δ: ••8.51-8.62 (m, 1H), 7.92 (d, J=3.26

Hz, 1H), 7.69 (d, J=3.26 Hz, 1H), 7.42 (dd, J=8.53, 6.27 Hz, 1H), 7.25 (dd, J=8.78, 2.51 Hz, 1H), 7.06 (td, J=8.34, 2.64 Hz, 1H), 6.17 (s, 1H), 4.59-4.71 (m, 2H), 4.33-4.53 (m, 2H), 3.55-3.69 (m, 4H).

LCMS (ESI) m/z: 449.1 [M+H$^+$]

Example 196

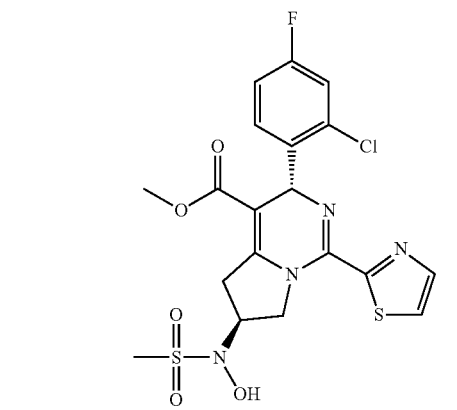

196

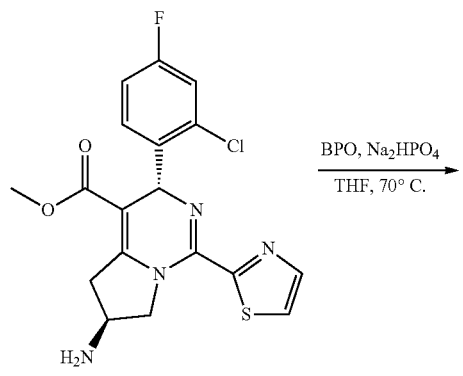

196-1

BPO, Na$_2$HPO$_4$
———————→
THF, 70° C.

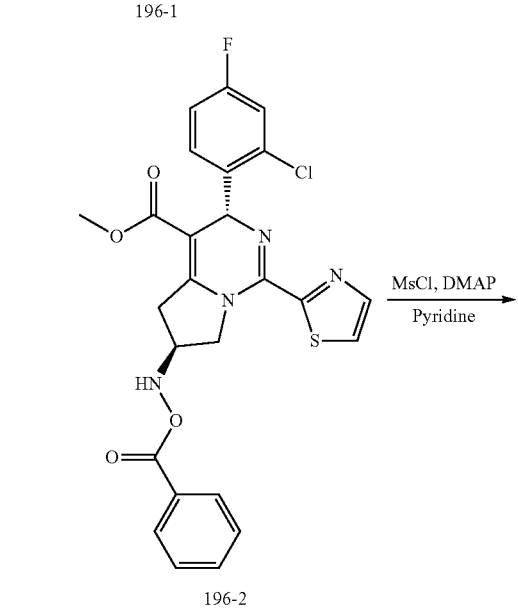

196-2

MsCl, DMAP
———————→
Pyridine

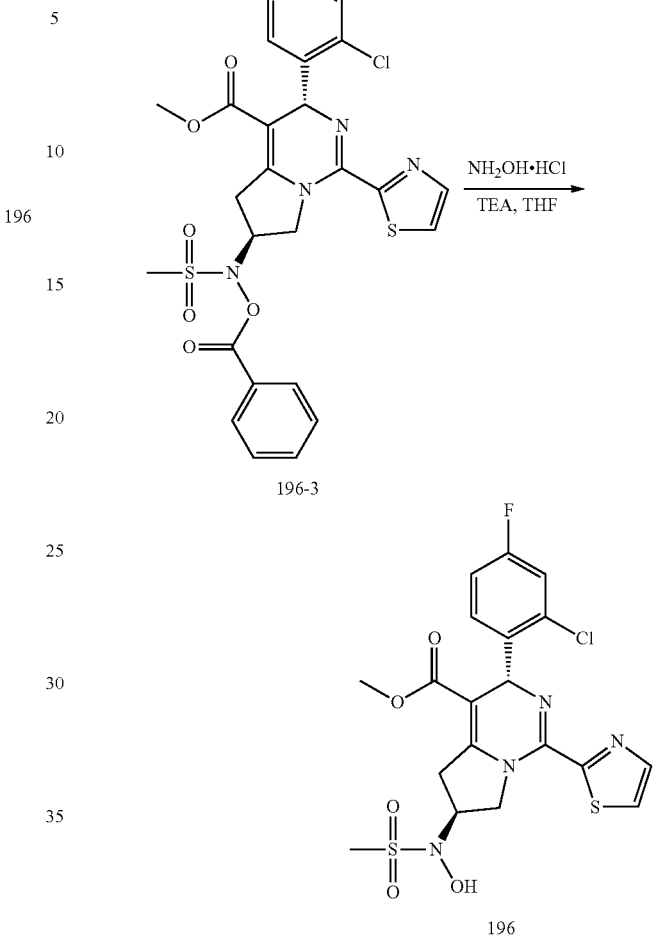

196-3

NH$_2$OH·HCl
———————→
TEA, THF

196

Step 1 Synthesis of (196-2)

Compound 196-1 (500 mg, 1.2 mmol, 1.0 eq.), BPO (327. mg, 1.35 mmol, 1.1 eq) was dissolved in anhydrous THF (5 mL), and at 25° C. was added Na$_2$HPO$_4$ (872 mg, 6.1 mmol, 5.0 eq). After the addition, the reaction mixture was warmed to 50° C., and stirred for 2 hours. With TLC showing completion of the reaction, the reaction mixture was concentrated under reduced pressure. The residue was washed with water (10 mL), and extracted with DCM (20 mL) for 3 times. The organic phases were washed with saturated brine, dried over anhydrous sodium sulfate, filtered, and concentrated under reduced pressure.

The residue was purified by column chromatograph with an eluent system of PE:EtOAc=1:1, to obtain 130 mg red solid, yield: 20%.

$^1$H NMR (400 MHz, CDCl3) •δ: ••8.05 (d, J=7.28 Hz, 2H), 7.84 (d, J=3.26 Hz, 1H), 7.60-7.69 (m, 1H), 7.51 (t, J=7.65 Hz, 2H), 7.41 (d, J=3.26 Hz, 1H), 7.31 (s, 1H), 7.14 (dd, J=2.51, 8.53 Hz, 1H), 6.94 (dt, J=2.51, 8.28 Hz, 1H), 6.19 (s, 1H), 4.79 (dd, J=3.51, 12.30 Hz, 1H), 4.44 (dd, J=6.15, 12.42 Hz, 1H), 4.12 (br. s., 1H), 3.61 (s, 3H), 3.42-3.52 (m, 2H)

Step 2 Synthesis of (196-3)

Compound 196-2 (130 mg, 246.7 umol, 1.0 eq.), methanesulfonyl chloride (141 mg, 1.2 mmol, 5.0 eq) were dissolved in pyridine (5 mL), and at 25° C. was added DMAP (90.4 mg, 740.1 μmol, 3.0 eq). After the addition, the reaction mixture was stirred for 16 hours at this temperature. With TLC showing completion of the reaction, the reaction mixture was concentrated under reduced pressure. The residue was washed with water (10 mL), and extracted with DCM (20 mL) for 3 times. The organic phases were washed with saturated brine, dried over anhydrous sodium sulfate, filtered, and concentrated under reduced pressure. The residue was purified by column chromatograph with an eluent system of PE:EtOAc=2:1, to obtain 130 mg pale yellow solid, yield: 87%.

$^1$H NMR (400 MHz, CDCl3) δ: 8.02 (d, J=7.53 Hz, 2H), 7.82 (d, J=3.01 Hz, 1H), 7.66-7.73 (m, 1H), 7.47-7.56 (m, 2H), 7.36 (d, J=2.51 Hz, 1H), 7.21 (dd, J=6.53, 8.53 Hz, 1H), 7.09 (dd, J=2.51, 8.53 Hz, 1H), 6.91 (dt, J=2.51, 8.03 Hz, 1H), 5.80 (br. s., 1H), 5.00 (quin, J=6.27 Hz, 1H), 4.78 (br. s., 1H), 4.56-4.66 (m, 1H), 3.45-3.79 (m, 5H), 3.14 (s, 3H)

Step 3 Synthesis of (196)

Compound 196-3 (130 mg, 214.85 μmol, 1.0 eq.), TEA (130 mg, 1.29 mmol, 6.0 eq) were dissolved in THF (5 mL), and at 25° C. was added hydroxylamine hydrochloride (59.7 mg, 859.4 μmol, 4.0 eq).

After the addition, the reaction mixture was stirred for 4 hours at this temperature. With TLC showing completion of the reaction, the reaction mixture was concentrated under reduced pressure. The residue was washed with water (10 mL), and extracted with EtOAc (10 mL) for 3 times. The organic phases were washed with saturated brine, dried over anhydrous sodium sulfate, filtered, and concentrated under reduced pressure. The residue was purified by instrumental separation (formic acid system) to obtain 14 mg white solid, yield: 13%.

NMR data of Example 196: $^1$H NMR (400 MHz, CDCl$_3$) δ: 7.85 (d, J=3.26 Hz, 1H), 7.43 (d, J=3.26 Hz, 1H), 7.24 (dd, J=6.02, 8.53 Hz, 1H), 7.16 (dd, J=2.51, 8.53 Hz, 1H), 6.95 (dt, J=2.51, 8.16 Hz, 1H), 6.18 (s, 1H), 4.64-4.77 (m, 2H), 4.39-4.51 (m, 1H), 3.64 (s, 3H), 3.56 (d, J=6.78 Hz, 2H), 3.10 (s, 3H)

LCMS (ESI) m/z: 501.1 [M+H$^+$]

Example 197

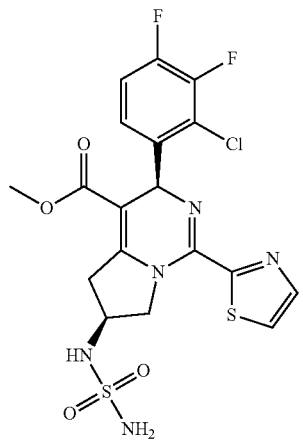

197

NMR data of Example 197: $^1$H NMR (400 MHz, MeOD-d$_4$) δ: 8.32 (dd, J=2.8, 12.8 Hz, 2H), 7.50-7.58 (m, 1H), 7.34-7.44 (m, 1H), 6.31 (s, 1H), 4.59 (br. s., 2H), 4.38 (d, J=2.8 Hz, 1H), 3.72-3.77 (m, 1H), 3.71 (s, 3H), 3.45 (dd, J=6.0, 18.4 Hz, 1H).

LCMS (ESI) m/z: 504.0 [M+H$^+$].

Example 198

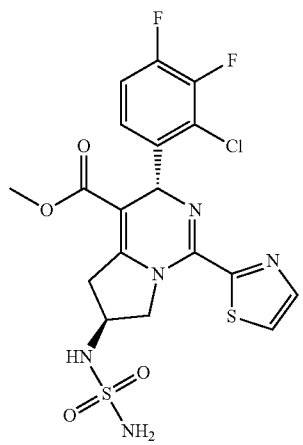

198

NMR data of Example 198: $^1$H NMR (400 MHz, MeOD-d4) δ: 8.29 (dd, J=2.64, 9.66 Hz, 2H), 7.52-7.59 (m, 1H), 7.38 (q, J=8.8 Hz, 1H), 6.33 (s, 1H), 4.55-4.63 (m, 1H), 4.46-4.53 (m, 1H), 4.32-4.41 (m, 1H), 3.69-3.75 (m, 1H), 3.68 (s, 3H), 3.36-3.43 (m, 1H), 3.35 (s, 3H).

LCMS (ESI) m/z: 504.0 [M+H$^+$].

Example 199

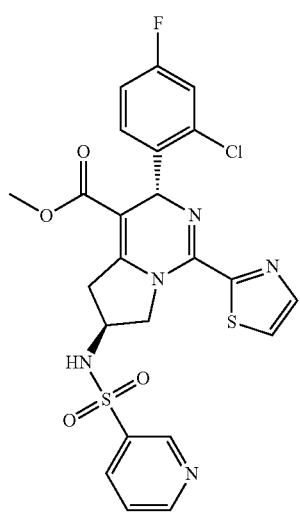

NMR data of Example 199: $^1$H NMR (400 MHz, CDCl3) δ: 9.14 (br. s., 1H), 8.84 (d, J=4.0 Hz, 1H), 8.20 (d, J=8.0 Hz, 1H), 7.77 (d, J=2.4 Hz, 1H), 7.46-7.54 (m, 1H), 7.38 (d, J=2.4 Hz, 1H), 7.15-7.22 (m, 1H), 7.12 (d, J=7.0 Hz, 1H), 6.91 (t, J=7.0 Hz, 1H), 6.11 (s, 1H), 5.81 (br. s., 1H), 4.40 (d, J=5.6 Hz, 2H), 4.16 (d, J=5.2 Hz, 1H), 3.57 (s, 3H), 3.46 (dd, J=7.2, 17.6 Hz, 1H), 3.11 (dd, J=6.4, 17.8 Hz, 1H).

LCMS (ESI) m/z: 548.1 [M+H$^+$].

Example 200

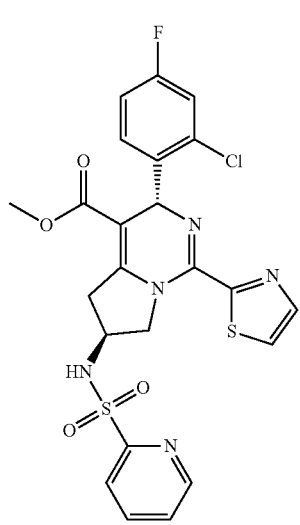

NMR data of Example 200: $^1$H NMR (400 MHz, CDCl3) δ: 8.71 (d, J=4.4 Hz, 1H), 8.02-8.09 (m, 1H), 7.96 (dt, J=1.2, 7.6 Hz, 1H), 7.75 (d, J=3.0 Hz, 1H), 7.54 (dd, J=5.0, 7.0 Hz, 1H), 7.37 (d, J=3.0 Hz, 1H), 7.19 (dd, J=6.0, 8.4 Hz, 1H), 7.11 (dd, J=2.4, 8.4 Hz, 1H), 6.90 (dt, J=2.4, 8.4 Hz, 1H), 6.11 (s, 1H), 5.77 (d, J=6.4 Hz, 1H), 4.40-4.48 (m, 1H), 4.25-4.38 (m, 2H), 3.57 (s, 3H), 3.48 (dd, J=6.4, 17.8 Hz, 1H), 3.12 (d, J=6.4, 18.0 Hz, 1H).

LCMS (ESI) m/z: 548.1 [M+H$^+$].

Example 201

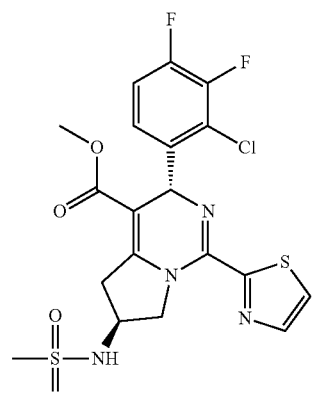

NMR data of Example 201: $^1$H NMR (400 MHz, MeOD-d4) δ: 8.31 (d, J=3.2 Hz, 2H), 7.62-7.52 (m, 1H), 7.46-7.34 (m, 1H), 6.35 (s, 1H), 4.67-4.55 (m, 1H), 4.51-4.36 (m, 2H), 3.83-3.64 (m, 4H), 3.36 (d, J=6.0 Hz, 1H), 3.08 (s, 3H).

LCMS (ESI) m/z: 503.0 [M+H$^+$].

Example 202

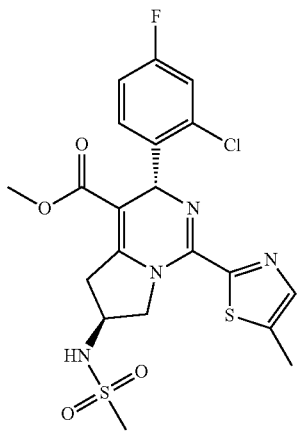

NMR data of Example 202: $^1$H NMR (400 MHz, CDCl3) δ: 7.45 (s, 1H), 7.22 (dd, J=6.4, 8.4 Hz, 1H), 7.13 (dd, J=2.4, 8.4 Hz, 1H), 6.93 (dt, J=2.4, 8.4 Hz, 1H), 6.13 (s, 1H), 4.88 (d, J=7.4 Hz, 1H), 4.42-4.57 (m, 2H), 4.21-4.35 (m, 1H), 3.63-3.70 (m, 1H), 3.61 (s, 3H), 3.12-3.19 (m, 1H), 3.07 (s, 3H), 2.44 (s, 3H). [M+1] LCMS (ESI) m/z: 499.1 [M+H$^+$].

Example 203

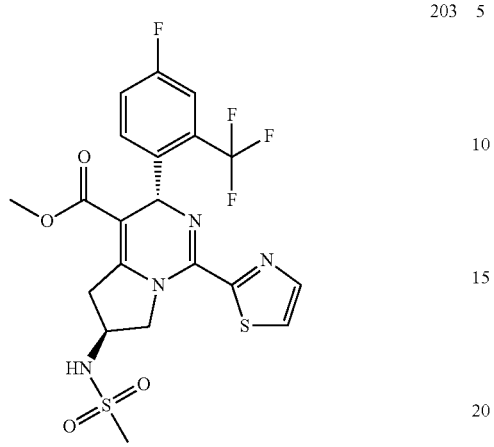

NMR data of Example 203: ¹H NMR (400 MHz, CDCl3) δ: 7.80 (d, J=3.2 Hz, 1H), 7.34-7.46 (m, 3H), 7.20 (td, J=8.0, 2.4 Hz, 1H), 6.13 (s, 1H), 4.69 (d, J=7.6 Hz, 1H), 4.62 (dd, J=11.6, 6.4 Hz, 1H), 4.41-4.48 (m, 1H), 4.30-4.37 (m, 1H), 3.73 (dd, J=17.6, 7.2 Hz, 1H), 3.56 (s, 3H), 3.19 (dd, J=18.0, 7.0 Hz, 1H), 3.08 (s, 3H).

LCMS (ESI) m/z: 519.3 [M+H⁺].

Example 204

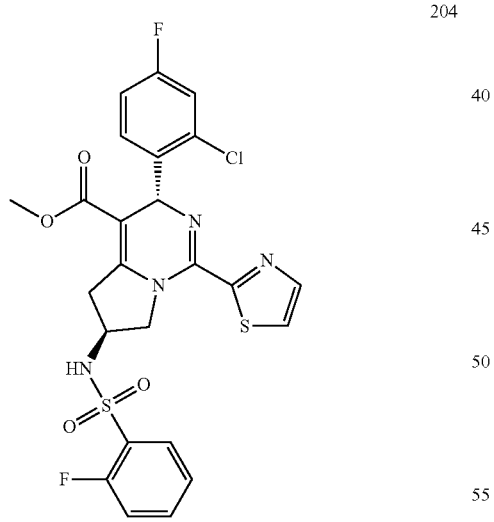

NMR data of Example 204: ¹H NMR (400 MHz, CDCl3) δ: 7.95 (t, J=7.6 Hz, 1H), 7.75 (d, J=3.0 Hz, 1H), 7.58-7.67 (m, 1H), 7.37 (d, J=3.0 Hz, 1H), 7.32 (t, J=7.6 Hz, 1H), 7.21-7.26 (m, 1H), 7.18 (dd, J=6.0, 8.4 Hz, 1H), 7.11 (dd, J=2.4, 8.4 Hz, 1H), 6.90 (dt, J=2.4, 8.4 Hz, 1H), 6.12 (s, 1H), 5.18 (br. s., 1H), 4.30-4.46 (m, 2H), 4.20 (sxt, J=6.8 Hz, 1H), 3.57 (s, 3H), 3.48 (dd, J=7.0, 18.0 Hz, 1H), 3.07 (d, J=7.0, 18.0 Hz, 1H).

LCMS (ESI) m/z: 565.3 [M+H⁺].

Example 205

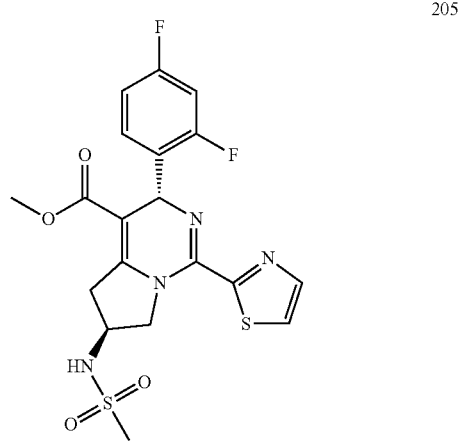 [SMILES: COC(=O)C1=C2C[C@H](NS(C)(=O)=O)CN2C(c2nccs2)=N[C@H]1c1ccc(F)cc1F]

NMR data of Example 205: ¹H NMR (400 MHz, CDCl3) δ: 7.86 (d, J=3.0 Hz, 1H), 7.44 (d, J=2.8 Hz, 1H), 7.23-7.28 (m, 1H), 6.76-6.89 (m, 2H), 5.99 (s, 1H), 4.64 (d, J=7.2 Hz, 1H), 4.56 (d, J=6.4 Hz, 2H), 4.27-4.36 (m, 1H), 3.66 (s, 3H), 3.59-3.65 (m, 1H), 3.14 (dd, J=18.0, 6.8 Hz, 1H), 3.10 (s, 3H).

LCMS (ESI) m/z: 469.2 [M+H⁺].

Example 206

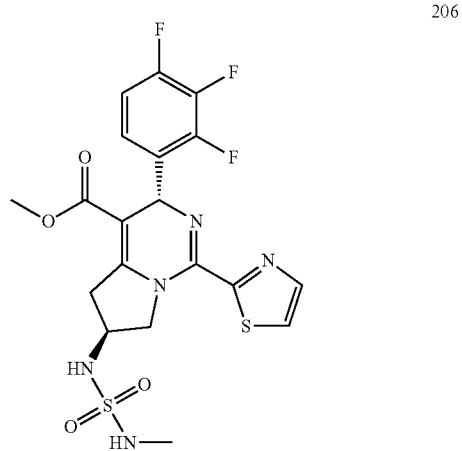 [SMILES: CNS(=O)(=O)N[C@H]1CC2=C(C(=O)OC)[C@H](c3ccc(F)c(F)c3F)N=C(c3nccs3)N2C1]

NMR data of Example 206: ¹H NMR (400 MHz, CDCl3) δ: 7.86 (d, J=3.0 Hz, 1H), 7.43 (d, J=3.0 Hz, 1H), 6.98-7.07 (m, 1H), 6.87-6.96 (m, 1H), 5.99 (s, 1H), 4.62-4.71 (m, 1H), 4.53 (d, J=6.8 Hz, 1H), 4.40-4.50 (m, 2H), 4.19 (qd, J=6.4, 12.8 Hz, 1H), 3.65 (s, 3H), 3.54 (dd, J=7.0, 18.0 Hz, 1H), 3.19 (dd, J=6.4, 18.0 Hz, 1H), 2.74 (d, J=5.2 Hz, 3H).

LCMS (ESI) m/z: 502.2 [M+H⁺].

Example 207

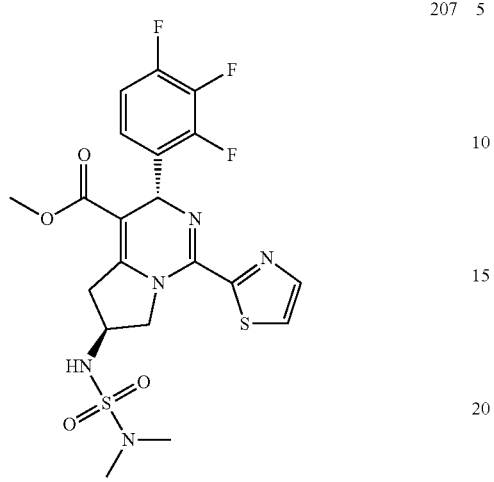

NMR data of Example 207: 1H NMR (400 MHz, CDCl3) δ: 7.85 (d, J=3.0 Hz, 1H), 7.42 (d, J=3.0 Hz, 1H), 6.97-7.08 (m, 1H), 6.85-6.96 (m, 1H), 5.99 (s, 1H), 4.53 (t, J=6.0 Hz, 2H), 4.35 (d, J=7.6 Hz, 1H), 4.13-4.23 (m, 1H), 3.64 (s, 3H), 3.57 (dd, J=18.0, 7.0 Hz, 1H), 3.13 (dd, J=17.8, 6.8 Hz, 1H), 2.84 (s, 6H).

LCMS (ESI) m/z: 516.3 [M+H$^+$].

Example 208

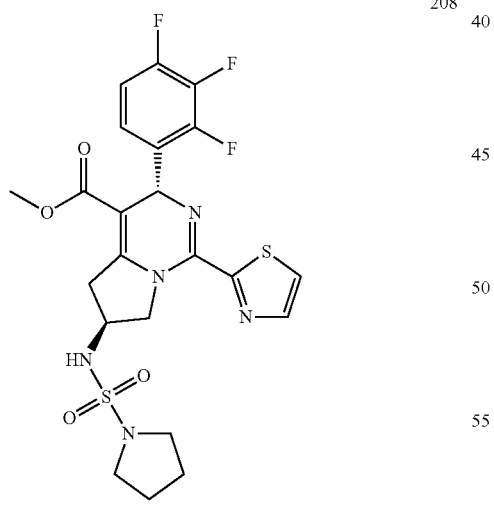

NMR data of Example 208: $^1$H NMR (400 MHz, CDCl3) δ: 7.84 (d, J=3.0 Hz, 1H), 7.42 (d, J=3.6 Hz, 1H), 6.97-7.06 (m, 1H), 6.86-6.95 (m, 1H), 5.99 (s, 1H), 4.46-4.59 (m, 3H), 4.13-4.25 (m, 1H), 3.64 (s, 3H), 3.56 (dd, J=18.0, 7.0 Hz, 1H), 3.31-3.34 (m, 4H), 3.13 (dd, J=17.8, 6.8 Hz, 1H), 1.94 (br. s., 4H).

LCMS (ESI) m/z: 542.1 [M+H$^+$].

Example 209

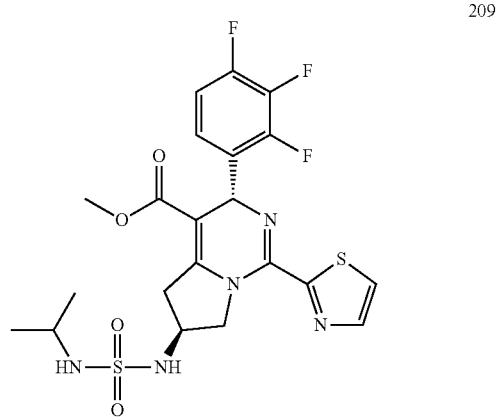 [SMILES: COC(=O)C1=C2C[C@H](NS(=O)(=O)NC(C)C)CN2C(c2nccs2)=N[C@H]1c1ccc(F)c(F)c1F]

NMR data of Example 209: $^1$H NMR (400 MHz, DMSO-d6) δ: 7.97 (d, J=3.0 Hz, 1H), 7.89 (d, J=3.2 Hz, 1H), 7.22-7.30 (m, 2H), 5.85-6.07 (m, 3H), 4.50 (dd, J=11.2, 6.9 Hz, 1H), 4.19 (dd, J=11.2, 6.4 Hz, 1H), 3.92-4.07 (m, 1H), 3.55 (s, 3H), 3.41-3.50 (m, 1H), 3.27-3.32 (m, 1H), 3.06 (dd, J=17.8, 6.9 Hz, 1H), 1.12 (dd, J=6.4, 3.14 Hz, 6H).

LCMS (ESI) m/z: 530.3 [M+H$^+$].

Example 210

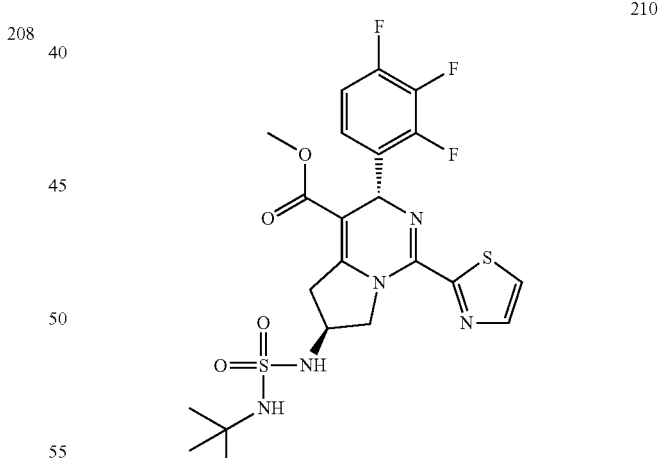

NMR data of Example 210: $^1$H NMR (400 MHz, CDCl3) δ: 7.84 (d, J=3.6 Hz, 1H), 7.41 (d, J=3.2 Hz, 1H), 6.98-7.08 (m, 1H), 6.84-6.96 (m, 1H), 5.99 (s, 1H), 4.55 (t, J=6.4 Hz, 2H), 4.44-4.50 (m, 1H), 4.24 (s, 1H), 4.13-4.22 (m, 1H), 3.64 (s, 3H), 3.57 (dd, J=18.0, 7.2 Hz, 1H), 3.14 (dd, J=17.6, 6.8 Hz, 1H), 1.37 (s, 9H).

LCMS (ESI) m/z: 544.3 [M+H$^+$].

Example 211

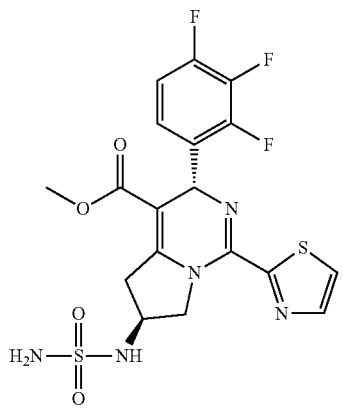

NMR data of Example 211: ¹H NMR (400 MHz, DMSO-d6) δ: 7.95 (d, J=3.0 Hz, 1H), 7.86 (d, J=3.2 Hz, 1H), 7.32-7.46 (m, 1H), 7.11-7.24 (m, 2H), 7.01 (t, J=7.6 Hz, 1H), 6.74 (s, 2H), 5.84 (s, 1H), 4.48 (dd, J=11.0, 6.8 Hz, 1H), 4.00-4.22 (m, 2H), 3.52 (s, 3H), 3.04 (dd, J=17.8, 7.2 Hz, 1H).

LCMS (ESI) m/z: 470.2 [M+H⁺].

Example 212

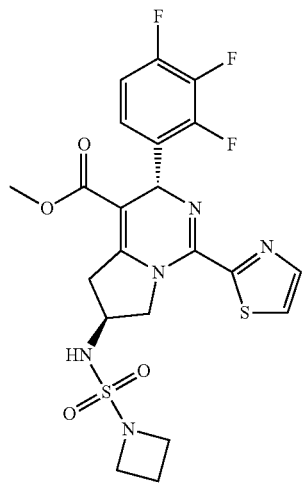

NMR data of Example 212: ¹H NMR (400 MHz, CDCl3) δ: 7.86 (d, J=3.0 Hz, 1H), 7.42 (d, J=3.0 Hz, 1H), 6.98-7.06 (m, 1H), 6.87-6.95 (m, 1H), 5.99 (s, 1H), 4.48-4.62 (m, 2H), 4.41 (d, J=7.6 Hz, 1H), 4.22 (qd, J=6.6, 13.2 Hz, 1H), 3.91 (t, J=7.6 Hz, 4H), 3.65 (s, 3H), 3.56 (dd, J=7.0, 18.0 Hz, 1H), 3.16 (dd, J=6.4, 18.0 Hz, 1H), 2.22 (quin, J=7.6 Hz, 2H)

LCMS (ESI) m/z: 528.2 [M+H⁺].

Example 213

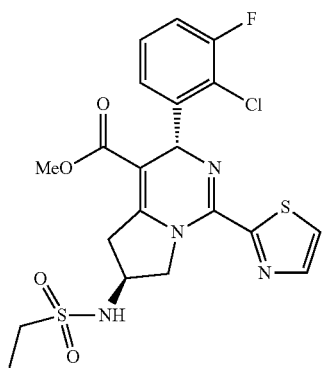

NMR data of Example 213: ¹H NMR (400 MHz, CDCl3) δ: 7.83 (d, J=3.0 Hz, 1H), 7.41 (d, J=3.0 Hz, 1H), 7.16-7.24 (m, 1H), 7.03-7.12 (m, 2H), 6.24 (s, 1H), 4.80 (d, J=7.2 Hz, 1H), 4.54-4.63 (m, 1H), 4.41-4.51 (m, 1H), 4.29 (sxt, J=7.0 Hz, 1H), 3.70 (dd, J=7.2, 17.8 Hz, 1H), 3.62 (s, 3H), 3.08-3.23 (m, 3H), 1.43 (t, J=7.2 Hz, 3H)

LCMS (ESI) m/z: 499.2 [M+H⁺].

Example 214

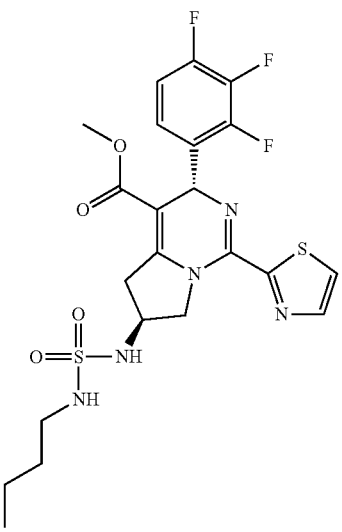

NMR data of Example 214: ¹H NMR (400 MHz, CDCl3) δ: 7.84 (d, J=3.6 Hz, 1H), 7.42 (d, J=3.2 Hz, 1H), 6.97-7.08 (m, 1H), 6.84-6.95 (m, 1H), 5.99 (s, 1H), 4.57-4.65 (m, 1H), 4.46-4.54 (m, 1H), 4.44 (d, J=7.2 Hz, 1H), 4.33 (t, J=6.0 Hz, 1H), 4.13-4.24 (m, 1H), 3.64 (s, 3H), 3.54 (dd, J=18.0, 7.2 Hz, 1H), 3.16 (dd, J=18.0, 6.8 Hz, 1H), 3.06 (q, J=6.8 Hz, 2H), 1.53 (d, J=7.6 Hz, 2H), 1.31-1.42 (m, 2H), 0.93 (t, J=7.2 Hz, 3H).

LCMS (ESI) m/z: 544.1 [M+H⁺].

Example 215

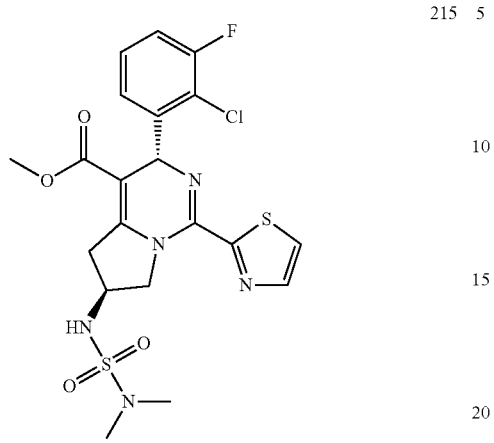

NMR data of Example 215: ¹H NMR (400 MHz, CDCl3) δ: 7.82 (d, J=3.0 Hz, 1H), 7.39 (d, J=3.6 Hz, 1H), 7.15-7.23 (m, 1H), 7.02-7.10 (m, 2H), 6.23 (s, 1H), 4.59 (d, J=7.0 Hz, 1H), 4.43-4.56 (m, 2H), 4.19 (qd, J=6.8, 13.6 Hz, 1H), 3.62-3.68 (m, 1H), 3.61 (s, 3H), 3.17 (dd, J=6.6, 18.0 Hz, 1H), 2.83 (s, 6H).

LCMS (ESI) m/z: 514.0 [M+H$^+$].

Example 216

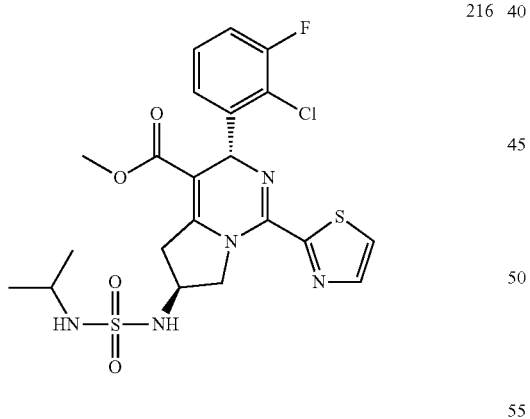

NMR data of Example 216: ¹H NMR (400 MHz, DMSO-d6) δ: 7.96 (d, J=3.0 Hz, 1H), 7.87 (d, J=3.0 Hz, 1H), 7.24-7.40 (m, 4H), 6.95 (d, J=7.6 Hz, 1H), 6.06 (s, 1H), 4.50 (dd, J=11.2, 6.8 Hz, 1H), 4.19 (dd, J=11.2, 6.4 Hz, 1H), 4.02 (q, J=6.4 Hz, 1H), 3.52 (s, 3H), 3.48 (d, J=7.2 Hz, 1H), 3.28-3.33 (m, 1H), 3.09 (dd, J=17.8, 6.8 Hz, 1H), 1.13 (t, J=5.6 Hz, 6H).

LCMS (ESI) m/z: 528.2 [M+H$^+$].

Example 217

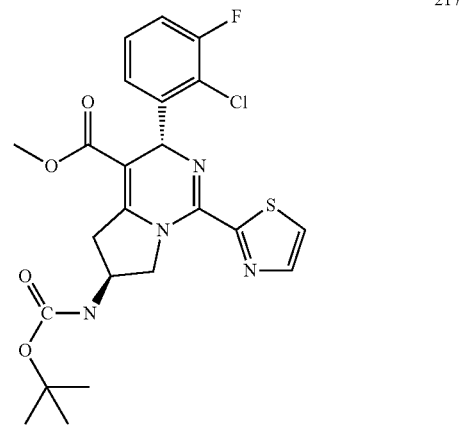

NMR data of Example 217: ¹H NMR (400 MHz, CDCl3) δ: 7.87 (d, J=3.0 Hz, 1H), 7.46 (d, J=3.0 Hz, 1H), 7.22 (dd, J=7.8, 5.2 Hz, 1H), 7.03-7.14 (m, 2H), 6.32 (s, 1H), 5.24 (br. s., 1H), 4.50 (d, J=7.0 Hz, 1H), 4.02 (dd, J=17.8, 9.8 Hz, 2H), 3.66 (s, 3H), 3.13 (dd, J=17.8, 7.2 Hz, 1H), 1.46 (s, 9H).

LCMS (ESI) m/z: 507.1 [M+H$^+$].

Example 218

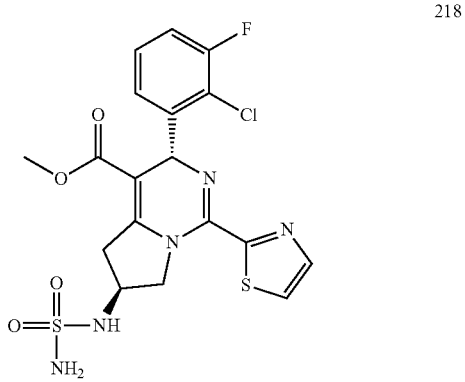 [SMILES: COC(=O)C1=C2C[C@H](NS(N)(=O)=O)CN2C(c2nccs2)=N[C@H]1c1cccc(F)c1Cl]

NMR data of Example 218: ¹H NMR (400 MHz, CDCl$_3$) δ: 7.89 (d, J=3.0 Hz, 1H), 7.65 (d, J=3.0 Hz, 1H), 7.19-7.37 (m, 2H), 7.13 (t, J=8.4 Hz, 1H), 6.18 (s, 1H), 4.53 (dd, J=6.8, 11.2 Hz, 1H), 4.33 (dd, J=6.4, 11.4 Hz, 1H), 4.11-4.28 (m, 1H), 3.66 (dd, J=7.4, 17.8 Hz, 1H), 3.59 (s, 3H), 3.17 (dd, J=7.0, 17.8 Hz, 1H).

LCMS (ESI) m/z: 486.1 [M+H$^+$].

Example 219

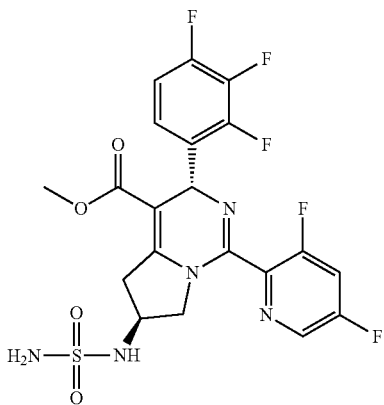

NMR data of Example 219: $^1$H NMR (400 MHz, CDCl3) δ: 8.35 (s, 1H), 7.28-7.36 (m, 1H), 7.03-7.13 (m, 1H), 6.88-6.98 (m, 1H), 6.01 (s, 1H), 5.46 (br. s., 1H), 5.01 (br. s., 2H), 4.19 (br. s., 1H), 3.87 (dd, J=10.8, 5.6 Hz, 1H), 3.57-3.72 (m, 4H), 3.49 (dd, J=18.0, 7.2 Hz, 1H), 3.22-3.36 (m, 1H).

LCMS (ESI) m/z: 518.1 [M+H$^+$].

Example 220

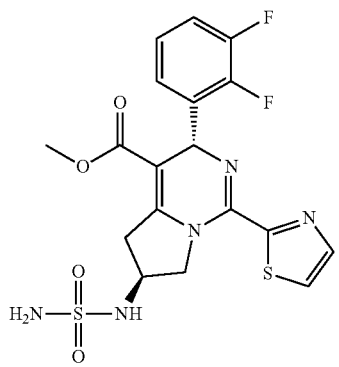

NMR data of Example 220: $^1$H NMR (400 MHz, CDCl3) δ: 7.85 (d, J=3.02 Hz, 1H), 7.42 (d, J=2.76 Hz, 1H), 6.93-7.17 (m, 3H), 6.04 (s, 1H), 5.37 (d, J=6.78 Hz, 1H), 5.19 (s, 2H), 4.64 (dd, J=11.68, 5.66 Hz, 1H), 4.46 (dd, J=11.80, 6.27 Hz, 1H), 4.24-4.33 (m, 1H), 3.62 (s, 3H), 3.52-3.60 (m, 1H), 3.23 (dd, J=18.08, 6.28 Hz, 1H).

LCMS (ESI) m/z: 470.0 [M+H$^+$].

Example 225: HBV In Vitro Dot-Blot Hybridization Test

1. Purpose of the test:
The content of HBV DNA in HepG2.2.15 cells was detected by dot-blot hybridization test to evaluate an inhibitory action of the compound on HBV with an $EC_{50}$ value as an indicator.

2. Experimental materials:
2.1 Cell lines: HepG2.2.15 Cells
HepG2.2.15 cell culture media (DMEM/F12, Invitrogen-11330057; 10% serum Invitrogen-10099141; 100 units/mL Penicillin and 10 μg/mL Streptomycin, Invitrogen-15140122; 1% non-essential amino acid, Invitrogen-11140076; 2 mM L-GLUTAMINE, Invitrogen-25030081; 300 g/ml Geneticin, Invitrogen-10131027

2.2 Reagents:
Trypsin (I Invitrogen-25300062)
DPBS (Hyclone-SH30028.01B)
DMSO (Sigma-D2650-100ML)
96-well cell-culture plate (Corning-3599)
$CO_2$ incubator (HERA-CELL-240)
20×SSC (Bio-serve Co. Ltd)
Tris-HCl (Aldirch-154563-1KG)
NaOH (Sinopharm 10019718)
NaCl (Sinopharm 10019308)
Hybridization solution (Major BioTech Co. Ltd, IMMUNE GOLD-HYB-500)
DIG Wash and Block Buffer set (Roche-11585762001)
Anti-digoxigenin-AP, Fab fragments from sheep (Roche-11093274910)

2.3 Materials and Instruments:
Positively-Charged Nylon Membrane (GE-RPN2250B)
Transfer Membrane Instrument (Bio-Rad, 170-6545)
Hybridization Oven (HL-2000 Hybrilinker)

3. Testing steps and Methods:
3.1 HepG2.2.15 cells (4×10$^4$ cells/well) were planted into a 96-well plate, and at 37° C., 5% $CO_2$ cultured overnight.
3.2 On Day 2, the compounds were diluted in totally 6 concentrations with a dilution gradient of five times. The compounds at different concentrations were added into the culture wells in duplicate. The final concentration of DMSO in the culture media was 1%. 1 μM GLS4 was used as 100% inhibition control; 1% DMSO as 0% inhibition control.
3.3 On Day 5, replacing with the fresh culture media containing the compound was performed.
3.4 On Day 8 and Day 9, the culture media in the culture wells was removed, and the cells were harvested for dot-blot hybridization.
The lysate was added into a culture well, and at 37° C. incubating for half an hour to disintegrate cells; the supernatant was obtained by centrifugation and transferred into a new microplate; a denaturation solution was added, after sufficient mixing the denatured sample was transferred and imprinted onto a Nylon membrane, the nucleic acid was fixed onto the membrane by UV cross-linking.
Pre-hybridization: the membrane was incubated at 60° C. in a hybridization solution for 1 hour.
Hybridization: heating the denatured digoxin-labelled HBV DNA probe and incubating at 60° C. overnight.
Membrane Washing: performing high strigency washing twice, low strigency washing for 3 times.
Blocking: incubating the membrane at room temperature in a blocking solution for 30-60 minutes.
Hybridization: diluting the Antibody Solution with the blocking solution, in which the membrane was placed and incubated at room temperature for 30-60 minutes.
Developing: washing the membrane in a Detection Buffer for 5 minutes, followed by adding a developing solution, pressing and exposing.
The photos was saved in tiff format, and a gray value of the dot was quantified with quantity one software.

3.5 Data Analysis:
3.5.1 The inhibition percentage was calculated: % Inh.=[1−(sample dot gray value−1 μM GLS4 dot gray value 1)/(DMSO control dot gray value−1 μM GLS4 dot gray value 1)]×100.
3.5.2 Calculating $EC_{50}$: the concentration of the compound for 50% inhibition of HBV ($EC_{50}$) was calculated by using GraphPad Prism Software.
4. Test Results
The test results were shown in Table 2:

TABLE 2

Testing Results of $EC_{50}$ by Dot-blot Hybridization Assay

| Tested Samples (Title Compound) | Concentration for 50% inhibition of HBV ($EC_{50}$) value |
|---|---|
| Example 1 | B |
| Example 2 | D |
| Example 3 | B |
| Example 4 | B |
| Example 5 | B |
| Example 6 | A |
| Example 7 | B |
| Example 8 | B |
| Example 9 | B |
| Example 10 | D |
| Example 11 | D |
| Example 12 | B |
| Example 13 | B |
| Example 14 | C |
| Example 15 | B |
| Example 16 | D |
| Example 17 | D |
| Example 18 | D |
| Example 19 | D |
| Example 20 | D |
| Example 21 | D |
| Example 22 | D |
| Example 23 | D |
| Example 24 | C |
| Example 25 | D |
| Example 26 | C |
| Example 27 | B |
| Example 28 | B |
| Example 29 | B |
| Example 30 | B |
| Example 31 | B |
| Example 32 | D |
| Example 33 | D |
| Example 34 | B |
| Example 35 | D |
| Example 36 | C |
| Example 37 | D |
| Example 38 | A |
| Example 39 | A |
| Example 40 | D |
| Example 41 | D |
| Example 42 | A |
| Example 43 | B |
| Example 44 | A |
| Example 45 | A |
| Example 46 | B |
| Example 47 | A |
| Example 48 | B |
| Example 49 | B |
| Example 50 | D |
| Example 51 | B |
| Example 52 | C |
| Example 53 | A |
| Example 54 | A |
| Example 55 | A |
| Example 56 | A |
| Example 57 | A |
| Example 58 | A |
| Example 59 | A |
| Example 60 | A |
| Example 61 | A |
| Example 62 | A |
| Example 63 | B |
| Example 64 | B |
| Example 65 | B |
| Example 66 | B |
| Example 67 | B |
| Example 68 | D |
| Example 69 | B |
| Example 70 | B |
| Example 71 | B |
| Example 72 | C |
| Example 73 | D |
| Example 74 | D |
| Example 75 | D |
| Example 76 | D |
| Example 77 | D |
| Example 78 | D |
| Example 79 | D |
| Example 80 | D |
| Example 81 | D |
| Example 82 | B |
| Example 83 | D |
| Example 84 | B |
| Example 85 | B |
| Example 86 | C |
| Example 87 | C |
| Example 88 | C |
| Example 89 | D |
| Example 90 | B |
| Example 91 | B |
| Example 92 | A |
| Example 93 | B |
| Example 94 | D |
| Example 95 | B |
| Example 96 | D |
| Example 97 | D |
| Example 98 | D |
| Example 99 | D |
| Example 100 | D |
| Example 101 | C |
| Example 102 | C |
| Example 103 | B |
| Example 104 | D |
| Example 105 | C |
| Example 106 | D |
| Example 107 | B |
| Example 108 | D |
| Example 109 | D |
| Example 110 | D |
| Example 111 | D |
| Example 112 | D |
| Example 113 | B |
| Example 114 | B |
| Example 115 | B |
| Example 116 | A |
| Example 117 | A |
| Example 118 | B |
| Example 119 | A |
| Example 120 | A |
| Example 121 | A |
| Example 122 | D |
| Example 123 | A |
| Example 124 | A |
| Example 125 | A |
| Example 126 | A |
| Example 127 | A |
| Example 128 | A |
| Example 129 | A |
| Example 130 | A |
| Example 131 | D |
| Example 132 | A |
| Example 133 | B |
| Example 134 | D |

TABLE 2-continued

Testing Results of EC$_{50}$ by Dot-blot Hybridization Assay

| Tested Samples (Title Compound) | Concentration for 50% inhibition of HBV (EC$_{50}$)value |
|---|---|
| Example 135 | C |
| Example 136 | C |
| Example 137 | D |
| Example 138 | A |
| Example 139 | D |
| Example 140 | C |
| Example 141 | C |
| Example 142 | B |
| Example 143 | B |
| Example 144 | A |
| Example 145 | C |
| Example 146 | D |
| Example 147 | D |
| Example 148 | B |
| Example 149 | A |
| Example 150 | B |
| Example 151 | A |
| Example 152 | B |
| Example 153 | A |
| Example 154 | B |
| Example 155 | A |
| Example 156 | A |
| Example 157 | A |
| Example 158 | A |
| Example 159 | A |
| Example 160 | A |
| Example 161 | A |
| Example 162 | B |
| Example 163 | A |
| Example 164 | D |
| Example 165 | A |

Bioactivity Definition: A: EC$_{50}$ ≤ 100 nM; B: 100 nM < EC$_{50}$ ≤ 500 nM; C: 500 nM < EC$_{50}$ ≤ 1000 nM; D: 1000 nM < EC$_{50}$ ≤ 5000 nM;
Conclusion: the compound of the invention showed a significantly inhibitory action on HBV DNA.

Example 226: HBV In Vitro Assay Quantitive qPCR Test

1 Purpose of the test:
The content of HBV DNA in HepG2.2.15 cells was detected by real time quantitive qPCR test to evaluate an inhibitory action of the compound on HBV with an EC$_{50}$ value of the compound as an indicator.

2 Experimental materials:

2.1 Cell lines: HepG2.2.15 Cells
HepG2.2.15 cell culture media (DMEM/F12, Invitrogen-11330057; 10% serum, Invitrogen-10099141; 100 units/ml Penicillin and 10 μg/ml Streptomycin, Invitrogen-15140122; 1% non-essential amino acid, Invitrogen-1140076; 2 mM L-GLUTAMINE, Invitrogen-25030081; 300 μg/ml Geneticin, Invitrogen-10131027

2.2 Reagents:
trypsin (Invitrogen-25300062)
DPBS (Hyclone-SH30028.01B)
DMSO (Sigma-D2650-100ML)
High-Throughput DNA Purification Kit (QIAamp 96 DNA Blood Kit, Qiagen-51162)
Quantitative Fast Start Universal Probe Reagent (Fast-Start Universal Probe Master, Roche-04914058001)

2.3 Materials and Instruments:
96-well cell culture plate (Corning-3599)
CO$_2$ Incubator (HERA-CELL-240)
Optical Sealing Membrane (ABI-4311971)
Quantitative PCR 96-well Plate (Applied Biosystems-4306737)
Fluorescent Quantitative PCR Instrument (Applied Biosystems-7500 real time PCR system)

3. Testing steps and Methods:

3.1 HepG2.2.15 cells (4×10$^4$ cells/well) were planted into a 96-well plate, and at 37° C., 5% CO$_2$ cultured overnight.

3.2 On Day 2, the compounds were diluted in totally 8 concentrations with a dilution gradient of three times. The compounds at different concentrations were added into the culture wells in duplicate. The final concentration of DMSO in the culture media was 1%. 1 μM GLS4 was used as 100% inhibition control; 1% DMSO as 0% inhibition control.

3.3 On Day 5, replacing with the fresh culture media containing the compound was performed.

3.4 On Day 8, the culture media in the culture wells was collected, and DNA was extracted with a High-Throughput DNA Purification Kit (Qiagen-51162), See Specification of the product for specific steps.

3.5 Preparation of PCR Reaction Mixture was shown in Table 1:

TABLE 1

Preparation of PCR Reaction Mixture

| Project | Volume Required for Preparing 1 well (μL) | Volume Required for Preparing 80 wells (μL) |
|---|---|---|
| Quantitative Fast Start Universal Probe Reagent | 12.5 | 1000 |
| Upstream primer (10 μmol) | 1 | 80 |
| Downstream primer (10 μmol) | 1 | 80 |
| Probe (10 μmol) | 0.5 | 40 |

Upstream primer sequence: GTGTCTGCGGCGTTTTATCA
Downstream primer sequence: GACAAACGGGCAACATACCTT
Probe sequence: 5' + FAM + CCTCTKCATCCTGCTGCTATGCCTCATC + TAMRA-3'

3.6 To each well of a 96-well PCR plate was added 15 μl reaction mixture, and then to each well was added 10 μl sample DNA or HBV DNA standard.

3.7 The reaction conditions of PCR were: heating at 95° C. for 10 minutes; then at 95° C. denaturing for 15 seconds, and at 60° C. extending for 1 minute, totally 40 cycles.

3.8 Data Analysis:

3.8.1 The inhibition percentage was calculated: % Inh.=[1−(DNA copy number in sample−DNA copy number in 1 μM GLS4)/(DNA copy number in DMSO control−DNA copy number in 1 μM GLS4)]×100.

3.8.2 Calculating EC$_{50}$: the concentration of the compound for 50% inhibition of HBV (EC$_{50}$) was calculated by using GraphPad Prism Software.

4 Testing Results

The testing results were shown in Table 3:

TABLE 3

Testing Results of $EC_{50}$ by qPCR Assay

| Tested Samples (Title Compound) | Concentration for 50% inhibition of HBV ($EC_{50}$) value |
|---|---|
| Example 166 | A |
| Example 167 | A |
| Example 168 | B |
| Example 169 | A |
| Example 170 | A |
| Example 171 | A |
| Example 172 | A |
| Example 173 | A |
| Example 174 | B |
| Example 175 | D |
| Example 176 | D |
| Example 177 | A |
| Example 178 | B |
| Example 179 | B |
| Example 180 | A |
| Example 181 | A |
| Example 182 | A |
| Example 183 | A |
| Example 184 | B |
| Example 185 | A |
| Example 186 | D |
| Example 187 | A |
| Example 188 | A |
| Example 189 | A |
| Example 190 | B |
| Example 191 | A |
| Example 192 | A |
| Example 193 | A |
| Example 194 | D |
| Example 195 | D |
| Example 196 | D |
| Example 197 | D |
| Example 198 | A |
| Example 199 | A |
| Example 200 | A |
| Example 201 | A |
| Example 202 | B |
| Example 203 | B |
| Example 204 | A |
| Example 205 | A |
| Example 206 | A |
| Example 207 | A |
| Example 208 | A |
| Example 209 | A |
| Example 210 | A |
| Example 211 | A |
| Example 212 | B |
| Example 213 | A |
| Example 214 | A |
| Example 215 | A |
| Example 216 | A |
| Example 217 | A |
| Example 218 | A |
| Example 219 | B |
| Example 220 | A |

Bioactivity definition: A: $EC_{50} \leq 100$ nM; B: $100$ nM $< EC_{50} \leq 500$ nM; C: $500$ nM $< EC_{50} \leq 1000$ nM; D: $1000$ nM $< EC_{50} \leq 5000$ nM;
Conclusion: the compound of the invention showed a significantly inhibitory action on HBV DNA.

We claim:

1. A compound represented by formula (I) or a pharmaceutically acceptable salt thereof,

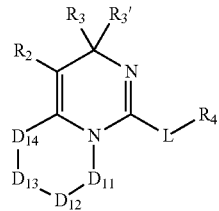

(I)

wherein, $D_{11}$ is a single bond $D_{12-14}$ are each independently —C($R_{d1}$)($R_{d2}$)—;

L is selected from a single bond, —O—, —S—, —NH—, —C(=O)—, —C(=S)—, —S(=O)—, —S(=O)$_2$—, —C(=O)N($R_{d3}$)—, —N($R_{d4}$)—, —[C($R_{d1}$)($R_{d2}$)]$_{0-6}$;

$R_2$ is selected from

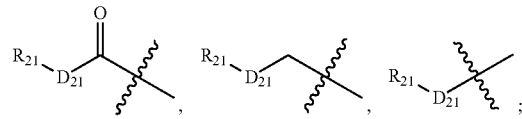

$D_{21}$ is selected from a single bond, —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, —[C($R_{d1}$)($R_{d2}$)]$_{0-6}$;

$R_3$ is selected from the following groups optionally substituted by $R_{01}$: 3-6 membered cycloalkyl or heterocycloalkyl, 6-10 membered aryl or heteroaryl;

$R_4$ is selected from the following groups optionally substituted by $R_{01}$: $C_{1-10}$alkyl or heteroalkyl, 3-6 membered cycloalkyl or heterocycloalkyl, 6-10 membered aryl or heteroaryl;

$R_3'$, $R_{21}$, $R_{d1-7}$ are separately and independently selected from H, F, Cl, Br, I, OH, NH$_2$, CN, —COOH, or selected from the following groups optionally substituted by $R_{01}$: $C_{1-4}$ alkyl, —$C_{0-4}$ alkylphenyl, —$C_{0-4}$ alkyl-3-6 membered heterocyclyl, 3-6 membered heterocyclocarbonyl- or benzenesulfonamido -$D_{01}$-$D_{02}$-$D_{03}$-H,

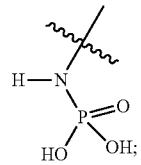

$D_{01}$ is selected from a single bond, —$C_{1-4}$ alkyl-;
$D_{02}$ is selected from O, S, NH, —C(=O)—, —S(=O)$_2$—, —C(=O)O—, —C(=O)NH—, —C(=S)NH—, —S(=O)$_2$NH—, —S(=O)NH—, —NHC(=O)O—, —NHC(=O)NH—, —NHS(=O)$_2$NH—, —C(=O)NHS(=O)$_2$—, —NHS(=O)NH—, —C(=O)NHS(=O)—, —NHS(=O)$_2$O—, —NHS(=O)O—, —C(=N)—, —NH—C(=N)—;
$D_{03}$ is selected from a single bond, —$C_{1-4}$ alkyl-, —$C_{2-4}$ alkenyl-, —$C_{3-6}$ cycloalkyl-, -3-6 membered heterocycloalkyl-, 5-6 membered aryl, 5-6 membered heteroaryl;

heteroalkyl in $R_4$ refers to an alkyl wherein one or more than one carbon atoms are replaced by a B, O, N or S heteroatom, provided that: the N or S heteroatoms are optionally oxidized; the N heteroatoms are optionally quaternized; the N and B heteroatoms are substituted with hydrogen or alkyl to fulfill their valency; and at most two heteroatoms are adjacent, where chemically possible;

heterocycloalkyl refers to a cycloalkyl wherein one or more than one carbon atoms are replaced by a B, O, N or S heteroatom, provided that: the N or S heteroatoms are optionally oxidized; the N heteroatoms are optionally quaternized; the N and B heteroatoms are substituted with hydrogen or alkyl to fulfill their valency; and at most two heteroatoms are adjacent, where chemically possible;

aryl refers to a polyunsaturated aromatic hydrocarbon substituent, which can be monosubstituted, disubstituted or multisubstituted, can be univalent, bivalent or multivalent, and can be monocyclic or polycyclic wherein at least one ring is aromatic; they are fused together or connected by a covalent linkage;

heteroaryl refers to an aryl containing 1 to 4 heteroatoms, the heteroatom is selected from the group consisting of B, N, O, and S, provided that: the nitrogen and sulfur atoms are optionally oxidized, and the nitrogen atom is optionally quaternized; the heteroaryl group can be connected to the rest part of a molecule via a heteroatom;

"hetero" in heterocyclocarbonyl and heterocycloalkylamino represents a heteroatom or heteroatom group, selected from —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, =O, =S, —C(=O)O—, —C(=O)—, —C(=S)—, —S(=O), —S(=O)$_2$— or/and —P(=O)(O$R_{d8}$)$_2$;

$R_{01}$ is selected from F, Cl, Br, I, CN, OH, SH, NH$_2$, CHO, COOH, =NH, =O, =S, or the following groups optionally substituted by $R_{001}$: $C_{1-10}$ alkyl, $C_{1-10}$alkylamino, N,N-di($C_{1-10}$ alkyl) amino, $C_{1-10}$alkoxy, $C_{1-10}$alkylacyl, $C_{1-10}$alkoxycarbonyl, —$C_{1-5}$ alkyl-C(=O)O—$C_{1-5}$ alkyl, $C_{1-10}$ alkylsulfonyl, $C_{1-10}$alkylsulfinyl, 3-10 membered cycloalkyl, 3-10 membered cycloalkylamino, 3-10 membered heterocycloalkylamino, 3-10 membered cycloalkoxy, 3-10 membered cycloalkylcarbonyl, 3-10 membered cycloalkoxycarbonyl, 3-10 membered cycloalkylsulfonyl, 3-10 membered cycloalkylsulfinyl;

$R_{001}$ is selected from F, Cl, Br, I, CN, OH, N(CH$_3$)$_2$, NH(CH$_3$), NH$_2$, CHO, COOH, =NH, =O, =S, trihalomethyl, dihalomethyl, monohalomethyl, aminomethyl, hydroxymethyl, methyl, methoxy, formyl, methoxycarbonyl, methylsulfonyl, methylsulfinyl;

in any of the above described cases, the number of $R_{01}$, $R_{001}$ is separately and independently selected from 0, 1, 2 or 3, and the number of heteroatom or heteroatom group is separately and independently selected from 1, 2 or 3.

2. A compound or pharmaceutically acceptable salt thereof, having a structure shown as formula (II):

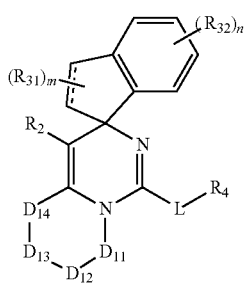

wherein, $R_{31-32}$ are separately and independently selected from H, F, Cl, Br, I, OH, NH$_2$, CN, —COOH, or selected from the following groups optionally substituted by 1, 2 or 3 $R_{01}$: $C_{1-4}$ alkyl, $C_{0-4}$ alkylphenyl, $C_{0-4}$ alkyl-3-6 membered heterocyclyl, 3-6 membered heterocyclocarbonyl or benzenesulfonamido, -$D_{01}$-$D_{02}$-$D_{03}$-H,

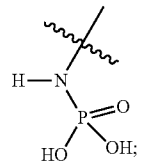 [SMILES: *NP(=O)(O)O]

$D_{01}$ is selected from a single bond, —$C_{1-4}$ alkyl-;
$D_{02}$ is selected from O, S, NH, —C(=O)—, —S(=O)$_2$—, —C(=O)O—, —C(=O)NH—, —C(=S)NH—, —S(=O)$_2$NH—, —S(=O)NH—, —NHC(=O)O—, —NHC(=O)NH—, —NHS(=O)$_2$NH—, —C(=O)NHS(=O)$_2$—, —NHS(=O)NH—, —C(=O)NHS(=O)—, —NHS(=O)$_2$O—, —NHS(=O)O—, —C(=N)—, —NH—C(=N)—;
$D_{03}$ is selected from a single bond, —$C_{1-4}$ alkyl-, —$C_{2-4}$ alkenyl-, —$C_{3-6}$ cycloalkyl-, -3-6 membered heterocycloalkyl-, 5-6 membered aryl, 5-6 membered heteroaryl;
m, n are separately and independently selected from 1 or 2;
===== represents a single bond or a double bond;
$D_{11}$ is a single bond;
$D_{12-14}$ are —C($R_{d1}$)($R_{d2}$)—;
L is selected from a single bond, —O—, —S—, —NH—, —C(=O)—, —C(=S)—, —S(=O)—, —S(=O)$_2$—, —C(=O)N($R_{d3}$)—, —N($R_{d4}$)—, —[C($R_{d1}$)($R_{d2}$)]$_{0-6}$;
$R_2$ is selected from

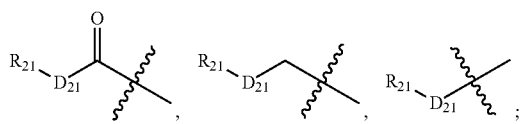

$D_{21}$ is selected from a single bond, —C(=O)N($R_{d3}$)—, —N($R_{d4}$)—, —C(=N$R_{d5}$)—, —S(=O)$_2$N($R_{d6}$)$_{0-6}$—, —S(=O)N($R_{d7}$)—, —O—, —S—, —[C($R_{d1}$)($R_{d2}$)]$_{0-6}$;
$R_4$ are separately and independently selected from the following groups optionally substituted by $R_{01}$; $C_{1-10}$ alkyl or heteroalkyl, 3-6 membered cycloalkyl or heterocycloalkyl, 6-10 membered aryl or heteroaryl;

$R_{21}$, $R_{d1-7}$ are separately and independently selected from H, F, Cl, Br, I, OH, $NH_2$, CN, —COOH, or selected from the following groups optionally substituted by $R_{01}$: $C_{1-4}$ alkyl, —$C_{0-4}$ alkylphenyl, —$C_{0-4}$ alkyl-3-6 membered heterocyclyl, 3-6 membered heterocyclocarbonyl-, benzenesulfonamido-, -$D_{01}$-$D_{02}$-$D_{03}$-H,

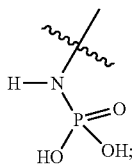

the heteroalkyl in $R_4$ refers to an alkyl wherein one or more than one carbon atoms are replaced by a B, O, N or S heteroatom, provided that: the N or S heteroatoms are optionally oxidized; the N heteroatoms are optionally quaternized; the N and B heteroatoms are substituted with hydrogen or alkyl to fulfill their valency; and at most two heteroatoms are adjacent, where chemically possible;

heterocycloalkyl refers to a cycloalkyl wherein one or more than one carbon atoms are replaced by a B, O, N or S heteroatom, provided that: the N or S heteroatoms are optionally oxidized; the N heteroatoms are optionally quaternized; the N and B heteroatoms are substituted with hydrogen or alkyl to fulfill their valency; and at most two heteroatoms are adjacent, where chemically possible;

aryl refers to a polyunsaturated aromatic hydrocarbon substituent, which can be monosubstituted, disubstituted or multisubstituted, can be univalent, bivalent or multivalent, and can be monocyclic or polycyclic wherein at least one ring is aromatic; they are fused together or connected by a covalent linkage;

heteroaryl refers to an aryl containing 1 to 4 heteroatoms, the heteroatom is selected from the group consisting of B, N, O, and S, provided that: the nitrogen and sulfur atoms are optionally oxidized, and the nitrogen atom is optionally quaternized; the heteroaryl group can be connected to the rest part of a molecule via a heteroatom;

"hetero" in heterocyclocarbonyl and heterocycloalkylamino represents a heteroatom or heteroatom group, selected from —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, =O, =S, —C(=O)O—, —C(=O)—, —C(=S)—, —S(=O), —S(=O)$_2$— or/and —P(=O)(O$R_{d8}$)$_2$;

$R_{01}$ is selected from F, Cl, Br, I, CN, OH, SH, $NH_2$, CHO, COOH, =NH, =O, =S, or the following groups optionally substituted by $R_{001}$: $C_{1-10}$ alkyl, $C_{1-10}$ alkylamino, N,N-di($C_{1-10}$ alkyl) amino, $C_{1-10}$ alkoxy, $C_{1-10}$ alkylacyl, $C_{1-10}$ alkoxycarbonyl, —$C_{1-5}$ alkyl-C(=O) O—$C_{1-5}$ alkyl, $C_{1-10}$ alkylsulfonyl, $C_{1-10}$ alkylsulfinyl, 3-10 membered cycloalkyl, 3-10 membered cycloalkylamino, 3-10 membered heterocycloalkylamino, 3-10 membered cycloalkoxy, 3-10 membered cycloalkylcarbonyl, 3-10 membered cycloalkoxycarbonyl, 3-10 membered cycloalkylsulfonyl, 3-10 membered cycloalkylsulfinyl;

$R_{001}$ is selected from F, Cl, Br, I, CN, OH, N($CH_3$)$_2$, NH($CH_3$), $NH_2$, CHO, COOH, =NH, =O, =S, trihalomethyl, dihalomethyl, monohalomethyl, aminomethyl, hydroxymethyl, methyl, methoxy, formyl, methoxycarbonyl, methylsulfonyl, methylsulfinyl;

in any of the above described cases, the number of $R_1$, $R_{001}$ is separately and independently selected from 0, 1, 2 or 3, and the number of heteroatom or heteroatom group is separately and independently selected from 1, 2 or 3.

3. The compound or pharmaceutically acceptable salt thereof according to claim 1, wherein $R_{01}$ is selected from halogen, CN, =NH, =O, =S, COOH, or the following groups optionally substituted by 1, 2 or 3 $R_{001}$: hydroxy, amino, $C_{1-4}$ alkyl, $C_{1-4}$ alkoxy, $C_{0-4}$ alkyl-C(=O)O—$C_{1-4}$ alkyl.

4. The compound or pharmaceutically acceptable salt thereof according to claim 1, wherein $R_3'$, $R_{21}$ and $R_{d1-d7}$ are separately and independently selected from H, F, Cl, Br, I, OH, $NH_2$, CN, —COOH, or selected from the following groups optionally substituted by 1, 2 or 3 $R_{01}$: $CH_3$,

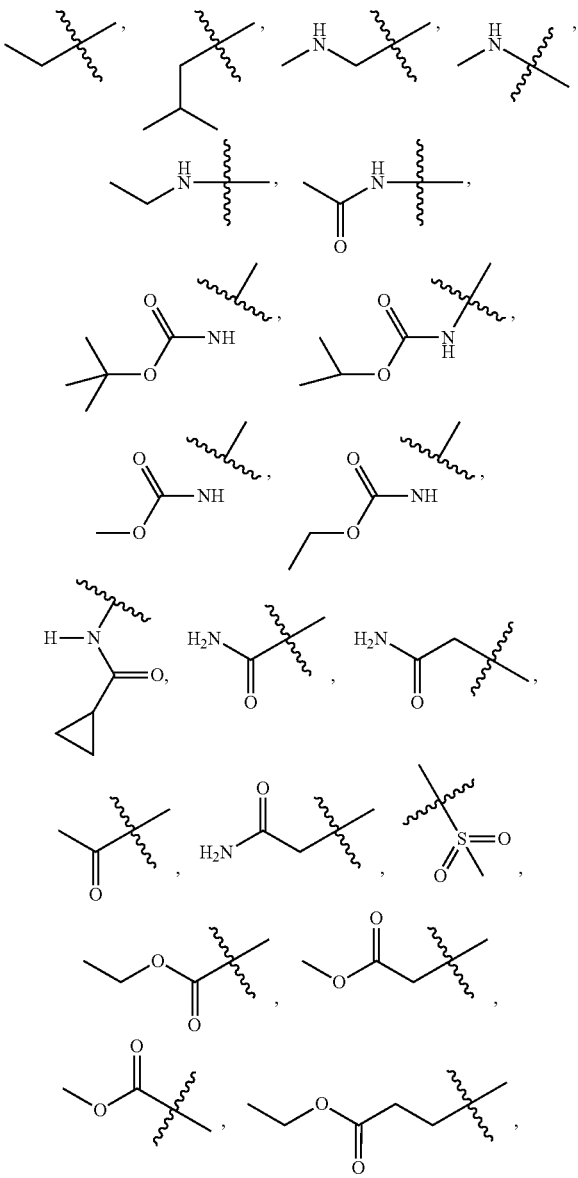

507
-continued
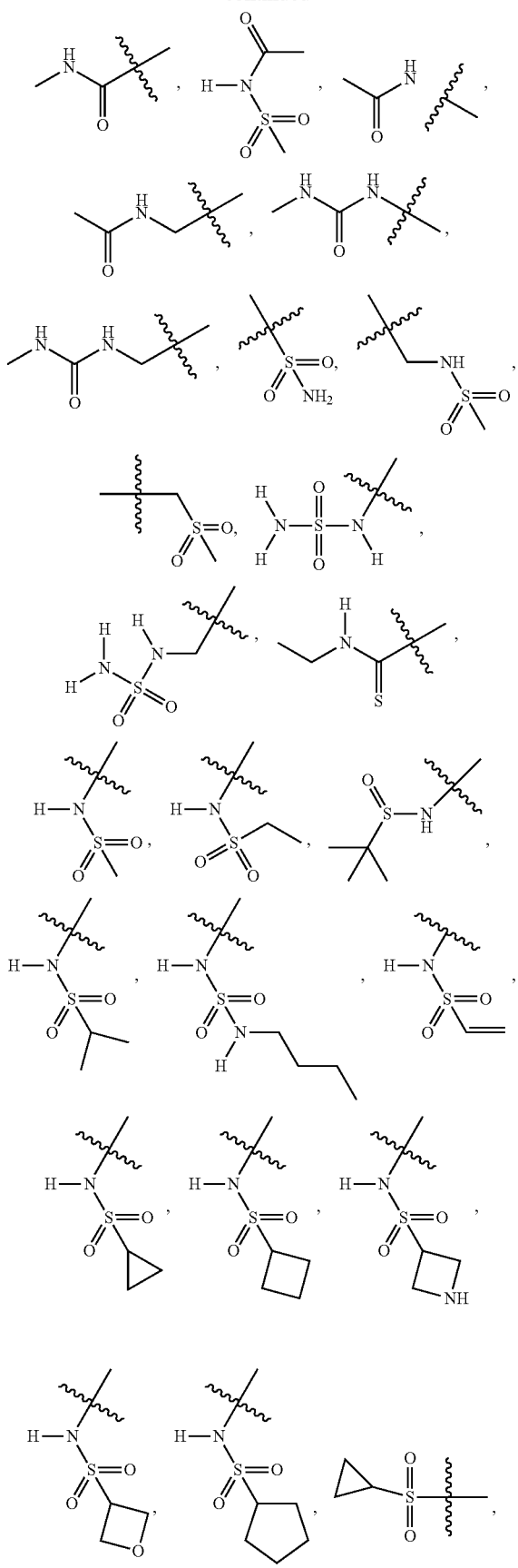
508
-continued
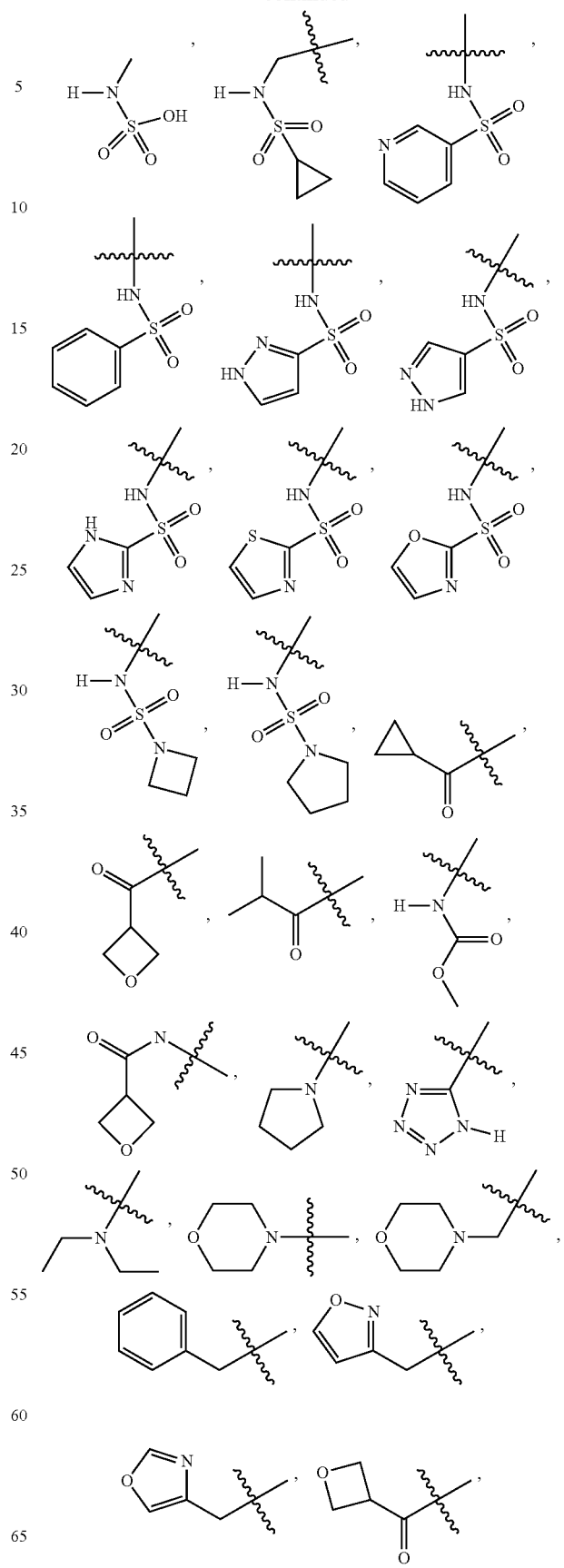

-continued
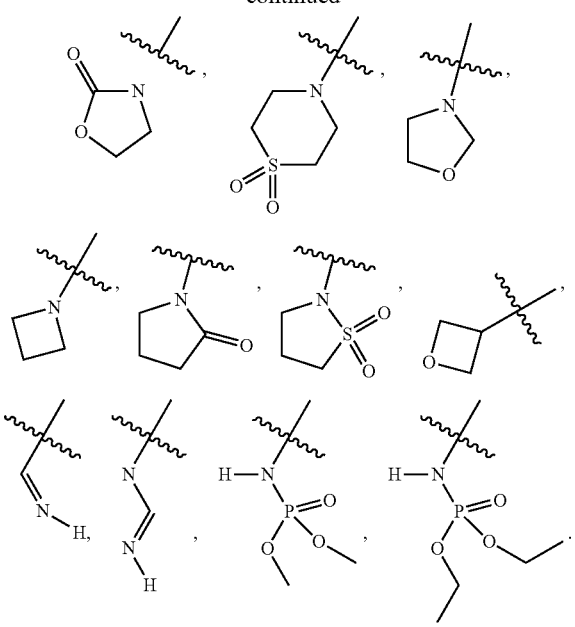
5. The compound or pharmaceutically acceptable salt thereof according to claim 4, wherein $R_3'$, $R_{21}$ and $R_{d1-d7}$ are separately and independently selected from: H, F, Cl, Br, I, OH, $NH_2$, CN, —COOH, $CH_3$,
-continued
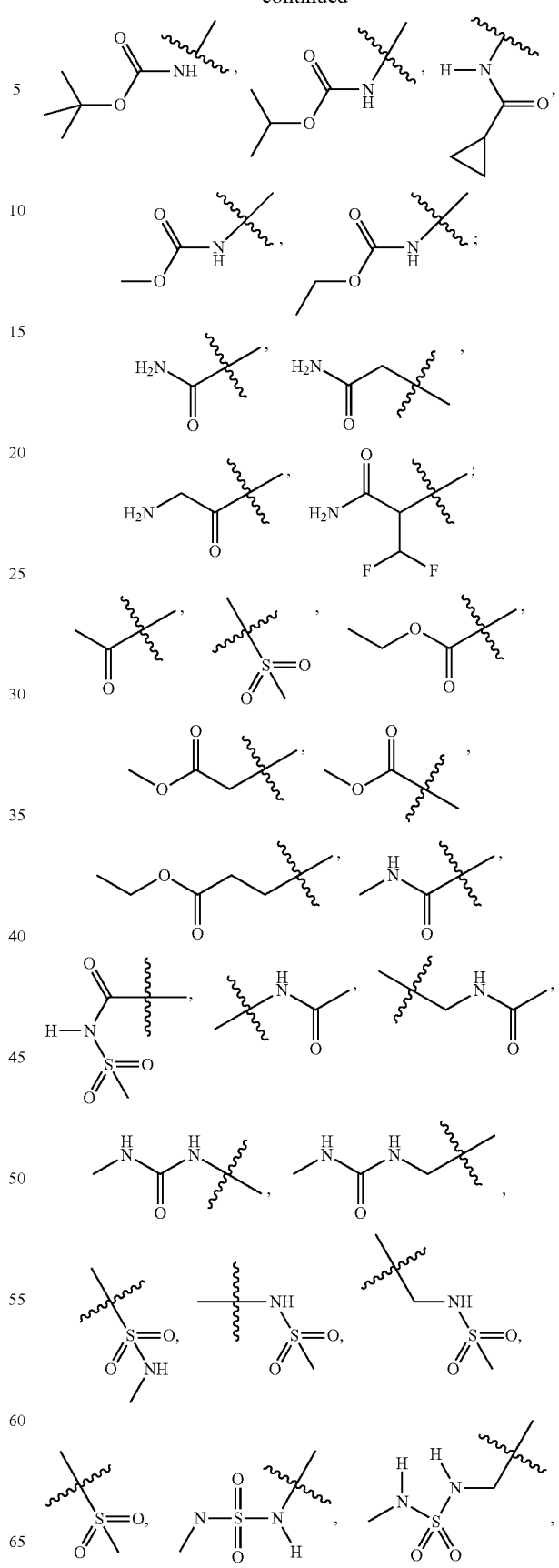

511
-continued
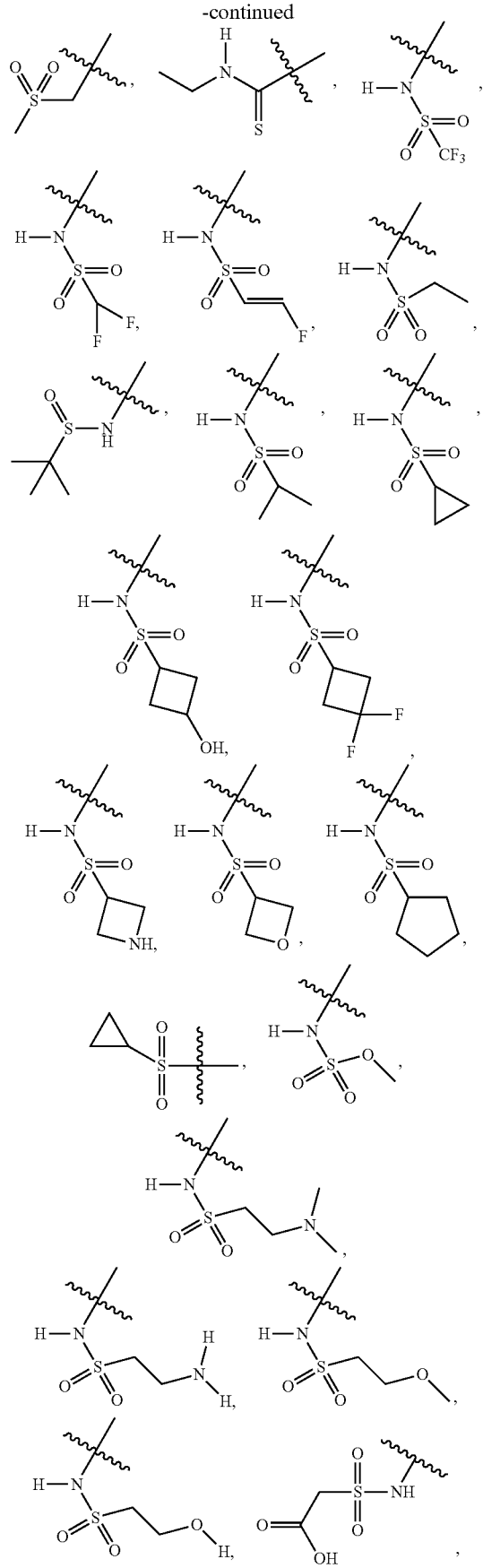
512
-continued
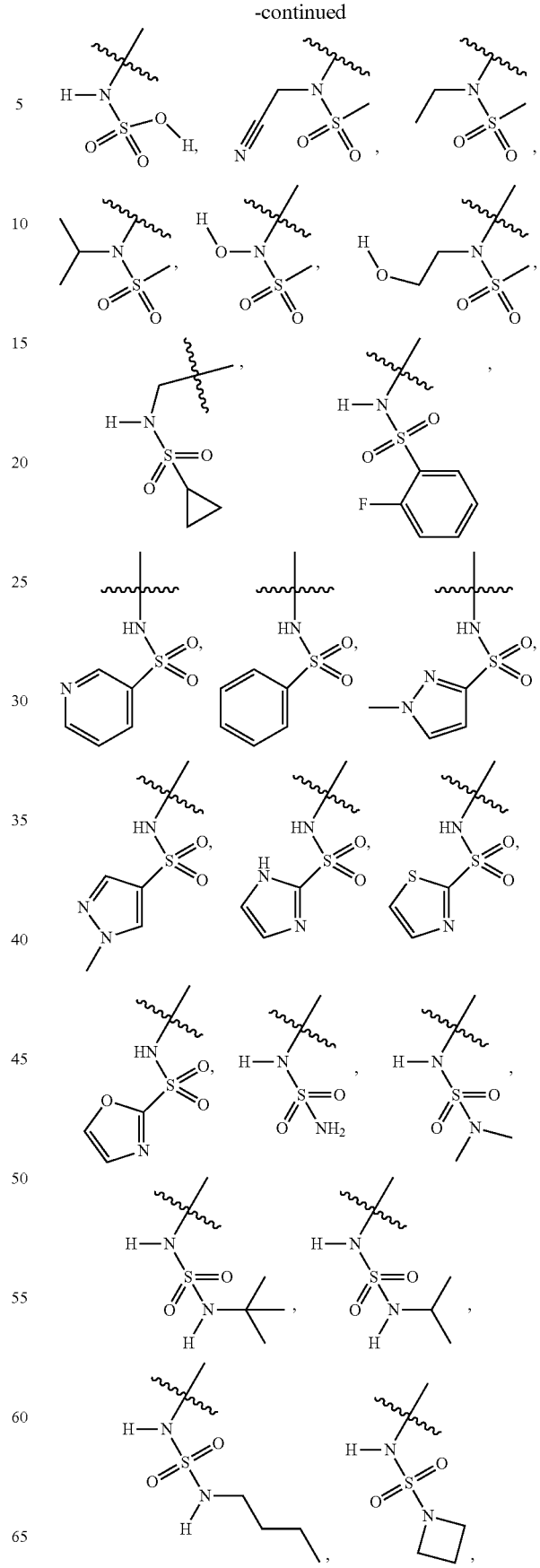

513
-continued
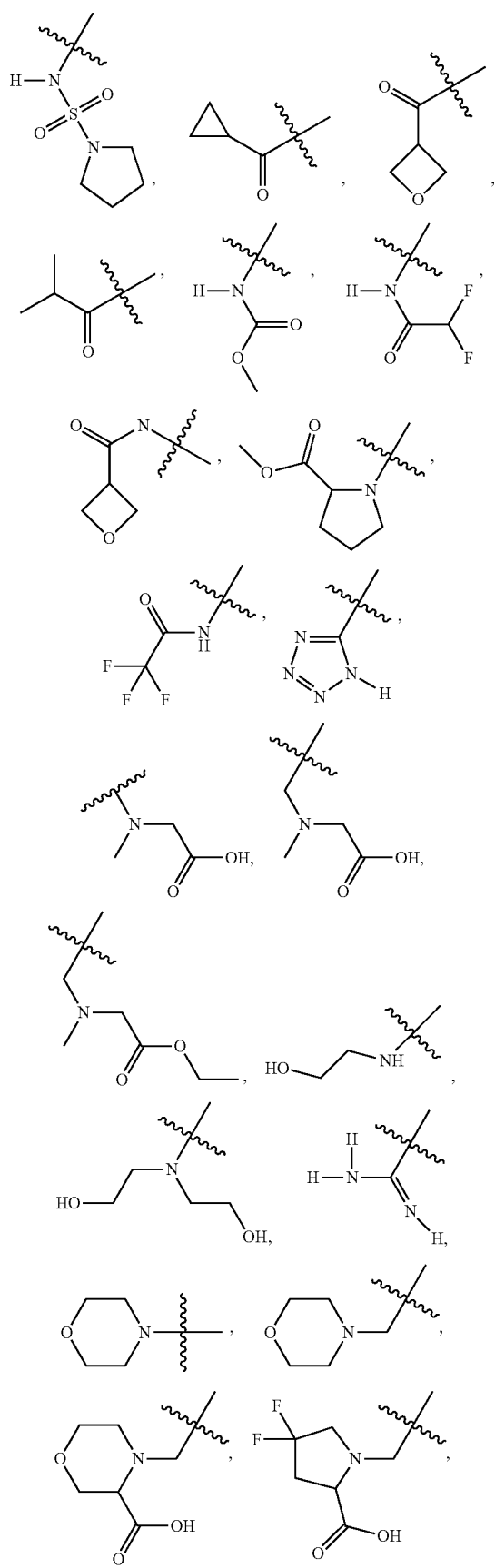
514
-continued
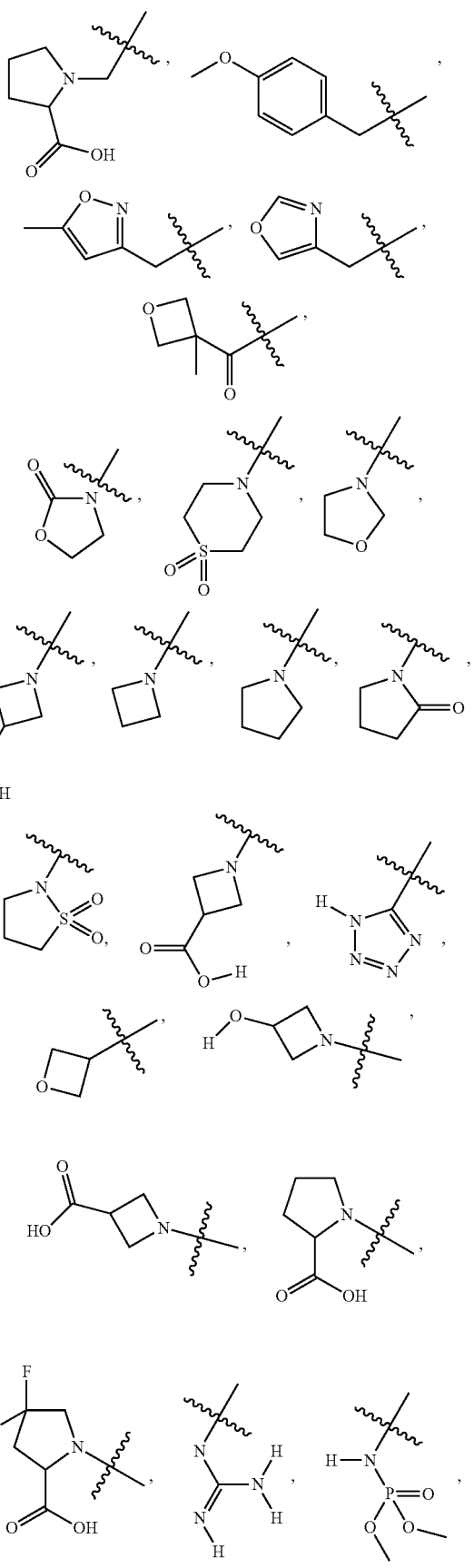

515
-continued
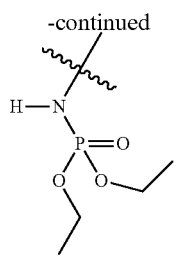
6. The compound or pharmaceutically acceptable salt thereof according to claim 1, wherein the structural unit
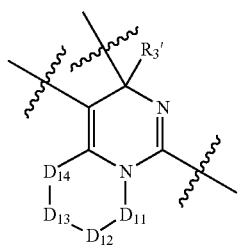
is selected from:
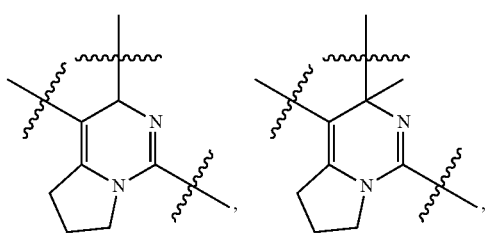
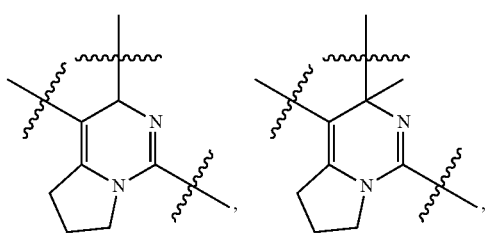
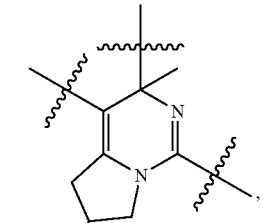
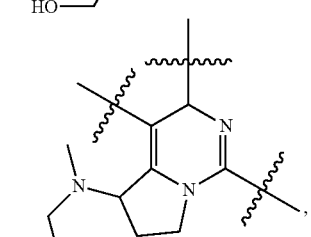
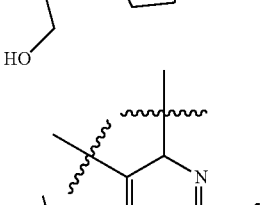
516
-continued
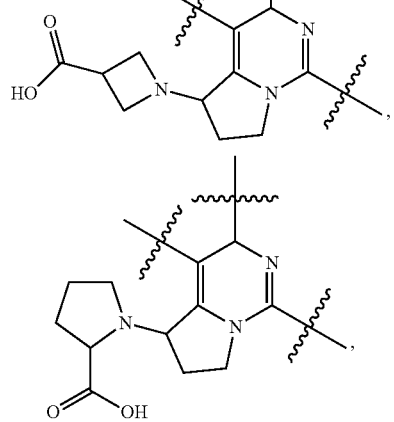
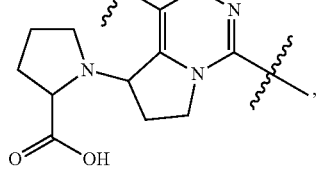
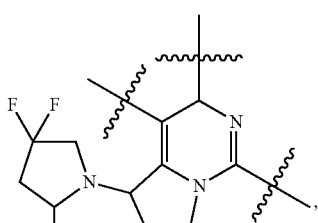
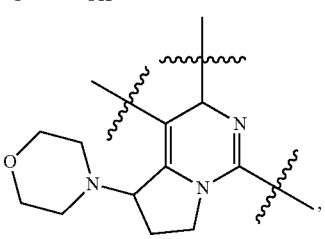
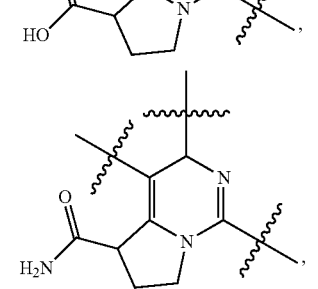

517
-continued
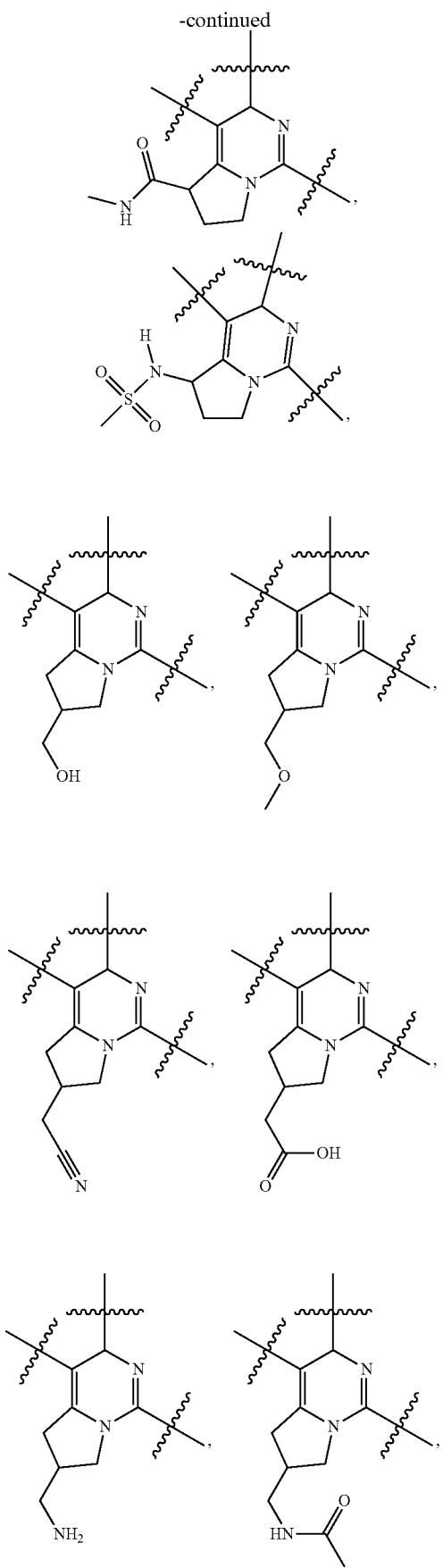
518
-continued
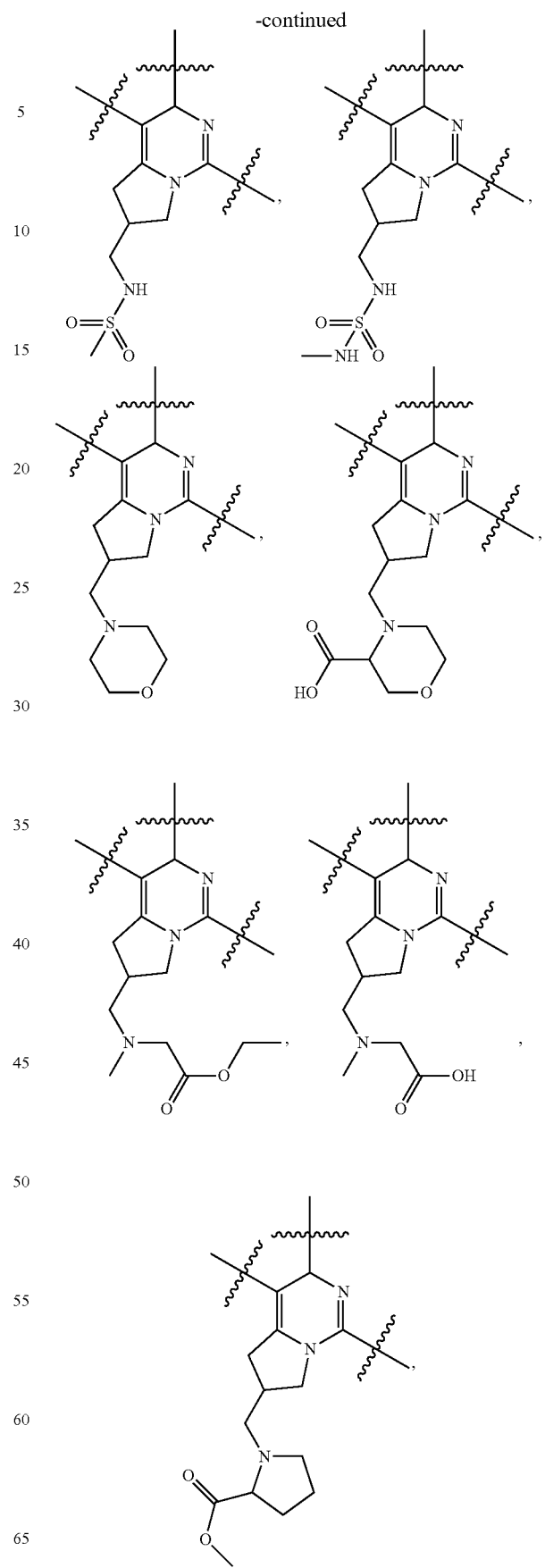

519
-continued
520
-continued
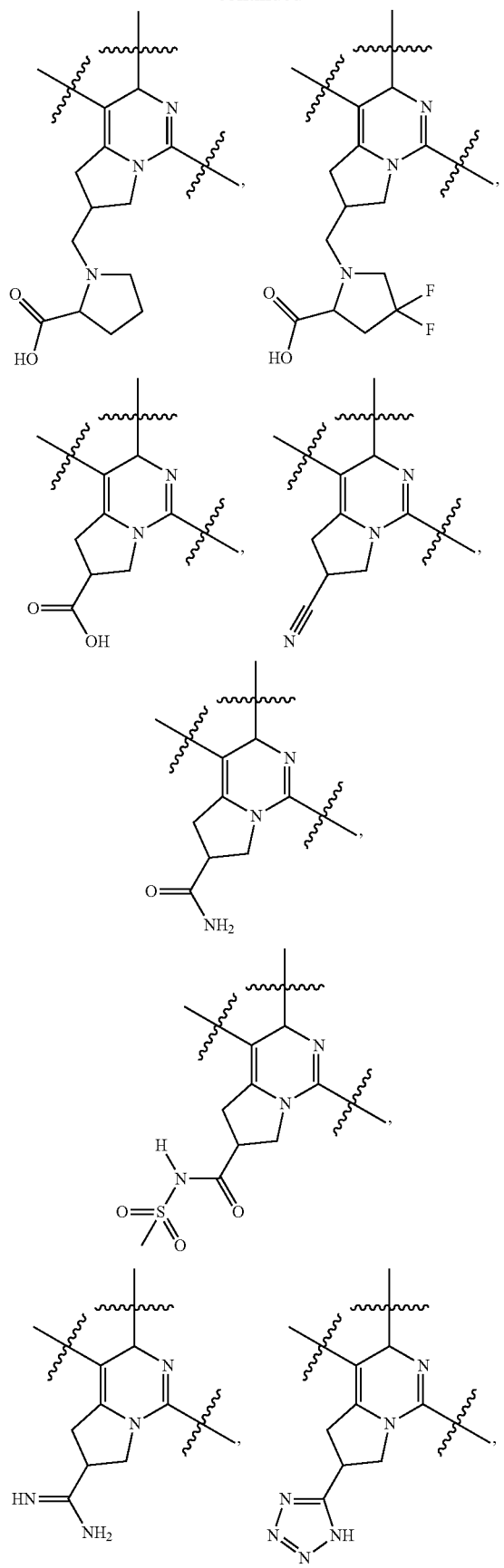
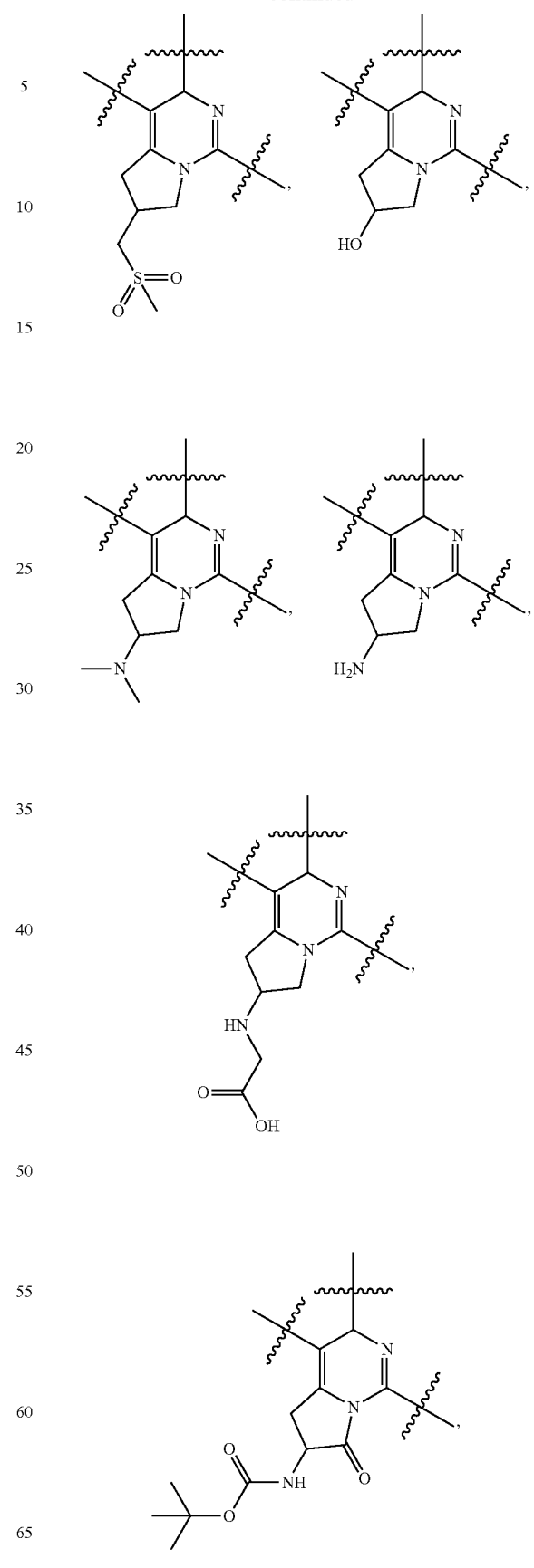

521
-continued
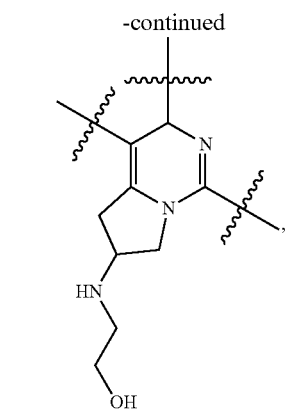
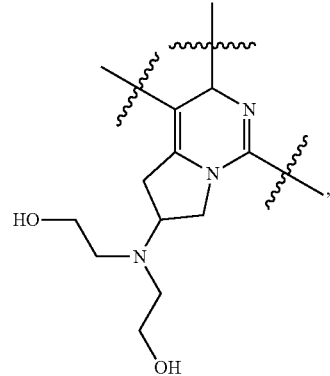
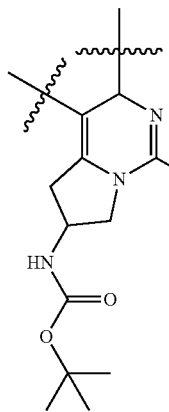 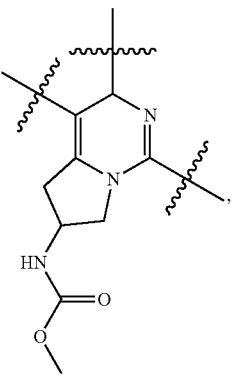
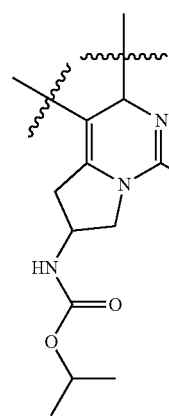 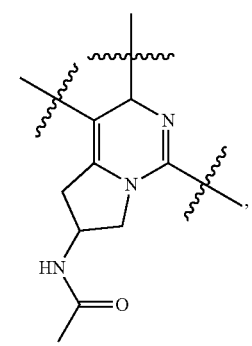
522
-continued
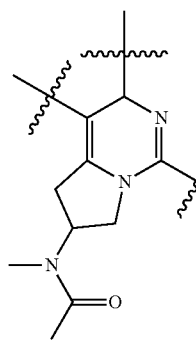 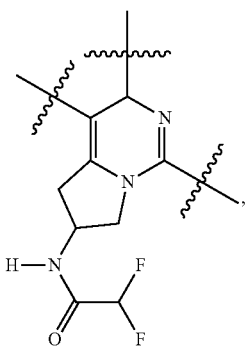
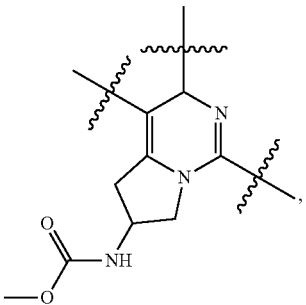
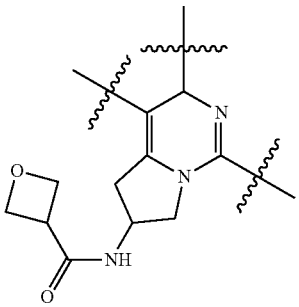 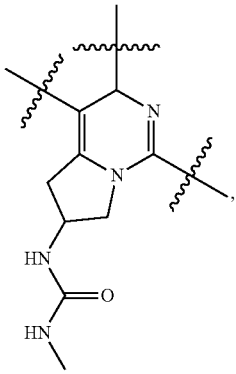
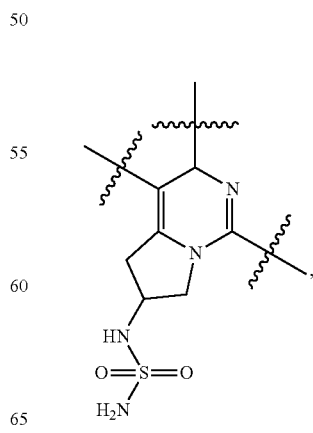 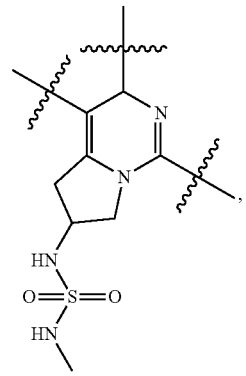

523
-continued
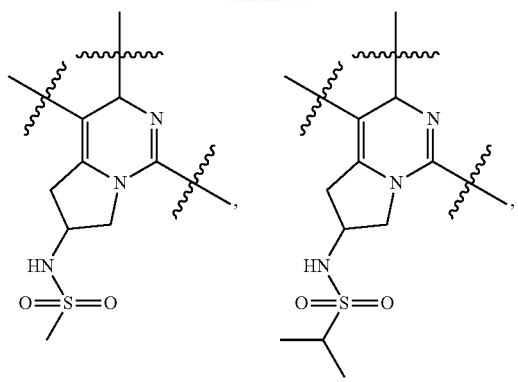
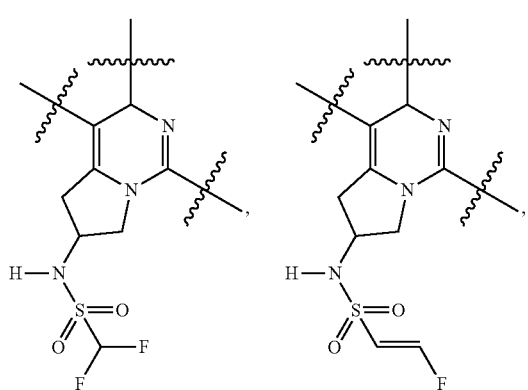
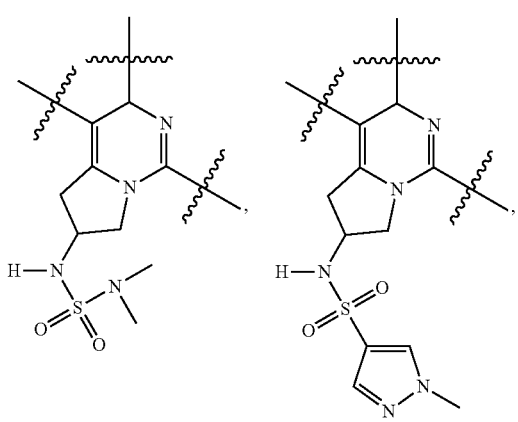
524
-continued
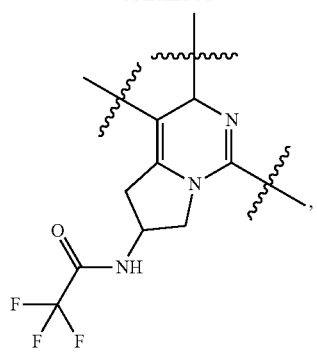
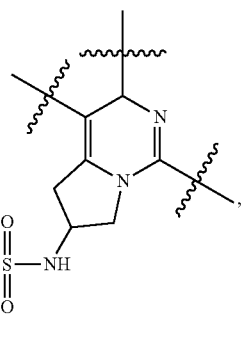
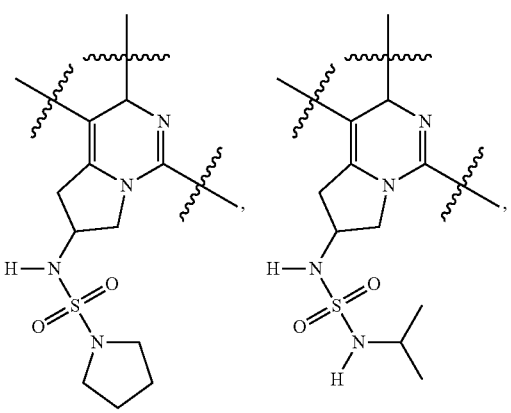
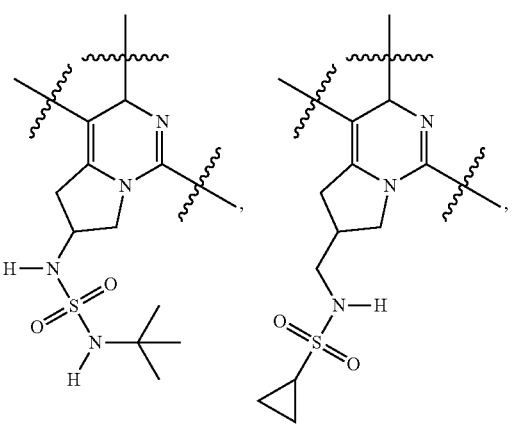
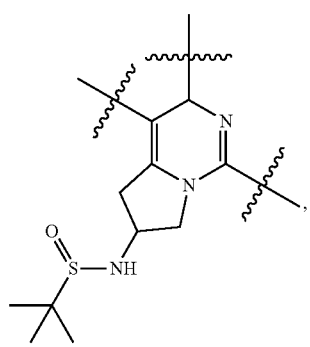

525
-continued
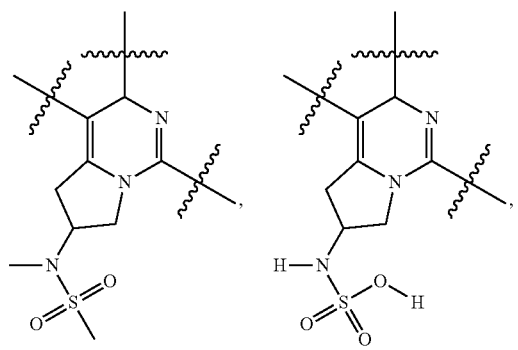
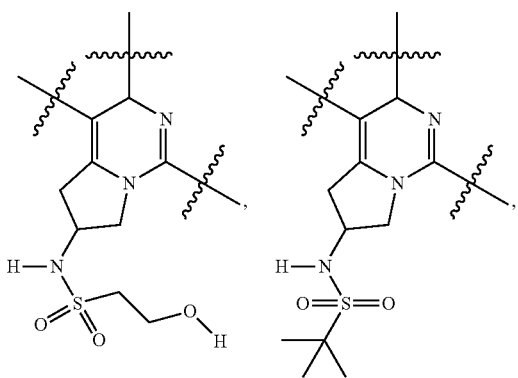
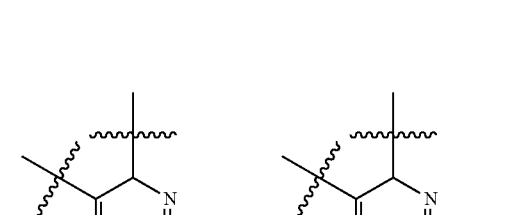
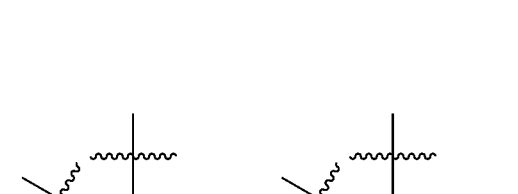
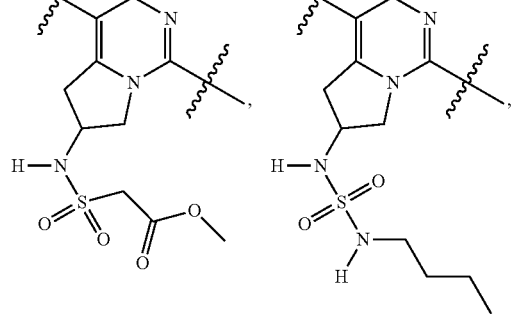
526
-continued
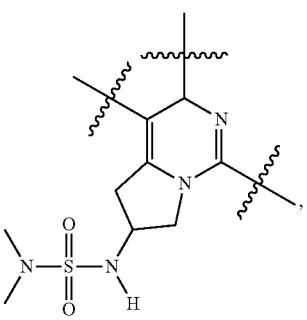
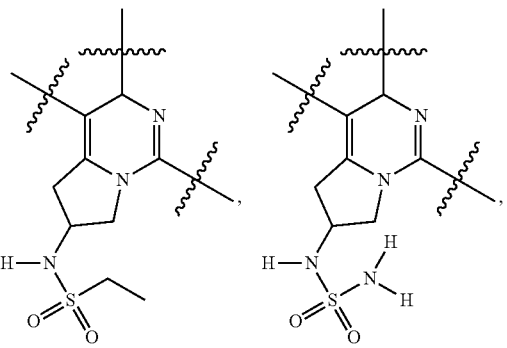
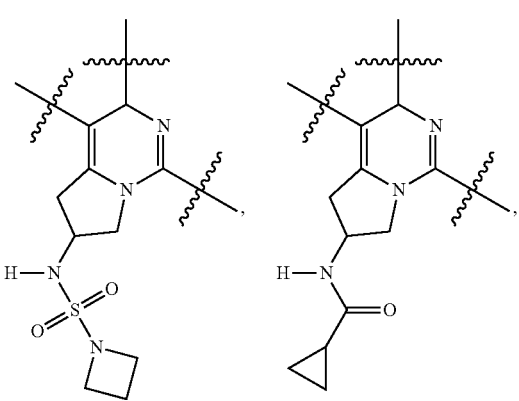
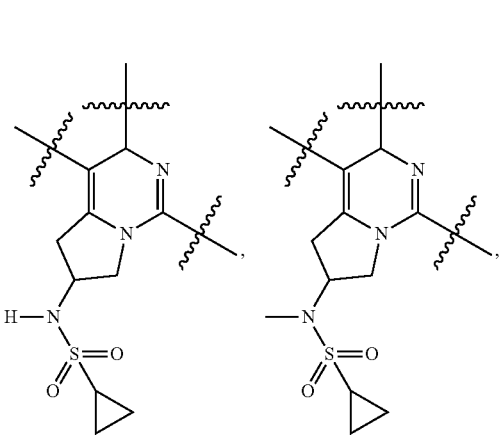

527
-continued
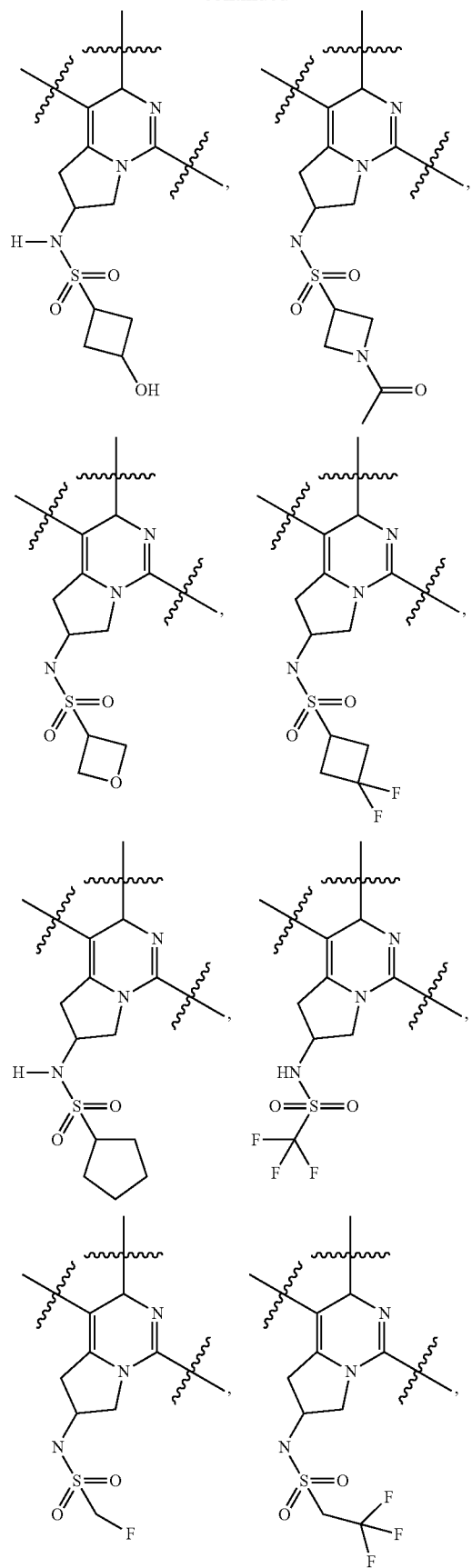
528
-continued
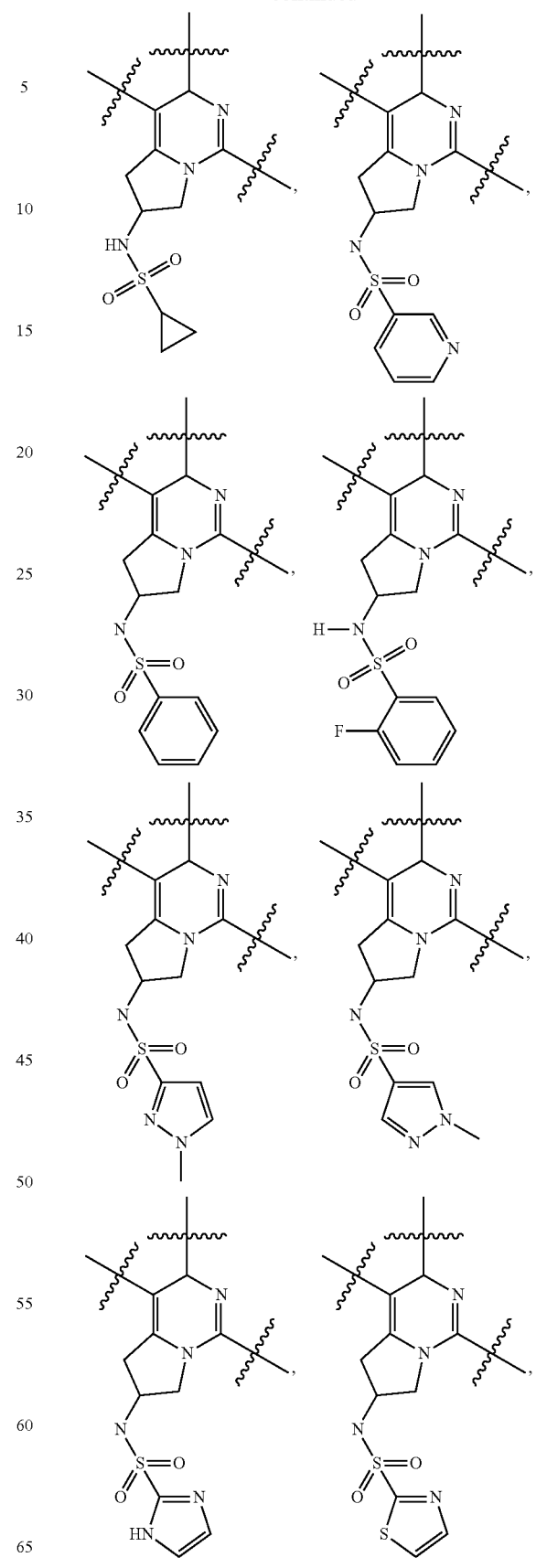

529
-continued
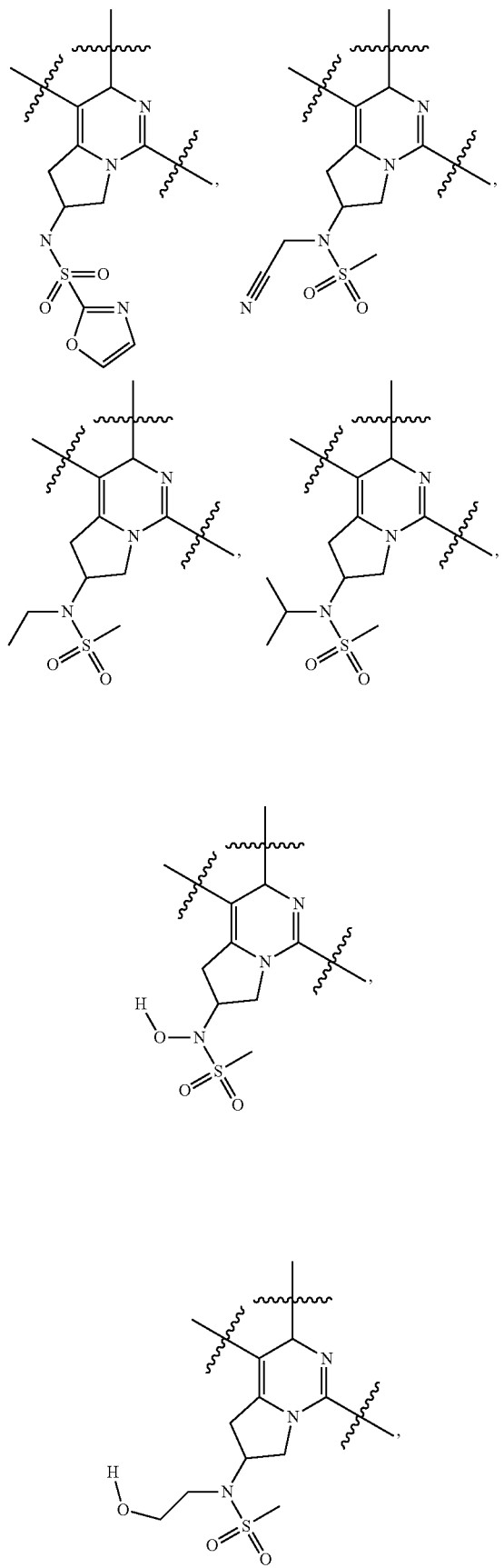
530
-continued
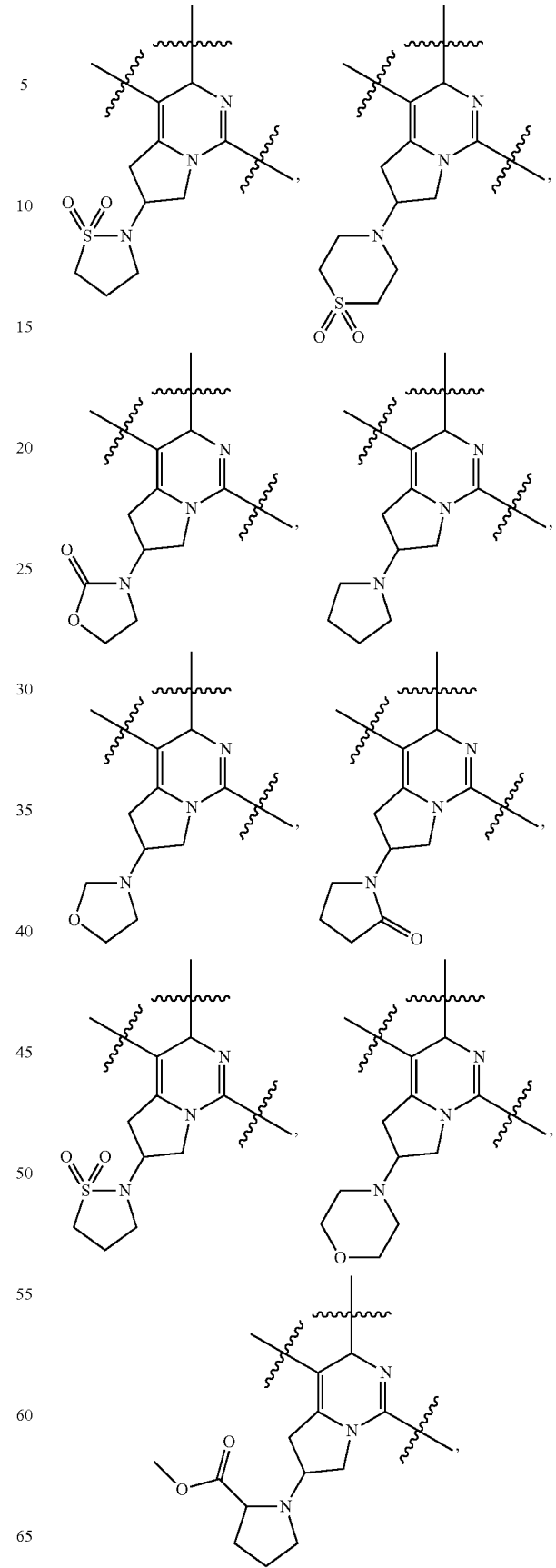

531
-continued
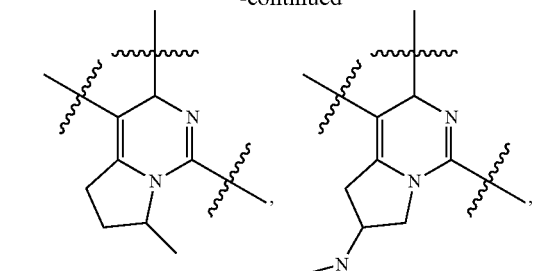
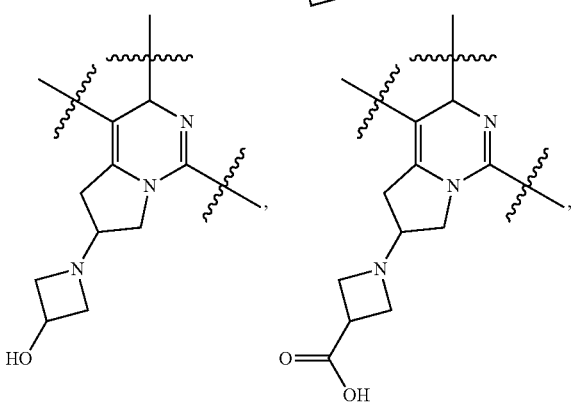
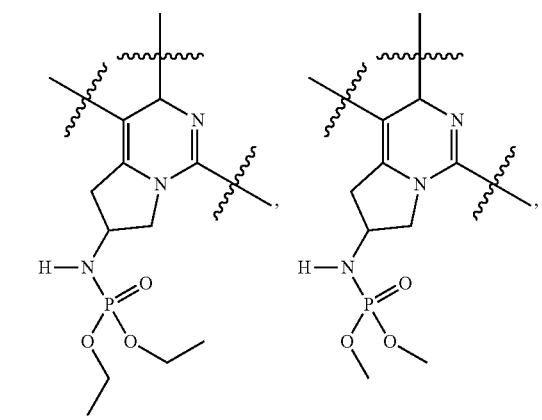
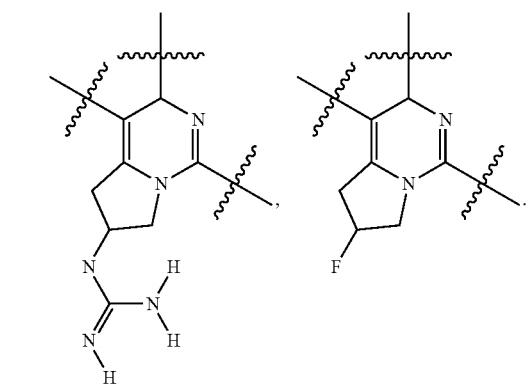
7. The compound or pharmaceutically acceptable salt thereof according to claim 6, wherein the structural unit
532
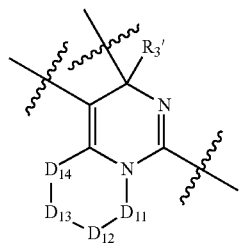
is selected from:
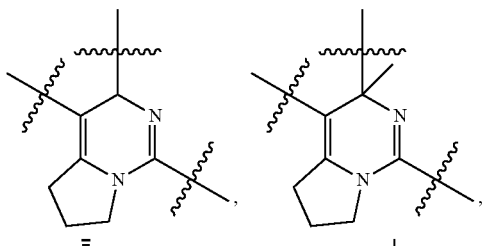
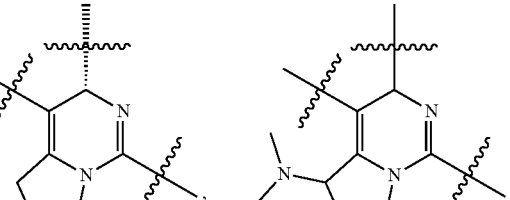
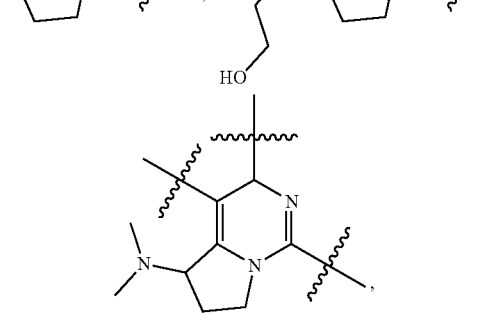
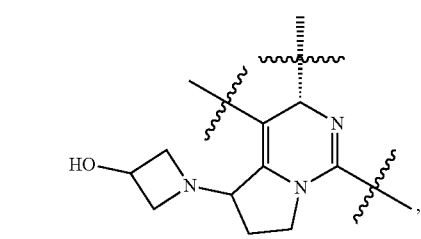
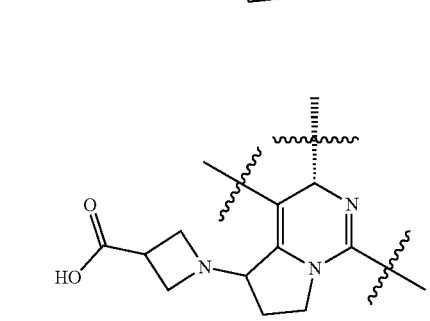

533
-continued
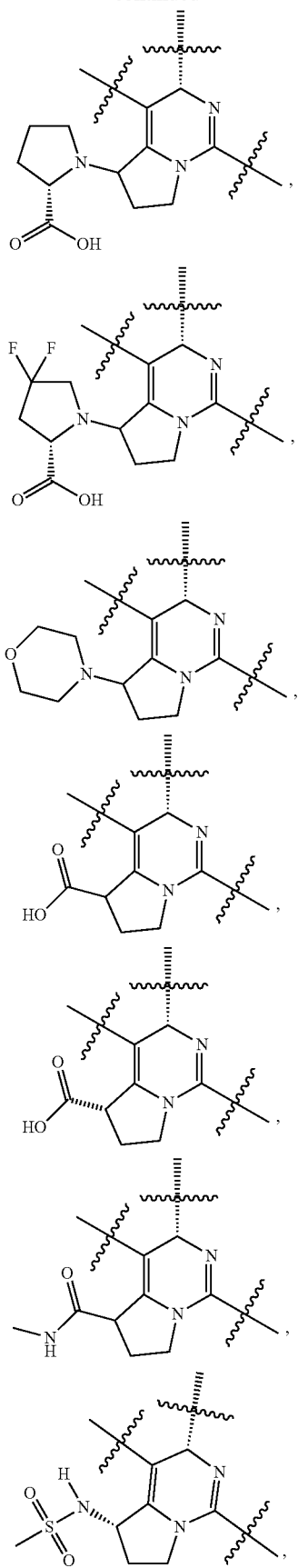
534
-continued
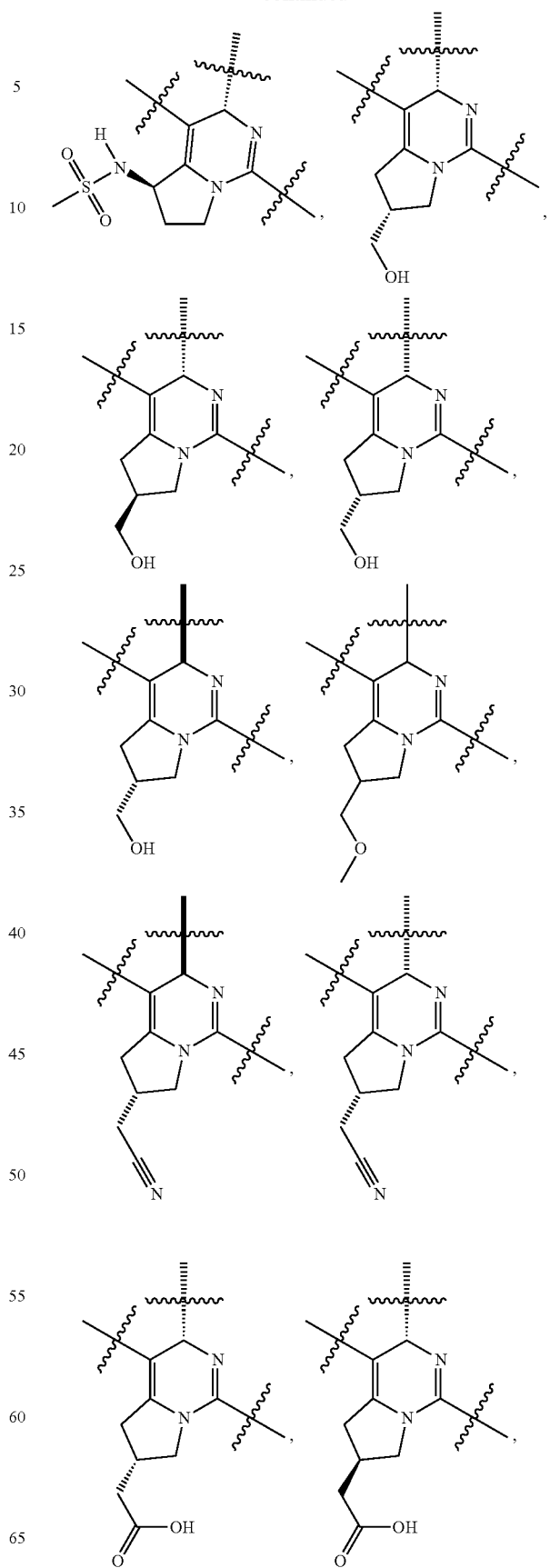

535
-continued
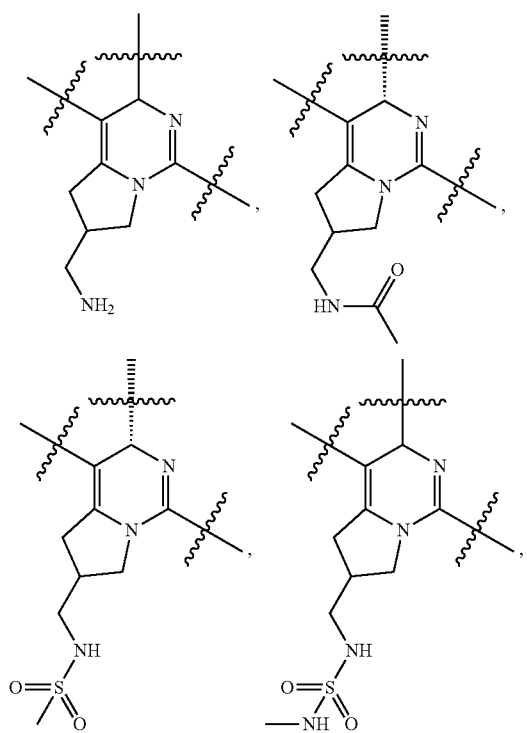
536
-continued
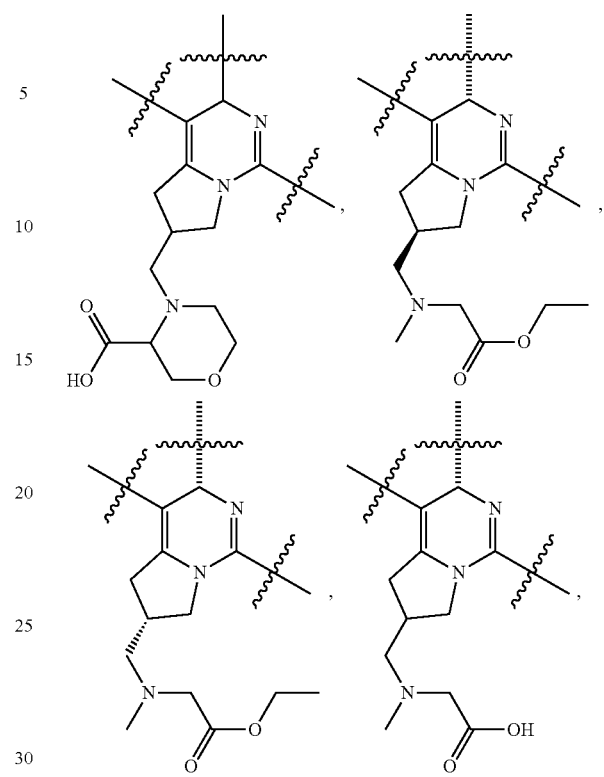
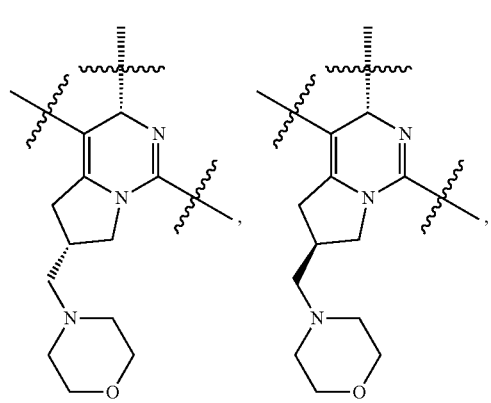
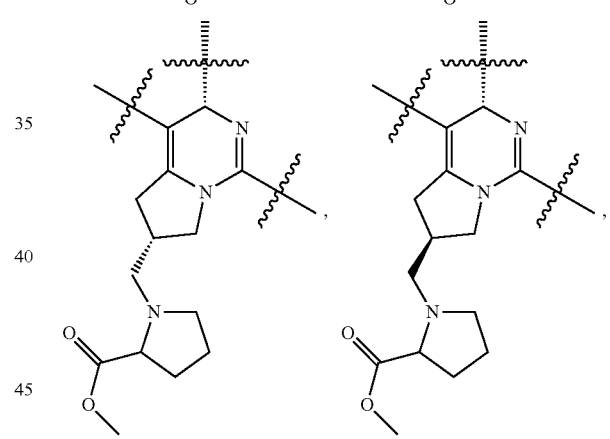
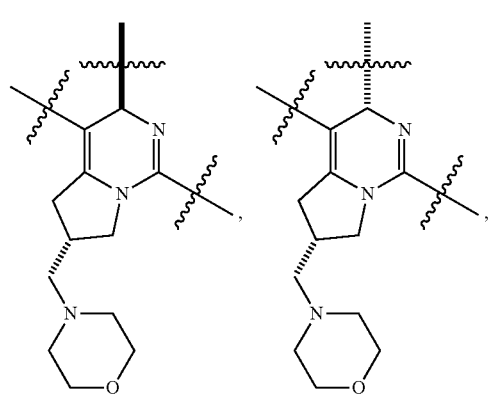
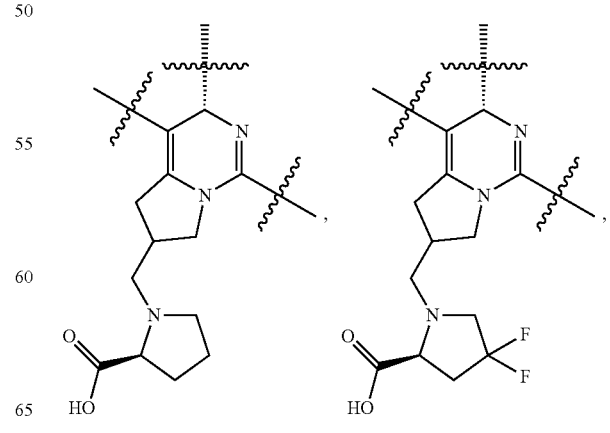

537
-continued
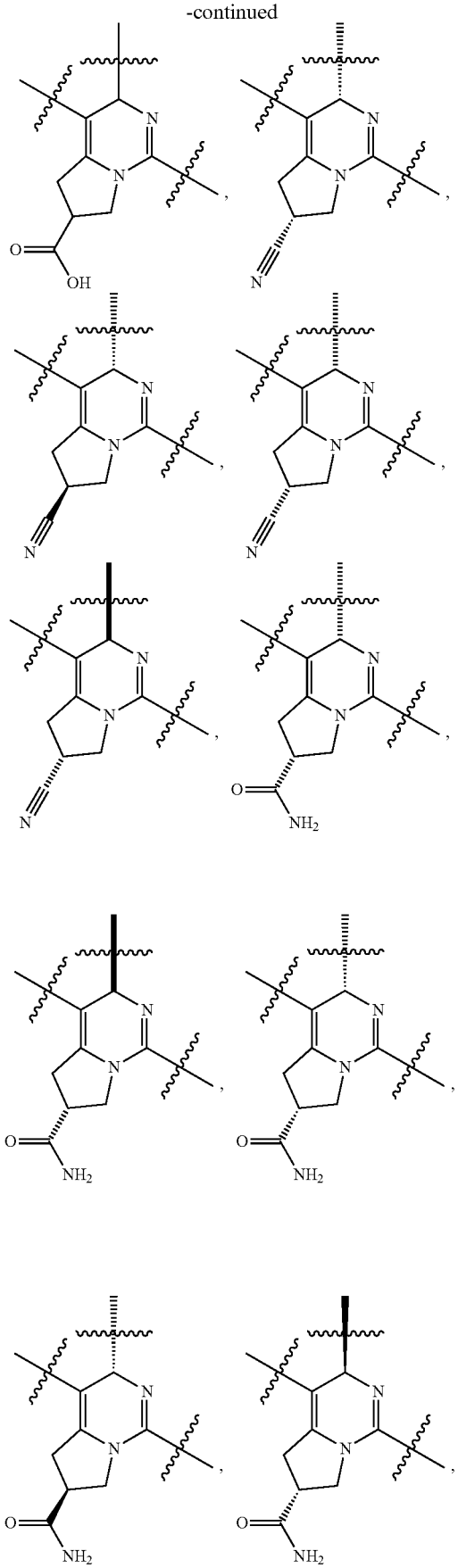
538
-continued
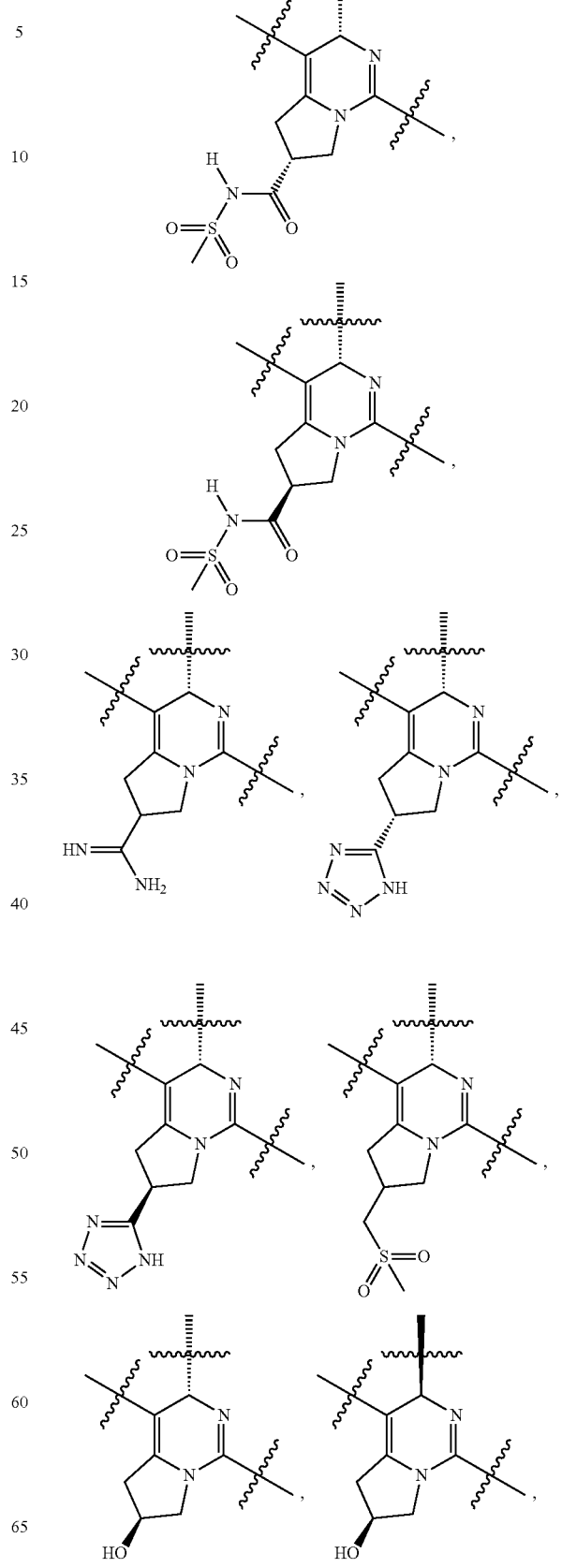

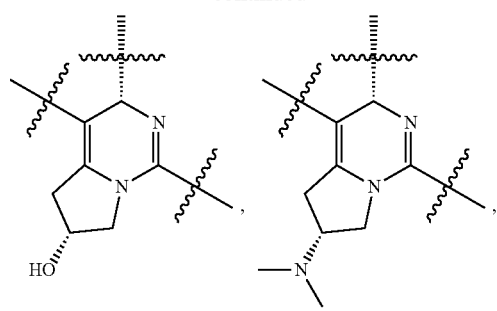
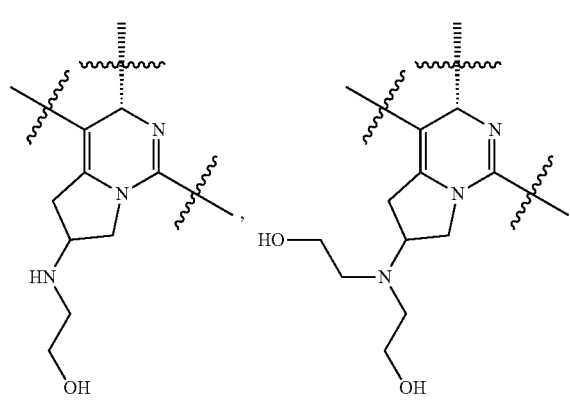
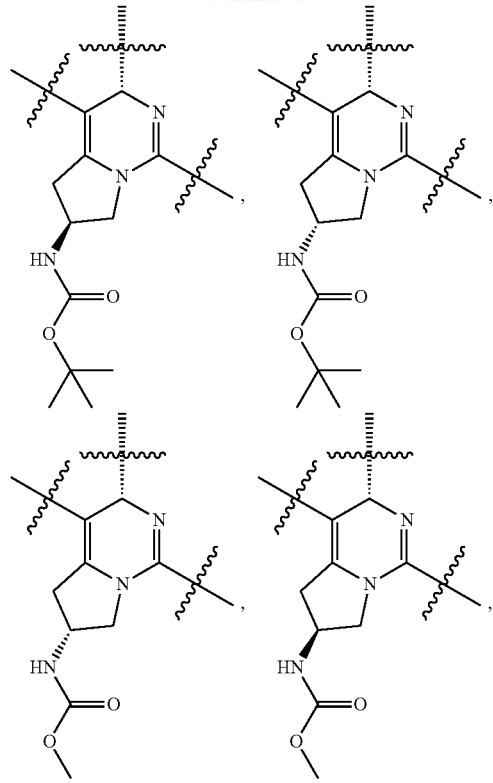
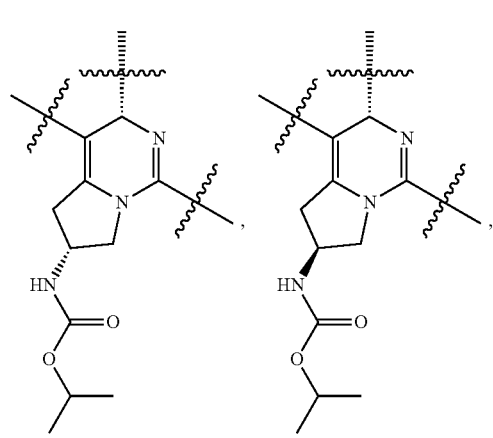
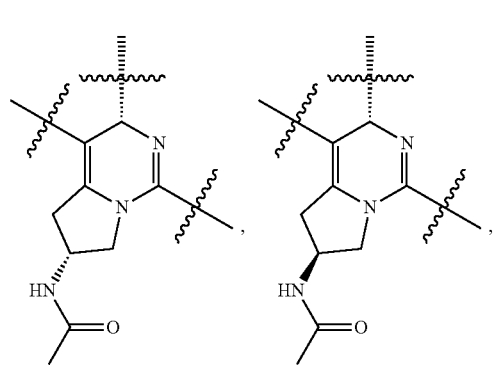

541
-continued
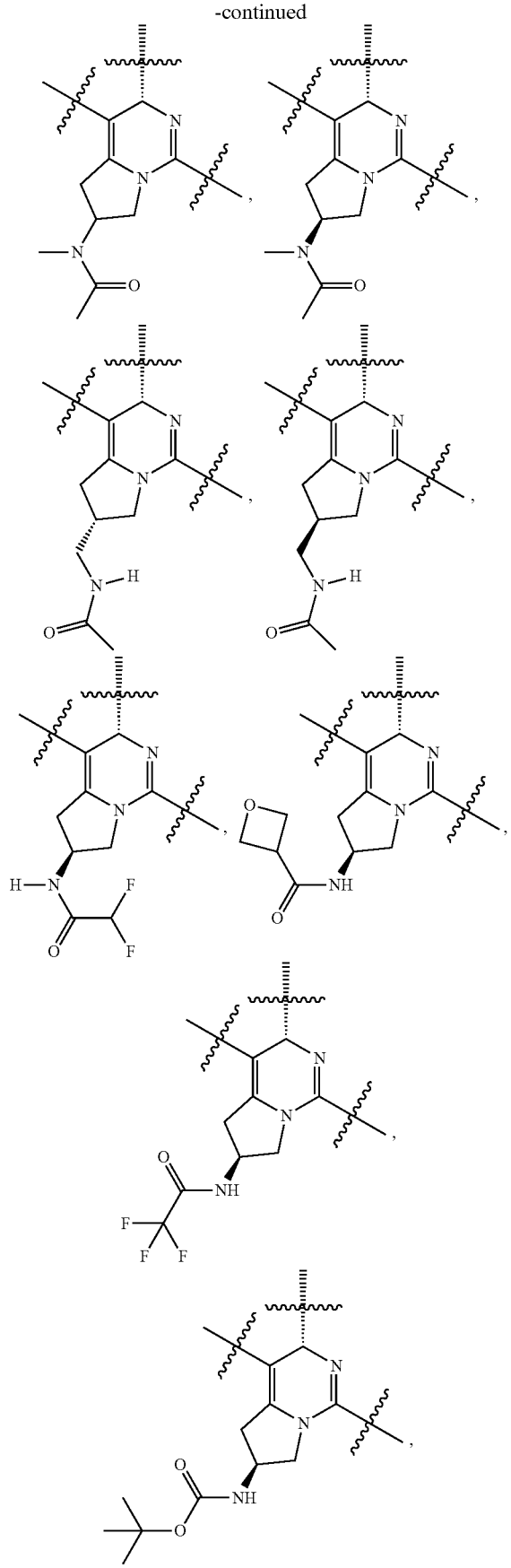
542
-continued
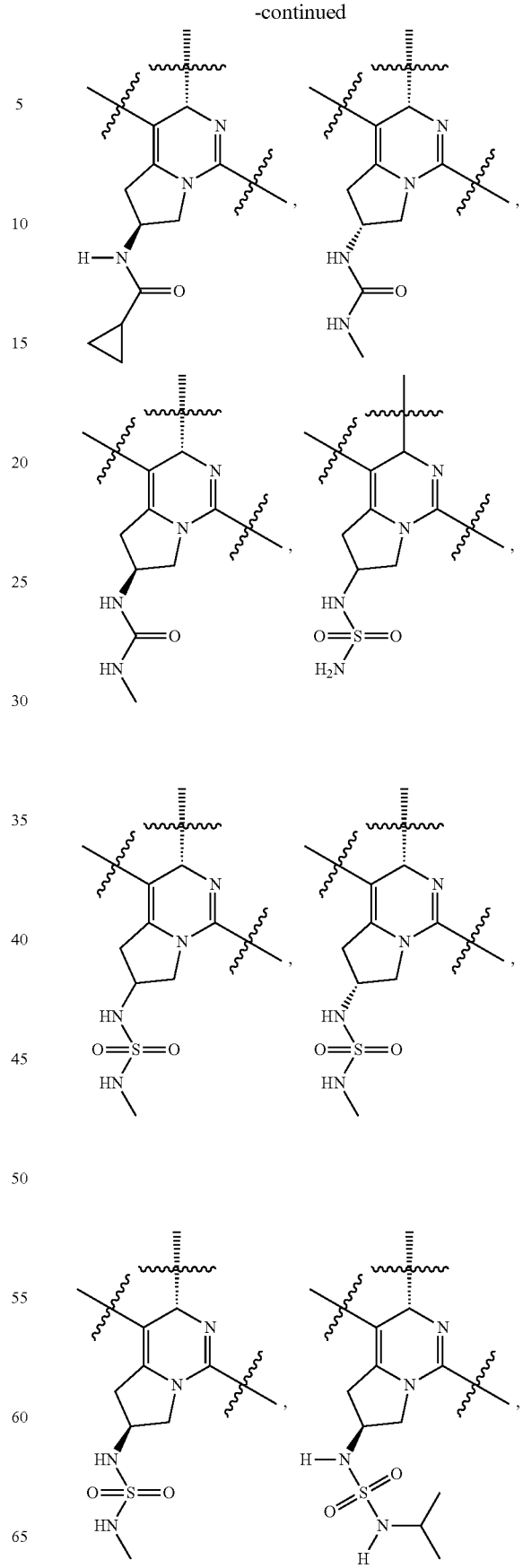

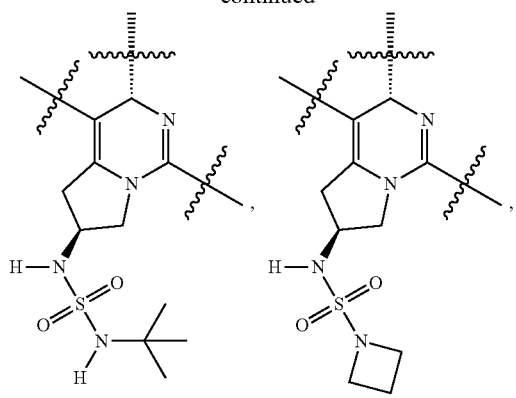
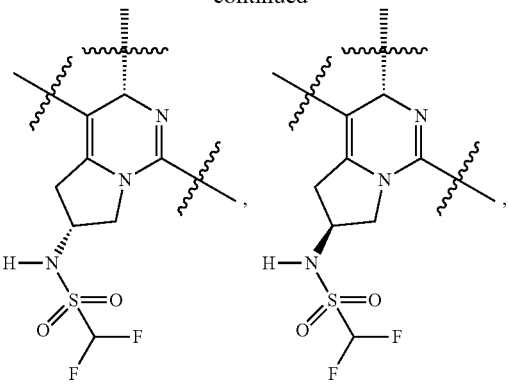
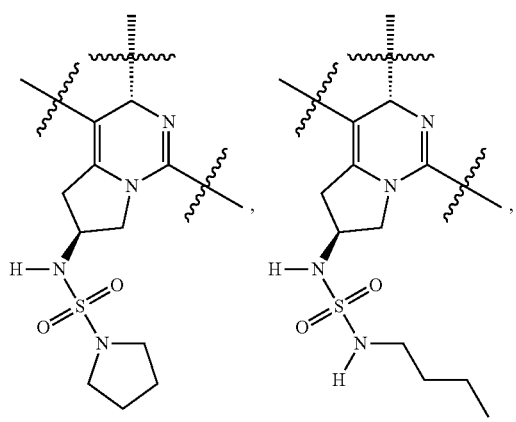
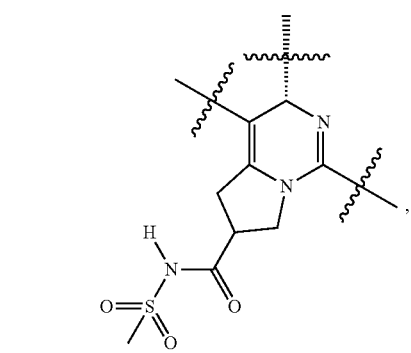
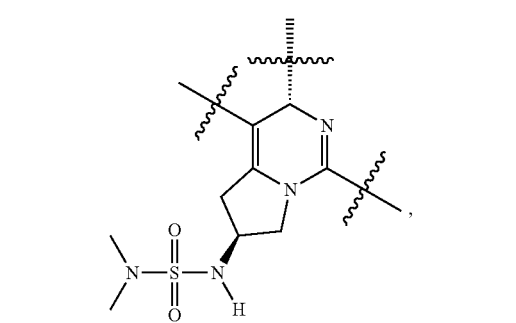
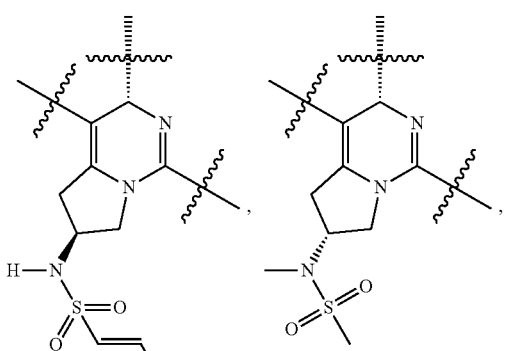
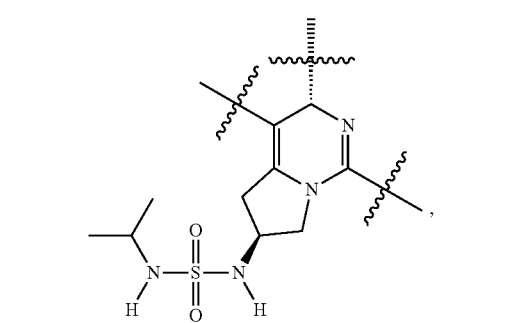
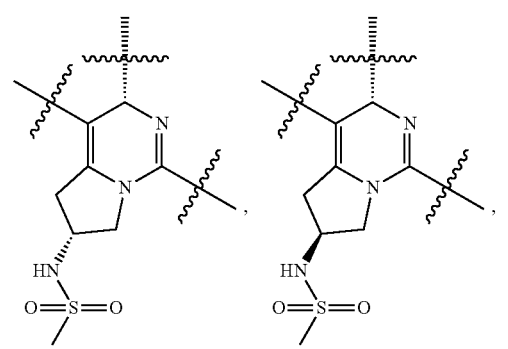

545
-continued
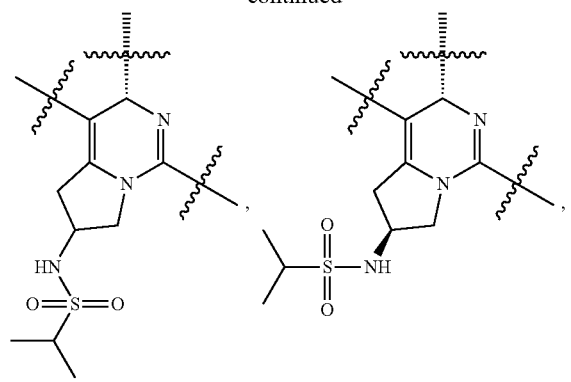
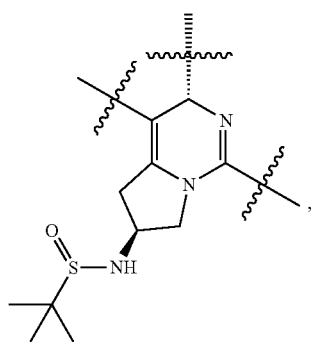
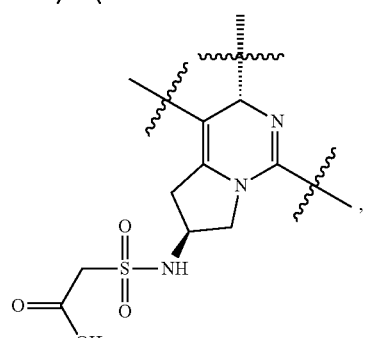
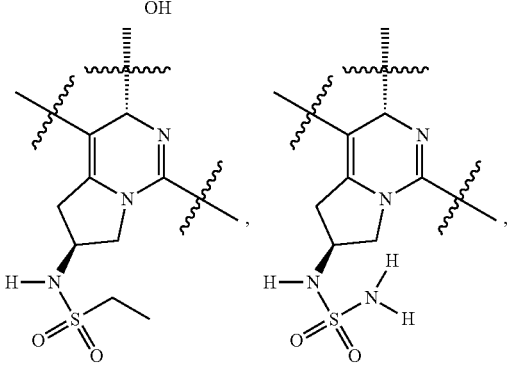
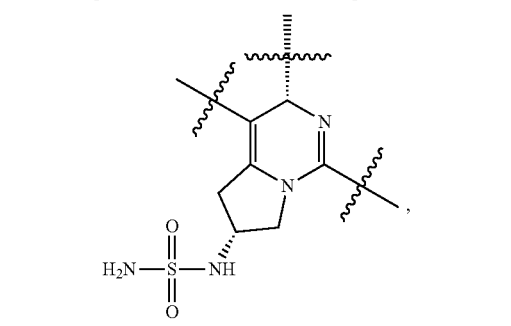
546
-continued
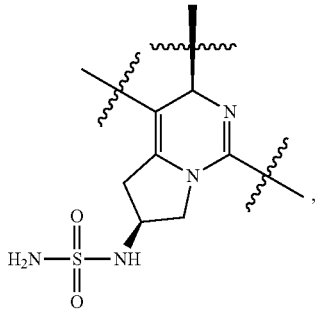
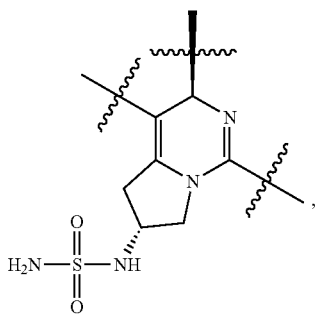
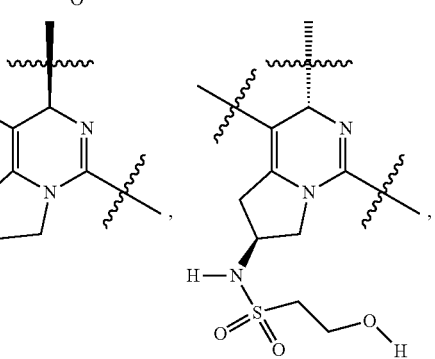
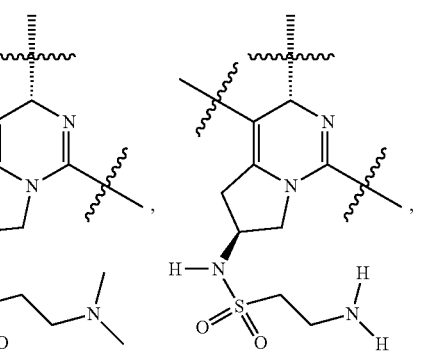
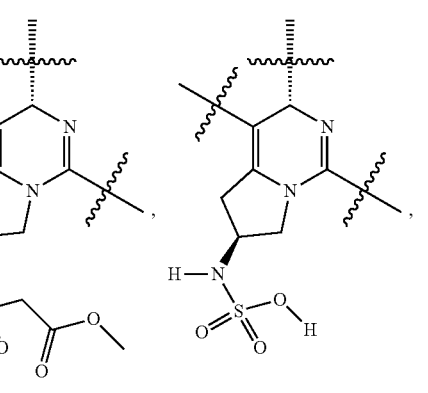
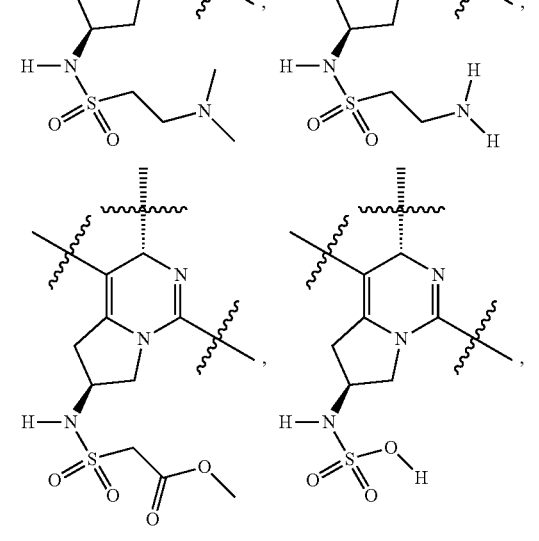

547
-continued
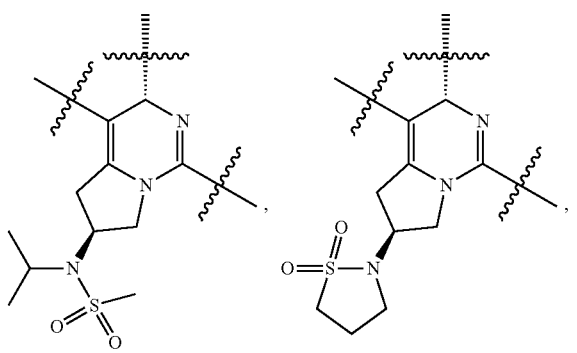
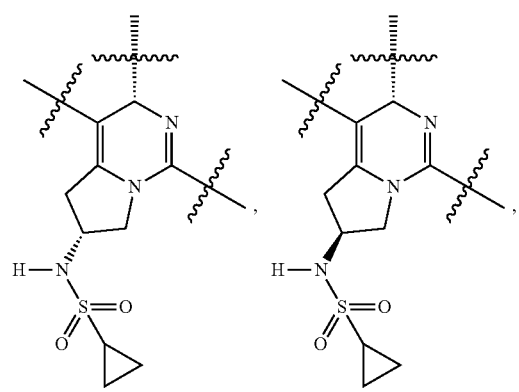
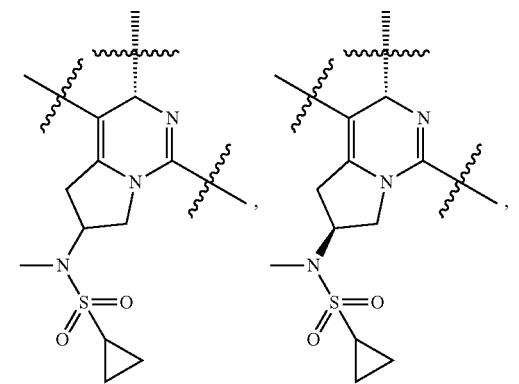
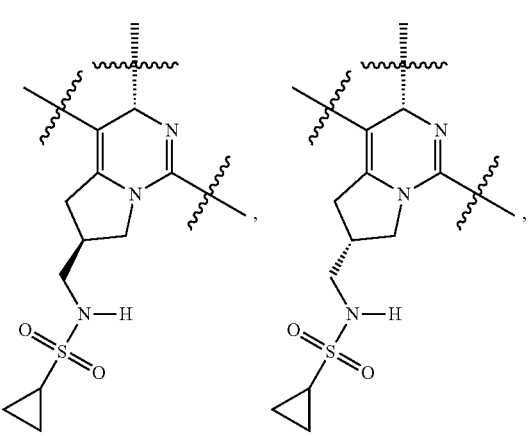
548
-continued
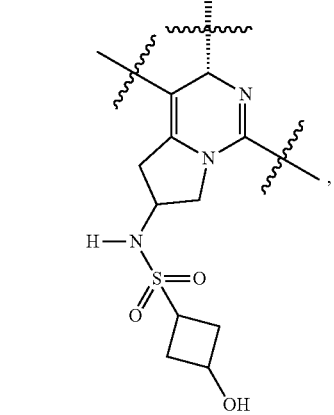
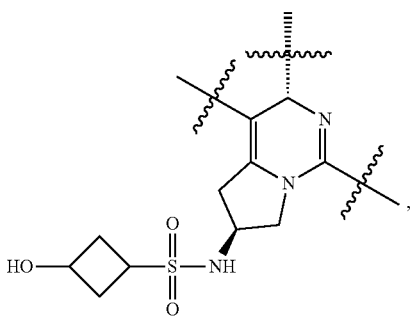
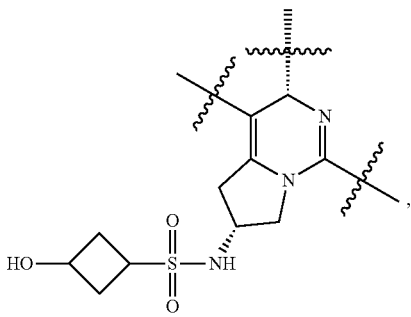
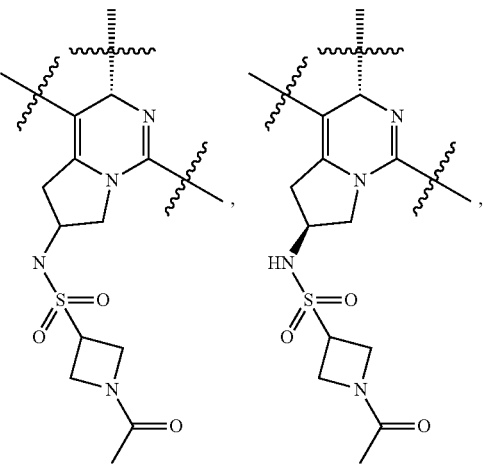

549
-continued
550
-continued
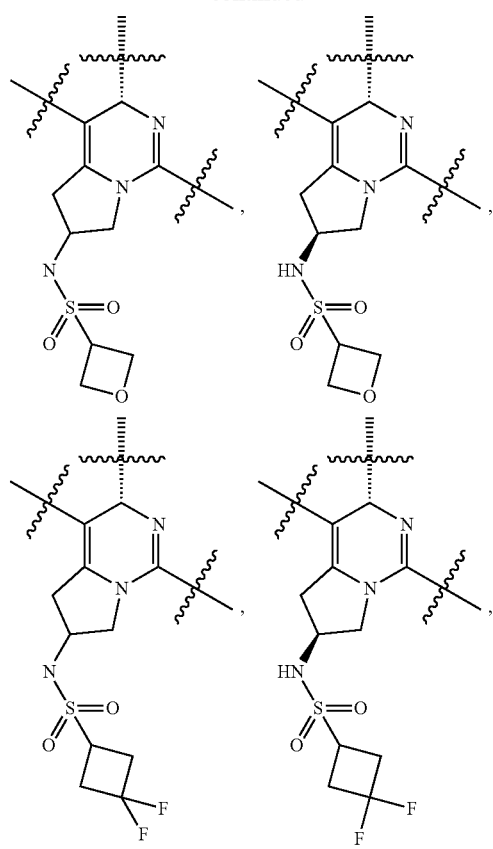
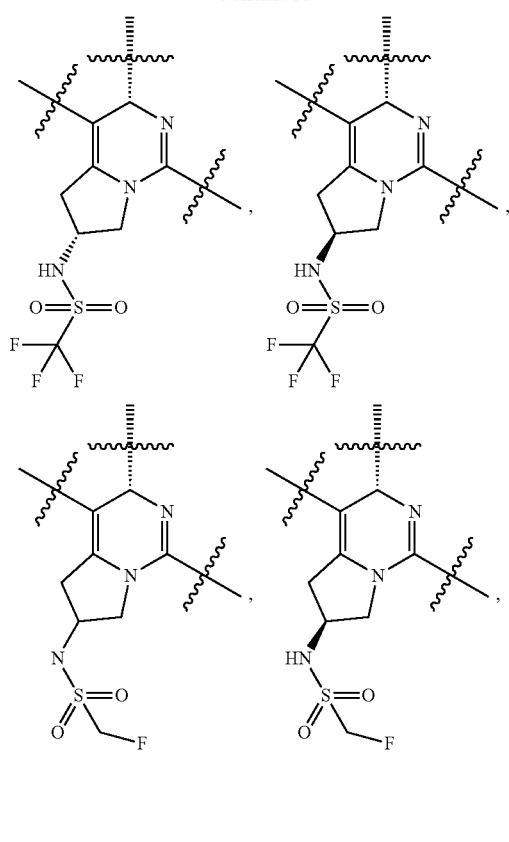
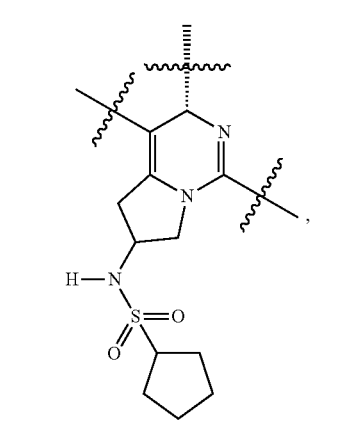
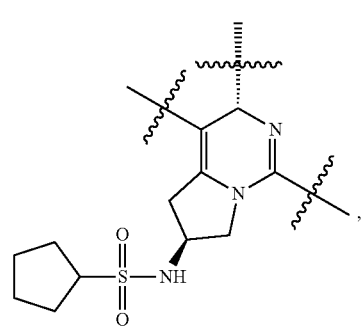

551
-continued
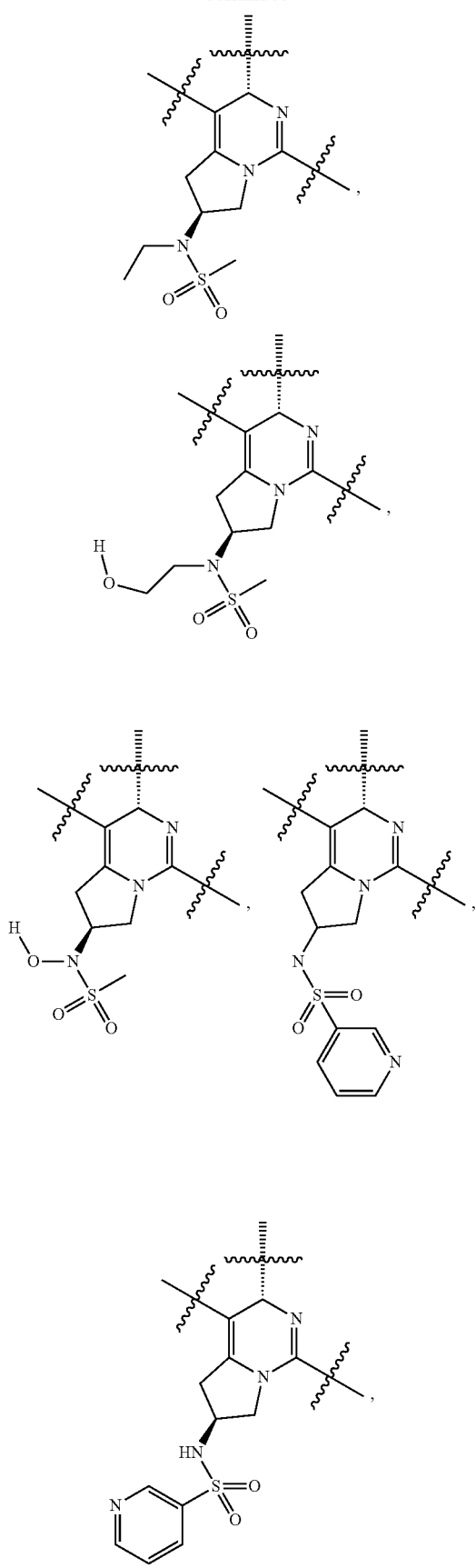
552
-continued
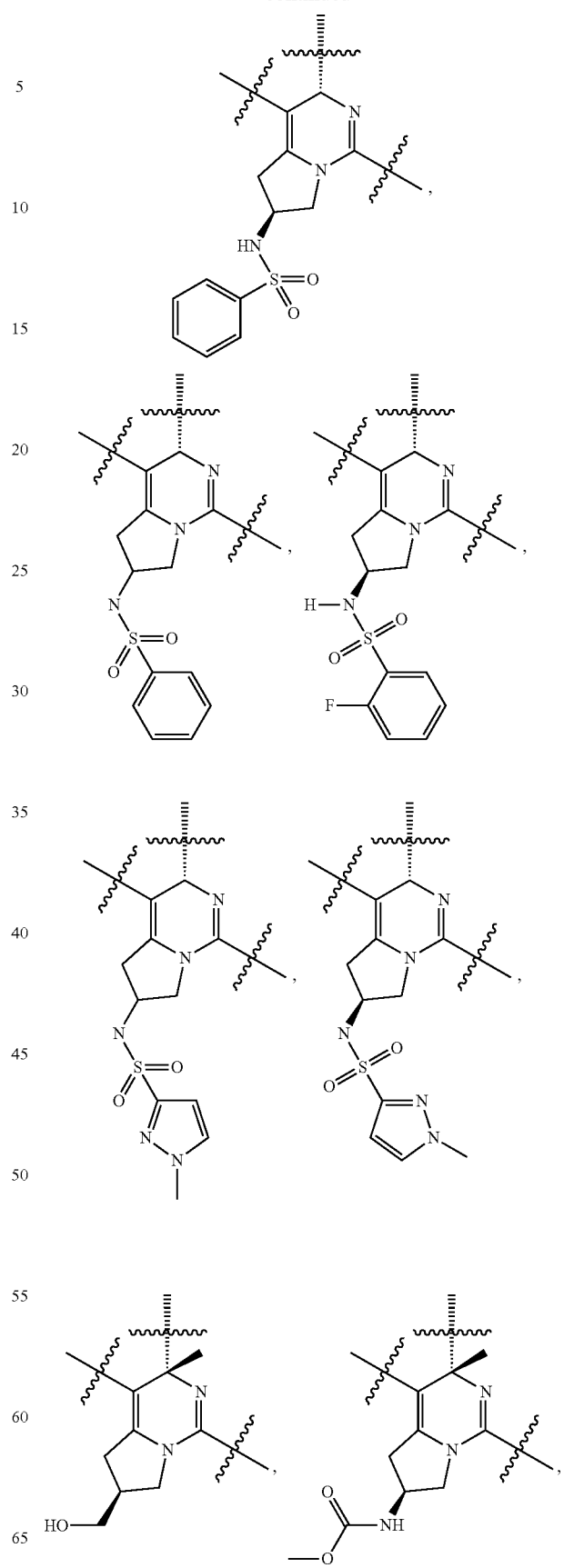

553
-continued
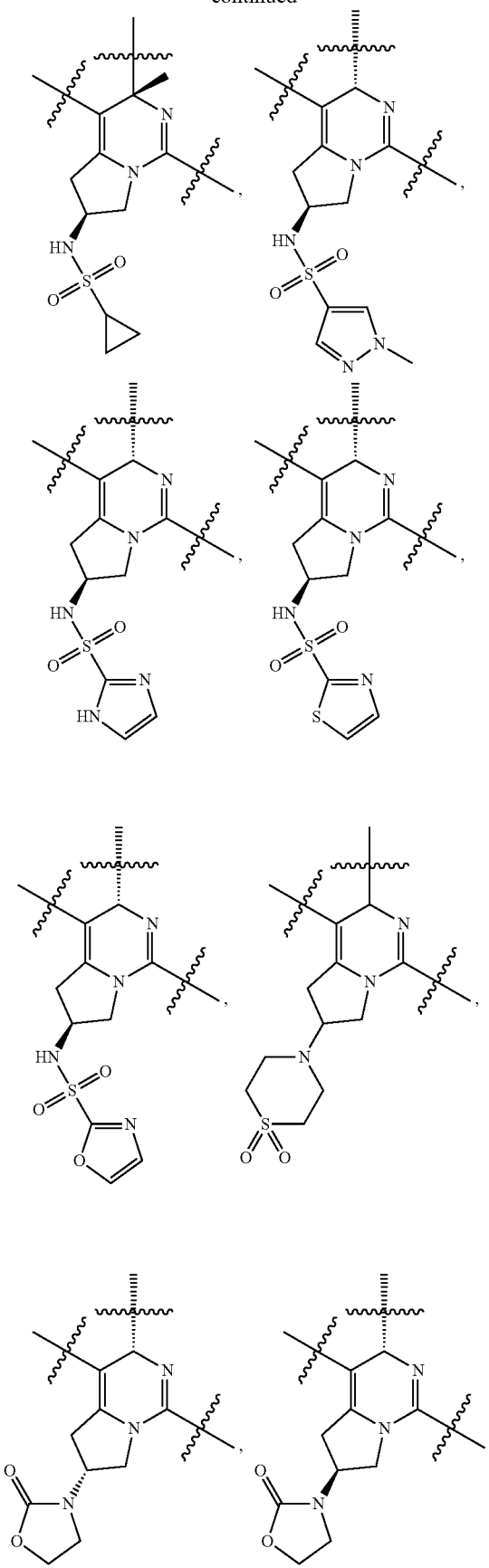
554
-continued
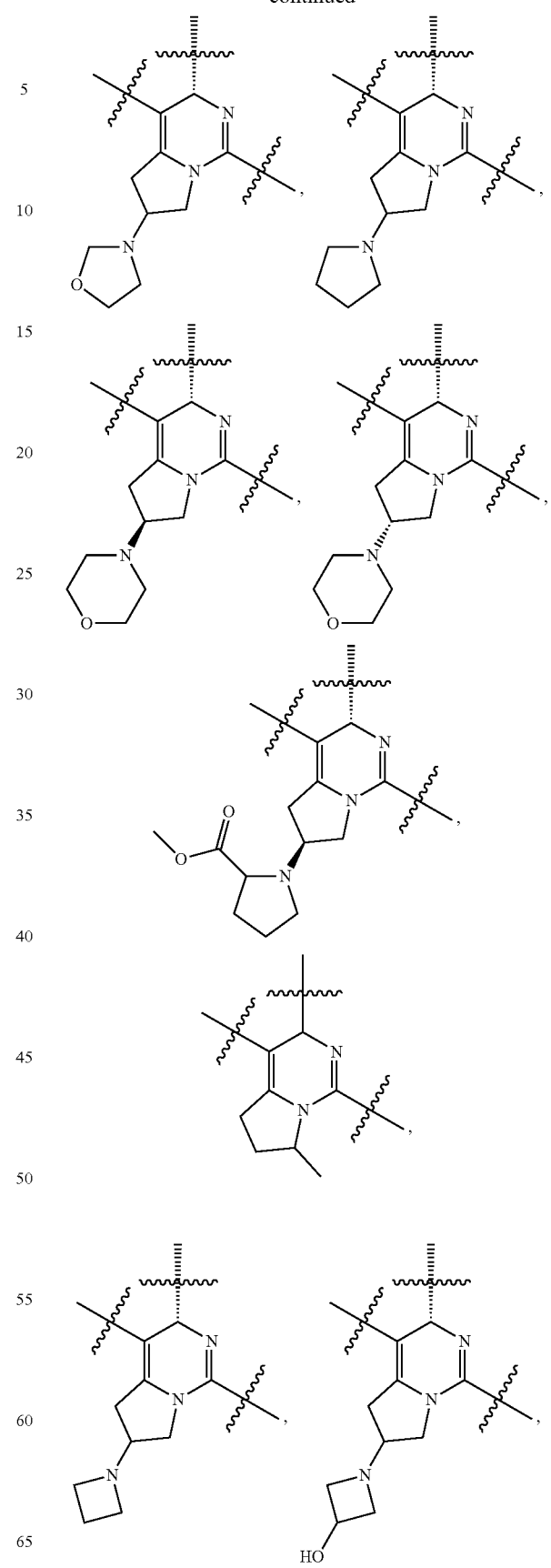

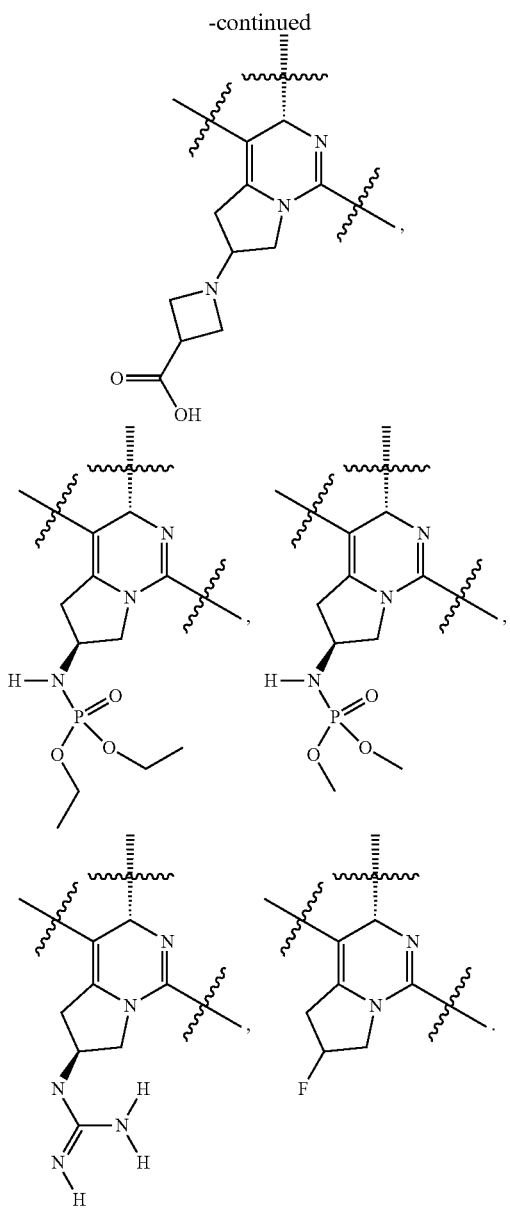

8. The compound or pharmaceutically acceptable salt thereof according to claim 1, wherein L, $D_{21}$ are selected from a single bond, —O—, —NH—; or $R_{21}$ is selected from $C_{1-4}$ alkyl, $C_{1-4}$ alkylamino, N,N-di($C_{1-4}$ alkyl) amino, $C_{1-4}$ alkylamino-$C_{1-4}$ alkyl-, N,N-di($C_{1-4}$ alkyl) amino-$C_{1-4}$ alkyl-, $C_{1-4}$ alkoxy, $C_{1-4}$ alkoxy-$C_{1-4}$ alkyl-, halo$C_{1-4}$ alkyl-, dihalo$C_{1-4}$ alkyl-, aminooxy $C_{1-4}$ alkyl-, hydroxyl $C_{1-4}$ alkyloxy-, hydroxyl $C_{1-3}$ alkylamino-.

9. The compound or pharmaceutically acceptable salt thereof according to claim 8, wherein $R_{21}$ is selected from methyl, ethyl, n-propyl, isopropyl, methylamino, ethylamino, propylamino, dimethylamino, diethylamino, dipropylamino, methylaminoethyl, ethylaminoethyl, propylaminoethyl, dimethylaminoethyl, diethylaminomethyl, dimethylaminomethyl, diethylaminoethyl, methoxymethyl, methoxyethyl, methoxypropyl, ethoxymethyl, propoxymethyl, ethoxyethyl, propoxypropyl, fluoromethyl, fluoroethyl, fluoropropyl, difluoromethyl, difluoroethyl, difluoropropyl, aminooxymethyl, aminooxyethyl, aminooxypropyl, hydroxymethyloxy, hydroxyethyloxy, hydroxypropoxy.

10. The compound or pharmaceutically acceptable salt thereof according to claim 9, wherein the structural unit

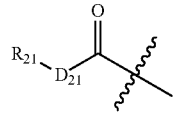

is selected from:

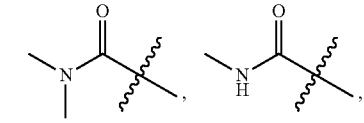

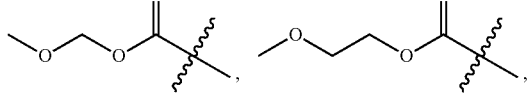

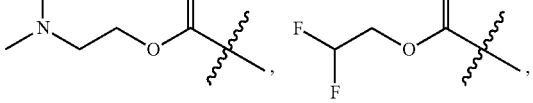

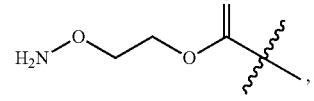

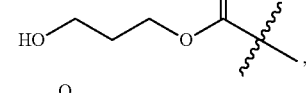

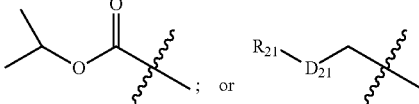

; or is selected from

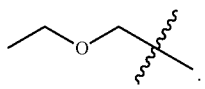 [SMILES: *COCC]

11. The compound or pharmaceutically acceptable salt thereof according to claim 1, wherein $R_3$ or $R_4$ is separately and independently selected from the following groups optionally substituted by 1, 2 or 3 $R_{001}$: phenyl, pyridyl, quinolyl, isoquinolyl, thiazolyl, thienyl, oxazolyl, isoxazolyl, pyrazolyl, isothiazole, furyl, pyrrolyl, pyrrolidinyl, 1,3-dioxolanyl, 2-pyrazolinyl, pyrazolidinyl, imidazolyl, 1,2,3-azolyl, 1,2,3-triazolyl, 1,2,4-triazolyl, 1,3,4-thiadiazolyl, piperidyl, 1,4-dioxanyl, morpholinyl, piperazinyl, piperidyl, pyrimidinyl, pyrazinyl, 1,3,5-trithianyl, 1,3,5-triazinyl, indenyl, naphthyl, benzofuranyl, benzothienyl, indolyl, benzimidazolyl, benzothiazolyl, benzocyclopentyl, or cyclopropyl.

12. The compound or pharmaceutically acceptable salt thereof according to claim 11, wherein $R_3$ is selected from 557
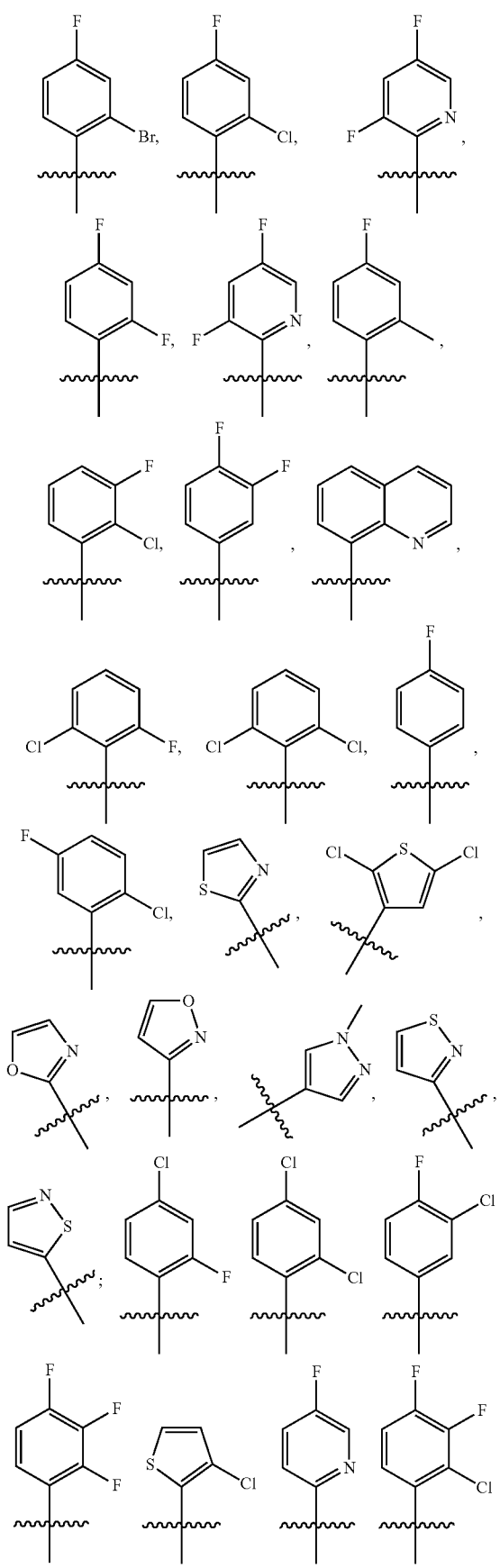
558
-continued
or OR₄ is selected from
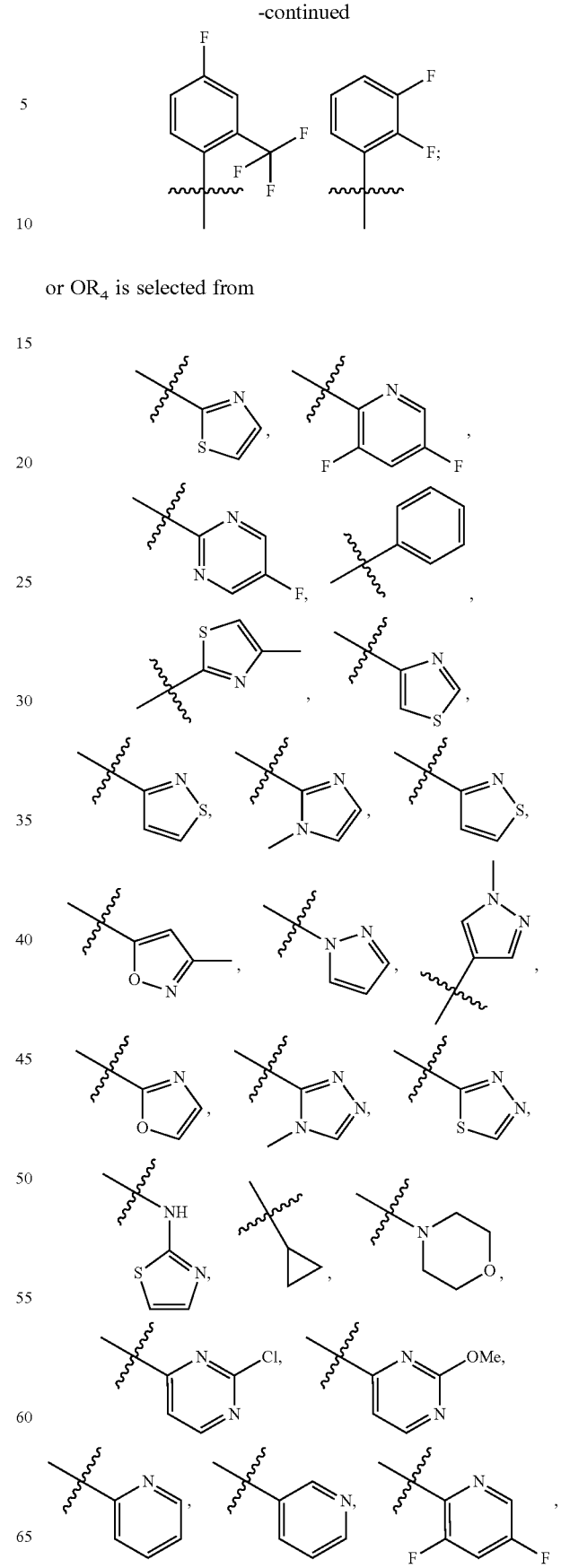

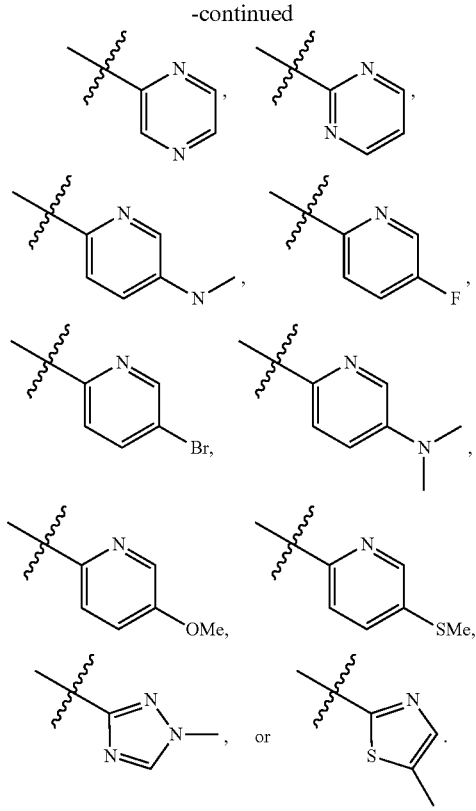
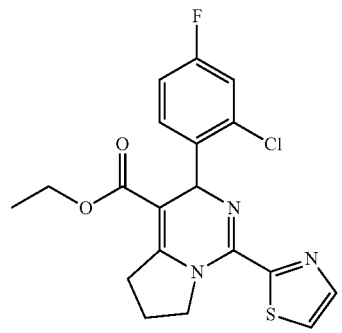
1
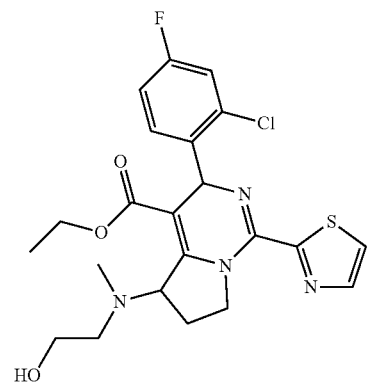
2
13. The compound or pharmaceutically acceptable salt thereof according to claim 1, wherein $R_{01}$ is selected from F, Cl, Br, I, OH, CN, $NH_2$, =NH, =O, =S, —SMe, Me, Et,
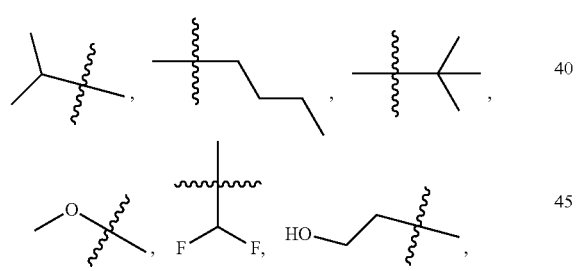
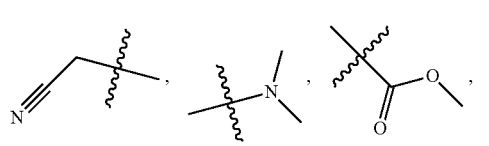
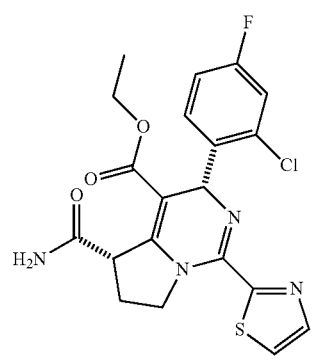
3
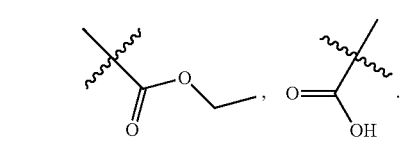
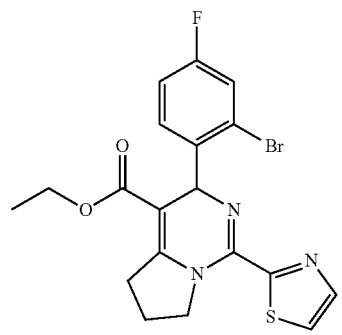
4
14. A compound or pharmaceutically acceptable salt thereof, selected from the following compounds:

561
-continued
5
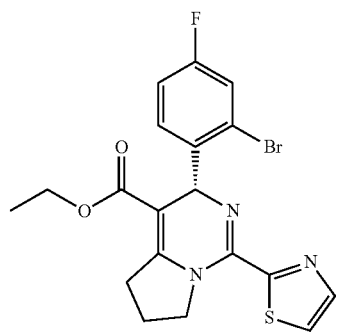
6
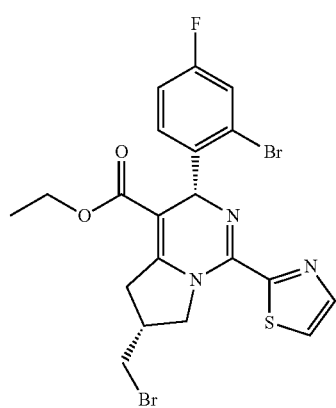
7
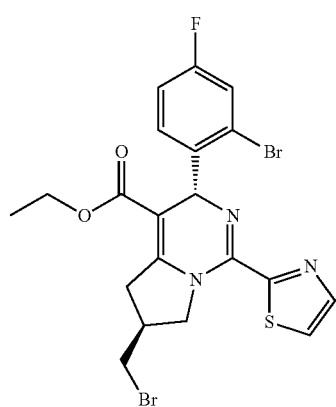
8
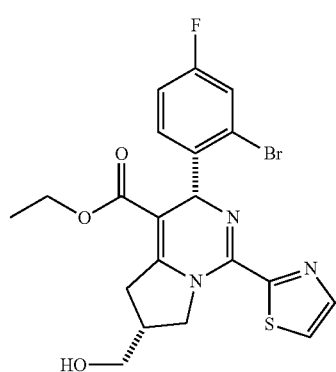
562
-continued
9
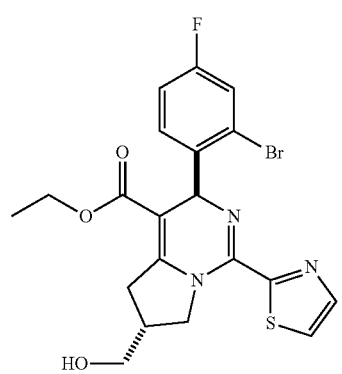
10
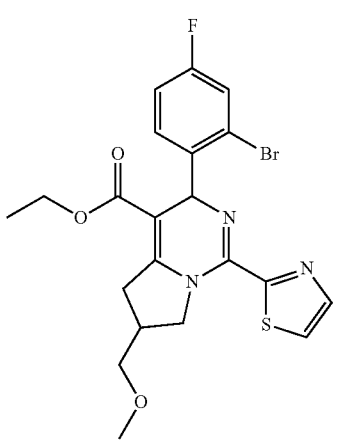
11
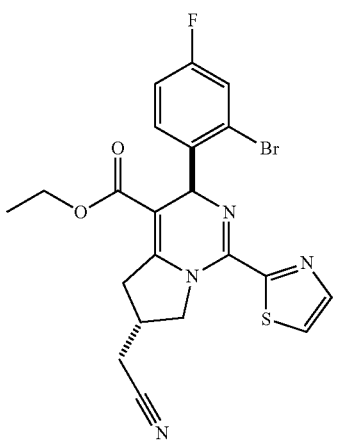

12
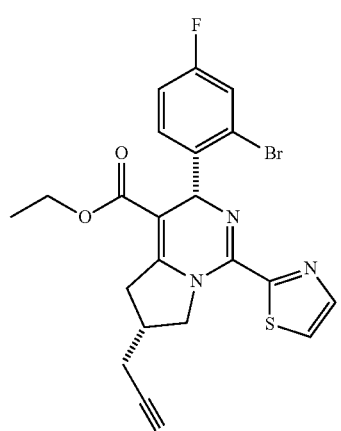
13
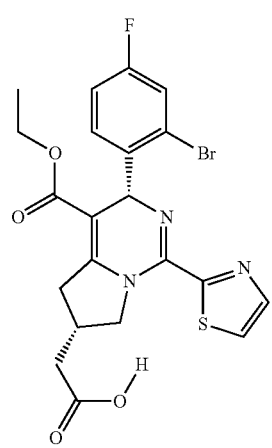
14
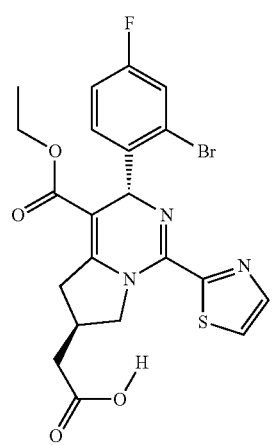
15
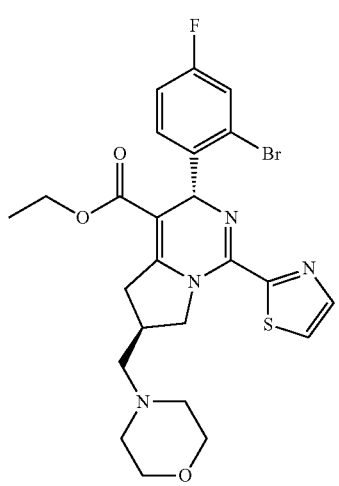
16
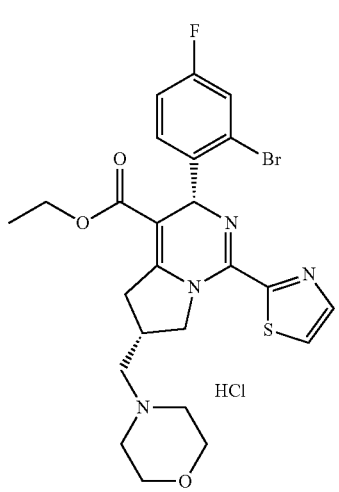
17
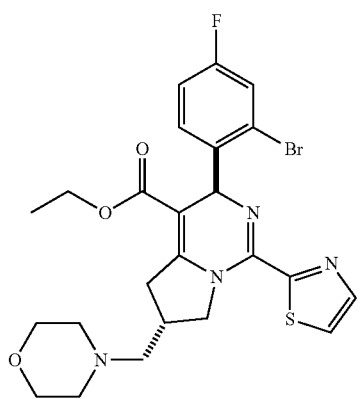

18
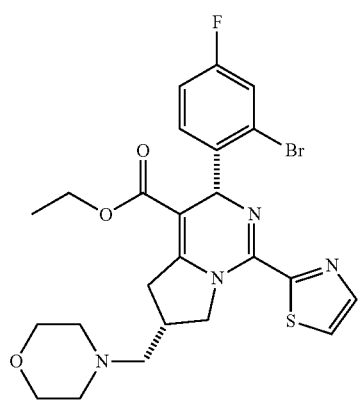
19
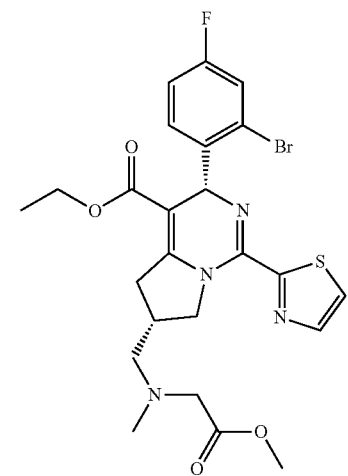
20
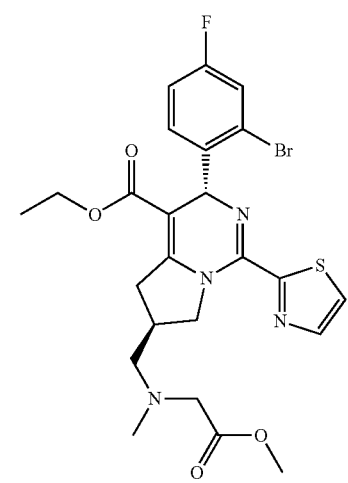
21
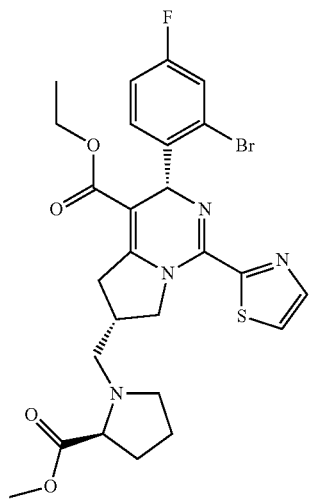
22
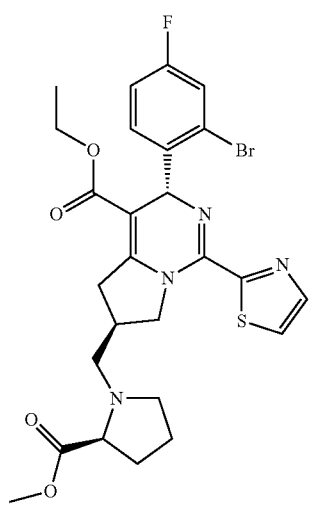
26
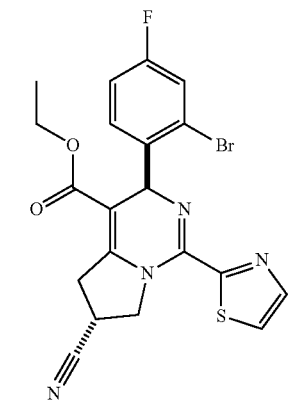

567
-continued
23
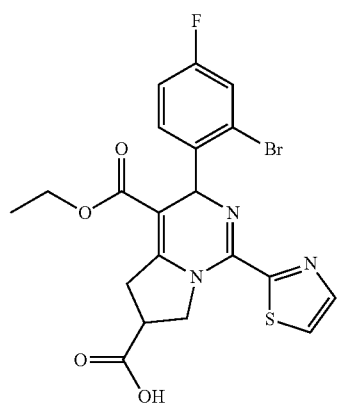
24
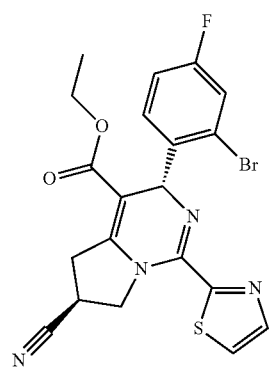
25
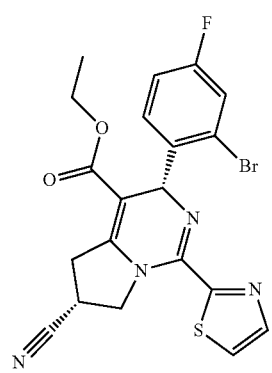
27
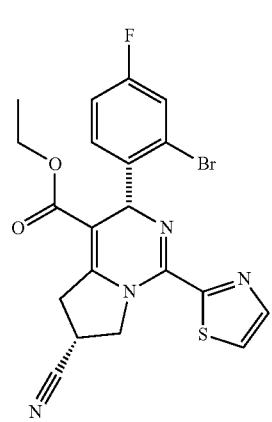
568
-continued
28
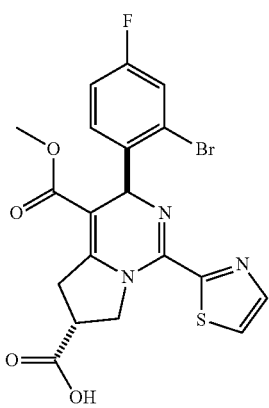
29
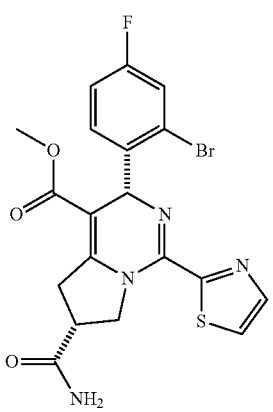
30
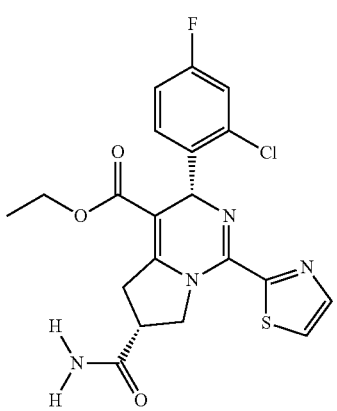
31
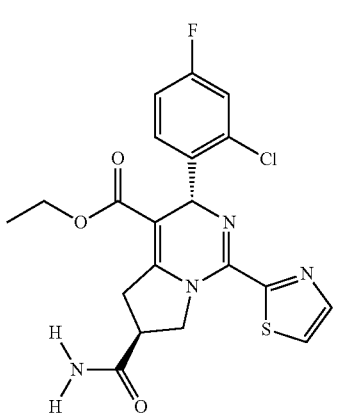

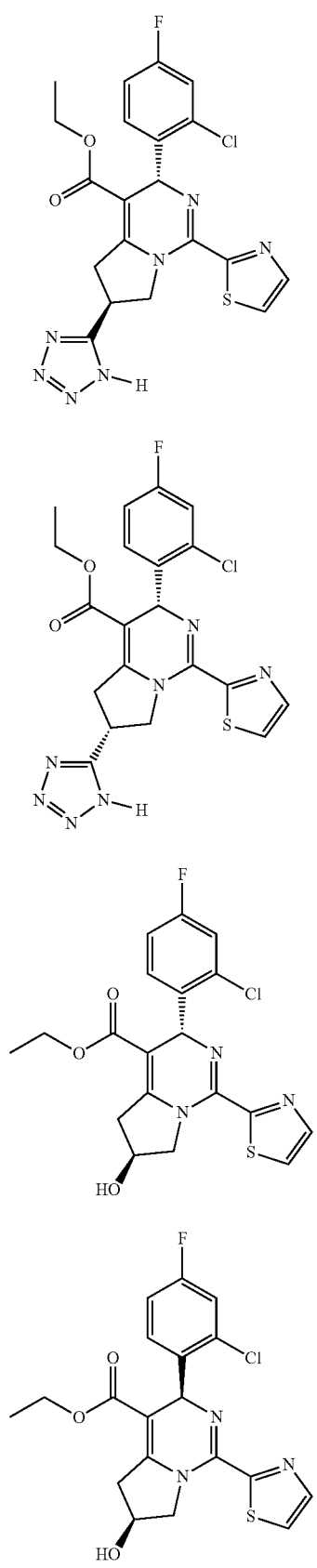
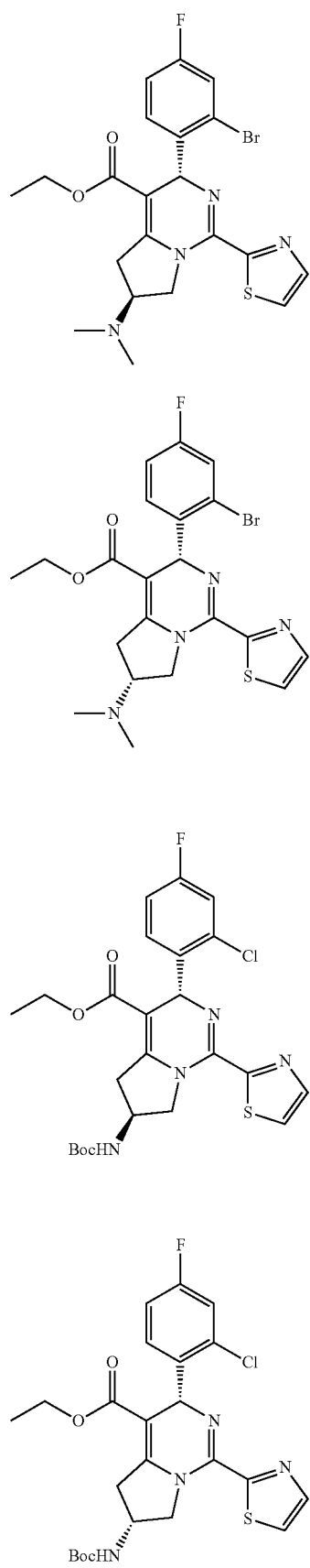

-continued
| | |
|---|---|
| 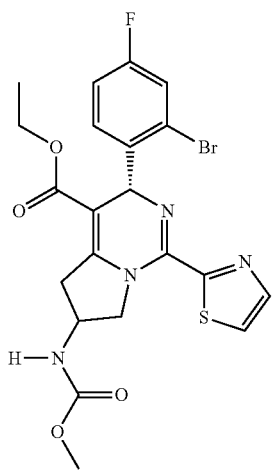 42 | 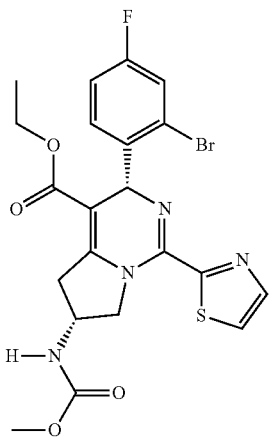 43 |
| 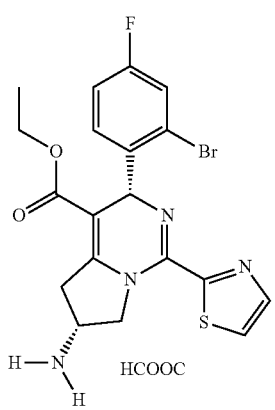 40 | 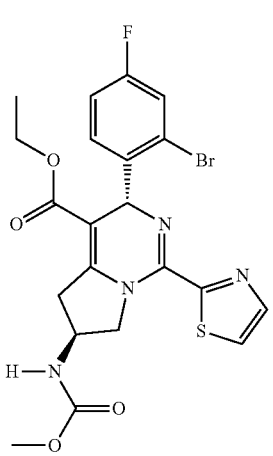 44 |
| 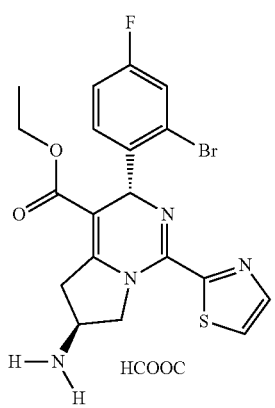 41 | 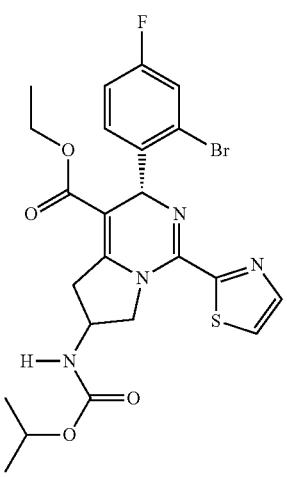 45 |

573
46
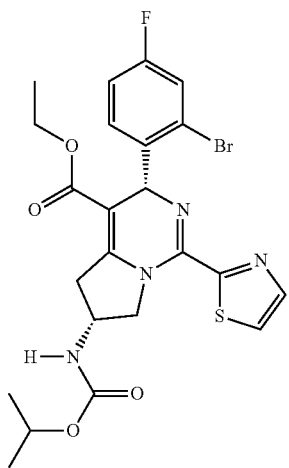
47
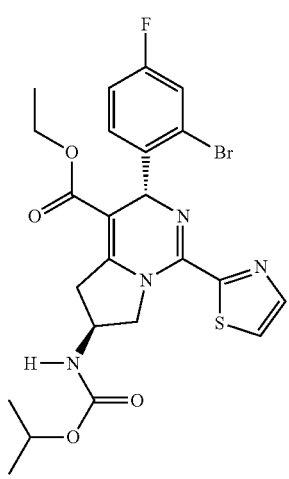
48
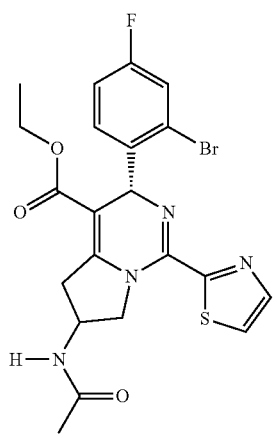
574
49
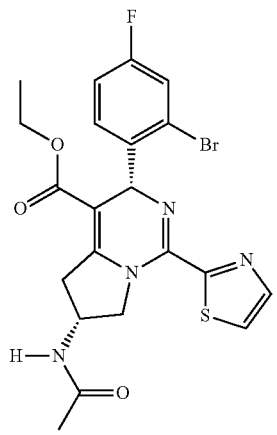
50
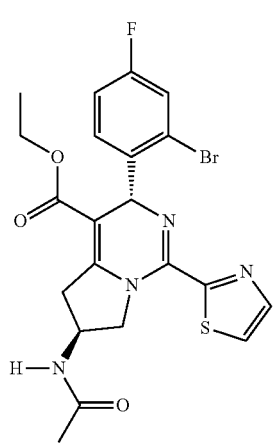
51
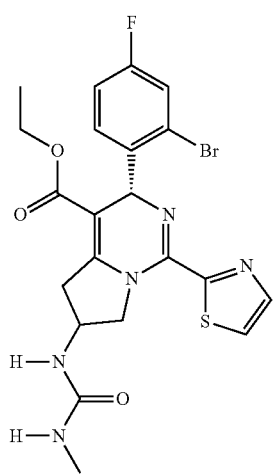

575
-continued
54
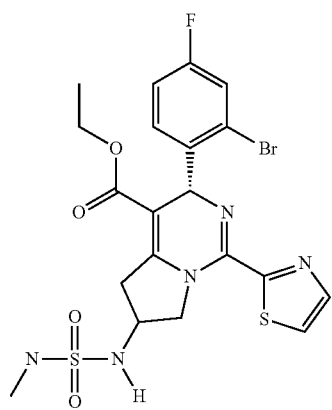
52
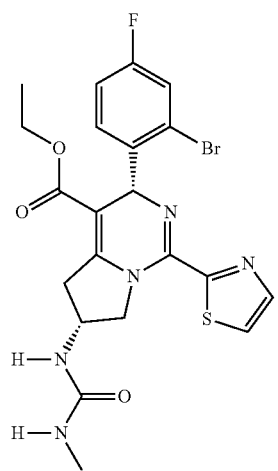
53
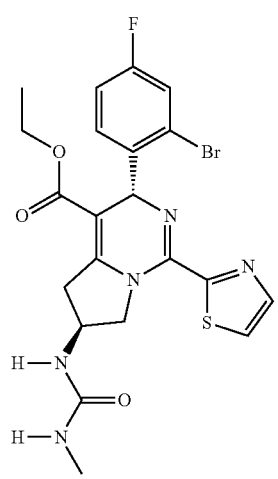
576
-continued
55
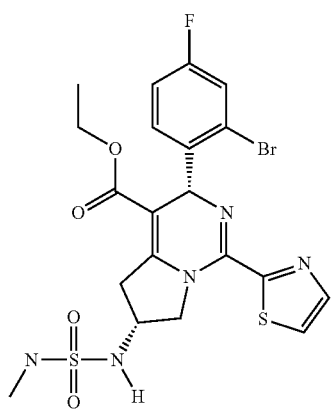
56
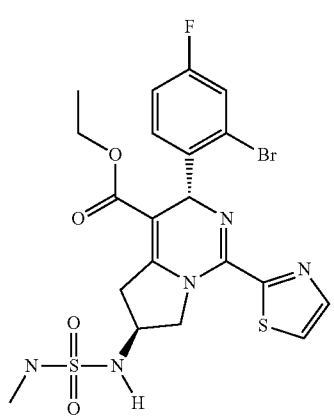
57
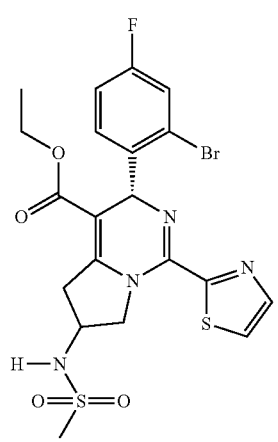

57
-continued
| | |
|---|---|
| 58 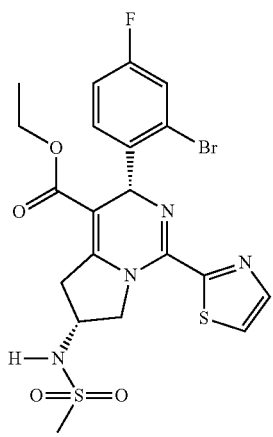 | 61 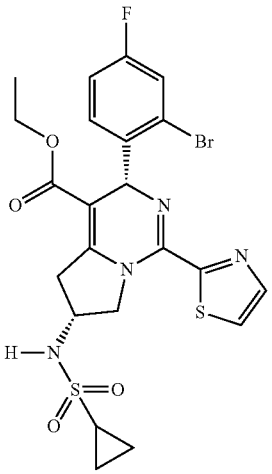 |
| 59 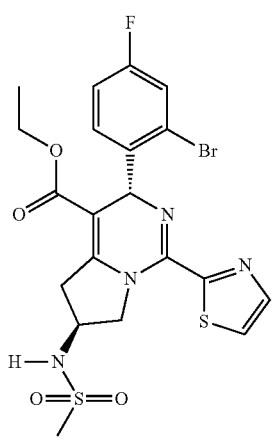 | 62 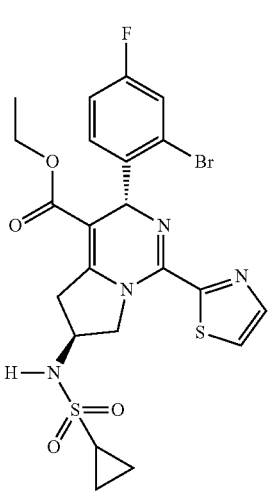 |
| 60 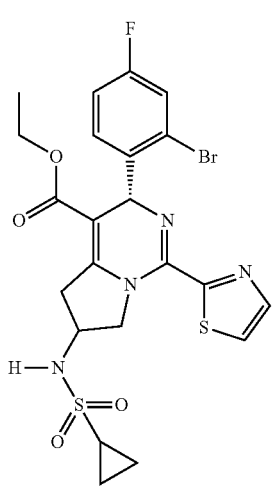 | 63 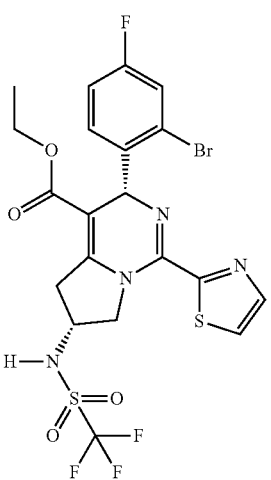 |

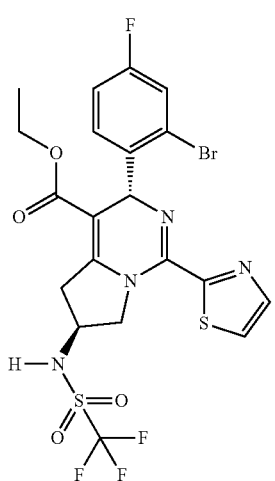
64
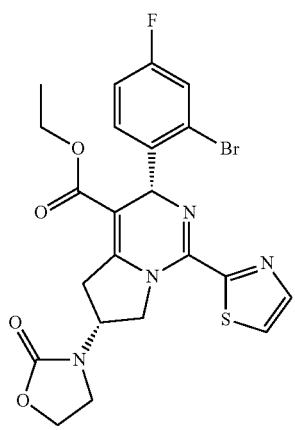
68
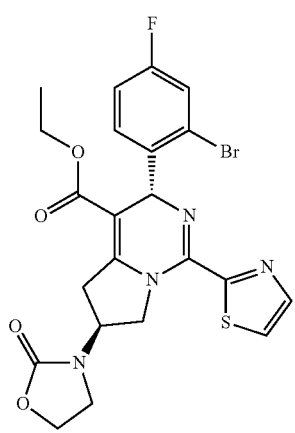
66
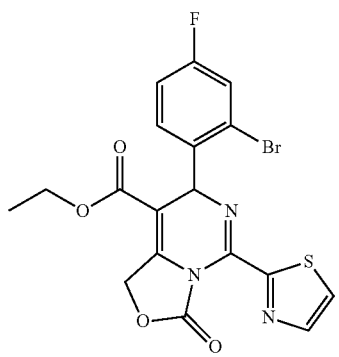
67
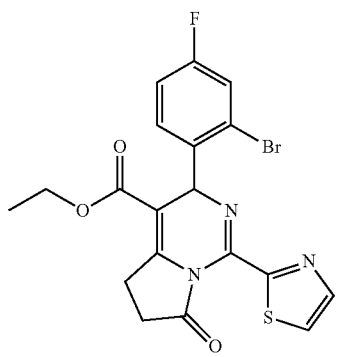
68
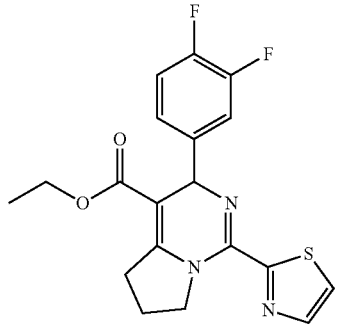
69
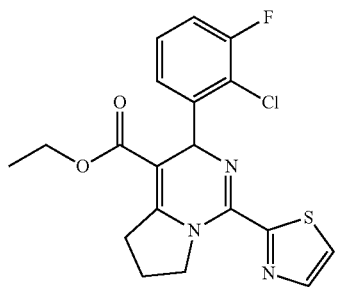
70

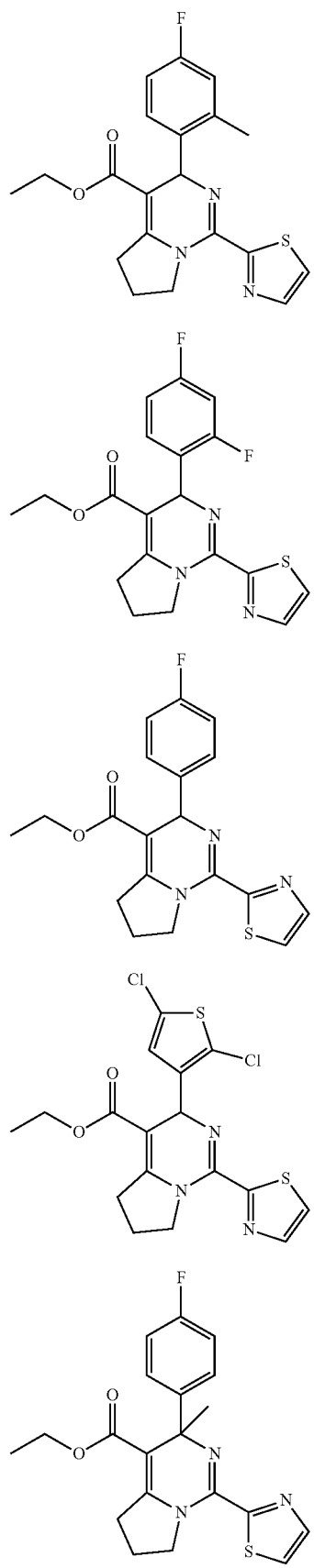
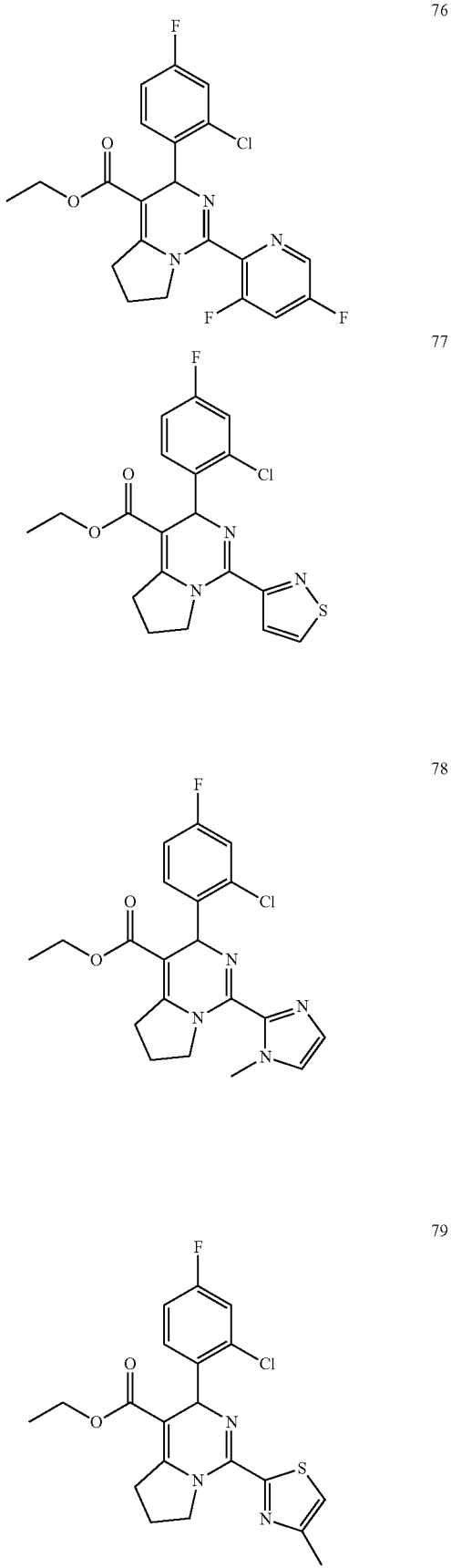

| 80 | 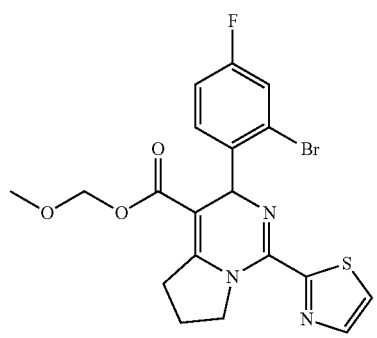 |
| --- | --- |
| 81 | 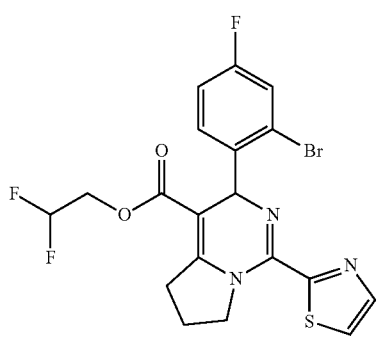 |
| 82 | 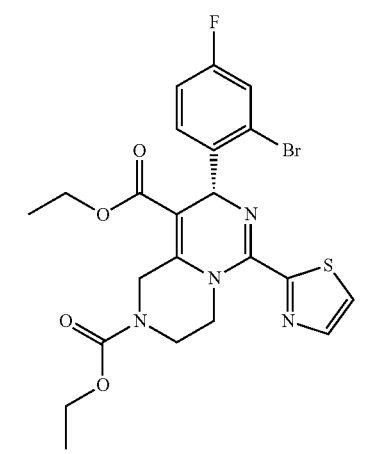 |
| 83 | 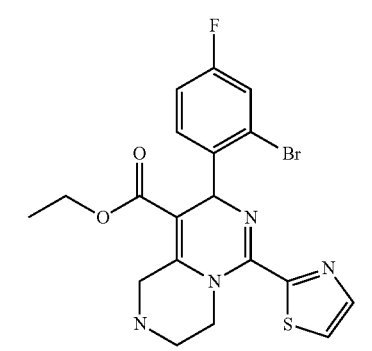 |
| 84 | 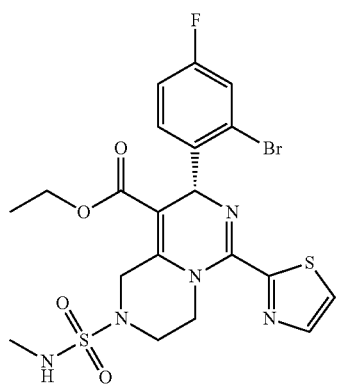 |
| 85 | 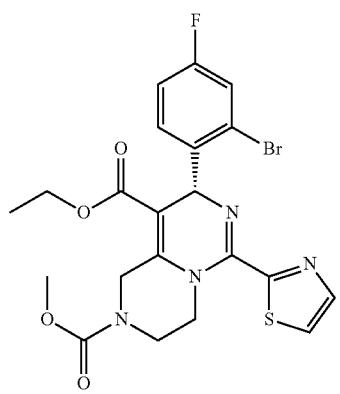 |
| 86 | 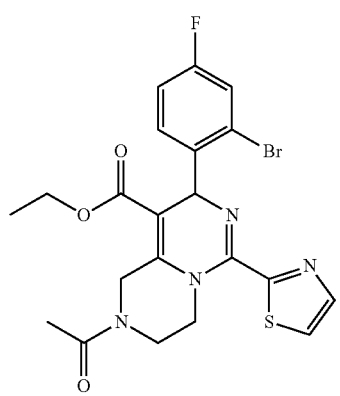 |
| 87 | 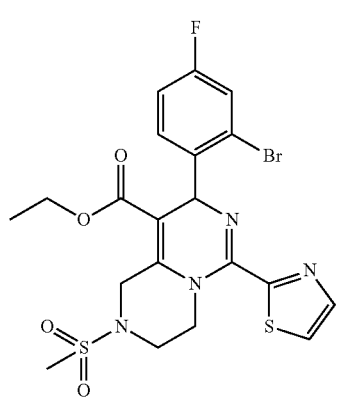 |

| 585 -continued | 586 -continued |
|---|---|
| 88 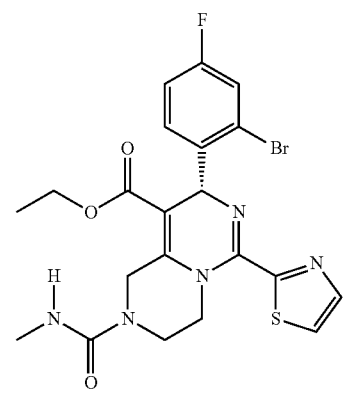 | 92 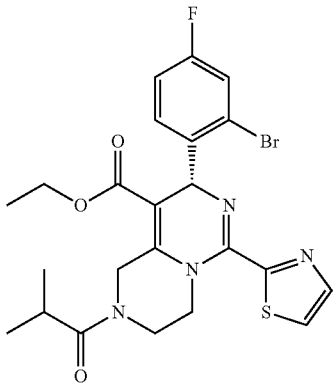 |
| 89 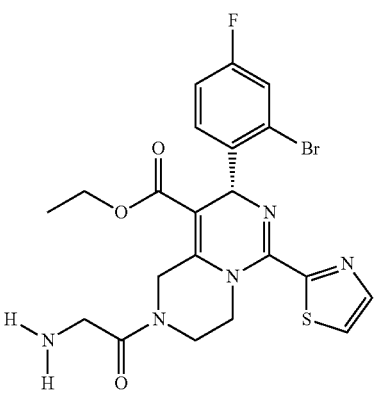 | 93 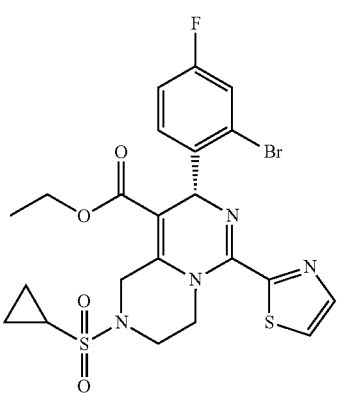 |
| 90 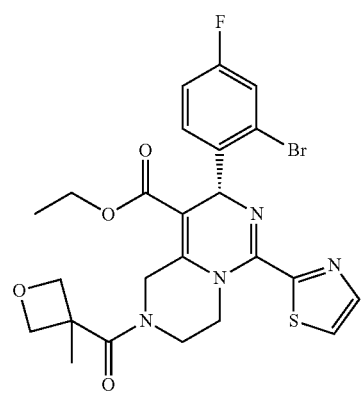 | 94 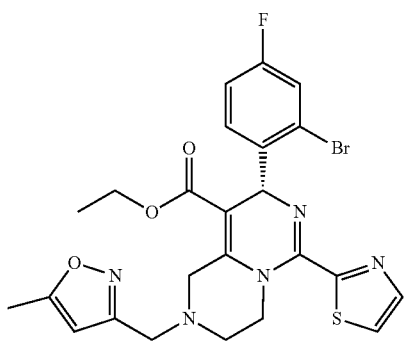 |
| 91 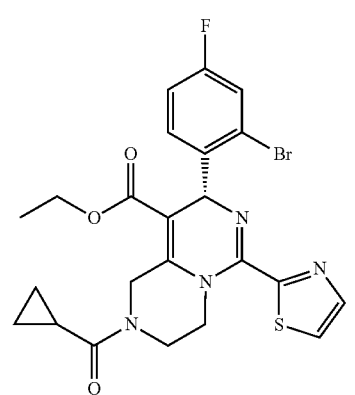 | 95 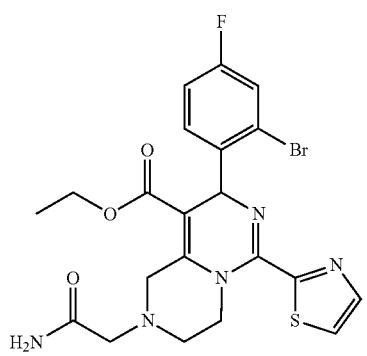 |

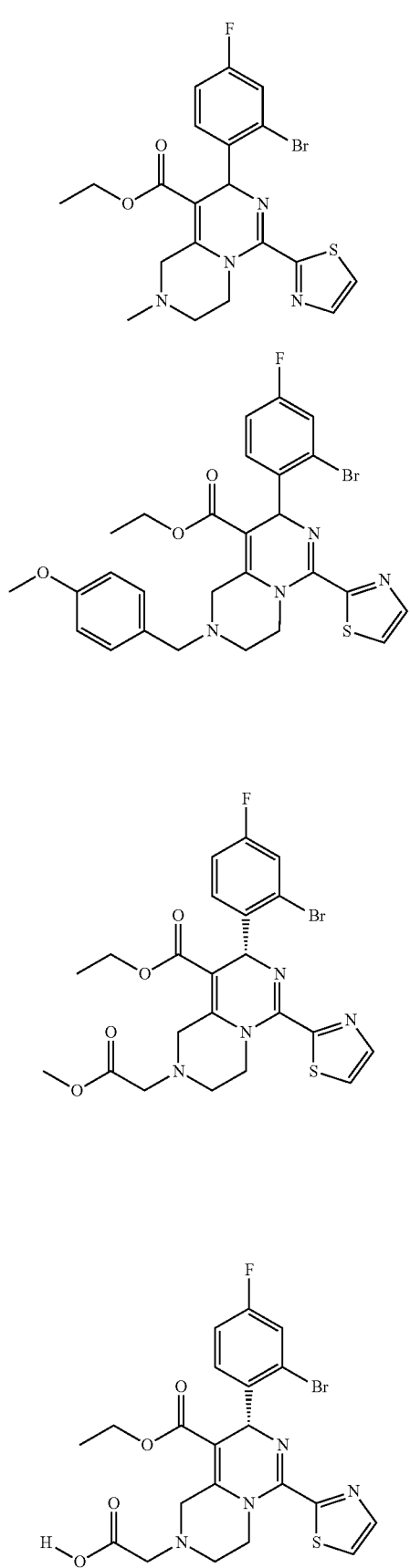
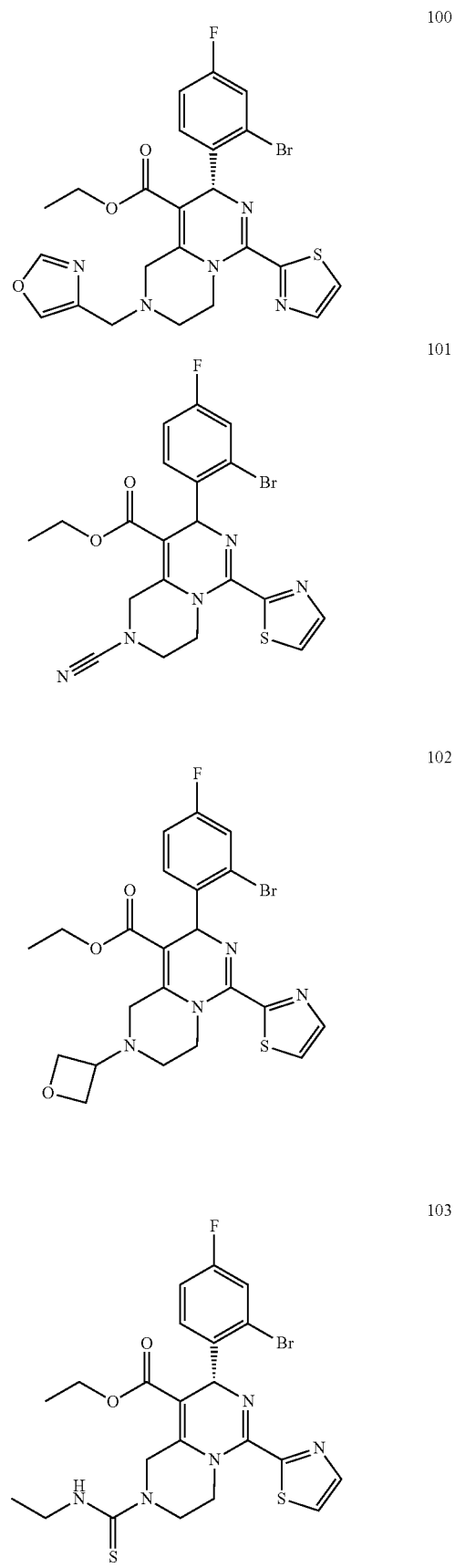

589
-continued
| | |
|---|---|
| 104 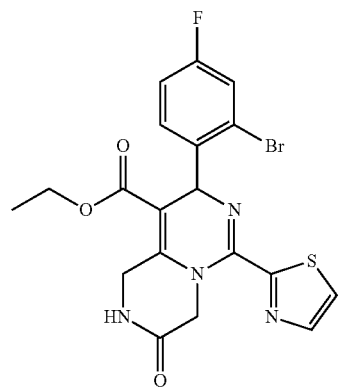 | 108 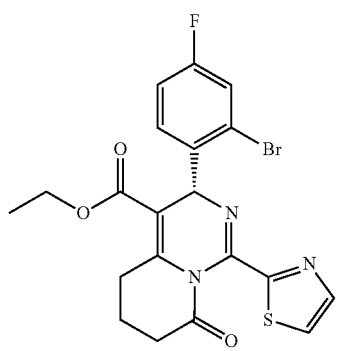 |
| 105 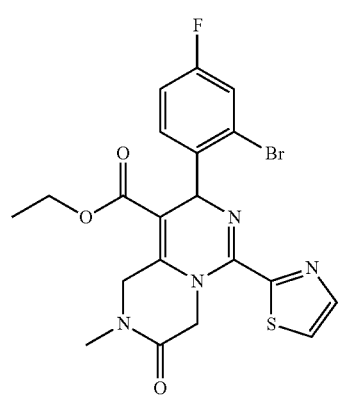 | 109 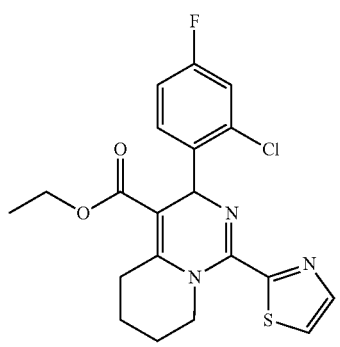 |
| 106 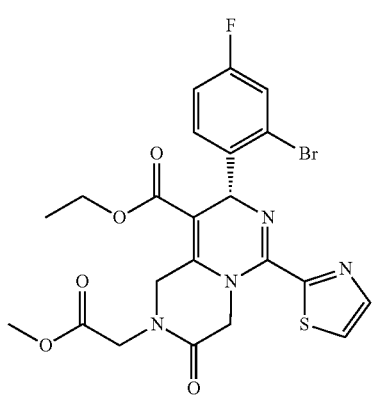 | 110 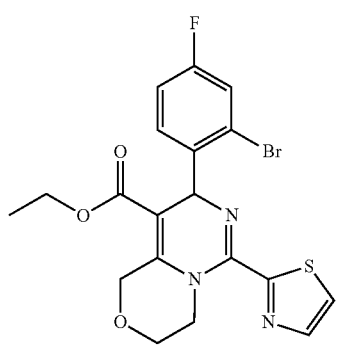 |
| 107 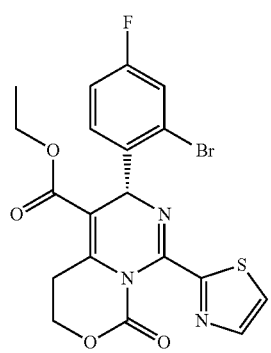 | 111 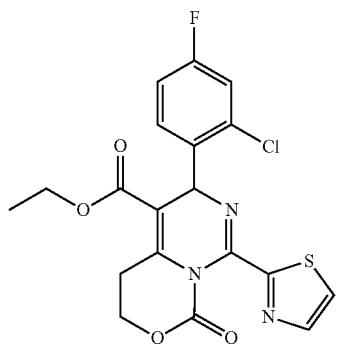 |
590
-continued

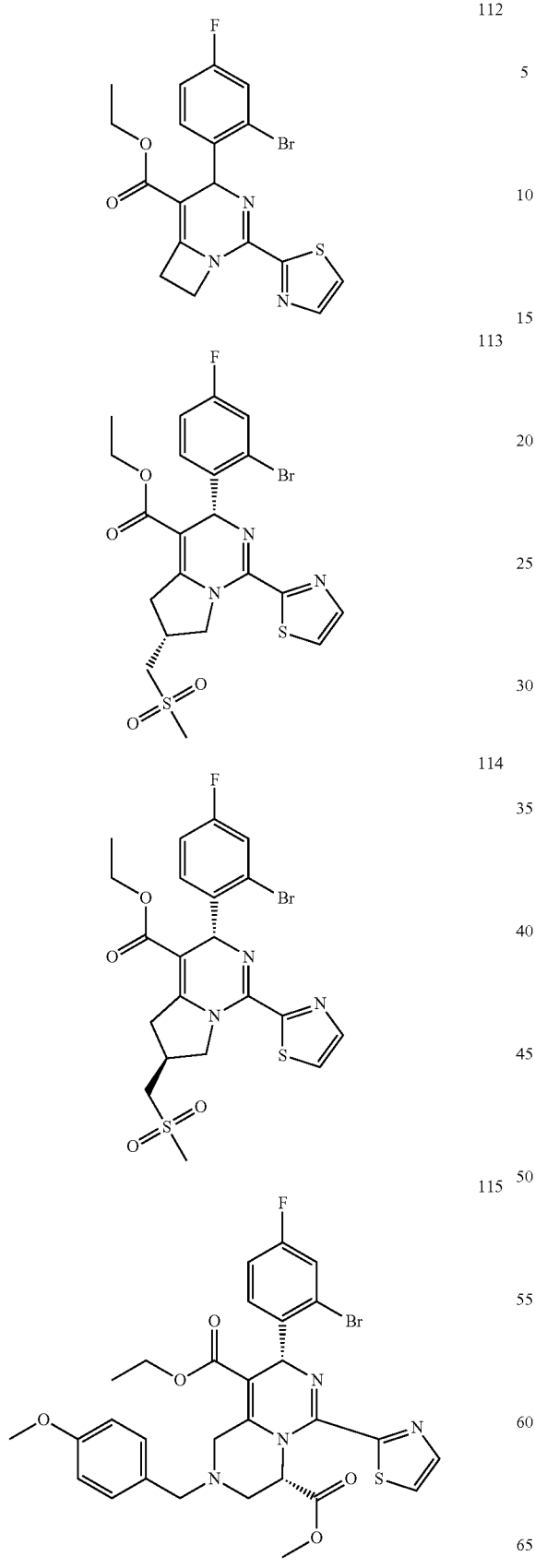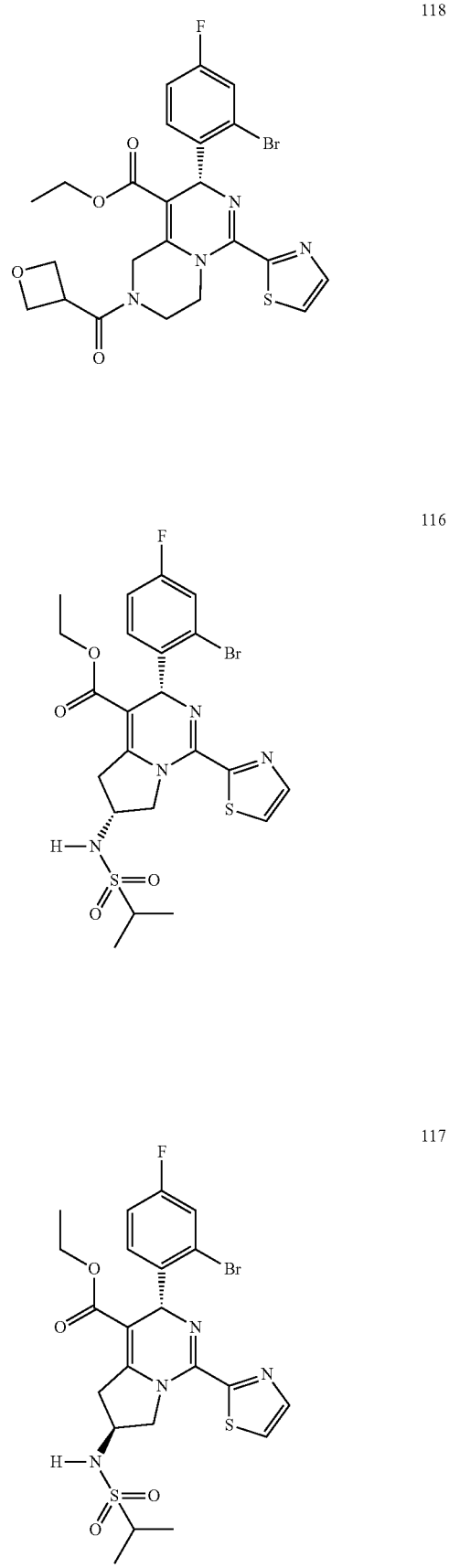

593
-continued
119
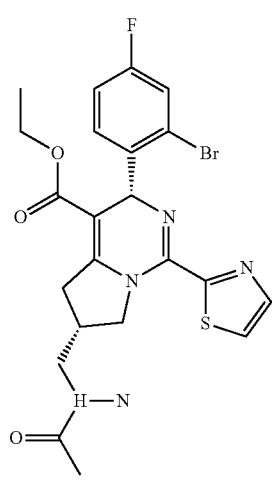
120
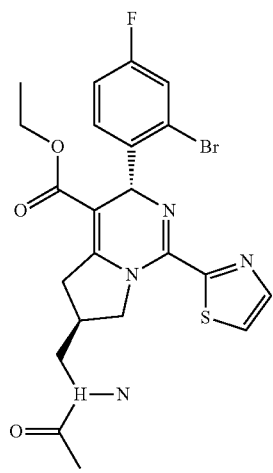
121
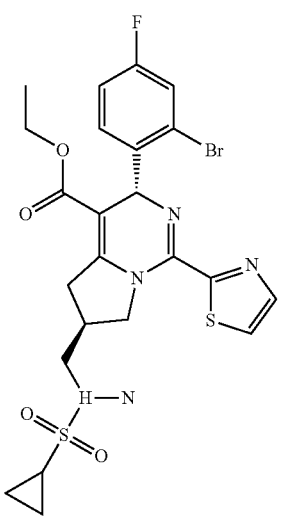
594
-continued
123
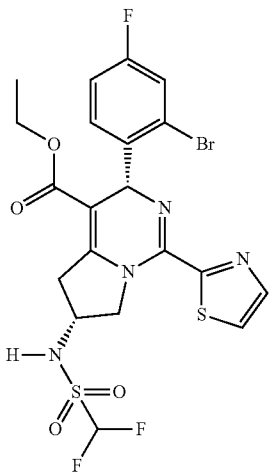
122
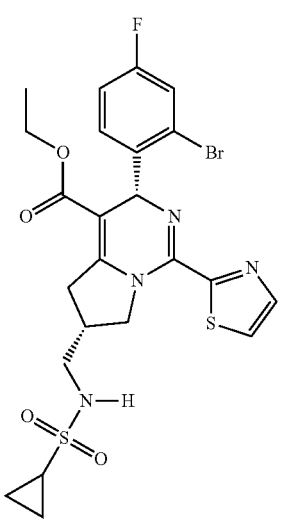
124
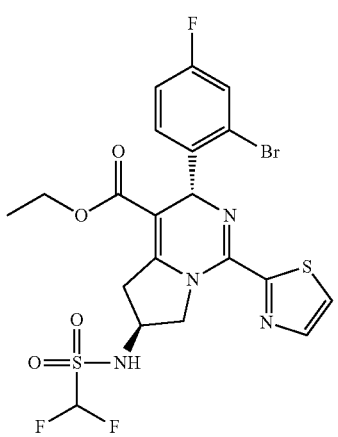

125 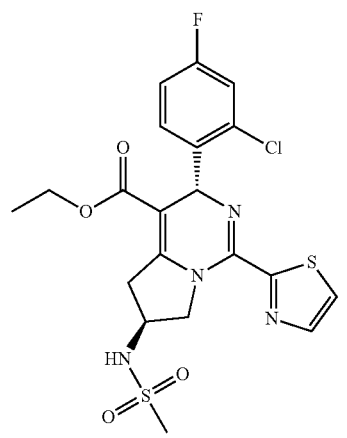
126 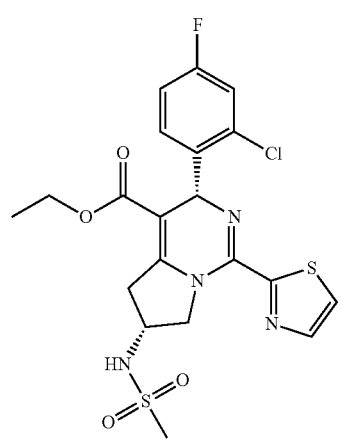
127 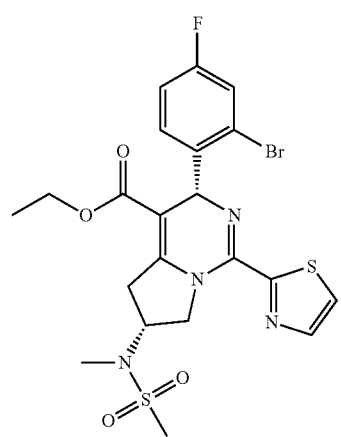
129 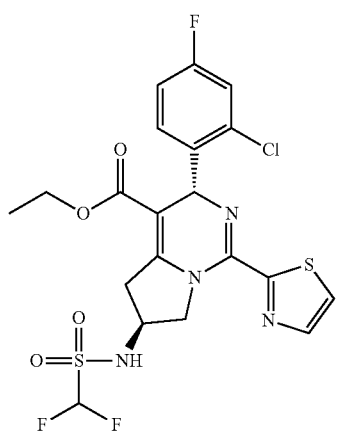
129 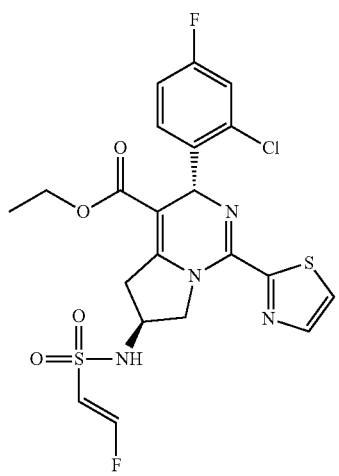
130 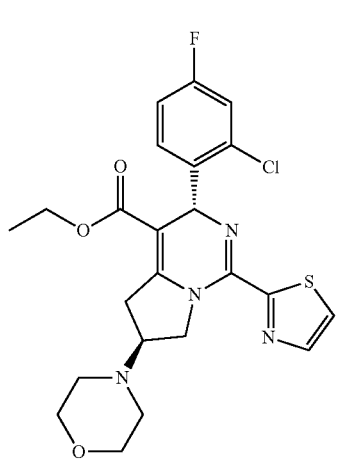

131 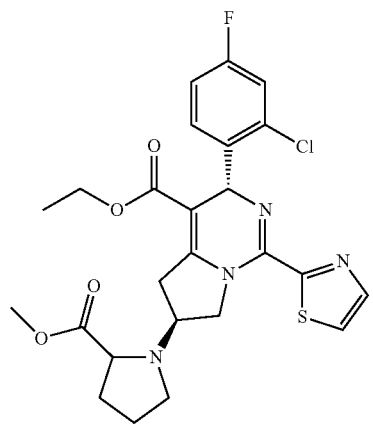
132 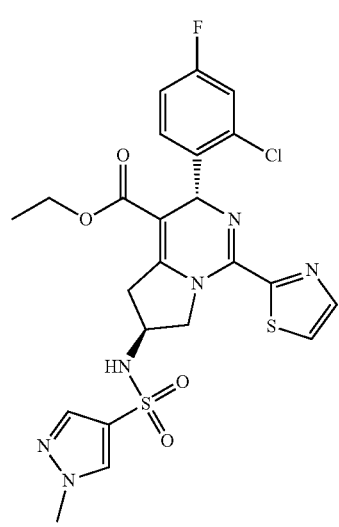
134 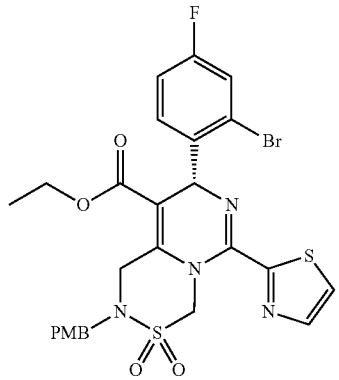
135 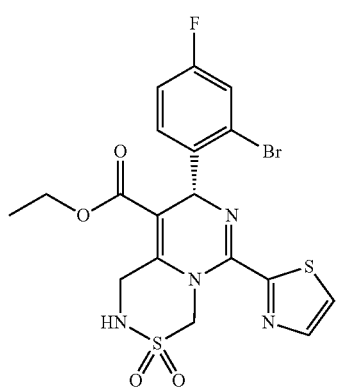
136 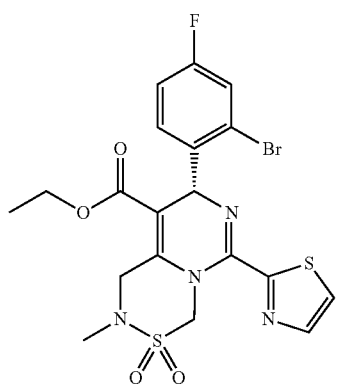
137 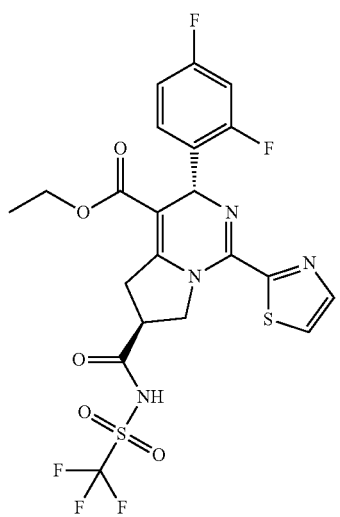

| 138 | 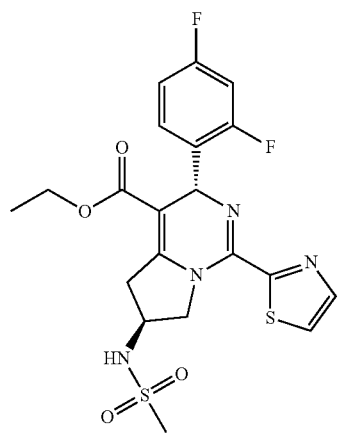 | 141 | 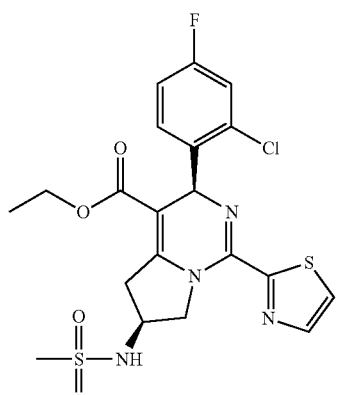 |
| 139 | 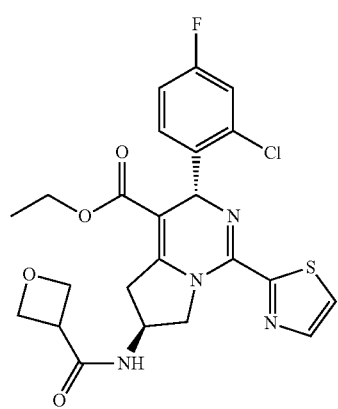 | 142 | 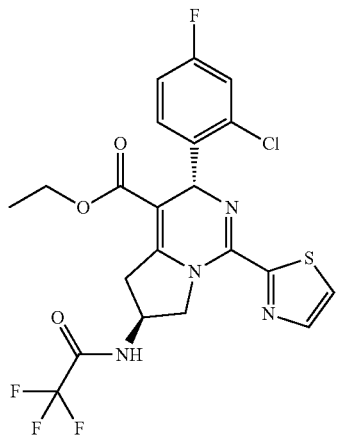 |
| 140 | 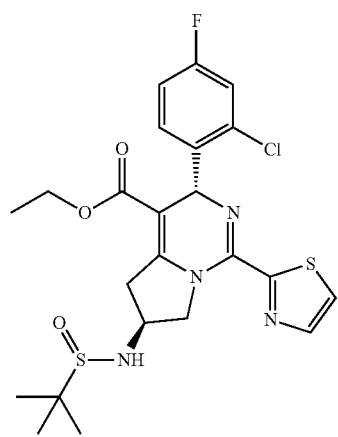 | 143 | 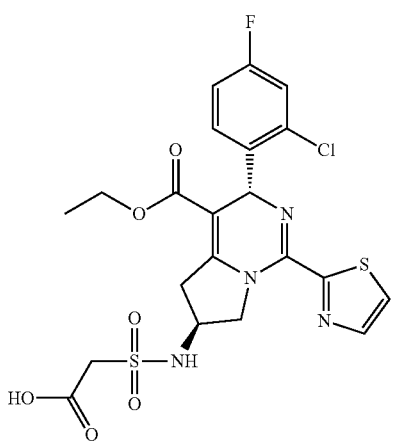 |

| 144 | 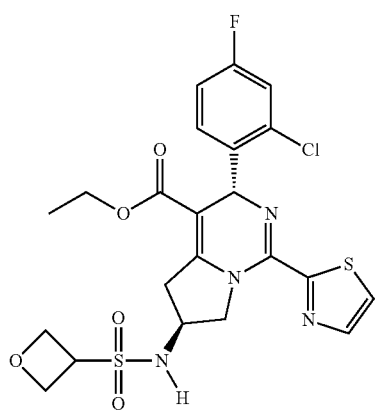 | 148 | 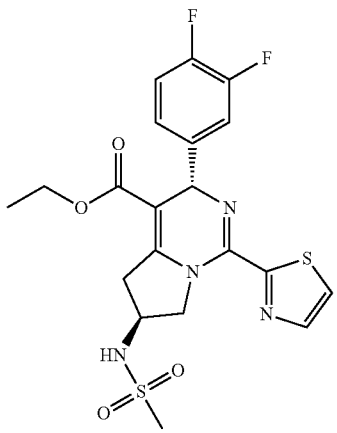 |
| 145 | 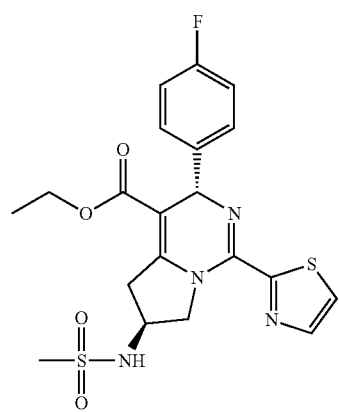 | 149 | 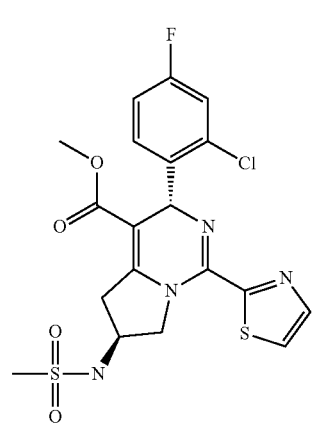 |
| 146 | 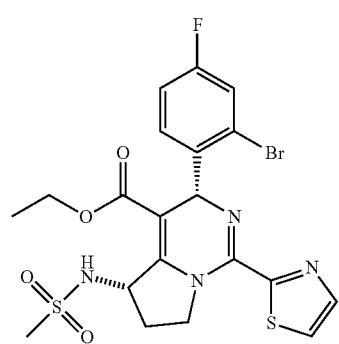 | 150 | 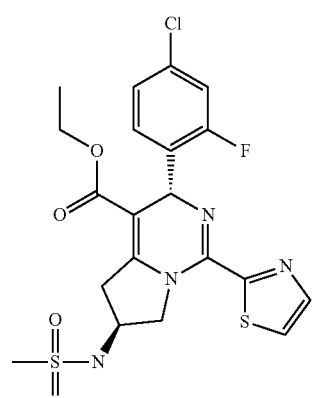 |
| 147 | 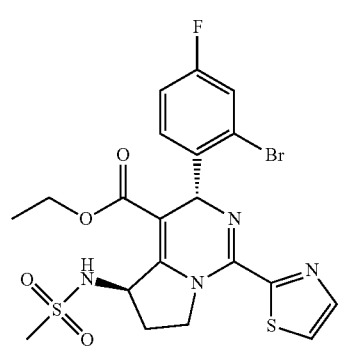 | 151 | 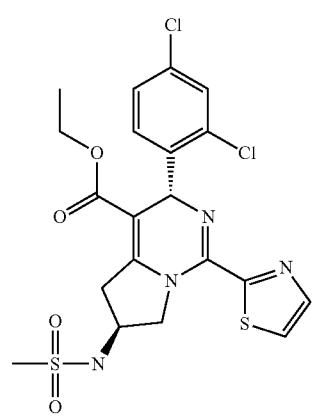 |

| 603 -continued | 604 -continued |
|---|---|
| 152 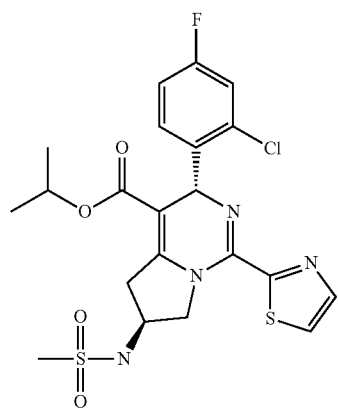 | 155 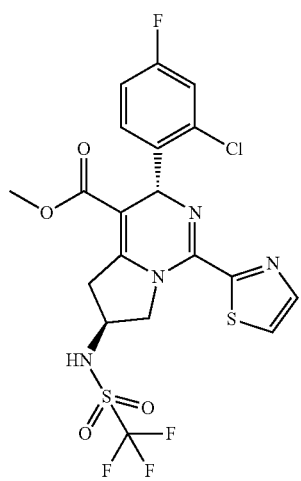 |
| 153 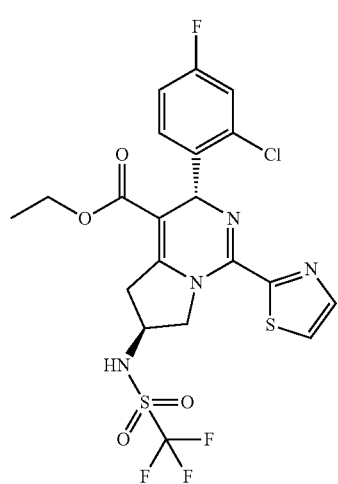 | 156 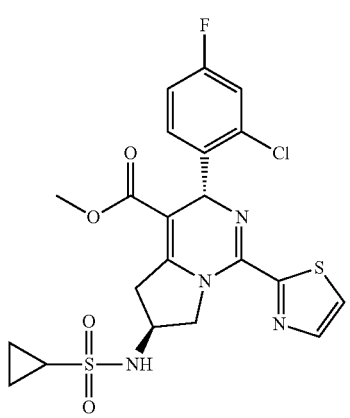 |
| 154 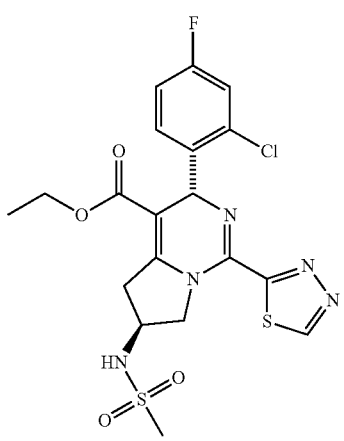 | 157 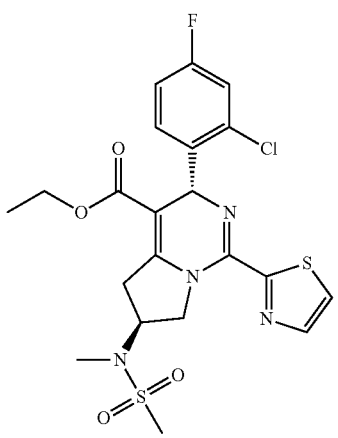 |

158
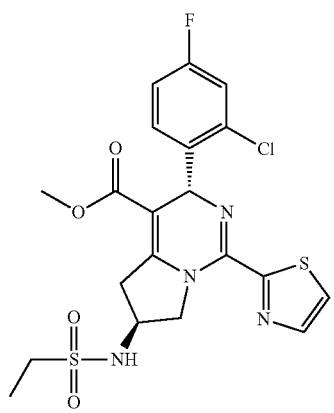
159
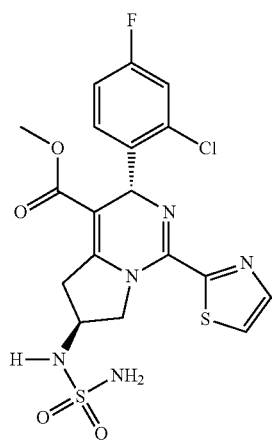
160
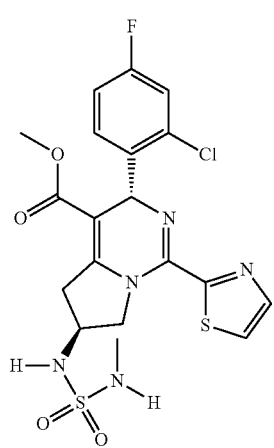
161
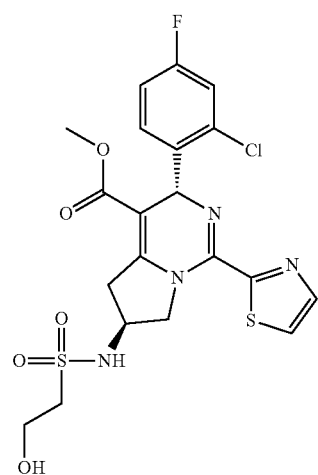
162
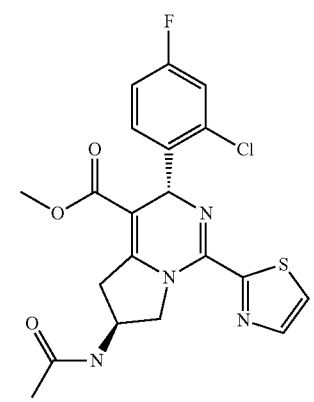
163
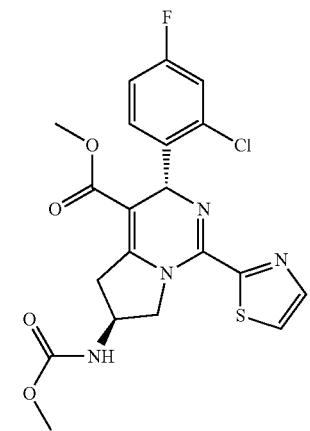

607
-continued
164
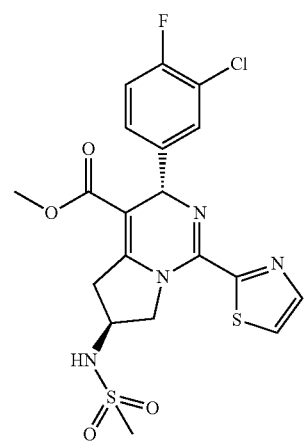
165
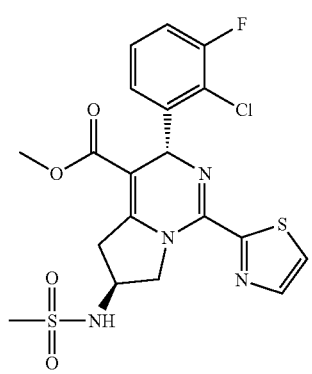
166
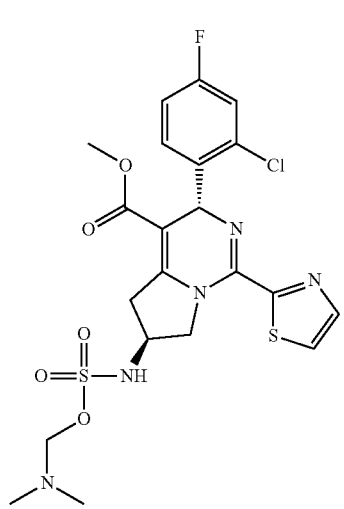
608
-continued
167
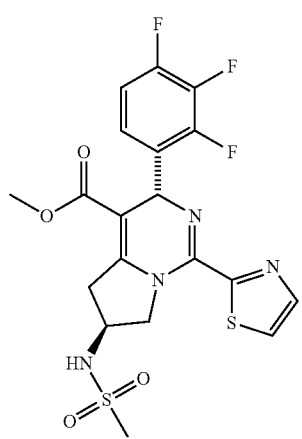
168
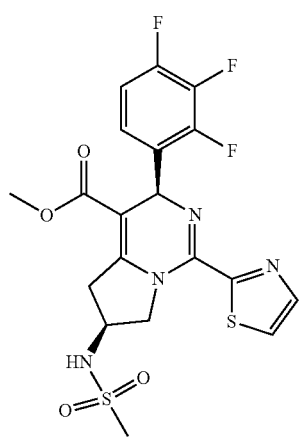
169
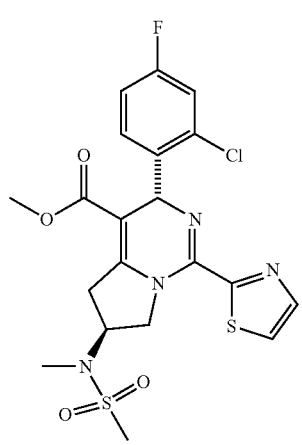

609
-continued
170
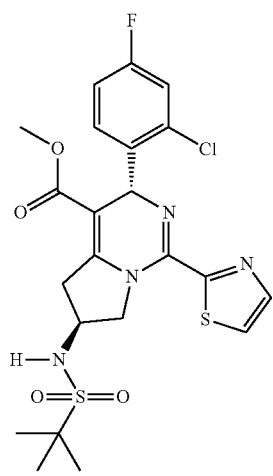
171
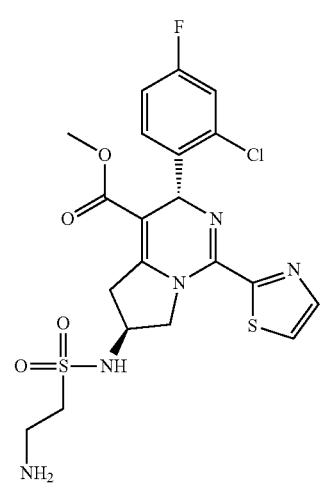
172
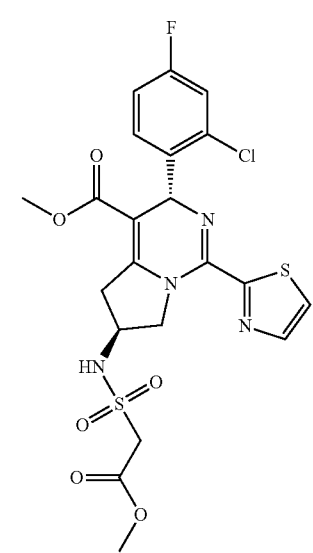
610
-continued
173
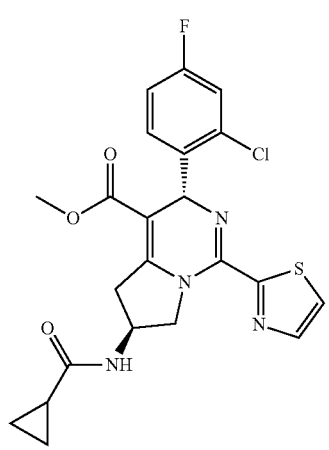
174
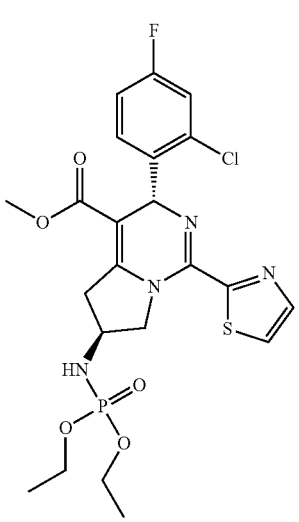
175
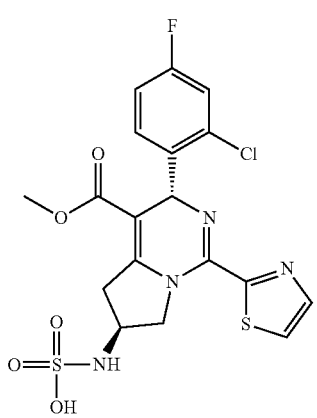

| 611 -continued | 612 -continued |
|---|---|
| 176 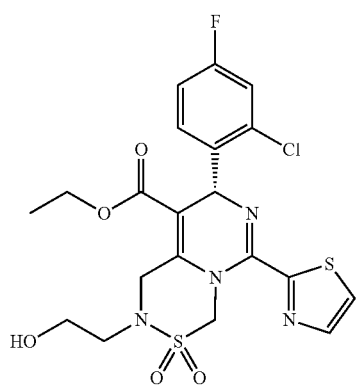 | 180 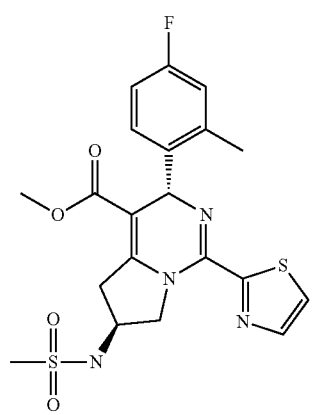 |
| 177 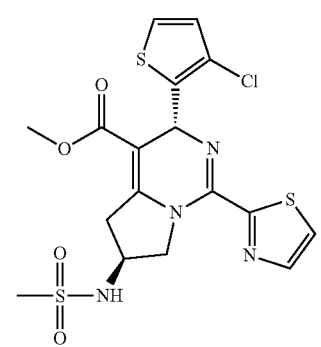 | |
| 178 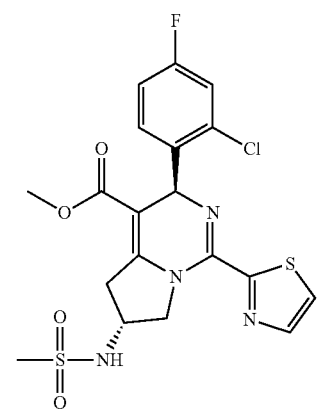 | 181 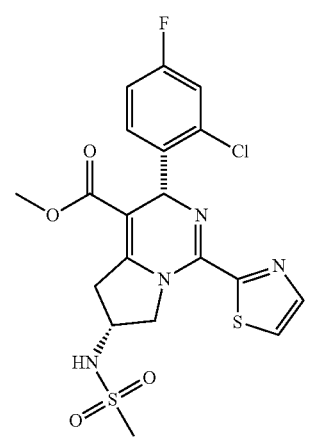 |
| 179 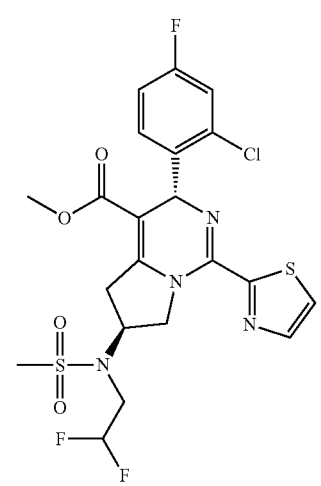 | 182 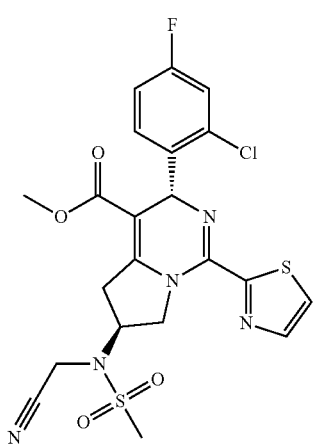 |

613
-continued
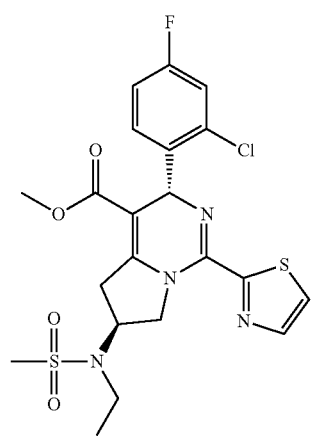
183
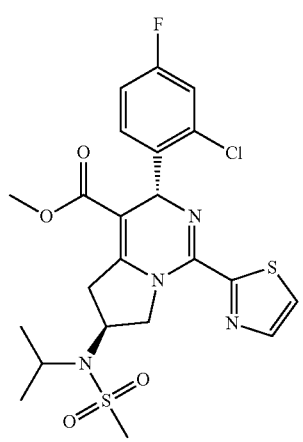
184
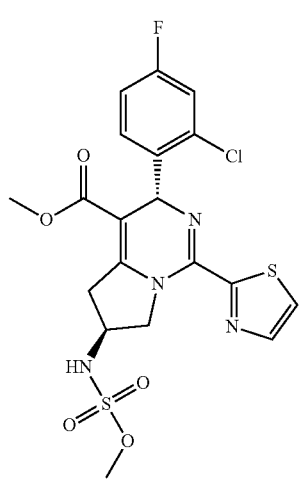
185
614
-continued
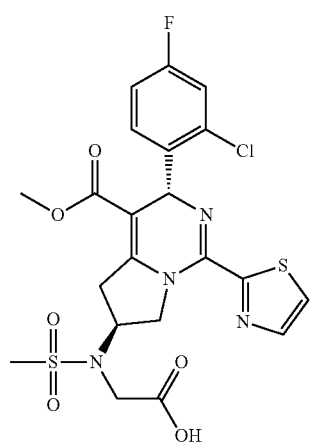
186
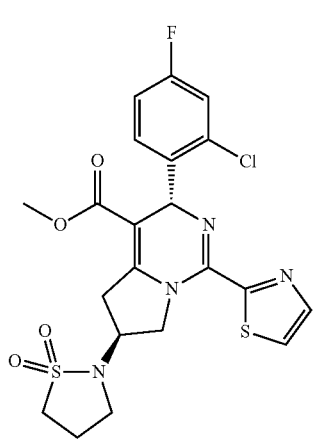
187
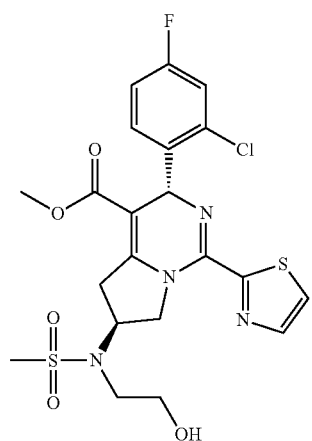
188

189
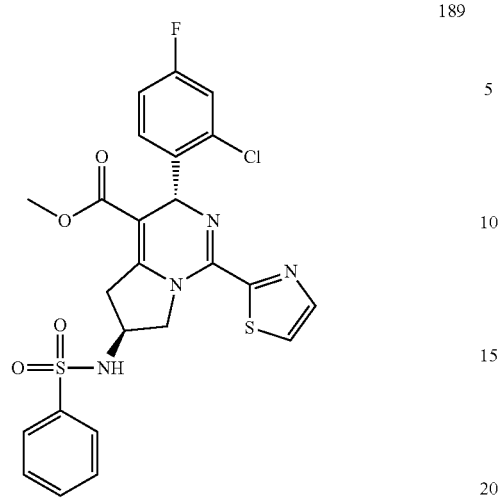
190
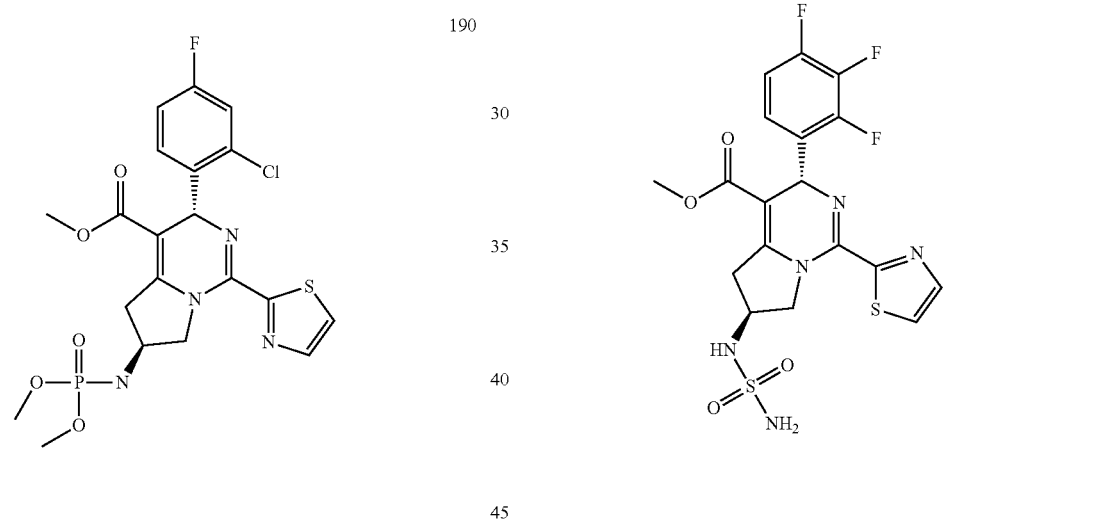
191
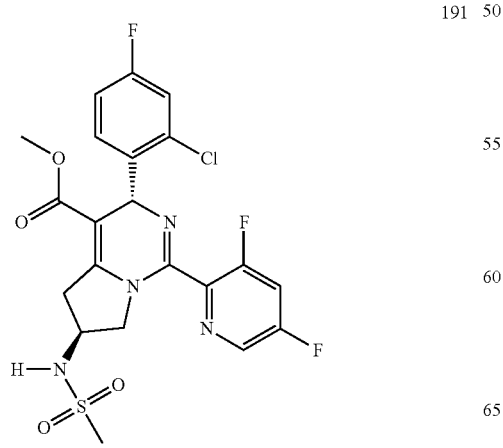
192
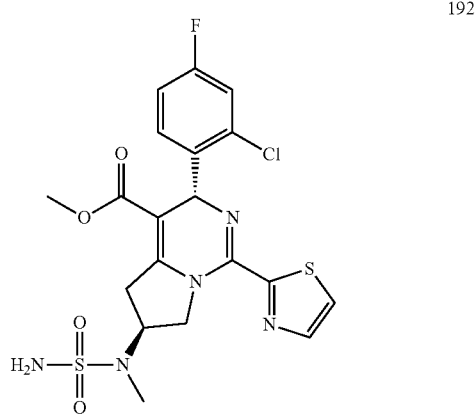
193
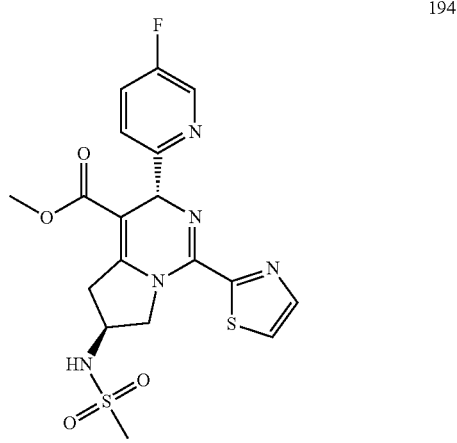
194

195
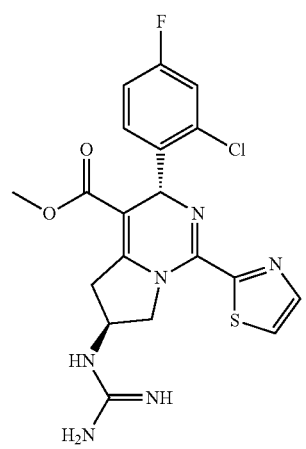
196
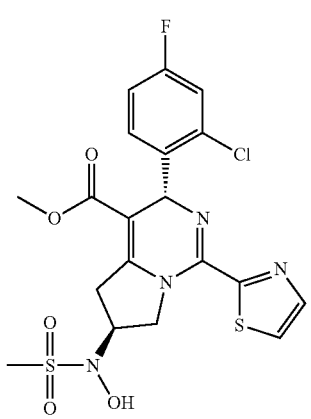
197
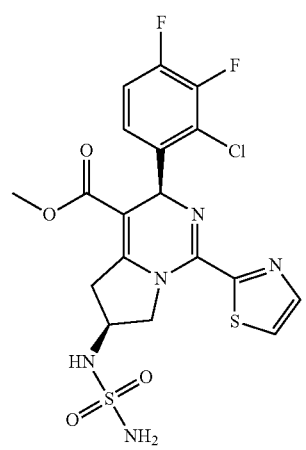
198
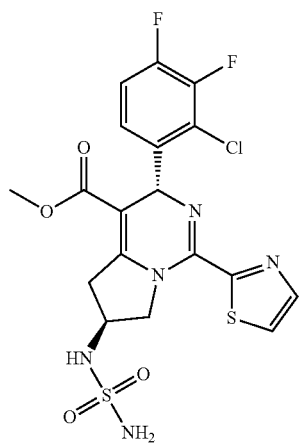
199
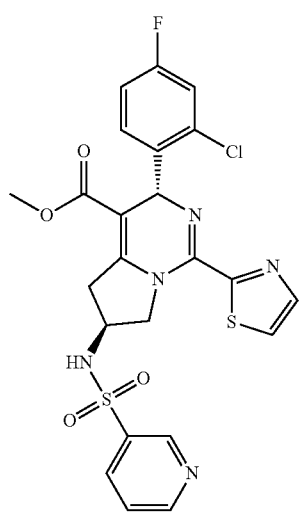
200
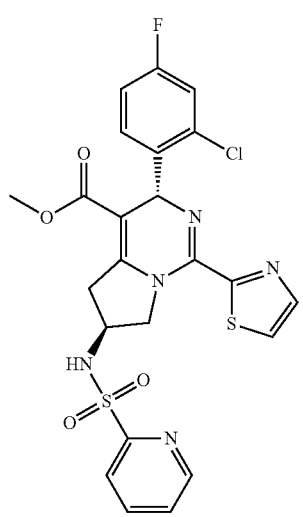

| 619 -continued | | 620 -continued | |
|---|---|---|---|
| 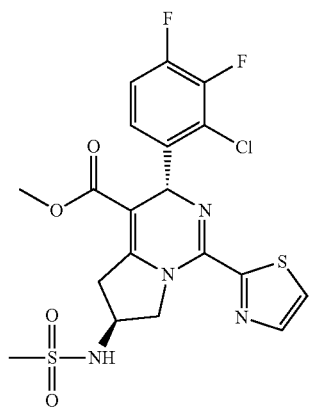 | 201 | 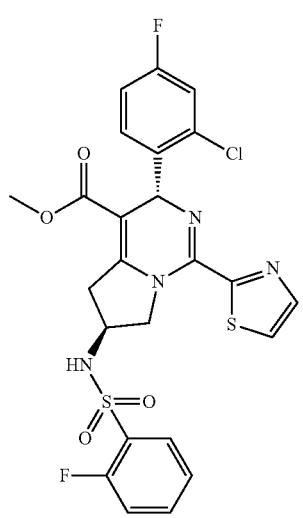 | 204 |
| 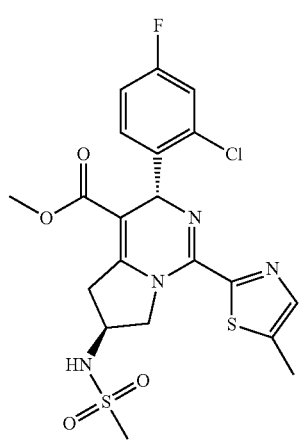 | 202 | 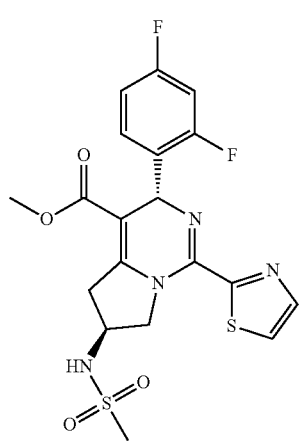 | 205 |
| | 203 | 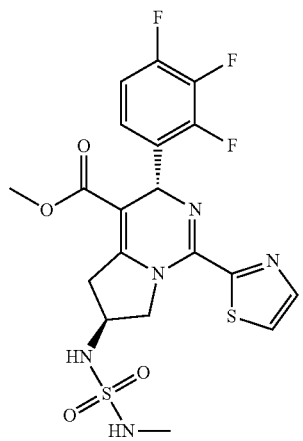 | 206 |

| 207 | 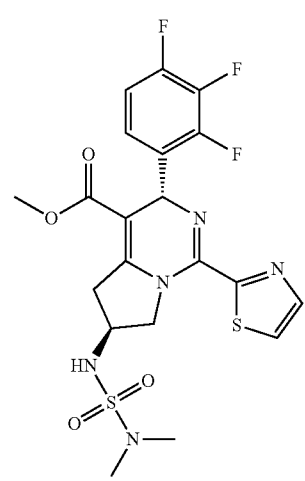 | 210 | 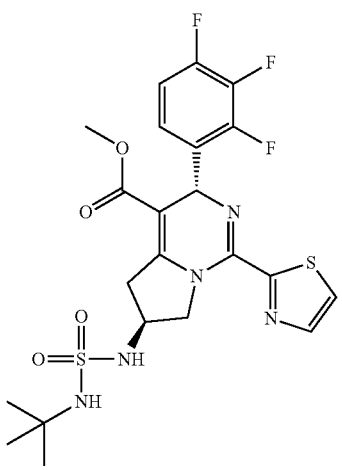 |
| --- | --- | --- | --- |
| 208 | 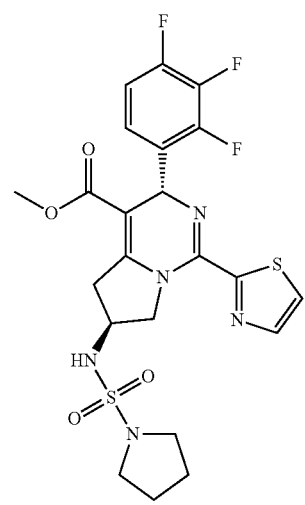 | 211 | 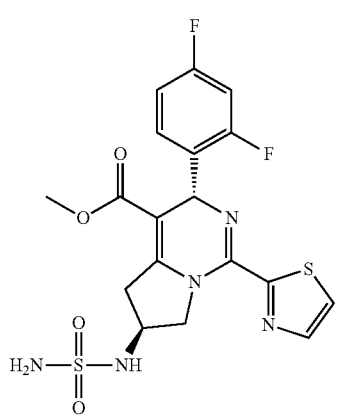 |
| 209 | 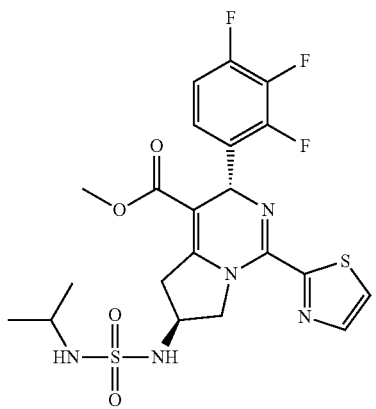 | 212 | 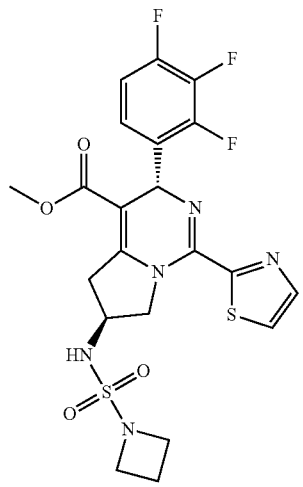 |

213 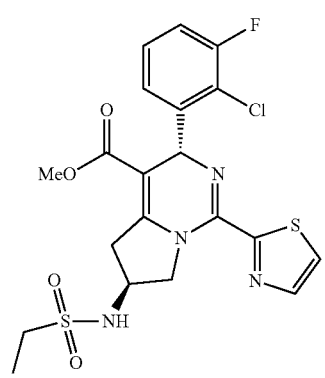
214 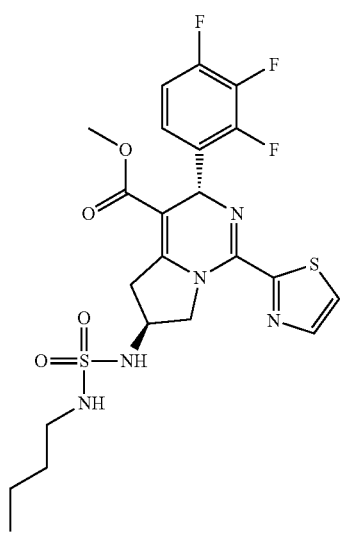
215 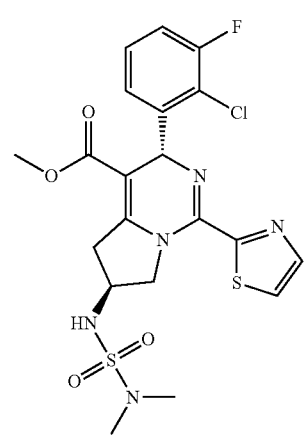
216 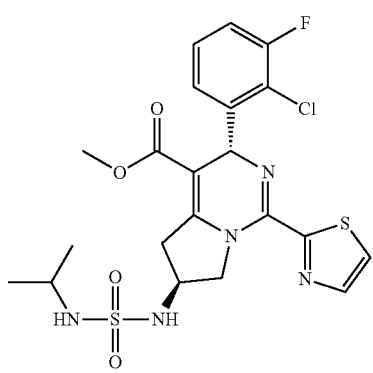
217 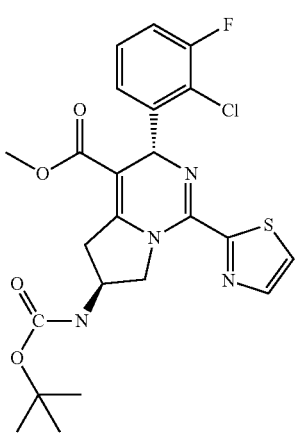
218 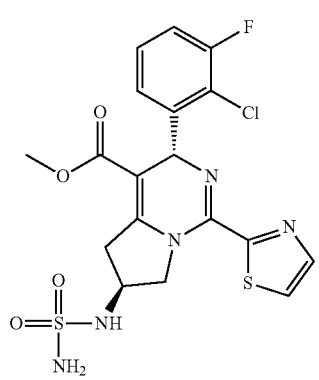
219 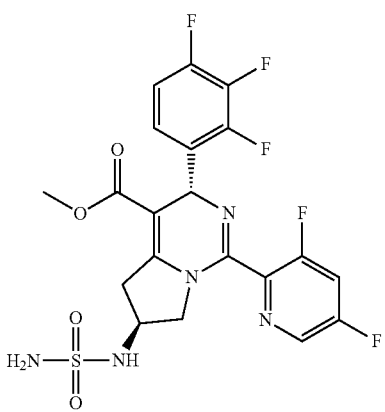

| 220 | 228 |
|---|---|
| 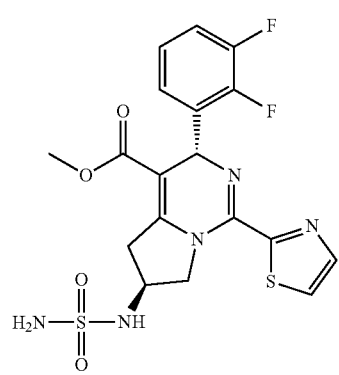 | 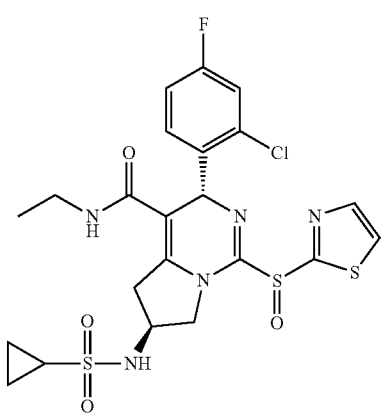 |
| 225 | |
| 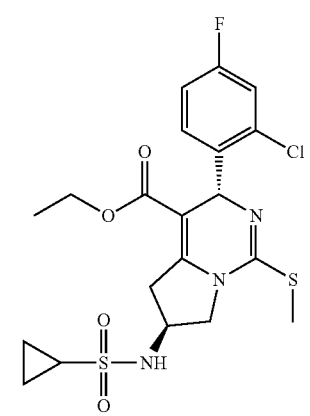 | 229 |
| 226 | 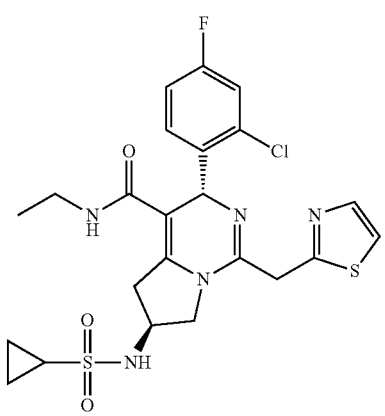 |
| 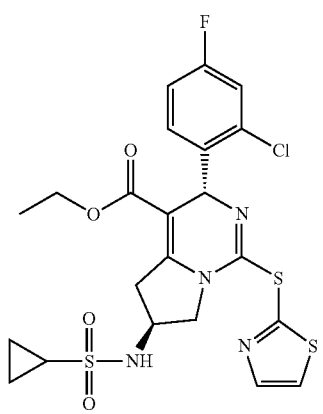 | 230 |
| 227 | 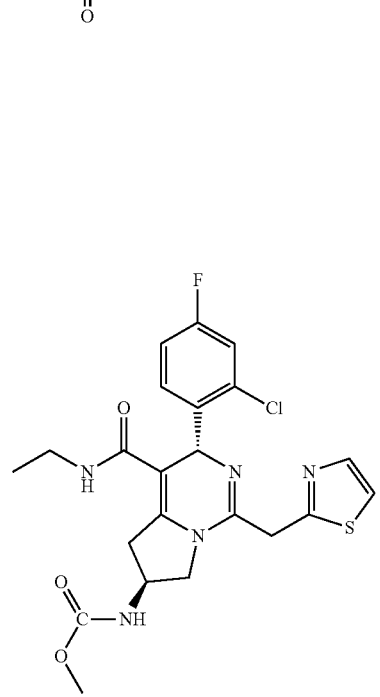 |
| 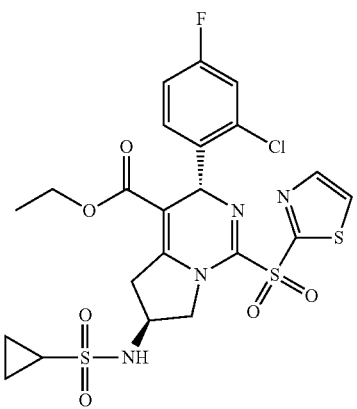 | |

231 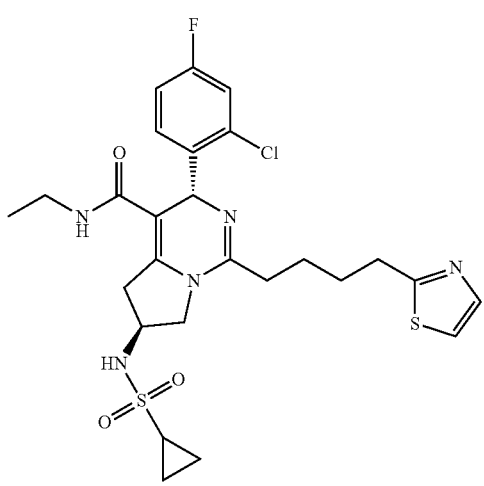
232 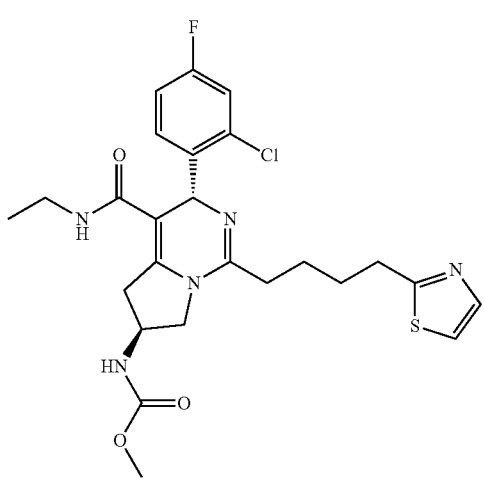
233 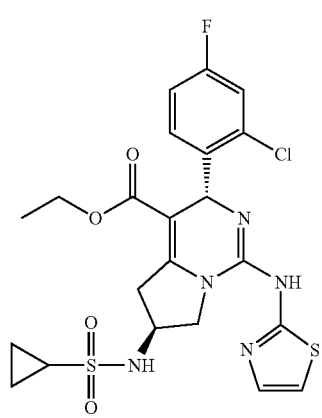
234 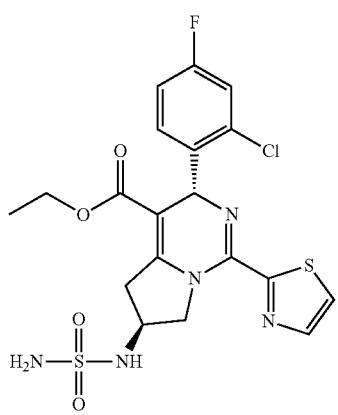
235 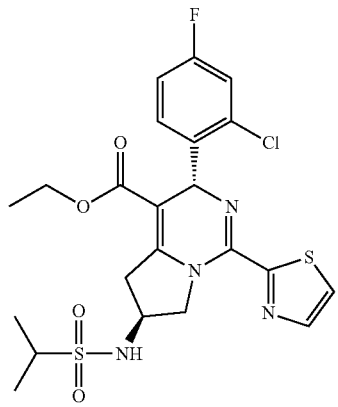
236 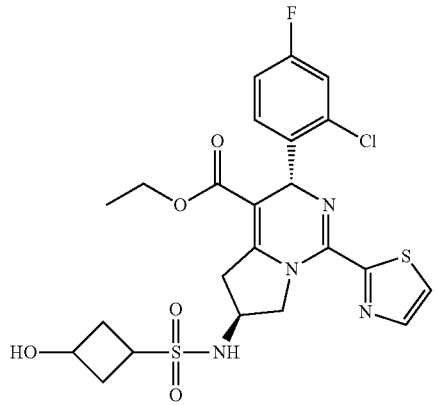
237 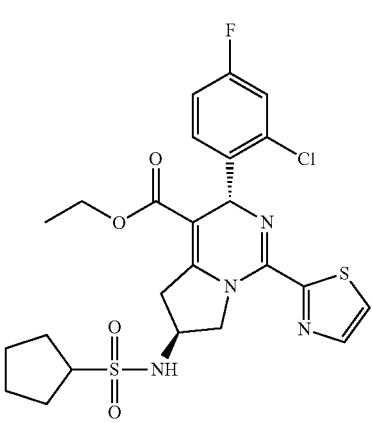

629
-continued
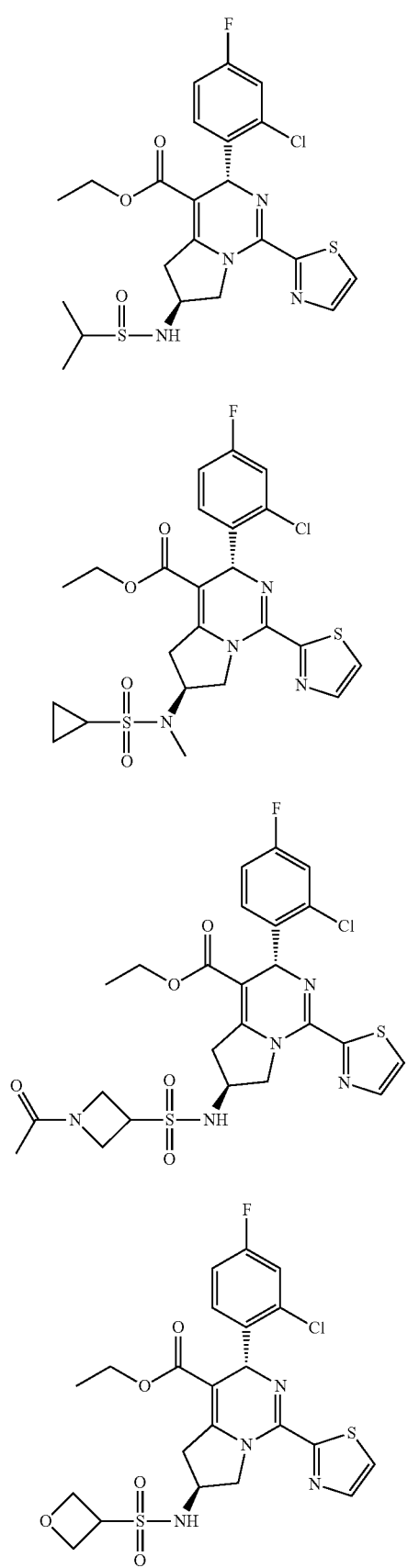
630
-continued
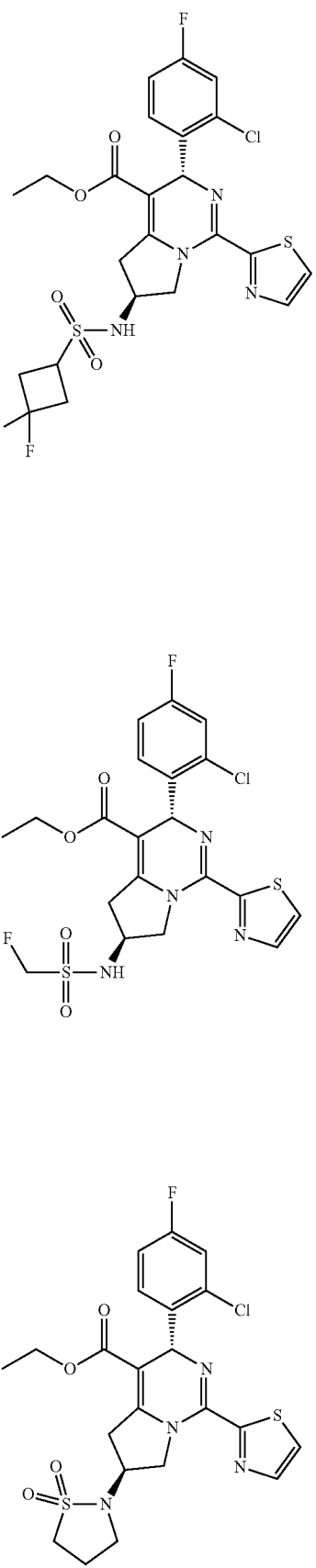

631
-continued
245
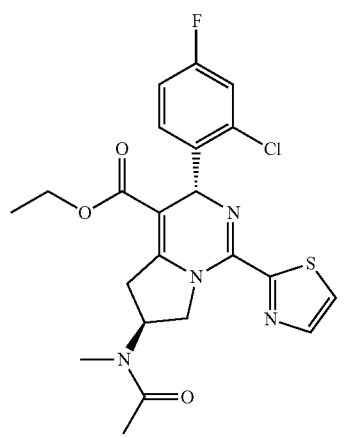
246
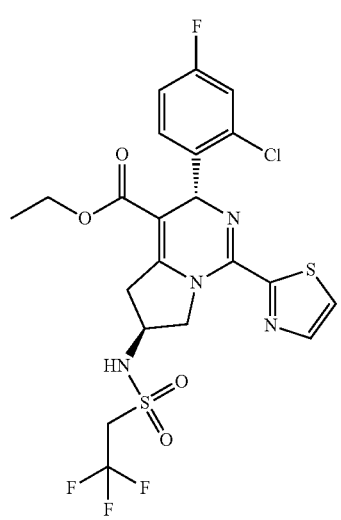
247
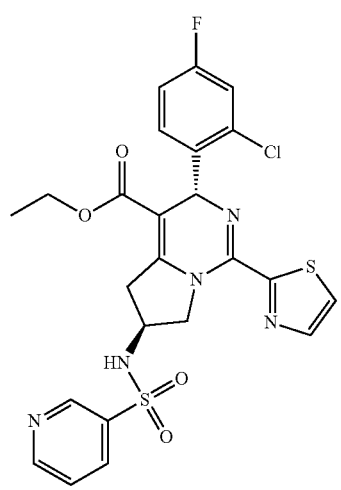
632
-continued
248
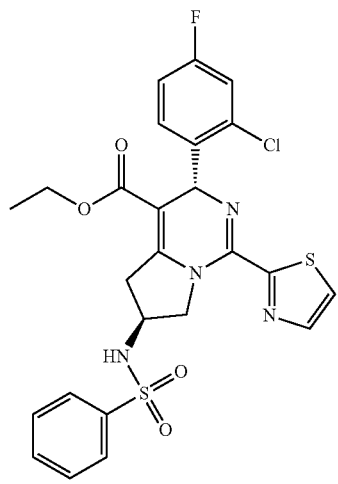
249
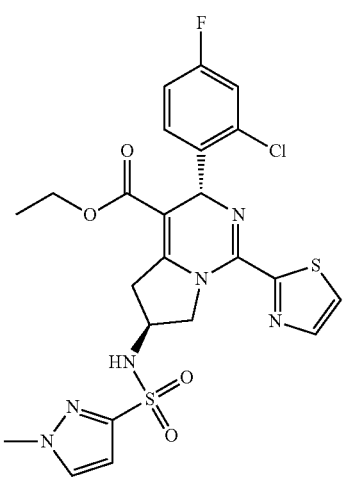
250
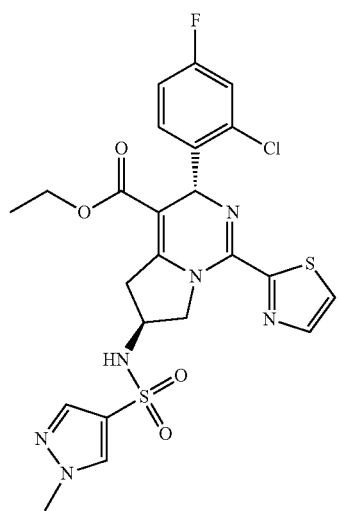

633
-continued
| | |
|---|---|
| 251 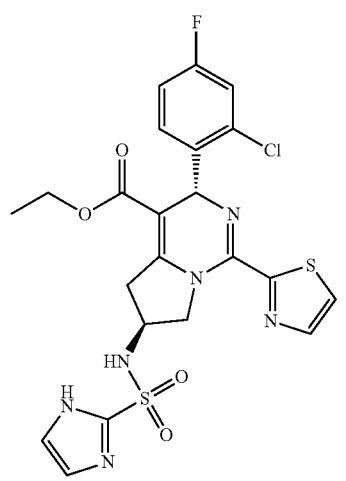 | 254 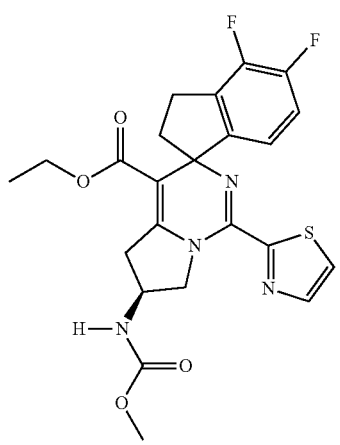 |
| 252 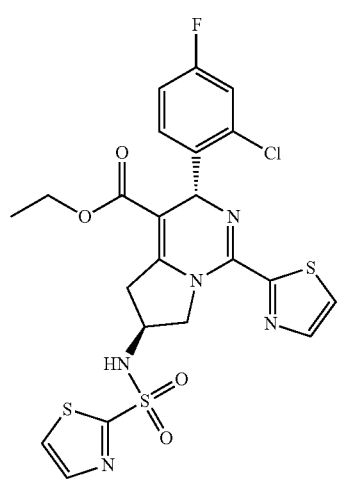 | 255 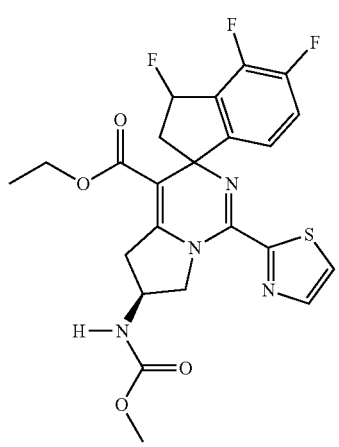 |
| 253 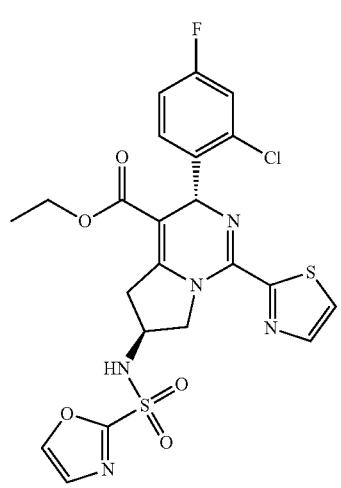 | 256 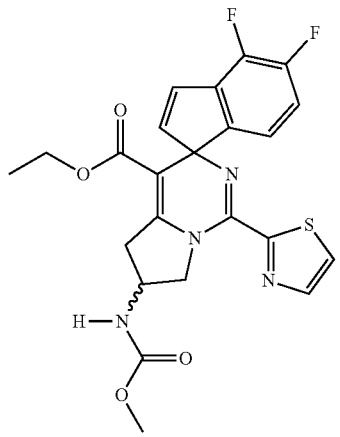 |
634
-continued 635
-continued
257
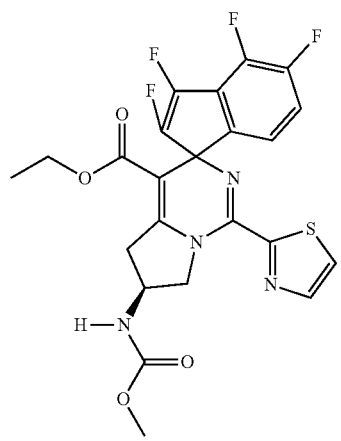
258
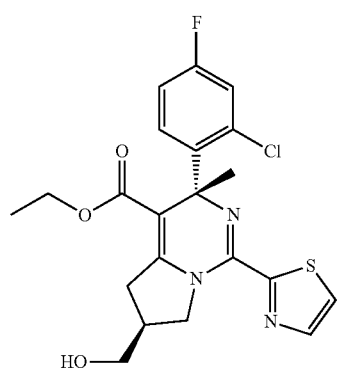
259
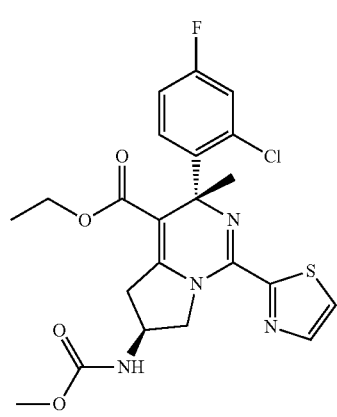
636
-continued
260
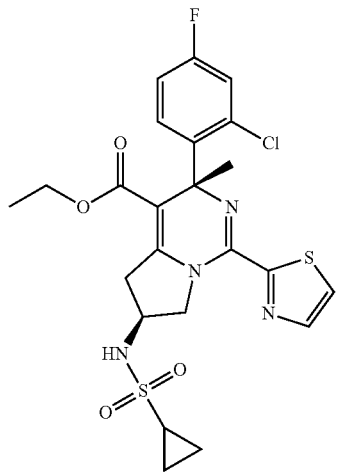
261
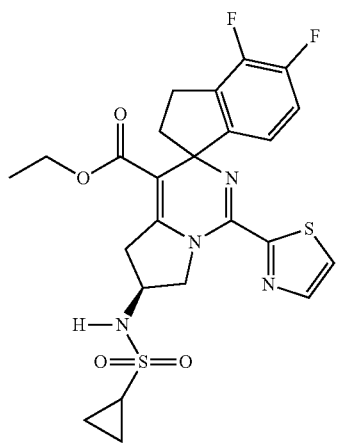
262
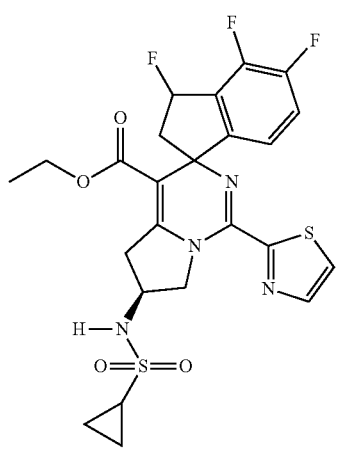

263
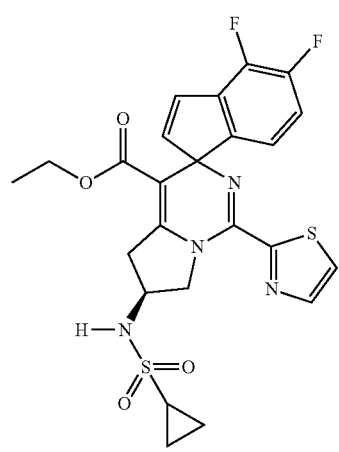
264
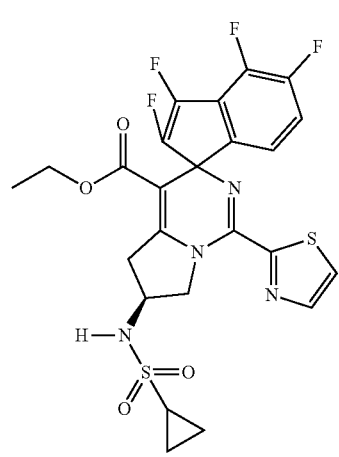
265
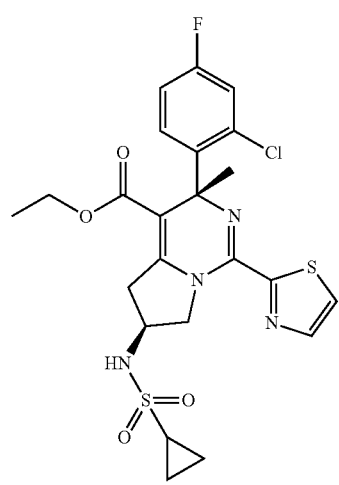
266
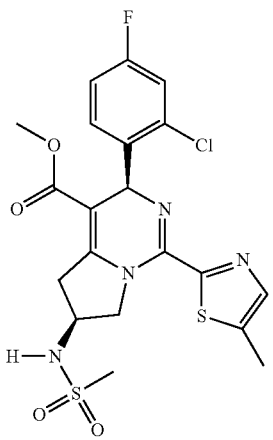
154a
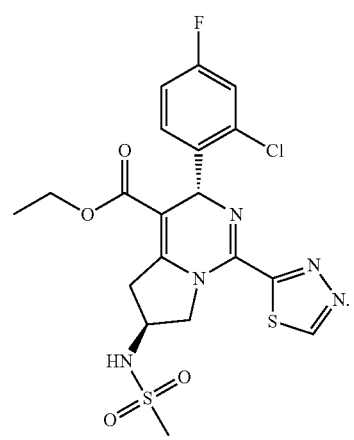
154a
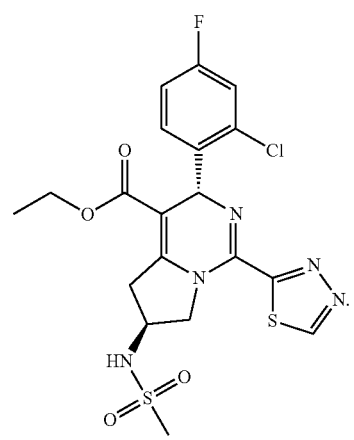
15. The compound or pharmaceutically acceptable salt thereof according to claim 2, wherein $R_{31\text{-}32}$ are separately and independently selected from H, F, Cl, Br, I, OH, $NH_2$, CN, —COOH, or selected from the following groups optionally substituted by 1, 2 or 3 $R_{01}$: $CH_3$,
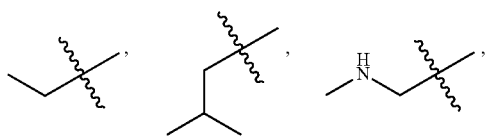

639
-continued
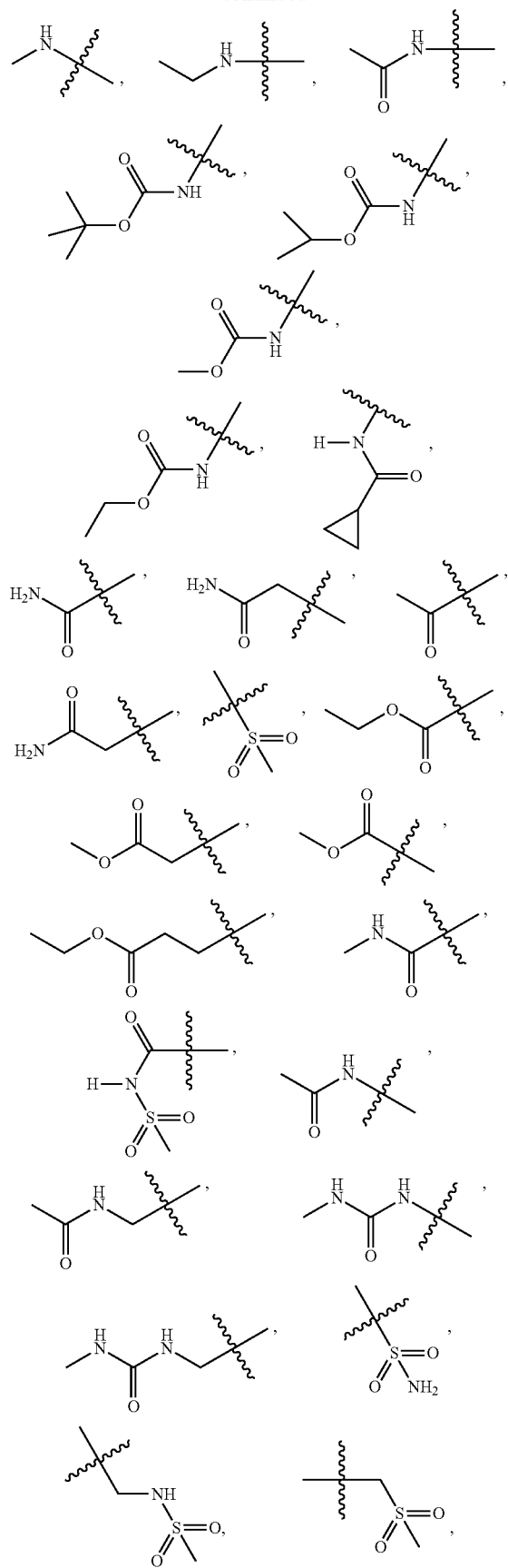
640
-continued
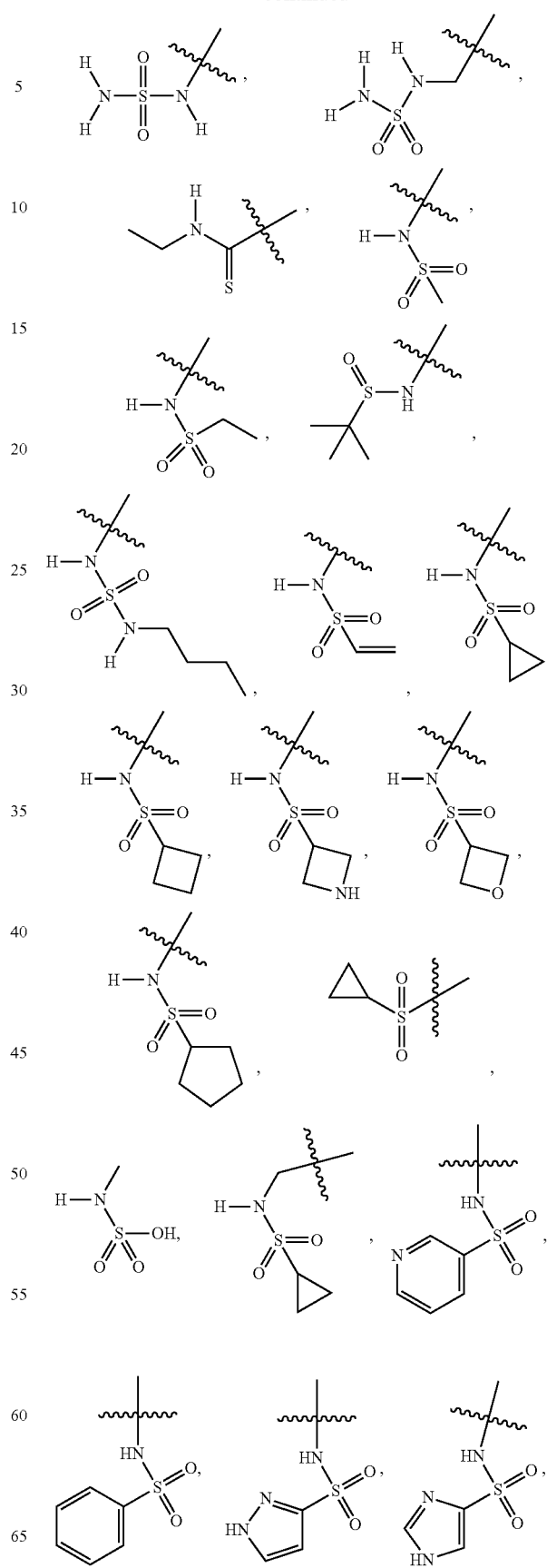

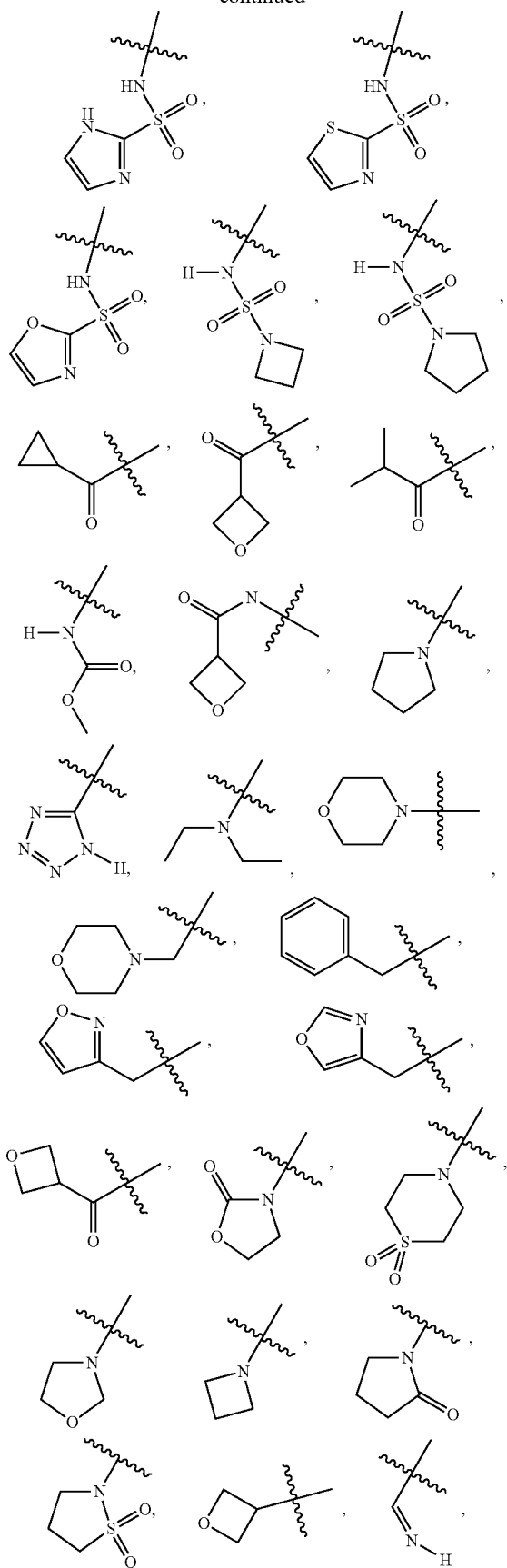
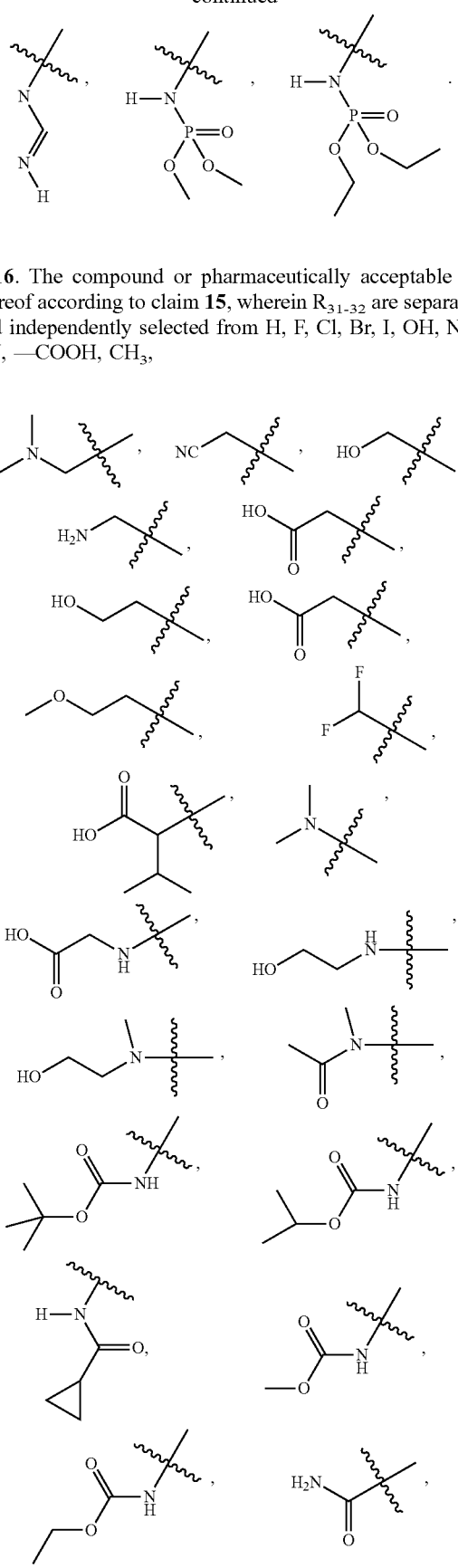
16. The compound or pharmaceutically acceptable salt thereof according to claim 15, wherein $R_{31\text{-}32}$ are separately and independently selected from H, F, Cl, Br, I, OH, $NH_2$, CN, —COOH, $CH_3$, 643
-continued
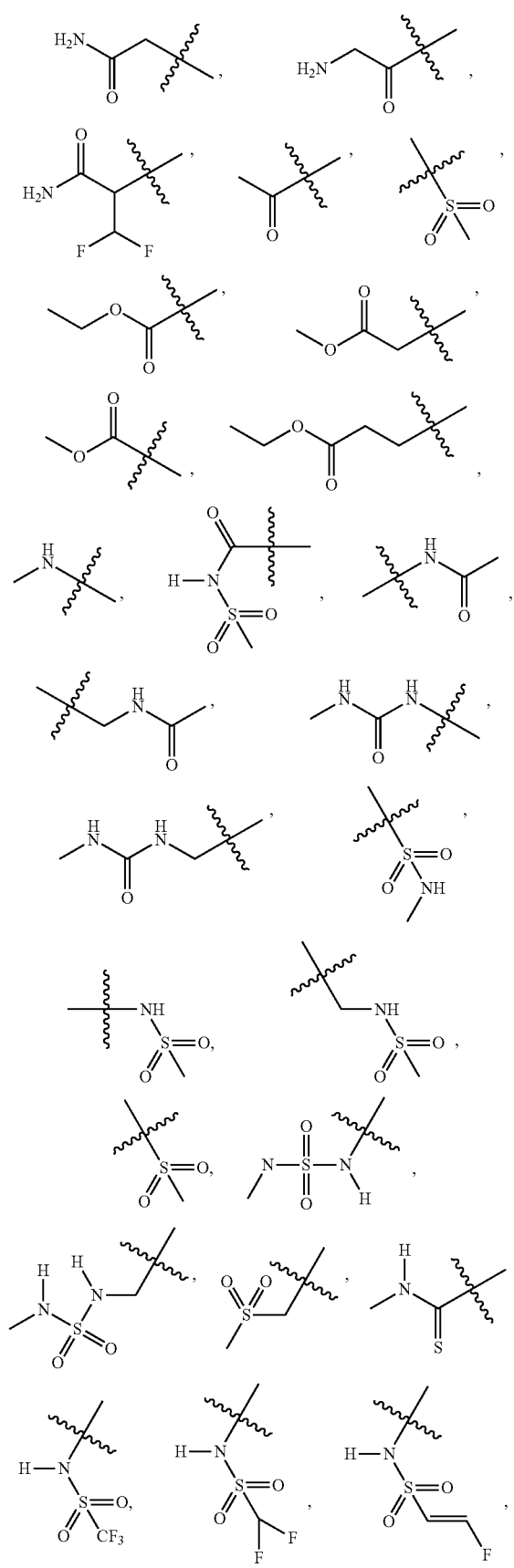
644
-continued
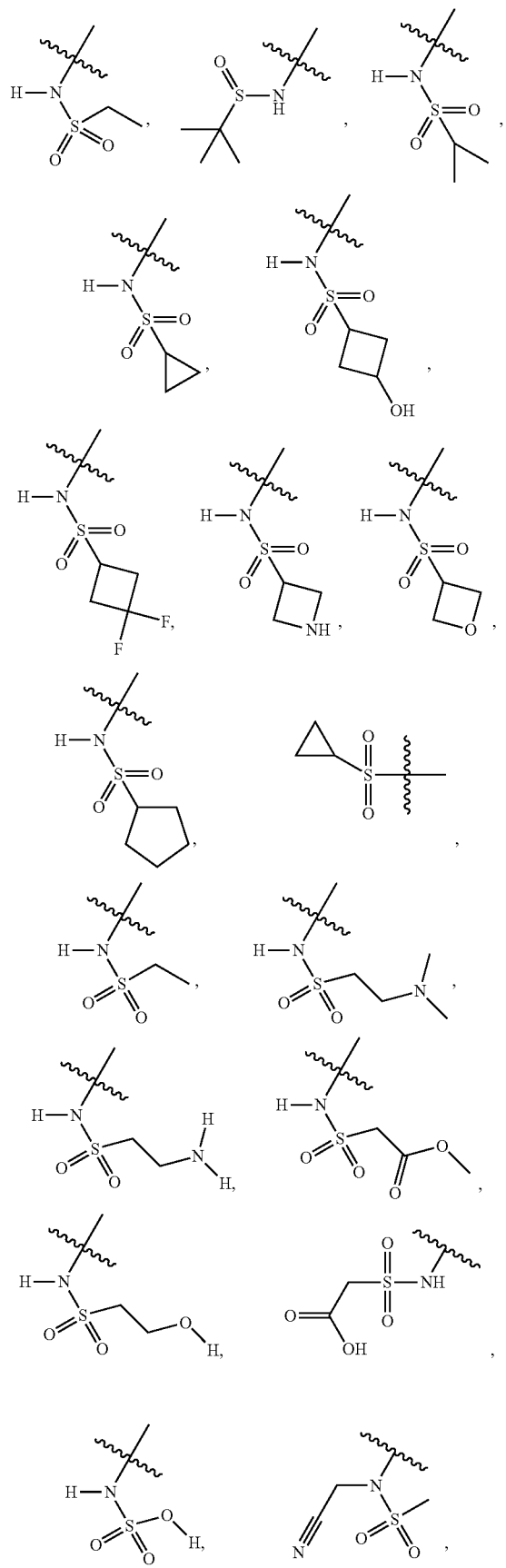

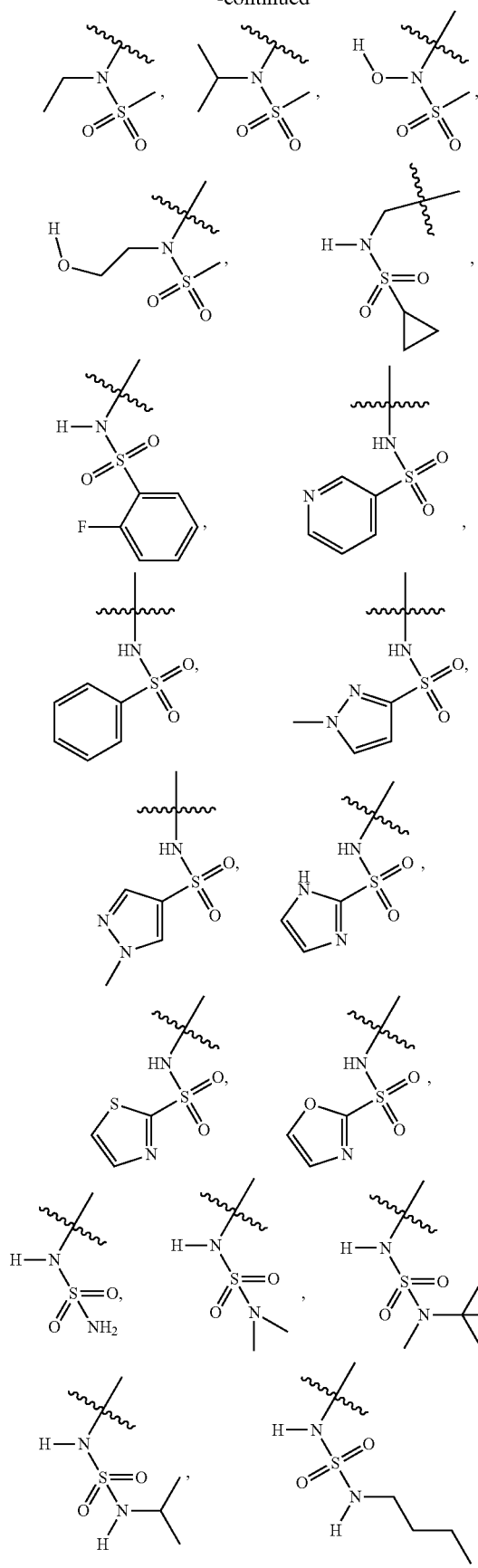
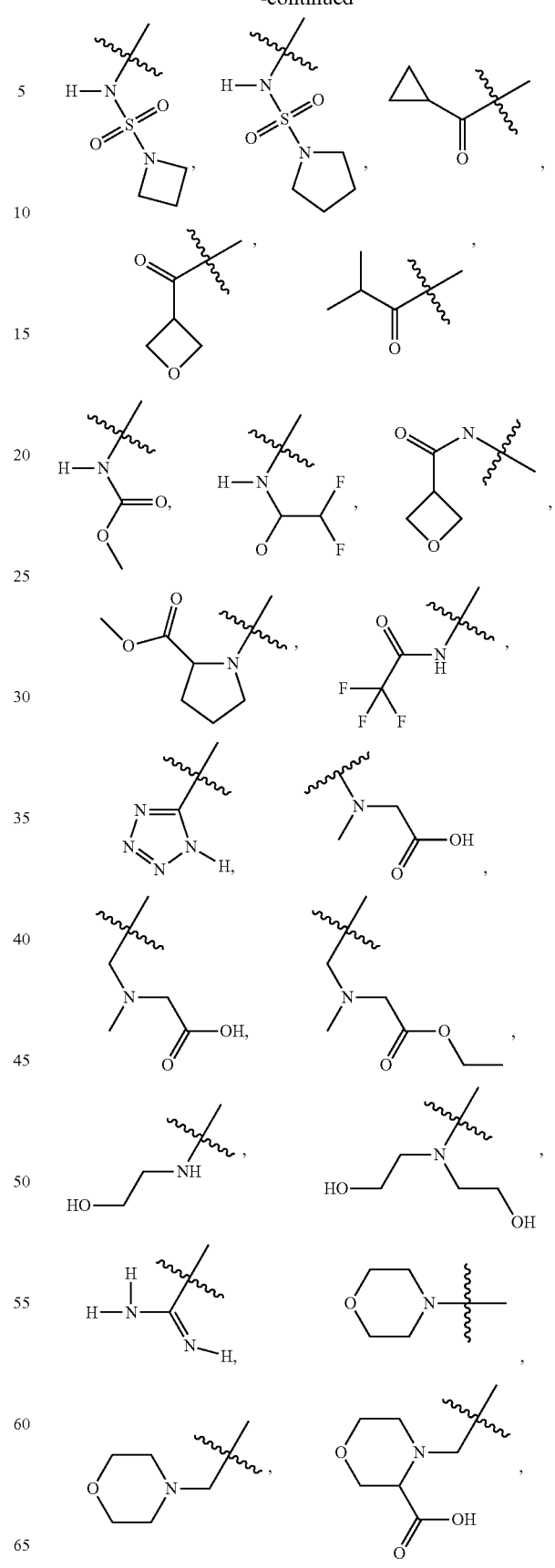

-continued
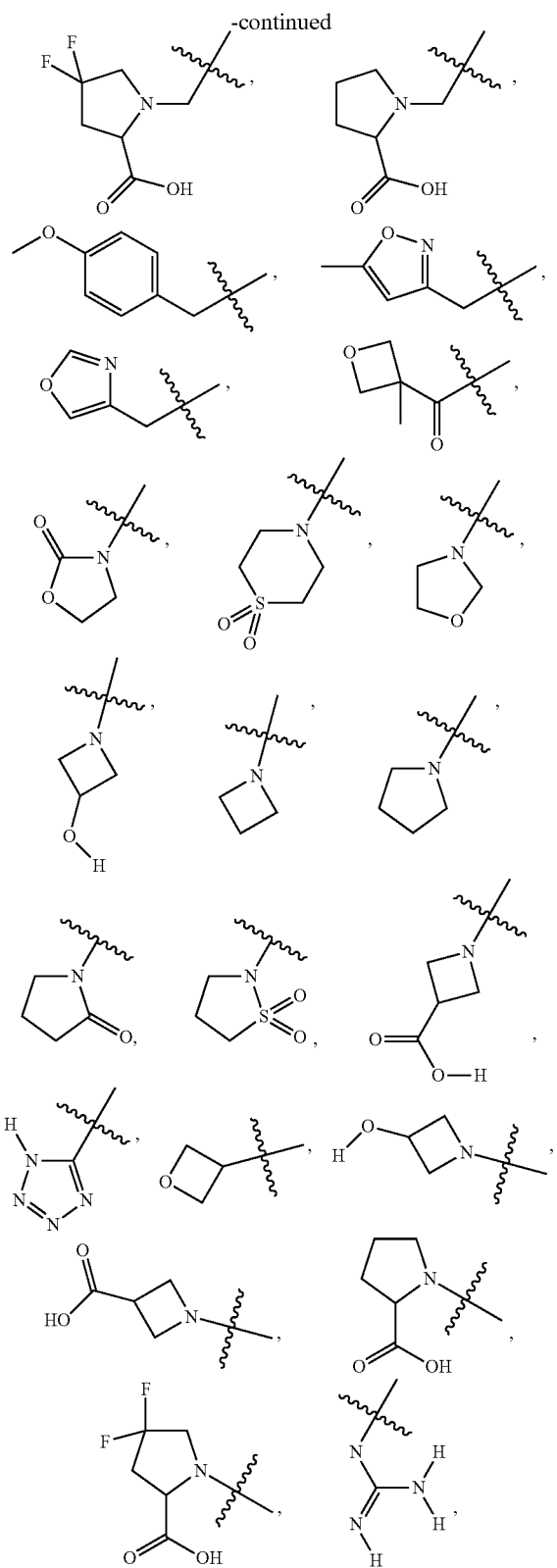
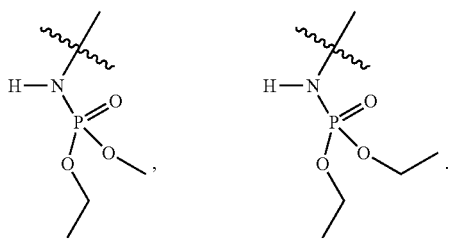
17. The compound or pharmaceutically acceptable salt thereof according to claim 2, wherein the structural unit
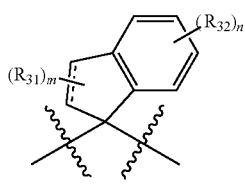
is selected from benzopentyl, indenyl which is optionally substituted by 1, 2 or 3 $R_{oo1}$.
18. The compound or pharmaceutically acceptable salt thereof according to claim 2, wherein the structural unit
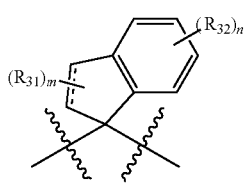
is selected from:
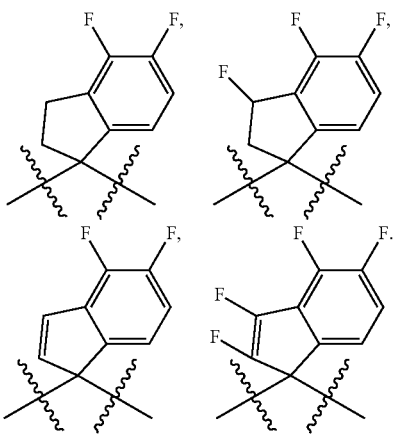
* * * * *